(12) United States Patent
Connors et al.

(10) Patent No.: US 10,047,148 B2
(45) Date of Patent: Aug. 14, 2018

(54) NEUTRALIZING GP41 ANTIBODIES AND THEIR USE

(71) Applicant: The United States of America, as represented by the Secretary, Department of Health and Human Services, Washington, DC (US)

(72) Inventors: Mark Connors, Bethesda, MD (US); Jinghe Huang, Bethesda, MD (US); Leo B. Laub, Richmond, VA (US); Peter Kwong, Washington, DC (US); Gary Nabel, Cambridge, MA (US); John R. Mascola, Rockville, MD (US); Baoshan Zhang, Bethesda, MD (US); Rebecca S. Rudicell, Silver Springs, MD (US); Ivelin Georgiev, Gaithersburg, MD (US); Yongping Yang, Potomac, MD (US); Jiang Zhu, Ashburn, VA (US); Gilad Ofek, Washington, DC (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 0 days.

(21) Appl. No.: 15/699,902

(22) Filed: Sep. 8, 2017

(65) Prior Publication Data

US 2018/0002406 A1   Jan. 4, 2018

Related U.S. Application Data

(62) Division of application No. 15/226,744, filed on Aug. 2, 2016, now Pat. No. 9,783,595, which is a division of application No. 14/356,557, filed as application No. PCT/US2012/063958 on Nov. 7, 2012, now Pat. No. 9,475,862.

(60) Provisional application No. 61/698,480, filed on Sep. 7, 2012, provisional application No. 61/672,708, filed on Jul. 17, 2012, provisional application No. 61/556,660, filed on Nov. 7, 2011, provisional application No. 61/702,703, filed on Sep. 18, 2012.

(51) Int. Cl.
| | |
|---|---|
| *A61K 39/395* | (2006.01) |
| *C07K 16/00* | (2006.01) |
| *A61K 39/42* | (2006.01) |
| *C07K 16/10* | (2006.01) |
| *A61K 39/00* | (2006.01) |
| *G01N 33/569* | (2006.01) |
| *A61K 45/06* | (2006.01) |
| *A61K 49/00* | (2006.01) |

(52) U.S. Cl.
CPC .......... *C07K 16/1063* (2013.01); *A61K 39/42* (2013.01); *A61K 45/06* (2013.01); *A61K 49/0004* (2013.01); *C07K 16/00* (2013.01); *C07K 16/1045* (2013.01); *G01N 33/56972* (2013.01); *G01N 33/56983* (2013.01); *G01N 33/56988* (2013.01); *A61K 2039/505* (2013.01); *C07K 2317/14* (2013.01); *C07K 2317/21* (2013.01); *C07K 2317/31* (2013.01); *C07K 2317/34* (2013.01); *C07K 2317/55* (2013.01); *C07K 2317/56* (2013.01); *C07K 2317/565* (2013.01); *C07K 2317/567* (2013.01); *C07K 2317/76* (2013.01); *G01N 2333/161* (2013.01)

(58) Field of Classification Search
CPC .............. A61K 2039/505; A61K 39/42; C07K 2317/565; C07K 2317/76; C07K 16/00
See application file for complete search history.

(56) References Cited

U.S. PATENT DOCUMENTS

| 7,378,276 B2 | 5/2008 | Ettinger et al. |
| 2011/0064760 A1 | 3/2011 | Cho et al. |

FOREIGN PATENT DOCUMENTS

| WO | WO 2005/111079 | 11/2005 |
| WO | WO 2006/117586 | 11/2006 |
| WO | WO 2010/089402 | 8/2010 |
| WO | WO 2011/038290 | 3/2011 |
| WO | WO 2011/046623 | 4/2011 |
| WO | WO 2013/163427 | 10/2013 |

OTHER PUBLICATIONS

Alam, et al. "Role of HIV membrane in neutralization by two broadly neutralizing antibodies." *Proceedings of the National Academy of Sciences*, 106.48 (2009): 20234-20239.

Bigott-Hennkens et al. "In vitro receptor binding assays: general methods and considerations," *The Quarterly Journal of Nuclear Medicine and Molecular Imaging*, vol. 52, No. 3 (Sep. 1, 2008): 245-253.

(Continued)

*Primary Examiner* — Barry A Chestnut
(74) *Attorney, Agent, or Firm* — Klarquist Sparkman, LLP

(57) ABSTRACT

Monoclonal neutralizing antibodies are disclosed that specifically bind to the HIV-1 gp41 membrane-proximal external region (MPER). Also disclosed are compositions including the disclosed antibodies that specifically bind gp41, nucleic acids encoding these antibodies, expression vectors including the nucleic acids, and isolated host cells that express the nucleic acids. The antibodies and compositions disclosed herein can be used for detecting the presence of HIV-1 in a biological sample, or detecting an HIV-1 infection or diagnosing AIDS in a subject. In additional, the broad neutralization breadth of the disclosed antibodies makes them ideal for treating a subject with an HIV infection. Thus, disclosed are methods of treating and/or preventing HIV infection.

25 Claims, 90 Drawing Sheets

(56) References Cited

OTHER PUBLICATIONS

Bonsignori, et al. "Analysis of a clonal lineage of HIV-1 envelope V2/V3 conformational epitope-specific broadly neutralizing antibodies and their inferred unmutated common ancestors." *Journal of virology*, 85.19 (2011): 9998-10009.
Burton, et al, "Efficient neutralization of primary isolates of HIV-1 by a recombinant human monoclonal antibody." *Science*, 266.5187 (1994): 1024-1027.
Cardoso, et al. "Broadly neutralizing anti-HIV antibody 4E10 recognizes a helical conformation of a highly conserved fusion-associated motif in gp41." *Immunity*, 22.2 (2005): 163-173.
Cardoso, et al. "Structural basis of enhanced binding of extended and helically, constrained peptide epitopes of the broadly neutralizing HIV-1 antibody 4E10." *Journal of molecular biology*, 365.5 (2007): 1533-1544.
Chakrabarti, et al. "Direct antibody access to the HIV-1 membrane-proximal external region positively correlates with neutralization sensitivity." *Journal of virology*, 85.16 (2011): 8217-8226.
Doria-Rose, et al. "Breadth of human immunodeficiency virus-specific neutralizing activity in sera: clustering analysis and association with clinical variables." *Journal of virology*, 84.3 (2010): 1631-1636.
Duebel, et al. "Handbook of Therapeutic Antibodies, Chapter 6." *Handbook of Therapeutic Antibodies*, Wiley-VCH, Weinheim (Jan. 1, 2007): 119-144.
Examination Report issued by the European Patent Office dated May 3, 2016, in corresponding EPC Patent Application No. 12847241.2, filed Jun. 10, 2014 (6 pages).
Extended European Search Report mailed by the European Patent Office dated Feb. 24, 2015 in European Patent Application No. 12847241.2 (11 pages).
Frey, et al. "A fusion-intermediate state of HIV-1 gp41 targeted by broadly neutralizing antibodies." *Proceedings of the National Academy of Sciences*, 105.10 (2008): 3739-3744.
Georgiev et al. "Antibodies VRC01 and 10E8 neutralize HIV-1 with high breadth and potency even with Ig-framework regions substantially reverted to germline," *J. Immunol.* 192 (2014): 1100-6.
Gray, et al. "Antibody specificities associated with neutralization breadth in plasma from human immunodeficiency virus type 1 subtype C-infected blood donors." *Journal of virology*, 83.17 (2009): 8925-8937.
Gray, et al. "Broad neutralization of human immunodeficiency virus type 1 mediated by plasma antibodies against the gp41 membrane proximal external region." *Journal of virology*, 83.21 (2009): 11265-11274.
Gray, et al. "Neutralizing antibody responses in acute human immunodeficiency virus type 1 subtype C infection." *Journal of virology*, 81.12 (2007): 6187-6196.
Haynes, et al. "B-cell-lineage immunogen design in vaccine development with HIV-1 as a case study." *Nature biotechnology*, 30.5 (2012): 423-433.
Haynes, et al. "Cardiolipin polyspecific autoreactivity in two broadly neutralizing HIV-1 antibodies." *Science*, 308.5730 (2005): 1906-1908.
Huang, et al. "Broad and potent HIV-1 neutralization by a human antibody that binds the gp41-gp120 interface," *Nature*, 515, (2014): 1-17.
Huang, et al. "Broad and potent neutralization of HIV-1 by a gp41-specific human antibody." *Nature*, 491, (2012): 406-412.
International Search Report issued by the Australian Patent Office dated Jan. 10, 2013, in Application PCT/US2012/063958 (5 pages).
Julien, et al. "Structural details of HIV-1 recognition by the broadly neutralizing monoclonal antibody 2F5: epitope conformation, antigen-recognition loop mobility, and anion-binding site." *Journal of molecular biology*, 384.2 (2008): 377-392.
Kershaw, et al. "Immunization against endogenous retroviral tumor-associated antigens." *Cancer research*, 61.21, (2001): 7920-7924.

Konforte, et al. "IL-21: an executor of B cell fate." *The Journal of Immunology*, 182.4, (2009): 1781-1787.
Li, et al. "Human immunodeficiency virus type 1 env clones from acute and early subtype B infections for standardized assessments of vaccine-elicited neutralizing antibodies." *Journal of virology*, 79.16 (2005): 10108-10125.
Liu, et al. "Potent and broad anti-HIV-1 activity exhibited by a glycosyl-phosphatidylinositol-anchored peptide derived from the CDR H3 of broadly neutralizing antibody PG16." *Journal of virology*, 85.17, (2011): 8467-8476.
Migueles, et al. "Lytic Granule Loading of $CD8^+$ T Cells Is Required for HIV-Infected Cell Elimination Associated with Immune Control." *Immunity*, 29.6 (2008): 1009-1021.
Montero, et al. "The membrane-proximal external region of the human immunodeficiency virus type 1 envelope: dominant site of antibody neutralization and target for vaccine design." *Microbiology and molecular biology reviews* 72.1 (2008): 54-84.
Morris, et al. "Isolation of a human anti-HIV gp41 membrane proximal region neutralizing antibody by antigen-specific single B cell sorting." *PloS one*, 6.9 (2011): e23532.
Muster, et al. "A conserved neutralizing epitope on gp41 of human immunodeficiency virus type 1." *Journal of virology*, 67.11 (1993): 6642-6647.
Nelson, et al. "An affinity-enhanced neutralizing antibody against the membrane-proximal external region of human immunodeficiency virus type 1 gp41 recognizes an epitope between those of 2F5 and 4E10." *Journal of virology*, 81.8, (2007): 4033-4043.
Ofek, et al. "Elicitation of structure-specific antibodies by epitope scaffolds." *Proceedings of the National Academy of Sciences*, 107.42 (2010): 17880-17887.
Ofek, et al. "Structure and mechanistic analysis of the anti-human immunodeficiency virus type 1 antibody 2F5 in complex with its gp41 epitope."*Journal of virology*, 78.19 (2004): 10724-10737.
Ohno et al. "Antigen-binding specificities of antibodies are primarily determined by seven residues of VH." *Proceedings of the National Academy of Sciences* 82, No. 9 (1985): 2945-2949.
Pegu et al. "Neutralizing antibodies to HIV-1 envelope protect more effectively in vivo than those to the CD4 receptor." *Science translational medicine* 6.243 (2014): 243ra88-243ra88.
Pejchal, et al. "A conformational switch in human immunodeficiency virus gp41 revealed by the structures of overlapping epitopes recognized by neutralizing antibodies." *Journal of virology*, 83.17, (2009): 8451-8462.
Rathinakumar, et al. "Binding of anti-membrane-proximal gp41 monoclonal antibodies to CD4-liganded and-unliganded human immunodeficiency virus type 1 and simian immunodeficiency virus virions." *Journal of virology*, 86.3 (2012): 1820-1831.
Rudikoff, et al. "Single amino acid substitution altering antigen-binding specificity." *Proceedings of the National Academy of Sciences* 79, No. 6 (1982): 1979-1983.
Scheid, et al. "A method for identification of HIV gp140 binding memory B cells in human blood." *Journal of immunological methods*, 343.2, (2009): 65-67.
Scheid, et al. "Broad diversity of neutralizing antibodies isolated from memory B cells in HIV-infected individuals." *Nature*, 458. 7238, (2009): 636-640.
Scheid, et al. "Sequence and structural convergence of broad and potent HIV antibodies that mimic CD4 binding." *Science*, 333.6049 (2011): 1633-1637.
Song, et al. "Broadly neutralizing anti-HIV-1 antibodies disrupt a hinge-related function of gp41 at the membrane interface." *Proceedings of the National Academy of Sciences*, 106.22, pp. 9057-9062 (2009): 9057-9062.
Story, et al. "Profiling antibody responses by multiparametric analysis of primary B cells." *Proceedings of the National Academy of Sciences*, 105.46 (2008): 17902-17907.
Tiller, et al. "Efficient generation of monoclonal antibodies from single human B cells by single cell RT-PCR and expression vector cloning." *Journal of immunological methods*, 329.1 (2008): 112-124.
Tomaras, et al. "Polyclonal B cell responses to conserved neutralization epitopes in a subset of HIV-1-infected individuals." *Journal of virology*, 85.21 (2011): 11502-11519.

(56) References Cited

OTHER PUBLICATIONS

Walker, et al. "A limited number of antibody specificities mediate broad and potent serum neutralization in selected HIV-1 infected individuals,"*PLoS pathogens*, 6.8 (2010): e1001028.
Walker, et al. "Broad and potent neutralizing antibodies from an African donor reveal a new HIV-1 vaccine target." *Science*, 326. 5950, (2009): 285-289.
Walker, et al. "Broad neutralization coverage of HIV by multiple highly potent antibodies." *Nature*, 477.7365 (2011): 466-470.
Walker, et al. "Rational antibody-based HIV-1 vaccine design: current approaches and future directions." *Current opinion in immunology*, 22.3 (2010): 358-366.
Written Opinion issued by the Australian Patent Office on Jan. 10, 2013, in Application PCT/US2012/063958 (5 pages).
Wu, et al. "Focused evolution of HIV-1 neutralizing antibodies revealed by structures and deep sequencing." *Science*, 333.6049 (2011): 1593-1602.
Wu, et al. "Rational design of envelope identifies broadly neutralizing human monoclonal antibodies to HIV-1." *Science*, 329.5993 (2010): 856-861.
Wu, et al. "Selection pressure on HIV-1 envelope by broadly neutralizing antibodies to the conserved CD4-binding site." *Journal of virology*, 86.10 (2012): 5844-5856.
Zhou et al. "Transplanting Supersites of HIV-1 Vulnerability." *PloS one* 9.7 (2014): e99881.
Zhu, et al. "Mining the antibodyome for HIV-1-neutralizing antibodies with next-generation sequencing and phylogenetic pairing of heavy/light chains." *Proceedings of the National Academy of Sciences* 110 (2013): 6470-6475.
Zhu, et al. "Somatic populations of PGT135-137 HIV-1-neutralizing antibodies identified by 454 pyrosequencing and bioinformatics." *Frontiers in microbiology*, 3 (2012).
Zwick, et al. "Anti-human immunodeficiency virus type 1 (HIV-1) antibodies 2F5 and 4E10 require surprisingly few crucial residues in the membrane-proximal external region of glycoprotein gp41 to neutralize HIV-1."*Journal of virology*, 79.2 (2005): 1252-1261.
Zwick, et al. "Broadly neutralizing antibodies targeted to the membrane-proximal external region of human immunodeficiency virus type 1 glycoprotein gp41." *Journal of virology*, 75.22 (2001): 10892-10905.

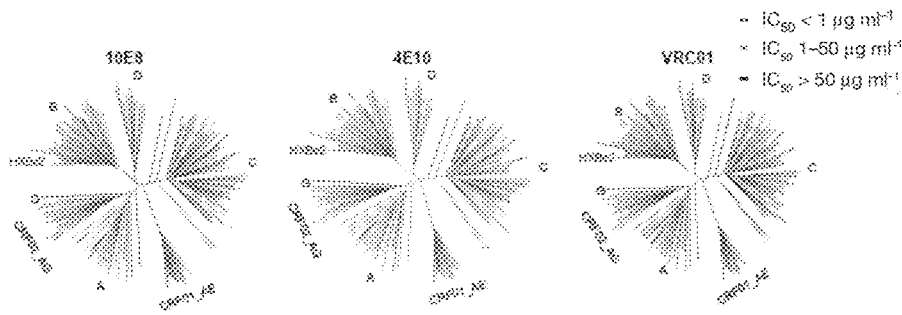

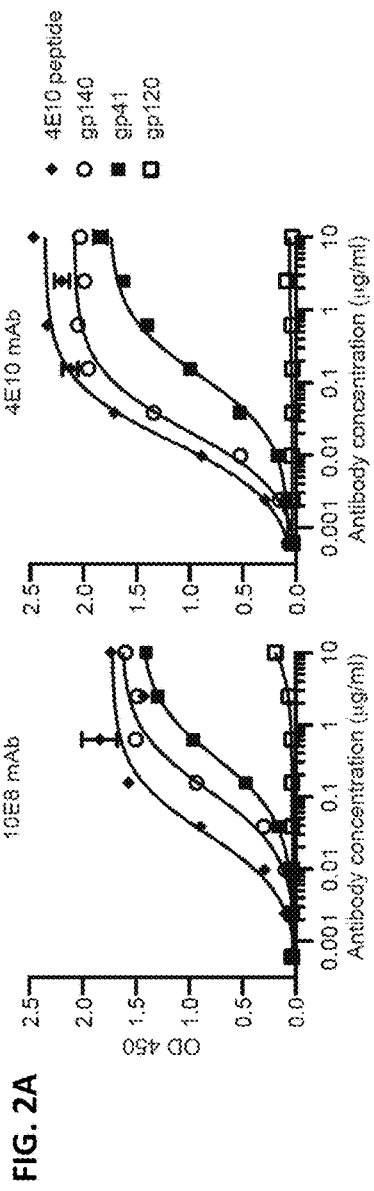
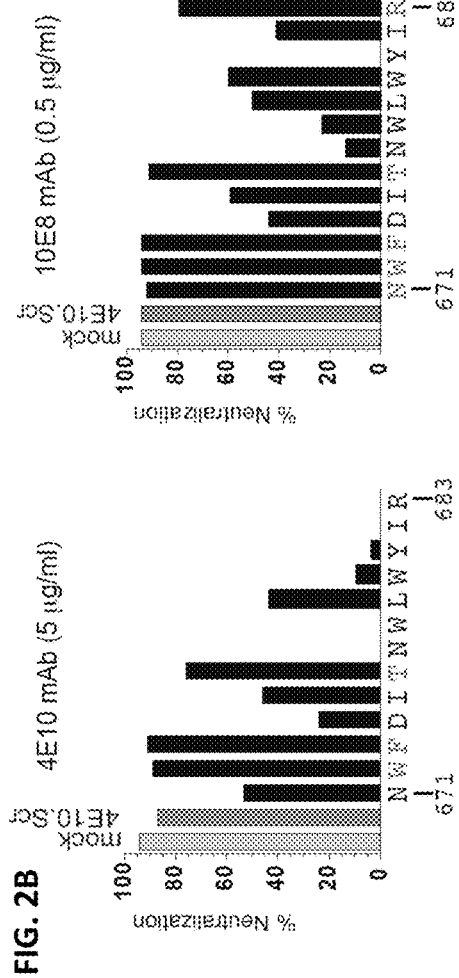
FIG. 2A
FIG. 2B

Buried contact surfaces

Epitope conservation

Paratope binding

Epitope binding

Paratope neutralization

Epitope neutralization

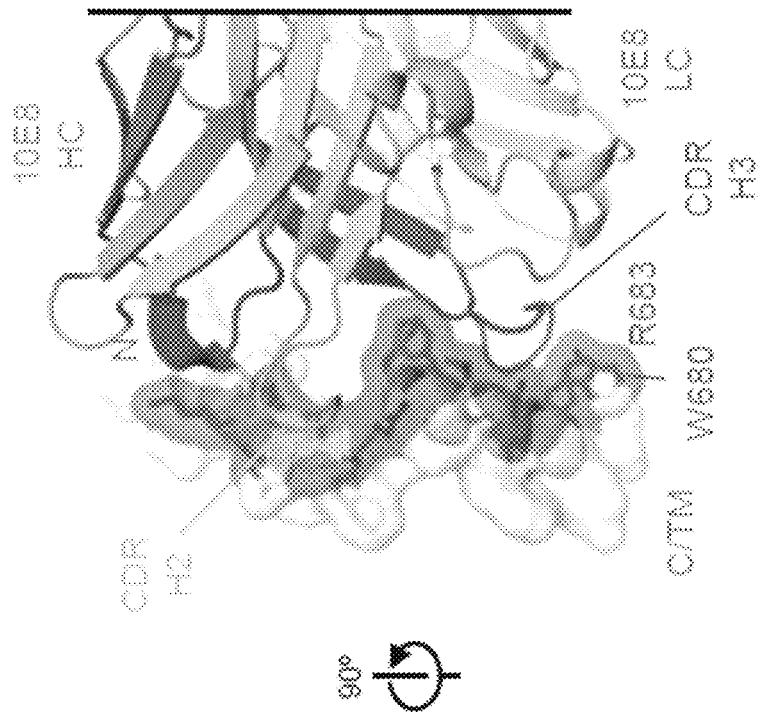
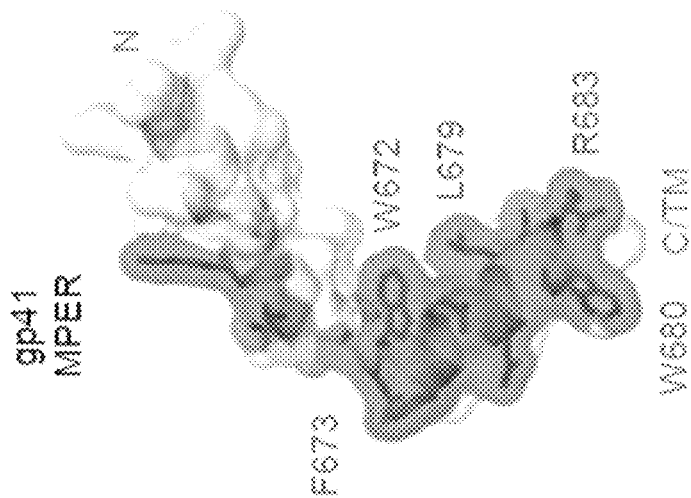
FIG. 5B

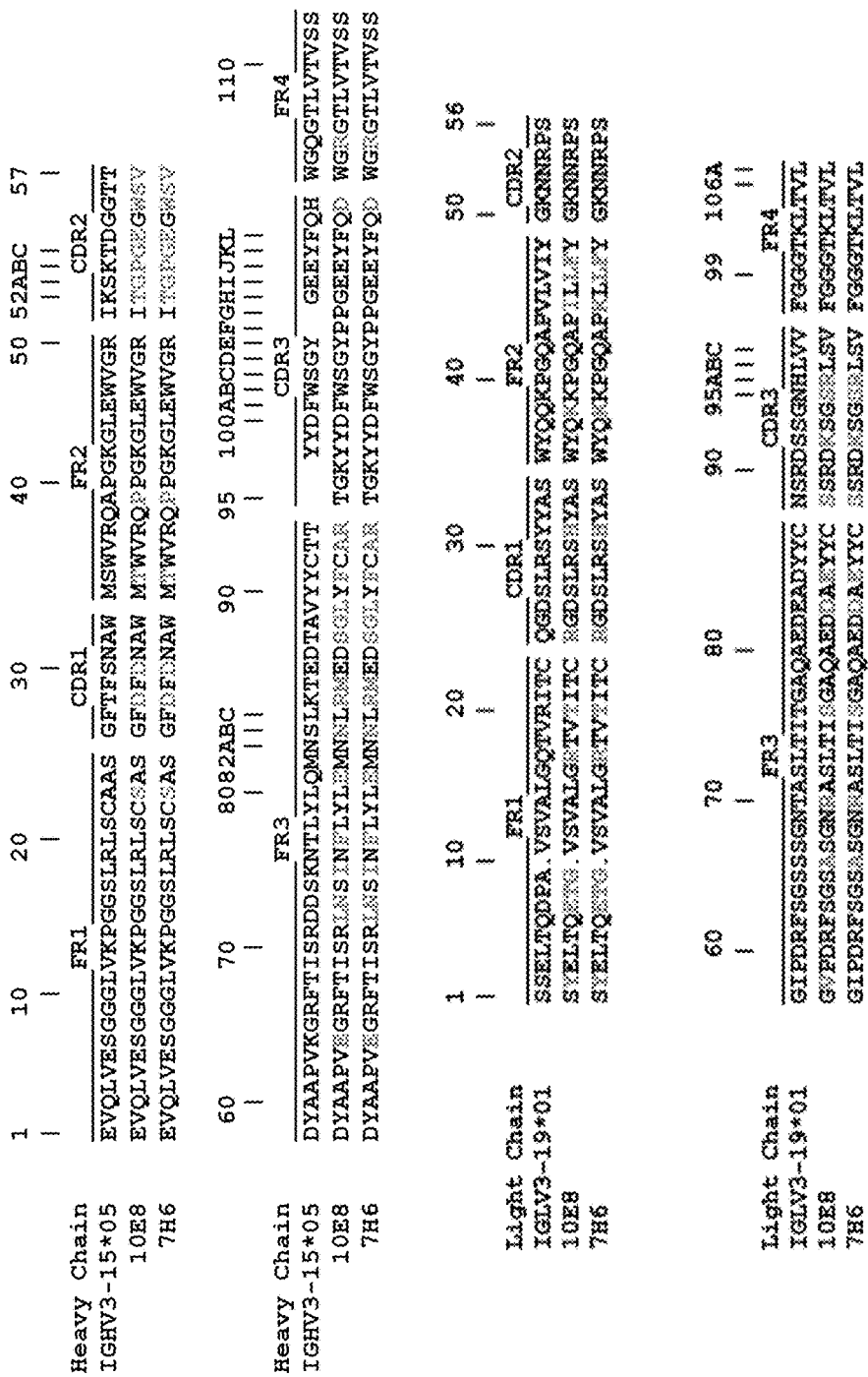

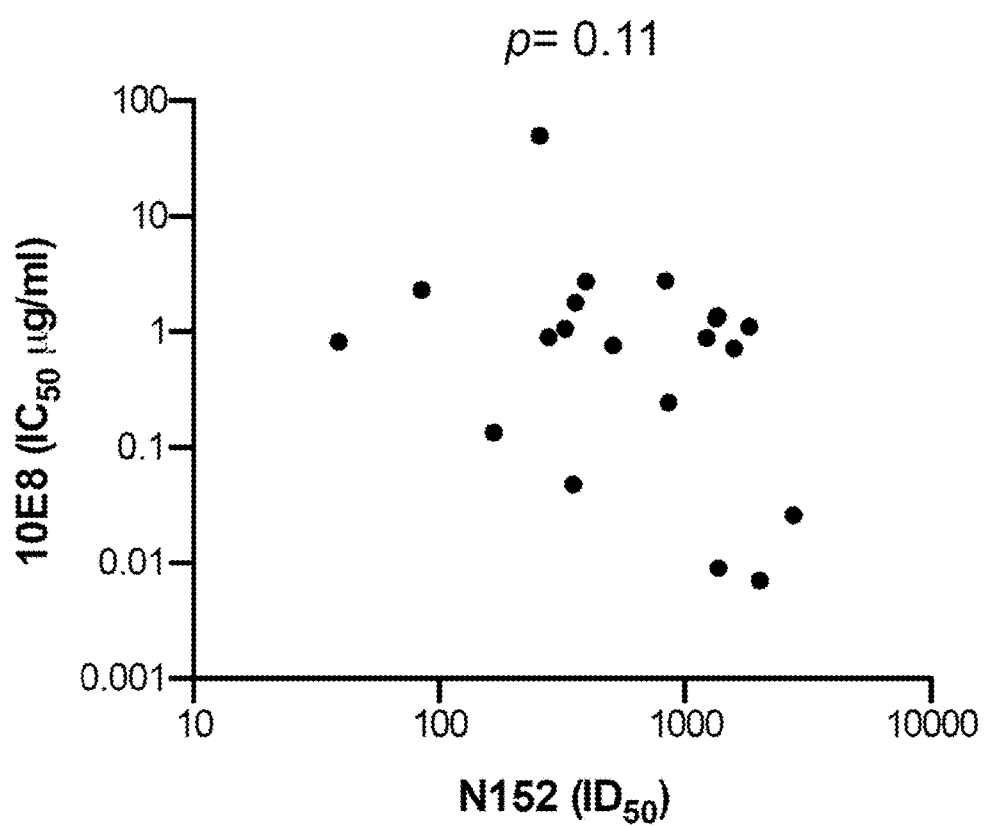

FIG. 8B

| Peptide | mAb IC50 (µg/ml) | | | | Fold Effect | | | |
|---|---|---|---|---|---|---|---|---|
| | 2F5 | 4E10 | Z13e1 | 10E8 | 2F5 | 4E10 | Z13e1 | 10E8 |
| mock | 0.068 | 0.188 | 0.523 | 0.002 | -- | -- | -- | -- |
| MPER.Scr | 0.072 | 0.318 | 0.694 | 0.002 | 1.1 | 1.7 | 1.3 | 1.0 |
| MPER | >5 | >5 | >50 | >0.1 | >74 | >27 | >96 | >50 |
| 2F5 | >5 | 0.229 | 0.564 | 0.002 | >74 | 1.2 | 1.1 | 1.0 |
| 4E10 | 0.082 | >5 | 1.94 | >0.1 | 1.2 | >27 | 3.7 | >50 |
| 4E10.19 | 0.048 | >5 | 0.59 | 0.001 | 0.7 | >27 | 1.2 | 3.8 |
| Z13e1 | 0.074 | 0.435 | 4.28 | 0.004 | 1.1 | 2.3 | 8.2 | 2.0 |

FIG. 8C

| Peptide | IC80 (µg/ml) | | | | Fold Effect | | | |
|---|---|---|---|---|---|---|---|---|
| | 2F5 | 4E10 | z13e1 | 10E8 | 2F5 | 4E10 | z13e1 | 10E8 |
| mock peptide | 0.278 | 0.822 | 1.61 | 0.006 | -- | -- | -- | -- |
| MPR.Scr.02 | 0.335 | 1.8 | 2.51 | 0.01 | 1.2 | 2.2 | 1.6 | 1.7 |
| MPR.03 | >5 | >5 | >50 | >0.1 | >18 | >6.1 | >31 | >17 |
| 2F5.01 | >5 | 1.17 | 1.67 | 0.006 | >18 | 1.4 | 1.0 | 1.0 |
| 4E10.22 | 0.304 | >5 | 6.82 | >0.1 | 1.1 | >6.1 | 4.2 | >17 |
| z13e1.01 | 0.313 | 3.33 | 20.5 | 0.02 | 1.1 | 4.1 | 13 | 3.3 |

| Analyte | ka (1/Ms) | SE* (ka) | kd (1/s) | SE (kd) | $K_D$ (M) | SE ($K_D$) |
|---|---|---|---|---|---|---|
| 10E8 Fab | 6.88E+04 | 49.0 | 0.00119 | 1.30E-06 | 1.73E-08 | 2.26E-11 |
| 2F5 Fab | 2.87E+05 | 2.20E+02 | 0.00109 | 2.00E-06 | 3.80E-09 | 7.56E-12 |
| 4E10 Fab | 1.27E+05 | 59.0 | 9.41E-05 | 8.00E-07 | 7.40E-10 | 6.30E-12 |

MPER Ligand: RRRNEQELLELDKWASLWNWFDITNWLWYIRRKK-biotin
*SE, standard error

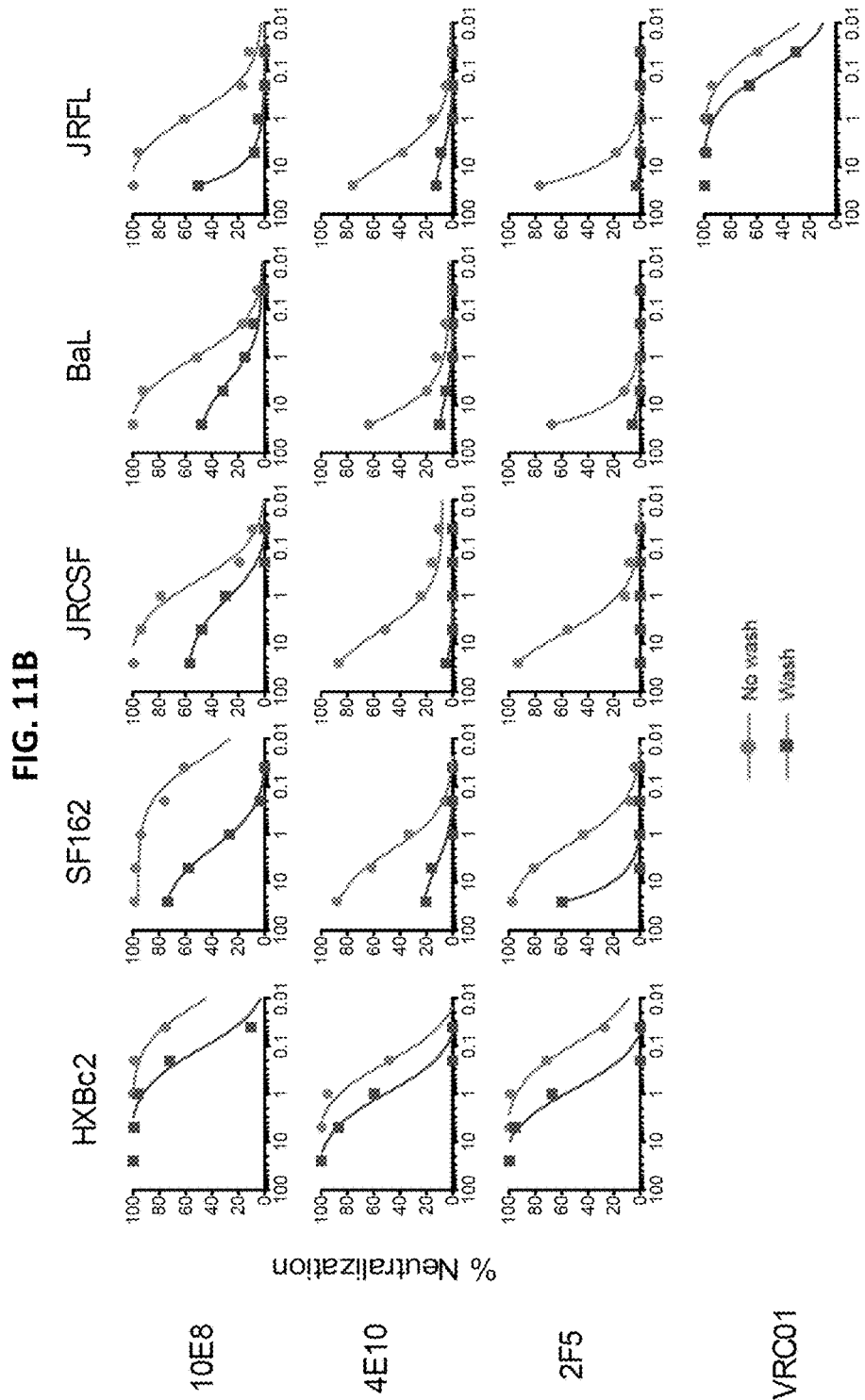

FIG. 11C

Antibody concentration (μg/ml)

| Antibody | HXB2 | | | SF162 | | | JRCSF | | | BaL | | | JRFL | | |
|---|---|---|---|---|---|---|---|---|---|---|---|---|---|---|---|
| | no wash | wash | fold change | no wash | wash | fold change | no wash | wash | fold change | no wash | wash | fold change | no wash | wash | fold change |
| 10E8 AUC | 2494.0 | 2457.0 | 1.0 | 2438.0 | 1499.0 | 1.6 | 2233.0 | 1213.0 | 1.9 | 2242.0 | 900.9 | 2.5 | 2312.0 | 611.6 | 3.8 |
| 4E10 AUC | 2449.0 | 2186.0 | 1.1 | 1707.0 | 398.7 | 4.3 | 1553.0 | 51.3 | 30.3 | 901.5 | 160.0 | 5.6 | 1259.0 | 230.9 | 5.5 |
| 2F5 AUC | 2476.0 | 2310.0 | 1.1 | 2057.0 | 596.0 | 3.5 | 1637.0 | 0.0 | NA | 823.8 | 62.1 | 13.3 | 992.5 | 29.6 | 33.5 |
| VRC01 AUC | - | - | - | - | - | - | - | - | - | - | - | - | 2491.0 | 2451.0 | 1.0 |
| 10E8 IC× | 80.0 | 27.0 | 3.0 | 80.0 | 3.6 | 22.1 | 80.0 | 34.1 | 2.3 | 60.0 | 16.6 | 3.6 | 75.0 | 3.9 | 19.6 |
| 4E10 IC× | 80.0 | 42.3 | 1.9 | 80.0 | 18.5 | 4.3 | 80.0 | 3.3 | 24.2 | 60.0 | 9.8 | 6.1 | 75.0 | 12.7 | 5.9 |
| 2F5 IC× | 80.0 | 26.1 | 3.1 | 80.0 | 9.2 | 8.7 | 80.0 | 0.0 | NA | 60.0 | 5.4 | 11.0 | 75.0 | 2.7 | 27.5 |
| VRC01 IC× | - | - | - | - | - | - | - | - | - | - | - | - | 75.0 | 43.2 | 1.7 |

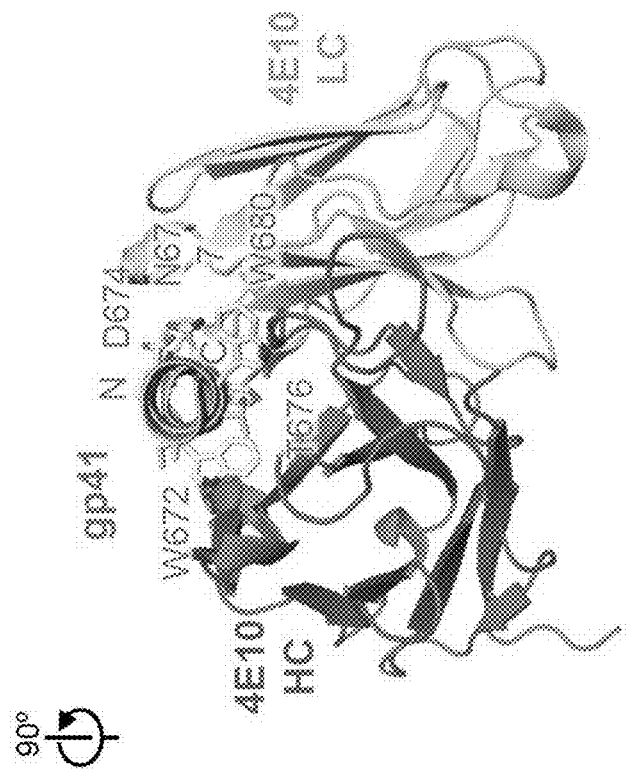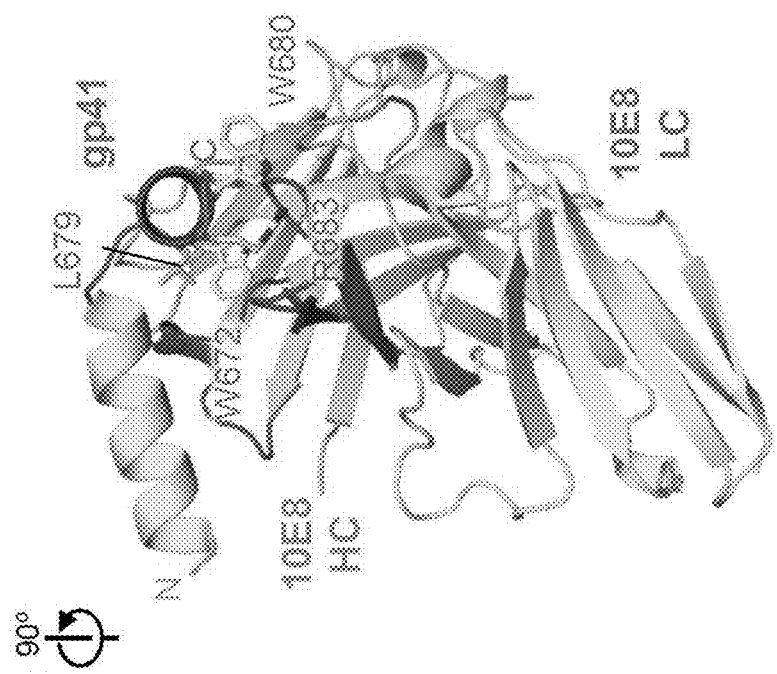
FIG. 15F
FIG. 15E

FIG. 17A

10E8 neutralizing properties
Neutralization 10E8 and 7H6 against a 5-isolate Env-pseudovirus mini-panel

| Virus ID | IC$_{50}$ (µg/ml)[a] | |
|---|---|---|
| | 10E8 | 7H6 |
| MN.03 | 0.002 | 0.002 |
| BaL.26 | 0.13 | 0.68 |
| THRO.18 | 0.145 | 0.285 |
| JRFL.JB | 0.2 | 0.897 |
| CAAN.A2 | 0.38 | 0.784 |

FIG. 17B

Neutralization profile of patient N152 serum and monoclonal antibodies

| Clade | Virus ID | Serum[a] N152 | Monoclonal antibody[b] | | | | |
|---|---|---|---|---|---|---|---|
| | | | 10E8 | 7H6 | 4E10 | 2F5 | VRC01 |
| A | KER2018 | 397 | 2.71 | 1.64 | 8.46 | 2.01 | |
| | RWO20.2 | | 1.3 | | 8.21 | 7.55 | |
| | Q168.a2 | 509 | | 1.51 | | 7.83 | |
| | Q769.d22 | | 1.11 | | 1.73 | | |
| | Q769.h5 | 836 | 2.74 | | 1.17 | >50 | |
| B | JRFL.JB | 660 | | | 5.37 | 7.84 | |
| | BaL.01 | | | | 3.52 | 4.13 | |
| | YU2.OG | 279 | | 1.36 | | >50 | |
| | PVO.04 | 359 | 1.78 | 1.47 | | >50 | |
| | TRO.11 | | | | 1.39 | >50 | |
| | CAAN.A2 | | 1.37 | 1.81 | | | 1.06 |
| | TRJO.58 | | | | 8.75 | >50 | |
| | THRO.18 | 351 | | | 4.68 | >50 | 4.42 |
| | BG1168.1 | 167 | | | 3.34 | 1.35 | |
| | 6101.1 | | | | | >50 | |
| C | ZA012.29 | 39 | | | 5.8 | >50 | |
| | DU156.12 | | | | | >50 | |
| | DU422.01 | 325 | 1.06 | | 1.65 | >50 | >50 |
| | ZM106.9 | 256 | >50 | >50 | | >50 | |
| | ZM55.28a | 85 | 2.31 | 1.86 | 8.79 | >50 | |
| Control | SIVmac251.SG3 | 5 | >50 | >50 | >50 | >50 | >50 |

FIG. 17C

Antibody neutralization data against 181 HIV-1 Env-pseudoviruses

| Virus ID | Clade | IC50 (μg/ml) | | | | | | | | IC80 (μg/ml) | | | | | | | |
|---|---|---|---|---|---|---|---|---|---|---|---|---|---|---|---|---|---|
| | | 10E8 | 4E10 | 2F5 | VRC01 | NIH 45-46 | 3BN C117 | PG9 | PG16 | 10E8 | 4E10 | 2F5 | VRC01 | NIH 45-46 | 3BN C117 | PG9 | PG16 |
| 286.36 | C | 1.05 | | >50 | | | | | | 7.74 | | >50 | | | 6.60 | | |
| 288.38 | C | | | >50 | 1.52 | | | 3.14 | | 4.73 | 9.25 | >50 | 6.86 | 1.06 | | >50 | >50 |
| 0013095-2.11 | C | | | >50 | | | | | | | | >50 | | | 2.33 | | |
| 001428-2.42 | C | | 9.10 | >50 | | | | | | 8.89 | >50 | >50 | | | | | |
| 0077_V1.C16 | C | 1.19 | | >50 | 1.04 | | >50 | | | | | >50 | 3.85 | 2.52 | >50 | | |
| 00836-2.5 | C | | 1.43 | >50 | | >50 | | >50 | | 2.61 | | >50 | | | >50 | >50 | >50 |
| 0921.V2.C14 | C | | 5.63 | | | | | | | 2.78 | | | | | | | |
| 16055-2.3 | C | | 4.12 | >50 | | | 3.24 | | | 3.73 | | >50 | | | | | |
| 16845-2.22 | C | | | >50 | 2.41 | 3.19 | | 2.36 | | | 5.03 | >50 | 9.07 | | >50 | | >50 |
| 16936-2.21 | C | | 1.79 | >50 | | | >50 | >50 | | 1.43 | | >50 | | | | >50 | >50 |
| 25710-2.43 | C | | | >50 | | | | | | | 3.10 | >50 | 1.56 | 1.22 | | | |
| 25711-2.4 | C | | 6.24 | | | | >50 | 1.50 | | 2.11 | | >50 | 1.70 | 7.52 | >50 | 5.27 | |
| 25925-2.22 | C | | 2.23 | >50 | | | | | | 1.38 | | >50 | 1.39 | | | | |
| 26191-2.48 | C | 1.07 | 4.20 | >50 | | | | 1.95 | | 4.80 | | >50 | | | | | >50 |
| 3168.V4.C10 | C | 1.23 | 2.63 | | | | | | | 6.87 | | >50 | | | | | |
| 3637.V5.C3 | C | 1.66 | 3.61 | >50 | 4.09 | 1.77 | | >50 | | 6.16 | | >50 | 6.60 | >50 | >50 | | |
| 3873.V1.C24 | C | 3.81 | 3.05 | >50 | | | 6.97 | >50 | | | | >50 | | 1.36 | >50 | >50 | >50 |
| 6322.V4.C1 | C | 1.80 | 7.95 | >50 | >50 | >50 | >50 | >50 | >50 | | | >50 | >50 | >50 | >50 | >50 | >50 |
| 6471.V1.C16 | C | 4.82 | | >50 | >50 | >50 | >50 | >50 | >50 | | | >50 | >50 | >50 | >50 | >50 | >50 |
| 6631.V3.C10 | C | | >50 | >50 | >50 | >50 | >50 | >50 | >50 | 3.11 | >50 | >50 | >50 | >50 | >50 | >50 | >50 |
| 6644.V2.C33 | C | | | >50 | | | | | | | 6.33 | >50 | | | | | >50 |
| 6785.V5.C14 | C | | 1.96 | >50 | | | | | | 2.27 | | >50 | | | | | |
| 6838.V1.C35 | C | | 1.66 | | | 1.52 | | | | 1.43 | 9.82 | | | | 8.46 | | |
| 96ZM651.02 | C | | | >50 | | 1.13 | >50 | >50 | | | | >50 | 1.94 | 1.39 | 1.77 | >50 | >50 |
| BR025.9 | C | | 3.73 | >50 | | >50 | | | | 1.31 | | >50 | 1.08 | 1.61 | >50 | | |
| CAP210.E8 | C | | 4.00 | >50 | >50 | >50 | 8.16 | | | 2.60 | | >50 | >50 | >50 | | | |
| CAP244.D3 | C | | 1.98 | >50 | | | | | | 1.48 | | >50 | 2.38 | 1.48 | | | |
| CAP45.G3 | C | | 2.36 | >50 | 9.47 | >50 | | | | 3.82 | | >50 | >50 | >50 | | | |
| CNE30 | C | | 1.73 | >50 | | | | >50 | >50 | 2.78 | | >50 | 2.59 | 2.27 | 1.05 | >50 | >50 |
| CNE31 | C | 1.14 | 3.12 | >50 | | | 6.95 | | 2.51 | 4.82 | | >50 | 2.24 | | >50 | >50 | >50 |
| CNE53 | C | | | >50 | | | | >50 | | 1.33 | 2.01 | >50 | | | | | >50 |
| CNE58 | C | | | >50 | 1.04 | | | | | 2.92 | 8.26 | >50 | | 3.46 | 1.41 | | |
| DU123.06 | C | | | >50 | | | | | | | 3.51 | >50 | >50 | >50 | 1.77 | | |
| DU151.02 | C | | 2.97 | >50 | 7.70 | >50 | >50 | | | 1.69 | | >50 | >50 | >50 | >50 | | |
| DU156.12 | C | | | >50 | | | | | | | | >50 | | | | | |
| DU172.17 | C | | | >50 | >50 | >50 | >50 | | | | | >50 | >50 | >50 | 2.46 | | |
| DU422.01 | C | 1.06 | 1.85 | >50 | >50 | >50 | >50 | >50 | | 2.49 | | >50 | >50 | >50 | >50 | | |
| MW965.26 | C | | | >50 | | | | | 1.99 | | | >50 | | | | | >50 |
| SO18.18 | C | | 8.73 | >50 | | | | | | 3.88 | | >50 | | | | | |
| TV1.29 | C | | 1.95 | 3.29 | >50 | >50 | >50 | | | 1.24 | 5.93 | | >50 | >50 | >50 | | |
| TZA125.17 | C | | | >50 | >50 | >50 | >50 | | | 1.98 | 5.44 | >50 | >50 | >50 | >50 | 1.21 | |
| TZB0.02 | C | 1.67 | 2.32 | >50 | | | | | | 8.15 | | >50 | | | >50 | 1.30 | |
| ZA012.29 | C | | 5.80 | >50 | | | | | | 3.80 | | >50 | | | | >50 | >50 |
| ZM106.9 | C | >50 | | >50 | | | | 1.10 | | >50 | >50 | >50 | | | | 9.58 | >50 |
| ZM109.4 | C | | | >50 | | | | 4.93 | | 1.05 | | >50 | | | | 2.64 | >50 |
| ZM135.10a | C | | | >50 | 1.26 | | >50 | >50 | | | | >50 | 5.16 | 2.69 | >50 | >50 | >50 |
| ZM176.66 | C | | | >50 | | | >50 | | | 1.82 | 8.44 | >50 | | | 1.30 | | |
| ZM197.7 | C | | | >50 | | | | | | | 3.93 | >50 | 1.55 | 1.29 | 1.92 | 6.67 | |
| ZM214.15 | C | 1.69 | 1.45 | >50 | | | | >50 | >50 | 7.87 | | >50 | 3.04 | 1.87 | >50 | >50 | >50 |
| ZM215.8 | C | | | >50 | | | | | | | 4.51 | >50 | | | | | >50 |
| ZM233.6 | C | | 2.06 | >50 | 4.25 | 5.44 | | | | | | >50 | | | >50 | | |
| ZM249.1 | C | | 2.75 | >50 | | | | | | 2.33 | 9.65 | >50 | | | | | 9.23 |
| ZM53.12 | C | 2.56 | 4.52 | >50 | | | | | | 9.38 | | >50 | 2.64 | 1.11 | 1.05 | | |
| ZM55.28a | C | 2.31 | 8.73 | >50 | | | | | >50 | 7.18 | | >50 | | | | | >50 |
| 3326.V4.C3 | CD | 1.18 | 1.93 | | | 4.27 | | | | 9.96 | | >50 | | | >50 | >50 | |
| 3337.V2.C6 | CD | 1.23 | 1.91 | 4.63 | | | >50 | >50 | | 6.59 | | >50 | | | | >50 | >50 |
| 3817.v2.c59 | CD | | 4.78 | 6.88 | | >50 | >50 | | | 4.27 | | >50 | >50 | >50 | | | |

FIG. 17F

| Virus ID | Clade | IC₅₀ (μg/ml) 10E8 | 4E10 | 2F5 | VRC01 | NIH 45-46 | 3BN C117 | PG9 | PG16 | IC₈₀ (μg/ml) 10E8 | 4E10 | 2F5 | VRC01 | NIH 45-46 | 3BN C117 | PG9 | PG16 |
|---|---|---|---|---|---|---|---|---|---|---|---|---|---|---|---|---|---|
| 231965.c1 | D | | 8.03 | | | | | 1.51 | 4.72 | | | | 1.55 | | | >50 | >50 |
| 247-23 | D | | 2.37 | 1.95 | | | | | >50 | 1.60 | | | >50 | >50 | | >50 | >50 |
| 3016.v5.c45 | D | | 4.80 | | | | | | >50 | 1.61 | | | >50 | >50 | 3.35 | >50 | >50 |
| 57128.vrc15 | D | | 1.93 | >50 | | | | | >50 | 3.33 | | >50 | >50 | >50 | 1.84 | >50 | >50 |
| 6405.v4.c34 | D | | 3.92 | 7.51 | 2.63 | | | | >50 | 1.88 | | | 7.36 | 2.81 | | >50 | >50 |
| A03349M1.vrc4a | D | | 3.12 | >50 | 4.66 | | | | >50 | 1.02 | | >50 | | | 2.34 | >50 | >50 |
| NKU3006.ec1 | D | | 5.83 | 1.10 | | | | | >50 | 2.56 | | | 1.78 | 2.34 | | >50 | >50 |
| UG021.16 | D | | | >50 | | | 1.48 | | >50 | 1.70 | | >50 | | | 5.09 | >50 | >50 |
| UG024.2 | D | | | | | | | 3.94 | >50 | | | | | | | >50 | >50 |
| X2088.c9 | G | | | | | | | >50 | >50 | >50 | >50 | >50 | >50 | >50 | >50 | >50 | >50 |
| SIVmac251.SG3 | Control | >50 | >50 | >50 | >50 | >50 | >50 | >50 | >50 | >50 | >50 | >50 | >50 | >50 | >50 | >50 | >50 |
| SVA.MLV | Control | >50 | >50 | >50 | >50 | >50 | >50 | >50 | >50 | >50 | >50 | >50 | >50 | >50 | >50 | >50 | >50 |

FIG. 18
Binding of 10E8 and 4E10 to gp41 MPER alanine scanned peptides, by ELISA

| gp41 MPER alanine peptide | $IC_{50}$ (μg/ml) 4E10 | $IC_{50}$ (μg/ml) 10E8 | Fold Change[a] 4E10 | Fold Change[a] 10E8 |
|---|---|---|---|---|
| Mock peptide | 0.031 | 0.016 | | |
| Control peptide | 59251 | 23562 | 1888779.1 | 1503637.5 |
| gp41 N671A | 0.049 | 0.684 | 1.6 | 43.7 |
| gp41 W672A | 3.373 | 6.207 | 107.5 | 396.1 |
| gp41 F673A | 1.723 | 18781 | 54.9 | 1198532.2 |
| gp41 D674A | 0.054 | 0.026 | 1.7 | 1.7 |
| gp41 I675A | 0.034 | 0.009 | 1.1 | 0.6 |
| gp41 T676A | 0.618 | 1.34 | 19.7 | 85.5 |
| gp41 N677A | 0.067 | 0.018 | 2.1 | 1.1 |
| gp41 W678A | 0.044 | 0.014 | 1.4 | 0.9 |
| gp41 L679A | 0.064 | 0.023 | 2 | 1.4 |
| gp41 W680A | 0.061 | 0.037 | 2 | 2.4 |
| gp41 Y681A | 0.061 | 0.015 | 1.9 | 1 |
| gp41 I682A | 0.064 | 0.023 | 2 | 1.4 |
| gp41 R683A | 0.086 | 0.983 | 2.7 | 62.7 |

FIG. 19

Neutralization of 10E8 against pseudotyped HIV-1$_{JR2}$ MPER alanine mutants

| JR2 MPER mutant | 10E8 | | 4E10 | |
|---|---|---|---|---|
| | IC$_{50}$[a] | IC$_{90}$ | IC$_{50}$ | IC$_{90}$ |
| WT | 0.28 | 2.49 | 2.56 | 24.98 |
| L660A | 0.01 | 0.07 | 0.28 | 3.06 |
| L661A | 0.01 | 0.15 | 0.50 | 4.63 |
| E662G | 1.31 | 9.28 | 8.01 | 47.21 |
| L663A | 0.02 | 0.25 | 0.61 | 6.11 |
| D664A | 1.24 | 13.35 | 10.07 | 53.04 |
| K665A | 0.35 | 3.27 | 4.22 | 29.96 |
| W666A | 0.00 | 0.03 | 0.11 | 1.41 |
| A667G | 0.39 | 3.56 | 3.16 | 24.47 |
| N668A | 0.43 | 3.96 | 3.12 | 28.22 |
| L669A | 0.00 | 0.04 | 0.16 | 2.04 |
| W670A | 0.01 | 0.11 | 0.48 | 3.58 |
| N671A | 0.09 | >20 | 0.23 | 17.24 |
| W672A | 0.05 | >20 | 1.60 | >100 |
| F673A | 0.24 | >20 | 1.73 | >100 |
| D674A | 0.76 | 5.66 | 4.57 | 38.28 |
| I675A | 0.00 | 0.05 | 0.10 | 1.11 |
| S676A | 0.03 | 0.39 | 1.64 | 33.46 |
| N677A | 0.10 | 1.12 | 1.54 | 16.35 |
| W678A | 0.01 | 0.07 | 0.07 | 0.93 |
| L679A | 0.01 | 0.11 | 0.52 | 5.52 |
| W680A | 0.15 | >20 | 0.59 | >100 |
| Y681A | 0.01 | 0.18 | 0.04 | 0.97 |
| I682A | 0.04 | 0.45 | 0.16 | 5.57 |
| K683A | 0.01 | >20 | 0.17 | 2.94 |

FIG. 20

Sequences of HIV-2/HIV-1 chimeras

| HIV-2/HIV-1 MPER Chimeric Virus | Grafted HIV-1 epitope | HIV-1 MPER residues | MPER Sequence[a] |
|---|---|---|---|
| 7312A (HIV-2 WT) | - | - | NMYELQKLNSWDVFGNWFDLASWVKYIQYGVYIV |
| C1 | Clade B MPER | 659-683 | NMYELLALDKWASLWNWFDITKWLWYIKYGVYIV |
| C1C | Clade C MPER | 659-683 | NMYELLALDSWKNLWNWFDITNWLWYIKYGVYIV |
| C3 | 2F5 | 659-674 | NMYELLALDKWASLWNWFDLASWVKYIQYGVYIV |
| C7 | 2F5 minimal | 662-667 | NMYELQALDKWAVFGNWFDLASWVKYIQYGVYIV |
| C6 | 4E10 minimal | 671-676 | NMYELQKLNSWDVFGNWFDISWIKYIQYGVYIV |
| C4 | 4E10 | 671-683 | NMYELQKLNSWDVFGNWFDITKWLWYIKYGVYIV |
| C4GW | Z13+4E10 | 670-683 | NMYELQKLNSWDVFWNWFDITKWLWYIKYGVYIV |
| C8 | Z13+4E10 | 669-683 | NMYELQKLNSWDSLWNWFDITKWLWYIKYGVYIV |

FIG. 21
Mapping anti-MPER neutralizing antibodies/sera with HIV-2/HIV-1 chimeras

| Ab/Serum ID | 7312A (HIV-2 WT) | HIV-2/HIV-1 Chimeras C1 (clade B MPER) | C1C (clade C MPER) | C3 (2F5) | C7 (2F5 minimal) | C6 (4E10 minimal) | C4 (4E10) | C4GW (Z13 + 4E10) | C8 (Z13 + 4E10) | Similar to |
|---|---|---|---|---|---|---|---|---|---|---|
| 2F5 | - | 0.449[a] | - | 1.057 | 0.458 | - | - | - | - | 2F5 |
| Z13 | - | 1.741 | 1.414 | - | - | - | - | 1.76 | 5.35 | Z13 |
| 4E10 | - | 0.133 | 0.036 | - | - | 0.16 | 0.161 | 0.195 | 0.169 | 4E10 |
| 10E8 | - | 0.003 | 0.004 | - | - | - | 0.002 | 0.002 | 0.002 | 10E8 |
| 137 | 45.1[b] | 11483 | 1539 | 133 | 98 | 662 | 1938 | 1912 | 1306 | 4E10 |
| N152 | 15.3 | 4159 | 1203 | 28 | 20 | 33 | 1809 | 2106 | 1054 | 10E8 |
| N158 | <10 | 3379 | 1144 | <10 | <10 | <10 | 1305 | 761 | 594 | 10E8 |
| Z208 | <10 | 579 | 218 | <10 | <10 | <10 | 236 | 517 | 164 | 10E8 |
| N69 | <10 | 1193 | 306 | <10 | <10 | <10 | 211 | 700 | 97 | 10E8 |
| 51 | 41 | 282 | 1642 | <10 | <10 | <10 | 121 | 182 | 158 | 10E8 |
| N200 | 12.5 | 2560 | 775 | 67 | 25 | 45 | 508 | 875 | 398 | 10E8 |
| N43 | <10 | 2356 | 925 | 42 | <10 | <10 | 452 | 882 | 552 | 10E8 |
| N91 | 15.7 | 1054 | 525 | 51 | 26 | 27 | 162 | 504 | 235 | 10E8 |
| N21 | <10 | 3846 | 892 | <10 | <10 | <10 | 56.1 | 3257 | 778 | Z13 |
| N30 | 67 | 3530 | 1819 | <10 | <10 | <10 | 206 | 1269 | 301 | Z13 |
| N13 | 35 | 880 | 696 | 20 | 12 | <10 | 106 | 586 | 88 | ND |
| N197 | <10 | 346 | 31 | 18 | <10 | <10 | 21 | 108 | 48 | ND |
| 59/E/N5 | <10 | 797 | 38 | <10 | <10 | 13 | 27 | 433 | 58 | ND |
| 35/ N14 | 107 | 1205 | 744 | 713 | 434 | 1347 | 681 | 398 | 427 | 2F5+4E10 |
| N209 | 42 | 482 | 898 | 99 | 161 | 213 | 1040 | 1438 | 720 | 2F5+4E10 |
| N55 | 72.5 | 2065 | 1143 | 213 | 164 | 146 | 414 | 1086 | 487 | ND |
| N44 | 160 | 1416 | 585 | 190 | 161 | 304 | 322 | 650 | 368 | ND |
| 52 | 36.7 | 1018 | 73 | 51 | 58 | 48 | 52 | 62 | 56 | ND |
| 125/D | <10 | 921 | 238 | <10 | <10 | <10 | <10 | <10 | 80.6 | ND |
| 30 | 308 | 1224 | 101 | <10 | <10 | <10 | 82 | 156 | 59 | ND |

FIG. 22

Blocking mAb- and serum-mediated neutralization of HIV-2/HIV-1 chimera C1 using MPER peptides

| | Ab/Serum ID | Blocking peptide[a] Control peptide | MPER | 2F5 | Z13e1 | 4E10 | 4E10 + Z13e1 | 4E10 + Z13e1 + 2F5 | Similar to |
|---|---|---|---|---|---|---|---|---|---|
| Fold change of $IC_{50}$ (μg/ml)[b] | 2F5 | 0.9 | >233 | >233 | 1.5 | 1.3 | 1.1 | >233 | 2F5 |
| | Z13 | 1.1 | >26 | 0.8 | 7.2 | 2.8 | 5 | 5.9 | Z13 |
| | 4E10 | 1.2 | >176 | 1.1 | 1.2 | >176 | >176 | >176 | 4E10 |
| | 10E8 | 1.7 | 375 | 1.5 | 0.7 | >597 | >597 | >597 | 10E8 |
| Fold change of $ID_{50}$[c] | 137 | 0.7 | 28.7 | 0.9 | 2.0 | 21.8 | 62.6 | 55.6 | 4E10 |
| | N152 | 2.0 | 7.4 | 0.6 | 2.4 | 11.1 | 53.0 | 48.5 | 10E8 |
| | N158 | 1.3 | 8.8 | 1.3 | 3.2 | 23.3 | 34.5 | 22.2 | 10E8 |
| | Z208 | 0.5 | >41 | 0.9 | 0.9 | 11.9 | 3.1 | >41 | 10E8 |
| | N69 | 1.1 | 25.1 | 0.8 | 4.4 | 7.5 | 3.6 | 3.4 | 10E8+Z13 |
| | 51 | 0.5 | 4 | 2.1 | 6.0 | 3.8 | 18.8 | >42.4 | 10E8+Z13 |
| | N200 | 0.7 | 48.2 | 0.9 | 5.8 | 3.0 | 7.4 | 7.9 | 10E8+Z13 |
| | N43 | 1.1 | 14.9 | 1.6 | 4.7 | 1.9 | 3.1 | 6.0 | Z13 |
| | N91 | 0.9 | 2.0 | 0.9 | 0.1 | 1.3 | 1.4 | 1.4 | ND |
| | N21 | 0.8 | 10.2 | 0.7 | 1.2 | 1.3 | 0.5 | 0.5 | ND |
| | N30 | 0.7 | 3.5 | 0.8 | 2.5 | 1.6 | 6.2 | 4.2 | Z13 |
| | N13 | 0.8 | 3.0 | 0.5 | 3.9 | 2.7 | 5.1 | 6.2 | Z13 |
| | N197 | 0.7 | 8.4 | 0.7 | 6.0 | 0.9 | 4.7 | >26 | Z13 |
| | 59/E/N5 | 1.0 | 7.9 | 1.3 | 3.9 | 1.9 | 4.1 | 6.7 | Z13 |
| | 35/ N14 | 1.0 | 2.3 | 0.7 | 1.8 | 0.5 | 1.1 | 2.2 | ND |
| | N209 | 1.0 | 2.3 | 0.6 | 1.1 | 1.5 | 1.3 | 5.9 | ND |
| | N55 | 1.1 | 3.9 | 1.4 | 1.4 | 1.5 | 1.3 | 4.8 | ND |
| | N44 | 0.6 | 2.6 | 0.6 | 1.6 | 0.7 | 0.5 | 0.8 | ND |
| | 52 | 1.2 | 2.4 | 0.9 | 1.1 | 1.2 | 3.8 | 2.7 | ND |
| | 125/D | 0.9 | 6.3 | 0.9 | 2.1 | 1.2 | 3.9 | 1.4 | ND |
| | 30 | 0.7 | 4.4 | 0.8 | 0.2 | 1.2 | 0.8 | 2.2 | ND |

FIG. 23  Reactivity of 10E8 with autoantigens

| Sample ID | µg/ml mAb | SSA | SSB | Sm | RNP | Scl 70 | Jo 1 | dsDNA | Cent B | Histone |
|---|---|---|---|---|---|---|---|---|---|---|
| Neg Control | | - | - | - | - | - | - | - | - | - |
| Pos Control 1 | | 630 | 436 | | | | | | 426 | 454 |
| Pos Control 2 | | | | | 423 | | 434 | 668 | | |
| Pos Control 3 | | | | 678 | | 427 | | | | |
| Anti-RSV | 50 | 3 | 1 | 2 | 2 | 1 | 3 | 2 | 2 | 1 |
| | 25 | 3 | 3 | 2 | 3 | 1 | 2 | 1 | 2 | 1 |
| | 12.5 | 2 | 3 | 3 | 2 | 2 | 2 | 0 | 1 | 1 |
| | 6.25 | 3 | 2 | 2 | 2 | 1 | 2 | 0 | 2 | 1 |
| 4E10 | 50 | 1117 | 768 | 461 | 256 | 73 | 690 | 124 | 521 | 304 |
| | 25 | 1117 | 643 | 381 | 227 | 60 | 532 | 81 | 449 | 210 |
| | 12.5 | 815 | 455 | 260 | 113 | 32 | 385 | 64 | 336 | 139 |
| | 6.25 | 656 | 345 | 177 | 79 | 23 | 274 | 46 | 243 | 92 |
| 2F5 | 50 | 165 | 96 | 42 | 41 | 38 | 158 | 150 | 345 | 196 |
| | 25 | 89 | 49 | 29 | 23 | 19 | 104 | 82 | 228 | 119 |
| | 12.5 | 54 | 31 | 23 | 15 | 11 | 78 | 55 | 141 | 69 |
| | 6.25 | 31 | 18 | 14 | 9 | 8 | 44 | 33 | 86 | 41 |
| 10E8 | 50 | 5 | 5 | 3 | 5 | 3 | 2 | 0 | 3 | 2 |
| | 25 | 4 | 4 | 3 | 5 | 2 | 2 | 0 | 3 | 2 |
| | 12.5 | 4 | 2 | 3 | 3 | 2 | 1 | 0 | 1 | 2 |
| | 6.25 | 3 | 3 | 2 | 1 | 2 | 3 | 2 | 2 | 2 |
| VRC01 | 50 | 3 | 3 | 3 | 3 | 1 | 3 | 2 | 1 | 1 |
| | 25 | 2 | 1 | 2 | 2 | 2 | 2 | 1 | 2 | 2 |
| | 12.5 | 2 | 2 | 2 | 2 | 2 | 1 | 0 | 1 | 1 |
| | 6.25 | 5 | 2 | 3 | 3 | 1 | 3 | 1 | 2 | 2 |
| 17b | 50 | 3 | 2 | 3 | 2 | 2 | 2 | 1 | 1 | 1 |
| | 25 | 3 | 3 | 2 | 1 | 1 | 2 | 0 | 2 | 2 |
| | 12.5 | 2 | 1 | 2 | 2 | 1 | 2 | 0 | 1 | 1 |
| | 6.25 | 3 | 3 | 3 | 2 | 1 | 3 | 3 | 1 | 2 |

FIG. 24

Data collection and refinement statistics

|  | 10E8 Fab + gp41 MPER 656-683 |
|---|---|
| PDB ID | 4G6F |
| Data collection | |
| Space group | $P2_1$ |
| Cell dimensions | |
| $a, b, c$ (Å) | 68.0, 71.4, 129.2 |
| $\alpha, \beta, \gamma$ (°) | 90, 104.5, 90 |
| Complexes per ASU | 2 |
| Resolution, Å* | 2.1 |
| $R_{sym}$* | 7.4 (24.2) |
| $I / \sigma I$* | 12.4 (2.4) |
| Completeness, %* | 88.6 (52.2) |
| Redundancy* | 2.7 (1.5) |
| Refinement | |
| Resolution (Å) | 2.1 |
| No. reflections | 61862 |
| $R_{work} / R_{free}$ (%) | 18.01/21.76 |
| No. atoms | |
| Protein | 7244 |
| Water | 535 |
| $B$-factors (mean) | |
| Protein | 51.5 |
| Water | 56.8 |
| R.m.s. deviations | |
| Bond lengths (Å) | 0.007 |
| Bond angles (°) | 1.064 |

FIG. 25 Phi-Psi angles of antibody-bound gp41 peptides

| gp41 Residue | 10E8 P Phi | 10E8 P Psi | 10E8 F Phi | 10E8 F Psi | 4E10[a] P Phi | 4E10[a] P Psi | Z13e1[b] P Phi | Z13e1[b] P Psi |
|---|---|---|---|---|---|---|---|---|
| ASN 656 | - | -27.1 | | | | | | |
| GLU 657 | -52.9 | -42.8 | | | | | | |
| GLN 658 | -63.0 | -33.4 | | | | | | |
| GLU 659 | -73.1 | -40.3 | - | -7.2 | | | | |
| LEU 660 | -59.5 | -47.4 | -60.7 | -16.5 | | | | |
| LEU 661 | -59.4 | -49.6 | -56.8 | -54.5 | | | | |
| GLU 662 | -54.5 | -42.8 | -73.8 | -24.0 | | | | |
| LEU 663 | -59.4 | -48.9 | -71.9 | -29.0 | | | | |
| ASP 664 | -57.8 | -37.4 | -70.9 | -37.6 | | | | |
| LYS 665 | -61.6 | -32.8 | -52.3 | -58.7 | | | | |
| TRP 666 | -73.3 | -40.1 | -59.4 | -39.5 | | | | |
| ALA 667 | -70.5 | -32.3 | -59.0 | -28.3 | | | | |
| SER 668 | -60.8 | -15.8 | -71.8 | -15.3 | | | | |
| LEU 669 | -71.7 | -16.9 | -93.6 | 14.1 | | | | |
| TRP 670 | -104 | 160 | -81.1 | 134 | | | | |
| ASN 671 | -82.0 | 112 | -76.7 | 121 | -53.3 | 117 | - | -18.7 |
| TRP 672 | -56.4 | -40.0 | -54.4 | -37.2 | -69.3 | -34.4 | -76.3 | -21.4 |
| PHE 673 | -64.7 | -36.8 | -70.5 | -41.0 | -104 | -4.00 | -120 | -23.8 |
| ASP 674 | -75.5 | -43.8 | -63.1 | -43.6 | -58.8 | -8.3 | -130 | 131 |
| ILE 675 | -54.7 | -50.6 | -56.4 | -55.3 | -63.4 | -48.1 | -64.8 | 109 |
| THR 676 | -62.5 | -42.5 | -64.0 | -40.8 | -66.8 | -28.8 | -60.0 | -12.9 |
| ASN 677 | -54.7 | -44.2 | -56.1 | -43.4 | -61.8 | -44.0 | -98.6 | 5.6 |
| TRP 678 | -71.6 | -41.7 | -70.3 | -42.8 | -59.3 | -45.0 | -80.6 | 168 |
| LEU 679 | -54.8 | -38.2 | -59.9 | -45.4 | -57.1 | -40.6 | -101 | - |
| TRP 680 | -67.9 | -38.9 | -58.3 | -44.3 | -62.1 | -49.1 | | |
| TYR 681 | -67.7 | -43.5 | -61.1 | -44.7 | -67.1 | -29.0 | | |
| ILE 682 | -56.1 | -42.9 | -71.7 | -17.8 | -67.1 | -60.8 | | |
| ARG 683 | -67.2 | -40.9 | -83.5 | -43.8 | -67.2 | -8.9 | | |

FIG. 26
Total buried surface areas on 10E8 and gp41

| Complex 1 | Buried surface on 10E8 (BSA³, Å²) | | | | | | | Contact surface on gp41 (Å²) |
|---|---|---|---|---|---|---|---|---|
| | FR1 | CDR1 | FR2 | CDR2 | FR3 | CDR3 | Subtotal | |
| 10E8 HC (H) | 0 | 106 | 6.4 | 148 | 6.4 | 423 | 689 | 706 |
| 10E8 LC (L) | 0 | 0 | 0 | 0 | 0 | 71 | 71 | 67 |
| Total | | | | | | | 760 | 773 |

| Complex 2 | Buried surface on 10E8 (BSA³, Å²) | | | | | | | Contact surface on gp41 (Å²) |
|---|---|---|---|---|---|---|---|---|
| | FR1 | CDR1 | FR2 | CDR2 | FR3 | CDR3 | Subtotal | |
| 10E8 HC (B) | 0 | 48 | 5.5 | 160 | 7.3 | 427 | 648 | 656 |
| 10E8 LC (D) | 0 | 0 | 0 | 0 | 0 | 62 | 62 | 64 |
| Total | | | | | | | 710 | 720 |

FIG. 27

Buried surface areas at interface between 10E8 heavy chain and gp41, by residue

| Chain | Residue | %Identity | Complex 1 ASA ($Å^2$) | Complex 1 BSA ($Å^2$) | Complex 1 % BSA | Complex 1 ΔG (kcal/mol) | Complex 2 ASA ($Å^2$) | Complex 2 BSA ($Å^2$) | Complex 2 % BSA | Complex 2 ΔG (kcal/mol) |
|---|---|---|---|---|---|---|---|---|---|---|
| gp41 Peptide | ASN 656 | 99.7 | 148 | | | | | | | |
| | GLU 657 | 99.4 | 141 | | | | | | | |
| | GLN 658 | 53.6 | 132 | | | | | | | |
| | GLU 659 | 41.2 | 112 | | | | 187 | | | |
| | LEU 660 | 99.8 | 92.5 | | | | 106 | | | |
| | LEU 661 | 99.4 | 311 | 3.52 | ▮ | 0.06 | 144 | | | |
| | GLU 662 | 38.1 | 107 | | | | 91.0 | | | |
| | LEU 663 | 98.6 | 109 | | | | 114 | | | |
| | ASP 664 | 96.8 | 82.8 | 0.30 | ▮ | 0.00 | 80.5 | | | |
| | LYS 665 | 67.3 | 128 | 44.0 | ▮▮ | 0.68 | 104 | | | |
| | TRP 666 | 99.9 | 157 | | | | 139 | | | |
| | ALA 667 | 64.1 | 59.6 | | | | 55.7 | | | |
| | SER 668 | 61.9 | 88.2 | 73.4 | ▮▮▮▮ | 0.02 | 83.3 | 34.4 | ▮▮ | 0.09 |
| | LEU 669 | 98.5 | 144 | 17.6 | ▮ | 0.09 | 130 | 39.0 | ▮▮ | 0.42 |
| | TRP 670 | 99.6 | 143 | 12.9 | ▮ | -0.07 | 137 | 10.5 | ▮ | -0.09 |
| | ASN 671 | 71.9 | 80.9 | 36.1 | ▮▮ | -0.07 | 73.4 | 32.5 | ▮▮ | 0.02 |
| | TRP 672 | 99.7 | 178 | 129 | ▮▮▮▮ | 1.37 | 179 | 139 | ▮▮▮▮ | 1.50 |
| | PHE 673 | 97.6 | 152 | 95.3 | ▮▮▮ | 1.52 | 148 | 93.0 | ▮▮▮ | 1.49 |
| | ASP 674 | 39.0 | 72.4 | | | | 67.3 | | | |
| | ILE 675 | 99.2 | 52.8 | | | | 45.7 | | | |
| | THR 676 | 65.2 | 47.9 | 47.9 | ▮▮▮▮ | 0.33 | 49.0 | 48.8 | ▮▮▮▮ | 0.43 |
| | ASN 677 | 57.3 | 98.9 | 19.7 | ▮ | -0.27 | 99.3 | 19.5 | ▮ | -0.30 |
| | TRP 678 | 99.9 | 158 | | | | 143 | | | |
| | LEU 679 | 99.7 | 102 | 42.3 | ▮▮ | 0.58 | 108 | 50.1 | ▮▮ | 0.69 |
| | TRP 680 | 98.9 | 162 | 64.1 | ▮▮ | 0.29 | 131 | 65.6 | ▮▮ | 0.22 |
| | TYR 681 | 99.7 | 144 | | | | 103 | | | |
| | ILE 682 | 99.6 | 129 | 14.9 | ▮ | 0.24 | 119 | 15.1 | ▮ | 0.23 |
| | ARG 683 | 21.3 | 181 | 105 | ▮▮▮ | 0.49 | 183 | 108 | ▮▮▮ | 0.15 |
| 10E8 Heavy Chain | ASP 28 | | 87.3 | 28.8 | ▮ | 0.07 | | | | |
| | ASN 31 | | 84.9 | 49.3 | ▮▮ | -0.14 | 85.7 | 17.1 | ▮ | |
| | TRP 33 | | 30.3 | 27.6 | ▮▮▮▮ | 0.44 | 33.4 | 30.7 | ▮▮▮▮ | |
| | ARG 50 | | 16.9 | 6.37 | ▮ | -0.22 | 14.1 | 5.30 | ▮ | |
| | THR 52 | | 3.85 | 3.85 | ▮▮▮▮▮ | 0.06 | 5.36 | 5.36 | ▮▮▮▮▮ | |
| | PRO 52B | | 68.6 | 17.5 | ▮ | 0.28 | 69.6 | 30.2 | ▮▮ | |
| | GLY 52C | | 73.6 | 57.3 | ▮▮▮ | 0.33 | 74.4 | 59.8 | ▮▮▮ | |
| | GLU 53 | | 79.3 | 61.7 | ▮▮▮ | 0.12 | 79.4 | 57.7 | ▮▮▮ | |
| | SER 56 | | 51.0 | 7.50 | ▮ | -0.07 | 52.6 | 6.76 | ▮ | |
| | ASP 58 | | 74.4 | 6.44 | ▮ | -0.07 | 71.8 | 7.30 | ▮ | |
| | LYS 97 | | 112 | 51.8 | ▮▮ | -0.00 | 111 | 40.4 | ▮▮ | |
| | TYR 98 | | 117 | 4.42 | ▮ | 0.02 | 118 | 3.81 | ▮ | |
| | TYR 99 | | 110 | 83.1 | ▮▮▮ | 0.65 | 111 | 81.7 | ▮▮▮ | |
| | PHE 100A | | 154 | 73.4 | ▮▮ | 0.87 | 155 | 86.8 | ▮▮ | |
| | TRP 100B | | 226 | 35.1 | ▮ | 0.12 | 225 | 29.3 | ▮ | |
| | SER 100C | | 94.3 | 4.03 | ▮ | 0.04 | 92.7 | 6.20 | ▮ | |
| | GLY 100D | | 26.5 | 15.8 | ▮▮ | -0.18 | 26.3 | 16.7 | ▮▮ | |
| | TYR 100E | | 173 | 24.3 | ▮ | 0.39 | 179 | 26.4 | ▮ | |
| | PRO 100F | | 86.4 | 66.4 | ▮▮▮ | 1.06 | 87.8 | 64.5 | ▮▮▮ | |
| | PRO 100G | | 131 | 59.6 | ▮▮ | 0.54 | 133 | 64.6 | ▮▮ | |
| | GLY 100H | | 15.3 | 0.17 | ▮ | 0.00 | | | | |
| | GLU 100I | | 94.9 | 1.57 | ▮ | -0.01 | 92.67 | 1.19 | ▮ | |
| | GLU 100J | | 58.8 | 5.09 | ▮ | -0.03 | 56.81 | 5.52 | ▮ | |

FIG. 28

Buried surface areas at interface between 10E8 light chain and gp41, by residue

| Chain | Residue | %Identity | Complex 1 ASA (Å²) | Complex 1 BSA (Å²) | Complex 1 % BSA | Complex 1 ΔG (kcal/mol) | Complex 2 ASA (Å²) | Complex 2 BSA (Å²) | Complex 2 % BSA | Complex 2 ΔG (kcal/mol) |
|---|---|---|---|---|---|---|---|---|---|---|
| gp41 Peptide | ASN 656 | 99.7 | 148 | | | | | | | |
| | GLU 657 | 99.4 | 141 | | | | | | | |
| | GLN 658 | 53.6 | 152 | | | | | | | |
| | GLU 659 | 43.2 | 112 | | | | | | | |
| | LEU 660 | 99.8 | 92.5 | | | | 187 | | | |
| | LEU 661 | 99.4 | 111 | | | | 106 | | | |
| | GLU 662 | 38.1 | 108 | | | | 144 | | | |
| | LEU 663 | 98.6 | 100 | | | | 91.0 | | | |
| | ASP 664 | 96.8 | 82.8 | | | | 114 | | | |
| | LYS 665 | 67.3 | 128 | | | | 80.5 | | | |
| | TRP 666 | 99.9 | 157 | | | | 105 | | | |
| | ALA 667 | 64.1 | 50.6 | | | | 159 | | | |
| | SER 668 | 61.9 | 88.2 | | | | 55.7 | | | |
| | LEU 669 | 98.5 | 144 | | | | 83.3 | | | |
| | TRP 670 | 99.6 | 143 | | | | 131 | | | |
| | ASN 671 | 71.9 | 80.9 | | | | 137 | | | |
| | TRP 672 | 99.7 | 178 | 9.85 | — | -0.07 | 73.4 | | | |
| | PHE 673 | 97.6 | 152 | 57.1 | ≡ | 0.91 | 179 | 11.9 | — | -0.10 |
| | ASP 674 | 59.0 | 72.4 | | | | 148 | 52.1 | ≡ | 0.83 |
| | ILE 675 | 99.2 | 52.8 | | | | 67.5 | | | |
| | THR 676 | 65.2 | 47.9 | | | | 45.7 | | | |
| | ASN 677 | 57.3 | 98.9 | | | | 49.0 | | | |
| | TRP 678 | 99.9 | 158 | | | | 99.2 | | | |
| | LEU 679 | 99.7 | 102 | | | | 144 | | | |
| | TRP 680 | 98.9 | 162 | | | | 108 | | | |
| | TYR 681 | 99.7 | 144 | | | | 131 | | | |
| | ILE 682 | 99.6 | 129 | | | | 103 | | | |
| | ARG 683 | 21.3 | 181 | | | | 119 | | | |
| | | | | | | | 183 | | | |
| 10E8 Light Chain | ARG 91 | | 84.1 | 15.9 | ≡ | -0.59 | 86.1 | 16.8 | ≡ | -0.62 |
| | ARG 95B | | 226 | 55.1 | ≡ | 0.61 | 220 | 44.8 | ≡ | 0.71 |

FIG. 29

Hydrogen Bonds and Salt Bridges between 10E8 and gp41

| gp41 Atom (Chain P) | 10E8 Atom (Chain H) | Distance Å |
|---|---|---|
| SER 668 [ O ] | GLY 52c [ N ] | 3.06 |
| TRP 672 [ N ] | GLU 53 [ OE2 ] | 2.79 |
| TRP 672 [ NE1 ] | PRO 100g [ O ] | 3.16 |
| ARG 683 [ NH2 ] | GLY 100d [ O ] | 2.92 |
| ARG 683 [ NE ] | PHE 100a [ O ] | 3.01 |

| gp41 Atom (Chain F) | 10E8 Atom (Chain B) | Distance Å |
|---|---|---|
| TRP 672 [ N ] | GLU 53 [ OE2 ] | 2.80 |
| TRP 672 [ NE1 ] | PRO 100g [ O ] | 2.69 |
| ARG 683 [ NH1 ] | GLY 100d [ O ] | 2.93 |
| ARG 683 [ NH1 ] | PHE 100a [ O ] | 3.08 |

FIG. 30
Van der Waals contacts between 10E8 and gp41

Complex 1

| Chain | Residue | # | Atom | Chain | Residue | # | Atom | Distance Å |
|---|---|---|---|---|---|---|---|---|
| P | SER | 668 | CB | H | ASN | 31 | CG | 3.79 |
| P | LEU | 669 | C | H | GLY | 52c | CA | 3.87 |
| P | TRP | 670 | C | H | GLY | 52c | CA | 3.74 |
| P | TRP | 672 | CH2 | H | TYR | 99 | CB | 3.83 |
| P | TRP | 672 | CZ2 | H | TYR | 99 | CB | 3.7 |
| P | TRP | 672 | CZ2 | H | TYR | 98 | C | 3.84 |
| P | TRP | 672 | CZ2 | H | LYS | 97 | CB | 3.81 |
| P | TRP | 672 | CE2 | H | LYS | 97 | CB | 3.87 |
| P | TRP | 672 | CD1 | H | TRP | 33 | CH2 | 3.76 |
| P | TRP | 672 | CB | H | TRP | 33 | CZ2 | 3.69 |
| P | PHE | 673 | CD1 | H | PRO | 100g | CB | 3.86 |
| P | PHE | 673 | CE2 | H | GLU | 53 | CG | 3.81 |
| P | PHE | 673 | CZ | H | TRP | 33 | CH2 | 3.71 |
| P | LEU | 679 | CB | H | TYR | 99 | CE2 | 3.84 |
| P | LEU | 679 | CD1 | H | TYR | 99 | CD2 | 3.85 |
| P | TRP | 680 | CD1 | H | PRO | 100f | CD | 3.44 |
| P | TRP | 680 | CG | H | PRO | 100f | CD | 3.52 |
| P | TRP | 680 | CB | H | PRO | 100f | CD | 3.71 |
| P | TRP | 680 | CB | H | PRO | 100f | CG | 3.86 |
| P | ARG | 683 | CD | H | TRP | 100b | CE3 | 3.82 |
| P | ARG | 683 | CD | H | TRP | 100b | C | 3.62 |
| P | ARG | 683 | CD | H | TRP | 100b | CA | 3.64 |
| P | PHE | 673 | CZ | L | ARG | 95b | CD | 3.59 |
| P | PHE | 673 | CE1 | L | ARG | 95b | CD | 3.41 |
| P | PHE | 673 | CD1 | L | ARG | 95b | CD | 3.61 |
| P | PHE | 673 | CE1 | L | ARG | 95b | CG | 3.48 |
| P | PHE | 673 | CD1 | L | ARG | 95b | CG | 3.7 |

Complex 2

| Chain | Residue | # | Atom | Chain | Residue | # | Atom | Distance Å |
|---|---|---|---|---|---|---|---|---|
| F | LEU | 669 | C | B | GLY | 52c | CA | 3.62 |
| F | LEU | 669 | CA | B | GLY | 52c | CA | 3.76 |
| F | TRP | 672 | CH2 | B | TYR | 99 | CB | 3.74 |
| F | TRP | 672 | CZ2 | B | TYR | 99 | CB | 3.77 |
| F | TRP | 672 | CH2 | B | TYR | 98 | C | 3.86 |
| F | TRP | 672 | CZ2 | B | TYR | 98 | C | 3.78 |
| F | TRP | 672 | CH2 | B | LYS | 97 | CB | 3.78 |
| F | TRP | 672 | CZ2 | B | LYS | 97 | CB | 3.74 |
| F | TRP | 672 | CE2 | B | LYS | 97 | CB | 3.82 |
| F | TRP | 672 | CH2 | B | LYS | 97 | C | 3.88 |
| F | TRP | 672 | CD1 | B | TRP | 33 | CH2 | 3.61 |
| F | TRP | 672 | CG | B | TRP | 33 | CH2 | 3.81 |
| F | TRP | 672 | CB | B | TRP | 33 | CH2 | 3.78 |
| F | TRP | 672 | CB | B | TRP | 33 | CZ2 | 3.52 |
| F | PHE | 673 | CD1 | B | PRO | 100g | CB | 3.56 |
| F | PHE | 673 | CZ | B | TRP | 33 | CH2 | 3.79 |
| F | THR | 676 | CG2 | B | TYR | 99 | CD1 | 3.85 |
| F | LEU | 679 | CB | B | TYR | 99 | CE2 | 3.69 |
| F | LEU | 679 | CD1 | B | TYR | 99 | CD2 | 3.84 |
| F | TRP | 680 | CD1 | B | PRO | 100f | CD | 3.53 |
| F | TRP | 680 | CG | B | PRO | 100f | CD | 3.49 |
| F | TRP | 680 | CB | B | PRO | 100f | CD | 3.58 |
| F | TRP | 680 | CB | B | PRO | 100f | CG | 3.81 |
| F | ARG | 683 | CD | B | TRP | 100b | C | 3.82 |
| F | PHE | 673 | CZ | D | ARG | 95b | CD | 3.58 |
| F | PHE | 673 | CE1 | D | ARG | 95b | CD | 3.37 |
| F | PHE | 673 | CD1 | D | ARG | 95b | CD | 3.77 |
| F | PHE | 673 | CE1 | D | ARG | 95b | CG | 3.53 |

FIG. 31 Binding affinities of 10E8 alanine variants to a soluble MPER peptide

| | 10E8 Variant | ka (1/Ms) | SE (ka) | kd (1/s) | SE (kd) | K_D (M) | SE (K_D) | Fold ka | Fold kd | Fold K_D[a] |
|---|---|---|---|---|---|---|---|---|---|---|
| Heavy Chain | D28A | 2.39E+04 | 2.10E+01 | 3.42E-04 | 2.00E-06 | 1.43E-08 | 8.45E-11 | 1.50 | 3.46 | 2.31 |
| | D30A | 4.47E+04 | 4.60E+01 | 5.27E-04 | 2.20E-06 | 1.18E-08 | 5.07E-11 | 2.80 | 5.32 | 1.90 |
| | N31A | 2.37E+04 | 6.10E+01 | 3.07E-04 | 1.90E-06 | 1.30E-08 | 5.69E-11 | 1.48 | 3.11 | 2.10 |
| | W33A | nb | | nb | | nb | | | | |
| | R50A | nb | | nb | | nb | | | | |
| | T52A | 3.62E+04 | 1.80E+02 | 3.95E-04 | 2.50E-06 | 1.09E-08 | 8.77E-11 | 2.27 | 3.99 | 1.76 |
| | G52cA | 3.00E+04 | 1.10E+02 | 3.35E-04 | 1.70E-06 | 1.11E-08 | 6.98E-11 | 1.88 | 3.38 | 1.80 |
| | E53A | 1.24E+04 | 2.90E+02 | 4.90E-03 | 9.20E-05 | 3.95E-07 | 1.18E-08 | 0.78 | 49.6 | 63.8 |
| | S56A | 3.70E+04 | 1.70E+02 | 4.02E-04 | 2.40E-06 | 1.09E-08 | 8.19E-11 | 2.31 | 4.07 | 1.76 |
| | D58A | 3.40E+04 | 1.80E+02 | 1.04E-03 | 3.60E-06 | 3.06E-08 | 1.94E-10 | 2.12 | 10.5 | 4.95 |
| | K97A | 3.26E+04 | 1.40E+02 | 8.08E-04 | 2.70E-06 | 2.48E-08 | 1.35E-10 | 2.04 | 8.17 | 4.01 |
| | Y98A | 2.00E+04 | 1.30E+02 | 5.39E-04 | 2.10E-06 | 2.70E-08 | 2.65E-10 | 1.25 | 5.45 | 4.36 |
| | Y99A | nb | | nb | | nb | | | | |
| | P100aA | 3.38E+03 | 3.30E+01 | 1.05E-02 | 6.40E-06 | 4.29E-07 | 4.59E-09 | 0.21 | 14.7 | 69.4 |
| | W100bA | 6.98E+03 | 4.60E+02 | 6.50E-04 | 2.30E-05 | 9.31E-08 | 6.97E-09 | 0.44 | 6.57 | 15.1 |
| | S100cA | 5.23E+04 | 4.10E+02 | 5.05E-04 | 4.00E-06 | 9.65E-09 | 1.08E-10 | 3.27 | 5.10 | 1.56 |
| | G100dA | 3.33E+04 | 1.10E+03 | 0.01047 | 3.30E-04 | 3.15E-07 | 1.44E-08 | 2.08 | 106 | 50.8 |
| | Y100eA | 8.74E+03 | 2.40E+01 | 6.63E-04 | 2.90E-06 | 7.59E-08 | 3.92E-10 | 0.55 | 6.71 | 12.3 |
| | P100fA | 1.86E+04 | 3.80E+03 | 1.41E-02 | 2.70E-03 | 7.57E-07 | 2.13E-07 | 1.16 | 142 | 122 |
| | P100gA | 5.37E+03 | 2.00E+02 | 3.71E-04 | 6.00E-05 | 6.91E-07 | 2.81E-08 | 0.34 | 37.5 | 112 |
| | G100hA | nb | | nb | | nb | | | | |
| | E100iA | 1.19E+04 | 2.10E+02 | 5.13E-03 | 7.70E-05 | 4.33E-07 | 1.01E-08 | 0.74 | 51.9 | 70.0 |
| | E100jA | 1.12E+04 | 2.60E+02 | 4.05E-03 | 7.30E-05 | 3.61E-07 | 1.06E-08 | 0.70 | 41.0 | 58.4 |
| Light Chain | R91A | nb | | nb | | nb | | | | |
| | R95bA | 2.80E+04 | 3.10E+02 | 8.01E-04 | 4.70E-06 | 2.86E-08 | 3.59E-10 | 1.75 | 8.10 | 4.62 |
| 10E8 | wt[b] | 3.27E+04 | 1.64E+02 | 1.99E-04 | 1.85E-06

FIG. 32

Neutralization IC50s and IC80s of 10E8 alanine variants

| | 10E8 Variant | HxB2.DG IC$_{50}$ | MN.3 IC$_{50}$ | REJO.67 IC$_{50}$ | QH0515.01 IC$_{50}$ | THRO.18 IC$_{50}$ | Mean IC$_{50}$* | Fold Effect |
|---|---|---|---|---|---|---|---|---|
| | wt | 0.0020 | 0.0003 | 0.0110 | 0.0090 | 0.2890 | 0.0620 | |
| Heavy Chain | D28A | 0.0020 | 0.0003 | 0.0110 | 0.0140 | 0.0730 | 0.0200 | 0.9616 |
| | D30A | 0.0020 | 0.0002 | 0.0090 | 0.0070 | 0.0920 | 0.0220 | 0.7162 |
| | N31A | 0.0020 | 0.0003 | 0.0150 | 0.0170 | 0.1170 | 0.0300 | 1.132 |
| | W33A | >5 | 0.0020 | 0.5000 | 4.060 | >25 | 1.501 | 616.6 |
| | R50A | >5 | 0.0070 | >25 | 0.8000 | >25 | 1.269 | 594.3 |
| | T52A | 0.0030 | 0.0003 | 0.0140 | 0.0110 | 0.0870 | 0.0230 | 1.059 |
| | G52cA | 0.0040 | 0.0003 | 0.0120 | 0.0300 | 0.1040 | 0.0300 | 1.557 |
| | E53A | 0.0020 | 0.0003 | 0.0130 | 0.0180 | 0.0750 | 0.0220 | 0.9349 |
| | S56A | 0.0040 | 0.0003 | 0.0290 | 0.0190 | 0.0960 | 0.0300 | 1.616 |
| | D58A | 0.0020 | 0.0002 | 0.0120 | 0.0100 | 0.0720 | 0.0190 | 0.824 |
| | K97A | 0.0060 | 0.0010 | 0.0130 | 0.0340 | 0.1560 | 0.0420 | 2.367 |
| | Y98A | 0.0100 | 0.0010 | 0.0370 | 0.1270 | 0.2760 | 0.0880 | 5.108 |
| | Y99A | >5 | 0.0390 | 20.00 | >25 | >25 | 10.02 | 1463 |
| | F100aA | 4.560 | 0.0090 | 0.2450 | >25 | >25 | 1.605 | 1039 |
| | W100bA | 2.940 | 0.1240 | 4.000 | >25 | >25 | 2.355 | 1022 |
| | S100cA | 0.0450 | 0.0030 | 0.0940 | 0.3390 | 0.6390 | 0.2240 | 16.19 |
| | G100dA | 0.5830 | 0.0040 | 0.2500 | 0.2000 | 3.340 | 0.8750 | 72.27 |
| | Y100eA | 0.0100 | 0.0007 | 0.0150 | 0.0020 | 0.2170 | 0.0490 | 1.934 |
| | P100fA | 0.0650 | 0.0010 | 0.1250 | 0.0490 | 1.080 | 0.2640 | 11.28 |
| | P100gA | 0.4670 | 0.0040 | 1.090 | 1.580 | 7.380 | 2.104 | 109.4 |
| | G100hA | >5 | 0.0370 | >25 | >25 | >25 | 0.0370 | 1552 |
| | E100iA | 0.1960 | 0.0040 | 0.1710 | >25 | 9.970 | 2.585 | 587.8 |
| | E100jA | 0.1640 | 0.0080 | 0.1380 | 0.5540 | 2.400 | 0.653 | 38.21 |
| Light Chain | R91A | >5 | 0.0160 | 0.3480 | >25 | >25 | 0.1820 | 1090 |
| | R95bA | 0.0010 | 0.0002 | 0.0180 | 0.0090 | 0.0570 | 0.0170 | 0.8001 |

| | 10E8 Variant | HxB2.DG IC$_{80}$ | MN.3 IC$_{80}$ | REJO.67 IC$_{80}$ | QH0515.01 IC$_{80}$ | THRO.18 IC$_{80}$ | Mean IC$_{80}$* | Fold Effect |
|---|---|---|---|---|---|---|---|---|
| | wt | 0.0130 | 0.0020 | 1.110 | 0.9780 | 1.470 | 0.7146 | |
| Heavy Chain | D28A | 0.0150 | 0.0010 | 0.2910 | 0.4040 | 0.3990 | 0.2220 | 0.5201 |
| | D30A | 0.0120 | 0.0010 | 0.4150 | 0.2940 | 0.4670 | 0.2378 | 0.4831 |
| | N31A | 0.0180 | 0.0020 | 0.6130 | 0.9490 | 0.5600 | 0.4284 | 0.8576 |
| | W33A | >5 | 0.0850 | >25 | >25 | >25 | 16.02 | 98.44 |
| | R50A | >5 | 0.1620 | >25 | >25 | >25 | 16.03 | 106.1 |
| | T52A | 0.0200 | 0.0020 | 0.3250 | 0.3470 | 0.5260 | 0.2440 | 0.7088 |
| | G52cA | 0.0210 | 0.0020 | 0.5210 | 0.8090 | 0.5350 | 0.3776 | 0.8552 |
| | E53A | 0.0120 | 0.0006 | 0.4340 | 0.6360 | 0.4790 | 0.3123 | 0.5180 |
| | S56A | 0.0250 | 0.0020 | 0.6590 | 0.8740 | 0.5730 | 0.4266 | 0.9600 |
| | D58A | 0.0140 | 0.0010 | 0.3290 | 0.3260 | 0.5490 | 0.2438 | 0.5160 |
| | K97A | 0.0370 | 0.0050 | 0.8330 | 1.690 | 0.9000 | 0.6930 | 1.687 |
| | Y98A | 0.0680 | 0.0070 | 1.920 | 3.930 | 1.680 | 1.521 | 3.124 |
| | Y99A* | >5 | 0.2960 | >25 | >25 | >25 | 16.06 | 119.5 |
| | F100bA | >5 | 0.1720 | >25 | >25 | >25 | 16.03 | 107.1 |
| | W100bA | >5 | 1.270 | >25 | >25 | >25 | 16.25 | 216.9 |
| | S100cA | 0.2000 | 0.0330 | 3.780 | 4.190 | 2.980 | 2.237 | 8.320 |
| | G100dA | 1.940 | 0.0640 | 8.850 | >25 | 22.00 | 11.57 | 45.95 |
| | Y100eA | 0.0720 | 0.0030 | 0.5740 | 2.060 | 1.380 | 0.8058 | 2.108 |
| | P100fA | 0.3130 | 0.0090 | 4.320 | 6.260 | 5.630 | 3.306 | 8.540 |
| | P100gA | 1.880 | 0.0410 | 12.60 | >25 | >25 | 12.90 | 43.81 |
| | G100hA | >5 | 1.470 | >25 | >25 | >25 | 16.29 | 236.9 |
| | E100iA | 4.040 | 0.0720 | >25 | >25 | >25 | 15.82 | 82.37 |
| | E100jA | 0.7030 | 0.0650 | 11.20 | >25 | 17.30 | 10.85 | 26.80 |
| Light Chain | R91A | >5 | 0.3000 | >25 | >25 | >25 | 16.02 | 99.94 |
| | R95bA | 0.0090 | 0.0009 | 0.6870 | 0.5920 | 0.5000 | 0.3578 | 0.5413 |

FIG. 33

Root-mean-square deviations (RMSD) of antibody-bound gp41 structures

| gp41 | Residues | RMSD 10E8 P (Å) Mainchain | All Atoms | RMSD 10E8 F (Å) Mainchain | All Atoms |
|---|---|---|---|---|---|
| 10E8 P | 659-683 | na | na | 1.45 | 2.92 |
|  | 659-670 | na | na | 0.65 | 2.55 |
|  | 670-672 | na | na | 0.18 | 1.04 |
|  | 672-683 | na | na | 0.25 | 0.76 |
| 4E10 | 671-683 | 0.93 | 2.49 | 0.96 | 2.23 |
| Z13e1 | 670-678 | 2.98 | 4.89 | 2.95 | 5.00 |
| 2F5 | 659-670 | 3.70 | 5.67 | 3.43 | 4.95 |

FIG. 34

Comparison of MPER-specific antibody buried surfaces on gp41

| Antibody | gp41 Residue Range | Buried surface on gp41 (Å²) |
|---|---|---|
| 10E8 | 656-683 | 773 (760) |
| | 658-683 | 725 (720) |
| | 671-683 | 621 (636) |
| 4E10 | 671-683 | 808 |
| Z13e1 | 670-676 | 550 |
| 2F5 | 659-670 | 855 |

FIG. 35

Comparison of direct contacts of antibodies 10E8 and 4E10 with gp41

| gp41 Residue | 10E8 (Complex 1) | 10E8 (Complex 2) | 4E10 (2FX7) | 4E10 (1TZG-P) | 4E10 (1TZG-Q) |
|---|---|---|---|---|---|
| ASN 656 | | | | | |
| GLU 657 | | | | | |
| GLN 658 | | | | | |
| GLU 659 | | | | | |
| LEU 660 | | | | | |
| LEU 661 | | | | | |
| GLU 662 | | | | | |
| LEU 663 | | | | | |
| ASP 664 | | | | | |
| LYS 665 | | | | | |
| TRP 666 | | | | | |
| ALA 667 | | | | | |
| SER 668 | HN | | | | |
| LEU 669 | N | N | | | |
| TRP 670 | N | | | | |
| ASN 671 | | | HN | | |
| TRP 672 | HN | HN | HN | HN | HN |
| PHE 673 | N | N | N | N | N |
| ASP 674 | | | | N | N |
| ILE 675 | | | N | N | N |
| THR 676 | | | HN | HN | HN |
| ASN 677 | | | N | N | N |
| TRP 678 | HN | N | | | |
| LEU 679 | N | N | N | | |
| TRP 680 | | | | | |
| TYR 681 | | | | | |
| ILE 682 | | | | | |
| ARG 683 | HN | HN | | | |

FIG. 36
Neutralization of pseudotyped COT6.15 (clade C) envelope MPER mutants

10E8

| COT6.15 | IC80 (ug/ml) | Mutant/WT |
|---|---|---|
| W666A | 0.006 | 0.09 |
| K667A | 0.018 | 0.29 |
| N668A | 0.057 | 0.90 |
| L669A | 0.009 | 0.14 |
| W670A | 0.009 | 0.14 |
| S671A | 0.083 | 1.32 |
| W672A | >2 | >31 |
| F673A | >2 | >31 |
| D674A | 0.332 | 5.30 |
| D674N | 0.054 | 0.87 |
| D674S | 0.100 | 1.60 |
| I675A | 0.009 | 0.14 |
| T676A | 0.012 | 0.19 |
| K677A | 0.061 | 0.97 |
| W678A | 0.011 | 0.18 |
| L679A | 0.072 | 1.15 |
| W680A | 0.022 | 0.35 |
| Y681A | 0.010 | 0.16 |
| I682A | 0.008 | 0.13 |
| K683A | 0.092 | 1.47 |
| K683R | 0.083 | 1.33 |
| Wild-type | 0.063 | 1.00 |

4E10

| COT6.15 | IC80 (ug/ml) | Mutant/WT |
|---|---|---|
| W666A | 0.193 | 0.07 |
| K667A | 0.541 | 0.18 |
| N668A | 3.407 | 1.16 |
| L669A | 0.271 | 0.09 |
| W670A | 0.669 | 0.23 |
| S671A | 5.055 | 1.72 |
| W672A | >25 | >8.3 |
| F673A | >25 | >8.3 |
| D674A | 14.140 | 4.81 |
| D674N | 2.412 | 0.82 |
| D674S | 20.060 | 6.83 |
| I675A | 0.387 | 0.13 |
| T676A | >25 | >8.3 |
| K677A | 1.868 | 0.64 |
| W678A | 0.457 | 0.16 |
| L679A | 8.501 | 2.89 |
| W680A | >25 | >8.3 |
| Y681A | 0.489 | 0.17 |
| I682A | 0.754 | 0.26 |
| K683A | 0.907 | 0.31 |
| K683R | 2.331 | 0.79 |
| Wild-type | 2.939 | 1.00 |

| 10E8 Ab | Clade C (use COT6.15 MPER mutants) | WKNLWSWFDITKWLWYIK (SEQ ID NO: 24) |
|---|---|---|
| | Clade B (use 4E10 mutant peptides) | CNWFDITNWLWYIRKKK SEQ ID NO: 14) |
| 4E10 Ab | Clade C (use COT6.15 MPER mutants) | WKNLWSWFDITKWLWYIK (SEQ ID NO: 24) |
| | Clade B (use 4E10 mutant peptides) | CNWFDITNWLWYIRKKK(SEQ ID NO: 14) |

FIG. 37

10E8, 7H6, 7N16 and their cross complementary combinations in neutralization assays

| IC50 (ug/ml) | BaL | CAAN | JRFL | Q168 | THRO | Z106.9 |
|---|---|---|---|---|---|---|
| 10E8 | 0.11 | 0.42 | 0.23 | 1.04 | 0.08 | 10.6 |
| 7H6 | 0.68 | 0.784 | 0.896 | 1.772 | 0.285 | 3.17 |
| *fold chage* | *6.18* | *1.87* | *3.90* | *1.70* | *3.56* | *0.30* |
| 7N16L | | | | | | |
| *fold chage* | | | | | | |
| **10E8*H*-7N16*L*** | 6.33 | 14 | 2.77 | >27 | 0.81 | >27 |
| *fold chage* | *56* | *33* | *12* | *>26* | *10* | *>2.5* |
| **7H6*H*-10E8*L*** | 0.17 | 0.32 | 0.46 | 2.27 | 0.1 | >20.5 |
| *fold change* | *1.5* | *-1.3* | *2* | *2* | *1.3* | *>2* |

10E8H-10E8L - the original 10E8
10E8-7N16L - one less mutation in the light chain of 7N16
7H6H-10E8L - one additional mutation in the heavy chain of 7H6

Mapping of 10e8-Variant Mutations

7H6 (yellow spheres):

Light Chain
FR2 aa51 I->K
FR3 aa71 V->I

7N16 (orange spheres):

Heavy Chain
FR1 aa3 Q->R
FR1 aa5 V->A
IGHJ1: TLVT->TLVI

Light Chain
CDR1 aa38 Y->H
FR3 aa71 V->I
IGLJ3: TKLT->TKLI

Comparison with other Anti-MPER Antibodies

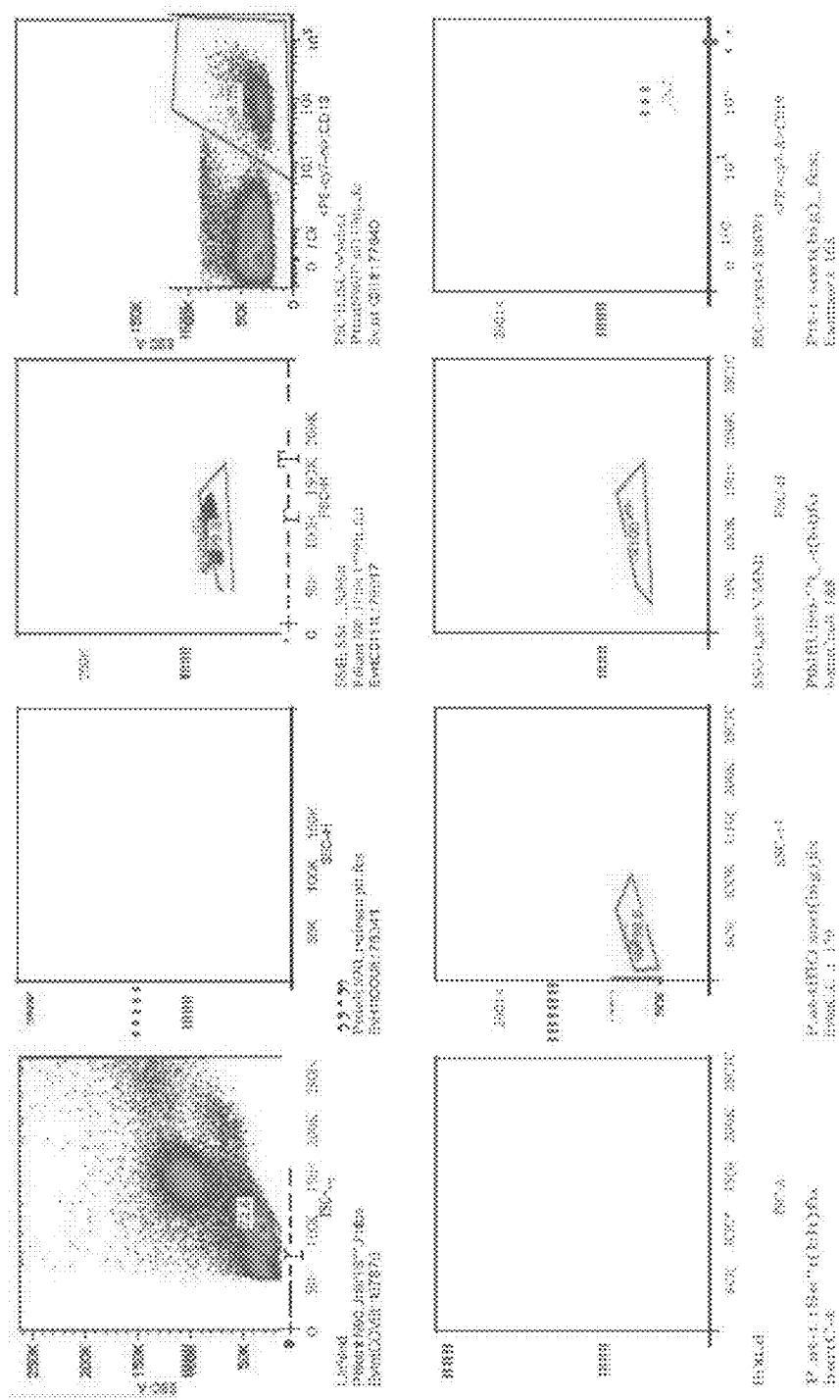
FIG. 42A  Isolation of CD19+IgGA-IgD-IgM- B cells

10E8 paratope residues shown in surface representation.

Mutations of 10E8 Heavy Chain (HC):

Based on relative co-planarity with gp41 epitope peptide, six residue positions within 10E8 heavy chain, along with heavy chain N-terminal extensions were selected for mutagenesis.

1. HC G54
2. HC D28
3. HC D30
4. HC N31
5. HC P52b
6. HC S74
7. HC E1 (-1)

These positions are addressed in the wild type background, in the revertant R3 background, as well as in combination with relevant residue positions obtained from the alanine scanning of the complete paratope.

Mutations of 10E8 Heavy Chain (HC):

Single, double, triple, and quadruple mutation combinations with substitutions to Trp or Phe:

| Hydrophobic Mutants | | | IC50 | | | | | IC80 | | | |
|---|---|---|---|---|---|---|---|---|---|---|---|
| | | BaL.01 | JRFL.JB | REJO.67 | QH0515.01 | THRO.18 | BaL.01 | JRFL.JB | REJO.67 | QH0515.01 | THRO.18 |
| Heavy Chain | D28W | 0.6 | 0.6 | 0.6 | 0.2 | 0.2 | 0.2 | 0.4 | 0.2 | 0.4 | 0.2 |
| | D30W | 0.4 | 0.7 | 1.0 | 1.0 | 0.2 | 0.4 | 0.5 | 0.5 | 0.5 | 0.3 |
| | N31W | 0.9 | 1.1 | 1.8 | 2.8 | 0.4 | 0.4 | 0.7 | 0.9 | 0.9 | 0.4 |
| | P52bW | 0.5 | 0.4 | 0.6 | 0.9 | 0.1 | 0.2 | 0.3 | 0.2 | 0.3 | 0.2 |
| | G54W | 0.6 | 0.6 | 0.6 | 0.6 | 0.3 | 0.3 | 0.5 | 0.3 | 0.2 | 0.4 |
| | S74W | 0.3 | 0.2 | 0.4 | 0.6 | 0.2 | 0.2 | 0.3 | 0.2 | 0.3 | 0.2 |
| D28W G54W | | 0.5 | 0.5 | 1.3 | 2.2 | 0.2 | 0.2 | 0.4 | 0.3 | 0.4 | 0.2 |
| D30W G54W | | 0.9 | 0.7 | 0.6 | 0.7 | 0.2 | 0.3 | 0.4 | 0.2 | 0.6 | 0.2 |
| N31W G54W | | 0.8 | 0.6 | 0.4 | 1.0 | 0.2 | 0.4 | 0.5 | 0.2 | 0.4 | 0.3 |
| P54W G54W | | 0.6 | 0.5 | 0.7 | 1.3 | 0.2 | 0.3 | 0.5 | 0.4 | 0.5 | 0.3 |
| D28W D30W | | 1.3 | 1.1 | 4.5 | 3.4 | 0.6 | 0.5 | 0.8 | 1.1 | 1.0 | 0.5 |
| D28W N31W | | 2.4 | 1.2 | 1.4 | 0.4 | 0.8 | 0.8 | 0.6 | 1.1 | 1.0 | 0.5 |
| D30W N31F | | 0.6 | 0.6 | 0.3 | 0.1 | 0.3 | 0.3 | 0.5 | 0.2 | 0.4 | 0.3 |

>3 fold increase in IC50/80 (loss of function)
>3 fold decrease in IC50/80 (gain of function)

Fold: IC50(Mutant)/IC50(10E8)

FIG. 48

| Virus ID | Clade | IC50 10e8-R1 | 10e8-R3 | 10e8-R H3L1 | 10e8-R H3L2 | 10e8 |
|---|---|---|---|---|---|---|
| JRFL.JB | B | 3.590 | | 1.780 | 1.010 | |
| BaL.01 | B | 1.610 | | 1.320 | | |
| YU2.DG | B | 9.520 | 1.850 | 7.240 | 3.910 | 2.300 |
| PVO.04 | B | 4.550 | | 6.680 | 3.770 | 1.410 |
| TRO.11 | B | | | | | |
| CAAN.A2 | B | | 1.940 | 8.600 | 4.540 | 2.700 |
| THRO.18 | B | | | | | |
| BG1168.01 | B | 1.090 | | 1.120 | | |
| 6101.10 | B | | | | | |
| KER2018.11 | A | 8.070 | 1.140 | 3.820 | 3.180 | 2.060 |
| GM IC50 | | 2.540 | 0.256 | 1.318 | 0.881 | 0.420 |
| fold improvement over WT | IC50(10E8)/IC50(Revertant) | 0.17 | 1.64 | 0.32 | 0.48 | 1.00 |
| | IC50(Revertant)/IC50(10E8) | | | | | 1.00 |

| Virus ID | Clade | IC80 10e8-R1 | 10e8-R3 | 10e8-R H3L1 | 10e8-R H3L2 | 10e8 |
|---|---|---|---|---|---|---|
| JRFL.JB | B | | 2.030 | 6.900 | 3.660 | 1.990 |
| BaL.01 | B | 9.610 | 1.740 | 9.160 | 4.520 | 2.090 |
| YU2.DG | B | >50 | 8.190 | | | |
| PVO.04 | B | >50 | 5.210 | >50 | | 8.160 |
| TRO.11 | B | 4.760 | | 1.120 | | |
| CAAN.A2 | B | >50 | 9.390 | >50 | | |
| THRO.18 | B | 2.800 | | 2.260 | 1.480 | |
| BG1168.01 | B | 6.730 | 1.460 | 5.070 | 3.250 | 2.330 |
| 6101.10 | B | 2.470 | | | | |
| KER2018.11 | A | | 5.830 | | | 8.280 |
| GM IC80 | | | 1.6318 | | 4.0817 | 2.241 |
| fold improvement over WT | IC50(10E8)/IC50(Revertant) | | 1.37 | | 0.55 | 1.00 |
| | IC50(Revertant)/IC50(10E8) | | | | | 1.00 |

FIG. 49

Heavy-chain grid-identified phylogenetic tree

Light-chain grid-identified phylogenetic tree

10E8 heavy-chain variant neutralization

10E8 light-chain variant neutralization

FIG. 51C

Functional 10E8 light chain variants

Light chain variants

FIG. 52A

| Heavy Chain | | Light Chain | | Matched | Symbol | Expression |
|---|---|---|---|---|---|---|
| Branch | Chain | Branch | Chain | | | (mg/L) |
| b1-H | gVRC-H1$_{dN152}$ | b1-L | gVRC-L1dN152 | Yes | | 24.8 |
| b2-H | gVRC-H8$_{dN152}$ | b1-L | gVRC-L1dN152 | No | | 13.6 |
| b3-H | gVRC-H6$_{dN152}$ | b1-L | gVRC-L1dN152 | No | | <0.5 |
| b4-H | gVRC-H11$_{dN152}$ | b1-L | gVRC-L1dN152 | No | | 33.6 |
| b1-H | gVRC-H1$_{dN152}$ | b3-L | gVRC-L10dN152 | No | | 21.6 |
| b2-H | gVRC-H8$_{dN152}$ | b3-L | gVRC-L10dN152 | No | | 9.6 |
| b3-H | gVRC-H6$_{dN152}$ | b3-L | gVRC-L10dN152 | Yes | | 15.2 |
| b4-H | gVRC-H11$_{dN152}$ | b3-L | gVRC-L10dN152 | No | | 15.2 |
| b1-H | gVRC-H1$_{dN152}$ | b2-L | gVRC-L19dN152 | No | | 24.0 |
| b2-H | gVRC-H8$_{dN152}$ | b2-L | gVRC-L19dN152 | Yes | | 2.4 |
| b3-H | gVRC-H6$_{dN152}$ | b2-L | gVRC-L19dN152 | No | | 6.4 |
| b4-H | gVRC-H11$_{dN152}$ | b2-L | gVRC-L19dN152 | No | | 23.2 |

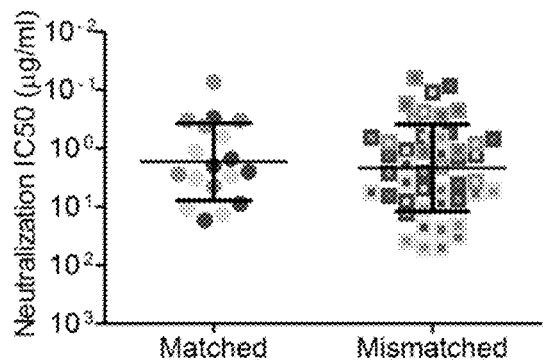

FIG. 52B

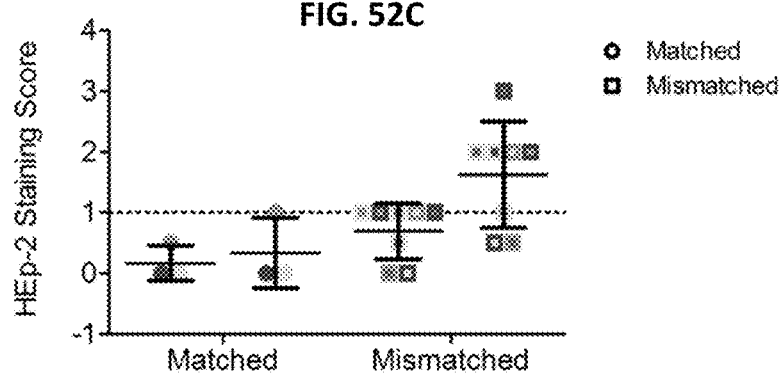

FIG. 52C

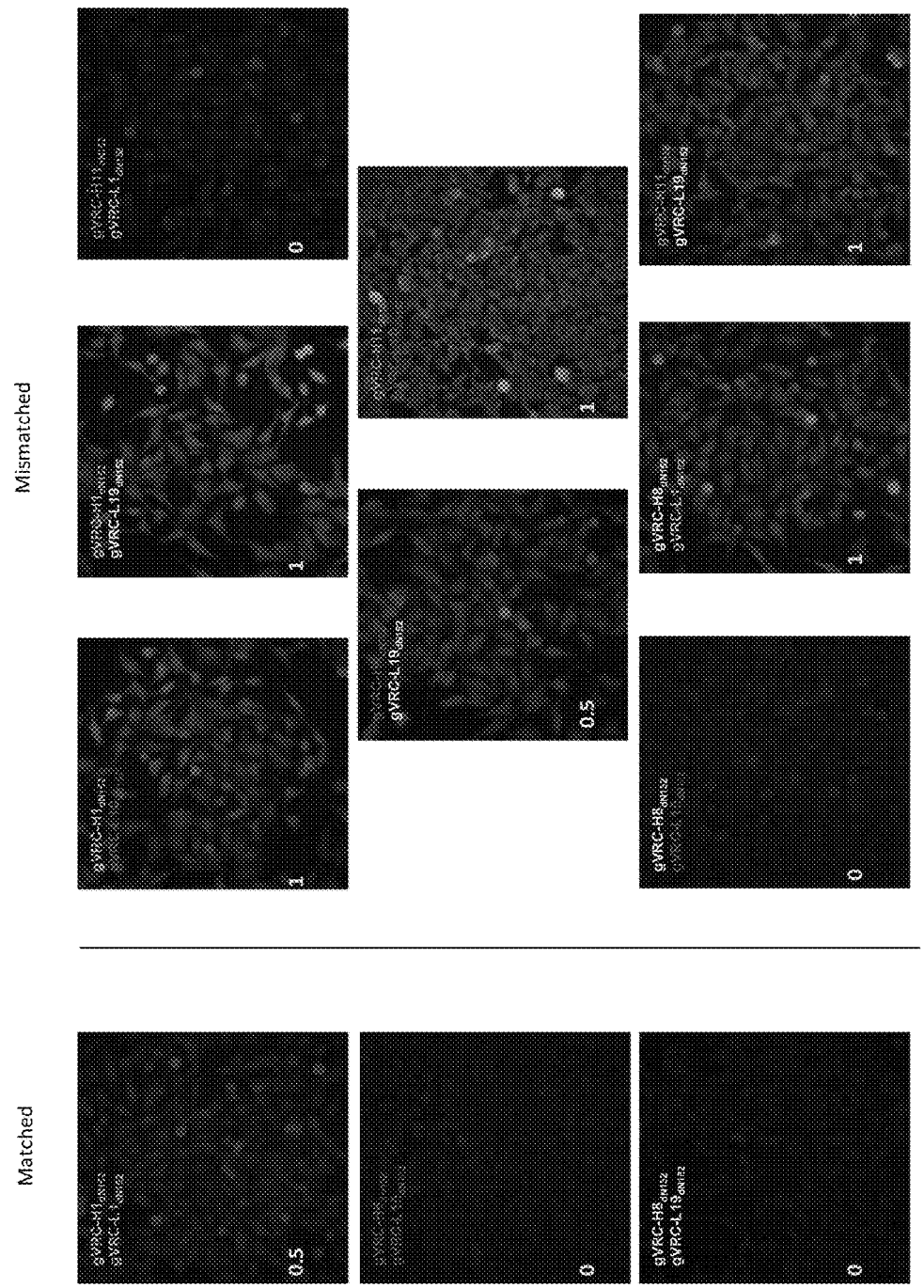

FIG. 53

| Antibody | Heavy chain | HC code | Light chain | LC code |
|---|---|---|---|---|
| 10e8-HC1-L | 10e8-HC1 | 85447 | 10e8-L | na |
| 10e8-HC6-L | 10e8-HC6 | 594928_corr | 10e8-L | na |
| 10e8-HC10-L | 10e8-HC10 | 48379 | 10e8-L | na |
| 10e8-HC6-S74W-L | 10e8-HC6-S74W | 594928_corr_S74W | 10e8-L | na |
| 10e8-HC10-S74W-L | 10e8-HC10-S74W | 48379_S74W | 10e8-L | na |
| 10e8-HC1-rL3 | 10e8-HC1 | 85447 | 10e8-rL3 | na |
| 10e8-HC6-rL3 | 10e8-HC6 | 594928_corr | 10e8-rL3 | na |
| 10e8-HC10-rL3 | 10e8-HC10 | 48379 | 10e8-rL3 | na |
| 10e8-HC1-LC16 | 10e8-HC1 | 85447 | 10e8-LC16 | 40147 |
| 10e8-HC6-LC16 | 10e8-HC6 | 594928_corr | 10e8-LC16 | 40147 |
| 10e8-HC10-LC16 | 10e8-HC10 | 48379 | 10e8-LC16 | 40147 |
| 10e8-HC1-LC22 | 10e8-HC1 | 85447 | 10e8-LC22 | 1044653 |
| 10e8-HC6-LC22 | 10e8-HC6 | 594928_corr | 10e8-LC22 | 1044653 |
| 10e8-HC10-LC22 | 10e8-HC10 | 48379 | 10e8-LC22 | 1044653 |
| 10e8-HC1-LC23 | 10e8-HC1 | 85447 | 10e8-LC23 | 99000 |
| 10e8-HC6-LC23 | 10e8-HC6 | 594928_corr | 10e8-LC23 | 99000 |
| 10e8-HC10-LC23 | 10e8-HC10 | 48379 | 10e8-LC23 | 99000 |

FIG. 54

| Antibody | Heavy chain | HC code | Light chain | LC code |
|---|---|---|---|---|
| 10e8-HC1-LC6 | 10e8-HC1 | 85447 | 10e8-LC6 | 1543 |
| 10e8-HC2-LC6 | 10e8-HC2 | 5908 | 10e8-LC6 | 1543 |
| 10e8-HC4-LC6 | 10e8-HC4 | 69791 | 10e8-LC6 | 1543 |
| 10e8-HC10-LC6 | 10e8-HC10 | 48379 | 10e8-LC6 | 1543 |
| 10e8-H-LC6 | 10e8-H | na | 10e8-LC6 | 1543 |
| 10e8-HC1-LC19 | 10e8-HC1 | 85447 | 10e8-LC19 | 903074 |
| 10e8-HC2-LC19 | 10e8-HC2 | 5908 | 10e8-LC19 | 903074 |
| 10e8-HC4-LC19 | 10e8-HC4 | 69791 | 10e8-LC19 | 903074 |
| 10e8-HC10-LC19 | 10e8-HC10 | 48379 | 10e8-LC19 | 903074 |
| 10e8-H-LC19 | 10e8-H | na | 10e8-LC19 | 903074 |
| 10e8-HC1-LC22 | 10e8-HC1 | 85447 | 10e8-LC22 | 1044653 |
| 10e8-HC2-LC22 | 10e8-HC2 | 5908 | 10e8-LC22 | 1044653 |
| 10e8-HC4-LC22 | 10e8-HC4 | 69791 | 10e8-LC22 | 1044653 |
| 10e8-HC10-LC22 | 10e8-HC10 | 48379 | 10e8-LC22 | 1044653 |
| 10e8-H-LC22 | 10e8-H | na | 10e8-LC22 | 1044653 |
| 10e8-HC1-10e8L | 10e8-HC1 | 85447 | 10e8L | na |
| 10e8-HC2-10e8L | 10e8-HC2 | 5908 | 10e8L | na |
| 10e8-HC4-10e8L | 10e8-HC4 | 69791 | 10e8L | na |
| 10e8-HC10-10e8L | 10e8-HC10 | 48379 | 10e8L | na |
| 10e8-H-10e8L | 10e8-H | na | 10e8L | na |

FIG. 55A

| IC50 μg/ml | | | | | | |
|---|---|---|---|---|---|---|
| clade | B | B | B | B | B | B |
| virus | JRFL.JB | BaL.01 | REJO.67 | QH0515.01 | YU2.DG | PVO.04 |
| sample name | | | | | | |
| 10e8 (lot #910) | 0.491 | 0.576 | 0.094 | 0.718 | 3.53 | 4.87 |
| 10e8-HC1-L | 0.073 | 0.117 | 0.033 | 0.136 | 0.681 | 0.505 |
| 10e8-HC6-L | 0.122 | 0.136 | 0.042 | 0.130 | 1.04 | 0.701 |
| 10e8-HC10-L | 0.119 | 0.112 | 0.059 | 0.122 | 0.811 | 0.697 |
| 10e8-HC6-S77W-L | 0.077 | 0.105 | 0.034 | 0.125 | 0.655 | 0.607 |
| 10e8-HC10-S77W-L | 0.050 | 0.096 | 0.016 | 0.117 | 0.367 | 0.522 |
| 10e8-HC1-rL3 | 0.092 | 0.052 | 0.023 | 0.088 | 0.576 | 0.410 |
| 10e8-HC6-rL3 | 0.154 | 0.109 | 0.049 | 0.205 | 0.803 | 1.10 |
| 10e8-HC10-rL3 | 0.227 | 0.132 | 0.082 | 0.264 | 1.03 | 1.72 |
| 10e8-HC1-LC16 | 0.119 | 0.132 | 0.039 | 0.083 | 0.537 | 0.726 |
| 10e8-HC6-LC16 | 0.197 | 0.187 | 0.041 | 0.109 | 1.33 | 1.44 |
| 10e8-HC10-LC16 | 0.261 | 0.194 | 0.061 | 0.096 | 1.54 | 1.79 |
| 10e8-HC1-LC22 | 0.326 | 0.181 | 0.103 | 0.167 | 1.41 | 1.29 |
| 10e8-HC6-LC22 | 0.396 | 0.421 | 0.163 | 0.341 | 2.01 | 4.18 |
| 10e8-HC10-LC22 | 0.352 | 0.299 | 0.097 | 0.110 | 2.01 | 2.05 |
| 10e8-HC1-LC23 | 0.172 | 0.122 | 0.057 | 0.065 | 0.958 | 0.794 |
| 10e8-HC6-LC23 | 0.333 | 0.313 | 0.136 | 0.225 | 2.03 | 2.27 |
| 10e8-HC10-LC23 | 0.298 | 0.407 | 0.102 | 0.339 | 2.05 | 2.16 |
| 10e8 (lot #910) | 0.940 | 1.16 | 0.386 | 1.71 | 4.00 | 5.71 |
| 10e8-HC1-LC6 | 0.691 | 0.539 | 0.086 | 1.31 | 4.17 | 6.55 |
| 10e8-HC2-LC6 | 0.630 | 1.07 | 0.111 | 1.32 | 4.90 | 8.16 |
| 10e8-HC4-LC6 | 1.52 | 2.52 | 0.302 | 1.99 | 8.97 | 17.0 |
| 10e8-HC10-LC6 | 1.43 | 2.60 | 0.657 | 2.67 | 7.57 | 12.9 |
| 10e8-H-LC6 | 2.84 | 2.72 | 0.432 | 3.92 | 14.2 | 23.9 |
| 10e8-HC1-LC19 | 5.22 | 5.93 | 0.615 | 24.6 | 32.6 | >50 |
| 10e8-HC2-LC19 | 1.14 | 3.24 | 0.623 | 11.0 | 2.97 | 13.6 |
| 10e8-HC4-LC19 | 1.90 | 3.84 | 1.24 | 5.68 | 8.82 | 22.4 |
| 10e8-HC10-LC19 | 5.43 | 10.7 | 0.644 | 21.3 | 38.6 | >50 |
| 10e8-H-LC19 | 8.21 | 9.96 | 0.695 | >50 | >50 | >50 |
| 10e8-HC1-LC22 | 0.175 | 0.270 | 0.063 | 0.224 | 1.15 | 1.11 |
| 10e8-HC2-LC22 | 0.331 | 0.797 | 0.240 | 0.841 | 2.08 | 3.71 |
| 10e8-HC10-LC22 | 0.329 | 0.411 | 0.073 | 0.334 | 2.79 | 4.46 |
| 10e8-H-LC22 | 0.419 | 0.508 | 0.101 | 0.262 | 3.55 | 3.69 |
| 10e8-HC1-10e8L | 0.106 | 0.158 | 0.050 | 0.139 | 0.725 | 0.940 |
| 10e8-HC2-10e8L | 0.232 | 0.461 | 0.145 | 0.454 | 1.03 | 2.21 |
| 10e8-HC4-10e8L | 0.289 | 0.374 | 0.074 | 0.557 | 2.04 | 2.80 |
| 10e8-HC10-10e8L | 0.383 | 0.235 | 0.064 | 0.356 | 2.28 | 1.83 |
| 10e8-H-10e8L | 0.565 | 0.679 | 0.230 | 0.853 | 3.52 | 4.40 |

FIG. 55B

| # Viruses Tested | 6 | | | | |
|---|---|---|---|---|---|
| Total VS Neutralized, IC50 | | % VS Neutralized, IC50 | | Median | Geometric |
| <50ug/ml | <1ug/ml | <50ug/ml | <1ug/ml | IC50 | Mean |
| 6 | 4 | 100 | 67 | 0.647 | 0.830 |
| 6 | 6 | 100 | 100 | 0.127 | 0.154 |
| 6 | 5 | 100 | 83 | 0.133 | 0.201 |
| 6 | 6 | 100 | 100 | 0.121 | 0.195 |
| 6 | 6 | 100 | 100 | 0.115 | 0.155 |
| 6 | 6 | 100 | 100 | 0.107 | 0.109 |
| 6 | 6 | 100 | 100 | 0.090 | 0.115 |
| 6 | 5 | 100 | 83 | 0.180 | 0.230 |
| 6 | 4 | 100 | 67 | 0.246 | 0.324 |
| 6 | 6 | 100 | 100 | 0.126 | 0.165 |
| 6 | 4 | 100 | 67 | 0.192 | 0.261 |
| 6 | 4 | 100 | 67 | 0.228 | 0.306 |
| 6 | 4 | 100 | 67 | 0.254 | 0.350 |
| 6 | 4 | 100 | 67 | 0.409 | 0.654 |
| 6 | 4 | 100 | 67 | 0.326 | 0.408 |
| 6 | 6 | 100 | 100 | 0.147 | 0.197 |
| 6 | 4 | 100 | 67 | 0.323 | 0.495 |
| 6 | 4 | 100 | 67 | 0.373 | 0.515 |
| 6 | 2 | 100 | 33 | 1.44 | 1.59 |
| 6 | 3 | 100 | 50 | 1.00 | 1.02 |
| 6 | 2 | 100 | 33 | 1.20 | 1.26 |
| 6 | 1 | 100 | 17 | 2.25 | 2.66 |
| 6 | 1 | 100 | 17 | 2.64 | 2.93 |
| 6 | 1 | 100 | 17 | 3.38 | 4.05 |
| 5 | 1 | 83 | 17 | 5.93 | 6.87 |
| 6 | 1 | 100 | 17 | 3.11 | 3.17 |
| 6 | 0 | 100 | 0 | 4.76 | 4.65 |
| 5 | 1 | 83 | 17 | 10.7 | 7.90 |
| 3 | 1 | 50 | 17 | 8.21 | 3.84 |
| 6 | 4 | 100 | 67 | 0.247 | 0.308 |
| 6 | 4 | 100 | 67 | 0.819 | 0.862 |
| 6 | 4 | 100 | 67 | 0.373 | 0.587 |
| 6 | 4 | 100 | 67 | 0.464 | 0.648 |
| 6 | 6 | 100 | 100 | 0.149 | 0.207 |
| 6 | 4 | 100 | 67 | 0.458 | 0.502 |
| 6 | 4 | 100 | 67 | 0.466 | 0.542 |
| 6 | 4 | 100 | 67 | 0.370 | 0.452 |
| 6 | 4 | 100 | 67 | 0.766 | 1.03 |

FIG. 55C

Fold Effect

| sample name | clade<br>virus | B<br>JRFL.JB | B<br>BaL.01 | B<br>REJO.67 | B<br>QH0515.01 | B<br>YU2.DG | B<br>PVO.04 | Mean |
|---|---|---|---|---|---|---|---|---|
| 10e8 | | | | | | | | |
| 10e8-HC1-L | | 0.15 | 0.20 | 0.35 | 0.19 | 0.19 | 0.10 | 0.20 |
| 10e8-HC6-L | | 0.25 | 0.24 | 0.45 | 0.18 | 0.29 | 0.14 | 0.26 |
| 10e8-HC10-L | | 0.34 | 0.19 | 0.63 | 0.17 | 0.23 | 0.14 | 0.27 |
| 10e8-HC6-S77W-L | | 0.16 | 0.18 | 0.36 | 0.17 | 0.19 | 0.12 | 0.20 |
| 10e8-HC10-S77W-L | | 0.10 | 0.17 | 0.17 | 0.16 | 0.10 | 0.11 | 0.14 |
| 10e8-HC1-rL3 | | 0.19 | 0.09 | 0.24 | 0.12 | 0.16 | 0.08 | 0.15 |
| 10e8-HC6-rL3 | | 0.31 | 0.19 | 0.52 | 0.29 | 0.23 | 0.23 | 0.29 |
| 10e8-HC10-rL3 | | 0.46 | 0.23 | 0.87 | 0.37 | 0.29 | 0.35 | 0.43 |
| 10e8-HC1-LC16 | | 0.24 | 0.23 | 0.41 | 0.12 | 0.15 | 0.15 | 0.22 |
| 10e8-HC6-LC16 | | 0.40 | 0.32 | 0.44 | 0.15 | 0.38 | 0.30 | 0.33 |
| 10e8-HC10-LC16 | | 0.53 | 0.34 | 0.65 | 0.13 | 0.44 | 0.37 | 0.41 |
| 10e8-HC1-LC22 | | 0.66 | 0.31 | 1.10 | 0.23 | 0.40 | 0.26 | 0.50 |
| 10e8-HC6-LC22 | | 0.81 | 0.73 | 1.73 | 0.47 | 0.57 | 0.66 | 0.86 |
| 10e8-HC10-LC22 | | 0.72 | 0.52 | 1.03 | 0.15 | 0.57 | 0.42 | 0.57 |
| 10e8-HC1-LC23 | | 0.35 | 0.21 | 0.61 | 0.09 | 0.27 | 0.16 | 0.28 |
| 10e8-HC6-LC23 | | 0.68 | 0.54 | 1.45 | 0.31 | 0.58 | 0.47 | 0.67 |
| 10e8-HC10-LC23 | | 0.61 | 0.71 | 1.09 | 0.47 | 0.58 | 0.44 | 0.65 |
| 10e8 | | | | | | | | |
| 10e8-HC1-LC6 | | 1.41 | 0.94 | 0.91 | 1.82 | 1.18 | 1.34 | 1.27 |
| 10e8-HC2-LC6 | | 1.28 | 1.86 | 1.18 | 1.84 | 1.39 | 1.68 | 1.54 |
| 10e8-HC4-LC6 | | 3.10 | 4.37 | 3.21 | 2.77 | 2.54 | 3.49 | 3.25 |
| 10e8-HC10-LC6 | | 2.91 | 4.51 | 6.99 | 3.72 | 2.15 | 2.65 | 3.82 |
| 10e8-H-LC6 | | 5.78 | 4.72 | 4.60 | 5.46 | 4.02 | 4.91 | 4.91 |
| 10e8-HC1-LC19 | | 10.64 | 10.30 | 6.54 | 34.26 | 9.24 | 20.53 | 15.25 |
| 10e8-HC2-LC19 | | 2.32 | 5.63 | 6.63 | 15.32 | 0.84 | 2.79 | 5.59 |
| 10e8-HC4-LC19 | | 3.87 | 6.67 | 13.19 | 7.91 | 2.50 | 4.60 | 6.46 |
| 10e8-HC10-LC19 | | 11.06 | 18.58 | 6.85 | 29.67 | 10.94 | 20.53 | 16.27 |
| 10e8-H-LC19 | | 16.72 | 17.29 | 7.39 | 139.28 | 28.34 | 20.53 | 38.26 |
| 10e8-HC1-LC22 | | 0.36 | 0.47 | 0.67 | 0.31 | 0.33 | 0.23 | 0.39 |
| 10e8-HC2-LC22 | | 0.67 | 1.38 | 2.55 | 1.17 | 0.59 | 0.76 | 1.19 |
| 10e8-HC10-LC22 | | 0.67 | 0.71 | 0.78 | 0.47 | 0.79 | 0.92 | 0.72 |
| 10e8-H-LC22 | | 0.85 | 0.68 | 1.07 | 0.38 | 1.01 | 0.76 | 0.82 |
| 10e8-HC1-10e8L | | 0.22 | 0.27 | 0.53 | 0.19 | 0.21 | 0.19 | 0.27 |
| 10e8-HC2-10e8L | | 0.47 | 0.80 | 1.54 | 0.63 | 0.29 | 0.45 | 0.70 |
| 10e8-HC4-10e8L | | 0.59 | 0.65 | 0.79 | 0.78 | 0.58 | 0.58 | 0.66 |
| 10e8-HC10-10e8L | | 0.78 | 0.41 | 0.68 | 0.50 | 0.65 | 0.38 | 0.56 |
| 10e8-H-10e8L | | 1.15 | 1.18 | 2.45 | 1.19 | 1.00 | 0.90 | 1.31 |

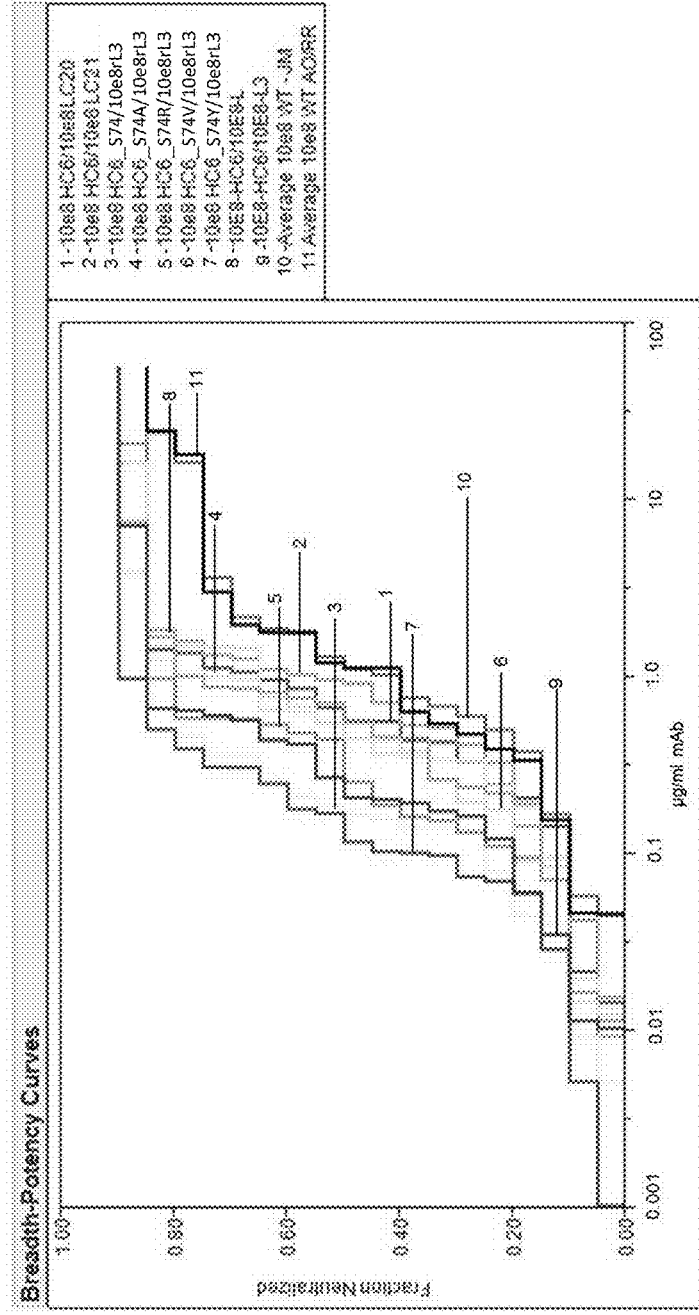

Breadth-Potency Curves – IC80
10e8 WT and selected variants against a panel of 20 viruses.
Average 10e8 WT – JM = Average IC80 of three runs using JM lab stock 10e8 WT
Average 10e8 WT AO/RR = Average IC80 of three runs using AO/RR-provided 10e8 WT
20 Virus Panel: Panel from clades A (6), B (8), C (4), AG (1), and G (1) selected to represent a range of 10e8 neutralization (and different from the VRC01/07 20 virus panel)

FIG. 59

Nomenclature and SEQ ID NOs for heavy and light chains of 10E8-like antibodies

| Name in FIGs. 79-83 | Name in FIGs. 76-78 | SEQ ID NO |
|---|---|---|
| \multicolumn{3}{c}{Heavy chains} | | |
| HC10 | VRC-H1dN152 | 153 |
| HC6 | VRC-H2dN152 | 154 |
| HC8 | VRC-H2dN152 | 154 |
| HC9 | VRC-H3dN152 | 155 |
| HC5 | VRC-H4dN152 | 156 |
| HC7 | VRC-H5dN152 | 157 |
| HC4 | VRC-H6dN152 | 158 |
| HC3 | VRC-H7dN152 | 159 |
| HC2 | VRC-H8dN152 | 160 |
| HC11 | VRC-H9dN152 | 161 |
| HC12 | VRC-H10dN152 | 162 |
| HC1 | VRC-H11dN152 | 163 |
| HC6-S74W | - | 154 with S54W substitution |
| HC10-S74W | - | 154 with S54W substitution |
| | Light Chains | |
| FIGs79-83 | FIGs. 76-78 | |
| LC22 | VRC-L1dN152 | 164 |
| LC16 | VRC-L2dN152 | 165 |
| LC20 | VRC-L3dN152 | 166 |
| LC23 | VRC-L4dN152 | 167 |
| LC21 | VRC-L5dN152 | 168 |
| LC4 | VRC-L6dN152 | 169 |
| LC8 | VRC-L7dN152 | 170 |
| LC7 | VRC-L7dN152 | 170 |
| LC9 | VRC-L7dN152 | 170 |
| LC15 | VRC-L8dN152 | 171 |
| LC13 | VRC-L9dN152 | 172 |
| LC6 | VRC-L10dN152 | 173 |
| LC5 | VRC-L10dN152 | 173 |
| LC14 | VRC-L11dN152 | 174 |
| LC3 | VRC-L12dN152 | 175 |
| LC12 | VRC-L13dN152 | 176 |
| LC1 | VRC-L14dN152 | 177 |
| LC27 | VRC-L15dN152 | 178 |
| LC11 | VRC-L16dN152 | 179 |
| LC26 | VRC-L17dN152 | 180 |
| LC24 | VRC-L18dN152 | 181 |
| LC19 | VRC-L19dN152 | 182 |
| LC10 | VRC-L20dN152 | 183 |
| LC25 | VRC-L21dN152 | 184 |
| LC18 | VRC-L22dN152 | 185 |
| LC17 | VRC-L23dN152 | 186 |

FIG. 60A

Summary of 16E5 Heavy Chain Variations

| A.A. Position (Kabat) | A.A. position (linear) | 16E5 sequence | Germline Revertant Mutations | 454 Mutants | Alanine scan mutants | Structure based mutants | Additional mutants |
|---|---|---|---|---|---|---|---|
| 1 | 1 | E | | | | | |
| 2 | 2 | V | | I | | | |
| 3 | 3 | Q | | R | | | |
| 4 | 4 | L | | | | | |
| 5 | 5 | V | | A | | | |
| 6 | 6 | E | | | | | |
| 7 | 7 | S | | | | | |
| 8 | 8 | G | | | | | |
| 9 | 9 | G | | | | | |
| 10 | 10 | G | | R, D | | | |
| 11 | 11 | L | | | | | |
| 12 | 12 | V | | | | | |
| 13 | 13 | K | | R | | | |
| 14 | 14 | P | | | | | |
| 15 | 15 | G | | | | | |
| 16 | 16 | G | | | | | |
| 17 | 17 | S | | | | | |
| 18 | 18 | L | | | | | Q |
| 19 | 19 | R | | | | | |
| 20 | 20 | L | | | | | |
| 21 | 21 | S | | | | | |
| 22 | 22 | C | | | | | |
| 23 | 23 | S | A | | | | A |
| 24 | 24 | A | | | | | |
| 25 | 25 | S | | | | | |
| 26 | 26 | G | | | | | |
| 27 | 27 | F | | | | | |
| 28 | 28 | D | | N, S | A | W | |
| 29 | 29 | F | | | | | |
| 30 | 30 | D | | K | A | W | A |
| 31 | 31 | N | | S, D | A | W, F | F, Y |
| 32 | 32 | A | | T | | | Q |
| 33 | 33 | W | | | | | |
| 34 | 34 | M | | | | | |
| 35 | 35 | T | | | | | |
| 36 | 36 | W | | | | | |
| 37 | 37 | V | | | | | |
| 38 | 38 | R | | | | | |
| 39 | 39 | Q | | | | | |
| 40 | 40 | P | A | A | | | |
| 41 | 41 | P | | | | | |
| 42 | 42 | G | | | | | |
| 43 | 43 | K | | | | | |
| 44 | 44 | G | | | | | |
| 45 | 45 | L | | | | | |
| 46 | 46 | E | | | | | |
| 47 | 47 | W | | | | | |
| 48 | 48 | V | | | | | |
| 49 | 49 | G | | | | | |
| 50 | 50 | R | | | | | |
| 51 | 51 | I | | | | | |
| 52 | 52 | T | | S | A | | |
| 52a | 53 | G | | | | | |
| 52b | 54 | P | | | | W | |
| 52c | 55 | G | | | | | |
| 53 | 56 | E | | | A | | A, F, L, M, V, W |
| 54 | 57 | G | | | | W | |
| 55 | 58 | W | | | | | K |
| 56 | 59 | S | | T | A | | R |
| 57 | 60 | V | | S | | | |
| 58 | 61 | D | | G | A | | |
| 59 | 62 | Y | | | | | |
| 60 | 63 | A | | | | | |
| 61 | 64 | A | | E | | | |
| 62 | 65 | P | | S, T | | | |
| 63 | 66 | V | | | | | |

FIG. 60B

| | | | | | | | |
|---|---|---|---|---|---|---|---|
| 64 | 77 | E | | K,Q | | | |
| 65 | 68 | G | | | | | |
| 66 | 69 | K | | | | | |
| 67 | 70 | F | | | | | |
| 68 | 71 | T | | I | | | |
| 69 | 72 | I | | | | | |
| 70 | 73 | S | | | | | |
| 71 | 74 | R | | | | | |
| 72 | 75 | L | D | M,I,N | | | D |
| 73 | 76 | N | D | | | | |
| 74 | 77 | S | | M | | W | W,F,L,M,Y,A,R,V |
| 75 | 78 | I | E | | | | K |
| 76 | 79 | N | | D | | | |
| 77 | 80 | F | T | M | | | T |
| 78 | 81 | L | | F | | | |
| 79 | 82 | Y | | | | | |
| 80 | 83 | L | | | | | |
| 81 | 84 | E | Q | | | | Q |
| 82 | 85 | M | | | | | |
| 83a | 86 | N | | | | | |
| 83b | 87 | N | S | R | | | S |
| 83c | 88 | L | | V | | | |
| 83 | 89 | K | K | K | | | K |
| 84 | 90 | M | T | T,I,P | | | T |
| 85 | 91 | E | | D | | | |
| 86 | 92 | Q | | | | | |
| 87 | 93 | S | T | T | | | T,W |
| 88 | 94 | G | A | | | | W |
| 89 | 95 | I | V | S,Y | | | V |
| 90 | 96 | Y | | | | | |
| 91 | 97 | F | Y | Y | | | Y |
| 92 | 98 | C | | | | | |
| 93 | 99 | A | T | V | | | |
| 94 | 100 | R | T | H | | | |
| 95 | 101 | T | | | | | |
| 96 | 102 | G | | E | | | |
| 97 | 103 | K | | | | | |
| 98 | 104 | Y | | H | | | |
| 99 | 105 | Y | | | | | |
| 100 | 106 | Q | | A,N | | | |
| 100a | 107 | F | | | | | |
| 100b | 108 | W | | | | | |
| 100c | 109 | S | | G,R | | | |
| 100d | 110 | G | | | | | |
| 100e | 111 | Y | | | A | | |
| 100f | 112 | P | | | | | |
| 100g | 113 | P | | | | | |
| 100h | 114 | G | | | | | |
| 100i | 115 | E | | | | | |
| 100j | 116 | E | | | | | |
| 100k | 117 | Y | | | | | |
| 100l | 118 | F | | L | | | |
| 101 | 119 | Q | | E | | | |
| 102 | 120 | D | | H | | | |
| 103 | 121 | W | | | | | |
| 104 | 122 | G | | | | | |
| 105 | 123 | R | Q | Q | | | Q |
| 106 | 124 | G | | | | | |
| 107 | 125 | T | | | | | |
| 108 | 126 | L | | Q | | | |
| 109 | 127 | V | | | | | |
| 110 | 128 | T | | I | | | |
| 111 | 129 | V | | | | | |
| 112 | 130 | S | | P | | | |
| 113 | 131 | S | | | | | |

FIG. 61A

Summary of 10E8 Light Chain Variations

| Amino Acid Position (Kabat) | Amino Acid position (linear) | 10E8 sequence | Germline Revertant Mutations | 454 Mutants |
|---|---|---|---|---|
| 1 | 1 | S | | A |
| 2 | 2 | Y | | S |
| 3 | 3 | E | | D |
| 4 | 4 | L | | |
| 5 | 5 | T | | |
| 6 | 6 | Q | | |
| 7 | 7 | E | D | D |
| 8 | 8 | T | P | P |
| 9 | 9 | G | A | A, T |
| 10 | 10 | V | | |
| 11 | 11 | S | | |
| 12 | 12 | V | | |
| 13 | 13 | A | | |
| 14 | 14 | L | | F |
| 15 | 15 | G | | K, E |
| 16 | 16 | R | Q | Q, K |
| 17 | 17 | T | | |
| 18 | 18 | V | | |
| 19 | 19 | T | R | R |
| 20 | 20 | I | | |
| 21 | 21 | T | | |
| 22 | 22 | C | | |
| 23 | 23 | R | | Q |
| 24 | 24 | G | | |
| 25 | 25 | D | | |
| 26 | 26 | S | | |
| 27 | 27 | L | | |
| 28 | 28 | R | | |
| 29 | 29 | S | | R, N |
| 30 | 30 | H | | Y |
| 31 | 31 | Y | | |
| 32 | 32 | A | | V, T |
| 33 | 33 | S | | G |
| 34 | 34 | W | | |
| 35 | 35 | Y | | |
| 36 | 36 | Q | | |
| 37 | 37 | R | Q | K, Q |
| 38 | 38 | K | | R |
| 39 | 39 | P | | T |
| 40 | 40 | G | | R |
| 41 | 41 | Q | | |
| 42 | 42 | A | | |
| 43 | 43 | P | | |
| 44 | 44 | I | V | V, E |
| 45 | 45 | L | | |
| 46 | 46 | L | | V |
| 47 | 47 | F | | V, I |
| 48 | 48 | Y | | |
| 49 | 49 | G | | P |
| 50 | 50 | K | | R |
| 51 | 51 | N | | D, H |
| 52 | 52 | N | | I |
| 53 | 53 | R | | |
| 54 | 54 | P | | |
| 55 | 55 | S | | S |
| 56 | 56 | G | | P |
| 57 | 57 | V | I | I |
| 58 | 58 | P | | H, S |
| 59 | 59 | D | | |
| 60 | 60 | R | | |
| 61 | 61 | F | | |
| 62 | 62 | S | | |
| 63 | 63 | G | | A |
| 64 | 64 | S | | F |

FIG. 61B

| | | | | |
|---|---|---|---|---|
| 65 | 65 | A | | T, S |
| 66 | 66 | S | | |
| 67 | 67 | G | | |
| 68 | 68 | N | | |
| 69 | 69 | R | T | T |
| 70 | 70 | A | | |
| 71 | 71 | S | | |
| 72 | 72 | L | | |
| 73 | 73 | T | | |
| 74 | 74 | I | | |
| 75 | 75 | S | T | A, T |
| 76 | 76 | Q | | |
| 77 | 77 | A | | |
| 78 | 78 | Q | | E |
| 79 | 79 | A | | G |
| 80 | 80 | E | | D |
| 81 | 81 | D | | |
| 82 | 82 | D | E | I |
| 83 | 83 | A | | |
| 84 | 84 | E | D | |
| 85 | 85 | Y | | |
| 86 | 86 | Y | | |
| 87 | 87 | C | | |
| 88 | 88 | S | | |
| 89 | 89 | S | | |
| 90 | 90 | R | | |
| 91 | 91 | D | | |
| 92 | 92 | K | | |
| 93 | 93 | S | | |
| 94 | 94 | G | | |
| 95 | 95 | S | | |
| 95A | 96 | R | | |
| 95B | 97 | L | | |
| 95C | 98 | S | | V |
| 96 | 99 | V | | T |
| 97 | 100 | F | | |
| 98 | 101 | G | | |
| 99 | 102 | G | | R |
| 100 | 103 | G | | |
| 101 | 104 | T | | |
| 102 | 105 | K | | E |
| 103 | 106 | L | | V, R |
| 104 | 107 | T | | S, A |
| 105 | 108 | V | | I, G |
| 106 | 109 | L | | V, P |

SEQUENCE LISTING

```
<160> NUMBER OF SEQ ID NOS: 209

<210> SEQ ID NO 1
<211> LENGTH: 131
<212> TYPE: PRT
<213> ORGANISM: Homo sapiens

<400> SEQUENCE: 1

Glu Val Gln Leu Val Glu Ser Gly Gly Gly Leu Val Lys Pro Gly Gly
1               5                   10                  15

Ser Leu Arg Leu Ser Cys Ser Ala Ser Gly Phe Asp Phe Asp Asn Ala
            20                  25                  30

Trp Met Thr Trp Val Arg Gln Pro Pro Gly Lys Gly Leu Glu Trp Val
        35                  40                  45

Gly Arg Ile Thr Gly Pro Gly Glu Gly Trp Ser Val Asp Tyr Ala Ala
    50                  55                  60

Pro Val Glu Gly Arg Phe Thr Ile Ser Arg Leu Asn Ser Ile Asn Phe
65                  70                  75                  80

Leu Tyr Leu Glu Met Asn Asn Leu Arg Met Glu Asp Ser Gly Leu Tyr
                85                  90                  95

Phe Cys Ala Arg Thr Gly Lys Tyr Tyr Asp Phe Trp Ser Gly Tyr Pro
            100                 105                 110

Pro Gly Glu Glu Tyr Phe Gln Asp Trp Gly Arg Gly Thr Leu Val Thr
        115                 120                 125

Val Ser Ser
    130

<210> SEQ ID NO 2
<211> LENGTH: 109
<212> TYPE: PRT
<213> ORGANISM: Homo sapiens

<400> SEQUENCE: 2

Ser Tyr Glu Leu Thr Gln Glu Thr Gly Val Ser Val Ala Leu Gly Arg
1               5                   10                  15

Thr Val Thr Ile Thr Cys Arg Gly Asp Ser Leu Arg Ser His Tyr Ala
            20                  25                  30

Ser Trp Tyr Gln Lys Lys Pro Gly Gln Ala Pro Ile Leu Leu Phe Tyr
        35                  40                  45

Gly Lys Asn Asn Arg Pro Ser Gly Val Pro Asp Arg Phe Ser Gly Ser
    50                  55                  60

Ala Ser Gly Asn Arg Ala Ser Leu Thr Ile Ser Gly Ala Gln Ala Glu
65                  70                  75                  80

Asp Asp Ala Glu Tyr Tyr Cys Ser Ser Arg Asp Lys Ser Gly Ser Arg
                85                  90                  95

Leu Ser Val Phe Gly Gly Gly Thr Lys Leu Thr Val Leu
            100                 105

<210> SEQ ID NO 3
<211> LENGTH: 131
<212> TYPE: PRT
<213> ORGANISM: Homo sapiens
```

<400> SEQUENCE: 3

Glu Val Gln Leu Val Glu Ser Gly Gly Gly Leu Val Lys Pro Gly Gly
1               5                   10                  15

Ser Leu Arg Leu Ser Cys Ser Ala Ser Gly Phe Asp Phe Asp Asn Ala
            20                  25                  30

Trp Met Thr Trp Val Arg Gln Pro Pro Gly Lys Gly Leu Glu Trp Val
        35                  40                  45

Gly Arg Ile Thr Gly Pro Gly Glu Gly Trp Ser Val Asp Tyr Ala Ala
    50                  55                  60

Pro Val Glu Gly Arg Phe Thr Ile Ser Arg Leu Asn Ser Ile Asn Phe
65                  70                  75                  80

Leu Tyr Leu Glu Met Asn Asn Leu Arg Met Glu Asp Ser Gly Leu Tyr
                85                  90                  95

Phe Cys Ala Arg Thr Gly Lys Tyr Tyr Asp Phe Trp Ser Gly Tyr Pro
            100                 105                 110

Pro Gly Glu Glu Tyr Phe Gln Asp Trp Gly Arg Gly Thr Leu Val Thr
        115                 120                 125

Val Ser Ser
    130

<210> SEQ ID NO 4
<211> LENGTH: 109
<212> TYPE: PRT
<213> ORGANISM: Homo sapiens

<400> SEQUENCE: 4

Ser Tyr Glu Leu Thr Gln Glu Thr Gly Val Ser Val Ala Leu Gly Arg
1               5                   10                  15

Thr Val Thr Ile Thr Cys Arg Gly Asp Ser Leu Arg Ser His Tyr Ala
            20                  25                  30

Ser Trp Tyr Gln Lys Lys Pro Gly Gln Ala Pro Lys Leu Leu Phe Tyr
        35                  40                  45

Gly Lys Asn Asn Arg Pro Ser Gly Ile Pro Asp Arg Phe Ser Gly Ser
    50                  55                  60

Ala Ser Gly Asn Arg Ala Ser Leu Thr Ile Ser Gly Ala Gln Ala Glu
65                  70                  75                  80

Asp Asp Ala Glu Tyr Tyr Cys Ser Ser Arg Asp Lys Ser Gly Ser Arg
                85                  90                  95

Leu Ser Val Phe Gly Gly Gly Thr Lys Leu Thr Val Leu
            100                 105

<210> SEQ ID NO 5
<211> LENGTH: 131
<212> TYPE: PRT
<213> ORGANISM: Homo sapiens

<400> SEQUENCE: 5

Glu Val Arg Leu Ala Glu Ser Gly Gly Gly Leu Val Lys Pro Gly Gly
1               5                   10                  15

Ser Leu Arg Leu Ser Cys Ser Ala Ser Gly Phe Asp Phe Asp Asn Ala
            20                  25                  30

Trp Met Thr Trp Val Arg Gln Pro Pro Gly Lys Gly Leu Glu Trp Val
        35                  40                  45

Gly Arg Ile Thr Gly Pro Gly Glu Gly Trp Ser Val Asp Tyr Ala Ala
    50                  55                  60

Pro Val Glu Gly Arg Phe Thr Ile Ser Arg Leu Asn Ser Ile Asn Phe

```
            65                  70                  75                  80
Leu Tyr Leu Glu Met Asn Asn Leu Arg Met Glu Asp Ser Gly Leu Tyr
                85                  90                  95

Phe Cys Ala Arg Thr Gly Lys Tyr Tyr Asp Phe Trp Ser Gly Tyr Pro
            100                 105                 110

Pro Gly Glu Glu Tyr Phe Gln Asp Trp Gly Arg Gly Thr Leu Val Ile
        115                 120                 125

Val Ser Ser
    130

<210> SEQ ID NO 6
<211> LENGTH: 109
<212> TYPE: PRT
<213> ORGANISM: Homo sapiens

<400> SEQUENCE: 6

Ser Tyr Glu Leu Thr Gln Glu Thr Gly Val Ser Val Ala Leu Gly Arg
1               5                   10                  15

Thr Val Thr Ile Thr Cys Arg Gly Asp Ser Leu Arg Ser His His Ala
            20                  25                  30

Ser Trp Tyr Gln Lys Lys Pro Gly Gln Ala Pro Ile Leu Leu Phe Tyr
        35                  40                  45

Gly Lys Asn Asn Arg Pro Ser Gly Ile Pro Asp Arg Phe Ser Gly Ser
    50                  55                  60

Ala Ser Gly Asn Arg Ala Ser Leu Thr Ile Ser Gly Ala Gln Ala Glu
65                  70                  75                  80

Asp Asp Ala Glu Tyr Tyr Cys Ser Ser Arg Asp Lys Ser Gly Ser Arg
                85                  90                  95

Leu Ser Val Phe Gly Gly Gly Thr Lys Leu Ile Val Leu
            100                 105

<210> SEQ ID NO 7
<211> LENGTH: 100
<212> TYPE: PRT
<213> ORGANISM: Homo sapiens

<400> SEQUENCE: 7

Glu Val Gln Leu Ala Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Thr Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr
            100

<210> SEQ ID NO 8
<211> LENGTH: 96
<212> TYPE: PRT
<213> ORGANISM: Homo sapiens

<400> SEQUENCE: 8
```

-continued

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
                20                  25                  30

Ser Trp Tyr Gln Gln Lys Pro Gly Gln Ala Pro Val Leu Val Ile Tyr
                35                  40                  45

Gly Lys Asn Asn Arg Pro Ser Gly Ile Pro Asp Arg Phe Ser Gly Ser
            50                  55                  60

Ser Ser Gly Asn Thr Ala Ser Leu Thr Ile Ser Gly Ala Gln Ala Glu
65                  70                  75                  80

Asp Glu Ala Asp Tyr Tyr Cys Asn Ser Arg Asp Ser Ser Gly Asn His
                85                  90                  95

<210> SEQ ID NO 9
<211> LENGTH: 7
<212> TYPE: PRT
<213> ORGANISM: Human immunodeficiency virus

<400> SEQUENCE: 9

Glu Leu Asp Lys Trp Ala Ser
1               5

<210> SEQ ID NO 10
<211> LENGTH: 6
<212> TYPE: PRT
<213> ORGANISM: Human immunodeficiency virus

<400> SEQUENCE: 10

Asn Trp Phe Asp Ile Thr
1               5

<210> SEQ ID NO 11
<211> LENGTH: 131
<212> TYPE: PRT
<213> ORGANISM: Homo sapiens
<220> FEATURE:
<221> NAME/KEY: misc_feature
<222> LOCATION: (3)..(3)
<223> OTHER INFORMATION: Xaa can be Q or R
<220> FEATURE:
<221> NAME/KEY: misc_feature
<222> LOCATION: (5)..(5)
<223> OTHER INFORMATION: Xaa can be V or A
<220> FEATURE:
<221> NAME/KEY: misc_feature
<222> LOCATION: (77)..(77)
<223> OTHER INFORMATION: Xaa can be S or Y
<220> FEATURE:
<221> NAME/KEY: misc_feature
<222> LOCATION: (128)..(128)
<223> OTHER INFORMATION: Xaa can be T or I

<400> SEQUENCE: 11

Glu Val Xaa Leu Xaa Glu Ser Gly Gly Gly Leu Val Lys Pro Gly Gly
1               5                   10                  15

Ser Leu Arg Leu Ser Cys Ser Ala Ser Gly Phe Asp Phe Asp Asn Ala
                20                  25                  30

Trp Met Thr Trp Val Arg Gln Pro Pro Gly Lys Gly Leu Glu Trp Val
                35                  40                  45

Gly Arg Ile Thr Gly Pro Gly Glu Gly Trp Ser Val Asp Tyr Ala Ala
            50                  55                  60

Pro Val Glu Gly Arg Phe Thr Ile Ser Arg Leu Asn Xaa Ile Asn Phe
65                  70                  75                  80

Leu Tyr Leu Glu Met Asn Asn Leu Arg Met Glu Asp Ser Gly Leu Tyr
            85                  90                  95

Phe Cys Ala Arg Thr Gly Lys Tyr Tyr Asp Phe Trp Ser Gly Tyr Pro
            100                 105                 110

Pro Gly Glu Glu Tyr Phe Gln Asp Trp Gly Arg Gly Thr Leu Val Xaa
        115                 120                 125

Val Ser Ser
    130

<210> SEQ ID NO 12
<211> LENGTH: 109
<212> TYPE: PRT
<213> ORGANISM: Homo sapiens
<220> FEATURE:
<221> NAME/KEY: misc_feature
<222> LOCATION: (31)..(31)
<223> OTHER INFORMATION: Xaa can be Y or H
<220> FEATURE:
<221> NAME/KEY: misc_feature
<222> LOCATION: (44)..(44)
<223> OTHER INFORMATION: Xaa can be I or K
<220> FEATURE:
<221> NAME/KEY: misc_feature
<222> LOCATION: (57)..(57)
<223> OTHER INFORMATION: Xaa can be V or I
<220> FEATURE:
<221> NAME/KEY: misc_feature
<222> LOCATION: (107)..(107)
<223> OTHER INFORMATION: Xaa can be T or I

<400> SEQUENCE: 12

Ser Tyr Glu Leu Thr Gln Glu Thr Gly Val Ser Val Ala Leu Gly Arg
1               5                   10                  15

Thr Val Thr Ile Thr Cys Arg Gly Asp Ser Leu Arg Ser His Xaa Ala
            20                  25                  30

Ser Trp Tyr Gln Lys Lys Pro Gly Gln Ala Pro Xaa Leu Leu Phe Tyr
        35                  40                  45

Gly Lys Asn Asn Arg Pro Ser Gly Xaa Pro Asp Arg Phe Ser Gly Ser
    50                  55                  60

Ala Ser Gly Asn Arg Ala Ser Leu Thr Ile Ser Gly Ala Gln Ala Glu
65                  70                  75                  80

Asp Asp Ala Glu Tyr Tyr Cys Ser Ser Arg Asp Lys Ser Gly Ser Arg
            85                  90                  95

Leu Ser Val Phe Gly Gly Gly Thr Lys Leu Xaa Val Leu
            100                 105

<210> SEQ ID NO 13
<211> LENGTH: 19
<212> TYPE: PRT
<213> ORGANISM: Human immunodeficiency virus

<400> SEQUENCE: 13

Lys Trp Ala Ser Leu Trp Asn Trp Phe Asp Ile Thr Asn Trp Leu Trp
1               5                   10                  15

Tyr Ile Arg

<210> SEQ ID NO 14
<211> LENGTH: 17
<212> TYPE: PRT
<213> ORGANISM: Artificial sequence
<220> FEATURE:
<223> OTHER INFORMATION: Synthetic MPER peptide mutants.

```
<400> SEQUENCE: 14

Cys Asn Trp Phe Asp Ile Thr Asn Trp Leu Trp Tyr Ile Arg Lys Lys
1               5                   10                  15

Lys

<210> SEQ ID NO 15
<211> LENGTH: 34
<212> TYPE: PRT
<213> ORGANISM: Artificial sequence
<220> FEATURE:
<223> OTHER INFORMATION: Synthetic MPER peptide mutants.

<400> SEQUENCE: 15

Asn Met Tyr Glu Leu Gln Lys Leu Asn Ser Trp Asp Val Phe Gly Asn
1               5                   10                  15

Trp Phe Asp Leu Ala Ser Trp Val Lys Tyr Ile Gln Tyr Gly Val Tyr
            20                  25                  30

Ile Val

<210> SEQ ID NO 16
<211> LENGTH: 34
<212> TYPE: PRT
<213> ORGANISM: Artificial sequence
<220> FEATURE:
<223> OTHER INFORMATION: Synthetic MPER peptide mutants.

<400> SEQUENCE: 16

Asn Met Tyr Glu Leu Leu Ala Leu Asp Lys Trp Ala Ser Leu Trp Asn
1               5                   10                  15

Trp Phe Asp Ile Thr Lys Trp Leu Trp Tyr Ile Lys Tyr Gly Val Tyr
            20                  25                  30

Ile Val

<210> SEQ ID NO 17
<211> LENGTH: 34
<212> TYPE: PRT
<213> ORGANISM: Artificial sequence
<220> FEATURE:
<223> OTHER INFORMATION: Synthetic MPER peptide mutants.

<400> SEQUENCE: 17

Asn Met Tyr Glu Leu Leu Ala Leu Asp Ser Trp Lys Asn Leu Trp Asn
1               5                   10                  15

Trp Phe Asp Ile Thr Lys Trp Leu Trp Tyr Ile Lys Tyr Gly Val Tyr
            20                  25                  30

Ile Val

<210> SEQ ID NO 18
<211> LENGTH: 34
<212> TYPE: PRT
<213> ORGANISM: Artificial sequence
<220> FEATURE:
<223> OTHER INFORMATION: Synthetic MPER peptide mutants.

<400> SEQUENCE: 18

Asn Met Tyr Glu Leu Leu Ala Leu Asp Lys Trp Ala Ser Leu Trp Asn
1               5                   10                  15

Trp Phe Asp Leu Ala Ser Trp Val Lys Tyr Ile Gln Tyr Gly Val Tyr
            20                  25                  30

Ile Val
```

<210> SEQ ID NO 19
<211> LENGTH: 34
<212> TYPE: PRT
<213> ORGANISM: Artificial sequence
<220> FEATURE:
<223> OTHER INFORMATION: Synthetic MPER peptide mutants.

<400> SEQUENCE: 19

Asn Met Tyr Glu Leu Gln Ala Leu Asp Lys Trp Ala Val Phe Gly Asn
1               5                   10                  15

Trp Phe Asp Leu Ala Ser Trp Val Lys Tyr Ile Gln Tyr Gly Val Tyr
            20                  25                  30

Ile Val

<210> SEQ ID NO 20
<211> LENGTH: 34
<212> TYPE: PRT
<213> ORGANISM: Artificial sequence
<220> FEATURE:
<223> OTHER INFORMATION: Synthetic MPER peptide mutants.

<400> SEQUENCE: 20

Asn Met Tyr Glu Leu Gln Lys Leu Asn Ser Trp Asp Val Phe Gly Asn
1               5                   10                  15

Trp Phe Asp Ile Thr Ser Trp Ile Lys Tyr Ile Gln Tyr Gly Val Tyr
            20                  25                  30

Ile Val

<210> SEQ ID NO 21
<211> LENGTH: 34
<212> TYPE: PRT
<213> ORGANISM: Artificial sequence
<220> FEATURE:
<223> OTHER INFORMATION: Synthetic MPER peptide mutants.

<400> SEQUENCE: 21

Asn Met Tyr Glu Leu Gln Lys Leu Asn Ser Trp Asp Val Phe Gly Asn
1               5                   10                  15

Trp Phe Asp Ile Thr Lys Trp Leu Trp Tyr Ile Lys Tyr Gly Val Tyr
            20                  25                  30

Ile Val

<210> SEQ ID NO 22
<211> LENGTH: 34
<212> TYPE: PRT
<213> ORGANISM: Artificial sequence
<220> FEATURE:
<223> OTHER INFORMATION: Synthetic MPER peptide mutants.

<400> SEQUENCE: 22

Asn Met Tyr Glu Leu Gln Lys Leu Asn Ser Trp Asp Val Phe Trp Asn
1               5                   10                  15

Trp Phe Asp Ile Thr Lys Trp

<400> SEQUENCE: 23

Asn Met Tyr Glu Leu Gln Lys Leu Asn Ser Trp Asp Ser Leu Trp Asn
1               5                   10                  15

Trp Phe Asp Ile Thr Lys Trp Leu Trp Tyr Ile Lys Tyr Gly Val Tyr
            20                  25                  30

Ile Val

<210> SEQ ID NO 24
<211> LENGTH: 19
<212> TYPE: PRT
<213> ORGANISM: Human immunodeficiency virus

<400> SEQUENCE: 24

Ala Leu Asp Ser Trp Lys Asn Leu Trp Ser Trp Phe Asp Ile Thr Lys
1               5                   10                  15

Trp Leu Trp

<210> SEQ ID NO 25
<211> LENGTH: 35
<212> TYPE: PRT
<213> ORGANISM: Artificial sequence
<220> FEATURE:
<223> OTHER INFORMATION: Synthetic MPER peptide mutants.

<400> SEQUENCE: 25

Arg Arg Arg Arg Asn Glu Gln Glu Leu Leu Glu Leu Asp Lys Trp Ala
1               5                   10                  15

Ser Leu Trp Asn Trp Phe Asp Ile Thr Asn Trp Leu Trp Tyr Ile Arg
            20                  25                  30

Arg Arg Arg
        35

<210> SEQ ID NO 26
<211> LENGTH: 28
<212> TYPE: PRT
<213> ORGANISM: Human immunodeficiency virus

<400> SEQUENCE: 26

Asn Glu Gln Glu Leu Leu Glu Leu Asp Lys Trp Ala Ser Leu Trp Asn
1               5                   10                  15

Trp Phe Asp Ile Thr Asn Trp Leu Trp Tyr Ile Arg
            20                  25

<210> SEQ ID NO 27
<211> LENGTH: 53
<212> TYPE: DNA
<213> ORGANISM: Artificial sequence
<220> FEATURE:
<223> OTHER INFORMATION: Synthetic Sequencing Primer.

<400> SEQUENCE: 27
ccatctcatc cctgcgtgtc tccgactcag aaggtgtcca gtgtgargtg cag      53

<210> SEQ ID NO 28
<211> LENGTH: 54
<212> TYPE: DNA
<213> ORGANISM: Artificial sequence
<220> FEATURE:
<223> OTHER INFORMATION: Synthetic Sequencing Primer.

<400> SEQUENCE: 28
ccatctcatc cctgcgtgtc tccgactcag gctattttaa aaggtgtcca atgt       54

<210> SEQ ID NO 29
<211> LENGTH: 56
<212> TYPE: DNA
<213> ORGANISM: Artificial sequence
<220> FEATURE:
<223> OTHER INFORMATION: Synthetic Sequencing Primer.

<400> SEQUENCE: 29
ccatctcatc cctgcgtgtc tccgactcag gtggcagctc ccagatgggt cctgtc     56

<210> SEQ ID NO 30
<211> LENGTH: 56
<212> TYPE: DNA
<213> ORGANISM: Artificial sequence
<220> FEATURE:
<223> OTHER INFORMATION: Synthetic Sequencing Primer.

<400> SEQUENCE: 30
ccatctcatc cctgcgtgtc tccgactcag gttgcagttt taaaaggtgt ccagtg     56

<210> SEQ ID NO 31
<211> LENGTH: 53
<212> TYPE: DNA
<213> ORGANISM: Artificial sequence
<220> FEATURE:
<223> OTHER INFORMATION: Synthetic Sequencing Primer.

<400> SEQUENCE: 31
ccatctcatc cctgcgtgtc tccgactcag gctctgtgac ctcctatgag ctg        53

<210> SEQ ID NO 32
<211> LENGTH: 54
<212> TYPE: DNA
<213> ORGANISM: Artificial sequence
<220> FEATURE:
<223> OTHER INFORMATION: Synthetic Sequencing Primer.

<400> SEQUENCE: 32
ccatctcatc cctgcgtgtc tccgactcag gcttactgca caggatccgt ggcc       54

<210> SEQ ID NO 33
<211> LENGTH: 54
<212> TYPE: DNA
<213> ORGANISM: Artificial sequence
<220> FEATURE:
<223> OTHER INFORMATION: Synthetic Sequencing Primer.

<400> SEQUENCE: 33
ccatctcatc cctgcgtgtc tccgactcag actctttgca taggttctgt ggtt       54

<210> SEQ ID NO 34
<211> LENGTH: 54
<212> TYPE: DNA
<213> ORGANISM: Artificial sequence
<220> FEATURE:
<223> OTHER INFORMATION: Synthetic Sequencing Primer.

<400> SEQUENCE: 34
ccatctcatc cctgcgtgtc tccgactcag tctcactgca caggctctgt gacc       54

<210> SEQ ID NO 35
<211> LENGTH: 393
<212> TYPE: DNA
<213> ORGANISM: Homo sapiens

<400> SEQUENCE: 35

```
gaggttcgat tggtggagtc tgggggaggc ttggtgaagc ctggaggatc ccttagactc      60
tcatgttcag cctctggttt cgacttcgat aacgcctaga tgacttgggt ccgccagcct     120
ccagggaagg gcctcgaatg ggttggtcgt attacgggtc caggtgaagg ttggtcagtg     180
gactatgctg cacccgtgga aggcagattt accatctcga gactcaattc aataaatttc     240
ttatatttgg agatgaacaa tttaagaatg gaagactcag gcctttactt ctgtgcccgc     300
acgggaaaat attatgattt tggagtggc tatccgccgg agaagaata cttccaagac       360
tggggccggg gcaccctagt catcgtctcc tca                                  393
```

<210> SEQ ID NO 36
<211> LENGTH: 393
<212> TYPE: DNA
<213> ORGANISM: Homo sapiens

<400> SEQUENCE: 36

```
gaggttcgac tggtggagtc tgggggacga ttggtgaggc ctgggggatc ccttagactc      60
tcatgttcag cctctggctt caatttcgat aacgcctgga tgacttgggt ccgccagcct     120
ccagggaagg gcctcgaatg ggttggtcgt ataacgggtc cgggtgaagg ttggtcagtg     180
gactatgctg catccgtaaa aggcagattt actatctcaa gaatgaattc aataaatttc     240
ttctatctgg agatgaacaa tttaaaaatc gaagacacag gcctttactt ctgtgcccgc     300
acgggaaaac attatgcttt tggggtggt taccgccgg agaagaata cctggaagac        360
tggggccagg gcacccttgt catcgtctct tca                                  393
```

<210> SEQ ID NO 37
<211> LENGTH: 393
<212> TYPE: DNA
<213> ORGANISM: Homo sapiens

<400> SEQUENCE: 37

```
gaggtgcgac tggtggagtc tgggggacga ttggtgaggc ctgggggatc ccttagactc      60
tcatgttcag cctctggctt caatttcgat aacgcctgga tgacttgggt ccgccagcct     120
ccagggaagg gcctcgaatg ggttggtcgt ataacgggtc cgggtgaagg ttggtcagtg     180
gactatgctg catccgtaaa aggcagattt actatctcaa gaatgaattc aataaatttc     240
ttctatctgg agatgaacaa tttaaaaatc gaagacacag gcctttactt ctgtgcccgc     300
acgggaaaac attatgcttt tggggtggt taccgccgg agaagaata cctggaagac        360
tggggccagg gcacccttgt catcgtctct tca                                  393
```

<210> SEQ ID NO 38
<211> LENGTH: 392
<212> TYPE: DNA
<213> ORGANISM: Homo sapiens

<400> SEQUENCE: 38

```
gaggttcgat tggcggagtc tgggggaggc ttggtgaagc ctggaggatc ccttagactc      60
tcatgttcag cctctggttt cgacttcgat aacgcctgga tgacttgggt ccgccagcct     120
ccagggaagg gcctcgaatg ggtcggtcgt attacgggtc caggtgaagg ttggtcagtg     180
gactatgctg cacccgtgga aggcagattt accatctcga gactcaattc aataaatttc     240
ttatatttgg agatgaacaa tttaagaatg gaagactcag gcctttactt ctgtgcccgc     300
```

```
acgggaaaat attatgattt ttggagtggc tatccgccgg agaagaatac ttccaagact    360
ggggccaggg caccctagtc atcgtctcct ca                                  392

<210> SEQ ID NO 39
<211> LENGTH: 393
<212> TYPE: DNA
<213> ORGANISM: Homo sapiens

<400> SEQUENCE: 39
gaggttcgat tggtggagtc tggggaggc ttggtgaagc ctggaggatc ccttagactc     60
tcatgttcag cctctggttt cgacttcgat aacgcctgga tgacttgggt ccgccagcct   120
ccagggaagg gcctcgaatg ggttggtcgt attacgggtc caggtgaagg ttggtcagtg   180
gactatgctg cacccgtgga aggcagattt accatctcga gactcaattc aataaatttc   240
ttatatttgg agatgaacaa tttaagaatg gaagactcag gcctttactt ctgtgcccgc   300
acgggaaaat attatgattt ttggagtggc tatccgccgg gagaagaata cttccaagac   360
tggggccagg gcaccctagt catcgtctcc tca                                393

<210> SEQ ID NO 40
<211> LENGTH: 393
<212> TYPE: DNA
<213> ORGANISM: Homo sapiens

<400> SEQUENCE: 40
gaggttcgat tggtggagtc tggggaggc ttggtgaagc ctggaggatc ccttagactc     60
tcatgttcag cctctggttt cgacttcgat aacgcctgga tgacttgggt ccgccagcct   120
ccagggaagg gcctcgaatg ggttggtcgt attacgggtc caggtgaagg ttggtcagtg   180
gactatgctg cacccgtgga aggcagattt accatctcga gactcaattc aataaatttc   240
ttatatttgg agatgaacaa tttaagaatg gaagactcag gcctttactt ctgtgcccgc   300
acgggaaaat attatgattt ttggagtggc tatccgccgg gagaagaata cttccaagac   360
tggggccggg gcaccctagt catcgtctcc tca                                393

<210> SEQ ID NO 41
<211> LENGTH: 393
<212> TYPE: DNA
<213> ORGANISM: Homo sapiens

<400> SEQUENCE: 41
gaggttcgat tggcggagtc tggggaggc ttggtgaagc ctggaggatc ccttagactc     60
tcatgttcag cctctggttt cgacttcgat aacgcctgga tgacttgggt ccgccagcct   120
ccagggaagg gcctcgaatg ggtcggtcgt attacgggtc caggtgaagg ttggtcagtg   180
gactatgctg cacccgtgga aggcagattt accatctcga gactcaattc aataaatttt   240
ctatatttgg agatgaacaa tttaagaatg gaagactcag gcctttactt ctgtgcccgc   300
acgggaaaat attatgattt ttggagtggc tatccgccgg gagaagaata cttccaagac   360
tggggccagg gcaccctagt catcgtcccc tca                                393

<210> SEQ ID NO 42
<211> LENGTH: 391
<212> TYPE: DNA
<213> ORGANISM: Homo sapiens

<400> SEQUENCE: 42
gaggtgcgac tggtggagtc tgggggacga ttggtgaggc ctgggggatc ccttagactc     60
```

```
tcatgttcag cctctggctt caatttcgat aacgcctgga tgacttgggt ccgccagcct    120
ccagggaagg gcctcgaatg ggttggtcgt ataacgggtc cggtgaagg ttggtcagtg     180 gactatgctg catccgtaaa aggcagattt actatctcaa gaatgaattc aataaatttc    240
ttctatctgg agatgaacaa tttaaaaatc gaagacacag gcctttactt ctgtgcccgc    300
acgggaaaac attatgcttt tggggtgtt acccgcggga gaagaatacc tggaagactg     360
gggccagggc acccttgtca tcgtctcttc a                                    391

<210> SEQ ID NO 43
<211> LENGTH: 392
<212> TYPE: DNA
<213> ORGANISM: Homo sapiens

<400> SEQUENCE: 43
gaggtgcgac tggtggagtc tgggggacga ttggtgaggc ctggggatc ccttagactc      60 tcatgttcag cctctggctt caatttcgat aacgcctgga tgacttgggt ccgccagcct   120
ccagggaagg gcctcgaatg ggttggtcgt ataacgggtc cggtgaagg ttggtcagtg    180 gactatgctg catccgtaaa aggcagattt actatctcaa gaatgaattc aataattct    240 ctctatctgg agatgaacaa tttaaaaatc gaagacacag gcctttactt ctgtgcccgc   300
acgggaaaac attatgcttt tggggtggt taccccgcggg agaagaatac ctggaagact   360
ggggccaggg caccccttgtc atcgtctctt ca                                 392

<210> SEQ ID NO 44
<211> LENGTH: 393
<212> TYPE: DNA
<213> ORGANISM: Homo sapiens

<400> SEQUENCE: 44
gaggttcgat tggtggagtc tgggggaggc ttggtgaagc ctggggatc ccttagactc     60 tcatgttcag cctctgggtt caatttcgat gacgcctgga tgacttgggt ccgccagcct  120
ccagggaagg gcctcgagtg ggttggtcgt atttcgggtc caggtgaagg ttggtcagtg   180
gactatgctg aatccgtaaa aggcagattt accatctcga gactcaattc aataaatttc  240
ttatatctgg agatgaacaa cgtaagaacc gaagacacag ggtattactt ctgtgcccgc  300
acgggaaaac attatgattt tggagtggt tatccgccgg gagaggagta cttccaggac   360
tggggccagg gcaccctggt catcgtctcc tca                                 393

<210> SEQ ID NO 45
<211> LENGTH: 392
<212> TYPE: DNA
<213> ORGANISM: Homo sapiens

<400> SEQUENCE: 45
gaggttcgat tggtggagtc tgggggaggc ttggtgaagc ctggaggatc ccttagactc    60
tcatgttcag cctctggttt cgacttcgat aacgcctgga tgacttgggt ccgccagcct  120
ccagggaagg gcctcgaatg ggttggtcgt attacgggtc caggtgaagg ttggtcagtg   180
gactatgctg cacccgtgga aggcagattt accatctcga gactcaattc aataaatttc  240
ttatatttgg agatgaacaa tttaagaatg gaagactcag gcctttactt ctgtgcccgc  300
acgggaaata ttatgatttt tggagtggct atccgccggg agaagaatac ttccaagact  360
ggggccgggg caccctagtc atcgtctcct ca                                  392
```

<210> SEQ ID NO 46
<211> LENGTH: 394
<212> TYPE: DNA
<213> ORGANISM: Homo sapiens

<400> SEQUENCE: 46

```
gaggttcgac tggtggagtc tgggggacga ttggtgaggc ctggggatc ccttagactc      60 tcatgttcag cctctggctt caatttcgat aacgcctgga tgacttgggt ccgccagcct    120
ccagggaagg gcctcgaatg ggttggtcgt ataacgggtc cgggtgaagg ttggtcagtg    180
gactatgctg catccgtaaa aggcagattt actatctcaa gaatgaattc aataaatttc    240
ttctatctgg agatgaacaa tttaaaaatc gaagacacag gcctttactt ctgtgcccgc    300
acgggaaaac attaatgctt tttggggtgg ttacccgccg ggagaagaat acctggaaga    360
ctggggccag ggcaccccttg tcatcgtctc ttca                                394
```

<210> SEQ ID NO 47
<211> LENGTH: 389
<212> TYPE: DNA
<213> ORGANISM: Homo sapiens
<220> FEATURE:
<221> NAME/KEY: misc_feature
<222> LOCATION: (326)..(326)
<223> OTHER INFORMATION: n is a, c, g, or t

<400> SEQUENCE: 47

```
gaggttcgac tggtggagtc tgggggacga ttggtgaggc ctggggatc ccttagactc      60 tcatgttcag cctctggctt caatttcgat aacgcctgga tgacttgggt ccgccagcct    120
ccagggaagg gcctcgaatg ggttggtcgt ataacgggtc cgggtgaagg ttggtcagtg    180
gactatgctg catccgtaaa aggcagattt actatctcaa gaatgaattc aataaatttc    240
ttctatctgg agatgaacaa tttaaaaatc gaagacacag gcctttactt ctgtgcccgc    300
acggaaaaca ttatgctttt tggggngtta cccgcggaga agaatacctg gaagactggg    360
gccagggcac ccttgtcatc gtctcttca                                      389
```

<210> SEQ ID NO 48
<211> LENGTH: 394
<212> TYPE: DNA
<213> ORGANISM: Homo sapiens
<220> FEATURE:
<221> NAME/KEY: misc_feature
<222> LOCATION: (344)..(344)
<223> OTHER INFORMATION: n is a, c, g, or t

<400> SEQUENCE: 48

```
gaggttcgat tggcggagtc tgggggaggc ttggtgaagc ctggaggatc ccttagactc      60
tcatgttcag cctctggttt cgacttcgat aacgcctgga tgacttgggt ccgccagcct    120
ccagggaagg gcctcgaatg ggtcggtcgt attacgggtc caggtgaagg ttggtcagtg    180
gactatgctg cacccgtgga aggcagattt accatctcga gactcaattc aataaatttc    240
ttatatttgg agatgaacaa tttaagaatg gaagactcag gcctttactt ctgtgcccgc    300
acggaaaaat attaatgatt tttggagtgg ctatccgccg gganaagaat acttccaaga    360
ctggggccag ggcaccctag tcatcgtctc ctca                                 394
```

<210> SEQ ID NO 49
<211> LENGTH: 394
<212> TYPE: DNA
<213> ORGANISM: Homo sapiens

<400> SEQUENCE: 49

```
gaggttcgac tggtggagtc tgggggacga ttggtgaggc ctgggggatc ccttagactc    60
tcatgttcag cctctggctt caatttcgat aacgcctgga tgacttgggt ccgccagcct   120
ccagggaagg gcctcgaatg ggttggtcgt ataacgggtc cgggtgaagg ttggtcagtg   180
gactatgctg catccgtaaa aggcagattt actatctcaa gaatgaattc aataaatttc   240
ttctatctgg agatgaacaa tttaaaaatc gaagacacag gcctttactt ctgtgcccgc   300
acgggaaaac attatgcttt ttggggtgg ttacccgccg ggagaagaat acctggaaga   360
ctggggccag ggcacccttg tcatcgtctc ttca                               394
```

<210> SEQ ID NO 50
<211> LENGTH: 393
<212> TYPE: DNA
<213> ORGANISM: Homo sapiens

<400> SEQUENCE: 50

```
gaggttcgat tggtggagtc tgggggaggc ttggtgaagc ctggaggatc ccttagactc    60
tcatgttcag cctctggttt cgacttcgat aacgcctgga tgacttgggt ccgccagcct   120
ccagggaagg gcctcgaatg ggttggtcgt attacgggtc caggtgaagg ttggtcagtg   180
gactatgctg cacccgtgga aggcagattt accatctcga gactcaattc aataaatttc   240
ttatatttgg agatgaacaa tttaagaatg gaagactcag gcctttactt ctgtgcccgc   300
acgggaaaat attatgattt ttggagtggc tatccgccgg gagaagaata cttccaagac   360
tggggccggg gcaccctagt catcgtctcc tca                                393
```

<210> SEQ ID NO 51
<211> LENGTH: 393
<212> TYPE: DNA
<213> ORGANISM: Homo sapiens

<400> SEQUENCE: 51

```
gaggttcgac tggtggagtc tgggggacga ttggtgaggc ctgggggatc ccttagactc    60
tcatgttcag cctctggctt caatttcgat aacgcctgga tgacttgggt ccgccagtct   120
ccagggaagg gcctcgaatg ggttggtcgt ataacgggtc cgggtgaagg ttggtcagtg   180
gactatgctg catccgtaaa aggcagattt actatctcaa gaatgaattc aataaatttc   240
ttctatctgg agatgaacaa tttaaaaatc gaagacacag gcctttactt ctgtgcccgc   300
acgggaaaac attatgcttt ttggggtggt tacccgccgg gagaagaata cctggaagac   360
tggggccagg gcacccttgt catcgtctct tca                                393
```

<210> SEQ ID NO 52
<211> LENGTH: 393
<212> TYPE: DNA
<213> ORGANISM: Homo sapiens

<400> SEQUENCE: 52

```
gaggttcgac tggtggagtc tgggggacga ttggtgaggc ctgggggatc ccttagactc    60
tcatgttcag cctctggctt caatttcgat aacgcctgga tgacttgggt ccgccagcct   120
ccagggaagg gcctcgaatg ggttggtcgt ataacgggtc cgggtgaagg ttggtcagtg   180
gactatgctg catccgtaaa aggcagattt actatctcaa gaatgaattc aataaatttc   240
ttctatctgg agatgaacaa tttaaaaatc gaagacacag gcctttactt ctgtgcccgc   300
```

```
acgggaaaac attatgcttt ttggggtggt tacccgccgg gagaagaata cctggaagac    360
tggggccagg gcacccttgt catcgtctct tca                                  393

<210> SEQ ID NO 53
<211> LENGTH: 392
<212> TYPE: DNA
<213> ORGANISM: Homo sapiens

<400> SEQUENCE: 53
gaggttcgac tggtggagtc tgggggacga ttggtgaggc ctgggggatc ccttagactc     60
tcatgttcag cctctggctt caatttcgat aacgcctgga tgacttgggt ccgccagtct   120
ccagggaagg gcctcgaatg ggttggtcgt ataacgggtc cggtgaagg ttggtcagtg    180 gactatgctg catccgtaaa aggcagattt actatctcaa gaatgaattc aataaatttc   240
ttctatctgg agatgaacaa tttaaaaatc gaagacacag gcctttactt ctgtgcccgc   300
acgggaaaca ttatgctttt tggggtggtt acccgccggg agaagaatac ctggaagact   360
ggggccaggg cacccttgtc atcgtctctt ca                                   392

<210> SEQ ID NO 54
<211> LENGTH: 394
<212> TYPE: DNA
<213> ORGANISM: Homo sapiens

<400> SEQUENCE: 54
gaggttcgac tggtggagtc tgggggacga ttggtgaggc ctgggggatc ccttagactc     60
tcatgttcag cctctggctt caatttcgat aacgcctgga tgacttgggt ccgccagcct   120
ccagggaagg gcctcgaatg ggttggtcgt ataacgggtc cggtgaagg ttggtcagtg    180 gactatgctg catccgtaaa aggcagattt actatctcaa gaatgaattc aataaatttc   240
ttctatctgg agatgaacaa tttaaaaatc gaagacacag gcctttactt ctgtgcccgc   300
acgggaaaac attaatgctt tttggggtgg ttacccgccg ggagaagaat acctggaaga   360
ctggggccag ggcacccttg tcatcgtctc ttca                                394

<210> SEQ ID NO 55
<211> LENGTH: 392
<212> TYPE: DNA
<213> ORGANISM: Homo sapiens

<400> SEQUENCE: 55
gaggttcgat tggtggagtc tgggggaggc ttggtgaagc ctggaggatc ccttagactc     60
tcatgttcag cctctggttt cgacttcgat aacgcctgga tgacttgggt ccgccagcct   120
ccagggaagg gcctcgaatg ggttggtcgt attacgggtc caggtgaagg ttggtcagtg   180
gactatgctg cacccgtgga aggcagattt accatctcga gactcaattc aataaatttc   240
ttatatttgg agatgaacaa tttaagaatg gaagactcag gcctttactt ctgtgcccgc   300
acgggaaata ttatgatttt tggagtggct atccgccggg agaagaatac ttccaagact   360
ggggccgggg caccctagtc atcgtctcct ca                                   392

<210> SEQ ID NO 56
<211> LENGTH: 392
<212> TYPE: DNA
<213> ORGANISM: Homo sapiens

<400> SEQUENCE: 56
gaggttcgac tggtggagtc tgggggacga ttggtgaggc ctgggggatc ccttagactc     60
```

```
tcatgttcag cctctggctt caatttcgat aacgcctgga tgacttgggt ccgccagcct    120
ccagggaagg gcctcgaatg ggttggtcgt ataacgggtc cgggtgaagg ttggtcagtg    180
gactatgctg catccgtaaa aggcagattt actatctcaa gaatgaattc aataaatttc    240
ttctatctgg agatgaacaa tttaaaaatc gaagacacag gcctttactt ctgtgcccgc    300
acgggaaaac attatgcttt tggggtggt  tacccgccgg agaagatac  ctggaagact    360 ggggccaggg cacccttgtc atcgtctctt ca                                   392
```

<210> SEQ ID NO 57
<211> LENGTH: 392
<212> TYPE: DNA
<213> ORGANISM: Homo sapiens

<400> SEQUENCE: 57

```
gaggttcgat tggcggagtc tgggggaggc ttggtgaagc ctggaggatc ccttagactc     60
tcatgttcag cctctggttt cgacttcgat aacgcctgga tgacttgggt ccgccagcct    120
ccagggaagg gcctcgaatg gtcggtcgt attacgggtc caggtgaagg ttggtcagtg     180
gactatgctg cacccgtgga aggcagattt accatctcga gactcaattc aataaatttt    240
ctatatttgg agatgaacaa tttaagaatg gaagactcag gcctttactt ctgtgcccgc    300
acgggaaaat attatgattt tggagtggc  tatccgcggg agaagaatac ttccaagact    360
ggggccgggg caccctagtc atcgtctcct ca                                   392
```

<210> SEQ ID NO 58
<211> LENGTH: 389
<212> TYPE: DNA
<213> ORGANISM: Homo sapiens

<400> SEQUENCE: 58

```
gaggttcgat tggcggagtc tgggggaggc ttggtgaagc ctggaggatc ccttagactc     60
tcatgttcag cctctggttt cgacttcgat aacgcctgga tgacttgggt ccgccagcct    120
ccagggaagg gcctcgaatg gtcggtcgt attacgggtc caggtgaagg ttggtcagtg     180
gactatgctg cacccgtgga aggcagattt accatctcga gactcaattc aataaatttc    240
ttatatttgg agatgaacaa tttaagaatg gaagactcag gcctttactt ctgtgcccgc    300
acgggaaaat attatgattt tggagtggct atccgcggag aagaatactc caagactggg    360
gccagggcac cctagtcatc gtctcctca                                        389
```

<210> SEQ ID NO 59
<211> LENGTH: 397
<212> TYPE: DNA
<213> ORGANISM: Homo sapiens

<400> SEQUENCE: 59

```
gaggttcgac tggtggagtc tgggggacga ttggtgaggc ctgggggatc ccttagactc     60
tcatgttcag cctctggctt caatttcgat aacgcctgga tgacttgggt ccgccagtct    120
ccagggaagg gcctcgaatg ggttggtcgt ataacgggtc cgggtgaagg ttggtcagtg    180
gactatgctg catccgtaaa aggcagattt actatctcaa gaatgaattc aataaatttc    240
ttctatctgg agatgaacaa tttaaaaatc gaagacacag gcctttaact tctgtgcccg    300
cacgggaaaa cattaatgct tttttggggt ggttacccccg ccgggagaag aatacctgga    360
agactggggc cagggcaccc ttgtcatcgt ctcttca                             397
```

<210> SEQ ID NO 60
<211> LENGTH: 397
<212> TYPE: DNA
<213> ORGANISM: Homo sapiens
<220> FEATURE:
<221> NAME/KEY: misc_feature
<222> LOCATION: (361)..(361)
<223> OTHER INFORMATION: n is a, c, g, or t

<400> SEQUENCE: 60
gaggttcgac tggtggagtc tgggggacga ttggtgaggc ctgggggatc ccttagactc      60
tcatgttcag cctctggctt caatttcgat aacgcctgga tgacttgggt ccgccagcct     120
ccagggaagg gcctcgaatg ggttggtcgt ataacgggtc cgggtgaagg ttggtcagtg     180
gactatgctg catccgtaaa aggcagattt actatctcaa gaatgaattc aataaatttc     240
ttctatctgg agatgaacaa tttaaaaatc gaagacacag gtcctttact tctgtgcccg     300
cacgggaaac attatgtcgt ttttggggtg gttacccgcc gggagaagaa tacctaggaa     360
nacgtggggc cagggcacct tggtcatcgt ctcttca                              397

<210> SEQ ID NO 61
<211> LENGTH: 397
<212> TYPE: DNA
<213> ORGANISM: Homo sapiens

<400> SEQUENCE: 61
gaggttcgac tggtggagtc tgggggacga ttggtgaggc ctgggggatc ccttagactc      60
tcatgttcag cctctggctt caatttcgat aacgcctgga tgacttgggt ccgccagcct     120
ccagggaagg gcctcgaatg ggttggtcgt ataacgggtc cgggtgaagg ttggtcagtg     180
gactatgctg catccgtaaa aggcagattt actatctcaa gaatgaattc aataaatttc     240
ttctatctgg agatgaacaa tttaaaaatc gaagacacag gcctttactt ctgtgcccgc     300
aacgggaaaa cattatgtcg tttttggggt ggttacccgc cgggagaaga atacctggaa     360
gacgtggggc cagggcaccc ttgtcatcgt ctcttca                              397

<210> SEQ ID NO 62
<211> LENGTH: 389
<212> TYPE: DNA
<213> ORGANISM: Homo sapiens

<400> SEQUENCE: 62
gagattcgat tggtggagtc tgggggaggc ctggtgaagc ctgggggatc ccttagattg      60
tcatgctcag cctctggctt caacttcgac agtgcctgga tgacttgggt ccgccagcct     120
ccagggaagg gcctcgaatg ggtcggtcgg attacgggtc caggtgaagg ttggtcagta     180
gactatgctg aatccgtaaa aggcagattt atcatctcga gaatcaattc aataaatttc     240
ttatatctgg agatgaacaa tcttagaccc gaagacacag ggtcttatttt ctgtgcccac     300 acgggaaaac attatgattt ttggcgtggt tatccgcggt gaagaatact tcaagactgg     360
gccagggcac ccaagtcatc gtctctcag                                       389

<210> SEQ ID NO 63
<211> LENGTH: 400
<212> TYPE: DNA
<213> ORGANISM: Homo sapiens

<400> SEQUENCE: 63
gaggttcgac tggtggagtc tgggggacga ttggtgaggc ctgggggatc ccttagactc      60

```
tcatgttcag cctctggctt caatttcgat aacgcctgga tgacttgggt ccgccagcct    120
ccagggaagg gcctcgaatg ggttggtcgt ataacgggtc cgggtgaagg ttggtcagtg    180
gactatgctg catccgtaaa aggcagattt actatctcaa gaatgaattc aataaatttc    240
ttctatctgg agatgaacaa tttaaaaatc gaagacacag gcctttactt ctgtgcccgc    300
acgggaaaac attatgtctt ttttggggtg gtttacccgg ccgggtagaa gaataccgta    360
ggaagactgg ggccagggca cccttgtcat cgtctcttca                          400

<210> SEQ ID NO 64
<211> LENGTH: 394
<212> TYPE: DNA
<213> ORGANISM: Homo sapiens

<400> SEQUENCE: 64
gaggttcgat tggtggagtc tgggggaggc ttggtgaagc ctggaggatc cctgagactc     60
tcatgttcag cctctggttt cgacttcgat aacgcctgga tgacttgggt ccgccagcct    120
ccagggaggg gcctcgaatg ggttggtcgt attacgggtc caggtgaagg ttggtcagtg    180
gactatgctg cacccgtgga aggcagattt accatctcga gactcaattc aataaatttc    240
ttatatttgg agatgaacaa tttaagaatg gaagactcag gccttttact tctgtgcccg    300
cacgggaaaa tattatgatt tttggagtgg ctctccgccg ggagaagaat acttccaaga    360
ctggggccag ggcacccctag tcatcgtctc ctca                               394

<210> SEQ ID NO 65
<211> LENGTH: 389
<212> TYPE: DNA
<213> ORGANISM: Homo sapiens

<400> SEQUENCE: 65
gaggttcgat tggtggagtc tgggggaggc ttggtgaagc ctggaggatc ccttagagtc     60
tcatgttcag cctctggttt cgacttcgat aacgcatgga tgacttgggt ccgccagcct    120
ccagggaagg gcctcgaatg ggttggtcgt attacgggtc caggtgaagg ttggtcagtg    180
gactatgctg cacccgtgga aggcagattt accatctcga gactcaattc aataaatttc    240
ttatatttgg agatgaacaa tttaagaatg gaagactcag gcctttactt ctgtgccgca    300
cgggaaaata ttatgatttt ggagtgctat cgccggagaa gaatactcca agacgtgggg    360
ccggggcacc ctagtcatcg tcccctca                                       389

<210> SEQ ID NO 66
<211> LENGTH: 394
<212> TYPE: DNA
<213> ORGANISM: Homo sapiens

<400> SEQUENCE: 66
gaggttcgac tggtggagtc tggggacga ttggtgaggc ctgggggtc ccttagactc       60 tcatgttcag cctctggctt caatttcgat aacgcctgga tgacttgggt ccgccagcct    120
ccagggaagg gcctcgaatg ggttggtcgt ataacgggtc cgggtgaagg ttggtcagtg    180
gactatgctg catccgtaaa aggcagattt actatctcaa gaatgaattc aataaatttc    240
ttctatctgg agatgaacaa tttaaaaatc gaagacacag gcctttactt ctgtgcccgc    300
acgggaaaac attatgtctt tttggggtgg ttacccgccg ggagaagaat acctggaaga    360
ctggggccag ggcacccttg tcatcgtctc ttca                                394
```

<210> SEQ ID NO 67
<211> LENGTH: 394
<212> TYPE: DNA
<213> ORGANISM: Homo sapiens
<220> FEATURE:
<221> NAME/KEY: misc_feature
<222> LOCATION: (311)..(311)
<223> OTHER INFORMATION: n is a, c, g, or t

<400> SEQUENCE: 67

```
gaggttcgac tggtggagtc tgggggacga ttggtgaggc ctgggggtc ccttagactc      60
tcatgttcag cctctggctt caatttcgat aacgcctgga tgacttgggt ccgccagtct   120
ccagggaagg gcctcgaatg ggttggtcgt ataacgggtc cgggtgaagg ttggtcagtg   180
gactatgctg catccgtaaa aggcagattt actatctcaa gaatgaattc aataaatttc   240
ttctatctgg agatgaacaa tttaaaaatc gaagacacag gccttttact ctgtgcccgc   300
acgggaaaac nttatgcttt ttggggtgg ttacccgccg ggagaagaat acctggaaga   360
ctggggccag ggcacccttg tcatcgtctc ttca                                394
```

<210> SEQ ID NO 68
<211> LENGTH: 392
<212> TYPE: DNA
<213> ORGANISM: Homo sapiens

<400> SEQUENCE: 68

```
gaggttcgac tggtggagtc tgggggacga ttggtgaggc ctgggggatc ccttagactc      60
tcatgttcag cctctggctt caatttcgat aacgcctgga tgacttgggt ccgccagcct   120
ccagggaagg gcctcgaatg ggttggtcgt atgacgggtc cgggtgaagg ttggtcagtg   180
gactatgctg catccgtaaa aggcagattt actatctcaa gaatgaattc aataaatttc   240
ttctatctgg agatgaacaa tttaaaaatc gaagacacag gcctttaact ctgtgcccgc   300
acgggaaaac attatgcttt ttggggtggt tacccgcgga agaagaatac ctggaagact   360
ggggccaggg caccttgcc atcgtctctt ca                                  392
```

<210> SEQ ID NO 69
<211> LENGTH: 394
<212> TYPE: DNA
<213> ORGANISM: Homo sapiens
<220> FEATURE:
<221> NAME/KEY: misc_feature
<222> LOCATION: (393)..(393)
<223> OTHER INFORMATION: n is a, c, g, or t

<400> SEQUENCE: 69

```
gaagtgcagc tggtggagtc tgggggaggc ttggtgaagc ctggaggatc ccttagactc      60
tcatgttcag cctctggttt cgacttcgat aacgcctgga tgacttgggt ccgccagcct   120
ccagggaagg gcctcgaatg ggttggtcgt attacgggtc caggtgaagg ttggtcagtg   180
gactatgctg cacccgtgga aggcagattt accatctcga gactcaattc aataaatttc   240
ttatatttgc agatgaacaa tttaagaatg gaagactcag gcctttactt ctgtgcccCg   300
cacgggaaaa tattatgatt tttggagtgg ctatccgccg ggagaagaat acttccaaga   360
cgtgggccgg ggcaccctag tcatcgtctc ctna                               394
```

<210> SEQ ID NO 70
<211> LENGTH: 393
<212> TYPE: DNA
<213> ORGANISM: Homo sapiens

<400> SEQUENCE: 70

```
gaggttcgac tggtggagtc tgggggacga ttggtgaggc tgggggatc ccttagactc    60
tcatgttcag cctctggctt caatttcgat aacgcctgga tgacttgggt ccgccagcct   120
ccagggaagg gcctcgaatg ggttggtcgt ataacgggtc cgggtgaagg ttggtcagtg   180
gactatgctg catccgtaaa aggcagattt actatctcaa gaatgaattc aataaatttc   240
ttctatctgg agatgaacaa tttaaaaatc gaagacacag gcctttactt ctgtgcccgc   300
acgggaaaac attatgcttt tggggtggt  tacccgccgg agaagaata  cctggaagac   360
tggggccagg gcacccttgt catcgtctct tca                                393
```

<210> SEQ ID NO 71
<211> LENGTH: 394
<212> TYPE: DNA
<213> ORGANISM: Homo sapiens

<400> SEQUENCE: 71

```
gaggttcgat tggtggagtc tgggggaggc ttggtgaagc ctggaggatc ccttagactc    60
tcatgttcag cctctggttt cgacttcgat aacgcctgga tgacttgggt ccgccagcct   120
ccagggaagg gcctcgaatg ggttggtcgt attacgggtc caggtgaagg ttggtcagtg   180
gactatgctg cacccgtgga aggcagattt accatctcga gactcaattc aataaatttc   240
ttatatttgg agatgaacaa tttaagaatg gaagactcag gcctttactt ctgtgcccgc   300
acgggaaaat attatgattt tttggagtgg ctatccgccg ggagaagaat acttccaaga   360
ctggggccgg ggcaccctag tcatcgtctc ctca                               394
```

<210> SEQ ID NO 72
<211> LENGTH: 394
<212> TYPE: DNA
<213> ORGANISM: Homo sapiens

<400> SEQUENCE: 72

```
gaggttcgac tggtggagtc tgggggacga ttggtgaggc tgggggatc ccttagactc    60
tcatgttcag cctctggctt caatttcgat aacgcctgga tgacttgggt ccgccagcct   120
ccagggaagg gcctcgaatg ggttggtcgt ataacgggtc cgggtgaagg ttggtcagtg   180
gactatgctg catccgtaaa aggcagattt actatctcaa gaatgaattc aataaatttc   240
ttctatctgg agatgaacaa tttaaaaatc gaagacacaa ggcctttact tctgtgcccg   300
cacgggaaaa cattaatgct ttttggggtg gttacccgcc gggagaagaa tacctggaag   360
actggggccag ggcacccttg tcatcgtctc ttca                              394
```

<210> SEQ ID NO 73
<211> LENGTH: 395
<212> TYPE: DNA
<213> ORGANISM: Homo sapiens

<400> SEQUENCE: 73

```
gaggttcgat tggcggagtc tggggggggc ttggtgaagc ctggaggatc ccttagactc    60
tcatgttcag cctctggttt cgacttcgat aacgcctgga tgacgtgggt ccgccagcct   120
ccagggaagg gcctcgaatg ggtcggtcgt attacgggtc caggtgaagg ttggtcagtg   180
gactatgctg cacccgtgga aggaagattt accatctcaa gactcaattc aattaaattt   240
ctttatttgg agatgaacaa tttaagaatg gaagactcag gcctgtactt ctgtgcccgc   300
```

```
acgggaaaac attaatgtat ttttggagtg gctatccgcc gggagaagaa tacttacaag    360
acgtggggcc gggcacccta gtcatcgtct cctca                              395
```

<210> SEQ ID NO 74
<211> LENGTH: 394
<212> TYPE: DNA
<213> ORGANISM: Homo sapiens

<400> SEQUENCE: 74

```
gaggttcgac tggtggagtc tgggggacga ttggtgaggc tgggggatc ccttagactc     60 tcatgttcag cctctggctt caatttcgat aacgcctgga tgacttgggt ccgccagcct   120
ccagggaagg gcctcgaatg ggttggtcgt ataacgggtc cggtgaagg ttggtcagtg    180 gactatgctg catccgtaaa aggcagattt actatctcaa gaatgaattc aataaattc    240 ttctatctgg agatgaacaa tttaaaaatc gaagacacag gccttttact tctgtgcccg   300
cacgggaaaa cattatgctt tttgggtgg ttacccgccg ggagaagaat acctggaaga    360
ctggggccag ggcacccttg tcatcgtctc ttca                               394
```

<210> SEQ ID NO 75
<211> LENGTH: 393
<212> TYPE: DNA
<213> ORGANISM: Homo sapiens

<400> SEQUENCE: 75

```
gaggttcgat tggcggagtc tgggggaggc ttggtgaagc ctggaggatc ccttagactc     60
tcatgttcag cctctggttt cgacttcgat aacgcctgga tgacttgggt ccgccagcct   120
ccagggaagg gcctcgaatg gtcggtcgt attacgggtc caggtgaagg ttggtcagtg    180
gactatgctg cacccgtgga aggcagattt accatctcga gactcaattc aataaattc    240 ttatatttgg agatgaacaa tttaagaatg gaagactcag gcctttactt ctgtgcccgc   300 acggaaaat attatgattt ttggagtggc tatccgccgg gagaagaata cttccaagac    360
tggggccggg gcaccctagt catcgtctcc tgt                                393
```

<210> SEQ ID NO 76
<211> LENGTH: 407
<212> TYPE: DNA
<213> ORGANISM: Homo sapiens

<400> SEQUENCE: 76

```
gaggttcgac tggtggagtc tgggggagga ttggtgaagc ctgggggatc ccttagactc     60
tcatgctcag cctctggctt caatttcgat aacgcctgga tgacttgggt ccgccagcct   120
ccagggaagg gcctcgaatg ggttggtcgt attacgggtc cggtgaagg ttggtcagtg    180 gactatgctg catccgtaaa aggcagattt actatctcaa ggatgaattc aataaattc    240 ttctatctgg agatgaacaa tttaagagtc gaagacacag gtcctttact tctgtcgccc   300
gcaacgggaa aacattagtg tcgttttttg ggggtagtta ctccggccgg gagaagaata   360
cctcgaagac gtcggggcca gggccacccg ttgtcatcgt ctcctgt                 407
```

<210> SEQ ID NO 77
<211> LENGTH: 397
<212> TYPE: DNA
<213> ORGANISM: Homo sapiens
<220> FEATURE:
<221> NAME/KEY: misc_feature
<222> LOCATION: (390)..(390)
<223> OTHER INFORMATION: n is a, c, g, or t
<220> FEATURE:
<221> NAME/KEY: misc_feature
<222> LOCATION: (393)..(393)
<223> OTHER INFORMATION: n is a, c, g, or t

<400> SEQUENCE: 77

```
gaggttcgat tggtggagtc tgggggaggc ttggtgaagc ctggaggatc ccttagactc      60
tcatgttcag cctctggttt cgacttcgat aacgcctgga tgacttgggt ccgccagcct     120
ccagggaagg gcctcgaatg ggttggtcgt attacgggtc caggtgaagg ttggtcagtg     180
gactatgctg cacccgtgga aggcagattt accatctcga gactcaattc aataaaattt     240
cttaatattt ggagatgaac aatttaaaga atggaagact caaggccttt acttctgtgc     300
ccgcacggga aaatattatg aattttttgga gtggctatcc gccggagaag aatacttcca    360
agactgggcc cagggcaccc tagtcatcgn tncagc                                397
```

<210> SEQ ID NO 78
<211> LENGTH: 399
<212> TYPE: DNA
<213> ORGANISM: Homo sapiens

<400> SEQUENCE: 78

```
gaggttcgac tggtggagtc tgggggacga ttggtgaggc ctgggggatc ccttagactc      60
tcatgttcag cctctggctt caatttcgat aacgcctgga tgacttgggt ccgccagtct     120
ccagggaagg gcctcgaatg ggttggtcgt ataacgggtc cggtgaagg ttggtcagtg      180
gactatgctg catccgtaaa aggcagattt actatctcaa gaatgaattc aataaatttc     240
ttctatctgg agatgaacaa tttaaaaatc gaagacacag gcctttactt ctgtgcccgc     300
acgggaaaac attaatgtct ttttgggggt ggttacccgc cgggagaaga ataccgtgga     360
agacgtgggc cagggccacc cgttgtcatc gtctcttca                            399
```

<210> SEQ ID NO 79
<211> LENGTH: 395
<212> TYPE: DNA
<213> ORGANISM: Homo sapiens

<400> SEQUENCE: 79

```
gaggttcgat tggcggagtc tgggggaggc ttggtgaagc ctggaggatc ccttagactc      60
tcatgttcag cctctggttt cgacttcgat aacgcctgga tgacttgggt ccgccagcct     120
ccagggaagg gcctcgaatg ggtcggtcgt attacgggtc caggtgaagg ttggtcagtg     180
gactatgctg cacccgtgga aggcagattt accatctcga gactcaattc aataatttct     240
ctatatttgg agatgaacaa tttaagaatg gaagactcag gcctttactt ctgtgcccgc     300
acggaaaaat attatgattt ttggagtggc tatccgccgg agaagaatac ttccaagact     360
aggggggcccg gggcacccta gtcaccgtct cctca                                395
```

<210> SEQ ID NO 80
<211> LENGTH: 394
<212> TYPE: DNA
<213> ORGANISM: Homo sapiens

<400> SEQUENCE: 80

```
gaggttcgat tggtggagtc tgggggaggc ttggtgaagc ctggaggatc ccttagactc      60
tcatgttcag cctctggttt cgacttcgat aacgcctgga tgacttgggt ccgccagcct     120
ccagggaagg gcctcgaatg ggttggtcgt attacgggtc caggtgaagg ttggtcagtg     180
```

```
gactatgctg cacccgtgga aggcagattt accatctcga gactcaattc aataaatttc    240
ttatatttgg agatgaacaa ttttaagaat aggaagactc aggcctttac ttctgtgccc    300
gcacgggaaa tattatgatt tttggagtgg ctagtccgcc ggagaagagt acttccaaga    360
ctgggggccg ggcaccctag tcatcgtctc ctca                                394
```

<210> SEQ ID NO 81
<211> LENGTH: 393
<212> TYPE: DNA
<213> ORGANISM: Homo sapiens

<400> SEQUENCE: 81

```
gaggttcgat tggtggagtc tggggaggc ttggtgaagc ctggaggatc ccttagactc     60
tcatgttcag cctctggttt cgacttcgat aacgcctgga tgacttgggt ccgccagcct    120
ccagggaagg gcctcgaatg ggttggtcgt attacgggtc caggtgaagg ttggtcagtg    180
gactatgctg cacccgtgga aggcagattt accatctcga gactcaattc aataaatttc    240
ttatatttgg agatgaacaa tttaagaatg gaagactcag gcctttactt ctgtgcccgc    300
acgggaaata ttatgtattt tggagtggc tatccgccgg gagaagaata cttacaagac    360
gtggggccgg gcaccctagt catcgtctcc tca                                 393
```

<210> SEQ ID NO 82
<211> LENGTH: 388
<212> TYPE: DNA
<213> ORGANISM: Homo sapiens

<400> SEQUENCE: 82

```
gaggttcgac tggtggagtc tgggggacga ttggtgaggc ctgggggatc ccttagactc     60
tcatgttcag cctctggctt caatttcgat aacgcctgga tgacttgggt ccgccagcct    120
ccagggaagg gcctcgaatg ggttggtcgt ataacgggtc cggtgaagg ttggtcagtg     180 gactatgctg catccgtaaa aggcagattt actatctcaa gaatgaattc aataaatttc    240
ttctatctgg agatgaacaa tttaaaaatc gaagacacag gcctttactt ctgtgcccgc    300
acgggaaaac attatgcttt tgggtgtta cccgcggaga agaatacctg aagactgggg    360
ccagggcacc cttgtcatcg tctcttca                                       388
```

<210> SEQ ID NO 83
<211> LENGTH: 393
<212> TYPE: DNA
<213> ORGANISM: Homo sapiens
<220> FEATURE:
<221> NAME/KEY: misc_feature
<222> LOCATION: (343)..(343)
<223> OTHER INFORMATION: n is a, c, g, or t

<400> SEQUENCE: 83

```
gagattcgat tggtggagtc tggggaggc ctggtgaagc ctgggggatc ccttagattg      60
tcatgctcag cctctggctt caacttcgac agtgcctgga tgacttgggt ccgccagcct    120
ccagggaagg gcctcgaatg ggtcggtcgg attacgggtc caggtgaagg ttggtcagta    180
ggctatgctg aatccgtaaa aggcagattt atcatctcga gaatcaattc aataaatttc    240
ttatatctgg agatgaacaa tcttagaccc gaagacacag ggtcttatt ctgtgcccac     300 acgggaaaac attatgattt ttggcgtggt tatccgccgg gtnaagaata cttccaagac    360
tggggccagg gcacccaagt catcgtctcc tca                                 393
```

<210> SEQ ID NO 84
<211> LENGTH: 393
<212> TYPE: DNA
<213> ORGANISM: Homo sapiens

<400> SEQUENCE: 84
gaggttcgat tggtggagtc tgggggaggc ttggtgaagc ctggaggatc ccttagactc      60
tcatgttcag cctctggttt cgacttcgat aacgcctgga tgacttgggt ccgccagcct     120
ccagggaagg gcctcgaatg ggttggtcgt attacgggtc aggtgaagg ttggtcagtg      180 gactatgctg cacccgtgga aggcagattt accatctcga gactcaattc aataaatttc     240
ttatatttgg agatgaacaa tttaagaatg gaagactcag gcctttactt ctgtgcccgc     300
acgggaaaat attatgattt tggagtggc tatccgccgg gagaagaata cttccaagac      360
tggggccggg gcaccctagt catcgtctcc tca                                  393

<210> SEQ ID NO 85
<211> LENGTH: 393
<212> TYPE: DNA
<213> ORGANISM: Homo sapiens

<400> SEQUENCE: 85
gaggttcgat tggcggagtc tgggggaggc ttggtgaagc ttggaggatc ccttagactc      60
tcatgttcag cctctggttt cgacttcgat aacgcctgga tgacttgggt ccgccagcct     120
ccagggaagg gcctcgaatg ggtcggtcgt attacgggtc aggtgaagg ttggtcagtg      180 gactatgctg cacccgtgga aggcagattt accatctcga gactcaattc aataaatttc     240
ttatatttgg agatgaacaa tttaagaatg gaagactcag gcctttactt ctgtgcccgc     300
acgggaaaat attatgattt tggagtggc tatccgccgg gagaagaata cttccaagac      360
tggggccagg gcaccctagt catcgtctcc tca                                  393

<210> SEQ ID NO 86
<211> LENGTH: 389
<212> TYPE: DNA
<213> ORGANISM: Homo sapiens

<400> SEQUENCE: 86
gaggttcgac tggtggagtc tgggggacga ttggtgaggc ctgggggatc ccttagactc      60
tcatgttcag cctctggctt caatttcgat aacgcctgga tgacttgggt ccgccagcct     120
ccagggaagg gcctcgaatg ggttggtcgt ataacgggtc cgggtgaagg ttggtcagtg     180
gactatgctg catccgtaaa aggcagattt actatctcaa gaatgaattc aataaatttc     240
ttctatctgg agatgaacaa tttaaaaatc gaagacacag gcctttactt ctgtgcccgc     300
acgggaaaac attatgcttt tggggtgtt acccgcggag aagaatacct gaagactggg      360
gccagggcac ccttgtcatc gtctcttca                                       389

<210> SEQ ID NO 87
<211> LENGTH: 393
<212> TYPE: DNA
<213> ORGANISM: Homo sapiens

<400> SEQUENCE: 87
gaggttcgat tggtggagtc tgggggaggc ttggtgaagc ctggaggatc ccttagactc      60
tcatgttcag cctctggttt cgacttcgat aacgcctgga tgacttgggt ccgccagcct     120
ccagggaagg gcctcgaatg ggttggtcgt attacgggtc aggtgaagg ttggtcagtg      180

```
gactatgctg cacccgtgga aggcagattt accatctcga gactcaattc aataaatttc    240
ttatattcgg agatgaacaa tttaagaatg gaagactcag gcctttactt ctgtgcccgc    300
acgggaaaat attatgattt tggagtggc tatccgccgg gagaagaata cttccaagac     360
tggggccggg gcaccctagt catcgtctcc tca                                 393

<210> SEQ ID NO 88
<211> LENGTH: 391
<212> TYPE: DNA
<213> ORGANISM: Homo sapiens

<400> SEQUENCE: 88
gagattcgat tggtggagtc tgggggaggc ctggtgaagc ctgggggatc ccttagattg    60
tcatgctcag cctctggctt caacttcgac agtgcctgga tgacttgggt ccgccagcct   120
ccagggaagg gcctcgaatg ggtcggtcgg attacgggtc caggtgaagg ttggtcagta   180
gactatgctg aatccgtaaa aggcagattt atcatctcga gaatcaattc aataaatttc   240
ttatatctgg agatgaacaa tcttagaccc gaagacacag ggtcttattt ctgtgcccac   300
acgggaaaac attatgattt tggcgtggt tatcgccggt gaagaatact tccaagactg    360
gggccagggc accaaggtca tcgtctcctc a                                  391

<210> SEQ ID NO 89
<211> LENGTH: 394
<212> TYPE: DNA
<213> ORGANISM: Homo sapiens

<400> SEQUENCE: 89
gaggttcgac tggtggagtc tgggggacga ttggtgaggc ctgggggatc ccttagactc    60
tcatgttcag cctctggctt caatttcgat aacgcctgga tgacttgggt ccgccagcct   120
ccagggaagg gcctcgaatg ggttggtcgt ataacgggtc cgggtgaagg ttggtcagtg   180
gactatgctg catccgtaaa aggcagattt actatctcaa gaatgaattc aataaatttc   240
ttctatctgg agatgaacaa tttaaaaatc gaagacacag gcctttactt ctgtgcccgc   300
acgggaaaac attatgtctt tttggggtgg ttacccgccg ggagaagaat acctggaaga   360
ctggggccag ggcacccttg tcatcgtctc ttca                               394

<210> SEQ ID NO 90
<211> LENGTH: 393
<212> TYPE: DNA
<213> ORGANISM: Homo sapiens

<400> SEQUENCE: 90
gaggttcgat tggcggagtc tgggggaggc ttggtgaagc ctggaggatc ccttagactc    60
tcatgttcag cctctggttt cgacttcgat aacgcctgga tgacttgggt ccgccagcct   120
ccagggaagg gcctcgaatg ggtcggtcgt attacgggtc caggtgaagg ttggtcagtg   180
gactatgctg cacccgtgga aggcagattt accatctcga gactcaattc aataaatttc   240
ttatatttgg agatgaacaa tttaagaatg gaagactcag gcctttactt ctgtgcccgc   300
acgggaaaat attatgattt tggagtggc tatccgccgg gagaagaata cttccaagac     360
tggggccggg gcaccctagt caccgtctcc tca                                 393

<210> SEQ ID NO 91
<211> LENGTH: 394
<212> TYPE: DNA
<213> ORGANISM: Homo sapiens
```

<400> SEQUENCE: 91

```
gaggttcgac tggtggagtc tggggacga ttggtgaggc tggggatc ccttagactc      60
tcatgttcag cctctggctt caatttcgat aacgcctgga tgacttgggt ccgccagcct   120
ccagggaagg gcctcgaatg ggttggtcgt ataacgggtc cgggtgaagg ttggtcagtg   180
gactatgctg catccgtaaa aggcagattt actatctcaa gaatgaattc aataaatttc   240
ttctatctgg agatgaacaa tttaaaaatc gaagacacag gcctttactt ctgtgcccgc   300
acgggaaaac attatgcttt ttggggtgg ttacccgccg ggagaagaat acctggaaga   360
ctggggccag ggcacccttg tcatcgtctc ttca                               394
```

<210> SEQ ID NO 92
<211> LENGTH: 393
<212> TYPE: DNA
<213> ORGANISM: Homo sapiens

<400> SEQUENCE: 92

```
gaggttcgat tggtggagtc tggggaggc ttggtgaagc ctggaggatc ccttagactc   60
tcatgttcag cctctggttt cgacttcgat aacgcctgga tgacttgggt ccgccagcct  120
ccagggaagg gcctcgaatg ggttggtcgt attacgggtc caggtgaagg ttggtcagtg  180
gactatgctg cacccgtgga aggcagattt accatctcga gactcaattc aataaatttc  240
ttatatttgg agatgaacaa tttaagaatg gaagactcag gcctttactt ctgtgcccgc  300
acgggaaaat attatgattt ttggagtggc tatccgccgg gagaagaata cttccaagac  360
tggggccagg gcaccctagt catcgtctcc tca                               393
```

<210> SEQ ID NO 93
<211> LENGTH: 393
<212> TYPE: DNA
<213> ORGANISM: Homo sapiens

<400> SEQUENCE: 93

```
gaggttcgat tggtggagtc tggggaggc ttggtgaagc ctggaggatc ccttagactc   60
tcatgttcag cctctggttt cgacttcgat aacgcctgga tgacttgggt ccgccagcct  120
ccagggaagg gcctcgaatg ggttggtcgt attacgggtc caggtgaagg ttggtcagtg  180
gactatgctg cacccgtgga aggcagattt accatctcga gactcaattc aataaatttc  240
ttatatttgg agatgaacaa tttaagaatg gaagactcag gcctttactt ctgtgcccgc  300
acgggaaaat attatgattt ttggagtggc tatccgccgg gagaagaata cttccaagac  360
tggggccggg gcaccctagt catcgtctcc tca                               393
```

<210> SEQ ID NO 94
<211> LENGTH: 393
<212> TYPE: DNA
<213> ORGANISM: Homo sapiens

<400> SEQUENCE: 94

```
gaggttcgat tggtggagtc tggggaggc ttggtgaagc ctggaggatc ccttagactc   60
tcatgttcag cctctggttt cgacttcgat aacgcctgga tgacttgggt ccgccagcct  120
ccagggaagg gcctcgaatg ggttggtcgt attacgggtc caggtgaagg ttggtcagtg  180
gactatgctg cacccgtgga aggcagattt accatctcga gactcaattc aataaatttc  240
ttatatttgg agatgaacaa tttaagaatg gaagactcag gcctttactt ctgtgcccgc  300
```

```
acgggaaaat attatgattt ttggagtggc tatccgccgg gagaagaata cttccaagac    360
tggggccggg gcaccctagt catcgtctcc tca                                 393

<210> SEQ ID NO 95
<211> LENGTH: 387
<212> TYPE: DNA
<213> ORGANISM: Homo sapiens

<400> SEQUENCE: 95
gaggttcgat tggcggagtc tggggaggc ttggtgaagc ctggaggatc ccttagactc     60
tcatgttcag cctctggttt cgacttcgat aacgcctgga tgacttgggt ccgccagcct   120
ccagggaagg gcctcgaatg ggtcggtcgt attacgggtc caggtgaagg ttggtcagtg   180
gactatgctg cacccgtgga aggcagattt accatctcga gactcaattc aataaatttc   240
ttatatttgg agatgaacaa tttaagaatg gaagactcag gcctttactt ctgtgcccgc   300
acgggaaaat attatgattt ttggagtggc tatcgccgga gaagatactt caagactggg   360
ccgggaaccc tagtcatcgt ctcctca                                       387

<210> SEQ ID NO 96
<211> LENGTH: 392
<212> TYPE: DNA
<213> ORGANISM: Homo sapiens

<400> SEQUENCE: 96
gaggttcgat tggtggagtc tggggaggc ttggtgaagc ctggaggatc ccttagactc     60
tcatgttcag cctctggttt cgacttcgat aacgcctgga tgacttgggt ccgccagcct   120
ccagggaagg gcctcgaatg ggttggtcgt attacgggtc caggtgaagg ttggtcagtg   180
gactatgctg cacccgtgga aggcagattt accatctcga gactcaattc aataaatttc   240
ttatatttgg agatgaacaa tttaagaatg gaagactcag gcctttactt ctgtgcccgc   300
acgggaaaat attatgattt ttggagtggc tatccgcggg agaagaatac ttccaagact   360
ggggccgggg caccctagtc atcgtctcct ca                                 392

<210> SEQ ID NO 97
<211> LENGTH: 393
<212> TYPE: DNA
<213> ORGANISM: Homo sapiens

<400> SEQUENCE: 97
gaggttcgat tggtggagtc tggggaggc ttggtgaagc ctggaggatc ccttagactc     60
tcatgttcag cctctggttt cgacttcgat aacgcctgga tgacttgggt ccgccagcct   120
ccagggaagg gcctcgaatg ggttggtcgt attacgggtc caggtgaagg ttggtcagtg   180
gactatgctg cacccgtgga aggcagattt accatctcga gactcaattc aataaatttc   240
ttatatttgg agatgaacaa tttaagaatg gaagactcag gcctttactt ctgtgcccgc   300
acgggaaaat attatgattt ttggagtggc tatccgccgg gagaagaata cttccaagac   360
tggggccggg gcaccctagt catcgtctcc tca                                393

<210> SEQ ID NO 98
<211> LENGTH: 393
<212> TYPE: DNA
<213> ORGANISM: Homo sapiens

<400> SEQUENCE: 98
gaggttcgac tggtggagtc tggggacga ttggtgaggc ctggggggatc ccttagactc    60
```

```
tcatgttcag cctctggctt caatttcgat aacgcctgga tgacttgggt ccgccagtct    120
ccagggaagg gcctcgaatg ggttggtcgt ataacgggtc cgggtgaagg ttggtcagtg    180
gactatgctg catccgtaaa aggcagattt actatctcaa gaatgaattc aataaatttc    240
ttctatctgg agatgaacaa tttaaaaatc gaagacacag gcctttactt ctgtgcccgc    300
acgggaaaac attatgcttt tggggtggt tacccgccgg gagaagaata cctggaagac    360
tggggccaag caccettgt categtctct tca                                  393

<210> SEQ ID NO 99
<211> LENGTH: 394
<212> TYPE: DNA
<213> ORGANISM: Homo sapiens

<400> SEQUENCE: 99
gaggttcgat tggcggagtc tgggggaggc ttggtgaagc ctggaggatc ccttagactc     60
tcatgttcag cctctggttt cgacttcgat aacgcctgga tgacttgggt ccgccagcct    120
ccagggaagg gcctcgaatg ggtcggtcgt attacgggtc caggtgaagg ttggtcagtg    180
gactatgctg cacccgtgga aggcagattt accatctcga gactcaattc aataaatttc    240
ttatatttgg agatgaacaa tttaagaata gaagactcag gcctttactt ctgtgcccgc    300
acgggaaaat attatgattt tttggagtgg ctatccgccg ggagaagaat acttccaaga    360
ctggggccag ggcaccctag tcatcgtctc ctca                                394

<210> SEQ ID NO 100
<211> LENGTH: 392
<212> TYPE: DNA
<213> ORGANISM: Homo sapiens

<400> SEQUENCE: 100
gaggttcgat tggcggagtc tgggggaggc ttggtgaagc ctggaggatc ccttagactc     60
tcatgttcag cctctggttt cgacttcgat aacgcctgga tgacttgggt ccgccagcct    120
ccagggaagg gcctcgaatg ggtcggtcgt attacgggtc caggtgaagg ttggtcagtg    180
gactatgctg cacccgtgga aggcagattt accatctcga gactcaattc aataaattt    240 ctatatttgg agatgaacaa tttaagaatg gaagactcag gcctttactt ctgtgcccgc    300
acgggaaata ttatgatttt tggagtggct atccgccggg agaagaatac ttccaagact    360
ggggccaggg caccctagtc atcgtctcct ca                                  392

<210> SEQ ID NO 101
<211> LENGTH: 392
<212> TYPE: DNA
<213> ORGANISM: Homo sapiens

<400> SEQUENCE: 101
gaggttcgat tggcggagtc tgggggaggc ttggtgaagc ctggaggatc ccttagactc     60
tcatgttcag cctctggttt cgacttcgat aacgcctgga tgacttgggt ccgccagcct    120
ccagggaagg gcctcgaatg ggtcggtcgt attacgggtc caggtgaagg ttggtcagtg    180
gactatgctg cacccgtgga aggcagattt accatctcga gactcaattc aataaatttc    240
ttatatttgg agatgaacaa tttaagaatg gaagactcag gcctttactt ctgtgcccgc    300
acgggaaata ttatgatttt tggagtggct atccgccagg agaagaatac ttccaagact    360
ggggccgggg caccctagtc atcgtctcct ca                                  392
```

<210> SEQ ID NO 102
<211> LENGTH: 391
<212> TYPE: DNA
<213> ORGANISM: Homo sapiens
<220> FEATURE:
<221> NAME/KEY: misc_feature
<222> LOCATION: (311)..(311)
<223> OTHER INFORMATION: n is a, c, g, or t

<400> SEQUENCE: 102

```
gaggttcgac tggtggagtc tgggggacga ttggtgaggc ctgggggatc ccttagactc      60
tcatgttcag cctctggctt caatttcgat aacgcctgga tgacttgggt ccgccagcct     120
ccagggaagg gcctcgaatg ggttggtcgt ataacgggtc cggtgaagg ttggtcagtg      180 gactatgctg catccgtaaa aggcagattt actatctcaa gaatgaattc aataaatttc     240
ttctatctgg agatgaacaa tttaaaaatc gaagacacag gcctttactt ctgtgcccgc     300
acgggaaaac nttaatgctt tttggggtgg ttacccgccg ggagaagaat acctggaaga    360
ctgggcaggc acccttgtca tcgtctcttc a                                   391
```

<210> SEQ ID NO 103
<211> LENGTH: 392
<212> TYPE: DNA
<213> ORGANISM: Homo sapiens

<400> SEQUENCE: 103

```
gaggttcgac tggtggagtc tgggggacga ttggtgaggc ctgggggatc ccttagactc      60
tcatgttcag cctctggctt caatttcgat aacgcctgga tgacttgggt ccgccagtct    120
ccagggaagg gcctcgaatg ggttggtcgt ataacgggtc cggtgaagg ttggtcagtg     180 gactatgctg catccgtaaa aggcagattt actatctcaa gaatgaattc aataaatttc    240
ttctatctgg agatgaacaa tttaaaaatc gaagacacag gcctttactt ctgtgcccgc    300
acgggaaaac attatgcttt ttggggtgtt acccgccggg agaagaatac ctggaagact   360
ggggccaggg caccttgtc atcgtctctt ca                                   392
```

<210> SEQ ID NO 104
<211> LENGTH: 395
<212> TYPE: DNA
<213> ORGANISM: Homo sapiens
<220> FEATURE:
<221> NAME/KEY: misc_feature
<222> LOCATION: (300)..(300)
<223> OTHER INFORMATION: n is a, c, g, or t

<400> SEQUENCE: 104

```
gaagtgcagc tggtggagtc tgggggagga ttggtgaagc ctggggggtc ccttagactc      60
tcatgctcag cctctggctt caatttcgat aacgcctgga tgacttgggt ccgccagcct    120
ccagggaagg gcctcgaatg ggttggtcgt attacgggtc cggtgaagg ttggtcagtg     180 gactatgctg catccgtaaa aggcagattt actatctcaa gaatgaattc aataaatttc    240
ttctatctgg agatgaacaa tttaagagtc gaagacacag gcctttactt ctgtgcccgn    300
acgggaaaac attatgtctt ttttggggt gttatccgcc ggagaagaa atacctgaag     360 actggggcca gggcacccctt gtcatcgtct cctca                              395
```

<210> SEQ ID NO 105
<211> LENGTH: 393
<212> TYPE: DNA
<213> ORGANISM: Homo sapiens

<400> SEQUENCE: 105

```
gaggttcgat tggcggagtc tgggggaggc ttggtgaagc ctggaggatc ccttagactc      60
tcatgttcag cctctggttt cgacttcgat aacgcctgga tgacttgggt ccgccagcct     120
ccagggaagg gcctcgaatg ggtcggtcgt attacgggtc caggtgaagg ttggtcagtg     180
gactatgctg cacccgtgga aggcagattt actatctcga gactcaattc aataaatttc     240
ttatatttgg agatgaacaa tttaagaatg gaagactcag gcctttactt ctgtgcccgc     300
acgggaaaat attatgattt tggagtggca tatccgccgg agaagaata cttccaagac      360
tggggccagg gcaccctagt catcgtctcc tca                                  393
```

<210> SEQ ID NO 106
<211> LENGTH: 391
<212> TYPE: DNA
<213> ORGANISM: Homo sapiens

<400> SEQUENCE: 106

```
gaagtgcagc tggtggagtc tgggggaggc tgggtaaagc ctggggggtc ccttagactc      60
tcctgtacag cctctggaat cactttcagt aacgcctgga tgagctgggt ccgccaggct     120
ccaggaaagg ggctggagtg ggttggccgg attacgggtc caggtgaagg ttggtcagta     180
gactatgctg aatccgtaaa aggcagattt atcatctcga gaatcaattc aataaatttc     240
ttatatctgg agatgaacaa tcttagaccc gaagacacag gtcttatttt ctgtgcccac     300
aacgggaaaa cagttatgta ttttttggcgt gttatcgccg gtgaagaata ctccaagact     360
gggccagggc acccaagtca tcgtctcctc a                                    391
```

<210> SEQ ID NO 107
<211> LENGTH: 388
<212> TYPE: DNA
<213> ORGANISM: Homo sapiens

<400> SEQUENCE: 107

```
gaggttcgac tggtggagtc tgggggacga ttggtgaggc ctgggggatc ccttagactc      60
tcatgttcag cctctggctt caatttcgat aacgcctgga tgacttgggt ccgccagcct     120
ccagggaagg gcctcgaatg ggttggtcgt ataacgggtc cgggtgaagg ttggtcagtg     180
gactatgctg catccgtaaa aggcagattt actatctcaa gaatgaattc aataaatttc     240
ttctatctgg agatgaacaa tttaaaaatc gaagacacag gcctttattt ctgtgcccgc     300
acgggaaaca ttatgctttt tgggtggtta cccgccggag aagaatacct gaagactggg     360
ccagggcacc cttgtcatcg tctcttca                                        388
```

<210> SEQ ID NO 108
<211> LENGTH: 394
<212> TYPE: DNA
<213> ORGANISM: Homo sapiens

<400> SEQUENCE: 108

```
gaggttcgat tggtggagtc tgggggaggc ttggtgaagc ctggaggatc ccttagactc      60
tcatgttcag cctctggttt cgacttcgat aacgcctgga tgacttgggt ccgccagcct     120
ccagggaagg gcctcgaatg ggttggtcgt attacgggtc caggtgaagg ttggtcagtg     180
gactatgctg cacccgtgga aggcagattt accatctcga gactcaattc aataaatttc     240
ttatatttgg agatgaacaa tttaagaatg gaagactcag gcctttactt ctgtgcccgc     300
```

```
acgggaaaat attatgtatt tttggagtgg ctatccgccg ggagaagaat acttccaaga        360
ctggggccag ggcaccctag tcatcgtctc ctca                                   394
```

<210> SEQ ID NO 109
<211> LENGTH: 395
<212> TYPE: DNA
<213> ORGANISM: Homo sapiens

<400> SEQUENCE: 109

```
gaggttcgac tggtggagtc tgggggacga ttggtgaggc ctgggggatc ccttagactc        60
tcatgttcag cctctggctt caatttcgat aacgcctgga tgacttgggt ccgccagcct       120
ccagggaagg gcctcgaatg ggttggtcgt ataacgggtc cgggtgaagg ttggtcagtg       180
gactatgctg catccgtaaa aggcagattt actatctcaa gaatgaattc aataaatttc       240
ttctatctgg agatgaacaa tttaaaaatc gaagacacag gcctttactt ctgtgcccgc       300
acgggaaaca ttatgctttt tggggtggt tacccgccgg gagaagaata ccgtggaaga       360
ctggggccga gggcacccett gtcatcgtct cttca                                  395
```

<210> SEQ ID NO 110
<211> LENGTH: 392
<212> TYPE: DNA
<213> ORGANISM: Homo sapiens

<400> SEQUENCE: 110

```
gaggttcgat tggtggagtc tgggggaggc ttggtgaagc ctggaggatc ccttagactc        60
tcatgttcag cctctggttt cgacttcgat aacgcctgga tgacttgggt ccgccagcct       120
ccagggaagg gcctcgaatg ggttggtcgt attacgggtc caggtgaagg ttggtcagtg       180
gactatgctg cacccgtgga aggcagattt accatctcga gactcaattc aataaatttc       240
ttatatttgg agatgaacaa tttaagaatg gaagactcag gcctttactt ctgtgcccgc       300
acgggaaaat attatgtatt tttggagtgg ctatcgccgg agaagaatac ttccaagact       360
ggggccgggg caccctagtc atcgtctcct ca                                      392
```

<210> SEQ ID NO 111
<211> LENGTH: 399
<212> TYPE: DNA
<213> ORGANISM: Homo sapiens
<220> FEATURE:
<221> NAME/KEY: misc_feature
<222> LOCATION: (311)..(311)
<223> OTHER INFORMATION: n is a, c, g, or t
<220> FEATURE:
<221> NAME/KEY: misc_feature
<222> LOCATION: (330)..(330)
<223> OTHER INFORMATION: n is a, c, g, or t

<400> SEQUENCE: 111

```
gaggttcgac tggtggagtc tgggggacga ttggtgaggc ctgggggatc ccttagactc        60
tcatgttcag cctctggctt caatttcgat aacgcctgga tgacttgggt ccgccagcct       120
ccagggaagg gcctcgaatg ggttggtcgt ataacgggtc cgggtgaagg ttggtcagtg       180
gactatgctg catccgtaaa aggcagattt actatctcaa gaatgaattc aataaatttc       240
ttctatctgg agatgaacaa tttaaaaatc gaagacacag gcctttactt ctgtgcccgc       300
acgggaaaac nttaatgtct tttttggggn ggtttacccc gccgggtaga agaatacctg       360
gaagactggg gccagggcac ccttgtcatc gtctcttca                              399
```

```
<210> SEQ ID NO 112
<211> LENGTH: 392
<212> TYPE: DNA
<213> ORGANISM: Homo sapiens

<400> SEQUENCE: 112
gaggttcgac tggtggagtc tgggggacga ttggtgaggc ctgggggatc ccttagactc      60
tcatgttcag cctctggctt caatttcgat aacgcctgga tgacttgggt ccgccagtct     120
ccagggaagg gcctcgaatg ggttggtcgt ataacgggtc cgggtgaagg ttggtcagtg     180
gactatgctg catccgtaaa aggcagattt actatctcaa gaatgaattc aataaatttc     240
ttctatctgg agatgaacaa tttaaaaaac gaagacacag gcctttaact tctgtgcccg     300
cacgggaaaa cattatgact ttttggggtg ttacccgccg gagaagaata cctggaagac     360
tgggccaggg cacccttgtc atcgtctctt ca                                   392

<210> SEQ ID NO 113
<211> LENGTH: 354
<212> TYPE: DNA
<213> ORGANISM: Homo sapiens

<400> SEQUENCE: 113
gaggttcgat tggtggagtc tgggggaggc ttggtgaagc ctggaggatc ccttagactc      60
tcatgttcag cctctggttt cgacttcgat aacgcctgga tgacttgggt ccgccagcct     120
ccaggtgaag gttggtcagt ggactatgct gcacccgtgg aaggcagatt taccatctcg     180
agactcaatt caataaattt cttatatttg gagatgaaca atttaagaat ggaagactca     240
ggcctttact tctgtgcccg cacgggaaaa tattatgatt tttggagtgg ctatccgccg     300
ggagaagaat acttccaaga ctggggccgg ggcaccctag tcatcgtctc ctca           354

<210> SEQ ID NO 114
<211> LENGTH: 393
<212> TYPE: DNA
<213> ORGANISM: Homo sapiens

<400> SEQUENCE: 114
gaggttcgat tggtggagtc tgggggaggc ttggtgaagc ctggaggatc ccttagactc      60
tcatgttcag cctctggttt cgacttcgat aacgcctgga tgacttgggt ccgccagcct     120
ccagggaagg gcctcgaatg ggttggtcgt attacgggtc caggtgaagg ttggtcagtg     180
gactatgctg cacccgtgga aggcagattt accatctcga gactcaattc aataaatttc     240
ttatatttgg agatgaacaa tttaagaatg gaagactcag gcctttactt ctgtgcccgc     300
acgggaaata ttatgtattt ttggagtggc tatccgccgg agaagaata cttccaagac      360 tggggccggg gcaccctagt catcgtctcc tca                                  393

<210> SEQ ID NO 115
<211> LENGTH: 397
<212> TYPE: DNA
<213> ORGANISM: Homo sapiens

<400> SEQUENCE: 115
gaggttcgat tggtggagtc tgggggaggc ttggtgaagc ctggaggatc ccttagactc      60
tcatgttcag cctctggttt cgacttcgat aacgcctgga tgacttgggt ccgccagcct     120
ccagggaagg gcctcgaatg ggttggtcgt attacgggtc caggtgaagg ttggtcagtg     180
gactatgctg cacccgtgga aggcagattt accatctcga gactcaattc aattaaattt     240
```

```
ctttatttgg agatgaacaa tttaagaatg aagagactcag gcctttactt ctgttgcccc    300
gcacgggaaa atattatgat tttttggagt tggctatccg ccgggagaag aatactacca    360
agactggggc cagggcaccc tagtcatcgt ctcctca                             397
```

<210> SEQ ID NO 116
<211> LENGTH: 330
<212> TYPE: DNA
<213> ORGANISM: Homo sapiens

<400> SEQUENCE: 116

```
gtttcctctg aactgactca ggagactggt gtctctgtgg ccttgggacg gacagtcaca     60
atcacgtgcc ggggagacag cctcagaagt cattatgcaa gttggtacca aaagaagcca    120
ggacaggccc ctaaacttct cttctatggt aaaaataatc gtccttcagg gatcccagac    180
cgattctctg gctccgcctc aggaaacaga gcttccttga ccatctctgg ggctcaggcg    240
gaagacgacg cggaatatta ttgtagttct cgagacaaga gtggcagccg tctgtcggcc    300
ttcggcgggg gaccgaaaact gactgtcctc                                    330
```

<210> SEQ ID NO 117
<211> LENGTH: 330
<212> TYPE: DNA
<213> ORGANISM: Homo sapiens

<400> SEQUENCE: 117

```
gtttcctctg aactgactca ggagactggt gtctctgtgg ccttgggacg gacagtcaca     60
atcacgtgcc ggggagacag cctcagaagt cattatgcaa gttggtacca aaagaagcca    120
ggacaggccc ctaaacttct cttctatggt aaaaataatc gtccttcagg gatcccagac    180
cgattctctg gctccgcctc aggaaacaga gcttccttga ccatctctgg ggctcaggcg    240
gaagacgacg cggaatatta ttgtagttct cgagacaaga gtggcagccg tctgtcggtc    300
ttcggcggag ggaccaaaact gaccgtcctc                                    330
```

<210> SEQ ID NO 118
<211> LENGTH: 330
<212> TYPE: DNA
<213> ORGANISM: Homo sapiens

<400> SEQUENCE: 118

```
gtttcctctg aactgactca ggagactggt gtctctgtgg ccttgggacg gacagtcaca     60
atcacgtgcc ggggagacag cctcagaagt cattatgcaa gttggtacca aaagaagcca    120
ggacaggccc ctaaacttct cttctatggt aaaaataatc gtccttcagg gatcccagac    180
cgattctctg gctccgcctc aggaaacaga gcttccttga ccatctctgg ggctcaggcg    240
gaagacgacg cggaatatta ttgtagttct cgagacaaga gtggcagccg tctgtcggcc    300
ttcggcgggg gaccgaaaact gactgtcctc                                    330
```

<210> SEQ ID NO 119
<211> LENGTH: 330
<212> TYPE: DNA
<213> ORGANISM: Homo sapiens

<400> SEQUENCE: 119

```
gtttcctctg aactgactca ggagactggt gtctctgtgg ccttgggacg gacagtcaca     60
atcacgtgcc ggggagacag cctcagaagt cattatgcaa gttggtacca aaagaagcca    120
ggacaggccc ctaaacttct cttctatggt aaaaataatc gtccttcagg gatcccagac    180
```
cgattctctg gcttcgcctc aggaaacaga gcttccttga ccatctctgg ggctcaggcg    240
gaagacgacg cggaatatta ttgtagttct cgagacaaga gtggcagccg tctgtcggtc    300
ttcggcgggg ggaccaaact gaccgtcctc                                     330

<210> SEQ ID NO 120
<211> LENGTH: 330
<212> TYPE: DNA
<213> ORGANISM: Homo sapiens

<400> SEQUENCE: 120
gtttcctctg aactgactca ggagactggt gtctctgtgg ccttgggacg gacagtcaca     60
atcacgtgcc ggggagacag cctcagaagt cattatgcaa gttggtacca aaagaagcca    120
ggacaggccc ctatacttct cttctatggt aaaaataatc gtccttcagg gatcccagac    180
cgattctctg gctccgcctc aggaaacaga gcttccttga ccatctctgg ggctcaggcg    240
gaagacgacg cggaatatta ttgtagttct cgagacaaga gtggcagccg tctgtcggtc    300
ttcggcgggg gaccgaaact gaccgtcctc                                     330

<210> SEQ ID NO 121
<211> LENGTH: 330
<212> TYPE: DNA
<213> ORGANISM: Homo sapiens

<400> SEQUENCE: 121
gtttcctctg aactgactca ggagactggt gtctctgtgg ccttgggacg gacagtcaca     60
atcacgtgcc ggggagacag cctcagaagt cattatgcaa gttggtacca aaagaagcca    120
ggacaggccc ctatacttct cttctatggt aaaaataatc gtccttcagg gatcccagac    180
cgattctctg gctccgcctc aggaaacaga gcttccttga ccatctctgg ggctcaggcg    240
gaagacgacg cggaatatta ttgtagttct cgagacaaga gtggcagccg tctgtcggtc    300
ttcggcgggg gaccgaaact gaccgtcctc                                     330

<210> SEQ ID NO 122
<211> LENGTH: 330
<212> TYPE: DNA
<213> ORGANISM: Homo sapiens

<400> SEQUENCE: 122
gtttcctctg aactgactca ggagactggt gtctctgtgg ccttgggacg gacagtcaca     60
atcacgtgcc ggggagacag cctcagaagt cattatgcaa gttggtacca aaagaagcca    120
ggacaggccc ctaaacttct cttctatggt aaaaataatc gtccttcagg gatcccagac    180
cgattctctg gctccgcctc aggaaacaga gcttccttga ccatctctgg ggctcaggcg    240
gaagacgacg cggaatatta ttgtagttct cgagacaaga gtggcagccg tctgtcggtc    300
ttcggcggag ggaccaaacc gaccgtcctc                                     330

<210> SEQ ID NO 123
<211> LENGTH: 330
<212> TYPE: DNA
<213> ORGANISM: Homo sapiens

<400> SEQUENCE: 123
gtttcctctg aactgactca ggagactggt gtctctgtgg ccttgggacg gacagtcaca     60
atcacgtgcc ggggagacag cctcagaagt cattatgcaa gttggtacca aaagaagcca    120

```
ggacaggccc ctaaacttct cttctatggt aaaaataatc gtccttcagg gatcccagac    180
cgattctctg gctccgcctc aggaaacaga gcttccttga ccatctctgg ggctcaggcg    240
gaagacgacg cggaatatta ttgtagttct cgagacaaga gtggcagccg tctgtcggtc    300
ttcggcgggg ggaccaaact gaccgtcctc                                     330
```

<210> SEQ ID NO 124
<211> LENGTH: 330
<212> TYPE: DNA
<213> ORGANISM: Homo sapiens

<400> SEQUENCE: 124

```
gtttcctctg aactgactca ggagactggt gtctctgtgg ccttgggacg dacagtcaca    60
atcacgtgcc ggggagacag cctcagaagt cattatgcaa gttggtacca aaagaagcca   120
ggacaggccc ctaaacttct cttctatggt aaaaataatc gtccttcagg gatcccagac   180
cgattctctg gctccgcctc aggaaacaga gcttccttga ccatctctgg ggctcaggcg   240
gaagacgacg cggaatatta atgtagttct cgagacaaga gtggcagccg tctgtcggtc   300
ttcggcggag ggaccaaact gaccgtcctc                                    330
```

<210> SEQ ID NO 125
<211> LENGTH: 330
<212> TYPE: DNA
<213> ORGANISM: Homo sapiens

<400> SEQUENCE: 125

```
gtttcctctg aactgactca ggagactggt gtctctgtgg ccttgggacg dacagtcaca    60
atcacgtgcc ggggagacag cctcagaagt cattatgcaa gttggtacca aaagaagcca   120
ggacaggccc ctaaacttct cttctatggt aaaaataatc gtccttcagg gatcccagac   180
cgattctctg gctccgcctc aggaaacaga gcttccttga ccatctctgg ggctcaggcg   240
gaagacgacg cggaatatat ctgtagttct cgagacaaga gtggcagccg tctgtcggtc   300
ttcggcggag ggaccaagct gaccgtcctc                                    330
```

<210> SEQ ID NO 126
<211> LENGTH: 330
<212> TYPE: DNA
<213> ORGANISM: Homo sapiens

<400> SEQUENCE: 126

```
gtttcctctg aactgactca ggagactggt gtctctgtgg ccttgggacg dacagtcaca    60
atcacgtgcc ggggagacag cctcagaagt cattatgcaa gttggtacca aaagaagcca   120
ggacaggccc ctaaacttct cttctatggt aaaaataatc gtccttcagg gatcccagac   180
cgattctctg gctccgcctc aggagacaga gcttccttga ccatctctgg ggcttaggcg   240
gaagacgacg cggaatatta ttgtagttct cgagacaaga gtggcagccg tctgtcggtc   300
ttcggcggag ggaccaagct gaccgtcctc                                    330
```

<210> SEQ ID NO 127
<211> LENGTH: 330
<212> TYPE: DNA
<213> ORGANISM: Homo sapiens

<400> SEQUENCE: 127

```
gtttcctctg aactgactca ggagactggt gtctctgtgg ccttgggaca dacagtcaca    60
atcacgtgcc ggggagacag cctcagaagt cattatgcaa gttggtacca aaagaagcca   120
```
ggacaggccc ctatacttct cttctatggt aaaaataatc gtccttcagg gatcccagac    180
cgattctctg gctccgcctc aggaaacaga gcttccttga ccatctctgg ggctcaggcg    240
gaagacgacg cggaatatta ttgtagttct cgagacaaga gtggcagccg tctgtcggtc    300
ttcggcgggg ggaccaaact gaccgtcctc                                     330

<210> SEQ ID NO 128
<211> LENGTH: 330
<212> TYPE: DNA
<213> ORGANISM: Homo sapiens

<400> SEQUENCE: 128
ggttcctctg aactgactca ggagactggt gtctctgtgg ccttgggacg gacagtcaca     60
atcacgtgcc ggggagacag cctcagaagt cattatgcaa gttggtacca aaagaagcca    120
ggacaggccc ctaaacttct cttctatggt aaaaataatc gtccttcagg gatcccagac    180
cgattctctg gctccgcctc aggaaacaga gcttccttga ccatctctgg ggctcaggcg    240
gaagacgacg cggaatatta ttgtagttct cgagacaaga gtggcagccg tctgtcggtc    300
ttcggcgggg ggaccaaact gaccgtcctc                                     330

<210> SEQ ID NO 129
<211> LENGTH: 330
<212> TYPE: DNA
<213> ORGANISM: Homo sapiens

<400> SEQUENCE: 129
gtttcctctg aactgactca ggagactggt gtctctgtgg ccttgggacg gacagtcaca     60
atcacgtgcc ggggagacag cctcagaagt cattatgcaa gttggtacca aaagaagcca    120
ggacaggccc ctaaacttct cttctatggt aaaaataatc gtccttcagg gatcccagac    180
cgattctctg gctccgcctc aggaaacaga gcttccttga ccatctctgg ggctcaggcg    240
gaagacgacg cggaatatta ttgtagttct cgagacaaga gtggcagccg tctgtcggtc    300
ttcggcgggg ggaccaaact gaccgtcctc                                     330

<210> SEQ ID NO 130
<211> LENGTH: 330
<212> TYPE: DNA
<213> ORGANISM: Homo sapiens

<400> SEQUENCE: 130
gtttcctctg aactgactca ggagactggt gtctctgtgg ccttgggacg gacagtcaca     60
atcacgtgcc ggggagacag cctcagaagt cattatgcaa gttggtacca aaagaagcca    120
ggacaggccc ctaaacttct cttctatggt aaaaataatc gtccttcagg gatcccagac    180
cgattctctg gctccgcctc aggaaacaga gcttccttga ccatctctgg ggctcaggcg    240
gaagacgacg cggaatatta ttgtagttct cgagacaaga gtggcagccg tctgtcggtc    300
ttcggcgggg ggaccaaact gaccgtcctc                                     330

<210> SEQ ID NO 131
<211> LENGTH: 330
<212> TYPE: DNA
<213> ORGANISM: Homo sapiens

<400> SEQUENCE: 131
gtttcctctg aactgactca ggagactggt gtctctgtgg ccttgggacg gacagtcaca     60

| | | |
|---|---|---|
| atcacgtgcc gggagacag cctcagaagt cattatgcaa gttggtacca aaagaagcca | 120 | |
| ggacaggccc ctaaacttct cttctatggt aaaaataatc gtccttcagg gatcccagac | 180 | |
| cgattctctg gctccgcctc aggaaacaga gcttccttga ccatctctgg ggctcaggcg | 240 | |
| gaagacgacg cggaatatta ttgtagttct cgagacaaga gtggcagccg tctgtcggtc | 300 | |
| ttcggcgggg ggaccaaact gaccgtcctc | 330 | |

<210> SEQ ID NO 132
<211> LENGTH: 330
<212> TYPE: DNA
<213> ORGANISM: Homo sapiens

<400> SEQUENCE: 132

| | | |
|---|---|---|
| gtttcctctg aactgactca ggagactggt gtctctgtgg ccttgggacg gacagtcaca | 60 | |
| atcacgtgcc gggagacag cctcagaagt cattatgcaa gttggtacca aaagaagcca | 120 | |
| ggacaggccc ctaaacttct cttctatggt aaaaataatc gtccttcagg gatcccagac | 180 | |
| cgattctctg gctccgcctc aggaaacaga gcttccttga ccatctctgg ggctcaggcg | 240 | |
| gaagacgacg cggaatatta ttgtagttct cgagacaaga gtggcagccg tctgtcggtc | 300 | |
| ttcggcgggg ggaccaaacc gaccgtcctc | 330 | |

<210> SEQ ID NO 133
<211> LENGTH: 330
<212> TYPE: DNA
<213> ORGANISM: Homo sapiens

<400> SEQUENCE: 133

| | | |
|---|---|---|
| gtttcctctg aactgactca ggagactggt gtctctgtgg ccttgggacg gacagtcaca | 60 | |
| atcacgtgcc gggagacag cctcagaagt cattatgcaa gttggtacca aaagaagcca | 120 | |
| ggacaggccc ctaaacttct cttctatggt aaaaataatc gtccttcagg gatcccagac | 180 | |
| cgattctctg gctccgcctc aggaaacaga gcttccttga ccatctctgg ggctcaggcg | 240 | |
| gaagacgacg cggaatatta ttgtagttct cgagacaaga gtggcagccg tctgtcggtc | 300 | |
| ttcggcgggg ggaccaaact gaccgtcctc | 330 | |

<210> SEQ ID NO 134
<211> LENGTH: 330
<212> TYPE: DNA
<213> ORGANISM: Homo sapiens

<400> SEQUENCE: 134

| | | |
|---|---|---|
| gtttcctctg aattgactca ggagactggt gtctctgtgg ccttgggacg gacagtcaca | 60 | |
| atcacgtgcc gggagacag cctcaaaagt cattatgcaa gttggtacca aaagaagcct | 120 | |
| ggacaggccc ctgtacttct cttctatggt aaaaataatc gtccttcagg gatcccagac | 180 | |
| cgattctctg gctccgcctc aggaaataga gcttcgttga ccatctcggg ggctcaggcg | 240 | |
| gaggacgacg cggaatatta ttgtagttct cgagacaaga gtggcagccg tctgtcggtc | 300 | |
| ttcggcgggg gaccaaaact gaccgtcctc | 330 | |

<210> SEQ ID NO 135
<211> LENGTH: 330
<212> TYPE: DNA
<213> ORGANISM: Homo sapiens

<400> SEQUENCE: 135

| | | |
|---|---|---|
| gtttcctctg aactgactca ggagactggt gtctctgtgg ccttgggacg gacagtcaca | 60 | |

```
atcacgtgcc ggggagacag cctcagaagt cattatgcaa gttggtacca aaagaagcca      120
ggacaggccc ctatacttct cttctatggt aaaaataatc gtccttcagg gatcccagac      180
cgattctctg gctccgcctc aggaaacaga gcttccttga ccatctctgg ggctcaggcg      240
gaagacggcg cggaatatta ttgtagttct cgagacaaga gtggcagccg tctgtcggtc      300
ttcggcggag ggaccaaatt gaccgtcctc                                       330
```

<210> SEQ ID NO 136
<211> LENGTH: 330
<212> TYPE: DNA
<213> ORGANISM: Homo sapiens

<400> SEQUENCE: 136

```
gtttcctctg aactgactca ggagactggt gtctctgtgg ccttgggacg gacagttaca       60
atcacgtgcc ggggagacag cctcagaagt cattatgcaa gttggtacca aaagaagcca      120
ggacaggccc ctaaacttct cttctatggt aaaaataatc gtccttcagg gatcccagac      180
cgattctctg gccccgcctc aggaaacaga gcttccttga ccatctctgg ggctcaggcg      240
gaagacgacg cggaatatta ttgtagttct cgagacaaga gtggcagccg tctgtcggtc      300
ttcggcgggg ggaccaaaact gaccgtcctc                                      330
```

<210> SEQ ID NO 137
<211> LENGTH: 330
<212> TYPE: DNA
<213> ORGANISM: Homo sapiens

<400> SEQUENCE: 137

```
gtttcctctg aactgactca ggagactggt gtctctgtgg ccttgggacg gacagtcaca       60
atcacgtgcc ggggagacag cctcagaagt cattatgcaa gttggtacca agagaagcca      120
gggcaggccc ctaaacttct cttctatggt aaaaataatc gtccttcagg gatcccagac      180
cgattctctg gctccgcctc aggaaacaga gcttccttga ccatctctgg ggctcaggcg      240
gaagacgacg cggaatatta ttgtagttct cgagacaaga gtggcagccg tctgtcggtc      300
ttcggcggag ggaccaaaact ggccgtcctc                                      330
```

<210> SEQ ID NO 138
<211> LENGTH: 330
<212> TYPE: DNA
<213> ORGANISM: Homo sapiens

<400> SEQUENCE: 138

```
gtttcctctg aactgactca ggagactggt gtctctgtgg ccttgggacg gacagtcaca       60
atcacgtgcc ggggagacag cctcagaagt cattatgcaa gttggtacca aaagaagcca      120
ggacaggccc ctatacttct cttctatggt aaaaataatc gcccttcagg gatcccagac      180
cgattctctg gctccgcctc aggaaacaga gcttccttga ccatctctgg ggctcaggcg      240
gaagacgacg cggaatatta ttgtagttct cgagacaaga gtggcagccg tctgtcggtc      300
ttcggcgggg ggaccaaaatt gaccgtcctc                                      330
```

<210> SEQ ID NO 139
<211> LENGTH: 330
<212> TYPE: DNA
<213> ORGANISM: Homo sapiens

<400> SEQUENCE: 139
gtttcctctg aactgactca ggagactggt gtctctgtgg ccttgggacg dacagtcaca    60
atcacgtgcc ggggagacag cctcagaagt cattatgcaa gttggtacca aaagaagcca   120
ggacaggccc ctaaacttct cttctatggt aaaaataatc gtccttcagg gatcccagac   180
cgattctctg gctccgcctc aggaaacaga gcttccttga ccatctctgg ggctcaggcg   240
gaagacgacg cggaatatta ttgtagtcct cgagacaaga gtggcagccg tctgtcggtc   300
ttcggcgggg ggaccaaact gaccgtccgt                                    330

<210> SEQ ID NO 140
<211> LENGTH: 330
<212> TYPE: DNA
<213> ORGANISM: Homo sapiens

<400> SEQUENCE: 140
gtttcctctg aactgactca ggagactggt gtctctgtgg ccttgggacg dacagtcaca    60
atcacgtgcc ggggagacag cctcagaagt cattatgcaa gttggtacca aaagaagcca   120
ggacaggccc ctaaacttct cttctatggt aaaaataatc gtccttcagg gatcccagac   180
cgattctctg gctccgcctc aggaaacaga gcttccttga ccatctctgg ggctcaggcg   240
gaagacgacg cggaatatta ttgtagttct cgagacaaga gtggcagccg tctgtcggtc   300
ttcggcgggg gaccgaaact gaccgtcctc                                    330

<210> SEQ ID NO 141
<211> LENGTH: 330
<212> TYPE: DNA
<213> ORGANISM: Homo sapiens

<400> SEQUENCE: 141
ggttcctctg aactgactca ggagactggt gtctctgtgg ccttgggacg dacagtcaca    60
atcacgtgcc ggggagacag cctcagaagt cattatgcaa gttggtacca aaagaagcca   120
ggacaggccc ctatacttct cttctatggt aaaaataatc gtccttcagg gatccacgac   180
cgattctctg gctccgcctc aggaaacaga gcttccttga ccatctctgg ggctcaggcg   240
gaagacgacg cggaatatta ttgtagttct cgagacaaga gtggcagccg tctgtcggtc   300
ttcggcggag ggaccaaatt gaccgtcctc                                    330

<210> SEQ ID NO 142
<211> LENGTH: 330
<212> TYPE: DNA
<213> ORGANISM: Homo sapiens

<400> SEQUENCE: 142
gtttcctctg aactgactca ggagactggt gtctctgtgg ccttgggacg dacagtcaca    60
atcacgtgcc ggggagacag cctcagaagt cattatgcaa gttggtacca aaagaagcca   120
ggacaggccc ctaaacttct cttctatggt aaaaataatc gtccttcagg gatcccagac   180
cgattctctg gctccgcctc aggaaacaga gcttccttga ccatctctgg ggctcaggcg   240
gaagacgacg cggaatatta ttgtagtcct cgagacaaga gtggcagccg tctgtcggtc   300
ttcggcgggg gaccgaaact agaccgtcct                                    330

<210> SEQ ID NO 143
<211> LENGTH: 330
<212> TYPE: DNA
<213> ORGANISM: Homo sapiens

<400> SEQUENCE: 143

```
gtttcctctg aactgactca ggagactggt gtctctgtgg ccttgggacg gacagtcaca      60
atcacgtgcc ggggagacag cctcagaagt cattatgcaa gttggtacca aaagaagcca     120
ggacaggccc ctaaacttct cttctatggt aaaaataatc gtccttcagg gatcccagac     180
cgattctctg gctccgcctc aggaaacaga gcttccttga ccatctctgg ggctcaggcg     240
gaagacgacg cggaatatta ttgtagttct cgagacaaga gtggcagccg tctgtcggtc     300
ttcggcgggg ggaccaaact gaccgtcctc                                      330
```

<210> SEQ ID NO 144
<211> LENGTH: 330
<212> TYPE: DNA
<213> ORGANISM: Homo sapiens

<400> SEQUENCE: 144

```
gtttcctctg aactgactca ggagactggt gtctctgtgg ccttgggacg gacagtcaca      60
atcacgtgcc ggggagacag cctcagaagt cattatgcaa gttggtacca aaagaagcca     120
ggacaggccc ctaaacttct cttctatggt aaaaataatc gtccttcagg gatcccagac     180
cgattctctg gctccgcctc aggaaacaga gcttccttga ccatctctgg ggctcagcgg     240
gaagacgacg cggaatatta ttgtagttct cgtgacaaga gtggcagccg tctgtcggtc     300
ttcggcgggg gaccgaaact gaccgtccta                                      330
```

<210> SEQ ID NO 145
<211> LENGTH: 329
<212> TYPE: DNA
<213> ORGANISM: Homo sapiens

<400> SEQUENCE: 145

```
ggttcctctg aactgactca ggagactggt gtctctgtgg ccttgggacg gacagtcaca      60
atcacgtgcc ggggagacag cctcagaagt cattatgcaa gttggtacca aaagaagcca     120
ggacaggccc ctatacttct cttctatggt aaaaataatc gtccttcagg gatcccagac     180
cgattctctg gctccgcctc aggaaacaga gcttccttga ccatctctgg ggctcaggcg     240
gaagacgacg cggaatatta ttgtagttct cgagacaaga gtggcagccg tctgtcggtc     300
ttcgggcggg ggaccaaaact tggaccgtc                                      329
```

<210> SEQ ID NO 146
<211> LENGTH: 131
<212> TYPE: PRT
<213> ORGANISM: Homo sapiens
<220> FEATURE:
<221> NAME/KEY: misc_feature
<222> LOCATION: (3)..(3)
<223> OTHER INFORMATION: X is Q or R
<220> FEATURE:
<221> NAME/KEY: misc_feature
<222> LOCATION: (5)..(5)
<223> OTHER INFORMATION: X is V or A
<220> FEATURE:
<221> NAME/KEY: misc_feature
<222> LOCATION: (28)..(28)
<223> OTHER INFORMATION: X is D or W
<220> FEATURE:
<221> NAME/KEY: misc_feature
<222> LOCATION: (30)..(30)
<223> OTHER INFORMATION: X is D or W
<220> FEATURE:
<221> NAME/KEY: misc_feature
<222> LOCATION: (31)..(31)
<223> OTHER INFORMATION: X is N or W
<220> FEATURE:

<221> NAME/KEY: misc_feature
<222> LOCATION: (57)..(57)
<223> OTHER INFORMATION: X is G or W
<220> FEATURE:
<221> NAME/KEY: misc_feature
<222> LOCATION: (128)..(128)
<223> OTHER INFORMATION: X is T or I

<400> SEQUENCE: 146

Glu Val Xaa Leu Xaa Glu Ser Gly Gly Gly Leu Val Lys Pro Gly Gly
1               5                   10                  15

Ser Leu Arg Leu Ser Cys Ser Ala Ser Gly Phe Xaa Phe Xaa Xaa Ala
            20                  25                  30

Trp Met Thr Trp Val Arg Gln Pro Pro Gly Lys Gly Leu Glu Trp Val
        35                  40                  45

Gly Arg Ile Thr Gly Pro Gly Glu Xaa Trp Ser Val Asp Tyr Ala Ala
    50                  55                  60

Pro Val Glu Gly Arg Phe Thr Ile Ser Arg Leu Asn Ser Ile Asn Phe
65                  70                  75                  80

Leu Tyr Leu Glu Met Asn Asn Leu Arg Met Glu Asp Ser Gly Leu Tyr
                85                  90                  95

Phe Cys Ala Arg Thr Gly Lys Tyr Tyr Asp Phe Trp Ser Gly Tyr Pro
            100                 105                 110

Pro Gly Glu Glu Tyr Phe Gln Asp Trp Gly Arg Gly Thr Leu Val Xaa
        115                 120                 125

Val Ser Ser
    130

<210> SEQ ID NO 147
<211> LENGTH: 131
<212> TYPE: PRT
<213> ORGANISM: homo sapiens

<400> SEQUENCE: 147

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Asp Phe Asp Asn Ala
            20                  25                  30

Trp Met Thr Trp Val Arg Gln Ala Pro Gly Lys Gly Leu Glu Trp Val
        35                  40                  45

Gly Arg Ile Thr Gly Pro Gly Glu Gly Trp Ser Val Asp Tyr Ala Ala
    50                  55                  60

Pro Val Glu Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Thr Gly Lys Tyr Tyr Asp Phe Trp Ser Gly Tyr Pro
            100                 105                 110

Pro Gly Glu Glu Tyr Phe Gln Asp Trp Gly Gln Gly Thr Leu Val Thr
        115                 120                 125

Val Ser Ser
    130

<210> SEQ ID NO 148
<211> LENGTH: 131
<212> TYPE: PRT
<213> ORGANISM: homo sapiens

<400> SEQUENCE: 148

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Asp Phe Asp Asn Ala
            20                  25                  30

Trp Met Thr Trp Val Arg Gln Pro Pro Gly Lys Gly Leu Glu Trp Val
            35                  40                  45

Gly Arg Ile Thr Gly Pro Gly Glu Gly Trp Ser Val Asp Tyr Ala Ala
        50                  55                  60

Pro Val Glu Gly Arg Phe Thr Ile Ser Arg Leu Asp Ser Ile Asn Phe
65                  70                  75                  80

Leu Tyr Leu Gln Met Asn Ser Leu Lys Met Glu Asp Thr Ala Val Tyr
                85                  90                  95

Tyr Cys Thr Thr Thr Gly Lys Tyr Tyr Asp Phe Trp Ser Gly Tyr Pro
            100                 105                 110

Pro Gly Glu Glu Tyr Phe Gln Asp Trp Gly Gln Gly Thr Leu Val Thr
            115                 120                 125

Val Ser Ser
        130

<210> SEQ ID NO 149
<211> LENGTH: 131
<212> TYPE: PRT
<213> ORGANISM: homo sapiens

<400> SEQUENCE: 149

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Asp Phe Asp Asn Ala
            20                  25                  30

Trp Met Thr Trp Val Arg Gln Pro Pro Gly Lys Gly Leu Glu Trp Val
            35                  40                  45

Gly Arg Ile Thr Gly Pro Gly Glu Gly Trp Ser Val Asp Tyr Ala Ala
        50                  55                  60

Pro Val Glu Gly Arg Phe Thr Ile Ser Arg Leu Asp Ser Ile Asn Phe
65                  70                  75                  80

Leu Tyr Leu Gln Met Asn Ser Leu Lys Met Glu Asp Thr Gly Val Tyr
                85                  90                  95

Tyr Cys Ala Arg Thr Gly Lys Tyr Tyr Asp Phe Trp Ser Gly Tyr Pro
            100                 105                 110

Pro Gly Glu Glu Tyr Phe Gln Asp Trp Gly Gln Gly Thr Leu Val Thr
            115                 120                 125

Val Ser Ser
        130

<210> SEQ ID NO 150
<211> LENGTH: 109
<212> TYPE: PRT
<213> ORGANISM: homo sapiens

<400> SEQUENCE: 150

Ser Tyr Glu Leu Thr Gln Asp Pro Ala Val Ser Val Ala Leu Gly Gln
1               5                   10                  15

Thr Val Arg Ile Thr Cys Arg Gly Asp Ser Leu Arg Ser His Tyr Ala
            20                  25                  30

Ser Trp Tyr Gln Gln Lys Pro Gly Gln Ala Pro Val Leu Leu Phe Tyr
            35                  40                  45
```

Gly Lys Asn Asn Arg Pro Ser Gly Ile Pro Asp Arg Phe Ser Gly Ser
        50                  55                  60

Ala Ser Gly Asn Thr Ala Ser Leu Thr Ile Thr Gly Ala Gln Ala Glu
 65                  70                  75                  80

Asp Glu Ala Asp Tyr Tyr Cys Ser Ser Arg Asp Lys Ser Gly Ser Arg
                 85                  90                  95

Leu Ser Val Phe Gly Gly Gly Thr Lys Leu Thr Val Leu
            100                 105

<210> SEQ ID NO 151
<211> LENGTH: 109
<212> TYPE: PRT
<213> ORGANISM: homo sapiens

<400> SEQUENCE: 151

Ser Tyr Glu Leu Thr Gln Asp Thr Gly Val Ser Val Ala Leu Gly Gln
 1               5                  10                  15

Thr Val Thr Ile Thr Cys Arg Gly Asp Ser Leu Arg Ser His Tyr Ala
                 20                  25                  30

Ser Trp Tyr Gln Gln Lys Pro Gly Gln Ala Pro Val Leu Leu Phe Tyr
             35                  40                  45

Gly Lys Asn Asn Arg Pro Ser Gly Ile Pro Asp Arg Phe Ser Gly Ser
        50                  55                  60

Ala Ser Gly Asn Arg Ala Ser Leu Thr Ile Thr Gly Ala Gln Ala Glu
 65                  70                  75                  80

Asp Glu Ala Asp Tyr Tyr Cys Ser Ser Arg Asp Lys Ser Gly Ser Arg
                 85                  90                  95

Leu Ser Val Phe Gly Gly Gly Thr Lys Leu Thr Val Leu
            100                 105

<210> SEQ ID NO 152
<211> LENGTH: 109
<212> TYPE: PRT
<213> ORGANISM: homo sapiens

<400> SEQUENCE: 152

Ser Tyr Glu Leu Thr Gln Asp Thr Gly Val Ser Val Ala Leu Gly Arg
 1               5                  10                  15

Thr Val Thr Ile Thr Cys Arg Gly Asp Ser Leu Arg Ser His Tyr Ala
                 20                  25                  30

Ser Trp Tyr Gln Lys Pro Gly Gln Ala Pro Val Leu Leu Phe Tyr
             35                  40                  45

Gly Lys Asn Asn Arg Pro Ser Gly Ile Pro Asp Arg Phe Ser Gly Ser
        50                  55                  60

Ala Ser Gly Asn Arg Ala Ser Leu Thr Ile Thr Gly Ala Gln Ala Glu
 65                  70                  75                  80

Asp Glu Ala Asp Tyr Tyr Cys Ser Ser Arg Asp Lys Ser Gly Ser Arg
                 85                  90                  95

Leu Ser Val Phe Gly Gly Gly Thr Lys Leu Thr Val Leu
            100                 105

<210> SEQ ID NO 153
<211> LENGTH: 131
<212> TYPE: PRT
<213> ORGANISM: homo sapiens

<400> SEQUENCE: 153

```
Glu Val Arg Leu Val Glu Ser Gly Gly Gly Leu Val Lys Pro Gly Gly
1               5                   10                  15

Ser Leu Arg Leu Ser Cys Ser Ala Ser Gly Phe Asp Phe Asp Asn Ala
            20                  25                  30

Trp Met Thr Trp Val Arg Gln Pro Pro Gly Lys Gly Leu Glu Trp Val
        35                  40                  45

Gly Arg Ile Thr Gly Pro Gly Glu Gly Trp Ser Val Asp Tyr Ala Ala
    50                  55                  60

Pro Val Glu Gly Arg Phe Thr Ile Ser Arg Leu Asn Ser Ile Asn Phe
65                  70                  75                  80

Leu Tyr Leu Glu Met Asn Asn Leu Arg Met Glu Asp Ser Gly Leu Tyr
                85                  90                  95

Phe Cys Ala Arg Thr Gly Lys Tyr Tyr Asp Phe Trp Ser Gly Tyr Pro
            100                 105                 110

Pro Gly Glu Glu Tyr Phe Gln Asp Trp Gly Arg Gly Thr Leu Val Ile
            115                 120                 125

Val Ser Ser
    130

<210> SEQ ID NO 154
<211> LENGTH: 131
<212> TYPE: PRT
<213> ORGANISM: homo sapiens

<400> SEQUENCE: 154

Glu Val Arg Leu Ala Glu Ser Gly Gly Gly Leu Val Lys Pro Gly Gly
1               5                   10                  15

Ser Leu Arg Leu Ser Cys Ser Ala Ser Gly Phe Asp Phe Asp Asn Ala
            20                  25                  30

Trp Met Thr Trp Val Arg Gln Pro Pro Gly Lys Gly Leu Glu Trp Val
        35                  40                  45

Gly Arg Ile Thr Gly Pro Gly Glu Gly Trp Ser Val Asp Tyr Ala Ala
    50                  55                  60

Pro Val Glu Gly Arg Phe Thr Ile Ser Arg Leu Asn Ser Ile Asn Phe
65                  70                  75                  80

Leu Tyr Leu Glu Met Asn Asn Leu Arg Met Glu Asp Ser Gly Leu Tyr
                85                  90                  95

Phe Cys Ala Arg Thr Gly Lys Tyr Tyr Asp Phe Trp Ser Gly Tyr Pro
            100                 105                 110

Pro Gly Glu Glu Tyr Phe Gln Asp Trp Gly Arg Gly Thr Leu Val Ile
            115                 120                 125

Val Ser Ser
    130

<210> SEQ ID NO 155
<211> LENGTH: 131
<212> TYPE: PRT
<213> ORGANISM: homo sapiens

<400> SEQUENCE: 155

Glu Val Arg Leu Val Glu Ser Gly Gly Gly Leu Val Lys Pro Gly Gly
1               5                   10                  15

Ser Leu Arg Leu Ser Cys Ser Ala Ser Gly Phe Asp Phe Asp Asn Ala
            20                  25                  30

Trp Met Thr Trp Val Arg Gln Pro Pro Gly Lys Gly Leu Glu Trp Val
        35                  40                  45
```

```
Gly Arg Ile Thr Gly Pro Gly Glu Gly Trp Ser Val Asp Tyr Ala Ala
        50                  55                  60

Pro Val Glu Gly Arg Phe Thr Ile Ser Arg Leu Asn Ser Ile Asn Phe
 65                  70                  75                  80

Leu Tyr Leu Glu Met Asn Asn Leu Arg Met Glu Asp Ser Gly Leu Tyr
                 85                  90                  95

Phe Cys Ala Arg Thr Gly Lys Tyr Tyr Asp Phe Trp Ser Gly Tyr Pro
            100                 105                 110

Pro Gly Glu Glu Tyr Phe Gln Asp Trp Gly Gln Gly Thr Leu Val Ile
        115                 120                 125

Val Ser Ser
    130

<210> SEQ ID NO 156
<211> LENGTH: 131
<212> TYPE: PRT
<213> ORGANISM: homo sapiens

<400> SEQUENCE: 156

Glu Val Arg Leu Val Glu Ser Gly Gly Gly Leu Val Lys Pro Gly Gly
 1               5                  10                  15

Ser Leu Arg Leu Ser Cys Ser Ala Ser Gly Phe Asp Phe Asp Asn Ala
                20                  25                  30

Trp Met Thr Trp Val Arg Gln Pro Pro Gly Lys Gly Leu Glu Trp Val
             35                  40                  45

Gly Arg Ile Thr Gly Pro Gly Glu Gly Trp Ser Val Asp Tyr Ala Ala
        50                  55                  60

Pro Val Glu Gly Arg Phe Thr Ile Ser Arg Leu Asn Ser Ile Asn Phe
 65                  70                  75                  80

Leu Tyr Leu Glu Met Asn Asn Leu Arg Met Glu Asp Ser Gly Leu Tyr
                 85                  90                  95

Phe Cys Ala Arg Thr Gly Lys Tyr Tyr Asp Phe Trp Ser Gly Tyr Pro
            100                 105                 110

Pro Gly Glu Glu Tyr Phe Gln Asp Trp Gly Gln Gly Thr Leu Val Ile
        115                 120                 125

Val Pro Ser
    130

<210> SEQ ID NO 157
<211> LENGTH: 131
<212> TYPE: PRT
<213> ORGANISM: homo sapiens

<400> SEQUENCE: 157

Glu Val Arg Leu Ala Glu Ser Gly Gly Gly Leu Val Lys Pro Gly Gly
 1               5                  10                  15

Ser Leu Arg Leu Ser Cys Ser Ala Ser Gly Phe Asp Phe Asp Asn Ala
                20                  25                  30

Trp Met Thr Trp Val Arg Gln Pro Pro Gly Lys Gly Leu Glu Trp Val
             35                  40                  45

Gly Arg Ile Thr Gly Pro Gly Glu Gly Trp Ser Val Asp Tyr Ala Ala
        50                  55                  60

Pro Val Glu Gly Arg Phe Thr Ile Ser Arg Leu Asn Ser Ile Asn Phe
 65                  70                  75                  80

Leu Tyr Leu Glu Met Asn Asn Leu Arg Met Glu Asp Ser Gly Leu Tyr
                 85                  90                  95
```

```
Phe Cys Ala Arg Thr Gly Lys Tyr Tyr Asp Phe Trp Ser Gly Tyr Pro
                100                 105                 110

Pro Gly Glu Glu Tyr Phe Gln Asp Trp Gly Gln Gly Thr Leu Val Ile
        115                 120                 125

Val Pro Ser
    130

<210> SEQ ID NO 158
<211> LENGTH: 131
<212> TYPE: PRT
<213> ORGANISM: homo sapiens

<400> SEQUENCE: 158

Glu Val Arg Leu Val Glu Ser Gly Gly Gly Leu Val Lys Pro Gly Gly
1               5                   10                  15

Ser Leu Arg Leu Ser Cys Ser Ala Ser Gly Phe Asn Phe Asp Asp Ala
            20                  25                  30

Trp Met Thr Trp Val Arg Gln Pro Pro Gly Lys Gly Leu Glu Trp Val
        35                  40                  45

Gly Arg Ile Ser Gly Pro Gly Glu Gly Trp Ser Val Asp Tyr Ala Glu
    50                  55                  60

Ser Val Lys Gly Arg Phe Thr Ile Ser Arg Leu Asn Ser Ile Asn Phe
65                  70                  75                  80

Leu Tyr Leu Glu Met Asn Asn Val Arg Thr Glu Asp Thr Gly Tyr Tyr
                85                  90                  95

Phe Cys Ala Arg Thr Gly Lys His Tyr Asp Phe Trp Ser Gly Tyr Pro
                100                 105                 110

Pro Gly Glu Glu Tyr Phe Gln Asp Trp Gly Gln Gly Thr Leu Val Ile
        115                 120                 125

Val Ser Ser
    130

<210> SEQ ID NO 159
<211> LENGTH: 131
<212> TYPE: PRT
<213> ORGANISM: homo sapiens

<400> SEQUENCE: 159

Glu Val Arg Leu Val Glu Ser Gly Gly Arg Leu Val Arg Pro Gly Gly
1               5                   10                  15

Ser Leu Arg Leu Ser Cys Ser Ala Ser Gly Phe Asn Phe Asp Asn Ala
            20                  25                  30

Trp Met Thr Trp Val Arg Gln Pro Pro Gly Lys Gly Leu Glu Trp Val
        35                  40                  45

Gly Arg Ile Thr Gly Pro Gly Glu Gly Trp Ser Val Asp Tyr Ala Ala
    50                  55                  60

Ser Val Lys Gly Arg Phe Thr Ile Ser Arg Met Asn Ser Ile Asn Phe
65                  70                  75                  80

Phe Tyr Leu Glu Met Asn Asn Leu Lys Ile Glu Asp Thr Gly Leu Tyr
                85                  90                  95

Phe Cys Ala Arg Thr Gly Lys His Tyr Ala Phe Trp Gly Tyr Pro
                100                 105                 110

Pro Gly Glu Glu Tyr Leu Glu Asp Trp Gly Gln Gly Thr Leu Val Ile
        115                 120                 125

Val Ser Ser
    130
```

<210> SEQ ID NO 160
<211> LENGTH: 131
<212> TYPE: PRT
<213> ORGANISM: homo sapiens

<400> SEQUENCE: 160

Glu Val Arg Leu Val Glu Ser Gly Gly Arg Leu Val Pro Gly Gly
1               5                   10                  15

Ser Leu Arg Leu Ser Cys Ser Ala Ser Gly Phe Asn Phe Asp Asn Ala
            20                  25                  30

Trp Met Thr Trp Val Arg Gln Pro Pro Gly Lys Gly Leu Glu Trp Val
        35                  40                  45

Gly Arg Ile Thr Gly Pro Gly Glu Gly Trp Ser Val Asp Tyr Ala Ala
    50                  55                  60

Ser Val Lys Gly Arg Phe Thr Ile Ser Arg Met Asn Ser Ile Asn Phe
65                  70                  75                  80

Phe Tyr Leu Glu Met Asn Asn Leu Lys Ile Glu Asp Thr Gly Leu Tyr
                85                  90                  95

Phe Cys Ala Arg Thr Gly Lys His Tyr Ala Phe Trp Gly Tyr Pro
            100                 105                 110

Pro Gly Glu Glu Tyr Leu Glu Asp Trp Gly Gln Gly Thr Leu Val Ile
        115                 120                 125

Val Ser Ser
    130

<210> SEQ ID NO 161
<211> LENGTH: 131
<212> TYPE: PRT
<213> ORGANISM: homo sapiens

<400> SEQUENCE: 161

Glu Ile Arg Leu Val Glu Ser Gly Gly Gly Leu Val Lys Pro Gly Gly
1               5                   10                  15

Ser Leu Arg Leu Ser Cys Ser Ala Ser Gly Phe Asn Phe Asp Ser Ala
            20                  25                  30

Trp Met Thr Trp Val Arg Gln Pro Pro Gly Lys Gly Leu Glu Trp Val
        35                  40                  45

Gly Arg Ile Thr Gly Pro Gly Glu Gly Trp Ser Val Asp Tyr Ala Glu
    50                  55                  60

Ser Val Lys Gly Arg Phe Ile Ile Ser Arg Ile Asn Ser Ile Asn Phe
65                  70                  75                  80

Leu Tyr Leu Glu Met Asn Asn Leu Arg Pro Glu Asp Thr Gly Ser Tyr
                85                  90                  95

Phe Cys Ala His Thr Gly Lys His Tyr Asp Phe Trp Arg Gly Tyr Pro
            100                 105                 110

Pro Gly Glu Glu Tyr Phe Gln Asp Trp Gly Gln Gly Thr Gln Val Ile
        115                 120                 125

Val Ser Ser
    130

<210> SEQ ID NO 162
<211> LENGTH: 131
<212> TYPE: PRT
<213> ORGANISM: homo sapiens

<400> SEQUENCE: 162

Glu Ile Arg Leu Val Glu Ser Gly Gly Gly Leu Val Lys Pro Gly Gly

```
                1               5                  10                 15
            Ser Leu Arg Leu Ser Cys Ser Ala Ser Gly Phe Asn Phe Asp Ser Ala
                            20                  25                  30

Trp Met Thr Trp Val Arg Gln Pro Gly Lys Gly Leu Glu Trp Val
                        35                  40                  45

Gly Arg Ile Thr Gly Pro Gly Glu Gly Trp Ser Val Gly Tyr Ala Glu
                        50                  55                  60

Ser Val Lys Gly Arg Phe Ile Ile Ser Arg Ile Asn Ser Ile Asn Phe
            65                  70                  75                  80

Leu Tyr Leu Glu Met Asn Asn Leu Arg Pro Glu Asp Thr Gly Ser Tyr
                            85                  90                  95

Phe Cys Ala His Thr Gly Lys His Tyr Asp Phe Trp Arg Gly Tyr Pro
                            100                 105                 110

Pro Gly Glu Glu Tyr Phe Gln Asp Trp Gly Gln Gly Thr Gln Val Ile
                        115                 120                 125

Val Ser Ser
                    130
```

<210> SEQ ID NO 163
<211> LENGTH: 131
<212> TYPE: PRT
<213> ORGANISM: homo sapiens

<400> SEQUENCE: 163

```
            Glu Val Gln Leu Val Glu Ser Gly Gly Asp Leu Val Lys Pro Gly Gly
            1               5                  10                  15

Ser Leu Arg Leu Ser Cys Ser Ala Ser Gly Phe Ser Phe Lys Asn Thr
                            20                  25                  30

Trp Met Thr Trp Val Arg Gln Ala Pro Gly Lys Gly Leu Glu Trp Val
                        35                  40                  45

Gly Arg Ile Thr Gly Pro Gly Glu Gly Trp Thr Ser Asp Tyr Ala Ala
                        50                  55                  60

Thr Val Gln Gly Arg Phe Thr Ile Ser Arg Asn Asn Met Ile Asp Met
            65                  70                  75                  80

Leu Tyr Leu Glu Met Asn Arg Leu Arg Thr Asp Thr Gly Leu Tyr
                            85                  90                  95

Tyr Cys Val His Thr Glu Lys Tyr Tyr Asn Phe Trp Gly Gly Tyr Pro
                            100                 105                 110

Pro Gly Glu Glu Tyr Phe Gln His Trp Gly Arg Gly Thr Leu Val Ile
                        115                 120                 125

Val Ser Ser
                    130
```

<210> SEQ ID NO 164
<211> LENGTH: 109
<212> TYPE: PRT
<213> ORGANISM: homo sapiens

<400> SEQUENCE: 164

```
            Ser Ser Glu Leu Thr Gln Glu Thr Gly Val Ser Val Ala Leu Gly Arg
            1               5                  10                  15

Thr Val Thr Ile Thr Cys Arg Gly Asp Ser Leu Arg Ser His Tyr Ala
                            20                  25                  30

Ser Trp Tyr Gln Lys Lys Pro Gly Gln Ala Pro Ile Leu Leu Phe Tyr
                        35                  40                  45

Gly Lys Asn Asn Arg Pro Ser Gly Ile His Asp Arg Phe Ser Gly Ser
```

```
                 50                  55                  60
Ala Ser Gly Asn Arg Ala Ser Leu Thr Ile Ser Gly Ala Gln Ala Glu
 65                  70                  75                  80

Asp Asp Ala Glu Tyr Tyr Cys Ser Ser Arg Asp Lys Ser Gly Ser Arg
                 85                  90                  95

Leu Ser Val Phe Gly Gly Gly Thr Lys Leu Thr Val Leu
                100                 105
```

<210> SEQ ID NO 165
<211> LENGTH: 109
<212> TYPE: PRT
<213> ORGANISM: homo sapiens

<400> SEQUENCE: 165

```
Ser Ser Glu Leu Thr Gln Glu Thr Gly Val Ser Val Ala Leu Gly Arg
 1               5                  10                  15

Thr Val Thr Ile Thr Cys Arg Gly Asp Ser Leu Arg Ser His Tyr Ala
                20                  25                  30

Ser Trp Tyr Gln Lys Lys Pro Gly Gln Ala Pro Lys Leu Leu Phe Tyr
                35                  40                  45

Gly Lys Asn Asn Arg Pro Ser Gly Ile Pro Asp Arg Phe Ser Gly Ser
 50                  55                  60

Ala Ser Gly Asn Arg Ala Ser Leu Thr Ile Ser Gly Ala Gln Ala Glu
 65                  70                  75                  80

Asp Asp Ala Glu Tyr Tyr Cys Ser Ser Arg Asp Lys Ser Gly Ser Arg
                 85                  90                  95

Leu Ser Val Phe Gly Gly Gly Thr Lys Leu Thr Val Leu
                100                 105
```

<210> SEQ ID NO 166
<211> LENGTH: 109
<212> TYPE: PRT
<213> ORGANISM: homo sapiens

<400> SEQUENCE: 166

```
Ser Ser Glu Leu Thr Gln Glu Thr Gly Val Ser Val Ala Leu Gly Arg
 1               5                  10                  15

Thr Val Thr Ile Thr Cys Arg Gly Asp Ser Leu Arg Ser His Tyr Ala
                20                  25                  30

Ser Trp Tyr Gln Lys Lys Pro Gly Gln Ala Pro Lys Leu Leu Phe Tyr
                35                  40                  45

Gly Lys Asn Asn Arg Pro Ser Gly Ile Pro Asp Arg Phe Ser Gly Ser
 50                  55                  60

Ala Ser Gly Asn Arg Ala Ser Leu Thr Ile Ser Gly Ala Gln Ala Glu
 65                  70                  75                  80

Asp Asp Ala Glu Tyr Ile Cys Ser Ser Arg Asp Lys Ser Gly Ser Arg
                 85                  90                  95

Leu Ser Val Phe Gly Gly Gly Thr Lys Leu Thr Val Leu
                100                 105
```

<210> SEQ ID NO 167
<211> LENGTH: 109
<212> TYPE: PRT
<213> ORGANISM: homo sapiens

<400> SEQUENCE: 167

```
Ser Ser Glu Leu Thr Gln Glu Thr Gly Val Ser Val Ala Leu Gly Arg
 1               5                  10                  15
```

```
Thr Val Thr Ile Thr Cys Arg Gly Asp Ser Leu Arg Ser His Tyr Ala
            20                  25                  30

Ser Trp Tyr Gln Lys Lys Pro Gly Gln Ala Pro Lys Leu Leu Phe Tyr
            35                  40                  45

Gly Lys Asn Asn Arg Pro Ser Gly Ile Pro Asp Arg Phe Ser Gly Phe
50                      55                  60

Ala Ser Gly Asn Arg Ala Ser Leu Thr Ile Ser Gly Ala Gln Ala Glu
65                  70                  75                  80

Asp Asp Ala Glu Tyr Tyr Cys Ser Ser Arg Asp Lys Ser Gly Ser Arg
                85                  90                  95

Leu Ser Val Phe Gly Gly Gly Thr Lys Leu Thr Val Leu
                100                 105
```

<210> SEQ ID NO 168
<211> LENGTH: 109
<212> TYPE: PRT
<213> ORGANISM: homo sapiens

<400> SEQUENCE: 168

```
Ser Ser Glu Leu Thr Gln Glu Thr Gly Val Ser Val Ala Leu Gly Arg
1               5                   10                  15

Thr Val Thr Ile Thr Cys Arg Gly Asp Ser Leu Arg Ser His Tyr Ala
            20                  25                  30

Ser Trp Tyr Gln Glu Lys Pro Gly Gln Ala Pro Lys Leu Leu Phe Tyr
            35                  40                  45

Gly Lys Asn Asn Arg Pro Ser Gly Ile Pro Asp Arg Phe Ser Gly Ser
50                      55                  60

Ala Ser Gly Asn Arg Ala Ser Leu Thr Ile Ser Gly Ala Gln Ala Glu
65                  70                  75                  80

Asp Asp Ala Glu Tyr Tyr Cys Ser Ser Arg Asp Lys Ser Gly Ser Arg
                85                  90                  95

Leu Ser Val Phe Gly Gly Gly Thr Lys Leu Ala Val Leu
                100                 105
```

<210> SEQ ID NO 169
<211> LENGTH: 109
<212> TYPE: PRT
<213> ORGANISM: homo sapiens

<400> SEQUENCE: 169

```
Ser Ser Glu Leu Thr Gln Asp Pro Gly Val Ser Val Ala Leu Lys Gln
1               5                   10                  15

Thr Val Thr Ile Thr Cys Arg Gly Asp Ser Leu Arg Ser His Tyr Val
            20                  25                  30

Ser Trp Tyr Gln Lys Lys Pro Gly Gln Ala Pro Val Leu Val Phe Tyr
            35                  40                  45

Gly Lys Asn Asn Arg Pro Ser Gly Ile Pro Asp Arg Phe Ser Gly Ser
50                      55                  60

Thr Ser Gly Asn Thr Ala Ser Leu Thr Ile Ala Gly Ala Gln Ala Glu
65                  70                  75                  80

Asp Asp Ala Asp Tyr Tyr Cys Ser Ser Arg Asp Lys Ser Gly Ser Arg
                85                  90                  95

Leu Ser Val Phe Gly Gly Gly Thr Lys Leu Thr Val Leu
                100                 105
```

<210> SEQ ID NO 170

<211> LENGTH: 109
<212> TYPE: PRT
<213> ORGANISM: homo sapiens

<400> SEQUENCE: 170

Ala Ser Glu Leu Thr Gln Asp Pro Gly Val Ser Val Ala Leu Lys Gln
1               5                   10                  15

Thr Val Thr Ile Thr Cys Arg Gly Asp Ser Leu Arg Ser His Tyr Val
            20                  25                  30

Ser Trp Tyr Gln Lys Lys Pro Gly Gln Ala Pro Val Leu Val Phe Tyr
        35                  40                  45

Gly Lys Asn Asn Arg Pro Ser Gly Ile Pro Asp Arg Phe Ser Gly Ser
    50                  55                  60

Thr Ser Gly Asn Thr Ala Ser Leu Thr Ile Ala Gly Ala Gln Ala Glu
65                  70                  75                  80

Asp Asp Ala Asp Tyr Tyr Cys Ser Ser Arg Asp Lys Ser Gly Ser Arg
                85                  90                  95

Leu Ser Val Phe Gly Gly Gly Thr Lys Leu Thr Val Leu
            100                 105

<210> SEQ ID NO 171
<211> LENGTH: 109
<212> TYPE: PRT
<213> ORGANISM: homo sapiens

<400> SEQUENCE: 171

Ala Ser Glu Leu Thr Gln Asp Pro Gly Val Ser Val Ala Leu Glu Gln
1               5                   10                  15

Thr Val Thr Ile Thr Cys Arg Gly Asp Ser Leu Arg Ser His Tyr Val
            20                  25                  30

Ser Trp Tyr Gln Lys Lys Pro Gly Gln Ala Pro Val Leu Val Phe Tyr
        35                  40                  45

Gly Lys Asn Asn Arg Pro Ser Gly Ile Pro Asp Arg Phe Ser Gly Ser
    50                  55                  60

Thr Ser Gly Asn Thr Ala Ser Leu Thr Ile Ala Gly Ala Gln Ala Glu
65                  70                  75                  80

Asp Asp Ala Asp Tyr Tyr Cys Ser Ser Arg Asp Lys Ser Gly Ser Arg
                85                  90                  95

Leu Ser Val Phe Gly Gly Gly Thr Lys Leu Thr Val Leu
            100                 105

<210> SEQ ID NO 172
<211> LENGTH: 109
<212> TYPE: PRT
<213> ORGANISM: homo sapiens

<400> SEQUENCE: 172

Ala Ser Glu Leu Thr Gln Asp Pro Gly Val Ser Val Ala Leu Lys Gln
1               5                   10                  15

Thr Val Thr Ile Thr Cys Arg Gly Asp Ser Leu Arg Ser His Tyr Val
            20                  25                  30

Ser Trp Tyr Gln Lys Arg Pro Gly Gln Ala Pro Val Leu Val Phe Tyr
        35                  40                  45

Gly Lys Asn Asn Arg Pro Ser Gly Ile Pro Asp Arg Phe Ser Gly Ser
    50                  55                  60

Thr Ser Gly Asn Thr Ala Ser Leu Thr Ile Ala Gly Ala Gln Ala Glu
65                  70                  75                  80

Asp Asp Ala Asp Tyr Tyr Cys Ser Ser Arg Asp Lys Ser Gly Ser Arg
            85                  90                  95

Leu Ser Val Phe Gly Gly Gly Thr Lys Leu Thr Val Leu
            100                 105

<210> SEQ ID NO 173
<211> LENGTH: 109
<212> TYPE: PRT
<213> ORGANISM: homo sapiens

<400> SEQUENCE: 173

Ala Ser Glu Leu Thr Gln Asp Pro Ala Val Ser Val Ala Leu Lys Gln
1               5                   10                  15

Thr Val Thr Ile Thr Cys Arg Gly Asp Ser Leu Arg Ser His Tyr Val
            20                  25                  30

Ser Trp Tyr Gln Lys Lys Pro Gly Gln Ala Pro Val Leu Val Phe Tyr
            35                  40                  45

Gly Lys Asn Asn Arg Pro Ser Gly Ile Pro Asp Arg Phe Ser Gly Ser
        50                  55                  60

Ser Ser Gly Asn Thr Ala Ser Leu Thr Ile Ala Gly Ala Gln Ala Glu
65                  70                  75                  80

Asp Asp Ala Asp Tyr Tyr Cys Ser Ser Arg Asp Lys Ser Gly Ser Arg
            85                  90                  95

Leu Ser Val Phe Gly Gly Gly Thr Lys Leu Thr Val Leu
            100                 105

<210> SEQ ID NO 174
<211> LENGTH: 109
<212> TYPE: PRT
<213> ORGANISM: homo sapiens

<400> SEQUENCE: 174

Ser Ser Glu Leu Thr Gln Asp Pro Gly Val Ser Val Ala Leu Lys Gln
1               5                   10                  15

Thr Val Thr Ile Thr Cys Arg Gly Asp Ser Leu Arg Ser His Tyr Val
            20                  25                  30

Ser Trp Tyr Gln Lys Lys Pro Gly Gln Ala Pro Val Leu Val Phe Tyr
            35                  40                  45

Gly Lys Asn Ile Gly Pro Ser Gly Ile Pro Asp Arg Phe Ser Gly Ser
        50                  55                  60

Thr Ser Gly Asn Thr Ala Ser Leu Thr Ile Ala Gly Ala Gln Ala Glu
65                  70                  75                  80

Asp Asp Ala Asp Tyr Tyr Cys Ser Ser Arg Asp Lys Ser Gly Ser Arg
            85                  90                  95

Leu Ser Val Phe Gly Gly Gly Thr Lys Leu Thr Val Leu
            100                 105

<210> SEQ ID NO 175
<211> LENGTH: 109
<212> TYPE: PRT
<213> ORGANISM: homo sapiens

<400> SEQUENCE: 175

Ala Ser Glu Leu Thr Gln Asp Pro Ala Val Ser Val Ala Leu Lys Gln
1               5                   10                  15

Thr Val Thr Ile Thr Cys Arg Gly Asp Ser Leu Arg Ser His Tyr Val
            20                  25                  30

Ser Trp Tyr Gln Gln Lys Pro Gly Gln Ala Pro Val Leu Val Phe Tyr

```
                35                  40                  45
Gly Lys Asn Asn Arg Pro Ser Gly Ile Pro Asp Arg Phe Ser Gly Ser
         50                  55                  60

Ser Ser Gly Asn Thr Ala Ser Leu Thr Ile Ala Gly Ala Gln Ala Glu
 65                  70                  75                  80

Asp Asp Ala Asp Tyr Tyr Cys Ser Ser Arg Asp Lys Ser Gly Ser Arg
                 85                  90                  95

Leu Ser Val Phe Gly Gly Gly Thr Lys Leu Thr Val Leu
            100                 105
```

<210> SEQ ID NO 176
<211> LENGTH: 109
<212> TYPE: PRT
<213> ORGANISM: homo sapiens

<400> SEQUENCE: 176

```
Ala Ser Glu Leu Thr Gln Asp Pro Ala Val Ser Val Ala Phe Glu Lys
 1               5                  10                  15

Thr Val Thr Ile Thr Cys Gln Gly Asp Ser Leu Arg Ser His Tyr Val
                 20                  25                  30

Ser Trp Tyr Gln Lys Arg Pro Gly Gln Ala Pro Val Leu Val Phe Tyr
                35                  40                  45

Gly Lys Asn Asn Arg Pro Ser Gly Ile Pro Asp Arg Phe Ser Gly Ser
         50                  55                  60

Thr Ser Gly Asn Thr Ala Ser Leu Thr Ile Ala Gly Ala Gln Ala Glu
 65                  70                  75                  80

Asp Asp Ala Asp Tyr Tyr Cys Ser Ser Arg Asp Lys Ser Gly Ser Arg
                 85                  90                  95

Leu Ser Val Phe Gly Gly Gly Thr Lys Leu Thr Val Pro
            100                 105
```

<210> SEQ ID NO 177
<211> LENGTH: 109
<212> TYPE: PRT
<213> ORGANISM: homo sapiens

<400> SEQUENCE: 177

```
Ser Ser Asp Leu Thr Gln Asp Pro Ala Val Ser Val Ala Leu Gly Gln
 1               5                  10                  15

Thr Val Arg Ile Thr Cys Gln Gly Asp Ser Leu Arg Arg Tyr Tyr Ala
                 20                  25                  30

Gly Trp Tyr Gln Gln Lys Pro Gly Gln Ala Pro Val Leu Val Val Tyr
                35                  40                  45

Gly Arg Asp Asn Arg Pro Ser Gly Ile Pro Asp Arg Phe Ser Gly Ser
         50                  55                  60

Thr Ser Gly Asn Thr Ala Ser Leu Thr Ile Ala Gly Ala Gln Ala Glu
 65                  70                  75                  80

Asp Asp Ala Asp Tyr Tyr Cys Ser Ser Arg Asp Lys Ser Gly Ser Arg
                 85                  90                  95

Leu Ser Val Phe Gly Gly Gly Thr Lys Leu Thr Val Leu
            100                 105
```

<210> SEQ ID NO 178
<211> LENGTH: 109
<212> TYPE: PRT
<213> ORGANISM: homo sapiens

<400> SEQUENCE: 178

Ala Ser Glu Leu Thr Gln Asp Pro Thr Val Ser Val Ala Leu Gly Gln
1               5                   10                  15

Thr Val Thr Ile Thr Cys Arg Gly Asp Ser Leu Arg Asn His Tyr Thr
            20                  25                  30

Ser Trp Tyr Gln Gln Lys Thr Gly Gln Ala Pro Ile Leu Leu Ile Tyr
        35                  40                  45

Pro Lys His Asn Arg Pro Pro Gly Ile Ser Asp Arg Phe Ser Ala Ser
    50                  55                  60

Ser Ser Gly Asn Thr Ala Ser Leu Thr Ile Thr Gly Ala Gln Thr Glu
65              70                  75                  80

Asp Glu Gly Asp Tyr Tyr Cys Ser Ser Arg Asp Lys Ser Gly Ser Arg
                85                  90                  95

Leu Val Thr Phe Gly Gly Gly Thr Lys Leu Thr Val Leu
            100                 105

<210> SEQ ID NO 179
<211> LENGTH: 109
<212> TYPE: PRT
<213> ORGANISM: homo sapiens

<400> SEQUENCE: 179

Ala Ser Glu Leu Thr Gln Asp Pro Thr Val Ser Val Ala Leu Gly Gln
1               5                   10                  15

Thr Val Thr Ile Thr Cys Arg Gly Asp Ser Leu Arg Asn Tyr Tyr Thr
            20                  25                  30

Ser Trp Tyr Gln Gln Lys Pro Gly Gln Ala Pro Val Leu Leu Ile Tyr
        35                  40                  45

Pro Lys His Asn Arg Pro Pro Gly Ile Ser Asp Arg Phe Ser Ala Ser
    50                  55                  60

Ser Ser Gly Asn Thr Ala Ser Leu Thr Ile Thr Gly Ala Gln Thr Glu
65              70                  75                  80

Asp Glu Gly Asp Tyr Tyr Cys Ser Ser Arg Asp Lys Ser Gly Ser Arg
                85                  90                  95

Leu Val Thr Phe Gly Gly Gly Thr Lys Leu Thr Val Leu
            100                 105

<210> SEQ ID NO 180
<211> LENGTH: 109
<212> TYPE: PRT
<213> ORGANISM: homo sapiens

<400> SEQUENCE: 180

Ala Ser Glu Leu Thr Gln Asp Pro Thr Val Ser Val Ala Leu Gly Gln
1               5                   10                  15

Thr Val Thr Ile Thr Cys Arg Gly Asp Ser Leu Arg Asn Tyr Tyr Thr
            20                  25                  30

Ser Trp Tyr Gln Gln Lys Pro Arg Gln Ala Pro Val Leu Leu Ile Tyr
        35                  40                  45

Pro Lys His Asn Arg Pro Pro Gly Ile Ser Asp Arg Phe Ser Ala Ser
    50                  55                  60

Ser Ser Gly Asn Thr Ala Ser Leu Thr Ile Thr Gly Ala Gln Thr Glu
65              70                  75                  80

Asp Glu Gly Asp Tyr Tyr Cys Ser Ser Arg Asp Lys Ser Gly Ser Arg
                85                  90                  95

Leu Val Thr Phe Gly Gly Gly Thr Lys Leu Thr Val Leu
            100                 105

<210> SEQ ID NO 181
<211> LENGTH: 109
<212> TYPE: PRT
<213> ORGANISM: homo sapiens

<400> SEQUENCE: 181

Ala Ser Glu Leu Thr Gln Asp Pro Thr Val Ser Val Ala Leu Gly Gln
1               5                   10                  15

Thr Val Thr Ile Thr Cys Arg Gly Asp Ser Leu Arg Asn His Tyr Thr
            20                  25                  30

Ser Trp Tyr Gln Gln Lys Thr Gly Gln Ala Pro Val Leu Leu Ile Tyr
        35                  40                  45

Pro Lys His Asn Arg Ser Pro Gly Ile Ser Asp Arg Phe Ser Ala Ser
    50                  55                  60

Ser Ser Gly Asn Thr Ala Ser Leu Thr Ile Thr Gly Ala Gln Thr Glu
65                  70                  75                  80

Asp Glu Gly Asp Tyr Tyr Cys Ser Ser Arg Asp Lys Ser Gly Ser Arg
                85                  90                  95

Leu Val Thr Phe Gly Gly Gly Thr Lys Val Thr Val Leu
            100                 105

<210> SEQ ID NO 182
<211> LENGTH: 109
<212> TYPE: PRT
<213> ORGANISM: homo sapiens

<400> SEQUENCE: 182

Ala Ser Glu Leu Thr Gln Asp Pro Thr Val Ser Val Ala Leu Gly Gln
1               5                   10                  15

Thr Val Thr Ile Thr Cys Arg Gly Asp Ser Leu Arg Asn Tyr Tyr Thr
            20                  25                  30

Ser Trp Tyr Gln Gln Lys Pro Gly Gln Ala Pro Val Leu Leu Ile Tyr
        35                  40                  45

Pro Lys His Asn Arg Pro Pro Gly Ile Ser Asp Arg Phe Ser Ala Ser
    50                  55                  60

Ser Ser Gly Asn Thr Ala Ser Leu Thr Ile Thr Gly Ala Gln Thr Glu
65                  70                  75                  80

Asp Glu Gly Asp Tyr Tyr Cys Ser Ser Arg Asp Lys Ser Gly Ser Arg
                85                  90                  95

Leu Val Thr Phe Gly Arg Gly Thr Lys Leu Thr Val Val
            100                 105

<210> SEQ ID NO 183
<211> LENGTH: 109
<212> TYPE: PRT
<213> ORGANISM: homo sapiens

<400> SEQUENCE: 183

Ala Ser Glu Leu Thr Gln Asp Pro Thr Val Ser Val Ala Leu Gly Gln
1               5                   10                  15

Thr Val Thr Ile Thr Cys Arg Gly Asp Ser Leu Arg Asn Tyr Tyr Thr
            20                  25                  30

Ser Trp Tyr Gln Gln Lys Pro Gly Gln Ala Pro Val Leu Leu Ile Tyr
        35                  40                  45

Pro Lys His Asn Arg Pro Pro Gly Ile Ser Asp Arg Phe Ser Ala Ser
    50                  55                  60

```
Ser Ser Gly Asn Thr Ala Ser Leu Thr Ile Thr Gly Ala Gln Thr Glu
 65                  70                  75                  80

Asp Glu Gly Asp Tyr Tyr Cys Ser Ser Arg Asp Lys Ser Gly Ser Arg
                 85                  90                  95

Leu Val Thr Phe Gly Gly Gly Thr Lys Val Thr Gly Leu
            100                 105
```

<210> SEQ ID NO 184
<211> LENGTH: 109
<212> TYPE: PRT
<213> ORGANISM: homo sapiens

<400> SEQUENCE: 184

```
Ala Ser Glu Leu Thr Gln Asp Pro Thr Val Ser Val Ala Leu Gly Gln
 1               5                   10                  15

Thr Val Thr Ile Thr Cys Arg Gly Asp Ser Leu Arg Asn His Tyr Thr
                 20                  25                  30

Ser Trp Tyr Gln Gln Lys Thr Gly Gln Ala Pro Val Leu Leu Ile Tyr
             35                  40                  45

Pro Lys His Asn Arg Ser Pro Gly Ile Ser Asp Arg Phe Ser Ala Ser
         50                  55                  60

Ser Ser Gly Asn Thr Ala Ser Leu Thr Ile Thr Gly Ala Gln Thr Glu
 65                  70                  75                  80

Asp Glu Gly Asp Tyr Tyr Cys Ser Ser Arg Asp Lys Ser Gly Ser Arg
                 85                  90                  95

Leu Val Thr Phe Gly Gly Gly Thr Lys Val Thr Val Val
            100                 105
```

<210> SEQ ID NO 185
<211> LENGTH: 109
<212> TYPE: PRT
<213> ORGANISM: homo sapiens

<400> SEQUENCE: 185

```
Ala Ser Glu Leu Thr Gln Asp Pro Thr Val Ser Val Ala Leu Gly Gln
 1               5                   10                  15

Thr Val Thr Ile Thr Cys Arg Gly Asp Ser Leu Arg Asn His Tyr Thr
                 20                  25                  30

Ser Trp Tyr Gln Gln Lys Thr Gly Gln Ala Pro Val Leu Leu Ile Tyr
             35                  40                  45

Pro Lys His Asn Arg Ser Pro Gly Ile Ser Asp Arg Phe Ser Ala Ser
         50                  55                  60

Ser Ser Gly Asn Thr Ala Ser Leu Thr Ile Thr Gly Ala Gln Thr Glu
 65                  70                  75                  80

Asp Glu Gly Asp Tyr Tyr Cys Ser Ser Arg Asp Lys Ser Gly Ser Arg
                 85                  90                  95

Leu Val Thr Phe Gly Gly Gly Thr Glu Val Thr Gly Leu
            100                 105
```

<210> SEQ ID NO 186
<211> LENGTH: 109
<212> TYPE: PRT
<213> ORGANISM: homo sapiens

<400> SEQUENCE: 186

```
Ala Ser Glu Leu Thr Gln Asp Pro Thr Val Ser Val Ala Leu Gly Gln
 1               5                   10                  15

Thr Val Thr Ile Thr Cys Arg Gly Asp Ser Leu Arg Asn His Tyr Thr
```

```
            20                  25                  30
Ser Trp Tyr Gln Gln Lys Thr Gly Gln Ala Pro Val Leu Leu Ile Tyr
         35                  40                  45

Pro Lys His Asn Arg Ser Pro Gly Ile Ser Asp Arg Phe Ser Arg Ser
     50                  55                  60

Ser Ser Gly Asn Thr Ala Ser Leu Thr Ile Thr Gly Ala Gln Thr Glu
 65                  70                  75                  80

Asp Glu Gly Asp Tyr Tyr Cys Ser Ser Arg Asp Lys Ser Gly Ser Arg
                 85                  90                  95

Leu Val Thr Phe Gly Gly Gly Thr Glu Arg Ser Thr Val
            100                 105
```

<210> SEQ ID NO 187
<211> LENGTH: 131
<212> TYPE: PRT
<213> ORGANISM: homo sapiens
<220> FEATURE:
<221> NAME/KEY: misc_feature
<222> LOCATION: (2)..(2)
<223> OTHER INFORMATION: Xaa can be V or I
<220> FEATURE:
<221> NAME/KEY: misc_feature
<222> LOCATION: (3)..(3)
<223> OTHER INFORMATION: Xaa can be Q or R
<220> FEATURE:
<221> NAME/KEY: misc_feature
<222> LOCATION: (5)..(5)
<223> OTHER INFORMATION: Xaa can be V or A
<220> FEATURE:
<221> NAME/KEY: misc_feature
<222> LOCATION: (10)..(10)
<223> OTHER INFORMATION: Xaa can be G, R, or D
<220> FEATURE:
<221> NAME/KEY: misc_feature
<222> LOCATION: (13)..(13)
<223> OTHER INFORMATION: Xaa can be K or R
<220> FEATURE:
<221> NAME/KEY: misc_feature
<222> LOCATION: (23)..(23)
<223> OTHER INFORMATION: Xaa can be S or A
<220> FEATURE:
<221> NAME/KEY: misc_feature
<222> LOCATION: (28)..(28)
<223> OTHER INFORMATION: Xaa can be D, N, S, A, or W
<220> FEATURE:
<221> NAME/KEY: misc_feature
<222> LOCATION: (30)..(30)
<223> OTHER INFORMATION: Xaa can be D, K, W or A
<220> FEATURE:
<221> NAME/KEY: misc_feature
<222> LOCATION: (31)..(31)
<223> OTHER INFORMATION: Xaa can be N, S, D, A, W, F, or Y
<220> FEATURE:
<221> NAME/KEY: misc_feature
<222> LOCATION: (32)..(32)
<223> OTHER INFORMATION: Xaa can be A, T, or Q
<220> FEATURE:
<221> NAME/KEY: misc_feature
<222> LOCATION: (40)..(40)
<223> OTHER INFORMATION: Xaa can be P, or A
<220> FEATURE:
<221> NAME/KEY: misc_feature
<222> LOCATION: (52)..(52)
<223> OTHER INFORMATION: Xaa can be T, S, or A
<220> FEATURE:
<221> NAME/KEY: misc_feature
<222> LOCATION: (54)..(54)
<223> OTHER INFORMATION: Xaa can be P or W
<220> FEATURE:
<221> NAME/KEY: misc_feature
<222> LOCATION: (56)..(56)
<223> OTHER INFORMATION: Xaa can be E, A, F, L, M, V, or W
<220> FEATURE:

```
<221> NAME/KEY: misc_feature
<222> LOCATION: (57)..(57)
<223> OTHER INFORMATION: Xaa can be G or W
<220> FEATURE:
<221> NAME/KEY: misc_feature
<222> LOCATION: (59)..(59)
<223> OTHER INFORMATION: Xaa can be S, T, A, or H
<220> FEATURE:
<221> NAME/KEY: misc_feature
<222> LOCATION: (60)..(60)
<223> OTHER INFORMATION: Xaa can be V or S
<220> FEATURE:
<221> NAME/KEY: misc_feature
<222> LOCATION: (61)..(61)
<223> OTHER INFORMATION: Xaa can be D, G, or A
<220> FEATURE:
<221> NAME/KEY: misc_feature
<222> LOCATION: (64)..(64)
<223> OTHER INFORMATION: Xaa can be A or E
<220> FEATURE:
<221> NAME/KEY: misc_feature
<222> LOCATION: (65)..(65)
<223> OTHER INFORMATION: Xaa can be P, S, or T
<220> FEATURE:
<221> NAME/KEY: misc_feature
<222> LOCATION: (67)..(67)
<223> OTHER INFORMATION: Xaa can be E, K, or Q
<220> FEATURE:
<221> NAME/KEY: misc_feature
<222> LOCATION: (71)..(71)
<223> OTHER INFORMATION: Xaa can be T or I
<220> FEATURE:
<221> NAME/KEY: misc_feature
<222> LOCATION: (75)..(75)
<223> OTHER INFORMATION: Xaa can be L, D, M, I, or N
<220> FEATURE:
<221> NAME/KEY: misc_feature
<222> LOCATION: (76)..(76)
<223> OTHER INFORMATION: Xaa can be N or D
<220> FEATURE:
<221> NAME/KEY: misc_feature
<222> LOCATION: (77)..(77)
<223> OTHER INFORMATION: Xaa can be S, M, W, F, L, or M
<220> FEATURE:
<221> NAME/KEY: misc_feature
<222> LOCATION: (78)..(78)
<223> OTHER INFORMATION: Xaa can be I or K
<220> FEATURE:
<221> NAME/KEY: misc_feature
<222> LOCATION: (79)..(79)
<223> OTHER INFORMATION: Xaa can be N or D
<220> FEATURE:
<221> NAME/KEY: misc_feature
<222> LOCATION: (80)..(80)
<223> OTHER INFORMATION: Xaa can be F, T. or M
<220> FEATURE:
<221> NAME/KEY: misc_feature
<222> LOCATION: (81)..(81)
<223> OTHER INFORMATION: Xaa can be L or F
<220> FEATURE:
<221> NAME/KEY: misc_feature
<222> LOCATION: (84)..(84)
<223> OTHER INFORMATION: Xaa can be E or Q
<220> FEATURE:
<221> NAME/KEY: misc_feature
<222> LOCATION: (87)..(87)
<223> OTHER INFORMATION: Xaa can be N, S, or R
<220> FEATURE:
<221> NAME/KEY: misc_feature
<222> LOCATION: (88)..(88)
<223> OTHER INFORMATION: Xaa can be L or V
<220> FEATURE:
<221> NAME/KEY: misc_feature
<222> LOCATION: (89)..(89)
<223> OTHER INFORMATION: Xaa can be R, or K
<220> FEATURE:
<221> NAME/KEY: misc_feature
<222> LOCATION: (90)..(90)
<223> OTHER INFORMATION: Xaa can be M, T, I, or P
```

```
<220> FEATURE:
<221> NAME/KEY: misc_feature
<222> LOCATION: (91)..(91)
<223> OTHER INFORMATION: Xaa can be E or D
<220> FEATURE:
<221> NAME/KEY: misc_feature
<222> LOCATION: (93)..(93)
<223> OTHER INFORMATION: Xaa can be S, T or W
<220> FEATURE:
<221> NAME/KEY: misc_feature
<222> LOCATION: (94)..(94)
<223> OTHER INFORMATION: Xaa can be G, A, or W
<220> FEATURE:
<221> NAME/KEY: misc_feature
<222> LOCATION: (95)..(95)
<223> OTHER INFORMATION: Xaa can be L, V, S or Y
<220> FEATURE:
<221> NAME/KEY: misc_feature
<222> LOCATION: (97)..(97)
<223> OTHER INFORMATION: Xaa can be F, or Y
<220> FEATURE:
<221> NAME/KEY: misc_feature
<222> LOCATION: (99)..(99)
<223> OTHER INFORMATION: Xaa can be A, T or V
<220> FEATURE:
<221> NAME/KEY: misc_feature
<222> LOCATION: (100)..(100)
<223> OTHER INFORMATION: Xaa can be R, T, or H
<220> FEATURE:
<221> NAME/KEY: misc_feature
<222> LOCATION: (102)..(102)
<223> OTHER INFORMATION: Xaa can be G or E
<220> FEATURE:
<221> NAME/KEY: misc_feature
<222> LOCATION: (104)..(104)
<223> OTHER INFORMATION: Xaa can be Y or H
<220> FEATURE:
<221> NAME/KEY: misc_feature
<222> LOCATION: (106)..(106)
<223> OTHER INFORMATION: Xaa can be D, A, or N
<220> FEATURE:
<221> NAME/KEY: misc_feature
<222> LOCATION: (109)..(109)
<223> OTHER INFORMATION: Xaa can be S, G, or R
<220> FEATURE:
<221> NAME/KEY: misc_feature
<222> LOCATION: (111)..(111)
<223> OTHER INFORMATION: Xaa can be Y or A
<220> FEATURE:
<221> NAME/KEY: misc_feature
<222> LOCATION: (118)..(118)
<223> OTHER INFORMATION: Xaa can be F or L
<220> FEATURE:
<221> NAME/KEY: misc_feature
<222> LOCATION: (119)..(119)
<223> OTHER INFORMATION: Xaa can be Q or E
<220> FEATURE:
<221> NAME/KEY: misc_feature
<222> LOCATION: (120)..(120)
<223> OTHER INFORMATION: Xaa can be D or H
<220> FEATURE:
<221> NAME/KEY: misc_feature
<222> LOCATION: (123)..(123)
<223> OTHER INFORMATION: Xaa can be R or Q
<220> FEATURE:
<221> NAME/KEY: misc_feature
<222> LOCATION: (126)..(126)
<223> OTHER INFORMATION: Xaa can be L or Q
<220> FEATURE:
<221> NAME/KEY: misc_feature
<222> LOCATION: (128)..(128)
<223> OTHER INFORMATION: Xaa can be T or I
<220> FEATURE:
<221> NAME/KEY: misc_feature
<222> LOCATION: (130)..(130)
<223> OTHER INFORMATION: Xaa can be S or P

<400> SEQUENCE: 187
```

```
Glu Xaa Xaa Leu Xaa Glu Ser Gly Gly Xaa Leu Val Xaa Pro Gly Gly
1               5                   10                  15

Ser Leu Arg Leu Ser Cys Xaa Ala Ser Gly Phe Xaa Phe Xaa Xaa Xaa
            20                  25                  30

Trp Met Thr Trp Val Arg Gln Xaa Pro Gly Lys Gly Leu Glu Trp Val
            35                  40                  45

Gly Arg Ile Xaa Gly Xaa Gly Xaa Xaa Trp Xaa Xaa Xaa Tyr Ala Xaa
        50                  55                  60

Xaa Val Xaa Gly Arg Phe Xaa Ile Ser Arg Xaa Xaa Xaa Xaa Xaa Xaa
65              70                  75                  80

Xaa Tyr Leu Xaa Met Asn Xaa Xaa Xaa Xaa Asp Xaa Xaa Xaa Tyr
            85                  90                  95

Xaa Cys Xaa Xaa Thr Xaa Lys Xaa Tyr Xaa Phe Trp Xaa Gly Xaa Pro
            100                 105                 110

Pro Gly Glu Glu Tyr Xaa Xaa Xaa Trp Gly Xaa Gly Thr Xaa Val Xaa
            115                 120                 125

Val Xaa Ser
    130

<210> SEQ ID NO 188
<211> LENGTH: 109
<212> TYPE: PRT
<213> ORGANISM: homo sapiens
<220> FEATURE:
<221> NAME/KEY: misc_feature
<222> LOCATION: (1)..(1)
<223> OTHER INFORMATION: X can be S or A
<220> FEATURE:
<221> NAME/KEY: misc_feature
<222> LOCATION: (2)..(2)
<223> OTHER INFORMATION: X can be Y or S
<220> FEATURE:
<221> NAME/KEY: misc_feature
<222> LOCATION: (3)..(3)
<223> OTHER INFORMATION: X can be E or D
<220> FEATURE:
<221> NAME/KEY: misc_feature
<222> LOCATION: (7)..(7)
<223> OTHER INFORMATION: X can be E or D
<220> FEATURE:
<221> NAME/KEY: misc_feature
<222> LOCATION: (8)..(8)
<223> OTHER INFORMATION: X can be T or P
<220> FEATURE:
<221> NAME/KEY: misc_feature
<222> LOCATION: (9)..(9)
<223> OTHER INFORMATION: X can be G, A, or T
<220> FEATURE:
<221> NAME/KEY: misc_feature
<222> LOCATION: (14)..(14)
<223> OTHER INFORMATION: X can be L or F
<220> FEATURE:
<221> NAME/KEY: misc_feature
<222> LOCATION: (15)..(15)
<223> OTHER INFORMATION: X can be G, K, or E
<220> FEATURE:
<221> NAME/KEY: misc_feature
<222> LOCATION: (16)..(16)
<223> OTHER INFORMATION: X can be R, Q, or K
<220> FEATURE:
<221> NAME/KEY: misc_feature
<222> LOCATION: (19)..(19)
<223> OTHER INFORMATION: X can be T or R
<220> FEATURE:
<221> NAME/KEY: misc_feature
<222> LOCATION: (23)..(23)
<223> OTHER INFORMATION: X can be R or Q
<220> FEATURE:
<221> NAME/KEY: misc_feature
<222> LOCATION: (29)..(29)
```

```
<223> OTHER INFORMATION: X can be S, R, or N
<220> FEATURE:
<221> NAME/KEY: misc_feature
<222> LOCATION: (30)..(30)
<223> OTHER INFORMATION: X can be H or Y
<220> FEATURE:
<221> NAME/KEY: misc_feature
<222> LOCATION: (32)..(32)
<223> OTHER INFORMATION: X can be A, V, or T
<220> FEATURE:
<221> NAME/KEY: misc_feature
<222> LOCATION: (33)..(33)
<223> OTHER INFORMATION: X can be S or G
<220> FEATURE:
<221> NAME/KEY: misc_feature
<222> LOCATION: (37)..(37)
<223> OTHER INFORMATION: X can be K, E, or Q
<220> FEATURE:
<221> NAME/KEY: misc_feature
<222> LOCATION: (38)..(38)
<223> OTHER INFORMATION: X can be K or R
<220> FEATURE:
<221> NAME/KEY: misc_feature
<222> LOCATION: (39)..(39)
<223> OTHER INFORMATION: X can be P or T
<220> FEATURE:
<221> NAME/KEY: misc_feature
<222> LOCATION: (40)..(40)
<223> OTHER INFORMATION: X can be G or R
<220> FEATURE:
<221> NAME/KEY: misc_feature
<222> LOCATION: (44)..(44)
<223> OTHER INFORMATION: X can be I, V,
<220> FEATURE:
<221> NAME/KEY: misc_feature
<222> LOCATION: (46)..(46)
<223> OTHER INFORMATION: X can be L or V
<220> FEATURE:
<221> NAME/KEY: misc_feature
<222> LOCATION: (47)..(47)
<223> OTHER INFORMATION: X can be F, V, or I
<220> FEATURE:
<221> NAME/KEY: misc_feature
<222> LOCATION: (49)..(49)
<223> OTHER INFORMATION: X can be G or P
<220> FEATURE:
<221> NAME/KEY: misc_feature
<222> LOCATION: (50)..(50)
<223> OTHER INFORMATION: X can be K or R
<220> FEATURE:
<221> NAME/KEY: misc_feature
<222> LOCATION: (51)..(51)
<223> OTHER INFORMATION: X can be N, D, or H
<220> FEATURE:
<221> NAME/KEY: misc_feature
<222> LOCATION: (52)..(52)
<223> OTHER INFORMATION: X can be N or I
<220> FEATURE:
<221> NAME/KEY: misc_feature
<222> LOCATION: (56)..(56)
<223> OTHER INFORMATION: X can be G, I, or P
<220> FEATURE:
<221> NAME/KEY: misc_feature
<222> LOCATION: (57)..(57)
<223> OTHER INFORMATION: X can be V or I
<220> FEATURE:
<221> NAME/KEY: misc_feature
<222> LOCATION: (58)..(58)
<223> OTHER INFORMATION: X can be P, H, or S
<220> FEATURE:
<221> NAME/KEY: misc_feature
<222> LOCATION: (63)..(63)
<223> OTHER INFORMATION: X can be G or A
<220> FEATURE:
<221> NAME/KEY: misc_feature
<222> LOCATION: (64)..(64)
<223> OTHER INFORMATION: X can be S or F
<220> FEATURE:
<221> NAME/KEY: misc_feature
```

```
<222> LOCATION: (65)..(65)
<223> OTHER INFORMATION: X can be A, T, or S
<220> FEATURE:
<221> NAME/KEY: misc_feature
<222> LOCATION: (69)..(69)
<223> OTHER INFORMATION: X can be R or T
<220> FEATURE:
<221> NAME/KEY: misc_feature
<222> LOCATION: (75)..(75)
<223> OTHER INFORMATION: X can be S, A, or T
<220> FEATURE:
<221> NAME/KEY: misc_feature
<222> LOCATION: (78)..(78)
<223> OTHER INFORMATION: X can be Q or E
<220> FEATURE:
<221> NAME/KEY: misc_feature
<222> LOCATION: (79)..(79)
<223> OTHER INFORMATION: X can be A or G
<220> FEATURE:
<221> NAME/KEY: misc_feature
<222> LOCATION: (80)..(80)
<223> OTHER INFORMATION: X can be E or D
<220> FEATURE:
<221> NAME/KEY: misc_feature
<222> LOCATION: (82)..(82)
<223> OTHER INFORMATION: X can be D, E, or I
<220> FEATURE:
<221> NAME/KEY: misc_feature
<222> LOCATION: (84)..(84)
<223> OTHER INFORMATION: X can be E or D
<220> FEATURE:
<221> NAME/KEY: misc_feature
<222> LOCATION: (98)..(98)
<223> OTHER INFORMATION: X can be S, V
<220> FEATURE:
<221> NAME/KEY: misc_feature
<222> LOCATION: (99)..(99)
<223> OTHER INFORMATION: X can be V, T
<220> FEATURE:
<221> NAME/KEY: misc_feature
<222> LOCATION: (102)..(102)
<223> OTHER INFORMATION: X can be G, R
<220> FEATURE:
<221> NAME/KEY: misc_feature
<222> LOCATION: (105)..(105)
<223> OTHER INFORMATION: X can be K or E
<220> FEATURE:
<221> NAME/KEY: misc_feature
<222> LOCATION: (106)..(106)
<223> OTHER INFORMATION: X can be L, V, or R
<220> FEATURE:
<221> NAME/KEY: misc_feature
<222> LOCATION: (107)..(107)
<223> OTHER INFORMATION: X can be T, S, or A
<220> FEATURE:
<221> NAME/KEY: misc_feature
<222> LOCATION: (108)..(108)
<223> OTHER INFORMATION: X can be V, T, or G
<220> FEATURE:
<221> NAME/KEY: misc_feature
<222> LOCATION: (109)..(109)
<223> OTHER INFORMATION: X can be L, V, or P

<400> SEQUENCE: 188

Xaa Xaa Xaa Leu Thr Gln Xaa Xaa Xaa Val Ser Val Ala Xaa Xaa Xaa
1               5                   10                  15

Thr Val Xaa Ile Thr Cys Xaa Gly Asp Ser Leu Arg Xaa Xaa Tyr Xaa
            20                  25                  30

Xaa Trp Tyr Gln Xaa Xaa Xaa Xaa Gln Ala Pro Xaa Leu Xaa Xaa Tyr
        35                  40                  45

Xaa Xaa Xaa Xaa Arg Pro Ser Xaa Xaa Xaa Asp Arg Phe Ser Xaa Xaa
    50                  55                  60

Xaa Ser Gly Asn Xaa Ala Ser Leu Thr Ile Xaa Gly Ala Xaa Xaa Xaa
65                  70                  75                  80
```

```
Asp Xaa Ala Xaa Tyr Tyr Cys Ser Ser Arg Asp Lys Ser Gly Ser Arg
            85                  90                  95

Leu Xaa Xaa Phe Gly Xaa Gly Thr Xaa Xaa Xaa Xaa Xaa
            100                 105
```

<210> SEQ ID NO 189
<211> LENGTH: 131
<212> TYPE: PRT
<213> ORGANISM: homosapiens

<400> SEQUENCE: 189

```
Glu Val Arg Leu Ala Glu Ser Gly Gly Gly Leu Val Lys Pro Gly Gly
1               5                   10                  15

Ser Leu Arg Leu Ser Cys Ser Ala Ser Gly Phe Asp Phe Asp Asn Ala
            20                  25                  30

Trp Met Thr Trp Val Arg Gln Pro Pro Gly Lys Gly Leu Glu Trp Val
        35                  40                  45

Gly Arg Ile Thr Gly Pro Gly Glu Gly Trp Ser Val Asp Tyr Ala Ala
    50                  55                  60

Pro Val Glu Gly Arg Phe Thr Ile Ser Arg Leu Asn Ala Ile Asn Phe
65                  70                  75                  80

Leu Tyr Leu Glu Met Asn Asn Leu Arg Met Glu Asp Ser Gly Leu Tyr
                85                  90                  95

Phe Cys Ala Arg Thr Gly Lys Tyr Tyr Asp Phe Trp Ser Gly Tyr Pro
            100                 105                 110

Pro Gly Glu Glu Tyr Phe Gln Asp Trp Gly Arg Gly Thr Leu Val Ile
        115                 120                 125

Val Ser Ser
    130
```

<210> SEQ ID NO 190
<211> LENGTH: 131
<212> TYPE: PRT
<213> ORGANISM: homosapiens

<400> SEQUENCE: 190

```
Glu Val Arg Leu Ala Glu Ser Gly Gly Gly Leu Val Lys Pro Gly Gly
1               5                   10                  15

Ser Leu Arg Leu Ser Cys Ser Ala Ser Gly Phe Asp Phe Asp Asn Ala
            20                  25                  30

Trp Met Thr Trp Val Arg Gln Pro Pro Gly Lys Gly Leu Glu Trp Val
        35                  40                  45

Gly Arg Ile Thr Gly Pro Gly Glu Gly Trp Ser Val Asp Tyr Ala Ala
    50                  55                  60

Pro Val Glu Gly Arg Phe Thr Ile Ser Arg Leu Asn Arg Ile Asn Phe
65                  70                  75                  80

Leu Tyr Leu Glu Met Asn Asn Leu Arg Met Glu Asp Ser Gly Leu Tyr
                85                  90                  95

Phe Cys Ala Arg Thr Gly Lys Tyr Tyr Asp Phe Trp Ser Gly Tyr Pro
            100                 105                 110

Pro Gly Glu Glu Tyr Phe Gln Asp Trp Gly Arg Gly Thr Leu Val Ile
        115                 120                 125

Val Ser Ser
    130
```

<210> SEQ ID NO 191

```
<211> LENGTH: 131
<212> TYPE: PRT
<213> ORGANISM: homosapiens

<400> SEQUENCE: 191

Glu Val Arg Leu Ala Glu Ser Gly Gly Gly Leu Val Lys Pro Gly Gly
1               5                   10                  15

Ser Leu Arg Leu Ser Cys Ser Ala Ser Gly Phe Asp Phe Asp Asn Ala
            20                  25                  30

Trp Met Thr Trp Val Arg Gln Pro Pro Gly Lys Gly Leu Glu Trp Val
        35                  40                  45

Gly Arg Ile Thr Gly Pro Gly Glu Gly Trp Ser Val Asp Tyr Ala Ala
    50                  55                  60

Pro Val Glu Gly Arg Phe Thr Ile Ser Arg Leu Asn Val Ile Asn Phe
65                  70                  75                  80

Leu Tyr Leu Glu Met Asn Asn Leu Arg Met Glu Asp Ser Gly Leu Tyr
                85                  90                  95

Phe Cys Ala Arg Thr Gly Lys Tyr Tyr Asp Phe Trp Ser Gly Tyr Pro
            100                 105                 110

Pro Gly Glu Glu Tyr Phe Gln Asp Trp Gly Arg Gly Thr Leu Val Ile
        115                 120                 125

Val Ser Ser
    130

<210> SEQ ID NO 192
<211> LENGTH: 131
<212> TYPE: PRT
<213> ORGANISM: homosapiens

<400> SEQUENCE: 192

Glu Val Arg Leu Ala Glu Ser Gly Gly Gly Leu Val Lys Pro Gly Gly
1               5                   10                  15

Ser Leu Arg Leu Ser Cys Ser Ala Ser Gly Phe Asp Phe Asp Asn Ala
            20                  25                  30

Trp Met Thr Trp Val Arg Gln Pro Pro Gly Lys Gly Leu Glu Trp Val
        35                  40                  45

Gly Arg Ile Thr Gly Pro Gly Glu Gly Trp Ser Val Asp Tyr Ala Ala
    50                  55                  60

Pro Val Glu Gly Arg Phe Thr Ile Ser Arg Leu Asn Tyr Ile Asn Phe
65                  70                  75                  80

Leu Tyr Leu Glu Met Asn Asn Leu Arg Met Glu Asp Ser Gly Leu Tyr
                85                  90                  95

Phe Cys Ala Arg Thr Gly Lys Tyr Tyr Asp Phe Trp Ser Gly Tyr Pro
            100                 105                 110

Pro Gly Glu Glu Tyr Phe Gln Asp Trp Gly Arg Gly Thr Leu Val Ile
        115                 120                 125

Val Ser Ser
    130

<210> SEQ ID NO 193
<211> LENGTH: 28
<212> TYPE: DNA
<213> ORGANISM: Artificial Sequence
<220> FEATURE:
<223> OTHER INFORMATION: oligonucleotide primer

<400> SEQUENCE: 193
tcttaggagc agcaggaagc actatggg                                          28
```

<210> SEQ ID NO 194
<211> LENGTH: 24
<212> TYPE: DNA
<213> ORGANISM: Artificial Sequence
<220> FEATURE:
<223> OTHER INFORMATION: oligonucleotide primer

<400> SEQUENCE: 194
gtaagtctct caagcggtgg tagc                                              24

<210> SEQ ID NO 195
<211> LENGTH: 30
<212> TYPE: DNA
<213> ORGANISM: Artificial Sequence
<220> FEATURE:
<223> OTHER INFORMATION: oligonucleotide primer

<400> SEQUENCE: 195
acaattattg tctggtatag tgcaacagca                                        30

<210> SEQ ID NO 196
<211> LENGTH: 25
<212> TYPE: DNA
<213> ORGANISM: Artificial Sequence
<220> FEATURE:
<223> OTHER INFORMATION: oligonucleotide primer

<400> SEQUENCE: 196
ccaccttctt cttcgattcc ttcgg                                             25

<210> SEQ ID NO 197
<211> LENGTH: 109
<212> TYPE: PRT
<213> ORGANISM: Homo sapiens

<400> SEQUENCE: 197

Ser Ser Glu Leu Thr Gln Asp Thr Gly Val Ser Val Ala Leu Gly Arg
1               5                   10                  15

Thr Val Thr Ile Thr Cys Arg Gly Asp Ser Leu Arg Ser His Tyr Ala
            20                  25                  30

Ser Trp Tyr Gln Lys Lys Pro Gly Gln Ala Pro Lys Leu Leu Phe Tyr
        35                  40                  45

Gly Lys Asn Asn Arg Pro Ser Gly Ile Pro Asp Arg Phe Ser Gly Ser
    50                  55                  60

Ala Ser Gly Asn Arg Ala Ser Leu Thr Ile Thr Gly Ala Gln Ala Glu
65                  70                  75                  80

Asp Glu Ala Asp Tyr Tyr Cys Ser Ser Arg Asp Lys Ser Gly Ser Arg
                85                  90                  95

Leu Ser Val Phe Gly Gly Gly Thr Lys Leu Thr Val Leu
            100                 105

<210> SEQ ID NO 198
<211> LENGTH: 109
<212> TYPE: PRT
<213> ORGANISM: Homo sapiens

<400> SEQUENCE: 198

Ser Tyr Glu Leu Thr Gln Asp Thr Gly Thr Ser Val Ala Ala Gly Arg
1               5                   10                  15

Thr Val Thr Ile Thr Cys Arg Gly Asp Ser Leu Arg Ser His Tyr Ala
            20                  25                  30

Ser Trp Tyr Gln Lys Lys Pro Gly Gln Ala Pro Val Leu Leu Phe Tyr
        35                  40                  45

Gly Lys Asn Asn Arg Pro Ser Gly Ile Pro Asp Arg Phe Ser Gly Ser
        50                  55                  60

Ala Ser Gly Asn Arg Ala Ser Leu Thr Ile Thr Gly Ala Gln Ala Glu
65                  70                  75                  80

Asp Glu Ala Asp Tyr Tyr Cys Ser Ser Arg Asp Lys Ser Gly Ser Arg
                85                  90                  95

Leu Ser Val Phe Gly Gly Gly Thr Lys Leu Thr Val Pro
            100                 105

<210> SEQ ID NO 199
<211> LENGTH: 109
<212> TYPE: PRT
<213> ORGANISM: Homo sapiens

<400> SEQUENCE: 199

Ser Ser Glu Leu Thr Gln Asp Thr Gly Thr Ser Val Ala Ala Gly Arg
1               5                   10                  15

Thr Val Thr Ile Thr Cys Arg Gly Asp Ser Leu Arg Ser His Tyr Ala
            20                  25                  30

Ser Trp Tyr Gln Lys Lys Pro Gly Gln Ala Pro Lys Leu Leu Phe Tyr
        35                  40                  45

Gly Lys Asn Asn Arg Pro Ser Gly Ile Pro Asp Arg Phe Ser Gly Ser
        50                  55                  60

Ala Ser Gly Asn Arg Ala Ser Leu Thr Ile Thr Gly Ala Gln Ala Glu
65                  70                  75                  80

Asp Glu Ala Asp Tyr Tyr Cys Ser Ser Arg Asp Lys Ser Gly Ser Arg
                85                  90                  95

Leu Ser Val Phe Gly Gly Gly Thr Lys Leu Thr Val Pro
            100                 105

<210> SEQ ID NO 200
<211> LENGTH: 131
<212> TYPE: PRT
<213> ORGANISM: Homo sapiens

<400> SEQUENCE: 200

Glu Val Arg Leu Ala Glu Ser Gly Gly Gly Leu Val Lys Pro Gly Gly
1               5                   10                  15

Ser Gln Arg Leu Ser Cys Ser Ala Ser Gly Phe Asp Phe Asp Asn Ala
            20                  25                  30

Trp Met Thr Trp Val Arg Gln Pro Pro Gly Lys Gly Leu Glu Trp Val
        35                  40                  45

Gly Arg Ile Thr Gly Pro Gly Glu Gly Trp Ser Val Asp Tyr Ala Ala
        50                  55                  60

Pro Val Glu Gly Arg Phe Thr Ile Ser Arg Leu Asn Tyr Ile Asn Phe
65                  70                  75                  80

Leu Tyr Leu Glu Met Asn Asn Leu Arg Thr Glu Asp Ser Gly Leu Tyr
                85                  90                  95

Phe Cys Ala Arg Thr Gly Lys Tyr Tyr Asp Phe Trp Ser Gly Tyr Pro
            100                 105                 110

Pro Gly Glu Glu Tyr Phe Gln Asp Trp Gly Arg Gly Thr Leu Val Ile
        115                 120                 125

Val Ser Ser
        130

<210> SEQ ID NO 201
<211> LENGTH: 131
<212> TYPE: PRT
<213> ORGANISM: Homo sapiens

<400> SEQUENCE: 201

Glu Val Arg Leu Ala Glu Ser Gly Gly Gly Leu Val Lys Pro Gly Gly
1               5                   10                  15

Ser Leu Arg Leu Ser Cys Ser Ala Ser Gly Phe Asp Phe Asp Asn Ala
            20                  25                  30

Trp Met Thr Trp Val Arg Gln Pro Pro Gly Lys Gly Leu Glu Trp Val
        35                  40                  45

Gly Arg Ile Thr Gly Pro Gly Glu Gly Trp Ser Val Asp Tyr Ala Ala
    50                  55                  60

Pro Val Glu Gly Arg Phe Thr Ile Ser Arg Asp Asn Tyr Lys Asn Thr
65                  70                  75                  80

Leu Tyr Leu Glu Met Asn Asn Leu Arg Thr Glu Asp Ser Gly Leu Tyr
                85                  90                  95

Phe Cys Ala Arg Thr Gly Lys Tyr Tyr Asp Phe Trp Ser Gly Tyr Pro
            100                 105                 110

Pro Gly Glu Glu Tyr Phe Gln Asp Trp Gly Arg Gly Thr Leu Val Ile
        115                 120                 125

Val Ser Ser
    130

<210> SEQ ID NO 202
<211> LENGTH: 131
<212> TYPE: PRT
<213> ORGANISM: Homo sapiens

<400> SEQUENCE: 202

Glu Val Arg Leu Ala Glu Ser Gly Gly Gly Leu Val Lys Pro Gly Gly
1               5                   10                  15

Ser Gln Arg Leu Ser Cys Ser Ala Ser Gly Phe Asp Phe Asp Asn Ala
            20                  25                  30

Trp Met Thr Trp Val Arg Gln Pro Pro Gly Lys Gly Leu Glu Trp Val
        35                  40                  45

Gly Arg Ile Thr Gly Pro Gly Glu Gly Lys Ser Val Asp Tyr Ala Ala
    50                  55                  60

Pro Val Glu Gly Arg Phe Thr Ile Ser Arg Leu Asn Tyr Ile Asn Phe
65                  70                  75                  80

Leu Tyr Leu Glu Met Asn Asn Leu Arg Thr Glu Asp Ser Gly Leu Tyr
                85                  90                  95

Phe Cys Ala Arg Thr Gly Lys Tyr Tyr Asp Phe Trp Ser Gly Tyr Pro
            100                 105                 110

Pro Gly Glu Glu Tyr Phe Gln Asp Trp Gly Arg Gly Thr Leu Val Ile
        115                 120                 125

Val Ser Ser
    130

<210> SEQ ID NO 203
<211> LENGTH: 131
<212> TYPE: PRT
<213> ORGANISM: Homo sapiens

<400> SEQUENCE: 203

Glu Val Arg Leu Ala Glu Ser Gly Gly Gly Leu Val Lys Pro Gly Gly
1               5                   10                  15

Ser Gln Arg Leu Ser Cys Ser Ala Ser Gly Phe Asp Phe Asp Asn Ala
            20                  25                  30

Trp Met Thr Trp Val Arg Gln Pro Pro Gly Lys Gly Leu Glu Trp Val
            35                  40                  45

Gly Arg Ile Thr Gly Pro Gly Glu Gly Lys Ser Val Asp Tyr Ala Ala
    50                  55                  60

Pro Val Glu Gly Arg Phe Thr Ile Ser Arg Asp Asn Tyr Lys Asn Thr
65                  70                  75                  80

Leu Tyr Leu Glu Met Asn Asn Leu Arg Thr Glu Asp Ser Gly Leu Tyr
                85                  90                  95

Phe Cys Ala Arg Thr Gly Lys Tyr Tyr Asp Phe Trp Ser Gly Tyr Pro
            100                 105                 110

Pro Gly Glu Glu Tyr Phe Gln Asp Trp Gly Arg Gly Thr Leu Val Ile
            115                 120                 125

Val Ser Ser
    130

<210> SEQ ID NO 204
<211> LENGTH: 131
<212> TYPE: PRT
<213> ORGANISM: Homo sapiens

<400> SEQUENCE: 204

Glu Val Arg Leu Ala Glu Ser Gly Gly Gly Leu Val Lys Pro Gly Gly
1               5                   10                  15

Ser Leu Arg Leu Ser Cys Ala Ala Ser Gly Phe Asp Phe Asp Asn Ala
            20                  25                  30

Trp Met Thr Trp Val Arg Gln Pro Pro Gly Lys Gly Leu Glu Trp Val
            35                  40                  45

Gly Arg Ile Thr Gly Pro Gly Glu Gly Trp Ser Val Asp Tyr Ala Ala
    50                  55                  60

Pro Val Glu Gly Arg Phe Thr Ile Ser Arg Leu Asp Tyr Ile Asn Phe
65                  70                  75                  80

Leu Tyr Leu Gln Met Asn Ser Leu Lys Met Glu Asp Thr Gly Val Tyr
                85                  90                  95

Tyr Cys Ala Arg Thr Gly Lys Tyr Tyr Asp Phe Trp Ser Gly Tyr Pro
            100                 105                 110

Pro Gly Glu Glu Tyr Phe Gln Asp Trp Gly Gln Gly Thr Leu Val Ile
            115                 120                 125

Val Ser Ser
    130

<210> SEQ ID NO 205
<211> LENGTH: 109
<212> TYPE: PRT
<213> ORGANISM: Homo sapiens

<400> SEQUENCE: 205

Ser Tyr Glu Leu Thr Gln Glu Thr Gly Val Ser Val Ala Leu Gly Arg
1               5                   10                  15

Thr Val Thr Ile Thr Cys Gln Gly Asp Ser Leu Arg Ser His Tyr Ala
            20                  25                  30

Ser Trp Tyr Gln Lys Lys Pro Gly Gln Ala Pro Ile Leu Leu Phe Tyr
            35                  40                  45

```
Gly Lys Asn Asn Arg Pro Ser Gly Val Pro Asp Arg Phe Ser Gly Ser
    50                  55                  60

Ala Ser Gly Asn Arg Ala Ser Leu Thr Ile Ser Gly Ala Gln Ala Glu
 65                  70                  75                  80

Asp Asp Ala Glu Tyr Tyr Cys Ser Ser Arg Asp Lys Ser Gly Ser Arg
                 85                  90                  95

Leu Ser Val Phe Gly Gly Gly Thr Lys Leu Thr Val Leu
                100                 105

<210> SEQ ID NO 206
<211> LENGTH: 109
<212> TYPE: PRT
<213> ORGANISM: Homo sapiens

<400> SEQUENCE: 206

Ser Tyr Glu Leu Thr Gln Asp Thr Gly Val Ser Val Ala Leu Gly Arg
 1               5                  10                  15

Thr Val Thr Ile Thr Cys Gln Gly Asp Ser Leu Arg Ser His Tyr Ala
             20                  25                  30

Ser Trp Tyr Gln Lys Lys Pro Gly Gln Ala Pro Val Leu Leu Phe Tyr
         35                  40                  45

Gly Lys Asn Asn Arg Pro Ser Gly Ile Pro Asp Arg Phe Ser Gly Ser
    50                  55                  60

Ala Ser Gly Asn Arg Ala Ser Leu Thr Ile Thr Gly Ala Gln Ala Glu
 65                  70                  75                  80

Asp Glu Ala Asp Tyr Tyr Cys Ser Ser Arg Asp Lys Ser Gly Ser Arg
                 85                  90                  95

Leu Ser Val Phe Gly Gly Gly Thr Lys Leu Thr Val Leu
                100                 105

<210> SEQ ID NO 207
<211> LENGTH: 109
<212> TYPE: PRT
<213> ORGANISM: Homo sapiens

<400> SEQUENCE: 207

Ser Ser Glu Leu Thr Gln Asp Thr Gly Val Ser Val Ala Leu Gly Arg
 1               5                  10                  15

Thr Val Thr Ile Thr Cys Gln Gly Asp Ser Leu Arg Ser His Tyr Ala
             20                  25                  30

Ser Trp Tyr Gln Lys Lys Pro Gly Gln Ala Pro Lys Leu Leu Phe Tyr
         35                  40                  45

Gly Lys Asn Asn Arg Pro Ser Gly Ile Pro Asp Arg Phe Ser Gly Ser
    50                  55                  60

Ala Ser Gly Asn Arg Ala Ser Leu Thr Ile Thr Gly Ala Gln Ala Glu
 65                  70                  75                  80

Asp Glu Ala Asp Tyr Tyr Cys Ser Ser Arg Asp Lys Ser Gly Ser Arg
                 85                  90                  95

Leu Ser Val Phe Gly Gly Gly Thr Lys Leu Thr Val Leu
                100                 105

<210> SEQ ID NO 208
<211> LENGTH: 109
<212> TYPE: PRT
<213> ORGANISM: Homo sapiens

<400> SEQUENCE: 208

Ser Tyr Glu Leu Thr Gln Asp Thr Gly Thr Ser Val Ala Ala Gly Arg
```

```
1               5                   10                  15
Thr Val Thr Ile Thr Cys Gln Gly Asp Ser Leu Arg Ser His Tyr Ala
                20                  25                  30

Ser Trp Tyr Gln Lys Lys Pro Gly Gln Ala Pro Val Leu Leu Phe Tyr
                35              40                  45

Gly Lys Asn Asn Arg Pro Ser Gly Ile Pro Asp Arg Phe Ser Gly Ser
            50                  55                  60

Ala Ser Gly Asn Arg Ala Ser Leu Thr Ile Thr Gly Ala Gln Ala Glu
65                  70                  75                  80

Asp Glu Ala Asp Tyr Tyr Cys Ser Ser Arg Asp Lys Ser Gly Ser Arg
                    85                  90                  95

Leu Ser Val Phe Gly Gly Gly Thr Lys Leu Thr Val Pro
                100                 105

<210> SEQ ID NO 209
<211> LENGTH: 109
<212> TYPE: PRT
<213> ORGANISM: Homo sapiens

<400> SEQUENCE: 209

Ser Ser Glu Leu Thr Gln Asp Thr Gly Thr Ser Val Ala Ala Gly Arg
1               5                   10                  15

Thr Val Thr Ile Thr Cys Gln Gly Asp Ser Leu Arg Ser His Tyr Ala
                20                  25                  30

Ser Trp Tyr Gln Lys Lys Pro Gly Gln Ala Pro Lys Leu Leu Phe Tyr
                35              40                  45

Gly Lys Asn Asn Arg Pro Ser Gly Ile Pro Asp Arg Phe Ser Gly Ser
            50                  55                  60

Ala Ser Gly Asn Arg Ala Ser Leu Thr Ile Thr Gly Ala Gln Ala Glu
65                  70                  75                  80

Asp Glu Ala Asp Tyr Tyr Cys Ser Ser Arg Asp Lys Ser Gly Ser Arg
                    85                  90                  95

Leu Ser Val Phe Gly Gly Gly Thr Lys Leu Thr Val Pro
                100                 105
```

NEUTRALIZING GP41 ANTIBODIES AND THEIR USE

CROSS REFERENCE TO RELATED APPLICATIONS

This application is a divisional of U.S. patent application Ser. No. 15/226,744 filed Aug. 2, 2016, which is a divisional of U.S. patent application Ser. No. 14/356,557 filed May 6, 2014, which is the U.S. National Stage of International Application No. PCT/US2012/063958 filed Nov. 7, 2012, which was published in English under PCT Article 21(2), which in turn claims the benefit of U.S. Provisional Application No. 61/702,703 filed Sep. 18, 2012, U.S. Provisional Application No. 61/698,480 filed Sep. 7, 2012, U.S. Provisional Application No. 61/672,708 filed Jul. 17, 2012, and U.S. Provisional Application No. 61/556,660 filed Nov. 7, 2011. Each of these prior applications is incorporated by reference in its entirety.

FIELD OF THE DISCLOSURE

This relates to the identification of monoclonal neutralizing antibodies, such as, but not limited to, antibodies that bind to the membrane-proximal region of HIV-1 gp41.

BACKGROUND

An effective Human Immunodeficiency Virus type 1 (HIV-1) vaccine will likely need to induce neutralizing antibodies (NAbs) that block HIV-1 entry into human cells. To be effective, vaccine-induced antibodies will have to be active against most circulating strains of HIV-1. Unfortunately, current HIV-1 vaccines are unable to induce potent and broadly reactive NAbs. One major obstacle to the design of better vaccines is the limited understanding of what region of the HIV-1 envelope glycoproteins, such as gp120 and gp41, are recognized by NAbs. A few neutralizing monoclonal antibodies (mAbs) have been isolated from HIV-1 infected individuals and these mAbs define specific regions (epitopes) on the virus that are vulnerable to NAbs.

Although the envelope glycoproteins are immunogenic and induce a variety of antibodies, the neutralizing antibodies that are induced are strain-specific, and the majority of the immune response is diverted to non-neutralizing determinants (Weiss, R. A., et al., *Nature*, 1985. 316 (6023): p. 69-72; Wyatt, R. and J. Sodroski, *Science*, 1998. 280 (5371): p. 1884-8). Broadly neutralizing antibodies have been isolated only rarely from natural HIV infection. Three examples of broadly neutralizing antibodies that bind gp41 are 2F5, 4E10 and Z13E1. These gp41 neutralizing antibodies recognize the membrane-proximal region (MPER) of the HIV-1 gp41 glycoprotein. Unfortunately, these antibodies are limited in their strain cross reactivity or their potency and therefore do not provide a viable choice for therapeutic intervention. Thus, the need exists for methods to prepare monoclonal broadly neutralizing antibodies that can provide protection from an infectious agent, such as HIV.

SUMMARY

Isolated human monoclonal neutralizing antibodies that specifically bind gp41 are provided herein. In certain examples, the binding and/or neutralization ability of these antibodies has been optimized. Also disclosed herein are compositions including the disclosed antibodies that specifically bind gp41, nucleic acids encoding these antibodies, expression vectors including the nucleic acids, and isolated host cells that express the nucleic acids. Antigen binding fragments of the isolated antibodies are also provided.

In some embodiments, an isolated human monoclonal antibody, or antigen binding fragment thereof, includes a heavy chain and a light chain, wherein the heavy chain includes an amino acid sequence at least about 80% identical to the amino acid sequence set forth as SEQ ID NO: 1. In several such embodiments, the antibody, or antigen binding fragment thereof, specifically binds to gp41 and contacts L, WF, LW and R in the amino acid sequence set forth as LWNWFDITNWLWYIR (SEQ ID NO: 26, residues 14-28), and is neutralizing. In additional embodiments, the antibody, or antigen binding fragment thereof, specifically binds to gp41 and contacts NWF, T, and R in the amino acid sequence set forth as NWFDITNWLWYIR (SEQ ID NO: 13, residues 7-19), and is neutralizing. In additional embodiments, an isolated monoclonal antibody or antigen binding fragment is provided that includes a heavy chain and a light chain, wherein the heavy chain includes amino acids 26-33 (heavy chain complementarity-determining region 1 (HCDR1)), 51-60 (HCDR2), or 99-120 (HCDR3) of SEQ ID NO: 11, wherein $X_1$ is Q or R, $X_2$ is V or A, $X_3$ is S or Y, and $X_4$ is T or I. The antibody or the antigen binding fragment specifically binds gp41 of HIV-1, and is neutralizing. In some such embodiments, the isolated human monoclonal antibody or antigen binding fragment includes a heavy chain including one or more of amino acids 26-33 (HCDR1), 51-60 (HCDR2), and 99-120 (HCDR3) of one of SEQ ID NOs: 1, 3, 5, 147-149, 189-192, or 200-204. In some such embodiments, the heavy chain of the isolated human monoclonal antibody includes an amino acid sequence at least 90% identical to the amino acid sequence set forth as one of SEQ ID NOs: 1, 3, 5, 147-149, 189-192, or 200-204. In other embodiments, the heavy chain of the isolated human monoclonal antibody or antigen binding fragment thereof, includes the amino acid sequence set forth as one of SEQ ID NOs: 1, 3, 5, 147-149, 189-192, or 200-204.

In additional embodiments, the isolated human monoclonal antibody or antigen binding fragment thereof includes a light chain at least about 80% identical to the amino acid sequence set forth as SEQ ID NO: 2. In further embodiments, the light chain includes amino acids 26-31 (light chain complementarity-determining region 1 (LCDR1)), 49-51 (LCDR2), and 88-99 (LCDR3) of SEQ ID NO: 12, where $X_4$ is E or D, $X_5$ is Y or H, $X_6$ is K or I, $X_7$ is V or I, $X_8$ is S or T, $X_9$ is D or E, $X_{10}$ is E or D, and $X_{11}$ is T or I. In additional embodiments, the light chain includes amino acids 26-31 (LCDR1), 49-51 (LCDR2), or 88-99 (LCDR3) of one of SEQ ID NO: 2, 4, 6, 12, 150-152, or 164-186. In some embodiments, the light chain of the isolated human monoclonal antibody or antigen binding fragment includes an amino acid sequence at least 90% identical to the amino acid sequence set forth as one of SEQ ID NO: 2, 4, 6, 12, 150-152, or 164-186. In one embodiment, the light chain of the isolated human monoclonal antibody or antigen binding fragment includes the amino acid sequence set forth as one of SEQ ID NO: 2, 4, 6, 12, 150-152, or 164-186.

In some embodiments, an isolated human monoclonal antibody or antigen binding fragment thereof is provided in which the heavy chain includes the amino acid sequence set forth as SEQ ID NO: 1 and the light chain includes the amino acid sequence set forth as SEQ ID NO: 2. The antibody specifically binds gp41 of HIV-1 and is neutralizing. In further embodiments, an isolated human monoclonal antibody or antigen binding fragment thereof is provided in which the heavy chain includes the amino acid sequence set forth as SEQ ID NO: 154 and the light chain includes the amino acid sequence set forth as SEQ ID NO: 152. The antibody specifically binds gp41 of HIV-1 and is neutralizing. In other embodiments, an isolated human monoclonal antibody or antigen binding fragment thereof is provided in which the heavy chain includes the amino acid sequence set forth as SEQ ID NO: 192 and the light chain includes the amino acid sequence set forth as SEQ ID NO: 152. The antibody specifically binds gp41 of HIV-1 and is neutralizing.

The antibodies and compositions disclosed herein can be used for a variety of purposes, such as for detecting the presence of HIV-1 in a biological sample or diagnosing AIDS. These methods can include contacting a sample from a subject with a human monoclonal antibody that specifically binds gp41, and detecting binding of the antibody to the sample. An increase in binding of the antibody to the sample relative to binding of the antibody to a control sample identifies the subject as a subject with HIV-1 infection and/or AIDS. In some non-limiting examples, an increase in binding of the antibody to the sample relative to a control sample detects the presence of HIV-1.

Method are also disclosed for treating a subject with an HIV infection, such as, but not limited to, a subject with AIDS. The methods include administering a therapeutically effective amount of a monoclonal antibody as described above to a subject.

The foregoing and other features and advantages of this disclosure will become more apparent from the following detailed description of several embodiments which proceeds with reference to the accompanying figures.

BRIEF DESCRIPTION OF THE FIGURES

FIGS. 1A-1C are as set of tables and a diagram illustrating analyses of 10E8 antibody sequence and neutralization. (A) Inferred germline genes encoding the variable regions of 10E8, 7H6 and 7N16. (B) Neutralizing activity of antibodies against a 181-isolate HIV-1 envelope protein (Env)-pseudovirus panel. Dendrograms indicate the gp160 protein distance of HIV-1 primary isolate Envs. (C) Data below the dendrogram show the number of tested viruses, the percentage of viruses neutralized, and the geometric mean IC50 for viruses neutralized with an IC50<50 µg/ml. Median titers are based on all tested viruses, including those with IC50>50 ug/ml, which were assigned a value of 100.

FIGS. 2A and 2B illustrate the binding specificity of 10E8. (A) Enzyme-Linked immunosorbant assay (ELISA) binding of mAb 10E8 or 4E10 to gp140, gp120, gp41, or 4E10 peptide. Error bars denote one standard error of the mean (SEM). (B) Inhibition of mAbs 10E8 or 4E10 neutralization of C1 HIV-2/HIV-1 MPER virus by 4E10 alanine scanning peptides. Peptide was incubated with mAb 4E10 or 10E8 for one hour prior to infecting TZM-b1 cells. Y-axis shows percent neutralization for each condition. $W_{672}$, $F_{673}$, $T_{676}$ and $R_{683}$ residues were positions for which the alanine mutant peptide did not block neutralization ($R_{683}$ only for the 10E8 antibody). Residues 16-28 of SEQ ID NO: 26 are shown.

FIGS. 5A and 5B are a table, a set of graphs and a schematic diagram illustrating a site of gp41 vulnerability. (A) Impact of sequence variation on 10E8 neutralization. Predicted amino acid sequences within the binding epitope of 10E8 for three 10E8 resistant viruses and the patient virus are shown. The 10E8 binding region and differences in sequence compared to the JR2 virus are labeled in light grey. IC50 and IC80 values that are >20-fold than JR2 wild-type pseudovirus are highlighted in light grey. Error bars denote one SEM. (B) Structural definition of a highly conserved region of gp41 recognized by neutralizing antibodies. Atoms of highly conserved residues that make direct contacts with 10E8 are shaded medium grey and shown in stick representation, atoms buried by 10E8 are shaded dark grey, and main chain-contacting atoms are shaded light grey. Semi-transparent surfaces of the gp41 MPER are shaded according to the underlying atoms. 90° views are shown, with bound antibody 10E8 in the right panel. The 10E8 CDR H3 interacts with highly conserved hydrophobic residues, whereas the CDR H2 contacts main chain atoms at the juncture between the N- and C-terminal helices. Many of the unbound residues of the MPER (grey) are hydrophobic, especially those within the C-terminal helix. In the structure of a late fusion intermediate (FIG. 16) these residues face towards the outside of a helical coiled-coil; in the pre-fusion conformation of the viral spike, these may interact with the viral membrane or with other hydrophobic regions of Env.

FIGS. 6A and 6B depict a sequence alignment of the heavy and light chains of gp41 antibodies 10E8 (SEQ ID NO: 1 and 2), 7H6 (SEQ ID NO: 3 and 4), 7N16 (SEQ ID NO: 5 and 6), IGHV3-15*05 (SEQ ID NO: 7) and the germline sequence of IGLV3-19*01 (SEQ ID NO: 8). Residues in light grey represent substitutions from the germline sequence. The dot symbol denotes the residue deletion. Kabat and IMGT numbering are shown and are used to identify specific residues in the 10E8 heavy and light chains.

FIG. 7 is a graph illustrating the correlation of neutralization potencies between N152 donor serum and antibody 10E8. Shown is a plot of the neutralization ID50s of N152 donor serum against neutralization IC50s of 10E8, assessed against a 20-pseudovirus panel. A non-parametric Spearman correlation was used to evaluate the correlation between IC50s of 10E8 and ID50s of N152.

FIGS. 8A-8C are a graph and a set of tables illustrating the binding specificity of 10E8. (A) ELISA binding of indicated mAbs to MPER, 2F5, Z13e1, 4E10 and 4E10.19 peptides Amino acid sequences of peptides are also shown (descending, SEQ ID NO: 26 with N- and C-terminal lysine triplicates, residues 1-16 of SEQ ID NO: 26, residues 11-21 of SEQ ID NO: 26 with a C-terminal lysine triplicate, residues 16-24 of SEQ ID NO: 26 with a C-terminal lysine triplicate and residues 16-28 of SEQ ID NO: 26 with a N-terminal cysteine and a C-terminal lysine triplicate). (B-C) Inhibition of mAb neutralization of C1 HIV-2/HIV-1 MPER chimeric virus by addition of MPER, 2F5, Z13e1, 4E10 and 4E10.19 peptides. Fold effect was calculated as the ratio of neutralization IC50 with mock peptide/IC50 (B), or the ratio of neutralization IC80 with mock peptide/IC80 (C), for the indicated peptide. Values>5 are shaded light grey.

FIGS. 11A-11C illustrate accessibility of 10E8 to the MPER. (A) Binding of 10E8, 4E10 and 2F5 to full-length HIV$_{JR-FL}$ envelope spikes, 4E10 mutant (Phe673Ser) or 2F5 mutant (Lys665Glu) expressed on 293T cell surface as measured by flow cytometry. Serially diluted antibody was incubated with cells for one hour. 2G12 and b12 antibodies were used as positive controls and F105 was used as a negative control. VRC01 is used as an additional control on JR-FL transfected cells. Relative binding percent is calculated as the mean fluorescence intensity (MFI) divided by the maximum MFI of the positive control 2G12×100. (B) MPER accessibility was determined by washing antibody-virion mixture prior to infecting TZM-b1 cells. Pseudoviruses were incubated with antibodies at 37° C. for 30 minutes, and antibody-virion mixture was washed or not washed prior to infecting target cells. (C) Impact of washing on antibody neutralization was measured by the area under the curve (AUC) or at the IC80. For BaL and JRF1 the IC80 was not achieved in the no-wash condition and the highest inhibitory concentration (IC60 and IC75, respectively) was used.

FIGS. 15A-15H illustrate recognition of a structurally conserved C-terminal MPER helix by 10E8 and 4E10. 10E8 and 4E10 use substantially different modes of recognition to bind a structurally conserved helix at the C-terminus of the gp41 MPER. (A) MPER conformation and buried surface for neutralizing antibodies 10E8, 2F5 (Protein DataBank (PDB) ID No. 1TJI, incorporated by reference herein as present in the database on Oct. 22, 2012), Z13e1 (PDB ID No. 3FN0, incorporated by reference herein as present in the database on Oct. 22, 2012), and 4E10 (PDB ID No. 2FX7, incorporated by reference herein as present in the database on Oct. 22, 2012). Cα-ribbon representations of the gp41 MPER bound by each antibody are shown, with bar graphs displaying the amount of buried surface per residue. The amino acid sequence of SEQ ID NO: 26 is shown below each bar graph. The sequence of the crystallized epitope is shown in uppercase letters. (B) Superposition of the MPER C-terminal helix, in the 10E8- (dark grey) and 4E10-bound (light grey) conformations, displayed at 90° orientations. Cα-ribbon representations are shown, with side chains displayed as sticks. (C-F) Comparison of 10E8 and 4E10 recognition of the C-terminal MPER helix, with molecules displayed in Cα-ribbon representations. (C) 10E8 variable domains in complex with the MPER, shaded according to FIG. 4A. (D) 4E10 variable domains in complex with the MPER (PDB ID No. 2FX7, incorporated by reference herein as present in the database on Oct. 22, 2012), in an orientation based on the alignment of gp41 C-terminal helices described in (B; left panel). gp41 is shaded off-white, 4E10 heavy chain, dark grey, and 4E10 light chain, medium grey. (E-F) 90° views of (C) and (D), looking down from C-terminus to N-terminus of the conserved MPER C-terminal helix. (G,H) Helical wheel representations of the 10E8- and 4E10-bound MPER C-terminal helices, reflecting the orientation displayed in (B; right panel). Highlighted antibody-contacting faces are based on direct contacts observed between the antibodies and gp41, as described in FIG. 35.

FIGS. 17A-17F are a set of tables illustrating 10E8 neutralizing properties. (A) Neutralization of 10E8 and 7H6 against a 5-isolate Env-pseudovirus mini-panel. IC50 values of less than 1 μg/ml are highlighted in grey. (B) Neutralization profile of patient N152 serum and monoclonal antibodies. [a]The data for N152 shows the ID50 (dose of virus required for 50% infection) of serum against each virus. ID50>1000 is highlighted in dark grey, 500<ID50<1000 is in medium grey, and 100<ID50<500 is in light grey. The data for the monoclonal antibodies shows the IC50. IC50<1 μg/ml is highlighted in medium grey; IC50 of 1-10 μg/ml is highlighted in light grey; and IC50 of 10-50 μg/ml is highlighted in dark grey. (C-F) Antibody neutralization data against 181 HIV-1 Env-pseudoviruses. IC50<1 μg/ml is highlighted in medium grey; IC50 of 1-10 μg/ml is highlighted in light grey; and IC50 of 10-50 μg/ml is highlighted in dark grey.

FIG. 18 is a table illustrating binding of 10E8 and 4E10 to gp41 MPER alanine scanned peptides, by ELISA. Fold change was calculated as peptide IC50/mock peptide IC50. Fold change values>10 are highlighted in light grey.

FIG. 19 is a table listing neutralization data for 10E8 against pseudotyped HIV-1$_{JR2}$ MPER alanine mutants. Concentration is μg/ml. IC50 and IC90 values>20-fold compared to JR2 wild-type for 10E8 or >100 fold for 4E10 are highlighted in light grey.

FIG. 20 is a table listing sequences of the HIV-2/HIV-1 chimeras used for neutralization assays. The sequences of 7312A, C1, C1C, C3, C7, C6, C4, C4GW and C8 are shown (SEQ ID NOs: 15-22, respectively). Fragments of the MPER sequence that correspond to the sequence of the HIV-1 MPER are underlined.

FIG. 21 is a table illustrating mapping anti-MPER neutralizing antibodies/sera with HIV-2/HIV-1 chimeras. [a]IC50 (μg/ml) is shown. [b]ID50 values are shown. Numbers are bolded and highlighted light grey if the ID50 of the HIV-2/HIV-1 chimera was both 3-fold greater than HIV-2 wild-type control and >100. "–" indicates no neutralization. "ND" indicates the serum classification could not be determined.

FIG. 22 is a table illustrating blocking mAb- and serum-mediated neutralization of the HIV-2/HIV-1 chimera C1 using mutant MPER peptides. The sequence of the blocking peptides is shown in FIG. 8A. [b]Fold change of IC50 refers to (peptide IC50)/(mock peptide IC50). [c]Fold change of ID50 refers to (Mock peptide ID50)/(peptide ID50). Light grey highlight indicates a 3-fold change in IC50/ID50 relative to the control peptide.

FIG. 23 is a table illustrating reactivity of 10E8 with autoantigens. Reactivity of 10E8 with autoantigens was detected by the Luminex assay. An anti-RSV monoclonal antibody, Synagis (MedImmune, Gaithersburg, Md.), was used as a negative control. The 4E10, 2F5, VRC01 and 17b antibodies were also tested for comparison. SSA refers to Sjogren's syndrome antigen A; SSB refers to Sjogren syndrome antigen B; Sm refers to Smith antigen; RNP refers to ribonucleoprotein; Scl 70 refers to scleroderma 70; Jo1 refers to antigen; CentrB refers to centromere B.

FIG. 24 is a table listing data collection and refinement statistics for the 10E8 crystal structure studies. The highest resolution shell is shown in parentheses. The dataset shown was collected from one crystal.

FIG. 25 is a table listing Phi-Psi angles of antibody-bound gp41 peptides. [a]For the 4E10:gp41 complex the structure of PDB ID No. 2FX7 was used (incorporated by reference herein as present in the database on Oct. 22, 2012). [b]For the Z13e1:gp41 complex the structure of PDB ID No. 3FN0 was used (incorporated by reference herein as present in the database on Oct. 22, 2012).

FIG. 26 is a table listing the total buried surface area on 10E8 and gp41. All interactions were performed using PISA (ebi.ac.uk/msd-srv/prot_int/cgi-bin/piserver). [§] BSA refers to Buried Surface Area, Å$^2$.

FIG. 27 is a table listing buried surface areas at interface between 10E8 heavy chain and gp41, by residue. All interactions were performed using PISA (ebi.ac.uk/msd-srv/prot_int/cgi-bin/piserver). [£]Percent identity of this residue in an analysis of 2870 HIV strains deposited in the Los Alamos HIV sequence database (as of December 2011). [‡]ASA refers to Accessible Surface Area, Å$^2$. [§] BSA refers to Buried Surface Area, Å$^2$. [§§] Bars represent buried area percentage, one bar per 10%. Δ$^i$G refers to Solvation energy effect, kcal/mol.

FIG. 28 is a table listing buried surface areas at interface between 10E8 light chain and gp41, by residue. All interactions were performed with PISA (ebi.ac.uk/msd-srv/prot_int/cgi-bin/piserver). [£]Percent identity of this residue in an analysis of 2870 HIV strains deposited in the Los Alamos HIV sequence database (as of December 2011). ASA refers to Accessible Surface Area, Å$^2$. BSA refers to Buried Surface Area, Å². Bars represent buried area percentage, one bar per 10%. Δ$^i$G refers to Solvation energy effect, kcal/mol.

FIG. 29 is a table listing hydrogen bonds and salt bridges between 10E8 and gp41. Hydrogen bonds were determined with the use of the program Ligplot (McDonald et al., *J Mol Biol* 238, 777-793, 1994). Chain H refers to heavy chain complex 1; Chain B refers to heavy chain complex 2; Chain P refers to gp41 peptide complex 1; Chain F refers to gp41 peptide complex 2.

FIG. 30 is a table listing Van der Waals contacts between 10E8 and gp41. Van der Waals contacts were determined with the use of the program Ligplot (McDonald et al., *J Mol Biol* 238, 777-793, 1994). Chain H and chain L refer to complex 1 heavy and light chains, respectively; Chain P refers to complex 1 gp41 peptide. Chain B and chain D refer to complex 2 heavy and light chains, respectively; Chain F refers to complex 2 gp41 peptide.

FIG. 31 is a table illustrating binding affinities of 10E8 alanine variants to a soluble MPER peptide. SE refers to standard error; nb refers to weak to undetectable binding at concentration range used. ^Fold is defined as fold-change relative to individual wild type 10E8 runs performed in parallel with variants. Mean of three individual wild type 10E8 runs. #Only those mutations that yielded effects greater than 10-fold were mapped onto the 10E8 buried surface in FIG. 4E (medium grey, >100×; light grey, 50×<100×; dark grey, 10×<50×). Heavy chain residues Y99A$_{HC}$ and G100hA$_{HC}$ showed almost no binding to soluble peptide, while mutations of additional residues of the CDR H3 (F100aA$_{HC}$, G100dA$_{HC}$, P100fA$_{HC}$, P100gA$_{HC}$, E100iA$_{HC}$, and E100jA$_{HC}$) decreased affinity 50-120 fold (Kabat numbering is used to identify specific residues in the 10E8 heavy and light chains). CDR H1 loop and framework region 2 mutations W33A$_{HC}$ and R50A$_{HC}$, respectively, which are present within the hydrophobic cleft, also knocked out binding to the MPER peptide, and the CDR H2 mutation E53A$_{HC}$ within the cleft decreased affinity for the MPER peptide by 60-fold. Light chain residue R91LC, which is located at the base of the hydrophobic cleft and forms direct interactions with residues of the CDR H3, knocks out binding when mutated to alanine possibly by destabilizing the cleft itself.

FIG. 32 is a table listing neutralization IC50s and IC80s of 10E8 alanine scanning variants. In cases where neutralization IC50 or IC80 were not achieved at the highest concentration of antibody, the highest concentration was used in calculation of the mean. ^Mean fold effect is defined as the average of the individual fold effects seen against each viral strain. &Mutations Y99A$_{HC}$, F100aA$_{HC}$, W100bA$_{HC}$, and G100hA$_{HC}$ all had detrimental effects on neutralization, decreasing potency by over 1000-fold. Other mutations also had strong effects on neutralization, including P100gA$_{HC}$ and E100iA$_{HC}$ of the CDR H3, and W33A$_{HC}$ and R50A$_{HC}$ within the hydrophobic cleft. Light chain mutation R91A$_{LC}$, similarly to its effects on binding to peptide, decreased neutralization potency by over 1000-fold.

FIG. 33 is a table illustrating root-mean-square deviations (RMSD) of antibody-bound gp41 structures. Alignments were performed with the use of the program LSQKAB (Winn, M. D. et al. *Acta Crystallogr D Biol Crystallogr*, 67, 235-242, 2011). For the 4E10:gp41 complex the structure of PDB ID No. 2FX7 was used (incorporated by reference herein as present in the database on Oct. 22, 2012). For the Z13e1:gp41 complex the structure of PDB ID No. 3FN0 was used (incorporated by reference herein as present in the database on Oct. 22, 2012). For the 2F5:gp41 complex the structure of PDB ID No. 1TJI was used).

FIG. 34 is a table showing comparison of MPER-specific antibody buried surfaces on gp41. The interaction studies were performed with PISA (ebi.ac.uk/msd-srv/prot_int/cgi-bin/piserver). Values in parentheses are for complex 2. For the 4E10:gp41 complex the structure of PDB ID No. 2FX7 was used (incorporated by reference herein as present in the database on Oct. 22, 2012). For the Z13e1:gp41 complex the structure of PDB ID No. 3FN0 was used (incorporated by reference herein as present in the database on Oct. 22, 2012). For the 2F5:gp41 complex the structure of PDB ID No. 1TJI was used (incorporated by reference herein as present in the database on Oct. 22, 2012). Despite recognizing a more extensive residue range, 10E8 has a smaller gp41 footprint than 4E10. If the comparison is limited to the overlapping peptide range, residues 671-683, the difference in the footprints is even more pronounced, with 10E8 burying roughly 25% less surface area on gp41 than 4E10.

FIG. 35 is a table showing comparison of direct contacts of antibodies 10E8 and 4E10 with gp41. Direct contacts were determined with the use of the program Ligplot (McDonald et al., *J Mol Biol* 238, 777-793, 1994). H refers to hydrogen bond; N refers to van der Waals contact.

FIG. 36 is a set of tables illustrating results from the neutralization of pseudotyped COT6.15 (clade C) envelope MPER mutants with 10E8 and 4E10 antibodies.

FIG. 37 is a table illustrating results of neutralization assays using the cross-complementation of the 10E8, 7H6 and 7N16 heavy and light chains.

FIGS. 42A and 42B are scattergram plots showing the results of FACS isolation of CD19$^+$IgA$^-$IgD$^-$IgM$^-$ B cells from a PBMC sample.

FIG. 45 is a table illustrating the results of neutralization assays on a panel of HIV-1 viruses using the structure-base 10E8 mutants described in FIGS. 44A and 44B and Example 8 (with reference to Kabat numbering).

FIG. 48 is a set of tables illustrating results of neutralization assays on a panel of HIV-1 viruses using the partial germline revertants of the 10E8 antibody as described in FIG. 47 and Example 8. "10E8-R1" refers to 10E8gH01 heavy chain (SEQ ID NO: 147) paired with 10E8gL01 light chain (SEQ ID NO: 150). "10E8-R3" refers to 10E8gH03 heavy chain (SEQ ID NO: 149) paired with 10E8gL03 light chain (SEQ ID NO: 152).

FIG. 49 is a set of tables illustrating results of neutralization assays on a panel of HIV-1 viruses using a series of 10E8 mutants on the 10E8gH03 heavy chain background (SEQ ID NO: 149) or the 10E8gL03 background (SEQ ID NO: 152) as shown in FIG. 47 and described in Example 8.

FIGS. 51A-51D are a series of sequence alignments and ribbon diagrams illustrating sequences and modeled structures of 10E8 variants that neutralize HIV-1. (A) Heavy-chain sequences (SEQ ID NOs: 1, and 153-163, descending; gVRC-H1$_{dN152}$ (SEQ ID NO: 153); gVRC-H2$_{dN152}$ (SEQ ID NO: 154); gVRC-H3$_{dN152}$ (SEQ ID NO: 155); gVRC-H4$_{dN152}$ (SEQ ID NO: 156); gVRC-H5$_{dN152}$ (SEQ ID NO: 157); gVRC-H6$_{dN152}$ (SEQ ID NO: 158); gVRC-H7$_{dN152}$ (SEQ ID NO: 159); gVRC-H8$_{dN152}$ (SEQ ID NO: 160); gVRC-H9$_{dN152}$ (SEQ ID NO: 161); gVRC-H10$_{dN152}$ (SEQ ID NO: 162) gVRC-H11$_{dN152}$ (SEQ ID NO: 163)). Sequences are arranged by genetic distance from 10E8, with sequence changes from 10E8 underlined. Framework and CDR residues are highlighted, as are residues that interact with the gp41 MPER epitope (open circle, mainchain interaction; open circle with rays, sidechain interactions; solid circle, both mainchain and sidechain interactions). (B) Modeled structures of heavy chain variants in complex with gp41 epitope. 10E8 variants with enhanced recognition (with heavy chains shaded according to phylogenetic distance as in 1B) were modeled onto the structure of 10E8 with the entire MPER region of HIV-1 gp41 (off-white). Structures are displayed as Cα-ribbons, with amino acid-side chains that vary from 10E8 highlighted in stick representation, dark grey. (C) Light-chain sequences (SEQ ID NOs: 2 and 164-182, descending; gVRC-L1$_{dN152}$ (SEQ ID NO: 164); gVRC-L2$_{dN152}$ (SEQ ID NO: 165); gVRC-L3$_{dN152}$ (SEQ ID NO: 166); gVRC-L4$_{dN152}$ (SEQ ID NO: 167); gVRC-L5$_{dN152}$ (SEQ ID NO: 168); gVRC-L6$_{dN152}$ (SEQ ID NO: 169); gVRC-L7$_{dN152}$ (SEQ ID NO: 170); gVRC-L8$_{dN152}$ (SEQ ID NO: 171); gVRC-L9$_{dN152}$ (SEQ ID NO: 172); gVRC-L10$_{dN152}$ (SEQ ID NO: 173); gVRC-L11$_{dN152}$ (SEQ ID NO: 174); gVRC-L12$_{dN152}$ (SEQ ID NO: 175); gVRC-L13$_{dN152}$ (SEQ ID NO: 176); gVRC-L14$_{dN152}$ (SEQ ID NO: 177); gVRC-L15$_{dN152}$ (SEQ ID NO: 178); gVRC-L16$_{dN152}$ (SEQ ID NO: 179); gVRC-L17$_{dN152}$ (SEQ ID NO: 180); gVRC-L18$_{dN152}$ (SEQ ID NO: 181); gVRC-L19$_{dN152}$ (SEQ ID NO: 182). Sequences are arranged by genetic distance from 10E8, with sequence changes from 10E8 underlined. Framework and CDR residues are highlighted, as are residues that interact with the gp41 MPER epitope (as described in (A). (D) Modeled structures of light chain variants in complex with gp41 epitope. 10E8 variants with enhanced recognition (with light chains shaded according to phylogenetic distance as in 1C) were modeled onto the structure of 10E8 with entire MPER region of HIV-1 gp41 (off-white). Structures are displayed as Cα-ribbons, with amino acid-side chains that vary from 10E8 highlighted in stick representation, dark grey.

FIGS. 52A-52D are a table and a set of graphs illustrating phylogenetic branch matching of heavy and light chain variants of 10E8. (A) Phylogenetic branch matching. From the phylogenetic trees of grid-identified antibodies (FIG. 1C,D) branches were named based on distance from 10E8, b1-H for heavy and b1-L for light for the branch containing 10E8, and in descending order, b2-H (b2-L), b3-H (b3-L), and b4-H for the farthest branch. The variant from each branch that displayed the most potent neutralization with a 10E8 wild-type partner was chosen, and a full matrix of 12 antibodies reconstituted. (B) HIV-1 neutralization. Neutralization was assessed on 5 isolates, for 10E8 variants from matched and mismatched branch pairings. (C) Hep2 Staining. Auto-reactivity was accessed with Hep2 cell staining, for 10E8 variants from matched and mismatched branch pairings.

FIG. 53 is a table illustrating 10E8 monoclonal antibodies composed of the indicated heavy and light chain variants based on the neutralization potency of the indicated variants when complemented with the 10E8 wild-type complementary chain.

FIG. 54 is a table illustrating 10E8 antibodies composed of the indicated heavy and light chain variants paired phylogenetically.

FIGS. 55A-55C shows a set of tables illustrating results of neutralization assays on a panel of HIV-1 viruses using the series of 10E8 variant paired by neutralization potency or pair phylogenetically as shown in FIGS. 53 and 54 and described in Example 8.

FIG. 56 is a set of tables illustrating results of autoreactivity assays on a panel of HIV-1 viruses using the series of 10E8 variant paired by neutralization potency or pair phylogenetically as shown in FIGS. 53 and 54 and described in Example 8.

FIG. 57 is a set of tables illustrating results of neutralization assays on a panel of HIV-1 viruses using the series of 10E8 variants paired by neutralization potency or paired phylogenetically as shown in FIGS. 53 and 54 and described in Example 8.

FIGS. 58A and 58B are a set of graphs illustrating results from neutralization assays testing the neutralization properties of the indicated series of antibodies, containing 10E8 heavy and light chains, or variants of 10E8 heavy and light chains, on a panel of 20 HIV viruses.

FIG. 59 is a table illustrating the nomenclature and SEQ ID NOs for the heavy and light chains of certain 10E8 antibody variants.

FIGS. 60A and 60B are a set of tables illustrating a summary of 10E8 heavy chain variants. "Germline revertant," "454," "Alanine Scan," "Structure-based," and "additional" mutants refer to the 10E8 heavy chain substitutions illustrated in Example 8.

FIGS. 61A and 61B are a set of tables illustrating a summary of 10E8 light chain variants. "Germline revertant" and "454" mutants refer to the 10E8 light chain substitutions illustrated in Example 8.

SEQUENCE LISTING

Figure 3A:
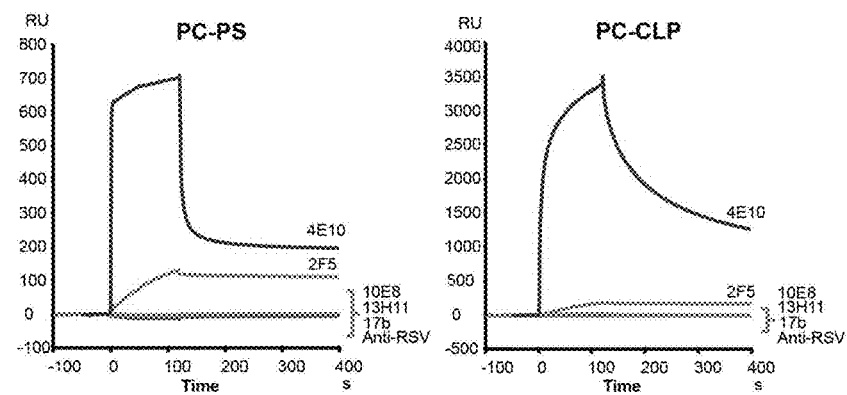
FIGS. 3A and 3B are a set of graphs and a set of digital images illustrating analysis of 10E8 autoreactivity. (A) Surface Plasmon Resonance (SPR) analysis of 10E8 binding to anionic phospholipids. 10E8 was injected over PC-CLP liposomes or PC-PS liposome immobilized on the BIACORE® L1 sensor chip. 4E10 and 2F5 were used as positive controls and 13H1, 17b, and anti-RSV F protein as negative controls. (B) Reactivity of 10E8 with HEP-2 epithelial cells. Controls are as above with VRC01 added as an additional negative control. Antibody concentration was 25 µg/ml. All pictures are shown at 400× magnification.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file in the form of the file named "Sequence.txt" (~160 kb), which was created on Sep. 1, 2017, which is incorporated by reference herein. In the accompanying sequence listing:

SEQ ID NO: 1 is the amino acid sequence of the heavy chain of the gp41-specific antibody 10E8.

SEQ ID NO: 2 is the amino acid sequence of the light chain of the gp41-specific antibody 10E8.

SEQ ID NO: 3 is the amino acid sequence of the heavy chain of the gp41-specific antibody 7H6.

SEQ ID NO: 4 is the amino acid sequence of the light chain of the gp41-specific antibody 7H6.

SEQ ID NO: 5 is the amino acid sequence of the heavy chain of the gp41-specific antibody 7N16.

SEQ ID NO: 6 is the amino acid sequence of the light chain of the gp41-specific antibody 7N16.

SEQ ID NO: 7 is the amino acid sequence of the heavy chain of IGHV3-15*05.

SEQ ID NO: 8 is the amino acid sequence of the light chain of IGLV3-19*01.

SEQ ID NOs: 9 and 10 are epitopes within the gp41 MPER.

SEQ ID NO: 11 is the amino acid sequence of the heavy chain of a gp41-specific antibody.

SEQ ID NO: 12 is the amino acid sequence of the light chain of a gp41-specific antibody.

SEQ ID NO: 13 is the amino acid sequence of a gp41 epitope that specifically binds 10E8 and 10E8 like antibodies.

SEQ ID NOs: 14-25 are the amino acid sequences of mutant gp41 MPER sequences.

SEQ ID NO: 26 is the amino acid sequence of a region of the gp41 MPER.

SEQ ID NOs: 27-34 are the nucleic acid sequences of sequencing primers.

SEQ ID NOs: 35-115 are the nucleic acid sequences of exemplary 10E8-like antibody heavy chains.

SEQ ID NOs: 116-145 are the nucleic acid sequences of exemplary 10E8-like antibody light chains.

SEQ ID NO: 146 is the consensus amino acid sequence of the heavy chain of a gp41-specific antibody.

SEQ ID NOs: 147-149 are the amino acid sequences of the heavy chains of germline revertants the 10E8 monoclonal antibody.

SEQ ID NOs: 150-152 are the amino acid sequences of the light chain variable regions of germline revertants of the 10E8 monoclonal antibody.

SEQ ID NOs: 153-163 are the amino acid sequences of the heavy chain variable regions of gp41-specific antibodies.

SEQ ID NOs: 164-186 are the amino acid sequences of the light chain variable regions of gp41-specific antibodies.

SEQ ID NO: 187 is the consensus amino acid sequence of the heavy chain variable region of a gp41-specific antibody.

SEQ ID NO: 188 is the consensus amino acid sequence of the heavy chain variable region of a gp41-specific antibody.

SEQ ID NOs: 189-192 are the amino acid sequences of the heavy chain variable regions of gp41-specific antibodies.

SEQ ID NOs: 193-196 are the nucleic acid sequences of primers.

SEQ ID NOs: 197-199 are the amino acid sequences of the light chain variable regions of gp41 specific antibodies.

SEQ ID NOs: 200-205 are the amino acid sequences of the heavy chain variable regions of gp41 specific antibodies.

SEQ ID NOs: 205-209 are the amino acid sequences of the light chain variable regions of gp41 specific antibodies.

DETAILED DESCRIPTION

I. Summary of Terms

Unless otherwise noted, technical terms are used according to conventional usage. Definitions of common terms in molecular biology can be found in Benjamin Lewin, Genes VII, published by Oxford University *Press,* 1999; Kendrew et al. (eds.), *The Encyclopedia of Molecular Biology*, published by Blackwell Science Ltd., 1994; and Robert A. Meyers (ed.), *Molecular Biology and Biotechnology: a Comprehensive Desk Reference*, published by VCH Publishers, Inc., 1995; and other similar references.

As used herein, the singular forms "a," "an," and "the," refer to both the singular as well as plural, unless the context clearly indicates otherwise. For example, the term "an antigen" includes single or plural antigens and can be considered equivalent to the phrase "at least one antigen."

As used herein, the term "comprises" means "includes." Thus, "comprising an antigen" means "including an antigen" without excluding other elements.

It is further to be understood that any and all base sizes or amino acid sizes, and all molecular weight or molecular mass values, given for nucleic acids or polypeptides are approximate, and are provided for descriptive purposes, unless otherwise indicated. Although many methods and materials similar or equivalent to those described herein can be used, particular suitable methods and materials are described below. In case of conflict, the present specification, including explanations of terms, will control. In addition, the materials, methods, and examples are illustrative only and not intended to be limiting.

To facilitate review of the various embodiments, the following explanations of terms are provided:

Administration: The introduction of a composition into a subject by a chosen route. Administration can be local or systemic. For example, if the chosen route is intravenous, the composition is administered by introducing the composition into a vein of the subject. In some examples, a disclosed antibody, or antigen binding fragment thereof, specific for an HIV gp41 polypeptide is administered to a subject.

Agent: Any substance or any combination of substances that is useful for achieving an end or result; for example, a substance or combination of substances useful for inhibiting HIV infection in a subject. Agents include proteins, nucleic acid molecules, compounds, small molecules, organic compounds, inorganic compounds, or other molecules of interest. An agent can include a therapeutic agent (such as an anti-retroviral agent), a diagnostic agent or a pharmaceutical agent. In some embodiments, the agent is a polypeptide agent (such as a HIV-neutralizing antibody), or an anti-viral agent. The skilled artisan will understand that particular agents may be useful to achieve more than one result.

Amino acid substitution: The replacement of one amino acid in polypeptide with a different amino acid.

Amplification: A technique that increases the number of copies of a nucleic acid molecule (such as an RNA or DNA). An example of amplification is the polymerase chain reaction, in which a biological sample is contacted with a pair of oligonucleotide primers, under conditions that allow for the hybridization of the primers to a nucleic acid template in the sample. The primers are extended under suitable conditions, dissociated from the template, and then re-annealed, extended, and dissociated to amplify the number of copies of the nucleic acid. The product of amplification can be characterized by electrophoresis, restriction endonuclease cleavage patterns, oligonucleotide hybridization or ligation, and/or nucleic acid sequencing using standard techniques. Other examples of amplification include strand displacement amplification, as disclosed in U.S. Pat. No. 5,744,311; transcription-free isothermal amplification, as disclosed in U.S. Pat. No. 6,033,881; repair chain reaction amplification, as disclosed in WO 90/01069; ligase chain reaction amplification, as disclosed in EP-A-320 308; gap filling ligase chain reaction amplification, as disclosed in U.S. Pat. No. 5,427,930; and NASBA™ RNA transcription-free amplification, as disclosed in U.S. Pat. No. 6,025,134.

Animal: Living multi-cellular vertebrate organisms, a category that includes, for example, mammals and birds. The term mammal includes both human and non-human mammals. Similarly, the term "subject" includes both human and veterinary subjects.

Antibody: A polypeptide substantially encoded by an immunoglobulin gene or immunoglobulin genes, or antigen binding fragments thereof, which specifically binds and recognizes an analyte (antigen) such as gp41 or an immunogenic fragment of gp41, for example the membrane-proximal region of gp41. Immunoglobulin genes include the kappa, lambda, alpha, gamma, delta, epsilon and mu constant region genes, as well as the myriad immunoglobulin variable region genes.

Antibodies exist, for example as intact immunoglobulins and as a number of well characterized antigen binding fragments produced by digestion with various peptidases. For instance, Fabs, Fvs, scFvs that specifically bind to gp41 or fragments of gp41 would be gp41-specific binding agents. A scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. The term also includes genetically engineered forms such as chimeric antibodies and heteroconjugate antibodies such as bispecific antibodies. See also, *Pierce Catalog and Handbook*, 1994-1995 (Pierce Chemical Co., Rockford, Ill.); Kuby, *Immunology*, 3$^{rd}$ Ed., W.H. Freeman & Co., New York, 1997.

Antibody fragments include, but are not limited to, the following: (1) Fab, the fragment which contains a monovalent antigen-binding fragment of an antibody molecule produced by digestion of whole antibody with the enzyme papain to yield an intact light chain and a portion of one heavy chain; (2) Fab', the fragment of an antibody molecule obtained by treating whole antibody with pepsin, followed by reduction, to yield an intact light chain and a portion of the heavy chain; two Fab' fragments are obtained per antibody molecule; (3) (Fab')$_2$, the fragment of the antibody obtained by treating whole antibody with the enzyme pepsin without subsequent reduction; (4) F(ab')2, a dimer of two Fab' fragments held together by two disulfide bonds; (5) Fv, a genetically engineered fragment containing the variable region of the light chain and the variable region of the heavy chain expressed as two chains; and (6) single chain antibody ("SCA"), a genetically engineered molecule containing the variable region of the light chain, the variable region of the heavy chain, linked by a suitable polypeptide linker as a genetically fused single chain molecule.

The term "antibody," as used herein, also includes antibody fragments either produced by the modification of whole antibodies or those synthesized de novo using recombinant DNA methodologies. In some examples, the term antibody includes the amino acid sequences of one or more of the CDRs from the antibody grafted onto a scaffold.

Typically, a naturally occurring immunoglobulin has heavy (H) chains and light (L) chains interconnected by disulfide bonds. There are two types of light chain, lambda (λ) and kappa (κ). There are five main heavy chain classes (or isotypes) which determine the functional activity of an antibody molecule: IgM, IgD, IgG, IgA and IgE. The disclosed antibodies can be class switched.

Each heavy and light chain contains a constant region and a variable region, (the regions are also known as "domains"). In several embodiments, the heavy and the light chain variable domains combine to specifically bind the antigen. In additional embodiments, only the heavy chain variable domain is required. For example, naturally occurring camelid antibodies consisting of a heavy chain only are functional and stable in the absence of light chain (see, e.g., Hamers-Casterman et al., *Nature*, 363:446-448, 1993; Sheriff et al., *Nat. Struct. Biol.*, 3:733-736, 1996). Light and heavy chain variable domains contain a "framework" region interrupted by three hypervariable regions, also called "complementarity-determining regions" or "CDRs" (see, e.g., Kabat et al., *Sequences of Proteins of Immunological Interest*, U.S. Department of Health and Human Services, 1991). The sequences of the framework regions of different light or heavy chains are relatively conserved within a species. The framework region of an antibody, that is the combined framework regions of the constituent light and heavy chains, serves to position and align the CDRs in three-dimensional space.

The CDRs are primarily responsible for binding to an epitope of an antigen. The amino acid sequence boundaries of a given CDR can be readily determined using any of a number of well-known schemes, including those described by Kabat et al. ("Sequences of Proteins of Immunological Interest," 5th Ed. Public Health Service, National Institutes of Health, Bethesda, Md., 1991; "Kabat" numbering scheme), Al-Lazikani et al., (JMB 273,927-948, 1997; "Chothia" numbering scheme), and Lefranc, et al. ("IMGT unique numbering for immunoglobulin and T cell receptor variable domains and Ig superfamily V-like domains," Dev. Comp. Immunol., 27:55-77, 2003; "IMGT" numbering scheme).

The CDRs of each chain are typically referred to as CDR1, CDR2, and CDR3 (from the N-terminus to C-terminus), and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found. Light chain CDRs are sometimes referred to as CDR L1, CDR L2, and CDR L3. Heavy chain CDRs are sometimes referred to as CDR H1, CDR H2, and CDR H3.

References to "$V_H$" or "VH" refer to the variable region of an immunoglobulin heavy chain, including that of an antibody fragment, such as Fv, scFv, dsFv or Fab. References to "$V_L$" or "VL" refer to the variable region of an immunoglobulin light chain, including that of an Fv, scFv, dsFv or Fab.

A "monoclonal antibody" is an antibody produced by a single clone of B-lymphocytes or by a cell into which the light and heavy chain genes of a single antibody have been transfected. Monoclonal antibodies are produced by methods known to those of skill in the art, for instance by making hybrid antibody-forming cells from a fusion of myeloma cells with immune spleen cells. These fused cells and their progeny are termed "hybridomas." Monoclonal antibodies include humanized monoclonal antibodies. In some examples monoclonal antibodies are isolated from a subject. The amino acid sequences of such isolated monoclonal antibodies can be determined.

A "humanized" immunoglobulin is an immunoglobulin including a human framework region and one or more CDRs from a non-human (such as a mouse, rat, or synthetic) immunoglobulin. The non-human immunoglobulin providing the CDRs is termed a "donor," and the human immunoglobulin providing the framework is termed an "acceptor." In one embodiment, all the CDRs are from the donor immunoglobulin in a humanized immunoglobulin. Constant regions need not be present, but if they are, they must be substantially identical to human immunoglobulin constant regions, such as at least about 85-90%, such as about 95% or more identical. Hence, all parts of a humanized immunoglobulin, except possibly the CDRs, are substantially identical to corresponding parts of natural human immunoglobulin sequences. A "humanized antibody" is an antibody including a humanized light chain and a humanized heavy chain immunoglobulin. A humanized antibody binds to the same antigen as the donor antibody that provides the CDRs. The acceptor framework of a humanized immunoglobulin or antibody may have a limited number of substitutions by amino acids taken from the donor framework. Humanized or other monoclonal antibodies can have additional conservative amino acid substitutions which have substantially no effect on antigen binding or other immunoglobulin functions. Humanized immunoglobulins can be constructed by means of genetic engineering (for example, see U.S. Pat. No. 5,585,089).

Antibody self-reactivity: A property of an antibody, whereby the antibody reacts with self-epitopes, that is epitopes of proteins and/or lipids that are produced by the subject. For example, an antibody, such as 10E8 that does not have self-reactivity does not bind to lipids present on the membrane of a cell from a subject, such as a cell infected with HIV and/or expressing gp41 on its surface. Methods of determining if an antibody reacts with self epitopes are known to the person of ordinary skill in the art and described herein (for example, in Examples 1 and 8). In one example, antibody self reactivity is evaluated using an anti-cardiolipin assay or an anti-nuclear antigen (ANA) assay.

Antibody Scaffold: Refers to a heterologous protein that is engrafted with one or more CDRs from an antibody of interest on its surface. Transplantation of the CDRs can performed computationally in a manner that preserves its relevant structure and conformation. Mutations within the acceptor scaffold are made in order to accommodate the CDR graft.

Antibodyome: The entire repertoire of expressed antibody heavy and light chain sequence in an individual. The individual can be an individual infected with a pathogen, for example, HIV.

Antigen: A polypeptide that can stimulate the production of antibodies or a T cell response in an animal, including polypeptides that are injected or absorbed into an animal. An antigen reacts with the products of specific humoral or cellular immunity, including those induced by heterologous antigens, such as the disclosed antigens. "Epitope" or "antigenic determinant" refers to the region of an antigen to which B and/or T cells respond. In one embodiment, T cells respond to the epitope, when the epitope is presented in conjunction with an MHC molecule. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5, about 9, or about 8-10 amino acids in a unique spatial conformation. Methods of determining spatial conformation of epitopes include, for example, x-ray crystallography and nuclear magnetic resonance.

Immunogenic polypeptides and immunogenic peptides are non-limiting examples of antigens. In some examples, antigens include polypeptides derived from a pathogen of interest, such as a virus. An antigen that can stimulate the production of antibodies or a T cell response in a subject to a polypeptide expressed by a virus is a viral antigen. An "HIV antigen" can stimulate the production of antibodies or a T cell response in a subject to a polypeptide expressed by HIV. In some embodiments, an HIV antigen is a polypeptide expressed by HIV, such as gp160, or a fragment thereof, such as gp145, gp140, gp120 or gp41.

A "target epitope" is a specific epitope on an antigen that specifically binds an antibody of interest, such as a monoclonal antibody. In some examples, a target epitope includes the amino acid residues that contact the antibody of interest, such that the target epitope can be selected by the amino acid residues determined to be in contact with the antibody of interest.

Anti-retroviral agent: An agent that specifically inhibits a retrovirus from replicating or infecting cells. Non-limiting examples of antiretroviral drugs include entry inhibitors (e.g., enfuvirtide), CCR5 receptor antagonists (e.g., aplaviroc, vicriviroc, maraviroc), reverse transcriptase inhibitors (e.g., lamivudine, zidovudine, abacavir, tenofovir, emtricitabine, efavirenz), protease inhibitors (e.g., lopivar, ritonavir, raltegravir, darunavir, atazanavir), maturation inhibitors (e.g., alpha interferon, bevirimat and vivecon).

Anti-retroviral therapy (ART): A therapeutic treatment for HIV infection involving administration of at least one anti-retroviral agents (e.g., one, two, three or four anti-retroviral agents) to an HIV infected individual during a course of treatment. Non-limiting examples of antiretroviral agents include entry inhibitors (e.g., enfuvirtide), CCR5 receptor antagonists (e.g., aplaviroc, vicriviroc, maraviroc), reverse transcriptase inhibitors (e.g., lamivudine, zidovudine, abacavir, tenofovir, emtricitabine, efavirenz), protease inhibitors (e.g., lopivar, ritonavir, raltegravir, darunavir, atazanavir), maturation inhibitors (e.g., alpha interferon, bevirimat and vivecon). One example of an ART regimen includes treatment with a combination of tenofovir, emtricitabine and efavirenz. In some examples, ART includes Highly Active Anti-Retroviral Therapy (HAART).

Atomic Coordinates or Structure coordinates: Mathematical coordinates derived from mathematical equations related to the patterns obtained on diffraction of a monochromatic beam of X-rays by the atoms (scattering centers) such as an antigen, or an antigen in complex with an antibody. In some examples that antigen can be gp41, a gp41:antibody complex, or combinations thereof in a crystal. The diffraction data are used to calculate an electron density map of the repeating unit of the crystal. The electron density maps are used to establish the positions of the individual atoms within the unit cell of the crystal. In one example, the term "structure coordinates" refers to Cartesian coordinates derived from mathematical equations related to the patterns obtained on diffraction of a monochromatic beam of X-rays, such as by the atoms of a gp41 in crystal form.

Those of ordinary skill in the art understand that a set of structure coordinates determined by X-ray crystallography is not without standard error. For the purpose of this disclosure, any set of structure coordinates that have a root mean square deviation of protein backbone atoms (N, Cα, C and 0) of less than about 1.0 Angstroms when superimposed, such as about 0.75, or about 0.5, or about 0.25 Angstroms, using backbone atoms, shall (in the absence of an explicit statement to the contrary) be considered identical.

B Cell and Memory B cell: B cells are a subset of lymphocytes, that is, white blood cells (leukocytes). Mature B cells differentiate into plasma cells, which produces antibodies, and memory B cells. A "B cell progenitor" is a cell that can develop into a mature B cell. B cell progenitors include stem cells, early pro-B cells, late pro-B cells, large pre-B cells, small pre-B cells, and immature B cells and transitional B cells. Generally, early pro-B cells (that express, for example, CD43 or B220) undergo immunoglobulin heavy chain rearrangement to become late pro B and pre B cells, and further undergo immunoglobulin light chain rearrangement to become an immature B cells. In humans, immature B cells (for example, immature peripheral transitional B cells) include $CD38^{hi}$, $IgD^+$, $CD10^+$, $CD24^{hi}$, $CD44^{lo}$, $CD23^{lo}$ and $CD1^{lo}$ cells. Thus, immature B cells include B220 (CD45R) expressing cells wherein the light and the heavy chain immunoglobulin genes are rearranged. In one embodiment, immature B cells express CD45R, class II, IgM, CD19 and CD40. Immature B cells can develop into mature B cells, which can produce immunoglobulins (e.g., IgA, IgG or IgM). Mature B cells have acquired surface IgM and IgD, are capable of responding to antigen, and express characteristic markers such as CD21 and CD23 ($CD23^{hi}CD21^{hi}$ cells). Plasma cells are terminally differentiated B cells that are the predominant antibody-secreting cells.

After a B cell progenitor (e.g., a pre-committed small lymphocyte) is stimulated by an antigen, it differentiates into a blast cell, which differentiates into an immature plasma cell that can differentiate into either a mature plasma cell or a memory B cell. A "mature plasma cell" secretes immunoglobulins in response to a specific antigen.

B cells can be activated by agents such as lippopolysaccharide (LPS) or IL-4 and antibodies to IgM. Common biological sources of B cells and B cell progenitors include bone marrow, peripheral blood, spleen and lymph nodes.

A "memory B cell" is a B cell that undergoes isotype switching and somatic hypermutation that are generally found during a secondary immune response (a subsequent antigen exposure following a primary exposure) but can also be detected during a primary antigen response. Generation of memory B cells generally requires helper T cells. The development of memory B cells takes place in germinal centers (GC) of lymphoid follicles where antigen-driven lymphocytes undergo somatic hypermutation and affinity selection, presumably under the influence of helper T cells. Typically, memory B cells express high affinity antigen specific immunoglobulin (B cell receptor) on their cell surface. In one embodiment, memory B cells include cells that express CD19, but do not express IgA, IgD or IgM ($CD19^+IgA^-IgD^-IgM^-$ cells).

Bispecific antibody: A recombinant molecule composed of two different antigen binding domains that consequently binds to two different antigenic epitopes. Bispecific antibodies include chemically or genetically linked molecules of two antigen-binding domains. The antigen binding domains can be linked using a linker. The antigen binding domains can be monoclonal antibodies, antigen-binding fragments (e.g., Fab, scFv), eAds, bispecific single chain antibodies or combinations thereof. A bispecific antibody can include one or more constant domains, but does not necessarily include a constant domain. An example of a bispecific antibody is a bispecific single chain antibody including a scFv that specifically binds to gp41 joined (via a peptide linker) to a scFv that specifically binds to an antigen other than gp41. Another example is a bispecific antibody including a Fab that specifically binds to gp41 joined to a scFv that specifically binds to an antigen other than gp41.

B cell repertoire: The B cells in a sample or in a subject specific for antigen of interest.

CD40: A costimulatory protein found an antigen presenting cells that is required for their activation. The binding of CD40 ligand (CD40L), also known as CD154, to CD40 activates antigen presenting cells. This receptor has been found to be essential in mediating a broad variety of immune and inflammatory responses including T cell-dependent immunoglobulin class switching, memory B cell development, and germinal center formation. An exemplary amino acid sequence for CD40, and an exemplary mRNA sequence encoding CD40 can be found in GENBANK® Accession No. NM_001250, (Jun. 10, 2012), which is incorporated herein by reference.

CD40 ligand (CD40L): A ligand that is also called CD154, that is expressed on activated T cells and is a member of the tumor necrosis superfamily of molecules. It binds to CD40 on antigen-presenting cells, which leads to many effects depending on the target cell type. In general, CD40L plays the role of a costimulatory molecule and induces activation in antigen-presenting cells in association with T cell receptor stimulation by MHC molecules on the antigen-presenting cells. In total CD40L has three binding partners: CD40, α5β1 integrin and αIIbβ3. CD154 is expressed on the surface of T cells. It regulates B cell function by engaging CD40 on the B cell surface. An exemplary amino acid sequence for CD40, and an exemplary mRNA sequence encoding CD40 can be found in GENBANK® Accession No. NM_000074.2, (Jun. 10, 2012), which is incorporated herein by reference.

Chimeric antibody: An antibody which includes sequences derived from two different antibodies, which typically are of different species. In some examples, a chimeric antibody includes one or more CDRs and/or framework regions from one human antibody and CDRs and/or framework regions from another human antibody. In some examples, a chimeric antibody is produced by grafting one or more CDRs into an antibody scaffold.

Clonal variant: Any sequence, which differs by one or more nucleotides or amino acids, in presence of V region with identical mutations compared to the germline, identical VDJ or VJ gene usage, and identical D and J length. The "germline" sequence is intended to be the sequence coding for the antibody/immunoglobulin (or of any fragment thereof) deprived of mutations, for example somatic mutations. The percentage of homology represents an indication of the mutational events which any type of heavy chain portion undergoes after contact with an antigen.

Computer readable storage media: Any medium or media, which can be read and accessed directly by a computer, so that the media is suitable for use in a computer system. Such media include, but are not limited to: magnetic storage media such as floppy discs, hard disc storage medium and magnetic tape; optical storage media such as optical discs or CD-ROM; electrical storage media such as RAM and ROM; and hybrids of these categories such as magnetic/optical storage media.

Computer system: Hardware that can be used to analyze atomic coordinate data and/or design an antigen using atomic coordinate data or to analyze an amino acid or nucleic acid sequence, for example to compare two or more sequences an calculate sequence similarity and/or divergence. The minimum hardware of a computer-based system typically includes a central processing unit (CPU), an input device, for example a mouse, keyboard, and the like, an output device, and a data storage device. Desirably a monitor is provided to visualize structure data. The data storage device may be RAM or other means for accessing computer readable. Examples of such systems are microcomputer workstations available from Silicon Graphics Incorporated and Sun Microsystems running Unix based Windows NT or IBM OS/2 operating systems.

Conjugate: A complex of two molecules linked together, for example, linked together by a covalent bond. In one embodiment, an antibody is linked to an effector molecule; for example, an antibody that specifically binds to gp41 covalently linked to an effector molecule or to a toxin. The linkage can be by chemical or recombinant means. In one embodiment, the linkage is chemical, wherein a reaction between the antibody moiety and the effector molecule has produced a covalent bond formed between the two molecules to form one molecule. A peptide linker (short peptide sequence) can optionally be included between the antibody and the effector molecule. Because conjugates can be prepared from two molecules with separate functionalities, such as an antibody and an effector molecule, they are also sometimes referred to as "chimeric molecules." In one embodiment, an antibody linked to an effector molecule is further joined to a lipid or other molecule to a protein or peptide to increase its half-life in the body.

Contacting: Placement in direct physical association; includes both in solid and liquid form, which can take place either in vivo or in vitro. Contacting includes contact between one molecule and another molecule, for example the amino acid on the surface of one polypeptide, such as an antigen, that contacts another polypeptide, such as an antibody. Contacting between polypeptides can include direct contacts between amino acids of two or more polypeptides (for example, hydrogen bonding or Van der Waals force interactions between polypeptides), as well as other interactions between polypeptides producing an interface between the polypeptides with reduced solvent accessibility (without all amino acids of the interface necessarily forming direct bonds). In some embodiments, a direct contact refers to forming a hydrogen bond or Van der Waals interaction with particularly a identified residue or residues in a sequence but not with the other residues in the sequence. The person of ordinary skill in the art is familiar with methods of determining contacts between polypeptides (see for example, Example 1). Contacting can also include contacting a cell for example by placing an antibody in direct physical association with a cell. In some embodiments, an antibody (e.g., 10E8) only contacts particular residues of an epitope on an antigen, such as the 10E8 epitope on gp41 as described herein.

Control: A reference standard. In some embodiments, the control is a sample obtained from a healthy patient. In other embodiments, the control is a tissue sample obtained from a patient diagnosed with HIV infection. In still other embodiments, the control is a historical control or standard reference value or range of values (such as a previously tested control sample, such as a group of HIV patients with known prognosis or outcome, or group of samples that represent baseline or normal values).

A difference between a test sample and a control can be an increase or conversely a decrease. The difference can be a qualitative difference or a quantitative difference, for example a statistically significant difference. In some examples, a difference is an increase or decrease, relative to a control, of at least about 5%, such as at least about 10%, at least about 20%, at least about 30%, at least about 40%, at least about 50%, at least about 60%, at least about 70%, at least about 80%, at least about 90%, at least about 100%, at least about 150%, at least about 200%, at least about 250%, at least about 300%, at least about 350%, at least about 400%, at least about 500%, or greater than 500%.

Cytokine/Interleukin (IL): A generic name for a diverse group of soluble proteins and peptides which act as humoral regulators at nano- to picomolar concentrations and which, either under normal or pathological conditions, modulate the functional activities of individual cells and tissues. These proteins also mediate interactions between cells directly and regulate processes taking place in the extracellular environment. Many growth factors and cytokines act as cellular survival factors by preventing programmed cell death. Cytokines and interleukins include both naturally occurring peptides and variants that retain full or partial biological activity. Although specific cytokines/interleukins are described in the specification, they are not limited to the specifically disclosed peptides.

Cytotoxicity: The toxicity of a molecule, such as an immunotoxin, to the cells intended to be targeted, as opposed to the cells of the rest of an organism. In one embodiment, in contrast, the term "toxicity" refers to toxicity of an immunotoxin to cells other than those that are the cells intended to be targeted by the targeting moiety of the immunotoxin, and the term "animal toxicity" refers to toxicity of the immunotoxin to an animal by toxicity of the immunotoxin to cells other than those intended to be targeted by the immunotoxin.

Detectable marker: A detectable molecule (also known as a label) that is conjugated directly or indirectly to a second molecule, such as an antibody, to facilitate detection of the second molecule. For example, the detectable marker can be capable of detection by ELISA, spectrophotometry, flow cytometry, microscopy or diagnostic imaging techniques (such as CT scans, MRIs, ultrasound, fiberoptic examination, and laparoscopic examination). Specific, non-limiting examples of detectable markers include fluorophores, fluorescent proteins, chemiluminescent agents, enzymatic linkages, radioactive isotopes and heavy metals or compounds (for example super paramagnetic iron oxide nanocrystals for detection by MRI). In one example, a "labeled antibody" refers to incorporation of another molecule in the antibody. For example, the label is a detectable marker, such as the incorporation of a radiolabeled amino acid or attachment to a polypeptide of biotinyl moieties that can be detected by marked avidin (for example, streptavidin containing a fluorescent marker or enzymatic activity that can be detected by optical or colorimetric methods). Various methods of labeling polypeptides and glycoproteins are known in the art and may be used. Examples of labels for polypeptides include, but are not limited to, the following: radioisotopes or radionuclides (such as $^{35}$S or $^{131}$I), fluorescent labels (such as fluorescein isothiocyanate (FITC), rhodamine, lanthanide phosphors), enzymatic labels (such as horseradish peroxidase, beta-galactosidase, luciferase, alkaline phosphatase), chemiluminescent markers, biotinyl groups, predetermined polypeptide epitopes recognized by a secondary reporter (such as a leucine zipper pair sequences, binding sites for secondary antibodies, metal binding domains, epitope tags), or magnetic agents, such as gadolinium chelates. In some embodiments, labels are attached by spacer arms of various lengths to reduce potential steric hindrance. Methods for using detectable markers and guidance in the choice of detectable markers appropriate for various purposes are discussed for example in Sambrook et al. (Molecular Cloning: A Laboratory Manual, Cold Spring Harbor, N.Y., 1989) and Ausubel et al. (In Current Protocols in Molecular Biology, John Wiley & Sons, New York, 1998).

Detecting: To identify the existence, presence, or fact of something. General methods of detecting are known to the skilled artisan and may be supplemented with the protocols and reagents disclosed herein. For example, included herein are methods of detecting a cell that expresses gp41 in a subject.

DNA sequencing: The process of determining the nucleotide order of a given DNA molecule. The general characteristics of "deep sequencing" are that genetic material is amplified, such as by polymerase chain reaction, and then the amplified products are ligated to a solid surface. The sequence of the amplified target genetic material is then performed in parallel and the sequence information is captured by a computer. Generally, the sequencing can be performed using automated Sanger sequencing (AB13730x1 genome analyzer), pyrosequencing on a solid support (454 sequencing, Roche), sequencing-by-synthesis with reversible terminations (ILLUMINA® Genome Analyzer), sequencing-by-ligation (ABI SOLiD®) or sequencing-by-synthesis with virtual terminators (HELISCOPE®).

In some embodiments, DNA sequencing is performed using a chain termination method developed by Frederick Sanger, and thus termed "Sanger based sequencing" or "SBS." This technique uses sequence-specific termination of a DNA synthesis reaction using modified nucleotide substrates. Extension is initiated at a specific site on the template DNA by using a short oligonucleotide primer complementary to the template at that region. The oligonucleotide primer is extended using DNA polymerase in the presence of the four deoxynucleotide bases (DNA building blocks), along with a low concentration of a chain terminating nucleotide (most commonly a di-deoxynucleotide). Limited incorporation of the chain terminating nucleotide by the DNA polymerase results in a series of related DNA fragments that are terminated only at positions where that particular nucleotide is present. The fragments are then size-separated by electrophoresis a polyacrylamide gel, or in a narrow glass tube (capillary) filled with a viscous polymer. An alternative to using a labeled primer is to use labeled terminators instead; this method is commonly called "dye terminator sequencing."

"Pyrosequencing" is an array based method, which has been commercialized by 454 Life Sciences (Branford, Conn.). In some embodiments of the array-based methods, single-stranded DNA is annealed to beads and amplified via EmPCR®. These DNA-bound beads are then placed into wells on a fiber-optic chip along with enzymes that produce light in the presence of ATP. When free nucleotides are washed over this chip, light is produced as the PCR amplification occurs and ATP is generated when nucleotides join with their complementary base pairs. Addition of one (or more) nucleotide(s) results in a reaction that generates a light signal that is recorded, such as by the charge coupled device (CCD) camera, within the instrument. The signal strength is proportional to the number of nucleotides, for example, homopolymer stretches, incorporated in a single nucleotide flow.

Effective amount: The amount of an agent (such as CD40L, IL-21 or IL-2) that alone, or together with one or more additional agents, induces the desired response.

Effector molecule: The portion of a chimeric molecule that is intended to have a desired effect on a cell to which the chimeric molecule is targeted. Effector molecule is also known as an effector moiety, therapeutic agent, or diagnostic agent, or similar terms.

Epitope: An antigenic determinant. These are particular chemical groups or peptide sequences on a molecule that are antigenic, such that they elicit a specific immune response, for example, an epitope is the region of an antigen to which B and/or T cells respond. In some examples, a disclosed antibody specifically binds to an epitope on the surface of gp41 from HIV.

Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5, about 9, or about 8-10 amino acids in a unique spatial conformation. Methods of determining spatial conformation of epitopes include, for example, x-ray crystallography and nuclear magnetic resonance.

Fc polypeptide: The polypeptide including the constant region of an antibody excluding the first constant region immunoglobulin domain. Fc region generally refers to the last two constant region immunoglobulin domains of IgA, IgD, and IgG, and the last three constant region immunoglobulin domains of IgE and IgM. An Fc region may also include part or all of the flexible hinge N-terminal to these domains. For IgA and IgM, an Fc region may or may not include the tailpiece, and may or may not be bound by the J chain. For IgG, the Fc region includes immunoglobulin domains Cgamma2 and Cgamma3 (Cγ2 and Cγ3) and the lower part of the hinge between Cgamma1 (Cγ1) and Cγ2. Although the boundaries of the Fc region may vary, the human IgG heavy chain Fc region is usually defined to include residues C226 or P230 to its carboxyl-terminus, wherein the numbering is according to the EU index as in Kabat. For IgA, the Fc region includes immunoglobulin domains Calpha2 and Calpha3 (Cα2 and Cα3) and the lower part of the hinge between Calpha1 (Cα1) and Cα2. Encompassed within the definition of the Fc region are functionally equivalent analogs and variants of the Fc region. A functionally equivalent analog of the Fc region may be a variant Fc region, including one or more amino acid modifications relative to the wild-type or naturally existing Fc region. Variant Fc regions will possess at least 50% homology with a naturally existing Fc region, such as about 80%, and about 90%, or at least about 95% homology. Functionally equivalent analogs of the Fc region may include one or more amino acid residues added to or deleted from the N- or C-termini of the protein, such as no more than 30 or no more than 10 additions and/or deletions. Functionally equivalent analogs of the Fc region include Fc regions operably linked to a fusion partner. Functionally equivalent analogs of the Fc region must include the majority of all of the Ig domains that compose the Fc region as defined above; for example IgG and IgA Fc regions as defined herein must include the majority of the sequence encoding $CH_2$ and the majority of the sequence encoding $CH_3$. Thus, the $CH_2$ domain on its own, or the $CH_3$ domain on its own, are not considered the Fc region. The Fc region may refer to this region in isolation, or this region in the context of an Fc fusion polypeptide (immunoadhesin, see below).

Framework Region: Amino acid sequences interposed between CDRs. Includes variable light and variable heavy framework regions. The framework regions serve to hold the CDRs in an appropriate orientation for antigen binding.

gp41: A specific HIV protein. The envelope protein of HIV-1 is initially synthesized as a longer precursor protein of 845-870 amino acids in size, designated gp160. gp160 forms a homotrimer and undergoes glycosylation within the Golgi apparatus. In vivo, it is then cleaved by a cellular protease into gp120 and gp41. The amino acid sequence of an example of gp41 is set forth in GENBANK® Accession No. CAD20975 (as available on Oct. 16, 2009) which is incorporated by reference herein. It is understood that the sequence of gp41 can vary from that given in GENBANK® Accession No. CAD20975. gp41 contains a transmembrane domain and typically remains in a trimeric configuration; it interacts with gp120 in a non-covalent manner.

HIV Envelope protein (Env): The HIV envelope protein is initially synthesized as a longer precursor protein of 845-870 amino acids in size, designated gp160. gp160 forms a homotrimer and undergoes glycosylation within the Golgi apparatus. In vivo, it is then cleaved by a cellular protease into gp120 and gp41. gp120 contains most of the external, surface-exposed, domains of the HIV envelope glycoprotein complex, and it is gp120 which binds both to cellular CD4 receptors and to cellular chemokine receptors (such as CCR5). gp41 contains a transmembrane domain and remains in a trimeric configuration; it interacts with gp120 in a non-covalent manner.

Host cells: Cells in which a vector can be propagated and its DNA expressed, for example a disclosed antibody can be expressed in a host cell. The cell may be prokaryotic or eukaryotic. The term also includes any progeny of the subject host cell. It is understood that all progeny may not be identical to the parental cell since there may be mutations that occur during replication. However, such progeny are included when the term "host cell" is used.

Human Immunodeficiency Virus (HIV): A retrovirus that causes immunosuppression in humans (HIV disease), and leads to a disease complex known as the acquired immunodeficiency syndrome (AIDS). "HIV disease" refers to a well-recognized constellation of signs and symptoms (including the development of opportunistic infections) in persons who are infected by an HIV virus, as determined by antibody or western blot studies. Laboratory findings associated with this disease include a progressive decline in T cells. HIV includes HIV type 1 (HIV-1) and HIV type 2 (HIV-2). Related viruses that are used as animal models include simian immunodeficiency virus (SIV), and feline immunodeficiency virus (FIV). Treatment of HIV-1 with HAART has been effective in reducing the viral burden and ameliorating the effects of HIV-1 infection in infected individuals.

HXB2 numbering system: A reference numbering system for HIV protein and nucleic acid sequences, using HIV-1 HXB2 strain sequences as a reference for all other HIV strain sequences. The person of ordinary skill in the art is familiar with the HXB2 numbering system, and this system is set forth in "Numbering Positions in HIV Relative to HXB2CG," Bette Korber et al., Human Retroviruses and AIDS 1998: A Compilation and Analysis of Nucleic Acid and Amino Acid Sequences. Korber B, Kuiken C L, Foley B, Hahn B, McCutchan F, Mellors J W, and Sodroski J, Eds. Theoretical Biology and Biophysics Group, Los Alamos National Laboratory, Los Alamos, N. Mex., which is incorporated by reference herein in its entirety. HXB2 is also known as: HXBc2, for HXB clone 2; HXB2R, in the Los Alamos HIV database, with the R for revised, as it was slightly revised relative to the original HXB2 sequence; and HXB2CG in GENBANK™, for HXB2 complete genome. The numbering used in gp41 polypeptides disclosed herein is relative to the HXB2 numbering scheme.

IgA: A polypeptide belonging to the class of antibodies that are substantially encoded by a recognized immunoglobulin alpha gene. In humans, this class or isotype includes $IgA_1$ and $IgA_2$. IgAn antibodies can exist as monomers, polymers (referred to as pIgA) of predominantly dimeric form, and secretory IgA. The constant chain of wild-type IgA contains an 18-amino-acid extension at its C-terminus called the tail piece (tp). Polymeric IgA is secreted by plasma cells with a 15-kDa peptide called the J chain linking two monomers of IgA through the conserved cysteine residue in the tail piece.

IgG: A polypeptide belonging to the class or isotype of antibodies that are substantially encoded by a recognized immunoglobulin gamma gene. In humans, this class includes $IgG_1$, $IgG_2$, $IgG_3$, and $IgG_4$.

Immune complex: The binding of antibody to a soluble antigen forms an immune complex. The formation of an immune complex can be detected through conventional methods known to the skilled artisan, for instance immunohistochemistry, immunoprecipitation, flow cytometry, immunofluorescence microscopy, ELISA, immunoblotting (for example, Western blot), magnetic resonance imaging, CT scans, X-ray and affinity chromatography. Immunological binding properties of selected antibodies may be quantified using methods well known in the art.

Immunoadhesin: A molecular fusion of a protein with the Fc region of an immunoglobulin, wherein the immunoglobulin retains specific properties, such as Fc receptor binding and increased half-life. An Fc fusion combines the Fc region of an immunoglobulin with a fusion partner, which in general can be any protein, polypeptide, peptide, or small molecule. In one example, an immunoadhesin includes the hinge, $CH_2$, and $CH_3$ domains of the immunoglobulin gamma 1 heavy chain constant region. In another example, the immunoadhesin includes the $CH_2$, and $CH_3$ domains of an IgG.

Immunogen: A compound, composition, or substance (for example, a protein or a portion thereof) that is capable of inducing an immune response in a mammal, such as a mammal infected or at risk of infection with a pathogen. Administration of an immunogen can lead to protective immunity and/or proactive immunity against a pathogen of interest. In some examples, an immunogen is an HIV antigen. Examples of immunogens include, but are not limited to, peptides, lipids, polysaccharides, combinations thereof, and nucleic acids containing antigenic determinants, such as those recognized by an immune cell. In some examples, immunogens include peptides derived from a pathogen of interest. Exemplary pathogens include bacteria, fungi, viruses and parasites. In specific examples, an immunogen is derived from HIV, such as a gp41 polypeptide derived from HIV or antigenic fragment thereof.

Immunological Probe: A molecule that can be used for selection of antibodies from sera which are directed against a specific epitope, including from human patient sera. The epitope scaffolds, along with related point mutants, can be used as immunological probes in both positive and negative selection of antibodies against the epitope graft. In some examples immunological probes are engineered variants of gp120.

Immunologically reactive conditions: Includes reference to conditions which allow an antibody raised against a particular epitope to bind to that epitope to a detectably greater degree than, and/or to the substantial exclusion of, binding to substantially all other epitopes. Immunologically reactive conditions are dependent upon the format of the antibody binding reaction and typically are those utilized in immunoassay protocols or those conditions encountered in vivo. See Harlow & Lane, infra, for a description of immunoassay formats and conditions. The immunologically reactive conditions employed in the methods are "physiological conditions" which include reference to conditions (e.g., temperature, osmolarity, and pH) that are typical inside a living mammal or a mammalian cell. While it is recognized that some organs are subject to extreme conditions, the intra-organismal and intracellular environment normally lies around pH 7 (e.g., from pH 6.0 to pH 8.0, more typically pH 6.5 to 7.5), contains water as the predominant solvent, and exists at a temperature above 0° C. and below 50° C. Osmolarity is within the range that is supportive of cell viability and proliferation.

Inhibiting or treating a disease: Inhibiting the full development of a disease or condition, for example, in a subject who is at risk for a disease such as acquired immunodeficiency syndrome (AIDS). "Treatment" refers to a therapeutic intervention that ameliorates a sign or symptom of a disease or pathological condition after it has begun to develop. The term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, a reduction in the viral load, an improvement in the overall health or well-being of the subject, or by other parameters well known in the art that are specific to the particular disease. A "prophylactic" treatment is a treatment administered to a subject who does not exhibit signs of a disease or exhibits only early signs for the purpose of decreasing the risk of developing pathology.

Interleukin-2 (IL-2): IL-2 is a cytokine that is necessary for the growth and function of T cells. Antigen binding to the T cell receptor (TCR) stimulates the secretion of IL-2, and the expression of IL-2 receptors IL-2R. The IL-2/IL-2R interaction then stimulates the growth, differentiation and survival of antigen-selected cytotoxic T cells via the activation of the expression of specific genes. As such, IL-2 is necessary for the development of T cell immunologic memory, which depends upon the expansion of the number and function of antigen-selected T cell clones. IL-2 is also necessary during T cell development in the thymus for the maturation of a subset of T cells that are termed regulatory T cells. An exemplary amino acid sequence of human IL-2 is provided in GENBANK® Accession No. NM_000586 (Jun. 10, 2012), which is incorporated by reference herein.

Interleukin-21 (IL-21): A cytokine cloned from a cDNA library derived from activated CD3+ T cells (Parrish-Novak et al., *Nature* 408:57-63, 2000). The IL-21 cDNA encodes a secreted protein of 131 amino acids protein most closely related to IL-2 and IL-15. The IL-21 gene has been mapped to human chromosome 4q26-q27 near the IL-2 gene.

IL-21 mRNA has been demonstrated to be expressed in activated CD4+ cells, but not in other T cells, B cells, or monocytes (Parrish-Novak et al., *Nature* 408:57-63, 2000). However, it has been demonstrated that IL-21 stimulates proliferation of B cells that are stimulated by cross-linking of the CD40 antigen and proliferation of B cells stimulated by IL-4 in addition to anti-IgM. IL-21 has also been shown to stimulate proliferation of naive (CD45RA (+)) cells, mediated by engagement of CD3. IL-21 has also been shown to stimulate the proliferation of bone marrow progenitor to cells and to enhance the expression of the NK cell marker CD56 in the presence of IL-15. (For review, see Horst Ibelgaufts' *COPE: Cytokines Online Pathfinder Encyclopedia*, available on the internet). The amino acid sequence of an exemplary human IL-21 is shown as SEQ ID NO: 1 in U.S. Published Patent Application No. 2003/0003545, which is incorporated herein, by reference. A representative clone containing all or most of the sequence for IL-21 (designated HTGED19) was deposited with the American Type Culture Collection ("ATCC") on Mar. 5, 1998, and was given the ATCC Deposit Number 209666 (see, e.g., U.S. Published Patent Application No. 2003/0003545).

The IL-21 receptor has been isolated and was found to be expressed by CD23+ B cells, B cell lines, a T cell leukemia line, and NK cell lines. The receptor gene has been mapped to human chromosome 16p12 (see Parrish-Novak et al., *Nature* 408:57-63, 2000; Ozaki et al., *Proc. Natl. Acad. Sci. USA* 97:11439-11444, 2000).

Interleukin 15 (IL-15): A cytokine with structural similarity to IL-2. IL-15 binds to and signals through the IL-2/IL-15 beta chain (CD122) and the common gamma chain (gamma-C, CD132). IL-15 is secreted by mononuclear phagocytes (and some other cells) following infection by virus(es). This cytokine induces cell proliferation of natural killer cells; cells of the innate immune system whose principal role is to kill virally infected cells.

Isolated: An "isolated" biological component (such as an antibody, for example, an antibody that specifically binds gp41, a nucleic acid, peptide, protein or antibody) has been substantially separated, produced apart from, or purified away from other biological components in the cell of the organism in which the component naturally occurs, such as, other chromosomal and extrachromosomal DNA and RNA, and proteins. Nucleic acids, peptides and proteins which have been "isolated" thus include nucleic acids and proteins purified by standard purification methods. The term also embraces nucleic acids, peptides, and proteins prepared by recombinant expression in a host cell as well as chemically synthesized nucleic acids or polypeptides. In some examples, an antibody, such as an antibody specific for gp41, can be isolated, for example, isolated from a subject infected with HIV.

An "isolated" cell is a cell that has been purified from the other cellular components of a tissue. Cells can be isolated by mechanical (such as by use FACS) and/or enzymatic methods. In several embodiments, an isolated population of cells (such as a B cell repertoire) includes greater than about 80%, about 85%, about 90%, about 95%, or greater than about 99% of the cells of interest. In another embodiment, an isolated population of cells is one in which no other cells of a different phenotype can be detected. In a further embodiment, an isolated population of cells is a population of cells that includes less than about 20%, about 15%, about 10%, about 5%, or less than about 1% of a cells of a different phenotype than the cells of interest.

$K_D$: The dissociation constant for a given interaction, such as a polypeptide ligand interaction or an antibody antigen interaction. For example, for the bimolecular interaction of an antibody (such as one disclosed herein) and an antigen (such as gp41) it is the concentration of the individual components of the bimolecular interaction divided by the concentration of the complex.

Linker: A bi-functional molecule that can be used to link two molecules into one contiguous molecule, for example, to link an effector molecule to an antibody. In some embodiments, a conjugate includes a linker between the effector molecule or detectable marker and an antibody. In some embodiments, the linker is cleavable under intracellular conditions, such that cleavage of the linker releases the effector molecule or detectable marker from the antibody in the intracellular environment. In yet other embodiments, the linker is not cleavable and the effector molecule or detectable marker can be released, for example, by antibody degradation. In some cases, a linker is a peptide within an antibody binding fragment (such as an Fv fragment) which serves to indirectly bond the variable heavy chain to the variable light chain.

The terms "conjugating," "joining," "bonding" or "linking" refer to making two polypeptides into one contiguous polypeptide molecule, to covalently attaching a radionuclide or other molecule to a polypeptide, such as an antibody that specifically binds gp41, or an antibody binding fragment thereof. In the specific context, the terms include reference to joining a ligand, such as an antibody moiety, to an effector molecule. The linkage can be either by chemical or recombinant means. "Chemical means" refers to a reaction between the antibody moiety and the effector molecule such that there is a covalent bond formed between the two molecules to form one molecule.

Membrane-proximal external region (MPER) of gp41: A region that is immediately N-terminal of the transmembrane region of gp41. The MPER is highly hydrophobic (50% of residues are hydrophobic) and is highly conserved across many HIV clades (Zwick, M. B., et al., *J Virol*, 75 (22): p. 10892-905, 2001). The conserved MPER of HIV-1 gp41 is a target of two neutralizing human monoclonal antibodies, 2F5 and 4E10. The core of the 2F5 epitope has been shown to be ELDKWAS (SEQ ID NO: 9). With this epitope, the residues D, K, and W were found to be most critical for recognition by 2F5. The core of the 4E10 epitope, NWFDIT (SEQ ID NO: 10), maps just C-terminal to the 2F5 epitope on the gp41 ectodomain.

Neutralizing antibody: An antibody which reduces the infectious titer of an infectious agent by binding to a specific antigen on the infectious agent. In some examples the infectious agent is a virus. In some examples, an antibody that is specific for gp41 neutralizes the infectious titer of HIV. A "broadly neutralizing antibody" is an antibody that binds to and inhibits the function of related antigens, such as antigens that share at least 85%, 90%, 95%, 96%, 97%, 98% or 99% identity antigenic surface of antigen. With regard to an antigen from a pathogen, such as a virus, the antibody can bind to and inhibit the function of an antigen from more than one class and/or subclass of the pathogen. For example, with regard to a human immunodeficiency virus, the antibody can bind to and inhibit the function of an antigen, such as gp41 from more than one Glade. In one embodiment, broadly neutralizing antibodies to HIV are distinct from other antibodies to HIV in that they neutralize a high percentage of the many types of HIV in circulation.

Nucleic acid: A polymer composed of nucleotide units (ribonucleotides, deoxyribonucleotides, related naturally occurring structural variants, and synthetic non-naturally occurring analogs thereof) linked via phosphodiester bonds, related naturally occurring structural variants, and synthetic non-naturally occurring analogs thereof. Thus, the term includes nucleotide polymers in which the nucleotides and the linkages between them include non-naturally occurring synthetic analogs, such as, for example and without limitation, phosphorothioates, phosphoramidates, methyl phosphonates, chiral-methyl phosphonates, 2-O-methyl ribonucleotides, peptide-nucleic acids (PNAs), and the like. Such polynucleotides can be synthesized, for example, using an automated DNA synthesizer. The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

Conventional notation is used herein to describe nucleotide sequences: the left-hand end of a single-stranded nucleotide sequence is the 5'-end; the left-hand direction of a double-stranded nucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand;" sequences on the DNA strand having the same sequence as an mRNA transcribed from that DNA and which are located 5' to the 5'-end of the RNA transcript are referred to as "upstream sequences;" sequences on the DNA strand having the same sequence as the RNA and which are 3' to the 3' end of the coding RNA transcript are referred to as "downstream sequences."

"cDNA" refers to a DNA that is complementary or identical to an mRNA, in either single stranded or double stranded form.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA produced by that gene produces the protein in a cell or other biological system. Both the coding strand, the nucleotide sequence of which is identical to the mRNA sequence and is usually provided in sequence listings, and non-coding strand, used as the template for transcription, of a gene or cDNA can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

"Recombinant nucleic acid" refers to a nucleic acid having nucleotide sequences that are not naturally joined together. This includes nucleic acid vectors including an amplified or assembled nucleic acid which can be used to transform a suitable host cell. A host cell that includes the recombinant nucleic acid is referred to as a "recombinant host cell." The gene is then expressed in the recombinant host cell to produce, e.g., a "recombinant polypeptide." A recombinant nucleic acid may serve a non-coding function (e.g., promoter, origin of replication, ribosome-binding site, etc.) as well.

A first sequence is an "antisense" with respect to a second sequence if a polynucleotide whose sequence is the first sequence specifically hybridizes with a polynucleotide whose sequence is the second sequence.

Operably linked: A first nucleic acid sequence is operably linked with a second nucleic acid sequence when the first nucleic acid sequence is placed in a functional relationship with the second nucleic acid sequence. For instance, a promoter, such as the CMV promoter, is operably linked to a coding sequence if the promoter affects the transcription or expression of the coding sequence. Generally, operably linked DNA sequences are contiguous and, where necessary to join two protein-coding regions, in the same reading frame.

Pharmaceutical agent: A chemical compound or composition capable of inducing a desired therapeutic or prophylactic effect when properly administered to a subject or a cell. In some examples a pharmaceutical agent includes one or more of the disclosed antibodies.

Pharmaceutically acceptable carriers: The pharmaceutically acceptable carriers of use are conventional. *Remington's Pharmaceutical Sciences*, by E. W. Martin, Mack Publishing Co., Easton, Pa., 19th Edition, 1995, describes compositions and formulations suitable for pharmaceutical delivery of the antibodies herein disclosed.

In general, the nature of the carrier will depend on the particular mode of administration being employed. For instance, parenteral formulations usually include injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Polypeptide: Any chain of amino acids, regardless of length or post-translational modification (e.g., glycosylation or phosphorylation). In one embodiment, the polypeptide is gp41 polypeptide. In one embodiment, the polypeptide is a disclosed antibody or a fragment thereof. A "residue" refers to an amino acid or amino acid mimetic incorporated in a polypeptide by an amide bond or amide bond mimetic. A polypeptide has an amino terminal (N-terminal) end and a carboxy terminal (C-terminal) end.

Promoter: A promoter is an array of nucleic acid control sequences that directs transcription of a nucleic acid. A promoter includes necessary nucleic acid sequences near the start site of transcription, for example, in the case of a polymerase II type promoter, a TATA element. A promoter also optionally includes distal enhancer or repressor elements which can be located as much as several thousand base pairs from the start site of transcription. Both constitutive and inducible promoters are included (see for example, Bitter et al., *Methods in Enzymology* 153:516-544, 1987).

Specific, non-limiting examples of promoters include promoters derived from the genome of mammalian cells (such as the metallothionein promoter) or from mammalian viruses (such as the retrovirus long terminal repeat; the adenovirus late promoter; the vaccinia virus 7.5K promoter) may be used. Promoters produced by recombinant DNA or synthetic techniques may also be used. A polynucleotide can be inserted into an expression vector that contains a promoter sequence which facilitates the efficient transcription of the inserted genetic sequence of the host. The expression vector typically contains an origin of replication, a promoter, as well as specific nucleic acid sequences that allow phenotypic selection of the transformed cells.

Purified: The term purified does not require absolute purity; rather, it is intended as a relative term. Thus, for example, a purified peptide preparation is one in which the peptide or protein (such as an antibody) is more enriched than the peptide or protein is in its natural environment within a cell. In one embodiment, a preparation is purified such that the protein or peptide represents at least 50% of the total peptide or protein content of the preparation.

Recombinant: A recombinant nucleic acid is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques.

Sequence identity: The similarity between amino acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs or variants of a polypeptide will possess a relatively high degree of sequence identity when aligned using standard methods.

Methods of alignment of sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. U.S.A.* 85:2444, 1988; Higgins and Sharp, *Gene* 73:237, 1988; Higgins and Sharp, *CABIOS* 5:151, 1989; Corpet et al., *Nucleic Acids Research* 16:10881, 1988; and Pearson and Lipman, *Proc. Natl. Acad. Sci. U.S.A.* 85:2444, 1988. Altschul et al., *Nature Genet.* 6:119, 1994, presents a detailed consideration of sequence alignment methods and homology calculations.

The NCBI Basic Local Alignment Search Tool (BLAST) (Altschul et al., *J. Mol. Biol.* 215:403, 1990) is available from several sources, including the National Center for Biotechnology Information (NCBI, Bethesda, Md.) and on the internet, for use in connection with the sequence analysis programs blastp, blastn, blastx, tblastn and tblastx. A description of how to determine sequence identity using this program is available on the NCBI website on the internet.

Homologs and variants of a $V_L$ or a $V_H$ of an antibody that specifically binds a polypeptide are typically characterized by possession of at least about 75%, for example at least about 80%, 85%, 90%, 91%, 92%, 93%, 94%, 95%, 96%, 97%, 98% or 99% sequence identity counted over the full length alignment with the amino acid sequence of interest. Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologs and variants will typically possess at least 80% sequence identity over short windows of 10-20 amino acids, and may possess sequence identities of at least 85% or at least 90% or 95% depending on their similarity to the reference sequence. Methods for determining sequence identity over such short windows are available at the NCBI website on the internet. One of skill in the art will appreciate that these sequence identity ranges are provided for guidance only; it is entirely possible that strongly significant homologs could be obtained that fall outside of the ranges provided.

Specifically bind: When referring to an antibody, refers to a binding reaction which determines the presence of a target protein, peptide, or polysaccharide in the presence of a heterogeneous population of proteins and other biologics. Thus, under designated conditions, an antibody binds preferentially to a particular target protein, peptide or polysaccharide (such as an antigen present on the surface of a pathogen, for example gp41) and do not bind in a significant amount to other proteins or polysaccharides present in the sample or subject. Specific binding can be determined by methods known in the art, such as by measuring the affinity of the antibody for an antigen. In one embodiment, affinity is calculated by a modification of the Scatchard method described by Frankel et al., *Mol. Immunol.*, 16:101-106, 1979. In another embodiment, binding affinity is measured by an antigen/antibody dissociation rate. In yet another embodiment, a high binding affinity is measured by a competition radioimmunoassay. With reference to an antibody antigen complex, specific binding of the antigen and antibody has a $K_d$ of less than about $10^{-6}$ Molar, such as less than about $10^{-6}$ Molar, $10^{-7}$ Molar, $10^{-8}$ Molar, $10^{-9}$, or even less than about $10^{-10}$ Molar.

Substantially purified: The term substantially purified indicates that the subject is substantially free of other molecular or cellular constituents with which it is naturally associated. Thus, a substantially purified population of cells (such as B cells, B cell progenitors, mature B cells, memory B cells, plasma cells, etc.) is substantially free of other cellular components of the tissue in which it is naturally found, such as bone marrow, peripheral blood, spleen, lymph node, etc. For example, a substantially pure population of B cells (e.g., a B cell progenitor, an immature B cell, a mature B cell, a memory B cell, a plasma cell, etc.) is at least 50%, for example at least about 80% or alternatively at least about 90% free of other cellular components. In an embodiment, the population of B cells is at least about 95% free of other cells. For example, a population of purified B cells, obtained from a tissue such as peripheral blood, is substantially free of red blood cells, T cells, platelets, and other cells typically found in peripheral blood.

T Cell: A white blood cell critical to the immune response. T cells include, but are not limited to, CD4+ T cells and CD8+ T cells. A CD4+ T lymphocyte is an immune cell that carries a marker on its surface known as "cluster of differentiation 4" (CD4). These cells, also known as helper T cells, help orchestrate the immune response, including antibody responses as well as killer T cell responses. CD8+ T cells carry the "cluster of differentiation 8" (CD8) marker. In one embodiment, a CD8 T cells is a cytotoxic T lymphocytes. In another embodiment, a CD8 cell is a suppressor T cell.

Therapeutic agent: Used in a generic sense, it includes treating agents, prophylactic agents, and replacement agents. A therapeutic agent is used to ameliorate a specific set of conditions in a subject with a disease or a disorder.

Therapeutically effective amount or effective amount: A quantity of a specific substance, such as a disclosed antibody, sufficient to achieve a desired effect in a subject being treated. For instance, this can be the amount necessary to inhibit HIV replication or treat AIDS. In several embodiments, a therapeutically effective amount is the amount necessary to reduce a sign or symptom of AIDS, and/or to decrease viral titer in a subject. When administered to a subject, a dosage will generally be used that will achieve target tissue concentrations that has been shown to achieve a desired in vitro effect.

Toxin: An effector molecule that induces cytotoxicity when it contacts a cell. Specific, non-limiting examples of toxins include, but are not limited to, abrin, ricin, auristatins (such as monomethyl auristatin E (MMAE; see for example, Francisco et al., Blood, 102: 1458-1465, 2003)) and monomethyl auristatin F (MMAF; see, for example, Doronina et al., BioConjugate Chem., 17: 114-124, 2006), maytansinoids (such as DM1; see, for example, Phillips et al., Cancer Res., 68:9280-9290, 2008), *Pseudomonas* exotoxin (PE, such as PE35, PE37, PE38, and PE40), diphtheria toxin (DT), botulinum toxin, saporin, restrictocin or gelonin, or modified toxins thereof, or other toxic agents that directly or indirectly inhibit cell growth or kill cells. For example, PE and DT are highly toxic compounds that typically bring about death through liver toxicity. PE and DT, however, can be modified into a form for use as an immunotoxin by removing the native targeting component of the toxin (such as the domain Ia of PE and the B chain of DT) and replacing it with a different targeting moiety, such as an antibody.

Under conditions sufficient for: A phrase that is used to describe any environment that permits a desired activity. In one example the desired activity is formation of an immune complex. In particular examples the desired activity is treatment of a tumor.

Vector: A nucleic acid molecule as introduced into a host cell, thereby producing a transformed host cell. A vector may include nucleic acid sequences that permit it to replicate in a host cell, such as an origin of replication. A vector may also include one or more selectable marker genes and other genetic elements known in the art.

Virus: Microscopic infectious organism that reproduces inside living cells. A virus consists essentially of a core of a single nucleic acid surrounded by a protein coat, and has the ability to replicate only inside a living cell. "Viral replication" is the production of additional virus by the occurrence of at least one viral life cycle. A virus may subvert the host cells' normal functions, causing the cell to behave in a manner determined by the virus. For example, a viral infection may result in a cell producing a cytokine, or responding to a cytokine, when the uninfected cell does not normally do so.

"Retroviruses" are RNA viruses wherein the viral genome is RNA. When a host cell is infected with a retrovirus, the genomic RNA is reverse transcribed into a DNA intermediate which is integrated very efficiently into the chromosomal DNA of infected cells. The integrated DNA intermediate is referred to as a provirus. The term "lentivirus" is used in its conventional sense to describe a genus of viruses containing reverse transcriptase. The lentiviruses include the "immunodeficiency viruses" which include human immunodeficiency virus (HIV) type 1 and type 2 (HIV-I and HIV-II), simian immunodeficiency virus (SIV), and feline immunodeficiency virus (FIV).

Suitable methods and materials for the practice or testing of this disclosure are described below. Such methods and materials are illustrative only and are not intended to be limiting. Other methods and materials similar or equivalent to those described herein can be used. For example, conventional methods well known in the art to which a disclosed invention pertains are described in various general and more specific references, including, for example, Sambrook et al., *Molecular Cloning: A Laboratory Manual*, 2d ed., Cold Spring Harbor Laboratory Press, 1989; Sambrook et al., *Molecular Cloning: A Laboratory Manual*, 3d ed., Cold Spring Harbor Press, 2001; Ausubel et al., *Current Protocols in Molecular Biology*, Greene Publishing Associates, 1992 (and supplements to 2012); Ausubel et al., *Short Protocols in Molecular Biology: A Compendium of Methods from Current Protocols in Molecular Biology*, 4th ed., Wiley & Sons, 1999; Harlow and Lane, *Antibodies: A Laboratory Manual*, Cold Spring Harbor Laboratory Press, 1990; and Harlow and Lane, *Using Antibodies: A Laboratory Manual*, Cold Spring Harbor Laboratory Press, 1999.

II. Description of Several Embodiments

A. Neutralizing Monoclonal Antibodies

Isolated human monoclonal antibodies that specifically bind gp41 are disclosed herein. The disclosed antibodies specifically bind the membrane-proximal extracellular region (MPER) of gp41. Also disclosed herein are compositions including these human monoclonal antibodies and a pharmaceutically acceptable carrier. Nucleic acids encoding these antibodies, expression vectors including these nucleic acids, and isolated host cells that express the nucleic acids are also provided.

Compositions including the human monoclonal antibodies specific for gp41 can be used for research, diagnostic and therapeutic purposes. For example, the human monoclonal antibodies disclosed herein can be used to detect HIV-1 in a biological sample or interfere with the HIV-1 activity, for example to diagnose or treat a subject having an HIV-1 infection and/or AIDS. For example, the antibodies can be used to determine HIV-1 titer in a subject. The antibodies disclosed herein also can be used to study the biology of the human immunodeficiency virus.

The disclosed antibodies that specifically bind gp41 bind the membrane proximal extracellular region (MPER) of gp41 at a previously uncharacterized epitope, that is designated herein as the 10E8 epitope, for the first member of this class of antibodies discovered (10E8-like antibodies). The crystal structure of the 10E8 antibody was solved in complex with a gp41 peptide (see Example 1), which allowed for detailed analysis of the binding of this class of the 10E8 antibody and gp41, and describe at the atomic level the binding of 10E8-like antibodies (such as 10E8) to the 10E8 epitope. This epitope, and thus the antibodies of this class (10E8-like antibodies), can be distinguished from other antibodies that bond gp41 by virtue of their binding to the 10E8 epitope. In several embodiments, the 10E8 epitope, e.g., KWASLWNWFDITNWLWYIR (SEQ ID NO: 13), extends C-terminal to the 2F5 epitope (although there is some overlap) on the gp41 ectodomain and is distinguished from the 4E10 and Z13E1 epitope by expanding the binding to C-terminal residues previously thought to be inaccessible (e.g. these residues were believed to be buried in the lipid bilayer). The person of ordinary skill in the art will understand that the 10E8 antibodies can specifically bind to gp41 MPER residues extending N-terminal to the above sequence. In some embodiments, the disclosed 10E8-like antibodies specifically bind to a polypeptide including an amino acid sequence set forth as residues 1-28, 2-28, 3-28, 4-28, 5-28, 6-28, 7-28, 8-28, 9-28, 10-28, 11-28, 12-28, 13-28 or 14-28 of SEQ ID NO: 26, which correspond to gp41 residues 656-683, 657-683, 658-683, 659-683, 660-683, 661-683, 662-683, 663-683, 664-683, 665-683, 666-683, 667-683, 668-683, or 669-683, respectively (HXB2 numbering system).

In some embodiments, residues believed to make contacts with the 10E8 antibody include the K, SLWNWF, TN, LW, and IR shown in bold above. Thus, in some embodiments a 10E8-like antibody specifically binds to one or more of K, SLWNWF, TN, LW, and IR of SEQ ID NO: 13, such as at least 1, at least 2, at least 3, at least 4, at least 5, at least 6, at least 7, at least 8, at least 9, at least 10, at least 11, at least 12 or even all 13 of these residues. In some examples, a 10E8-like antibody binds to the NWF, T and R resides shown in bold in the following sequence NWFDITNWL-WYIR (residues 7-19 of SEQ ID NO: 13).

In additional embodiments, the antibody or antigen binding fragment contacts L, WF, LW and R shown in bold in the amino acid sequence set forth as LWNWFDITNWLWYIR (SEQ ID NO: 26, residues 14-28). In additional embodiments, the disclosed antibody contacts LW, WF, LW and R shown in bold in the amino acid sequence set forth as LWNWFDITNWLWYIR (SEQ ID NO: 26, residues 14-28). In additional embodiments, the disclosed antibody contacts SLW, WF, LW and R shown in bold in the amino acid sequence set forth as SLWNWFDITNWLWYIR (SEQ ID NO: 26, residues 13-28). In additional embodiments, the disclosed antibody contacts L, DK, SLWNWF, TN, LW and IR shown in bold in the amino acid sequence set forth as LELDKWASLWNWFDITNWLWYIR (SEQ ID NO: 26, residues 6-28). In additional embodiments, the disclosed antibody contacts NWF, T, and R shown in bold in the amino acid sequence set forth as NWFDITNWLWYIR (SEQ ID NO: 13, residues 7-19). In additional embodiments, the disclosed antibody contacts K, SLNWF, T, and IR shown in bold in the amino acid sequence set forth as KWASLWN-WFDITNWLWYIR (SEQ ID NO: 13). In additional embodiments, the disclosed antibody the antibody specifically binds to residues NWF, T, and R shown in bold in the amino acid sequence set forth as NWFDITNWLWYIR (SEQ ID NO: 13, residues 7-19). In additional embodiments, the disclosed antibody specifically binds to residues K, SLNWF, T, and IR shown in bold in the amino acid sequence set forth as KWASLWNWFDITNWLWYIR (SEQ ID NO: 13). In several such embodiments, the antibody directly contacts the gp41 MPER at the indicated residues when specifically bound to gp41, for example, through hydrogen bond contacts and/or Van der Waals contacts. In additional embodiments, the antibody contacts the gp41 MPER at the indicated residues when specifically bound to gp41, for example through hydrogen bond contacts, Van der Waals contacts, and/or interactions that cause reduced solvent access between the antibody and gp41 (i.e., buried surface area). As shown in FIGS. 27 and 28, residues in the 10E8 and 10E8-like antibodies that are important for binding to the 10E8 epitope include Kabat residues 28, 31, 33, 50, 52, 52B, 52C, 53, 56, 58, and 97-100J of the heavy chain and Kabat residues 91 and 95B of the light chain. These residues correspond to residues 28, 31, 33, 50, 52, 54, 55, 56, 59, 61, 103-116 of the heavy chain (the residue numbers are given relative to SEQ ID NO: 1), and 91 and 97 of the light chain (the residue numbers are given relative to SEQ ID NO: 2). In some embodiments, a 10E8-like antibody specifically binds to gp41, and one or more of residues 28, 31, 33, 50, 52, 54, 55, 56, 59, 61, and/or 103-116 from the heavy chain (relative to SEQ ID NO: 1), such as at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, or even all 27 of these residues contact gp41. In some embodiments, a 10E8-like antibody specifically binds to gp41 and at least one of residues 91 and 97 from the light chain (relative to SEQ ID NO: 2) contact gp41.

In some embodiments, the class of 10E8-like antibodies do not exhibit self-reactivity, that is they do not bind self-antigens, such as human protein. Without being bound by theory, examination of the crystal structure of 10E8 in complex with an MPER gp41 peptide shows that 10E8 binds to the MPER in a manner that may not require any hydrophobic interaction with membrane. Other known neutralizing antibodies that bind the MPER of gp41, such as 2F5 and 4E10, include hydrophobic residues in the CDR H3 that do not contact the epitope and are believed to make specific contacts with the lipid membrane in which gp41 is situated.

While not being bound by theory, it is believed that the neutralization breadth of the 10E8-like antibodies can tolerate conservative changes to the epitope while still maintaining binding. For example, while the C-terminal residue is shown as an arginine, antibodies of this class can tolerate a lysine substitution at this site, and still maintain high binding affinity. In addition, one of ordinary skill in the art can formulate a consensus sequence for the 10E8 epitope using the sequences of all of HIV gp41 variations for the HIV isolates listed in FIG. 17B or FIGS. 17C-17F. In some embodiments, the antibodies in this class (10E8-like antibodies) can also be distinguished by neutralization breadth. In some embodiments, a 10E8-like antibody can neutralize at least 95% (such as at least 96%, at least 97%, at least 98% or at least 99%) of the HIV-1 isolates listed in FIG. 17B or FIGS. 17C-17F with an IC50 of less than 50 μg/ml. In some embodiments, a 10E8-like antibody can neutralize at least 65% (such as at least 66%, at least 67%, at least 68%, at least 69%, at least 70%, at least 71%, at least 72%, at least 73%, at least 74%, at least 75%, or at least 80%) of the HIV-1 isolates listed in FIG. 17B or FIGS. 17C-17F with an IC50 of less than 1 μg/ml. In specific embodiments, a 10E8-like antibody is not the Z13E1, 4E10 or 2F5 antibody.

The discussion of monoclonal antibodies below refers to isolated monoclonal antibodies that include heavy and light chain variable domains including a CDR1, CDR2 and CDR3. The person of ordinary skill in the art will understand that various CDR numbering schemes (such as the Kabat, Chothia or IMGT numbering schemes) can be used to determine CDR positions. The heavy chain CDR positions of the 10E8 monoclonal antibody according to the Kabat and IMGT numbering scheme are shown in FIG. 6A (Kabat) and FIG. 6B (IMGT). In several embodiments, reference to particular amino acid substitutions in the heavy or light chains of the disclosed antibodies is made according to the Kabat or IMGT numbering schemes. For example, the amino acid substitution S74W in 10E8 referenced herein refers to the Kabat numbering scheme. Using the IMGT numbering scheme this substitution would be referred to as S82W. In both cases, this substation refers to substitution of the serine residue at position 77 of SEQ ID NO: 1. The person of skill in the art will readily understand use of various CDR numbering schemes when referencing particular amino acids of the antibodies disclosed herein.

In some embodiments, an isolated antibody that specifically binds gp41 includes a heavy chain with one or more of amino acids 26-33 (complementarity-determining region 1 (CDR1)), amino acids 51-60 (CDR2), and/or 99-120 (CDR3) of SEQ ID NO: 11: EV$X_1$L$X_2$ ESGGGLVKPGG-SLRLSCSASGFDFDNAWMTWVRQPPGK-GLEWVGRITGPGEGWSVDYAA PVEGRFTISRLN$X_3$INFLYLEMNNLRMEDSGLYFCA RTGKYYDFWSGYPPGEEYFQDWGRGTLV$X_4$V SS (SEQ ID NO: 11), where $X_1$ is Q or R, $X_2$ is V or A, $X_3$ is S or Y, and $X_4$ is T or I. In some embodiments, an isolated human monoclonal antibody that specifically binds gp41 includes a heavy chain with amino acids 26-33 (CDR1), 51-60 (CDR2), and 99-120 (CDR3) of SEQ ID NO: 11. In specific examples, the heavy chain of the human monoclonal antibody includes SEQ ID NO: 11.

In some embodiments, an isolated antibody that specifically binds gp41 includes a heavy chain with one or more of amino acids 26-33 (complementarity-determining region 1 (CDR1)), amino acids 51-60 (CDR2), and/or 99-120 (CDR3) of SEQ ID NO: 146:

EV$X_1$L$X_2$ESGGGLVKPGGSLRLSCSASGF$X_3$F$X_4X_5$ AWMTWVRQPPGKGLEWVGRITGPGE$X_6$WSVDYAA PVEGRFTISRLNSINFLYLEMNNLRMEDSGLYFCART-GKYYDFWSGYPPGEEYFQDWGR GTLV$X_7$VSS (SEQ ID NO: 146), where $X_1$ is Q or R, $X_2$ is V or A, $X_3$ is D or W, $X_4$ is D or W, $X_5$ is N or W, $X_6$ is G or W and $X_7$ is T or I). In some embodiments, an isolated human monoclonal antibody that specifically binds gp41 includes a heavy chain with amino acids 26-33 (CDR1), 51-60 (CDR2), and 99-120 (CDR3) of SEQ ID NO: 146. In specific examples, the heavy chain of the human monoclonal antibody includes SEQ ID NO: 146.

In some embodiments, an isolated antibody that specifically binds gp41 includes a heavy chain with one or more of amino acids 26-33 (complementarity-determining region 1 (CDR1)), amino acids 51-60 (CDR2), and/or 99-120 (CDR3) of SEQ ID NO: 187. SEQ ID NO: 187 is set forth as E$X_1X_2$L$X_3$ESGG$X_4$LV$X_5$PGGSLRLSC$X_6$ASGF$X_7$F$X_8$ $X_9X_{10}$WMTWVRQ$X_{11}$PGKGLEWVGRI$X_{12}$G$X_{13}$G$X_{14}$ $X_{15}$W$X_{16}X_{17}X_{18}$YA$X_{19}X_{20}$V$X_{21}$GRF$X_{22}$ISR$X_{23}X_{24}X_{25}$ $X_{26}X_{27}X_{28}X_{29}$YL$X_{30}$MN$X_{31}X_{32}X_{33}X_{34}X_{35}$D$X_{36}X_{37}X_{38}$ Y$X_{39}$C$X_{40}X_{41}$T$X_{42}$K$X_{43}$Y$X_{44}$FW$X_{45}$G$X_{46}$PPGEEY$X_{47}$ $X_{48}X_{49}$WGX50GT$X_{51}$V$X_{52}$V$X_{53}$S, wherein $X_1$ is V or I; $X_2$ is Q or R; $X_3$ is V or A; $X_4$ is G, R, or D; $X_5$ is K or R; $X_6$ is S or A; $X_7$ is D, N, S, A, or W; $X_8$ is D, K, W or A; $X_9$ is N, S, D, A, W, F, or Y; $X_{10}$ is A, T, or Q; $X_{11}$ is P, or A; $X_{12}$ is T, S, or A; $X_{13}$ is P or W; $X_{14}$ is E, A, F, L, M, V, or W; $X_{15}$ is G or W; $X_{16}$ is S, T, A, or H; $X_{17}$ is V or S; $X_{18}$ is D, G, or A; $X_{19}$ is A or E; $X_{20}$ is P, S, or T; $X_{21}$ is E, K or Q; $X_{22}$ is T or I; $X_{23}$ is L, D, M, I, or N; $X_{24}$ is N or D; $X_{25}$ is S, M, W, F, L, or M; $X_{26}$ is I or K; $X_{27}$ is N or D; $X_{28}$ is F, T. or M; $X_{29}$ is L or F; $X_{30}$ is E or Q; $X_{31}$ is N, S, or R; $X_{32}$ is L or V; $X_{33}$ is R, or K; $X_{34}$ is M, T, I, or P; $X_{35}$ is E or D; $X_{36}$ is S, T or W; $X_{37}$ is G, A, or W; $X_{38}$ is L, V, S or Y; $X_{39}$ is F, or Y; $X_{40}$ is A, T or V; $X_{41}$ is R, T, or H; $X_{42}$ is G or E; $X_{43}$ is Y or H; $X_{44}$ is D, A, or N; $X_{45}$ is S, G, or R; $X_{46}$ is Y or A; $X_{47}$ is F or L; $X_{48}$ is Q or E; $X_{49}$ is D or H; X50 is R or Q; $X_{51}$ is L or Q; $X_{52}$ is T or I; and $X_{53}$ is S or P.) In some embodiments, an isolated human monoclonal antibody that specifically binds gp41 includes a heavy chain with amino acids 26-33 (CDR1), 51-60 (CDR2), and 99-120 (CDR3) of SEQ ID NO: 187. In additional embodiments, an isolated antibody that specifically binds gp41 includes a heavy chain variable region including the amino acid sequence set forth as SEQ ID NO: 187.

In several embodiments, the isolated antibody that specifically binds gp41, is neutralizing, and includes a heavy chain including one or more of the heavy chain complementarity determining regions (CDRs) of one of the heavy chain variable region sequences set forth as SEQ ID NOs: 1, 3, 5, 11, 146, 147-149, 187, 189-192, and 200-204, according to the Kabat, IMGT, or Clothia numbering systems. In some embodiments, an isolated antibody that specifically binds gp41 and is neutralizing, includes a heavy chain including the CDR1, CDR2, and CDR3 of one of the heavy chain variable region sequences set forth as SEQ ID NOs: 1, 3, 5, 11, 146, 147-149, 187, 189-192, or 200-204, according to the Kabat, IMGT, or Clothia numbering systems.

Thus in some embodiments, an isolated antibody that specifically binds gp41 includes one or more of amino acids 26-33 (CDR1), amino acids 51-60 (CDR2), and/or 99-120 (CDR3) of one of SEQ ID NOs: 1, 3, 5, 11, 146, 147-149, 187, 189-192, and 200-204. In some embodiments, an isolated human monoclonal antibody that specifically binds gp41 includes a heavy chain with amino acids 26-33 (CDR1), 51-60 (CDR2), and 99-120 (CDR3) of one of SEQ ID NOs: 1, 3, 5, 11, 146, 147-149, 187, 189-192, and 200-204. In specific examples, the heavy chain of the human monoclonal antibody includes one of SEQ ID NOs: 1, 3, 5, 11, 146, 147-149, 187, 189-192, and 200-204.

Figure 6B:
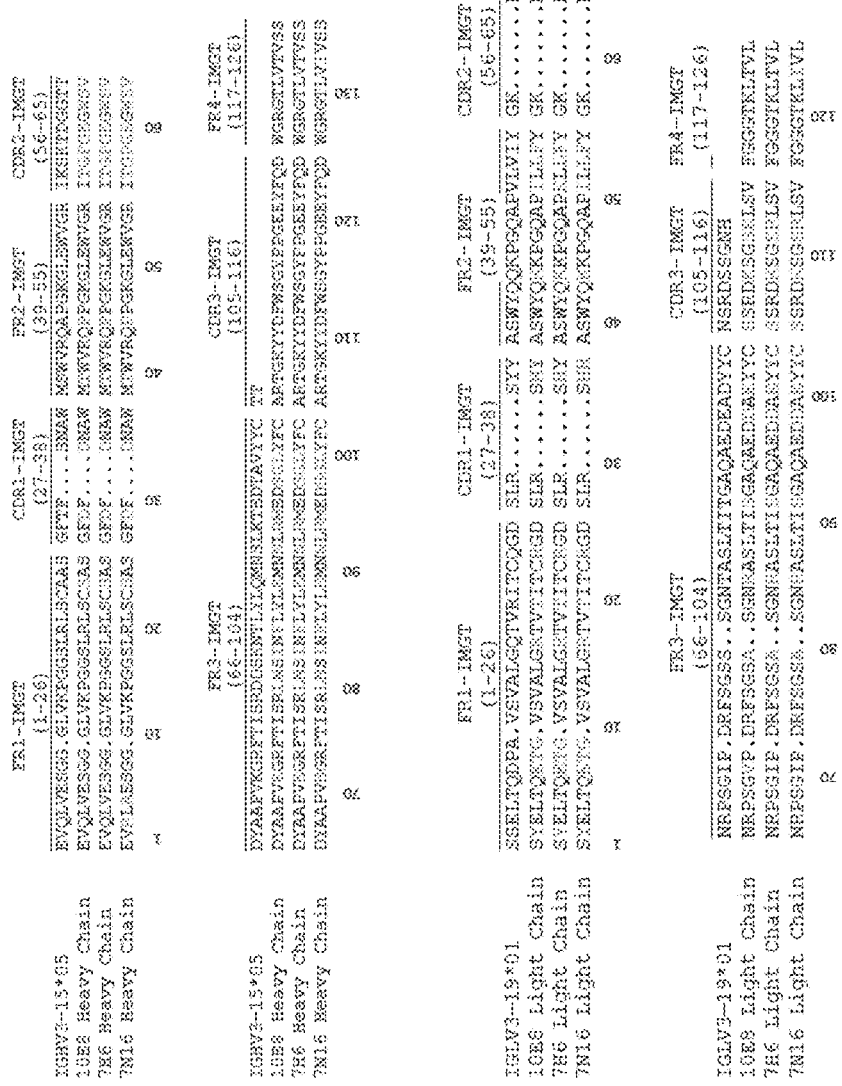

For example, in some embodiments, an isolated antibody that specifically binds gp41 includes a heavy chain including one or more of the heavy chain complementarity determining regions (CDRs) from gp41 antibody 10E8, 7H6 and/or 7N16. The heavy chain of gp41 antibody 10E8 is set forth as SEQ ID NO: 1. In some embodiments, an isolated antibody that specifically binds gp41 includes one or more of amino acids 26-33 (27-38 in FIG. 6B) (CDR1), amino acids 51-60 (56-65 in FIG. 6B) (CDR2), and/or 99-120 (105-126 in FIG. 6B) (CDR3) of SEQ ID NO: 1. In some embodiments, an isolated human monoclonal antibody that specifically binds gp41 includes a heavy chain with amino acids 26-33 (CDR1), 51-60 (CDR2), and 99-120 (CDR3) of SEQ ID NO: 1. In specific examples, the heavy chain of the human monoclonal antibody includes SEQ ID NO: 1. The heavy chain of gp41 antibody 7H6 is set forth as SEQ ID NO: 3. Thus, in some embodiments, an isolated antibody that specifically binds gp41 includes one or more of amino acids 26-33 (CDR1), 51-60 (CDR2), and/or 99-120 (CDR3) of SEQ ID NO: 3. In some embodiments, an isolated human monoclonal antibody that specifically binds gp41 includes a heavy chain with amino acids 26-33 (CDR1), 51-60 (CDR2), and 99-120 (CDR3) of SEQ ID NO: 3. In specific examples, the heavy chain of the human monoclonal antibody includes SEQ ID NO: 3. The heavy chain of gp41 antibody 7N16 is set forth as SEQ ID NO: 5. Thus in some embodiments, an isolated antibody that specifically binds gp41 includes one or more of amino acids 26-33 (CDR1), 51-60 (CDR2), and/or 99-120 (CDR3) of SEQ ID NO: 5. In some embodiments, an isolated human monoclonal antibody that specifically binds gp41 includes a heavy chain with amino acids 26-33 (CDR1), 51-60 (CDR2), and 99-120 (CDR3) of SEQ ID NO: 5. In specific examples, the heavy chain of the human monoclonal antibody includes SEQ ID NO: 5.

In additional embodiments, an isolated antibody that specifically binds gp41 includes a heavy chain including the amino acid sequence of any one of the 10E8-like heavy chains disclosed herein and further including an amino acid substitution at position 77 (position 74 according to Kabat numbering), such as a S77Y substitution (S74Y according to Kabat numbering). In additional embodiments, an isolated antibody that specifically binds gp41 includes a heavy chain including one or more of the heavy chain complementarity determining regions (CDRs) from any one of the 10E8-like heavy chains disclosed herein and further including an amino acid substitution at position 77 (position 74 according to Kabat numbering), such as a S77Y substitution (S74Y according to Kabat numbering). In additional embodiments, an isolated antibody that specifically binds gp41 includes a heavy chain including one or more of the heavy chain complementarity determining regions (CDRs) from one of gp41 antibodies gVRC-H2dN152 or gVRC-H2dN152 with an amino acid substitution at position 77 (position 74 according to Kabat numbering). In some examples the amino acid substitution is a serine to tyrosine substitution. The heavy chain of gp41 antibody gVRC-H2dN152 is set forth as SEQ ID NO: 154. Thus in some embodiments, an isolated antibody that specifically binds gp41 includes one or more of amino acids 26-33 (CDR1), 51-60 (CDR2), and/or 99-120 (CDR3) of SEQ ID NO: 154. In some embodiments, an isolated human monoclonal antibody that specifically binds gp41 includes a heavy chain with amino acids 26-33 (CDR1), 51-60 (CDR2), and 99-120 (CDR3) of SEQ ID NO: 154. In specific examples, the heavy chain of the human monoclonal antibody includes SEQ ID NO: 154. The heavy chain of gp41 antibody gVRC-H2dN152 with serine to tyrosine substitution at position 77 (position 74 using Kabat numbering) is set forth as SEQ ID NO: 192. Thus in some embodiments, an isolated antibody that specifically binds gp41 includes one or more of amino acids 26-33 (CDR1), 51-60 (CDR2), and/or 99-120 (CDR3) of SEQ ID NO: 192. In some embodiments, an isolated human monoclonal antibody that specifically binds gp41 includes a heavy chain with amino acids 26-33 (CDR1), 51-60 (CDR2), and 99-120 (CDR3) of SEQ ID NO: 192. In specific examples, the heavy chain of the human monoclonal antibody includes SEQ ID NO: 192.

In some embodiments, an isolated antibody that specifically binds gp41 includes one or more of the light chain complementarity determining regions (CDRs) of amino acids 26-31 (CDR1), 49-51 (CDR2), and/or 88-99 (CDR3) of SEQ ID NO: 12: SYELTQX$_1$ TGVSVAL GRTVVTITCRGDSLRSHX$_2$ASWYQKKPGQAPX$_3$LL FYGKNNRPSGX$_4$PDRFSGSASGNRASLTIX$_5$GAQAE DX$_6$AX$_7$YYCSSRDKSGSRLSVFGGGTKLX$_8$VL (SEQ ID NO: 12), where X$_1$ is E or D, X$_2$ is Y or H, X$_3$ is V or I, X$_4$ is V or I, X$_5$ is S or T, X$_6$ is D or E, X$_7$ is E or D, and X$_8$ is T or I. In some embodiments, an isolated human monoclonal antibody that specifically binds gp41 includes a light chain with amino acids 26-31 (CDR1), 49-51 (CDR2), and 88-99 (CDR3) of SEQ ID NO: 12. In specific examples, the light chain of the human monoclonal antibody includes SEQ ID NO: 12.

In some embodiments, an isolated antibody that specifically binds gp41 includes one or more of the light chain complementarity determining regions (CDRs) of amino acids 26-31 (CDR1), 49-51 (CDR2), and/or 88-99 (CDR3) of SEQ ID NO: 188: X$_1$X$_2$X$_3$LTQX$_4$X$_5$X$_6$ VSVAX$_7$X$_8$X$_9$TVX$_{10}$ITCX$_{11}$GDSLRX$_{12}$X$_{13}$YX$_{14}$X$_{15}$ WYQX$_{16}$X$_{17}$X$_{18}$X$_{19}$QAPX$_{20}$-LX$_{21}$X$_{22}$YX$_{23}$X$_{24}$X$_{25}$X$_{26}$ RPSX$_{27}$ X$_{28}$X$_{29}$DRFSX$_{30}$X$_{31}$X$_{32}$SGNX$_{33}$ASLTIX$_{34}$ GAX$_{35}$ X$_{36}$X$_{37}$DX$_{38}$AX$_{39}$YYCSSRD KSGSRLX$_{40}$X$_{41}$ FGX$_{42}$GTX$_{43}$X$_{44}$X$_{45}$X$_{46}$X$_{47}$, wherein X$_1$ is S or A; X$_2$ is Y or S; X$_3$ is E or D; X$_4$ is E or D; X$_5$ is T or P; X$_6$ is G, A, or T; X$_7$ is L or F; X$_8$ is G, K, or E; X$_9$ is R, Q, or K; X$_{10}$ is T or R; X$_{11}$ is R or Q; X$_{12}$ is S, R, or N; X$_{13}$ is H or Y; X$_{14}$ is A, V, or T; X$_{15}$ is S or G; X$_{16}$ is K, E, or Q; X$_{17}$ is K or R; X$_{18}$ is P or T; X$_{19}$ is G or R; X$_{20}$ is I, V, or K; X$_{21}$ is L or V; X$_{22}$ is F, V, or I; X$_{23}$ is G or P; X$_{24}$ is K or R; X$_{25}$ is N, D, or H; X$_{26}$ is N or I; X$_{27}$ is G, or P; X$_{28}$ is V or I; X$_{29}$ is P, H, or S; X$_{30}$ is G or A; X$_{31}$ is S or F; X$_{32}$ is A, T, or S; X$_{33}$ is R or T; X$_{34}$ is S, A, or T; X$_{35}$ is Q or E; X$_{36}$ is A or G; X$_{37}$ is E or D; X$_{38}$ is D, E, or I; X$_{39}$ is E or D; X$_{40}$ is 5, V; X$_{41}$ is V, T; X$_{42}$ is G, R; X$_{43}$ is K or E; X$_{44}$ is L, V, or R; X$_{45}$ is T, S, or A; X$_{46}$ is V, T, or G; and X$_{47}$ is L, V, or P. In some embodiments, an isolated human monoclonal antibody that specifically binds gp41 includes a light chain with amino acids 26-31 (CDR1), 49-51 (CDR2), and 88-99 (CDR3) of SEQ ID NO: 188. In additional embodiments, an isolated antibody that specifically binds gp41 includes a light chain variable region including the amino acid sequence set forth as SEQ ID NO: 188.

Several embodiments include an isolated antibody that specifically binds gp41, is neutralizing, and includes a light chain including one or more of the light chain complementarity determining regions (CDRs) of one of the light chain variable region sequences set forth as SEQ ID NOs: 2, 4, 6, 12, 150-152, 164-186, 188, or 197-199, according to the Kabat, IMGT, or Clothia numbering systems. In some embodiments, an isolated antibody that specifically binds gp41 and is neutralizing, includes a light chain including the CDR1, CDR2, and CDR3 of one of the light chain variable region sequences set forth as SEQ ID NOs: 2, 4, 6, 12, 150-152, 164-186, 188, or 197-199, according to the Kabat, IMGT, or Clothia numbering systems. In additional embodiments, an isolated antibody that specifically binds gp41 includes one or more of amino acids 26-31 (27-38 in FIG. 6B) (CDR1), 49-51 (56-65 in FIG. 6B) (CDR2), and/or 88-99 (105-116 in FIG. 6B) (CDR3) of one of SEQ ID NOs: 2, 4, 6, 12, 150-152, 164-186, 188, or 197-199. In further embodiments, an isolated human monoclonal antibody that specifically binds gp41 includes a light chain with amino acids 26-31 (CDR1), 49-51 (CDR2), and 88-99 (CDR3) of one of SEQ ID NOs: 2, 4, 6, 12, 150-152, 164-186, 188, or 197-199. In specific examples, the light chain of the human monoclonal antibody includes one of SEQ ID NOs: 2, 4, 6, 12, 150-152, 164-186, 188, or 197-199.

For example, in some embodiments, an isolated antibody that specifically binds gp41 includes one or more of the light chain complementarity determining regions (CDRs) from gp41 antibody 10E8, 7H6 and/or 7N16. The light chain of gp41 antibody 10E8 is set forth as SEQ ID NO: 2. Thus in some embodiments, an isolated antibody that specifically binds gp41 includes one or more of amino acids 26-31 (27-38 in FIG. 6B) (CDR1), 49-51 (56-65 in FIG. 6B) (CDR2), and/or 88-99 (105-116 in FIG. 6B) (CDR3) of SEQ ID NO: 2. In some embodiments, an isolated human monoclonal antibody that specifically binds gp41 includes a light chain with amino acids 26-31 (CDR1), 49-51 (CDR2), and 88-99 (CDR3) of SEQ ID NO: 2. In specific examples, the light chain of the human monoclonal antibody includes SEQ ID NO: 2. The light chain of gp41 antibody 7H6 is set forth as SEQ ID NO: 4. Thus in some embodiments, an isolated antibody that specifically binds gp41 includes one or more of amino acids 26-31 (CDR1), 49-51 (CDR2), and/or 88-99 (CDR3) of SEQ ID NO: 4. In some embodiments, an isolated human monoclonal antibody that specifically binds gp41 includes a light chain with amino acids 26-31 (CDR1), 49-51 (CDR2), and 88-99 (CDR3) of SEQ ID NO: 4. In specific examples, the light chain of the human monoclonal antibody includes SEQ ID NO: 4. The light chain of gp41 antibody 7N16 is set forth as SEQ ID NO: 6. Thus in some embodiments, an isolated antibody that specifically binds gp41 includes one or more of amino acids 26-31 (CDR1), 49-51 (CDR2), and/or 88-99 (CDR3) of SEQ ID NO: 6. In some embodiments, an isolated human monoclonal antibody that specifically binds gp41 includes a heavy chain with amino acids 26-31 (CDR1), 49-51 (CDR2), and 88-99 (CDR3) of SEQ ID NO: 6. In specific examples, the heavy chain of the human monoclonal antibody includes SEQ ID NO: 6.

In additional embodiments, an isolated antibody that specifically binds gp41 includes a heavy chain including one or more of the heavy chain complementarity determining regions (CDRs) from gp41 antibody 10E8gL03. The light chain of gp41 antibody 10E8gH03 is set forth as SEQ ID NO: 152. Thus in some embodiments, an isolated antibody that specifically binds gp41 includes one or more of amino acids 26-31 (CDR1), 49-51 (CDR2), and/or 88-99 (CDR3) of SEQ ID NO: 152. In some embodiments, an isolated human monoclonal antibody that specifically binds gp41 includes a heavy chain with amino acids 26-31 (CDR1), 49-51 (CDR2), and 88-99 (CDR3) of SEQ ID NO: 152. In specific examples, the heavy chain of the human monoclonal antibody includes SEQ ID NO: 152.

Additional embodiments include an isolated antibody that specifically binds gp41 and is neutralizing, and includes a heavy chain including one or more of the heavy chain complementarity determining regions (CDRs) of one of the heavy chain variable region sequences set forth as SEQ ID NOs: 1, 3, 5, 11, 146, 147-149, 187, 189-192, and 200-204, according to the Kabat, IMGT, or Clothia numbering systems, and one or more of the light chain complementarity determining regions (CDRs) of one of the light chain variable region sequences set forth as SEQ ID NOs: 2, 4, 6, 12, 150-152, 164-186, 188, or 197-199, according to the Kabat, IMGT, or Clothia numbering systems, respectively. Additional embodiments include an isolated antibody that specifically binds gp41 and is neutralizing, and includes a heavy chain including the heavy chain complementarity determining region 1 (HCRD1), HCRD2, and HCDR3 of one of the heavy chain variable region sequences set forth as SEQ ID NOs: 1, 3, 5, 11, 146, 147-149, 187, 189-192, and 200-204, according to the Kabat, IMGT, or Clothia numbering systems, and the light chain complementarity determining region 1 (HCRD1), HCRD2, and HCDR3 of one of the light chain variable region sequences set forth as SEQ ID NOs: 2, 4, 6, 12, 150-152, 164-186, 188, or 197-199, according to the Kabat, IMGT, or Clothia numbering systems, respectively.

Thus in some embodiments, an isolated antibody that specifically binds gp41 includes a heavy chain including amino acids 26-33 (27-38 in FIG. 6B) (CDR1), amino acids 51-60 (56-65 in FIG. 6B) (CDR2), and/or 99-120 (105-126 in FIG. 6B) (CDR3) of one of SEQ ID NOs: 1, 3, 5, 11, 146, 147-149, 187, 189-192, and 200-204, and a light chain including amino acids 26-31 (27-38 in FIG. 6B) (CDR1), 49-51 (56-65 in FIG. 6B) (CDR2), and/or 88-99 (105-116 in FIG. 6B) (CDR3) of one of SEQ ID NOs: 2, 4, 6, 12, 150-152, 164-186, 188, or 197-199. In additional embodiments, an isolated antibody that specifically binds gp41 includes a heavy chain including amino acids 26-33 (27-38 in FIG. 6B) (CDR1), amino acids 51-60 (56-65 in FIG. 6B) (CDR2), and 99-120 (105-126 in FIG. 6B) (CDR3) of one of SEQ ID NOs: 1, 3, 5, 11, 146, 147-149, 187, 189-192, and 200-204, and a light chain including amino acids 26-31 (27-38 in FIG. 6B) (CDR1), 49-51 (56-65 in FIG. 6B) (CDR2), and 88-99 (105-116 in FIG. 6B) (CDR3) of one of SEQ ID NOs: 2, 4, 6, 12, 150-152, 164-186, 188, or 197-199.

In some embodiments, an isolated antibody that specifically binds gp41 includes a heavy chain including amino acids 26-33 (27-38 in FIG. 6B) (CDR1), amino acids 51-60 (56-65 in FIG. 6B) (CDR2), and/or 99-120 (105-126 in FIG. 6B) (CDR3) of SEQ ID NO: 1, and a light chain including amino acids 26-31 (27-38 in FIG. 6B) (CDR1), 49-51 (56-65 in FIG. 6B) (CDR2), and/or 88-99 (105-116 in FIG. 6B) (CDR3) of SEQ ID NO: 2. In some embodiments, an isolated antibody that specifically binds gp41 includes a heavy chain including amino acids 26-33 (27-38 in FIG. 6B) (CDR1), amino acids 51-60 (56-65 in FIG. 6B) (CDR2), and/or 99-120 (105-126 in FIG. 6B) (CDR3) of SEQ ID NO: 154, and a light chain including amino acids 26-31 (27-38 in FIG. 6B) (CDR1), 49-51 (56-65 in FIG. 6B) (CDR2), and/or 88-99 (105-116 in FIG. 6B) (CDR3) of SEQ ID NO: 152. In some embodiments, an isolated antibody that specifically binds gp41 includes a heavy chain including amino acids 26-33 (27-38 in FIG. 6B) (CDR1), amino acids 51-60 (56-65 in FIG. 6B) (CDR2), and/or 99-120 (105-126 in FIG. 6B) (CDR3) of SEQ ID NO: 192, and a light chain including amino acids 26-31 (27-38 in FIG. 6B) (CDR1), 49-51 (56-65 in FIG. 6B) (CDR2), and/or 88-99 (105-116 in FIG. 6B) (CDR3) of SEQ ID NO: 152.

In additional examples, an isolated antibody that specifically binds gp41 and is neutralizing includes a heavy chain variable region and a light chain variable region, wherein the heavy chain variable region includes the amino acid sequence set forth as one of SEQ ID NOs: 1, 3, 5, 11, 146, 147-149, 187, 189-192, or 200-204, and the light chain variable region includes the amino acid sequence set forth as one of SEQ ID NOs: 2, 4, 6, 12, 150-152, 164-186, 188, or 197-199. In one example, the heavy chain variable region includes the amino acid sequence set forth as SEQ ID NO: 1, and the light chain variable region includes the amino acid sequence set forth as SEQ ID NO: 2. In another example, the heavy chain variable region includes the amino acid sequence set forth as SEQ ID NO: 192, and the light chain variable region includes the amino acid sequence set forth as SEQ ID NO: 152. In a further example, the heavy chain variable region includes the amino acid sequence set forth as SEQ ID NO: 154, and the light chain variable region includes the amino acid sequence set forth as SEQ ID NO: 152.

In further embodiments, an isolated antibody that specifically binds gp41 includes a heavy chain variable region including an amino acid sequence including no more than 10 (such as more than 1, 2, 3, 4, 5, 6, 7, 8, or no more than 9) amino acid substitutions compared to one of SEQ ID NOs: 1, 3, 5, 11, 146, 147-149, 187, 189-192, and 200-204. In additional embodiments, an isolated antibody that specifically binds gp41 includes a light chain variable region including an amino acid sequence including no more than 10 (such as more than 1, 2, 3, 4, 5, 6, 7, 8, or no more than 9) amino acid substitutions compared to one of SEQ ID NOs: 2, 4, 6, 12, 150-152, 164-186, 188, or 197-199. In other embodiments, an isolated antibody that specifically binds gp41 includes a heavy chain variable region including an amino acid sequence including no more than 10 (such as more than 1, 2, 3, 4, 5, 6, 7, 8, or no more than 9) amino acid substitutions compared to one of SEQ ID NOs: 1, 3, 5, 11, 146, 147-149, 187, 189-192, and 200-204, and a light chain variable region including an amino acid sequence including no more than 10 (such as more than 1, 2, 3, 4, 5, 6, 7, 8, or no more than 9) amino acid substitutions compared to one of SEQ ID NOs: 2, 4, 6, 12, 150-152, 164-186, 188, or 197-199.

In other embodiments, an isolated antibody that specifically binds gp41 includes a heavy chain variable region including an amino acid sequence including no more than 10 (such as more than 1, 2, 3, 4, 5, 6, 7, 8, or no more than 9) amino acid substitutions compared to one of SEQ ID NO: 1, and a light chain variable region including an amino acid sequence including no more than 10 (such as more than 1, 2, 3, 4, 5, 6, 7, 8, or no more than 9) amino acid substitutions compared to SEQ ID NO: 2.

In further embodiments, an isolated antibody that specifically binds gp41 includes a heavy chain variable region including the amino acid sequence set forth as SEQ ID NO: 187, wherein the amino acid sequence includes no more than 25 (such as more than 1, 2, 3, 4, 5, 6, 7, 8, 9, 10, 11, 12, 13, 14, 15, 16, 17, 18, 19, 20, 21, 22, 23, or no more than 24) amino acid substitutions compared to SEQ ID NO: 1. In additional embodiments, an isolated antibody that specifically binds gp41 includes a light chain variable region including the amino acid sequence set forth as SEQ ID NO: 188, wherein the amino acid sequence includes no more than 33 (such as more than 1, 2, 3, 4, 5, 6, 7, 8, 9, 10, 11, 12, 13, 14, 15, 16, 17, 18, 19, 20, 21, 22, 23, 24, 35, 36, 37, 38, 39, 30, 31, 32 or no more than 33) amino acid substitutions compared to SEQ ID NO: 2. In other embodiments, an isolated antibody that specifically binds gp41 includes a heavy chain including the amino acid sequence set forth as SEQ ID NO: 187, wherein the amino acid sequence includes no more than 25 (such as more than 1, 2, 3, 4, 5, 6, 7, 8, 9, 10, 11, 12, 13, 14, 15, 16, 17, 18, 19, 20, 21, 22, 23, or no more than 24) amino acid substitutions compared to SEQ ID NO: 1, and a light chain including the amino acid sequence set forth as SEQ ID NO: 188, wherein the amino acid sequence includes no more than 33 (such as more than 1, 2, 3, 4, 5, 6, 7, 8, 9, 10, 11, 12, 13, 14, 15, 16, 17, 18, 19, 20, 21, 22, 23, 24, 35, 36, 37, 38, 39, 30, 31, 32 or no more than 33) amino acid substitutions compared to SEQ ID NO: 2.

In further embodiments, an isolated antibody that specifically binds gp41 includes a heavy chain variable region including an amino acid sequence having no more than 10 (such as more than 1, 2, 3, 4, 5, 6, 7, 8, or no more than 9) amino acid substitutions compared to one of SEQ ID NOs: 1, 3, 5, 11, 146, 147-149, 187, 189-192, and 200-204, and wherein the substitutions are selected from the amino acid substitutions listed in FIGS. 60A and 60B. In additional embodiments, an isolated antibody that specifically binds gp41 includes a light chain variable region including an amino acid sequence including no more than 10 (such as more than 1, 2, 3, 4, 5, 6, 7, 8, or no more than 9) amino acid substitutions compared to one of the amino acid sequence set forth as one of SEQ ID NOs: 2, 4, 6, 12, 150-152, 164-186, 188, or 197-199, wherein the, and wherein the substitutions are selected from the amino acid substitutions shown in FIGS. 61A and 61B. In other embodiments, an isolated antibody that specifically binds gp41 includes a heavy chain variable region including an amino acid sequence having no more than 10 (such as more than 1, 2, 3, 4, 5, 6, 7, 8, or no more than 9) amino acid substitutions compared to one of SEQ ID NOs: 1, 3, 5, 11, 146, 147-149, 187, 189-192, and 200-204, wherein the substitutions are selected from the amino acid substitutions shown in FIGS. 60A and 60B, and a light chain variable region including an amino acid sequence including no more than 10 (such as more than 1, 2, 3, 4, 5, 6, 7, 8, or no more than 9) amino acid substitutions compared to one of the amino acid sequence set forth as one of SEQ ID NOs: 2, 4, 6, 12, 150-152, 164-186, 188, or 197-199, and wherein the substitutions are selected from the amino acid substitutions listed in FIGS. 61A and 61B. In other embodiments, an isolated antibody that specifically binds gp41 includes a heavy chain variable region including an amino acid sequence having no more than 10 (such as more than 1, 2, 3, 4, 5, 6, 7, 8, or no more than 9) amino acid substitutions compared to SEQ ID NO: 1, wherein the substitutions are selected from the amino acid substitutions listed in FIGS. 60A and 60B, and a light chain variable region including an amino acid sequence having no more than 10 (such as more than 1, 2, 3, 4, 5, 6, 7, 8, or no more than 9) amino acid substitutions compared to SEQ ID NO: 2, and wherein the substitutions are selected from the amino acid substitutions listed in FIGS. 61A and 61B.

In further embodiments, an isolated antibody that specifically binds gp41 includes a heavy chain with at most one, at most two, at most three or at most four amino acid substitutions in amino acids 26-31 (CDR1), 49-51 (CDR2), and 87-98 (CDR3) of SEQ ID NO: 11, and a light chain. In some embodiments, an isolated antibody that specifically binds gp41 includes a heavy chain with at most one, at most two, at most three, at most four amino acid or at most five amino acid substitutions in amino acids 26-33 (CDR1), 51-60 (CDR2), and 99-120 (CDR3) of SEQ ID NO: 1.

In some embodiments, the antibody can include a heavy chain with at most one, at most two, at most three, at most four amino acid or at most five amino acid substitutions in amino acids 26-33 (CDR1), 51-60 (CDR2), and 99-120 (CDR3) of SEQ ID NO: 3. In some embodiments, the antibody can include a heavy chain with at most one, at most two, at most three, at most four amino acid or at most five amino acid substitutions in amino acids 26-33 (CDR1), 51-60 (CDR2), and 99-120 (CDR3) of SEQ ID NO: 5. In some embodiments, the antibody can include a heavy chain with at most one, at most two, at most three, at most four amino acid or at most five amino acid substitutions in amino acids 26-33 (CDR1), 51-60 (CDR2), and 99-120 (CDR3) of SEQ ID NO: 154.

In further embodiments, an isolated antibody that specifically binds gp41, and includes a light chain with at most one, at most two, at most three or at most four amino acid substitutions in amino acids 26-31 (CDR1), 49-51 (CDR2), and 88-99 (CDR3) of SEQ ID NO: 12. In some embodiments, an isolated antibody that specifically binds gp41, and includes a light chain with at most one, at most two, at most three or at most four amino acid substitutions in amino acids 26-31 (CDR1), 49-51 (CDR2), and 88-99 (CDR3) of SEQ ID NO: 2. In some embodiments, the antibody can include a light chain with at most one, at most two, at most three or at most four amino acid substitutions in amino acids 26-31 (CDR1), 49-51 (CDR2), and 88-99 (CDR3) of SEQ ID NO: 4. In some embodiments, the antibody can include a light chain with at most one, at most two, at most three or at most four amino acid substitutions in amino acids 26-31 (CDR1), 49-51 (CDR2), and 88-99 (CDR3) of SEQ ID NO: 6. In some embodiments, the antibody can include a light chain with at most one, at most two, at most three or at most four amino acid substitutions in amino acids 26-31 (CDR1), 49-51 (CDR2), and 88-99 (CDR3) of SEQ ID NO: 152.

In some embodiments, an isolated antibody that specifically binds gp41 as disclosed herein includes up to 10 amino acid substitutions (such as up to 1, 2, 3, 4, 5, 6, 7, 8, or up to 9 amino acid substitutions) in the framework regions (for example, according to the Kabat, Clothia or IMGT numbering systems) of the heavy chain of the antibody, the light chain of the antibody, or the heavy and light chains of the antibody.

In some embodiments, an isolated antibody that specifically binds gp41 includes a heavy chain variable region including no more than 10 (such as 1, 2, 3, 4, 5, 6, 7, 8 or 9) amino acid substitutions in the framework regions of one of SEQ ID NOs: 1, 3, 5, 11, 146, 147-149, 187, 189-192, and 200-204. Framework regions of SEQ ID NOs: 1, 3, 5, 11, 146, 147-149, 187, 189-192, and 200-204 include amino acids 1-25 (FR1), 34-50 (FR2), 61-66 (FR3) and 121-131 (FR4) of SEQ ID NOs: 1, 3, 5, 11, 146, 147-149, 187, 189-192, and 200-204, respectively (according to Kabat numbering). In some embodiments, an isolated antibody that specifically binds gp41 includes a light chain variable region including no more than 10 (such as 1, 2, 3, 4, 5, 6, 7, 8 or 9) amino acid substitutions in the framework regions of SEQ ID NOs: 2, 4, 6, 12, 150-152, 164-186, 188, or 197-199, respectively. Framework regions of SEQ ID NO: 2 include amino acids 1-25 (LFR2), 32-48 (LFR2), 52-87 (LFR3) and 99-108 (OFR4) of SEQ ID NO: 2, 4, 6, 12, 150-152, 164-186, 188, or 197-199, respectively (according to Kabat numbering).

In further embodiments, an isolated antibody that specifically binds gp41 includes a heavy chain variable region including no more than 10 (such as 1, 2, 3, 4, 5, 6, 7, 8 or 9) amino acid substitutions in the framework regions of SEQ ID NO: 1 and a light chain variable region including no more than 10 (such as 1, 2, 3, 4, 5, 6, 7, 8 or 9) amino acid substitutions in the framework regions of SEQ ID NOs: 2. In further embodiments, an isolated antibody that specifically binds gp41 includes a heavy chain variable region including no more than 10 (such as 1, 2, 3, 4, 5, 6, 7, 8 or 9) amino acid substitutions in the framework regions of SEQ ID NO: 154 and a light chain variable region including no more than 10 (such as 1, 2, 3, 4, 5, 6, 7, 8 or 9) amino acid substitutions in the framework regions of SEQ ID NO: 152. In further embodiments, an isolated antibody that specifically binds gp41 includes a heavy chain variable region including no more than 10 (such as 1, 2, 3, 4, 5, 6, 7, 8 or 9) amino acid substitutions in the framework regions of SEQ ID NO: 192 and a light chain variable region including no more than 10 (such as 1, 2, 3, 4, 5, 6, 7, 8 or 9) amino acid substitutions in the framework regions of SEQ ID NO: 152.

In some embodiments, the heavy chain of the human monoclonal antibody includes an amino acid sequence having at least 80% (such as at least 85%, 90%, 91%, 92%, 93%, 94%, 95%, 96%, 97%, 98%, or at least 99%) sequence identity with the amino acid sequence set forth as one of SEQ ID NOs: 1, 3, 5, 11, 146, 147-149, 187, 189-192, or 200-204. In additional examples, the heavy chain includes the amino acid sequence set forth as one of SEQ ID NOs: 1, 3, 5, 11, 146, 147-149, 187, 189-192, or 200-204. In some examples, the light chain of the human monoclonal antibody includes the amino acid sequence having at least 80% (such as at least 85%, 90%, 91%, 92%, 93%, 94%, 95%, 96%, 97%, 98%, or at least 99%) sequence identity with the amino acid sequence set forth as one of SEQ ID NOs: 2, 4, 6, 12, 150-152, 164-186, 188, or 197-199. In further embodiments, an isolated antibody that specifically binds gp41 includes a heavy chain variable region and a light chain variable region, wherein the heavy chain variable region includes the amino acid sequence having at least 80% (such as at least 85%, 90%, 91%, 92%, 93%, 94%, 95%, 96%, 97%, 98%, or at least 99%) sequence identity with the amino acid sequence set forth as one of SEQ ID NOs: 1, 3, 5, 11, 146, 147-149, 187, 189-192, or 200-204, and the light chain variable region includes the amino acid sequence having at least 80% (such as at least 85%, 90%, 91%, 92%, 93%, 94%, 95%, 96%, 97%, 98%, or at least 99%) sequence identity with the amino acid sequence set forth as one of SEQ ID NOs: 2, 4, 6, 12, 150-152, 164-186, 188, or 197-199.

As disclosed herein, deep sequencing was used to identify additional antibodies that bind to substantially similar epitopes on the surface of gp41 in substantially the same orientation that 10E8, 7H6, and/or 7N16 bind. Exemplary nucleic acid sequences encoding antibody heavy chains are set forth as SEQ ID NOs: 35-115 in the accompanying sequence listing. These encode antibody heavy chain variable regions at least about 80% identical to the 10E8 antibody heavy chain variable region (SEQ ID NO: 1). Thus, disclosed herein are nucleic acid molecules encoding antibody heavy chain variable regions that are at least about 80% identical to the heavy chain variable region set forth as SEQ Id NO: 1, such as at least about 80%, at least about 81%, at least about 82%, at least about 83%, at least about 84%, at least about 85% at least about 86%, at least about 87%, at least about 88%, or even at least about 89% at least about 90%, at least about 91%, at least about 92%, at least about 93%, at least about 94%, at least about 95% at least about 96%, at least about 97%, at least about 98%, or even at least about 99% identical to SEQ ID NO: 1. Exemplary nucleic acid sequences encoding 10E8-like antibody light chains are set forth as SEQ ID NOs: 116-145 in the accompanying sequence listing. Exemplary nucleic acid sequences encoding antibody light chains are set forth as SEQ ID NOs: 116-145 in the accompanying sequence listing. These encode antibody light chain variable regions at least about 80% identical to the 10E8 antibody light chain variable region (SEQ ID NO: 2). Thus, disclosed herein are nucleic acid molecules encoding antibody light chain variable regions that are at least about 80% identical to the heavy chain variable region set forth as SEQ ID NO: 2, such as at least about 80%, at least about 81%, at least about 82%, at least about 83%, at least about 84%, at least about 85% at least about 86%, at least about 87%, at least about 88%, or even at least about 89% at least about 90%, at least about 91%, at least about 92%, at least about 93%, at least about 94%, at least about 95% at least about 96%, at least about 97%, at least about 98%, or even at least about 99% identical to SEQ ID NO: 2.

In some embodiments, an isolated antibody that specifically binds gp41 includes one or more of the heavy chain complementarity determining regions (CDRs) encoded by the nucleic acid sequence set forth as one of SEQ ID NOs: 35-115. In some embodiments, an isolated human monoclonal antibody that specifically binds gp41 includes a heavy chain withal of the CDRs encoded by the nucleic acid sequence set forth as one of SEQ ID NOs: 35-115. In specific examples, the heavy chain of the human monoclonal antibody includes the amino acid sequence encoded by the nucleic acid sequence set forth as one of SEQ ID NOs: 35-115.

In some embodiments, an isolated antibody that specifically binds gp41 includes one or more of the light chain complementarity determining regions (CDRs) encoded by the nucleic acid sequence set forth as one of SEQ ID NOs: 116-145. In some embodiments, an isolated human monoclonal antibody that specifically binds gp41 includes a light chain with all of the CDRs antibody encoded by the nucleic acid sequence set forth as one of SEQ ID NOs: 116-145. In specific examples, the light chain of the human monoclonal antibody includes the amino acid sequence encoded by the nucleic acid sequence set forth as one of SEQ ID NOs: 116-145.

In some embodiments, an isolated antibody that specifically binds gp41 includes a heavy chain variable region encoded by a nucleic acid derived from the IGHV3-15 germline allelic origin, for example the IGHV3-15*01, IGHV3-15*02, IGHV3-15*03, IGHV3-15*04, IGHV3-15*05, IGHV3-15*06, IGHV3-15*07, IGHV3-15*08, IGHV3-15*09, IGHV3-15*10, IGHV3-15*11, IGHV3-15*12, IGHV3-15*13, IGHV3-15*14, or IGHV3-15*15 germline allelic origin. In some embodiments, the heavy chain variable region is encoded by a nucleic acid derived from the IGHV3-15 germline allelic origin, for example the IGHV3-15*01, IGHV3-15*02, IGHV3-15*03, IGHV3-15*04, IGHV3-15*05, IGHV3-15*06, IGHV3-15*07, IGHV3-15*08, IGHV3-15*09, IGHV3-15*10, IGHV3-15*11, IGHV3-15*12, IGHV3-15*13, IGHV3-15*14, or IGHV3-15*15 germline allelic origin, and is about 10%, 15%, 20%, 25%, 30%, 35% or 40%, such as about 15% to 40% divergent from the respective heavy chain germline sequence.

In some embodiments, an isolated antibody that specifically binds gp41 includes a light chain variable region encoded by a nucleic acid derived from the IGLV3-19 germline allelic origin, such as an IGLV3-19*01 germline allelic origin. In some embodiments, the light chain is encoded by a nucleic acid derived from the IGLV3-19 germline allelic origin, such as an IGLV3-19*01 germline allelic origin, and is about 10%, 15%, 20%, 25%, 30%, 35% or 40%, such as about 15% to 40% divergent from the respective light chain germline sequence.

In some examples, the heavy chain variable domain is a clonal variant from donor N152, with a heavy chain encoded by VH3-15 gene and VJ-1 J genes. In other examples, the light chain variable domain is a clonal variant from donor N152, with a light chain encoded by a LV3-19 V gene and a LJ-3 J gene. The isolated monoclonal antibody can include a heavy chain and a light chain, wherein the heavy chain variable region is a clonal variant from donor N152 with a heavy chain variable region amino acid sequence set forth as SEQ ID NO: 1. The a heavy chain is derived from a VH3-15 gene and LJ-3 J genes. The light chain variable domain is a clonal variant from donor N152 with a light chain variable region amino acid sequence set forth as SEQ ID NO: 2. The light chain is derived a LV3-19 V gene and a LJ-3 J gene, the monoclonal antibody specifically binds gp41, competes with 10E8 for binding to gp41, and is neutralizing.

In some embodiments, the heavy chain of a 10E8-like antibody can be complemented by the light chain of the 10E8, 7H6, and/or 7N16 antibody and still retain binding for gp41, for example retain specific binding for the 10E8 epitope. In some embodiments, the light chain of a 10E8-like antibody can be complemented by the heavy chain of the 10E8, 7H6, and/or 7N16 antibody and still retain binding for gp41, for example retain specific binding for the 10E8 epitope. Thus, disclosed herein are 10E8-like antibodies that can be identified by complementation of the heavy or light chains of 10E8, 7H6, and/or 7N16.

Once a heavy or light chain variable domain of interest is identified, binding to gp41 or an epitope of interest (such as the 10E8 epitope) can be determined using a cross complementation analysis. Briefly, if the variable domain of interest is a heavy chain variable domain, the amino acid sequence of this heavy chain variable domain is produced. The heavy chain variable domain is then paired with a reference sequence light chain variable domain, such as 10E8 (SEQ ID NO: 2), 7H6 (SEQ ID NO: 4), and/or 7N16 (SEQ ID NO: 6), light chain variable domain, and it is determined if the antibody specifically binds the antigen (or epitope) with a specified affinity, such as a $K_D$ of $10^{-8}$, $10^{-9}$ or $10^{-10}$. Similarly, if the variable domain of interest is a light chain variable domain, this amino acid sequence is produced. The variable light chain variable domain is then paired with a reference sequence heavy chain variable domain, such as variable domain is then paired with a reference sequence light chain variable domain, such as 10E8 (SEQ ID NO: 1), 7H6 (SEQ ID NO: 3), and/or 7N16 (SEQ Id NO: 5) heavy chain variable domain, and it is determined if the antibody specifically binds the antigen (or epitope) with a specified affinity, such as a $K_D$ of $10^{-8}$, $10^{-9}$ or $10^{-10}$.

Fully human monoclonal antibodies include human framework regions. Thus, any of the antibodies that specifically bind gp41 herein can include the human framework region and can include the framework regions of the amino acid sequence set forth as one of SEQ ID NO; 1-6, 11, 12, and/or 146-192 or encoded by one of SEQ ID NOs: 35-145. However, the framework regions can be from another source. Additional examples of framework sequences that can be used include the amino acid framework sequences of the heavy and light chains disclosed in PCT Publication No. WO 2006/074071 (see, for example, SEQ ID NOs: 1-16), which is herein incorporated by reference.

In some embodiments, one or more of the heavy and/or light chain complementarity determining regions (CDRs) from gp41 antibody set forth one of 1-6, 11, 12, and/or 146-192 or encoded by SEQ ID NOs: 35-145 is expressed on the surface of another protein, such as a scaffold protein. The expression of domains of antibodies on the surface of a scaffolding protein are known in the art (see e.g. Liu et al., *J. Virology* 85(17): 8467-8476, 2011). Such expression creates a chimeric protein that retains the binding for gp41, such as specific binding to the 10E8 epitope. As described in Example 1, the 10E8 class of antibodies makes most of its contacts through the heavy chain CDRs (see, for example, the tables given as FIGS. 27-30, and the molecular models shown in FIGS. 4, 5, 12, 15, 16 and 39-41A). Thus, in some specific embodiments, one or more of the heavy chain CDRs is grafted onto a scaffold protein, such as one or more of heavy chain CDR1, CDR2, and/or CDR3 set forth as one of SEQ ID NO; 1, 3, 5, 11, 146-149, 153-163, 187, 189-192, or 200-204 or encoded by one of SEQ ID NOs: 35-115.

The monoclonal antibody can be of any isotype. The monoclonal antibody can be, for example, an IgM or an IgG antibody, such as $IgG_1$, $IgG_2$, $IgG_3$, or $IgG_4$. The class of an antibody that specifically binds gp41 can be switched with another. In one aspect, a nucleic acid molecule encoding $V_L$ or $V_H$ is isolated using methods well-known in the art, such that it does not include any nucleic acid sequences encoding the constant region of the light or heavy chain, respectively.

In particular examples, the $V_H$ amino acid sequence is set forth as one of SEQ ID NO: 1, 3, 5, 11, 146-149, 153-163, 187, 189-192, or 200-204 or encoded by one of SEQ ID NOs: 35-115. In other examples, the $V_L$ amino acid sequence is set forth as one of SEQ ID NO: 2, 4, 6, 12, 150-152, 164-186, 188, or 197-199 or encoded by one of SEQ ID NOs: 116-145. The nucleic acid molecule encoding $V_L$ or $V_H$ is then operatively linked to a nucleic acid sequence encoding a $C_L$ or $C_H$ from a different class of immunoglobulin molecule. This can be achieved using a vector or nucleic acid molecule that includes a $C_L$ or $C_H$ chain, as known in the art. For example, an antibody that specifically binds gp41, that was originally IgM may be class switched to an IgG. Class switching can be used to convert one IgG subclass to another, such as from $IgG_1$ to $IgG_2$, $IgG_3$, or $IgG_4$.

In some examples, the disclosed antibodies are oligomers of antibodies, such as dimers, trimers, tetramers, pentamers, hexamers, septamers, octomers and so on. In some examples, the antibodies are pentamers.

In some examples, the antibodies, or an antibody binding fragment thereof is modified such that it is directly cytotoxic to infected cells, or uses natural defenses such as complement, antibody dependent cellular cytotoxicity (ADCC), or phagocytosis by macrophages.

Antibody fragments are encompassed by the present disclosure, such as Fab, F(ab')$_2$, and Fv which include a heavy chain and light chain variable region and specifically bind gp41. These antibody fragments retain the ability to selectively bind with the antigen and are "antigen-binding" fragments. These fragments include:

(1) Fab, the fragment which contains a monovalent antigen-binding fragment of an antibody molecule, can be produced by digestion of whole antibody with the enzyme papain to yield an intact light chain and a portion of one heavy chain;

(2) Fab', the fragment of an antibody molecule can be obtained by treating whole antibody with pepsin, followed by reduction, to yield an intact light chain and a portion of the heavy chain; two Fab' fragments are obtained per antibody molecule;

(3) (Fab')$_2$, the fragment of the antibody that can be obtained by treating whole antibody with the enzyme pepsin without subsequent reduction; F(ab')$_2$ is a dimer of two Fab' fragments held together by two disulfide bonds;

(4) Fv, a genetically engineered fragment containing the variable region of the light chain and the variable region of the heavy chain expressed as two chains; and (5) Single chain antibody (such as scFv), defined as a genetically engineered molecule containing the variable region of the light chain, the variable region of the heavy chain, linked by a suitable polypeptide linker as a genetically fused single chain molecule.

(6) A dimer of a single chain antibody (scFV$_2$), defined as a dimer of a scFV. This has also been termed a "miniantibody."

Methods of making these fragments are known in the art (see for example, Harlow and Lane, *Antibodies: A Laboratory Manual*, Cold Spring Harbor Laboratory, New York, 1988).

In a further group of embodiments, the antibodies are Fv antibodies, which are typically about 25 kDa and contain a complete antigen-binding site with three CDRs per each heavy chain and each light chain. To produce these antibodies, the $V_H$ and the $V_L$ can be expressed from two individual nucleic acid constructs in a host cell. In particular examples, the $V_H$ amino acid sequence includes the CDRs from one of SEQ ID NOs: 1, 3, 5, 11, 146-149, 153-163, 187 or 189-192 or encoded by one of SEQ ID NOs: 35-115. In other examples, the $V_L$ amino acid sequence includes the CDRs from SEQ ID NOs: 2, 4, 6, 12, 150-152, 164-186, 188, or 197-199 or encoded by one of SEQ ID NOs: 116-145. In additional examples, the $V_H$ amino acid sequence includes the amino acid sequence set forth as one of SEQ ID NOs: 1, 3, 5, 11, 146-149, 153-163, 187 or 189-192 or encoded by one of SEQ ID NOs: 35-115. In other examples, the $V_L$ amino acid sequence includes the amino acid sequence set forth as SEQ ID NOs: 2, 4, 6, 12, 150-152, 164-186, 188, or 197-199 or encoded by one of SEQ ID NOs: 116-145.

If the $V_H$ and the $V_L$ are expressed non-contiguously, the chains of the Fv antibody are typically held together by noncovalent interactions. However, these chains tend to dissociate upon dilution, so methods have been developed to crosslink the chains through glutaraldehyde, intermolecular disulfides, or a peptide linker. Thus, in one example, the Fv can be a disulfide stabilized Fv (dsFv), wherein the heavy chain variable region and the light chain variable region are chemically linked by disulfide bonds.

In an additional example, the Fv fragments include $V_H$ and $V_L$ chains connected by a peptide linker. These single-chain antigen binding proteins (scFv) are prepared by constructing a structural gene including DNA sequences encoding the $V_H$ and $V_L$ domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing scFvs are known in the art (see Whitlow et al., *Methods: a Companion to Methods in Enzymology*, Vol. 2, page 97, 1991; Bird et al., *Science* 242:423, 1988; U.S. Pat. No. 4,946,778; Pack et al., *Bio/Technology* 11:1271, 1993; and Sandhu, supra). Dimers of a single chain antibody ($scFV_2$), are also contemplated.

Antibody fragments can be prepared by proteolytic hydrolysis of the antibody or by expression in *E. coli* of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted $F(ab')_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly (see U.S. Pat. No. 4,036,945 and U.S. Pat. No. 4,331,647, and references contained therein; Nisonhoff et al., *Arch. Biochem. Biophys.* 89:230, 1960; Porter, *Biochem. J.* 73:119, 1959; Edelman et al., *Methods in Enzymology*, Vol. 1, page 422, Academic Press, 1967; and Coligan et al. at sections 2.8.1-2.8.10 and 2.10.1-2.10.4).

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

One of skill will realize that conservative variants of the antibodies can be produced. Such conservative variants employed in antibody fragments, such as dsFv fragments or in scFv fragments, will retain critical amino acid residues necessary for correct folding and stabilizing between the $V_H$ and the $V_L$ regions, and will retain the charge characteristics of the residues in order to preserve the low pI and low toxicity of the molecules Amino acid substitutions (such as at most one, at most two, at most three, at most four, or at most five amino acid substitutions) can be made in the $V_H$ and the $V_L$ regions to increase yield. In particular examples, the $V_H$ sequence is SEQ ID NOs: 1, 3, 5, 11, 146-149, 153-163, 187 or 189-192 or encoded by one of SEQ ID NOs: 35-115. In other examples, the $V_L$ sequence is SEQ ID NOs: 2, 4, 6, 12, 150-152, 164-186, 188, or 197-199 or encoded by one of SEQ ID NOs: 116-145. Conservative amino acid substitution tables providing functionally similar amino acids are well known to one of ordinary skill in the art. The following six groups are examples of amino acids that are considered to be conservative substitutions for one another:
 1) Alanine (A), Serine (S), Threonine (T);
 2) Aspartic acid (D), Glutamic acid (E);
 3) Asparagine (N), Glutamine (Q);
 4) Arginine (R), Lysine (K);
 5) Isoleucine (I), Leucine (L), Methionine (M), Valine (V); and
 6) Phenylalanine (F), Tyrosine (Y), Tryptophan (W).

The antibodies disclosed herein can be isolated using cloaked antigens, as described in PCT Publication No. WO 2009/100376. Briefly, antigens are cloaked to target antigenicity of the antigen to a specific epitope that specifically bound by the antibody of interest, such as a neutralizing antibody.

Additional recombinant human neutralizing antibodies that specifically bind the same epitope of gp41 bound by the antibodies disclosed herein that specifically bind gp41, can be isolated by screening of a recombinant combinatorial antibody library, such as a Fab phage display library (see, for example, U.S. Patent Application Publication No. 2005/0123900). In some cases the phage display libraries are prepared using cDNAs of the variable regions of heavy and light chains prepared from mRNA derived from human lymphocytes. Methodologies for preparing and screening such libraries are known in the art. There are commercially available kits for generating phage display libraries (for example, the Pharmacia Recombinant Phage Antibody System, Catalog No. 27-9400-01; and the Stratagene SurfZAP™ phage display kit, catalog no. 240612). There are also other methods and reagents that can be used in generating and screening antibody display libraries (see, for example, U.S. Pat. No. 5,223,409; PCT Publication No. WO 92/18619; PCT Publication No. WO 91/17271; PCT Publication No. WO 92/20791; PCT Publication No. WO 92/15679; PCT Publication No. WO 93/01288; PCT Publication No. WO 92/01047; PCT Publication No. WO 92/09690; Fuchs et al., *Bio/Technology* 9:1370-1372, 1991; Hay et al., *Hum. Antibod. Hybridomas* 3:81-85, 1992; Huse et al., *Science* 246:1275-1281, 1989; McCafferty et al., *Nature* 348:552-554, 1990; Griffiths et al., *EMBO J.* 12:725-734, 1993)

In one embodiment, to isolate additional human antibodies that specifically bind gp41, a neutralizing antibody that specifically binds gp41, as described herein, is first used to select human heavy and light chain sequences having similar binding activity toward gp41, such as using the epitope imprinting methods disclosed in PCT Publication No. WO 93/06213. The antibody libraries used in this method are scFv libraries prepared and screened, using methods such as those as described in PCT Publication No. WO 92/01047, McCafferty et al., *Nature* 348:552-554, 1990; and/or Griffiths et al., *EMBO J.* 12:725-734, 1993 using gp120.

Once initial human variable light chain ($V_L$) and variable heavy chain ($V_H$) segments are selected, "mix and match" experiments, in which different pairs of the initially selected $V_L$ and $V_H$ segments are screened for gp41 binding are performed to select $V_L/V_H$ pair combinations of interest. Additionally, to increase binding affinity of the antibody, the $V_L$ and $V_H$ segments can be randomly mutated, such as within H-CDR3 region or the L-CDR3 region, in a process analogous to the in vivo somatic mutation process responsible for affinity maturation of antibodies during a natural immune response. Thus in vitro affinity maturation can be accomplished by amplifying $V_H$ and $V_L$ regions using PCR primers complementary to the H-CDR3 or L-CDR3, respectively. In this process, the primers have been "spiked" with a random mixture of the four nucleotide bases at certain positions such that the resultant PCR products encode $V_H$ and $V_L$ segments into which random mutations have been introduced into the $V_H$ and/or $V_L$ CDR3 regions. These randomly mutated $V_H$ and $V_L$ segments can be tested to determine the binding affinity for gp41. In particular examples, the $V_H$ amino acid sequence is SEQ ID NOs: 1, 3, 5, or 11, 146-149, 153-163, 187, 189-192, or 200-204 or encoded by one of SEQ ID NOs: 35-115. In other examples, the $V_L$ amino acid sequence is SEQ ID NOs: 2, 4, 6, 12, 150-152, 164-186, 188, or 197-199 or encoded by one of SEQ ID NOs: 116-145.

Following screening and isolation of an antibody that binds gp41 from a recombinant immunoglobulin display library, nucleic acid encoding the selected antibody can be recovered from the display package (for example, from the phage genome) and subcloned into other expression vectors by standard recombinant DNA techniques, as described herein. If desired, the nucleic acid can be further manipulated to create other antibody fragments, also as described herein. To express a recombinant antibody isolated by screening of a combinatorial library, the DNA encoding the antibody is cloned into a recombinant expression vector and introduced into a mammalian host cells, as described herein.

Effector molecules, such as therapeutic, diagnostic, or detection moieties can be linked to an antibody of interest, using any number of means known to those of skill in the art. Both covalent and noncovalent attachment means may be used. The procedure for attaching an effector molecule to an antibody varies according to the chemical structure of the effector. Polypeptides typically contain a variety of functional groups; such as carboxylic acid (COOH), free amine (—$NH_2$) or sulfhydryl (—SH) groups, which are available for reaction with a suitable functional group on an antibody to result in the binding of the effector molecule. Alternatively, the antibody is derivatized to expose or attach additional reactive functional groups. The derivatization may involve attachment of any of a number of linker molecules such as those available from Pierce Chemical Company, Rockford, Ill. The linker can be any molecule used to join the antibody to the effector molecule. The linker is capable of forming covalent bonds to both the antibody and to the effector molecule. Suitable linkers are well known to those of skill in the art and include, but are not limited to, straight or branched-chain carbon linkers, heterocyclic carbon linkers, or peptide linkers. Where the antibody and the effector molecule are polypeptides, the linkers may be joined to the constituent amino acids through their side groups (such as through a disulfide linkage to cysteine) or to the alpha carbon amino and carboxyl groups of the terminal amino acids.

In some circumstances, it is desirable to free the effector molecule from the antibody when the immunoconjugate has reached its target site. Therefore, in these circumstances, immunoconjugates will include linkages that are cleavable in the vicinity of the target site. Cleavage of the linker to release the effector molecule from the antibody may be prompted by enzymatic activity or conditions to which the immunoconjugate is subjected either inside the target cell or in the vicinity of the target site.

In view of the large number of methods that have been reported for attaching a variety of radiodiagnostic compounds, radiotherapeutic compounds, label (such as enzymes or fluorescent molecules) drugs, toxins, and other agents to antibodies one skilled in the art will be able to determine a suitable method for attaching a given agent to an antibody or other polypeptide.

The antibodies or antibody fragments disclosed herein can be derivatized or linked to another molecule (such as another peptide or protein). In general, the antibody or portion thereof is derivatized such that the binding to gp41 is not affected adversely by the derivatization or labeling. For example, the antibody can be functionally linked (by chemical coupling, genetic fusion, noncovalent association or otherwise) to one or more other molecular entities, such as another antibody (for example, a bispecific antibody or a diabody), a detection agent, a pharmaceutical agent, and/or a protein or peptide that can mediate associate of the antibody or antibody portion with another molecule (such as a streptavidin core region or a polyhistidine tag).

One type of derivatized antibody is produced by crosslinking two or more antibodies (of the same type or of different types, such as to create bispecific antibodies). Suitable crosslinkers include those that are heterobifunctional, having two distinctly reactive groups separated by an appropriate spacer (such as m-maleimidobenzoyl-N-hydroxysuccinimide ester) or homobifunctional (such as disuccinimidyl suberate). Such linkers are available from Pierce Chemical Company (Rockford, Ill.).

An antibody that specifically binds gp41 can be labeled with a detectable moiety. Useful detection agents include fluorescent compounds, including fluorescein, fluorescein isothiocyanate, rhodamine, 5-dimethylamine-1-napthalenesulfonyl chloride, phycoerythrin, lanthanide phosphors and the like. Bioluminescent markers are also of use, such as luciferase, Green fluorescent protein, Yellow fluorescent protein. An antibody can also be labeled with enzymes that are useful for detection, such as horseradish peroxidase, β-galactosidase, luciferase, alkaline phosphatase, glucose oxidase and the like. When an antibody is labeled with a detectable enzyme, it can be detected by adding additional reagents that the enzyme uses to produce a reaction product that can be discerned. For example, when the agent horseradish peroxidase is present the addition of hydrogen peroxide and diaminobenzidine leads to a colored reaction product, which is visually detectable. An antibody may also be labeled with biotin, and detected through indirect measurement of avidin or streptavidin binding. It should be noted that the avidin itself can be labeled with an enzyme or a fluorescent label.

An antibody may be labeled with a magnetic agent, such as gadolinium. Antibodies can also be labeled with lanthanides (such as europium and dysprosium), and manganese. Paramagnetic particles such as superparamagnetic iron oxide are also of use as labels. An antibody may also be labeled with a predetermined polypeptide epitopes recognized by a secondary reporter (such as leucine zipper pair sequences, binding sites for secondary antibodies, metal binding domains, epitope tags). In some embodiments, labels are attached by spacer arms of various lengths to reduce potential steric hindrance.

An antibody can also be labeled with a radiolabeled amino acid. The radiolabel may be used for both diagnostic and therapeutic purposes. Examples of labels for polypeptides include, but are not limited to, the following radioisotopes or radionucleotides: $^{3}H$, $^{14}C$, $^{15}N$, $^{35}S$, $^{90}Y$, $^{99}Tc$, $^{111}In$, $^{125}I$, $^{131}I$.

An antibody can also be derivatized with a chemical group such as polyethylene glycol (PEG), a methyl or ethyl group, or a carbohydrate group. These groups may be useful to improve the biological characteristics of the antibody, such as to increase serum half-life or to increase tissue binding.

Means of detecting such labels are well known to those of skill in the art. Thus, for example, radiolabels may be detected using photographic film or scintillation counters, fluorescent markers may be detected using a photodetector to detect emitted illumination. Enzymatic labels are typically detected by providing the enzyme with a substrate and detecting the reaction product produced by the action of the enzyme on the substrate, and colorimetric labels are detected by simply visualizing the colored label.

The present disclosure also relates to the crystals obtained from the 10E8, 7H6, and/or 7N16, antibody or portions thereof in complex with gp41 (or gp41 peptides), the crystal structures of the 10E8, 7H6, and/or 7N16 antibody or portions thereof in complex with gp41 (or gp41 peptides), the three-dimensional coordinates of the 10E8, 7H6, and/or 7N16 antibody or portions thereof in complex with gp41 (or gp41 peptides) and three-dimensional structures of models of the 10E8, 7H6, and/or 7N16 antibody or portions thereof in complex with gp41 (or gp41 peptides).

Those of skill in the art will understand that a set of structure coordinates for the 10E8, 7H6, and/or 7N16 antibody or portions thereof in complex with gp41 or a portion thereof, is a relative set of points that define a shape in three dimensions. Thus, it is possible that an entirely different set of coordinates could define a similar or identical shape. Moreover, slight variations in the individual coordinates will have little effect on overall shape. The variations in coordinates discussed above may be generated because of mathematical manipulations of the structure coordinates.

This disclosure further provides systems, such as computer systems, intended to generate structures and/or perform rational drug or compound design for an antigenic compound capable of eliciting an immune response in a subject. The system can contain one or more or all of: atomic co-ordinate data according to 10E8, 7H6, and/or 7N16 antibody complex or a subset thereof, and the figures derived therefrom by homology modeling, the data defining the three-dimensional structure of a 10E8, 7H6, and/or 7N16 antibody complex or at least one sub-domain thereof, or structure factor data for gp41, the structure factor data being derivable from the atomic co-ordinate data of 10E8, 7H6, and/or 7N16 antibody complex or a subset thereof and the figures.

B. Polynucleotides and Expression

Nucleic acid molecules (also referred to as polynucleotides) encoding the polypeptides provided herein (including, but not limited to antibodies) can readily be produced by one of skill in the art. For example, these nucleic acids can be produced using the amino acid sequences provided herein (such as the CDR sequences, heavy chain and light chain sequences).

One of skill in the art can readily use the genetic code to construct a variety of functionally equivalent nucleic acids, such as nucleic acids which differ in sequence but which encode the same antibody sequence, or encode a conjugate or fusion protein including the $V_L$ and/or $V_H$ nucleic acid sequence.

Nucleic acid sequences encoding the antibodies that specifically bind gp41 can be prepared by any suitable method including, for example, cloning of appropriate sequences or by direct chemical synthesis by methods such as the phosphotriester method of Narang et al., *Meth. Enzymol.* 68:90-99, 1979; the phosphodiester method of Brown et al., *Meth. Enzymol.* 68:109-151, 1979; the diethylphosphoramidite method of Beaucage et al., *Tetra. Lett.* 22:1859-1862, 1981; the solid phase phosphoramidite triester method described by Beaucage & Caruthers, *Tetra. Letts.* 22(20):1859-1862, 1981, for example, using an automated synthesizer as described in, for example, Needham-VanDevanter et al., *Nucl. Acids Res.* 12:6159-6168, 1984; and, the solid support method of U.S. Pat. No. 4,458,066. Chemical synthesis produces a single stranded oligonucleotide. This can be converted into double stranded DNA by hybridization with a complementary sequence or by polymerization with a DNA polymerase using the single strand as a template. One of skill would recognize that while chemical synthesis of DNA is generally limited to sequences of about 100 bases, longer sequences may be obtained by the ligation of shorter sequences.

Exemplary nucleic acids can be prepared by cloning techniques. Examples of appropriate cloning and sequencing techniques, and instructions sufficient to direct persons of skill through many cloning exercises are found in Sambrook et al., supra, Berger and Kimmel (eds.), supra, and Ausubel, supra. Product information from manufacturers of biological reagents and experimental equipment also provide useful information. Such manufacturers include the SIGMA Chemical Company (Saint Louis, Mo.), R&D Systems (Minneapolis, Minn.), Pharmacia Amersham (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersburg, Md.), Fluka Chemica-Biochemika Analytika (Fluka Chemie AG, Buchs, Switzerland), Invitrogen (Carlsbad, Calif.), and Applied Biosystems (Foster City, Calif.), as well as many other commercial sources known to one of skill.

Nucleic acids can also be prepared by amplification methods. Amplification methods include polymerase chain reaction (PCR), the ligase chain reaction (LCR), the transcription-based amplification system (TAS), the self-sustained sequence replication system (3SR). A wide variety of cloning methods, host cells, and in vitro amplification methodologies are well known to persons of skill.

Any of the nucleic acids encoding any of the antibodies, $V_H$ and/or $V_L$, disclosed herein (or fragment thereof) can be expressed in a recombinantly engineered cell such as bacteria, plant, yeast, insect and mammalian cells. These antibodies can be expressed as individual $V_H$ and/or $V_L$ chain, or can be expressed as a fusion protein. An immunoadhesin can also be expressed. Thus, in some examples, nucleic acids encoding a $V_H$ and $V_L$, and immunoadhesin are provided. The nucleic acid sequences can optionally encode a leader sequence.

To create a single chain antibody, (scFv) the $V_H$- and $V_L$-encoding DNA fragments are operatively linked to another fragment encoding a flexible linker, e.g., encoding the amino acid sequence $(Gly_4$-$Ser)_3$, such that the $V_H$ and $V_L$ sequences can be expressed as a contiguous single-chain protein, with the $V_L$ and $V_H$ domains joined by the flexible linker (see, e.g., Bird et al., *Science* 242:423-426, 1988; Huston et al., *Proc. Natl. Acad. Sci. USA* 85:5879-5883, 1988; McCafferty et al., *Nature* 348:552-554, 1990). Optionally, a cleavage site can be included in a linker, such as a furin cleavage site.

The nucleic acid encoding the $V_H$ and/or the $V_L$ optionally can encode an Fc domain (immunoadhesin). The Fc domain can be an IgA, IgM or IgG Fc domain. The Fc domain can be an optimized Fc domain, as described in U.S. Published Patent Application No. 20100/093979, incorporated herein by reference. In one example, the immunoadhesin is an $IgG_1$ Fc. In one example, the immunoadhesin is an $IgG_3$ Fc.

The single chain antibody may be monovalent, if only a single $V_H$ and $V_L$ are used, bivalent, if two $V_H$ and $V_L$ are used, or polyvalent, if more than two $V_H$ and $V_L$ are used. Bispecific or polyvalent antibodies may be generated that bind specifically to gp120 and to another molecule, such as gp41. The encoded $V_H$ and $V_L$ optionally can include a furin cleavage site between the $V_H$ and $V_L$ domains.

It is expected that those of skill in the art are knowledgeable in the numerous expression systems available for expression of proteins including *E. coli*, other bacterial hosts, yeast, and various higher eukaryotic cells such as the COS, CHO, HeLa and myeloma cell lines.

The host cell can be a gram positive bacteria including, but are not limited to, *Bacillus, Streptococcus, Streptomyces,*

*Staphylococcus, Enterococcus, Lactobacillus, Lactococcus, Clostridium, Geobacillus,* and *Oceanobacillus*. Methods for expressing protein in gram positive bacteria, such as *Lactobaccillus* are well known in the art, see for example, U.S. Published Patent Application No. 20100/080774. Expression vectors for *lactobacillus* are described, for example in U.S. Pat. No. 6,100,388, and U.S. Pat. No. 5,728,571. Leader sequences can be included for expression in *Lactobacillus*. Gram negative bacteria include, but not limited to, *E. coli, Pseudomonas, Salmonella, Campylobacter, Helicobacter, Flavobacterium, Fusobacterium, Ilyobacter, Neisseria,* and *Ureaplasma*.

One or more DNA sequences encoding the antibody or fragment thereof can be expressed in vitro by DNA transfer into a suitable host cell. The cell may be prokaryotic or eukaryotic. The term also includes any progeny of the subject host cell. It is understood that all progeny may not be identical to the parental cell since there may be mutations that occur during replication. Methods of stable transfer, meaning that the foreign DNA is continuously maintained in the host, are known in the art. Hybridomas expressing the antibodies of interest are also encompassed by this disclosure.

The expression of nucleic acids encoding the isolated proteins described herein can be achieved by operably linking the DNA or cDNA to a promoter (which is either constitutive or inducible), followed by incorporation into an expression cassette. The promoter can be any promoter of interest, including a cytomegalovirus promoter and a human T cell lymphotrophic virus promoter (HTLV)-1. Optionally, an enhancer, such as a cytomegalovirus enhancer, is included in the construct. The cassettes can be suitable for replication and integration in either prokaryotes or eukaryotes. Typical expression cassettes contain specific sequences useful for regulation of the expression of the DNA encoding the protein. For example, the expression cassettes can include appropriate promoters, enhancers, transcription and translation terminators, initiation sequences, a start codon (i.e., ATG) in front of a protein-encoding gene, splicing signal for introns, sequences for the maintenance of the correct reading frame of that gene to permit proper translation of mRNA, and stop codons. The vector can encode a selectable marker, such as a marker encoding drug resistance (for example, ampicillin or tetracycline resistance).

To obtain high level expression of a cloned gene, it is desirable to construct expression cassettes which contain, at the minimum, a strong promoter to direct transcription, a ribosome binding site for translational initiation (internal ribosomal binding sequences), and a transcription/translation terminator. For *E. coli*, this includes a promoter such as the T7, trp, lac, or lambda promoters, a ribosome binding site, and preferably a transcription termination signal. For eukaryotic cells, the control sequences can include a promoter and/or an enhancer derived from, for example, an immunoglobulin gene, HTLV, SV40 or cytomegalovirus, and a polyadenylation sequence, and can further include splice donor and/or acceptor sequences (for example, CMV and/or HTLV splice acceptor and donor sequences). The cassettes can be transferred into the chosen host cell by well-known methods such as transformation or electroporation for *E. coli* and calcium phosphate treatment, electroporation or lipofection for mammalian cells. Cells transformed by the cassettes can be selected by resistance to antibiotics conferred by genes contained in the cassettes, such as the amp, gpt, neo and hyg genes.

When the host is a eukaryote, such methods of transfection of DNA as calcium phosphate coprecipitates, conventional mechanical procedures such as microinjection, electroporation, insertion of a plasmid encased in liposomes, or virus vectors may be used. Eukaryotic cells can also be cotransformed with polynucleotide sequences encoding the antibody, labeled antibody, or antibody binding fragment thereof, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein (see for example, Eukaryotic Viral Vectors, Cold Spring Harbor Laboratory, Gluzman ed., 1982). One of skill in the art can readily use an expression systems such as plasmids and vectors of use in producing proteins in cells including higher eukaryotic cells such as the COS, CHO, HeLa and myeloma cell lines.

Modifications can be made to a nucleic acid encoding a polypeptide described herein without diminishing its biological activity. Some modifications can be made to facilitate the cloning, expression, or incorporation of the targeting molecule into a fusion protein. Such modifications are well known to those of skill in the art and include, for example, termination codons, a methionine added at the amino terminus to provide an initiation, site, additional amino acids placed on either terminus to create conveniently located restriction sites, or additional amino acids (such as poly His) to aid in purification steps. In addition to recombinant methods, the immunoconjugates, effector moieties, and antibodies of the present disclosure can also be constructed in whole or in part using standard peptide synthesis well known in the art.

Once expressed, the recombinant immunoconjugates, antibodies, and/or effector molecules can be purified according to standard procedures of the art, including ammonium sulfate precipitation, affinity columns, column chromatography, and the like (see, generally, R. Scopes, PROTEIN PURIFICATION, Springer-Verlag, N.Y., 1982). The antibodies, immunoconjugates and effector molecules need not be 100% pure. Once purified, partially or to homogeneity as desired, if to be used therapeutically, the polypeptides should be substantially free of endotoxin.

Methods for expression of antibodies and/or refolding to an appropriate active form, including single chain antibodies, from bacteria such as *E. coli* have been described and are well-known and are applicable to the antibodies disclosed herein. See, Buchner et al., *Anal. Biochem.* 205:263-270, 1992; Pluckthun, *Biotechnology* 9:545, 1991; Huse et al., *Science* 246:1275, 1989 and Ward et al., *Nature* 341:544, 1989.

Often, functional heterologous proteins from *E. coli* or other bacteria are isolated from inclusion bodies and require solubilization using strong denaturants, and subsequent refolding. During the solubilization step, as is well known in the art, a reducing agent must be present to separate disulfide bonds. An exemplary buffer with a reducing agent is: 0.1 M Tris pH 8, 6 M guanidine, 2 mM EDTA, 0.3 M DTE (dithioerythritol). Reoxidation of the disulfide bonds can occur in the presence of low molecular weight thiol reagents in reduced and oxidized form, as described in Saxena et al., *Biochemistry* 9: 5015-5021, 1970, and especially as described by Buchner et al., supra.

Renaturation is typically accomplished by dilution (for example, 100-fold) of the denatured and reduced protein into refolding buffer. An exemplary buffer is 0.1 M Tris, pH 8.0, 0.5 M L-arginine, 8 mM oxidized glutathione (GSSG), and 2 mM EDTA.

As a modification to the two chain antibody purification protocol, the heavy and light chain regions are separately solubilized and reduced and then combined in the refolding solution. An exemplary yield is obtained when these two proteins are mixed in a molar ratio such that a 5-fold molar excess of one protein over the other is not exceeded. Excess oxidized glutathione or other oxidizing low molecular weight compounds can be added to the refolding solution after the redox-shuffling is completed.

In addition to recombinant methods, the antibodies, labeled antibodies and antibody binding fragments thereof that are disclosed herein can also be constructed in whole or in part using standard peptide synthesis. Solid phase synthesis of the polypeptides of less than about 50 amino acids in length can be accomplished by attaching the C-terminal amino acid of the sequence to an insoluble support followed by sequential addition of the remaining amino acids in the sequence. Techniques for solid phase synthesis are described by Barany & Merrifield, *The Peptides: Analysis, Synthesis, Biology. Vol. 2: Special Methods in Peptide Synthesis, Part A*. pp. 3-284; Merrifield et al., *J. Am. Chem. Soc.* 85:2149-2156, 1963, and Stewart et al., *Solid Phase Peptide Synthesis*, 2nd ed., Pierce Chem. Co., Rockford, Ill., 1984. Proteins of greater length may be synthesized by condensation of the amino and carboxyl termini of shorter fragments. Methods of forming peptide bonds by activation of a carboxyl terminal end (such as by the use of the coupling reagent N, N'-dicylohexylcarbodimide) are well known in the art.

C. Compositions and Therapeutic Methods

Methods are disclosed herein for the prevention or treatment of an HIV infection, such as an HIV-1 infection. Prevention can include inhibition of infection with HIV-1. The methods include contacting a cell with an effective amount of the human monoclonal antibodies disclosed herein that specifically binds gp41, or an antibody binding fragment thereof or an nucleic acid encoding such antibodies or antibody binding fragments thereof. The method can also include administering to a subject a therapeutically effective amount of the human monoclonal antibodies to a subject, or an antibody binding fragment thereof or an nucleic acid encoding such antibodies or antibody binding fragments thereof, for example the antibody binding fragment can be one or more of the CDRs grafted onto a protein scaffold. In some examples, the antibodies, or an antibody binding fragment thereof or an nucleic acid encoding such antibodies or antibody binding fragments thereof, can be used in post-exposure prophylaxis. In some examples, antibodies, or an antibody binding fragment thereof or an nucleic acid encoding such antibodies or antibody binding fragments thereof, can be used to eliminate the viral reservoir. For example a therapeutically effective amount of the antibodies, or an antibody binding fragment thereof or an nucleic acid encoding such antibodies or antibody binding fragments thereof can be administered to a subject being treated with anti-viral therapy. In some examples the antibodies, or an antibody binding fragment thereof is modified such that it is directly cytotoxic to infected cells, or uses natural defenses such as complement, antibody dependent cellular cytotoxicity (ADCC), or phagocytosis by macrophages.

Methods to assay for neutralization activity include, but are not limited to, a single-cycle infection assay as described in Martin et al. (2003) *Nature Biotechnology* 21:71-76. In this assay, the level of viral activity is measured via a selectable marker whose activity is reflective of the amount of viable virus in the sample, and the IC50 is determined. In other assays, acute infection can be monitored in the PM1 cell line or in primary cells (normal PBMC). In this assay, the level of viral activity can be monitored by determining the p24 concentrations using ELISA. See, for example, Martin et al. (2003) *Nature Biotechnology* 21:71-76.

HIV infection does not need to be completely eliminated for the composition to be effective. For example, a composition can decrease HIV infection by a desired amount, for example by at least 10%, at least 20%, at least 50%, at least 60%, at least 70%, at least 80%, at least 90%, at least 95%, at least 98%, or even at least 100% (elimination of detectable HIV infected cells), as compared to HIV infection in the absence of the composition. In example, the cell is also contacted with an effective amount of an additional agent, such as anti-viral agent. The cell can be in vivo or in vitro. The methods can include administration of one on more additional agents known in the art. In additional examples, HIV replication can be reduced or inhibited by similar methods. HIV replication does not need to be completely eliminated for the composition to be effective. For example, a composition can decrease HIV replication by a desired amount, for example by at least 10%, at least 20%, at least 50%, at least 60%, at least 70%, at least 80%, at least 90%, at least 95%, at least 98%, or even at least 100% (elimination of detectable HIV), as compared to HIV replication in the absence of the composition. In one example, the cell is also contacted with an effective amount of an additional agent, such as anti-viral agent. The cell can be in vivo or in vitro.

Compositions are provided that include one or more of the antibodies that specifically bind gp41, or an antibody binding fragment thereof or an nucleic acid encoding such antibodies or antibody binding fragments thereof, that are disclosed herein in a carrier. The compositions can be prepared in unit dosage forms for administration to a subject. The amount and timing of administration are at the discretion of the treating physician to achieve the desired purposes. The antibody can be formulated for systemic or local administration. In one example, the antibody that specifically binds gp41, or an antibody binding fragment thereof or a nucleic acid encoding such antibodies or antibody binding fragments thereof, is formulated for parenteral administration, such as intravenous administration.

The compositions for administration can include a solution of the antibody that specifically binds gp41, or an antibody binding fragment thereof or an nucleic acid encoding such antibodies or antibody binding fragments thereof, dissolved in a pharmaceutically acceptable carrier, such as an aqueous carrier. A variety of aqueous carriers can be used, for example, buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of antibody in these formulations can vary widely, and will be selected primarily based on fluid volumes, viscosities, body weight and the like in accordance with the particular mode of administration selected and the subject's needs.

A typical pharmaceutical composition for intravenous administration includes about 0.1 to 10 mg of antibody per subject per day. Dosages from 0.1 up to about 100 mg per subject per day may be used, particularly if the agent is administered to a secluded site and not into the circulatory or lymph system, such as into a body cavity or into a lumen of an organ. Actual methods for preparing administrable compositions will be known or apparent to those skilled in the art and are described in more detail in such publications as *Remington's Pharmaceutical Science,* 19*th ed.*, Mack Publishing Company, Easton, Pa. (1995).

Antibodies, or an antibody binding fragment thereof or an nucleic acid encoding such antibodies or antibody binding fragments thereof, may be provided in lyophilized form and rehydrated with sterile water before administration, although they are also provided in sterile solutions of known concentration. The antibody solution, or an antibody binding fragment thereof or an nucleic acid encoding such antibodies or antibody binding fragments thereof, is then added to an infusion bag containing 0.9% sodium chloride, USP, and typically administered at a dosage of from 0.5 to 15 mg/kg of body weight. Considerable experience is available in the art in the administration of antibody drugs, which have been marketed in the U.S. since the approval of RITUXAN® in 1997. Antibodies, or an antibody binding fragment thereof or an nucleic acid encoding such antibodies or antibody binding fragments thereof, can be administered by slow infusion, rather than in an intravenous push or bolus. In one example, a higher loading dose is administered, with subsequent, maintenance doses being administered at a lower level. For example, an initial loading dose of 4 mg/kg may be infused over a period of some 90 minutes, followed by weekly maintenance doses for 4-8 weeks of 2 mg/kg infused over a 30 minute period if the previous dose was well tolerated.

A therapeutically effective amount of a human gp41-specific antibody, or an antibody binding fragment thereof or an nucleic acid encoding such antibodies or antibody binding fragments thereof, will depend upon the severity of the disease and/or infection and the general state of the patient's health. A therapeutically effective amount of the antibody is that which provides either subjective relief of a symptom(s) or an objectively identifiable improvement as noted by the clinician or other qualified observer. These compositions can be administered in conjunction with another therapeutic agent, either simultaneously or sequentially.

In one embodiment, administration of the antibody, or an antibody binding fragment thereof or an nucleic acid encoding such antibodies or antibody binding fragments thereof, results in a reduction in the establishment of HIV infection and/or reducing subsequent HIV disease progression in a subject. A reduction in the establishment of HIV infection and/or a reduction in subsequent HIV disease progression encompass any statistically significant reduction in HIV activity. In some embodiments, methods are disclosed for treating a subject with an HIV-1 infection. These methods include administering to the subject a therapeutically effective amount of an antibody, or a nucleic acid encoding the antibody, thereby preventing or treating the HIV-1 infection.

Studies have shown that the rate of HIV transmission from mother to infant is reduced significantly when zidovudine is administered to HIV-infected women during pregnancy and delivery and to the offspring after birth (Connor et al., 1994 *Pediatr Infect Dis J* 14: 536-541). Several studies of mother-to-infant transmission of HIV have demonstrated a correlation between the maternal virus load at delivery and risk of HIV transmission to the child. The present disclosure provides isolated human monoclonal antibodies that are of use in decreasing HIV-transmission from mother to infant. Thus, in some examples, a therapeutically effective amount of a human gp41-specific antibody, or an antibody binding fragment thereof or an nucleic acid encoding such antibodies or antibody binding fragments thereof, is administered in order to prevent transmission of HIV, or decrease the risk of transmission of HIV, from a mother to an infant. In some examples, a therapeutically effective amount of the antibody, or an antibody binding fragment thereof or an nucleic acid encoding such antibodies or antibody binding fragments thereof, is administered to mother and/or to the child at childbirth. In other examples, a therapeutically effective amount of the antibody is administered to the mother and/or infant prior to breast feeding in order to prevent viral transmission to the infant or decrease the risk of viral transmission to the infant. In some embodiments, both a therapeutically effective amount of the antibody and a therapeutically effective amount of another agent, such as zidovudine, is administered to the mother and/or infant.

For any application, the antibody, or an antibody binding fragment thereof or an nucleic acid encoding such antibodies or antibody binding fragments thereof, can be combined with anti-retroviral therapy. Anti-retroviral drugs are broadly classified by the phase of the retrovirus life-cycle that the drug inhibits. The disclosed antibodies can be administered in conjunction with nucleoside analog reverse-transcriptase inhibitors (such as zidovudine, didanosine, zalcitabine, stavudine, lamivudine, abacavir, emtricitabine, entecavir, and apricitabine), nucleotide reverse transcriptase inhibitors (such as tenofovir and adefovir), non-nucleoside reverse transcriptase inhibitors (such as efavirenz, nevirapine, delavirdine, etravirine, and rilpivirine), protease inhibitors (such as saquinavir, ritonavir, indinavir, nelfinavir, amprenavir, lopinavir, fosamprenavir, atazanavir, tipranavir, and darunavir), entry or fusion inhibitors (such as maraviroc and enfuvirtide), maturation inhibitors, (such as bevirimat and vivecon), or a broad spectrum inhibitors, such as natural antivirals. In some examples, a disclosed antibody or active fragment thereof or nucleic acids encoding such is administered in conjunction with IL-15, or conjugated to IL-15.

In some examples, a subject is further administered one or more additional antibodies that bind HIV glycoproteins, such as gp120 and gp41. Examples of neutralizing antibodies that can be administered in conjunction with the disclosed antibodies can be found in International Patent Publication No. WO 2011/038290, published Mar. 31, 2011, which is specifically incorporated herein by reference in its entirety.

Single or multiple administrations of the compositions including the antibodies disclosed herein are administered depending on the dosage and frequency as required and tolerated by the patient. In any event, the composition should provide a sufficient quantity of at least one of the antibodies disclosed herein to effectively treat the patient. The dosage can be administered once, but may be applied periodically until either a therapeutic result is achieved or until side effects warrant discontinuation of therapy. In one example, a dose of the antibody is infused for thirty minutes every other day. In this example, about one to about ten doses can be administered, such as three or six doses can be administered every other day. In a further example, a continuous infusion is administered for about five to about ten days. The subject can be treated at regular intervals, such as monthly, until a desired therapeutic result is achieved. Generally, the dose is sufficient to treat or ameliorate symptoms or signs of disease without producing unacceptable toxicity to the patient.

Controlled-release parenteral formulations can be made as implants, oily injections, or as particulate systems. For a broad overview of protein delivery systems see, Banga, A. J., *Therapeutic Peptides and Proteins: Formulation, Processing, and Delivery Systems*, Technomic Publishing Company, Inc., Lancaster, Pa., (1995). Particulate systems include microspheres, microparticles, microcapsules, nanocapsules, nanospheres, and nanoparticles. Microcapsules contain the therapeutic protein, such as a cytotoxin or a drug, as a central core. In microspheres the therapeutic is dispersed throughout the particle. Particles, microspheres, and microcapsules smaller than about 1 µm are generally referred to as nanoparticles, nanospheres, and nanocapsules, respectively. Capillaries have a diameter of approximately 5 µm so that only nanoparticles are administered intravenously. Microparticles are typically around 100 µm in diameter and are administered subcutaneously or intramuscularly. See, for example, Kreuter, J., *Colloidal Drug Delivery Systems*, J. Kreuter, ed., Marcel Dekker, Inc., New York, N.Y., pp. 219-342 (1994); and Tice & Tabibi, *Treatise on Controlled Drug Delivery*, A. Kydonieus, ed., Marcel Dekker, Inc. New York, N.Y., pp. 315-339, (1992).

Polymers can be used for ion-controlled release of the antibody compositions disclosed herein. Various degradable and nondegradable polymeric matrices for use in controlled drug delivery are known in the art (Langer, *Accounts Chem. Res.* 26:537-542, 1993). For example, the block copolymer, polaxamer 407, exists as a viscous yet mobile liquid at low temperatures but forms a semisolid gel at body temperature. It has been shown to be an effective vehicle for formulation and sustained delivery of recombinant interleukin-2 and urease (Johnston et al., *Pharm. Res.* 9:425-434, 1992; and Pec et al., *J. Parent. Sci. Tech.* 44(2):58-65, 1990). Alternatively, hydroxyapatite has been used as a microcarrier for controlled release of proteins (Ijntema et al., *Int. J. Pharm.* 112:215-224, 1994). In yet another aspect, liposomes are used for controlled release as well as drug targeting of the lipid-capsulated drug (Betageri et al., *Liposome Drug Delivery Systems*, Technomic Publishing Co., Inc., Lancaster, Pa. (1993)). Numerous additional systems for controlled delivery of therapeutic proteins are known (see U.S. Pat. No. 5,055,303; U.S. Pat. No. 5,188,837; U.S. Pat. No. 4,235,871; U.S. Pat. No. 4,501,728; U.S. Pat. No. 4,837,028; U.S. Pat. No. 4,957,735; U.S. Pat. No. 5,019,369; U.S. Pat. No. 5,055,303; U.S. Pat. No. 5,514,670; U.S. Pat. No. 5,413,797; U.S. Pat. No. 5,268,164; U.S. Pat. No. 5,004,697; U.S. Pat. No. 4,902,505; U.S. Pat. No. 5,506,206; U.S. Pat. No. 5,271,961; U.S. Pat. No. 5,254,342 and U.S. Pat. No. 5,534,496).

In some examples, a subject is administered the DNA encoding the antibody or antibody binding fragments thereof, for example the antibody binding fragment can be one or more of the CDRs grafted onto a protein scaffold, to provide in vivo antibody production, for example using the cellular machinery of the subject. Immunization by nucleic acid constructs is well known in the art and taught, for example, in U.S. Pat. No. 5,643,578, and U.S. Pat. No. 5,593,972 and U.S. Pat. No. 5,817,637. U.S. Pat. No. 5,880,103 describes several methods of delivery of nucleic acids encoding to an organism. The methods include liposomal delivery of the nucleic acids. Such methods can be applied to the production of an antibody, or antibody binding fragments thereof, by one of ordinary skill in the art.

One approach to administration of nucleic acids is direct administration with plasmid DNA, such as with a mammalian expression plasmid. The nucleotide sequence encoding the disclosed antibody, or antibody binding fragments thereof, can be placed under the control of a promoter to increase expression.

In another approach to using nucleic acids, a disclosed antibody, or antibody binding fragments thereof can also be expressed by attenuated viral hosts or vectors or bacterial vectors. Recombinant vaccinia virus, adeno-associated virus (AAV), herpes virus, retrovirus, cytomegalovirus or other viral vectors can be used to express the antibody. For example, vaccinia vectors and methods useful protocols are described in U.S. Pat. No. 4,722,848. BCG (*Bacillus Calmette Guerin*) provides another vector for expression of the disclosed antibodies (see Stover, *Nature* 351:456-460, 1991).

In one embodiment, a nucleic acid encoding a disclosed antibody, or antibody binding fragments thereof, is introduced directly into cells. For example, the nucleic acid can be loaded onto gold microspheres by standard methods and introduced into the skin by a device such as Bio-Rad's HELIOS™ Gene Gun. The nucleic acids can be "naked," consisting of plasmids under control of a strong promoter.

Typically, the DNA is injected into muscle, although it can also be injected directly into other sites. Dosages for injection are usually around 0.5 µg/kg to about 50 mg/kg, and typically are about 0.005 mg/kg to about 5 mg/kg (see, e.g., U.S. Pat. No. 5,589,466).

D. Diagnostic Methods and Kits

A method is provided herein for the detection of the expression of gp41 in vitro or in vivo. In one example, expression of gp41 is detected in a biological sample, and can be used to detect HIV-1 infection as the presence of HIV-1 in a sample. The sample can be any sample, including, but not limited to, tissue from biopsies, autopsies and pathology specimens. Biological samples also include sections of tissues, for example, frozen sections taken for histological purposes. Biological samples further include body fluids, such as blood, serum, plasma, sputum, spinal fluid or urine.

In several embodiments, a method is provided for detecting AIDS and/or an HIV-1 infection in a subject. The disclosure provides a method for detecting HIV-1 in a biological sample, wherein the method includes contacting a biological sample with the antibody under conditions conducive to the formation of an immune complex, and detecting the immune complex, to detect the gp41 in the biological sample. In one example, the detection of gp41 in the sample indicates that the subject has an HIV infection. In another example, the detection of gp41 in the sample indicates that the subject has AIDS. In another example, detection of gp41 in the sample confirms a diagnosis of AIDS and/or an HIV-1 infection in a subject.

In some embodiments, the disclosed antibodies are used to test vaccines. For example to test if a vaccine composition assumes the same conformation as a gp41 peptide. Thus provided herein is a method for testing a vaccine, wherein the method includes contacting a sample containing the vaccine, such as a gp41 immunogen, with the antibody under conditions conducive to the formation of an immune complex, and detecting the immune complex, to detect the vaccine in the sample. In one example, the detection of the immune complex in the sample indicates that vaccine component, such as such as a gp41 immunogen assumes a conformation capable of binding the antibody.

In one embodiment, the antibody is directly labeled with a detectable label. In another embodiment, the antibody that binds gp41 (the first antibody) is unlabeled and a second antibody or other molecule that can bind the antibody that binds gp41 is utilized. As is well known to one of skill in the art, a second antibody is chosen that is able to specifically bind the specific species and class of the first antibody. For example, if the first antibody is a human IgG, then the secondary antibody may be an anti-human-IgG. Other molecules that can bind to antibodies include, without limitation, Protein A and Protein G, both of which are available commercially.

Suitable labels for the antibody or secondary antibody are described above, and include various enzymes, prosthetic groups, fluorescent materials, luminescent materials, magnetic agents and radioactive materials. Non-limiting examples of suitable enzymes include horseradish peroxidase, alkaline phosphatase, beta-galactosidase, or acetylcholinesterase. Non-limiting examples of suitable prosthetic group complexes include streptavidin/biotin and avidin/biotin. Non-limiting examples of suitable fluorescent materials include umbelliferone, fluorescein, fluorescein isothiocyanate, rhodamine, dichlorotriazinylamine fluorescein, dansyl chloride or phycoerythrin. A non-limiting exemplary luminescent material is luminol; a non-limiting exemplary a magnetic agent is gadolinium, and non-limiting exemplary radioactive labels include $^{125}$I, $^{131}$I, $^{35}$S or $^{3}$H.

The immunoassays and methods disclosed herein can be used for a number of purposes. Kits for detecting a polypeptide will typically include an antibody that binds gp41, such as any of the antibodies disclosed herein. In some embodiments, an antibody fragment, such as an Fv fragment or a Fab is included in the kit. In a further embodiment, the antibody is labeled (for example, with a fluorescent, radioactive, or an enzymatic label).

In one embodiment, a kit includes instructional materials disclosing means of use. The instructional materials may be written, in an electronic form (such as a computer diskette or compact disk) or may be visual (such as video files). The kits may also include additional components to facilitate the particular application for which the kit is designed. Thus, for example, the kit may additionally contain means of detecting a label (such as enzyme substrates for enzymatic labels, filter sets to detect fluorescent labels, appropriate secondary labels such as a secondary antibody, or the like). The kits may additionally include buffers and other reagents routinely used for the practice of a particular method. Such kits and appropriate contents are well known to those of skill in the art.

In one embodiment, the diagnostic kit includes an immunoassay. Although the details of the immunoassays may vary with the particular format employed, the method of detecting gp41 in a biological sample generally includes the steps of contacting the biological sample with an antibody which specifically reacts, under immunologically reactive conditions, to gp41. The antibody is allowed to specifically bind under immunologically reactive conditions to form an immune complex, and the presence of the immune complex (bound antibody) is detected directly or indirectly.

E. Methods of Identifying Antibodies of Interest

Methods are provided for producing a monoclonal antibody that specifically binds to a target antigen. These methods include isolating a population of memory B cells from a subject that has been exposed to the target antigen, wherein the memory B cells are CD19+IgA−IgD−IgM− B cells. The population of the isolated memory B cells is contacted with an effective amount of IL-21, IL-2 and CD40 ligand (CD40L), and mRNA is isolated from the population of isolated memory B cells. Nucleic acids encoding the variable heavy chains and the variable light chains of antibodies are isolated from cells, and the variable heavy chains and the variable light chains are expressed. A monoclonal antibody including a variable heavy chain and a variable light chain that specifically binds to the target antigen is then selected from combinations of the variable heavy chains and the variable light chains.

In some embodiments, a population of memory B cells is isolated from a biological sample from a subject that has been previously exposed to the antigen of interest. The population of memory B cells is divided into sub-populations which are contacted with an effective amount of CD40L, IL-2 and IL-21 for a sufficient amount of time for the memory B cells to undergo cell division and produce antibodies. The presence or absence of antibodies that specifically binds to the antigen of interest is determined for the subpopulations of memory B cells. If it is determined that a subpopulation of memory B cells produces antibodies that specifically bind to the antigen of interest, then that subpopulation is selected. The nucleic acid sequence encoding the heavy and light chain variable domains of the antibodies produced by memory B cells of the selected subpopulation can be determined, and monoclonal antibodies containing the heavy and light chain variable regions of antibodies produced by the selected subpopulation of memory B cells produced. The monoclonal antibodies are assayed for specific binding to the antigen on interest, and antibodies that specifically bind to the antigen of interest are selected, thereby identifying an antibody that specifically binds to the antigen of interest.

Methods are also provided for isolating the repertoire of B cells specific for a target antigen from a subject. These methods include isolating a population of memory B cells from a subject that has been exposed to the target antigen, wherein the memory B cells are CD19+IgA−IgD−IgM− B cells. The population of the isolated memory B cells is contacted with an effective amount of IL-21, IL-2 and CD40, and B cells are selected from the population that expresses antibodies that specifically bind the target antigen. These methods can also include isolating the library of nucleic acids encoding the variable heavy chains and the variable light chains of immunoglobulins are isolated from nucleic acids. The library of variable heavy chains and the variable light chains are then expressed to isolate the repertoire of B cells specific for the target antigen from the subject.

A humoral repertoire, including but not limited to the full humoral repertoire, to an entity, such as a pathogen or vaccine, can provide multi-dimensional information (e.g. specificities, affinities, stabilities, gene segment sequence preferences, etc) that could be considered a "profile" of a subject's humoral response. Quantitation of these parameters (Story et al., 2008 PNAS 105(46):17902-17907) can be used to correlate with protection from a pathogen or failure to protect. This information could then inform vaccine design in an iterative fashion, provide the basis for a multi-parameter diagnostic assay for specific antigens, or be directly used to identify single or multiple neutralizing antibodies against a given pathogen.

In some embodiments, the antibodies can be characterized. For example, multiparametric datasets can be collected that describe the characteristics, e.g. specificities, affinities, stabilities, isotypes, gene segment sequence preferences, etc. (Story et al., 2008 PNAS 105(46):17902-17907. In some representative, non-limiting embodiments, the profile or multiparametric dataset can be used to inform vaccine design in an iterative fashion, provide the basis for a multi-parameter diagnostic assay for specific antigens, or be directly used to identify single or multiple neutralizing antibodies against a given pathogen.

Thus, the methods disclosed herein can be used to isolate one or more monoclonal antibodies that specifically bind a target antigen, and/or can be used to isolate the B cell repertoire that bind the target antigen in a sample or in a subject. The target antigen can be from a pathogen, including viruses, parasites, fungi and bacteria. In some embodiments, pathogen is a virus, such as, but not limited to a virus from one of the following families: Retroviridae (for example, human immunodeficiency virus (HIV); human T-cell leukemia viruses (HTLV); Picornaviridae (for example, polio virus, hepatitis A virus; hepatitis C virus; enteroviruses, human coxsackie viruses, rhinoviruses, echoviruses; foot-and-mouth disease virus); Calciviridae (such as strains that cause gastroenteritis); Togaviridae (for example, equine encephalitis viruses, rubella viruses); Flaviridae (for example, dengue viruses; yellow fever viruses; West Nile virus; St. Louis encephalitis virus; Japanese encephalitis virus; and other encephalitis viruses); Coronaviridae (for example, coronaviruses; severe acute respiratory syndrome (SARS) virus; Rhabdoviridae (for example, vesicular stomatitis viruses, rabies viruses); Filoviridae (for example, Ebola viruses); Paramyxoviridae (for example, parainfluenza viruses, mumps virus, measles virus, respiratory syncytial virus (RSV)); Orthomyxoviridae (for example, influenza viruses); Bunyaviridae (for example, Hantaan viruses; Sin Nombre virus, Rift Valley fever virus; bunya viruses, phleboviruses and Nairo viruses); Arena viridae (hemorrhagic fever viruses; Machupo virus; Junin virus); Reoviridae (e.g., reoviruses, orbiviurses and rotaviruses); Birnaviridae; Hepadnaviridae (Hepatitis B virus); Parvoviridae (parvoviruses); Papovaviridae (papilloma viruses, polyoma viruses; BK-virus); Adenoviridae (most adenoviruses); Herpesviridae (herpes simplex virus (HSV)-1 and HSV-2; cytomegalovirus (CMV); Epstein-Barr virus (EBV); varicella zoster virus (VZV); and other herpes viruses, including HSV-6); Poxviridae (variola viruses, vaccinia viruses, pox viruses); and Iridoviridae (such as African swine fever virus); Filoviridae (for example, Ebola virus; Marburg virus); Caliciviridae (for example, Norwalk viruses) and unclassified viruses (for example, the etiological agents of Spongiform encephalopathies, the agent of delta hepatitis (thought to be a defective satellite of hepatitis B virus); and astroviruses).

In other embodiments, the target antigen is an antigen from a bacteria, such as, but not limited to, *Helicobacter pyloris, Borelia burgdorferi, Legionella pneumophilia, Mycobacteria* sps (such as. *M. tuberculosis, M. avium, M. intracellulare, M. kansaii, M. gordonae), Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (*viridans* group), *Streptococcus faecalis, Streptococcus bovis, Streptococcus* (anaerobic sps.), *Streptococcus pneumoniae*, pathogenic *Campylobacter* sp., *Enterococcus* sp., *Haemophilus influenzae, Bacillus anthracis, corynebacterium diphtheriae, corynebacterium* sp., *Erysipelothrix rhusiopathiae, Clostridium perfringers, Clostridium tetani, Enterobacter aerogenes, Klebsiella pneumoniae, Pasteurella multocida, Bacteroides* sp., *Fusobacterium nucleatum, Streptobacillus moniliformis, Treponema pallidum, Treponema pertenue, Leptospira,* or *Actinomyces israelii*.

In further embodiments, the antigen is from a fungus, such as *Cryptococcus neoformans, Histoplasma capsulatum, Coccidioides immitis, Blastomyces dermatitidis, Chlamydia trachomatis,* or *Candida albicans*. In other embodiments, antigen is from a parasite, such as, but not limited to, *Plasmodium falciparum* or *Toxoplasma gondii*.

In some embodiments, the antigen is a cancer antigen. The cancer can be a solid tumor or a hematogenous cancer. In particular examples, the solid tumor is a sarcoma or a carcinoma, such as fibrosarcoma, myxosarcoma, liposarcoma, chondrosarcoma, osteogenic sarcoma, or another sarcoma, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, bladder carcinoma, or a CNS tumor (such as a glioma, astrocytoma, medulloblastoma, craniopharyogioma, ependymoma, pinealoma, hemangioblastoma, acoustic neuroma, oligodendroglioma, menangioma, melanoma, neuroblastoma or retinoblastoma).

In some examples, the hematogenous cancer is a leukemia, such as an acute leukemia (such as acute lymphocytic leukemia, acute myelocytic leukemia, acute myelogenous leukemia and myeloblastic, promyelocytic, myelomonocytic, monocytic and erythroleukemia); a chronic leukemia (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia or myelodysplasia.

Tumor antigens are well known in the art and include, for example, carcinoembryonic antigen (CEA), human chorionic gonadotropin (HCG), alpha-fetoprotein (AFP), lectin-reactive AFP, (AFP-L3), thyroglobulin, RAGE-1, MN-CA IX, human telomerase reverse transcriptase (hTERT), RU1, RU2 (AS), intestinal carboxyl esterase, mut hsp70-2, M-CSF, prostase, prostate-specific antigen (PSA), PAP, NY-ESO-1, LAGE-1a, p53, prostein, PSMA, Her2/neu, survivin and telomerase, prostate-carcinoma tumor antigen-1 (PCTA-1), melanoma-associated antigen (MAGE), ELF2M, neutrophil elastase, ephrinB2 and CD22. The CH2 or CH3 domain molecules can also bind any cancer-related proteins, such IGF-I, IGF-II, IGR-IR or mesothelin. Additional tumor associated antigens are provided in the Table below:

| Exemplary tumors and their tumor antigens | |
|---|---|
| Tumor | Tumor Associated Target Antigens |
| Acute myelogenous leukemia | Wilms tumor 1 (WT1), preferentially expressed antigen of melanoma (PRAME), PR1, proteinase 3, elastase, cathepsin G |
| Chronic myelogenous leukemia | WT1, PRAME, PR1, proteinase 3, elastase, cathepsin G |
| Myelodysplastic syndrome | WT1, PRAME, PR1, proteinase 3, elastase, cathepsin G |
| Acute lymphoblastic leukemia | PRAME |
| Chronic lymphocytic leukemia | Survivin |
| Non-Hodgkin's lymphoma | Survivin |
| Multiple myeloma | New York esophagus 1 (NY-Eso1) |
| Malignant melanoma | MAGE, MART, Tyrosinase, PRAME GP100 |
| Breast cancer | WT1, Herceptin |
| Lung cancer | WT1 |
| Prostate cancer | Prostate-specific antigen (PSA) |
| Colon cancer | Carcinoembryonic antigen (CEA) |
| Renal cell carcinoma (RCC) | Fibroblast growth factor 5 (FGF-5) |

In some embodiments, the antigen is a self antigen. The antigen can be an antigen associated with an autoimmune disease, such as rheumatoid arthritis, juvenile oligoarthritis, collagen-induced arthritis, adjuvant-induced arthritis, Sjögren's syndrome, multiple sclerosis, experimental autoimmune encephalomyelitis, inflammatory bowel disease (for example, Crohn's disease, ulcerative colitis), autoimmune gastric atrophy, pemphigus vulgaris, psoriasis, vitiligo, type 1 diabetes, non-obese diabetes, myasthenia gravis, Grave's disease, Hashimoto's thyroiditis, sclerosing cholangitis, sclerosing sialadenitis, systemic lupus erythematosis, autoimmune thrombocytopenia purpura, Goodpasture's syndrome, Addison's disease, systemic sclerosis, polymyositis, dermatomyositis, autoimmune hemolytic anemia or pernicious anemia.

Isolating B Cells

In several embodiments, a population of cells including memory B cells is obtained from a subject. Typically, a substantially pure population of memory B cells (such as $CD19^+IgA^-$, $IgD^-$, $IgM^-$ B cells) are isolated. Typically, the isolated population of cells is enriched for memory B cells.

The population of cells including memory B cells can be isolated from a biological sample obtained from a subject of interest. Exemplary biological samples for use with the present methods include bone marrow, spleen, lymph node, blood, e.g., peripheral blood. However, the biological sample can also include any other source from which memory B cells can be isolated, including: tissue biopsy, surgical specimens, fine needle aspirates, autopsy material, and the like. In several embodiments, the biological sample is obtained from a subject that has been exposed to an antigen of interest. The subject may be any animal, preferably a mammal or a human. The subject may have a disease or a condition including a tumor, an infectious disease, or an autoimmune disease, or have been immunized. In certain aspects, the subject may recover or survive from a disease or a condition such as a tumor, an infectious disease, or an autoimmune disease. In further aspects, the subject may be under or after prevention and treatment for a disease or a condition, such as cancer therapy or infection disease therapy, or vaccination. For example, the subject has or has been exposed to an antigen which is an infectious agent, a tumor antigen, a tumor cell, an allergen or a self-antigen. Such an infectious agent may be any *pathogenic* viruses, *pathogenic* bacteria, fungi, protozoa, multicellular parasites, and aberrant proteins such as prions, as wells as nucleic acids or antigens derived therefrom. An allergen could be any nonparasitic antigen capable of stimulating a type-I hypersensitivity reaction in individuals, such as many common environmental antigens.

Fluorescence activated cell sorting (FACS) can be used to sort (isolate) cells, such as populations of memory B cells, by contacting the cells with an appropriately labeled antibody and sorting the cells based on binding of the labeled antibody to the cell. In one embodiment, several antibodies (such as antibodies that bind CD19, IgA, IgD, and/or IgM) and FACS sorting can be used to produce substantially purified populations of memory B cells. These methods are known in the art, and exemplary protocols are described herein.

FACS employs a plurality of color channels, low angle and obtuse light-scattering detection channels, and impedance channels, among other more sophisticated levels of detection, to separate or sort cells labeled or not labeled with a detectable marker. Any FACS technique can be employed as long as it is not detrimental to the viability of the desired cells. (For exemplary methods of FACS see U.S. Pat. No. 5,061,620). In one example, a FACSARIA III® cell sorter (Becton Dickinson, Franklin Lakes, N.J.) is used. Antibodies can be conjugated to biotin, which then can be removed with avidin or streptavidin bound to a support, or fluorochromes, which can be used with a FACS, to enable cell separation.

However, other techniques of differing efficacy can be employed to purify and isolate desired populations of cells. The separation techniques employed should maximize the retention of viability of the fraction of the cells to be collected. The particular technique employed will, of course, depend upon the efficiency of separation, cytotoxicity of the method, the ease and speed of separation, and what equipment and/or technical skill is required.

Separation procedures include magnetic separation, using antibody-coated magnetic beads, affinity chromatography, cytotoxic agents, either joined to a monoclonal antibody or used in conjunction with complement, and "panning," which utilizes a monoclonal antibody attached to a solid matrix, or another convenient technique. Antibodies attached to magnetic beads and other solid matrices, such as agarose beads, polystyrene beads, hollow fiber membranes and plastic petri dishes, allow for direct separation. Cells that are bound by the antibody can be removed from the cell suspension by simply physically separating the solid support from the cell suspension. The exact conditions and duration of incubation of the cells with the solid phase-linked antibodies will depend upon several factors specific to the system employed. The selection of appropriate conditions, however, is well within the skill in the art.

The unbound cells then can be collected (when negative selection for binding to the immunobeads) is being used) or washed away with physiologic buffer (when positive selection is benign used for binding to the immunobeads) after sufficient time has been allowed for the cells expressing a marker of interest (e.g., CD19) to bind to the solid-phase linked antibodies. The bound cells are then separated from the solid phase by any appropriate method, depending mainly upon the nature of the solid phase and the antibody employed. After a first round of selection using magnet beads, a second round (and additional rounds) can be used to further isolate a cell population of interest.

In some embodiments, cells expressing CD19 are separated from other cells by positive selection for the cell-surface expression of CD19. In one specific, non-limiting example, CD19+ cells are positively selected using FACS by labeling $CD19^+$ cells with a CD19 specific antibody conjugated to a detectable marker, and then using FACS to select cells labeled with the antibody conjugated to the detectable marker. CD19 specific antibodies conjugated to detectable markers are known and are commercially available, for example from BD Bioscience, Franklin Lakes, N.J. In another specific, non-limiting example, $CD19^+$ cells are positively selected by magnetic bead separation, wherein magnetic beads are coated with CD19 reactive monoclonal antibodies, and cell that are captured by the CD19 reactive immunobeads are collected. The $CD19^+$ cells are then removed from the magnetic beads.

In other embodiments, cells that do not express IgA on the cell surface are separated from other cells by the lack of cell-surface expression of IgA. In one specific, non-limiting example, $IgA^-$ cells are negatively selected using FACS by labeling IgA cells with an IgA specific antibody conjugated to a detectable marker, and then using FACS to select cells that are not labeled with the IgA specific antibody conjugated to the detectable marker. IgA specific antibodies conjugated to detectable markers are known and are commercially available, for example from Jackson ImmunoResearch Laboratories, Inc. West Grove, Pa. In another specific, non-limiting example, $IgA^-$ cells are negatively selected by magnetic bead separation, wherein magnetic beads are coated with IgA reactive monoclonal antibody and cells that are not captured by the immunobeads are collected.

In other embodiments, cells that do not express IgD on the cell surface are separated from other cells by the lack of cell-surface expression of IgD. In one specific, non-limiting example, IgD⁻ cells are negatively selected using FACS by labeling IgD⁺ cells with an IgD specific antibody conjugated to a detectable marker, and then using FACS to select cells that are not labeled with the IgD specific antibody conjugated to the detectable marker. IgD specific antibodies conjugated to detectable markers are known and are commercially available, for example from BD Pharmingen, Franklin Lakes, N.J. In another specific, non-limiting example, IgD⁻ cells are negatively selected by magnetic bead separation, wherein magnetic beads are coated with IgD reactive monoclonal antibody and cells that are not captured by the immunobeads are collected.

In other embodiments, cells that do not express IgM on the cell surface are separated from other cells by the lack of cell-surface expression of IgM. In one specific, non-limiting example, IgM⁻ cells are negatively selected using FACS by labeling IgM⁺ cells with an IgM specific antibody conjugated to a detectable marker, and then using FACS to select cells that are not labeled with the IgM specific antibody conjugated to the detectable marker. IgM specific antibodies conjugated to detectable markers are known and are commercially available, for example from Jackson ImmunoResearch Laboratories, Inc. West Grove, Pa. In another specific, non-limiting example, IgM⁻ cells are negatively selected by magnetic bead separation, wherein magnetic beads are coated with IgM reactive monoclonal antibody and cells that are not captured by the immunobeads are collected.

In further embodiments, cells that express CD19, but do not express IgA, IgD or IgM on the cell surface are separated from other cells by positively selecting for CD19 cell surface expression and negatively selecting for IgA, IgD and IgM expression on the cell surface. Using such methods, CD19⁺IgA⁻IgD⁻IgM⁻ cells can be collected. In one specific, non-limiting example, CD19⁺IgA⁻IgD⁻IgM⁻ cells are selected using FACS by labeling cells with four antibodies specific to CD19, IgA, IgD, and IgM, each of which is conjugated to a detectable marker that can be differentially detected using FACS analysis. FACS is then used to sort CD19⁺IgA⁻IgD⁻IgM⁻ cells. One of skill in the art can readily use FACS and set appropriate gates to isolate CD19⁺ IgA⁻IgD⁻IgM⁻ cells.

Contacting B Cells with CD40L, IL-2 and IL-21

In several embodiments, isolated memory B cells are contacted with CD40L, IL-2 and IL-21 for a sufficient amount of time for the memory B cells to undergo cell division and produce antibodies. In some a population of isolated memory B cells is contacted with CD40L, IL-2 and IL-21 by incubating the isolated population of memory B cells with CD40L, IL-2 and IL-21 for about 10 to about 15 days. In additional embodiments, the isolated population of memory B cells is incubated with CD40L, IL-2 and IL-21 for about 13 days. In several embodiments, the B cells are contacted with the CD40L, IL-2 and IL-21 for a sufficient amount of time for the memory B cells to undergo cell division and produce antibodies. In this context, a sufficient amount of time can be at least 5 days, such as 6, 7, 8, 9, 10, 11, 12, 13, 14, 15, 16, 17, 18, 19, 20, 21 or 22 days, for example from 5-22, 5-21, 10-20, 10-15, 11-16, or 13-15 days. The B cells can be contacted with the CD40L, IL-2 and IL-21 in the presence of growth media, such as Iscove's Modified Dulbecco's Medium, (IMDM) with 10% Fetal Bovine Serum, or other tissue culture growth media for use in culturing B cells. The person of ordinary skill in the art is familiar with such media.

CD40L (also known as CD40 ligand or CD154) is a protein that is primary expressed, for example, on activated T cells, but is also found in soluble form. CD40L binds to CD40 on the cell surface of B cells, a binding event that can result in the activation of B cells, differentiation of mature B cells into plasma cells and memory cells, and production of antibodies. The person of ordinary skill in the art is familiar with CD40L, and CD40L is available commercially (see, for example, Life Technologies Cat. No. PHP0024). In some embodiments, B cells are contacted with CD40L by culturing the B cells with a cell line that expresses CD40L, such as a CD40L feeder cell line. CD40L feeder cell lines are known in the art (see, for example, Kershaw et al., Cancer Res., 61: 7920-7924, 2001). Exemplary concentrations of CD40L for use in the disclosed methods include 1-2000 international units per milliliter, such as 100 international units per milliliter. Exemplary nucleic acid and polypeptide sequences for human CD40L are available at the NCBI website as GENBANK® Accession No. NM_000074.2 and GENBANK® Accession No. NP_000065.1, respectively, (as available on Jun. 13, 2012) which are incorporated herein by reference IL-2 is available commercially (see, for example, Life Technologies, Grand Island, N.Y., Cat. No. PHP0021). Exemplary nucleic acid and polypeptide sequences for human IL-2 are available at the NCBI website as GENBANK® Accession No. NM_000586.3 and GENBANK® Accession No. NP_000577.2, respectively (as available on Jun. 13, 2012) which are incorporated herein by reference. Exemplary concentrations of IL-2 for use in the disclosed methods include 10-200 international units per milliliter, such as 100 international units per milliliter.

IL-21 is also available commercially (see, for example, Life Technologies, Grand Island, N.Y., Cat. No. PHC0211). Exemplary nucleic acid and polypeptide sequences for human IL-21 are available at the NCBI website as GENBANK® Accession No. NM021803 and GENBANK® Accession No. AF254069, respectively. These GENBANK® entries are incorporated by reference herein. In several embodiments, the isolated B cells are contacted with about 10-100 ng/ml IL-21, such as about 10, 20, 30, 40, 50, 60, 70, 80, 90, or 100 ng/ml IL-21, for example the memory B cells can be contacted with from 10-100, 20-90, 30-80, 40-70, 40-60 or 45-55 ng/ml IL-21. Exemplary concentrations of IL-2 for use in the disclosed methods include 5-500 ng/ml IL-21, such as 50 ng/ml IL-21.

In several embodiments, contacting the memory B cells with the combination of CD40L, IL-2 and IL21 provides synergy, that is, the amount of cell division and antibody production observed by the memory B cells contacted with these three molecules is greater in combination then than the sum of the effect that results from using the molecules separately.

Selecting B Cells that Produce the Antibody of Interest

In some embodiments, the subpopulations of B cells that have been contacted with CD40L, IL-2 and IL-21 for a period of time sufficient for the memory B cells to undergo cell division and produce antibodies are assayed for expression of antibodies that specifically bind to the antigen of interest. Methods for determining if an antibody binds to an antigen of interest are familiar to the person of ordinary skill in the art, and include ELISA and neutralization assays.

Three representative general classes of screening methods that can be employed (a) antibody capture assays; (b)

antigen capture assays; and (c) functional screens. Combinations can also be employed. In antibody capture assays, the antigen can be bound to a solid phase, monoclonal antibodies to be tested are allowed to bind to the antigen, unbound antibodies are removed by washing, and then the bound antibodies are detected, e.g. by a secondary reagent such as a labeled antibody that specifically recognizes the antibody. For an antigen capture assay, the antigen can be labeled directly. In one embodiment, monoclonal antibodies to be tested can be bound to a solid phase and then reacted with the optionally labeled antigen. Alternatively, the antibody-antigen complex can be allowed to form by immunoprecipitation prior to binding of the monoclonal antibody to be tested to a solid phase. Once the antibody-antigen complexes are bound to the solid phase, unbound antigen can be removed by washing and positives can be identified by detecting the antigen.

Various functional screens exist for identifying monoclonal antibodies with desired activities. Examples include a virus neutralization assay; the agonistic activity assay and blocking assay; keratinocyte monolayer adhesion assay and the mixed lymphocyte response (MLR) assay (Werther et al. J. Immunol. 157:4986-4995 (1996)); tumor cell growth inhibition assays (as described in PCT Publication No. WO 89/06692, for example); antibody-dependent cellular-1-cytotoxicity (ADCC) and complement-mediated cytotoxicity (CDC) assays (U.S. Pat. No. 5,500,362); and hematopoiesis assays (see WO 95/27062). The class/subclass of the antibodies can be determined, e.g., by double-diffusion assays; antibody capture on antigen-coated plates; and/or antibody capture on anti-IgG antibodies.

To screen for antibodies which bind to a particular epitope on the antigen of interest, a routine cross-blocking assay such as that described in Antibodies, A Laboratory Manual, Cold Spring Harbor Laboratory, Ed Harlow and David Lane (1988), can be performed. Alternatively, epitope mapping, e.g., as described in Champe et al. (J. Biol. Chem. 270: 1388-1394 (1995)) can be performed to determine whether the antibody binds an epitope of interest.

If it is determined that a subpopulation of memory B cells produces antibodies that specifically bind to the antigen of interest, then additional steps can be taken to isolate the a monoclonal antibody that specifically binds to the antigen of interest from the subpopulation. For example, the variable region of the heavy chain and the light chain of the immunoglobulin genes from the B cells in the subpopulation are isolated, monoclonal antibodies containing the variable region of the heavy chain and the light chains are generating, and the specific binding acidity of the monoclonal antibodies for the antigen of interest is assay (for example, by ELISA or neutralization assay).

In certain aspects, sequence information of nucleic acid sequences can be obtained. Obtaining the nucleic acid sequence information may include determining the nucleic acid sequence. For determining the nucleic acid sequences, any nucleic acid sequencing methods known in the art may be used, including high throughput DNA sequencing. Non-limiting examples of high-throughput sequencing methods include sequencing-by-synthesis (e.g., 454 sequencing), sequencing-by-ligation, sequencing-by-hybridization, single molecule DNA sequencing, multiplex polony sequencing, nanopore sequencing, or a combination thereof.

In a further embodiment the method can include (a) isolating RNA from a sub-population of B cells; (b) transcribing said RNA to cDNA; (c) amplifying from said cDNA said first pool of DNA molecules using a first mixture of oligonucleotides including at least two oligonucleotides capable of amplifying heavy chain variable domain coding regions; (d) amplifying from said cDNA said second pool of DNA molecules using a second mixture of oligonucleotides including at least two oligonucleotides capable of amplifying light chain variable domain coding regions; and optionally (e) linking specimens of said first and said second pool of DNA molecules to each other by a DNA encoding said linker region (LR).

The cloning of variable regions is a standard procedure generally known in the art and has been described for various species, including humans, non-human primates, mouse, rabbit, and chicken. For review see Barbas III et al. (eds.), Phage Display—A Laboratory manual, Cold Spring Harbour Press, 2001, in particular the chapter Andris-Widhopf et al., Generation of Antibody Libraries: PCR Amplification and Assembly of Light- and Heavy-chain Coding Sequences, therein. Andris-Widhopf et al. discloses sequences of oligonucleotides capable of amplifying variable region coding regions (VR coding regions), preferably have chain variable domain coding regions or light chain variable domain coding regions. Furthermore, oligonucleotides capable of amplifying heavy chain variable domain coding regions or light chain variable domain coding regions, preferably human heavy chain variable domain coding regions or light chain variable domain coding regions, can be designed by the artisan by comparing known sequences of antibody coding regions which are available from databases such as, for example, Immunogenetics (imgt.cines.fr/), Kabat (Kabatdatabase.com), and Vbase (vbase.mrc-cpe.cam.ac.uk/), and by identifying consensus sequences suitable for primer design. Oligonucleotides capable of amplifying heavy chain variable domain coding regions or light chain variable domain coding regions, wherein the primers can include suitable restriction sites for the cloning of the amplified products and wherein the oligonucleotides also encode a linker region are known in the art. Additional strategies for amplifying and cloning variable domains are described in Sblattero and Bradbury (1998) Immunotechnology 3:271-278 and Weitkamp et al. (2003), J. Immunol. Meth. 275:223-237.

In some examples, the variable region of the heavy chain and the light chain of the immunoglobulin genes can be amplified by RT-PCR using known methods (see, e.g., Tiller et al., J. Immunological Methods, 329:112-124, 2008). PCR product including the $V_H$ or $V_L$-region DNA can be cloned into corresponding Igγ1, Igκ and Igλ, expression vectors, which can be used to co-transfected into a permissive cell line (such as 293T cells) for expression and production of monoclonal antibody. In some examples, full-length IgG1 can be purified using standard procedures, and then tested for binding to the antigen of interest (for example using ELISA or neutralization assay). The person of ordinary skill in the art will understand that the expression vectors can be expressed in any permissive cell line or subject for testing (for example in a mammalian cell line, a plant cell line, or using a viral expression vector for expression in a cell line or organism. Further, proteins including the sequence encoded by the $V_H$ or $V_L$-region DNA can be produced synthetically for testing.

Several Embodiments Concerning Methods of Identifying Antibodies of Interest

Several embodiments include a method for producing a monoclonal antibody that specifically binds to a target antigen, wherein the method includes: (a) isolating a population of memory B cells from a subject that has been exposed to the target antigen, wherein the memory B cells are CD19+IgA−IgD−IgM− B cells; (b) contacting the isolated population of memory B cells with an effective amount of IL-21, IL-2 and CD40; (c) isolating nucleic acid molecules from the isolated population of memory B cells; (d) amplifying nucleic acids encoding the variable heavy chains and the variable light chains from the nucleic acids; (e) expressing the variable heavy chains and the variable light chains from the nucleic acids to produce antibody molecules from the variable heavy chains and the variable light chains; and (f) selecting an monoclonal antibody that specifically binds to the target antigen.

Some embodiments, include a method for isolating the repertoire of B cells specific for a target antigen from a subject, including: (a) isolating a population of memory B cells from a subject that has been exposed to the target antigen, wherein the memory B cells are CD19+IgA–IgD–IgM– B cells; (b) contacting the isolated population of memory B cells with an effective amount of IL-21, IL-2 and CD40; and (c) selecting B cells from the population that express antibodies that specifically bind the target antigen, thereby isolating the repertoire of B cells specific for the target antigen from the subject.

In several embodiments, the target antigen is an antigen from a pathogen, such as a virus, a fungus, a parasite or a bacteria. The antigen can be from a virus, for example, human immunodeficiency virus (HIV), such as HIV-1. In some embodiments, the antigen can be HIV-1 gp41. In some embodiments wherein the target antigen is a HIV antigen, the subject is as subject infected with a HIV, such as HIV-1. In other embodiments, the target antigen is a cancer antigen. In some such embodiments, the subject is a subject with cancer. In still other embodiments, the target antigen is a self-antigen. For example, in some embodiments, the target antigen is a toxin, such as a bacterial toxin, for example, anthrax toxin. In additional embodiments, the target antigen is an antigen included in a vaccine. The person of ordinary skill in the art will appreciate that the target antigen can be any antigen to which a subject is capable of producing a B cell response that results in the production of memory B cells that produce antibody that specifically binds to the target antigen.

In some embodiments, the isolated population of memory B cells is representative of the repertoire of B cells in the subject that are specific to the target antigen.

In some embodiments of the disclosed methods, contacting the isolated population of memory B cells with CD40L includes incubating the isolated memory B cells with a feeder cell that expresses the CD40L.

In additional embodiments of the disclosed methods, contacting the isolated population of isolated memory B cells with CD40L, IL-2 and IL-21 includes incubating the isolated population of memory B cells with CD40L, IL-2 and IL-21 for about 10 to about 15 days, such as about 13 days.

EXAMPLES

The following examples are provided to illustrate particular features of certain embodiments, but the scope of the claims should not be limited to those features exemplified.

Example 1

Isolation and Characterization of Broadly Neutralizing MPER-Specific Monoclonal Antibodies This example illustrates isolation and characterization of HIV-1 gp41-specific binding antibodies from a subject infected with HIV-1.

Abstract.

Characterization of human monoclonal antibodies has provided considerable insight into mechanisms of broad HIV-1 neutralization. This example described isolation of an HIV-1 gp41 membrane-proximal external region (MPER)-specific antibody, named 10E8, which neutralizes ~98% of tested viruses. An analysis of sera from 78 healthy HIV-1-infected donors demonstrated that 27% contained MPER-specific antibodies and 8% contained 10E8-like specificities. In contrast to other neutralizing MPER antibodies, 10E8 did not bind phospholipids, was not autoreactive, and bound cell-surface envelope. The structure of 10E8 in complex with the complete MPER revealed a site-of-vulnerability including a narrow stretch of highly conserved gp41-hydrophobic residues and a critical Arg/Lys just prior to the transmembrane region. Analysis of resistant HIV-1 variants confirmed the importance of these residues for neutralization. The highly conserved MPER is a target of potent, non-self-reactive neutralizing antibodies, suggesting that HIV-1 vaccines should aim to induce antibodies to this region of HIV-1 Env.

Introduction.

Induction of an antibody response capable of neutralizing diverse HIV-1 isolates is a critical goal for vaccines that protect against HIV-1 infection. Potentially the greatest obstacle to achieving this goal is the extraordinary diversity that develops in the target of neutralizing antibodies, the envelope glycoprotein (Env). Although vaccines have thus far failed to induce broadly neutralizing antibody responses, there are examples of chronically infected patients with sera that neutralize highly diverse HIV-1 isolates. These individuals provide evidence that it is possible for the human antibody response to neutralize highly diverse strains of HIV-1, though the mechanisms by which such responses are induced or mediated remain incompletely understood (Haynes et al., *Nat Biotechnol* 30, 423-433, 2012; Walker et al., *Curr Opin Immunol* 22, 358-366, 2010).

Recently, isolation and characterization of human monoclonal antibodies from cells of chronically infected patients have provided considerable advances in understanding the specificities and mechanisms underlying broadly neutralizing antibody responses to HIV-1. Env exists on the virion and infected-cell surface as a trimer of heterodimers made up of gp120 and gp41 subunits. For some time, only a small number of broadly neutralizing monoclonal antibodies (mAbs) had been isolated consisting of one antibody that binds the CD4-binding site on gp120 (b12), one that binds a glycan configuration on the outer domain of gp120 (2G12) and three that bind the membrane-proximal external region (MPER) on gp41 (2F5, Z13e1, and 4E10; Zwick et al., *J Virol* 75, 10892-10905, 2001; Burton et al., *Science* 266, 1024-1027, 1994; Muster et al., *J Virol* 67, 6642-6647, 1993). More recently, considerably more broad and potent antibodies have been discovered that target the CD4-binding site of the envelope protein (for which VRC01 is a prototype; Bonsignori et al., *J Virol* 86, 4688-4692, 2012; Wu et al, *Science* 333, 1593-1602, 2011; Scheid et al., *Science* 333, 1633-1637, 2011; Wu et al., *Science* 329, 856-861, 2010) and glycan containing regions of the V1/V2 and V3 regions of gp120 (for which PG9 and PGT128 are prototypes; Walker et al., *PLoS Pathog* 6, e1001028, 2010; Walker et al., *Nature* 477, 466-470, 2011; Bonsignori et al., *J Virol* 85, 9998-10009, 2011; Walker et al., *Science* 326, 285-289, 2009). The specificities of these new antibodies are providing important information regarding antigen targets on Env to which the humoral immune response might be directed to mediate broad and potent neutralization. However, evidence for these specificities in many chronically infected patients within the cohort is lacking, suggesting that broad and potent neutralization may be mediated by other specificities.

This example describes isolation of a broad and potent gp41 MPER-specific human mAb, 10E8, from an HIV-1-infected individual with high neutralization titers. 10E8 is among the most broad and potent antibodies thus far described, and lacks many of the characteristics previously thought to limit the usefulness of MPER-specific antibodies in vaccines or passive therapies, including lipid binding and autoreactivity. In addition, the crystal structure of 10E8, along with biochemical binding studies, demonstrate that the breadth of 10E8 is mediated by its unique mode of recognition of a structurally conserved site-of-vulnerability within the gp41 MPER.

10E8 Isolation and Neutralizing Properties.

Figure 17D:
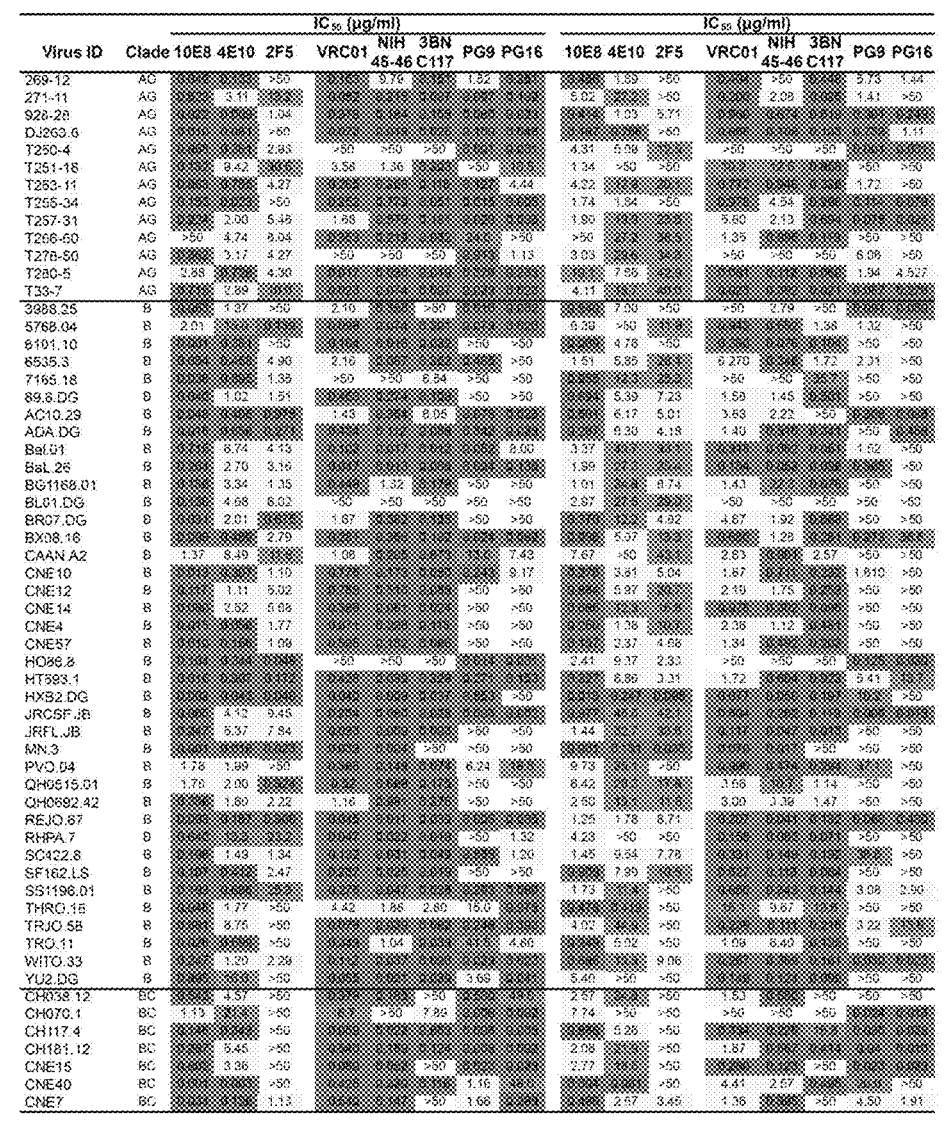

To understand the specificities and binding characteristics that underlie a broadly neutralizing antibody response techniques were developed that permitted isolation of human monoclonal antibodies without prior knowledge of specificity. Serum from one donor, N152, exhibited neutralizing breadth and potency in the top 1% of the cohort against a 20 cross-clade pseudovirus panel (FIG. 17; Doria-Rose et al., *J Virol* 84, 1631-1636, 2010). Peripheral blood CD19+IgM−IgD−IgA− memory B cells from this patient were sorted and expanded for 13 days with IL-2, IL-21, and CD40-ligand expressing feeder cells. The supernatants of ~16,500 B cell cultures were screened and IgG genes from wells with neutralization activity were cloned and re-expressed (Tiller et al., *Journal of immunological methods* 329, 112-124, 2008) and two novel antibodies (10E8 and 7H6) were isolated.

Nucleotide sequence analysis of DNA encoding 10E8 and 7H6 revealed that both were IgG3 antibodies and were somatic variants of the same IgG clone. These antibodies were derived from IGHV3-15*05 and IGLV3-19*01 germline genes, and were highly somatically mutated in variable genes of both heavy chain (21%) and lambda light chain (14%) compared to germline. These antibodies also possessed a long heavy-chain complementarity-determining region (CDR H3) loop composed of 22 amino acids (FIG. 1A). The heavy chains of 10E8 and 7H6 were identical and there were only two residue differences in the light chain (FIG. 6).

To assess neutralization activity of the clonal variants, they were initially tested against 5 Env-pseudoviruses (FIG. 17A), and mAb 10E8 was selected for further study. To determine if the neutralization activity of 10E8 was representative of the overall neutralization specificity present in patient N152 donor serum, the neutralization panel was expanded to 20 Env-pseudoviruses, and 10E8 was tested in parallel with N152 donor serum. Although there were some similarities in the pattern of neutralization of highly resistant variants, a correlation of the neutralization IC50 of mAb 10E8 and ID50 of N152 serum did not achieve statistical significance (p=0.11; FIGS. 7 and 17B). This finding suggests that although 10E8 may play a major role, the full breadth of neutralization of by N152 serum is likely mediated by an amalgam of 10E8-like or other antibodies.

To compare the neutralization potency and breadth of 10E8 with other broadly neutralizing anti-HIV-1 antibodies, 10E8 was then tested in a 181-isolate Env-pseudovirus panel in parallel with 4E10, 2F5, VRC01, NIH45-46, 3BNC117, PG9, and PG16 (FIG. 1B and FIGS. 17C-17F). At an IC50 below 50 μg/ml, 10E8 neutralized 98% of the tested pseudoviruses compared to 98% for 4E10 and 89% for VRC01. However, at an IC50 below 1 μg/ml, 10E8 neutralized 72% of the tested viruses compared to 37% for 4E10. The median and geometric mean IC50 values for 10E8 were below 1 ug/ml. Thus, 10E8 mediates broad and potent neutralization against a large range of viruses and the potency is comparable to some of the best available monoclonal antibodies.

10E8 Epitope Specificity and Binding.

Figure 8A:
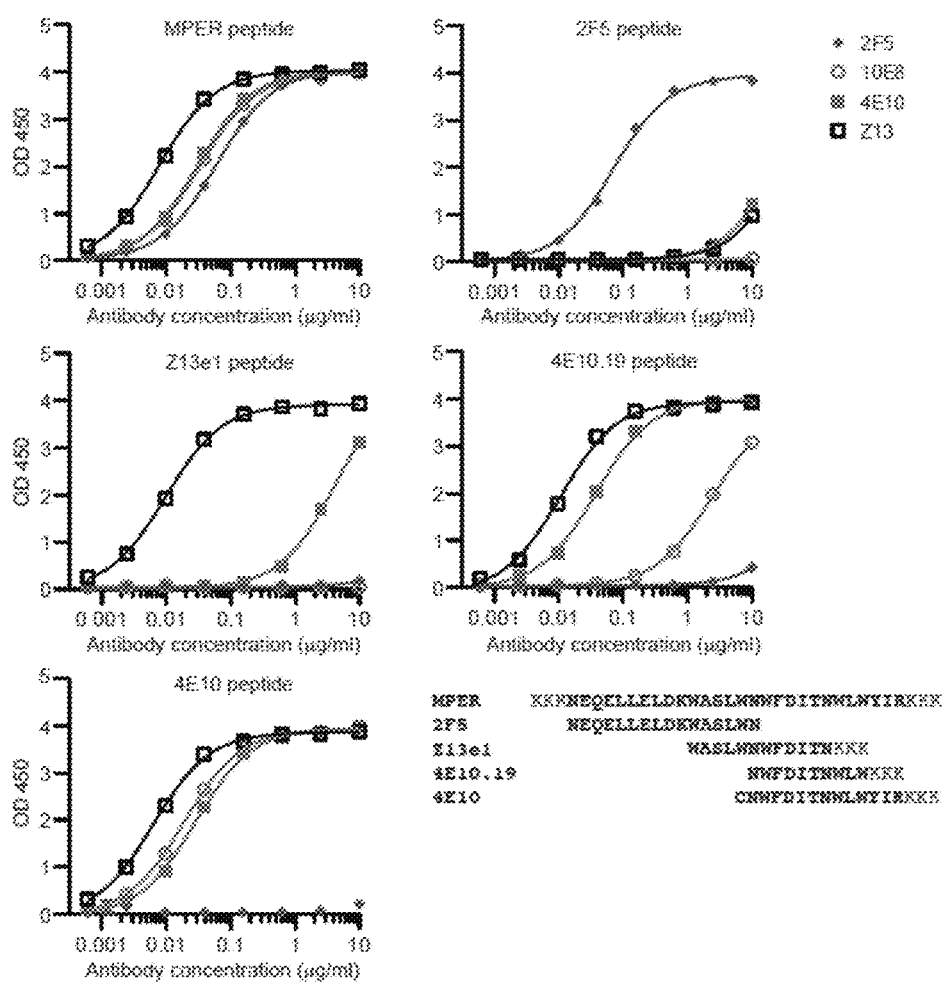

To map the epitope of the 10E8 antibody, binding to different subregions of Env by enzyme-linked immunosorbent assay was tested (ELISA). 10E8 bound strongly to gp140, gp41, and the 4E10-specific MPER peptide, but not to gp120 (FIG. 2A). To further map the 10E8 epitope within the MPER, binding of 10E8 to overlapping peptides corresponding to the 2F5 (656-671), Z13e1 (666-677), and 4E10 (671-683) specificities was examined. 10E8 bound to the full MPER and the 4E10-specific peptides, but not 2F5- or Z13e1-specific peptides. Within the 4E10 epitope, when a peptide with a truncated C-terminus was tested, 4E10.19 (671-680), 10E8 binding was weakened considerably, suggesting that the three terminal amino acids of the MPER, Tyr681, Ile682, and Arg683, were crucial for 10E8 binding (FIG. 8A). Consistent with these results, only the full MPER and 4E10-specific peptides blocked 10E8-mediated neutralization of the chimeric C1 virus, which contains the HIV-2 Env with the HIV-1 MPER (FIG. 8B). Taken together, these data suggest that the minimal 10E8 epitope is located within residues 671-683 of the MPER although additional contacts toward the amino terminus of the MPER could not be excluded.

To more precisely map the epitope of 10E8, a panel of alanine mutant peptides scanning MPER residues 671-683 was used to block 10E8 neutralization of the chimeric C1 virus in a TZM-b1 assay (FIG. 2B; Brunel et al., *J Virol* 80, 1680-1687, 2006). For these assays, the base peptide was 4E10.22 MPER peptide (CNWFDITNWLWYIRKKK; SEQ ID NO: 14) with the indicated alanine substitutions. MPER peptides with alanine substitutions at Trp672, Phe673 or Thr676 failed to block 4E10 or 10E8 neutralization, suggesting that these residues are critical for both 4E10 and 10E8 binding. Residue Asn671 and residue Arg683, both of which are not required for 4E10 binding, were found to be critical for 10E8 binding and neutralization (FIGS. 2B and 18). The ability of 10E8 to neutralize HIV-1$_{JR2}$ pseudoviruses with alanine substitutions in MPER residues 660-683 was also tested (FIG. 19). Consistent with the effects of alanine substitutions on peptide binding, residues Asn671 and Arg683 were critical for 10E8, but not 4E10, neutralization. Individual alanine substitutions at residues 671-673, 680 and 683 resulted in reduced neutralization sensitivity to 10E8 most apparent at the IC90 level rather than the IC50 level. Although the mechanism for this phenomenon is unclear, a similar effect has been observed previously when MPER mutations cause partial resistance to 4E10 (Zwick et al., *J Virol* 79, 1252-1261, 2005). Taken together, these results suggested that 10E8 recognized a novel epitope, which overlaps the known 4E10 and Z13e1 epitopes, but differs in a critical dependence on binding to Asn671 and Arg683, the last residue of the MPER.

Figures 9A, 9B:
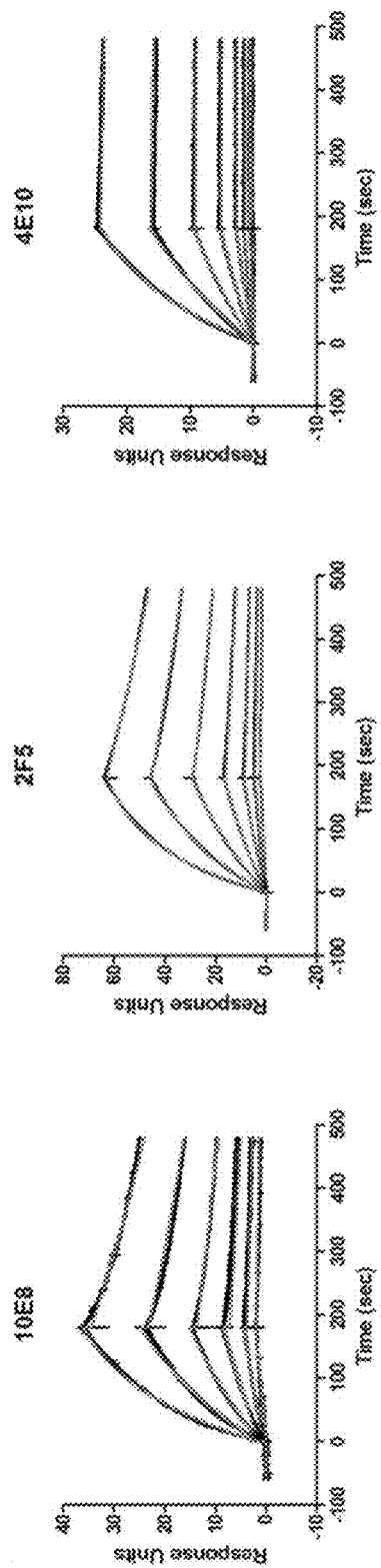
FIGS. 9A and 9B illustrate surface-plasmon resonance analysis of binding of 10E8, 2F5 and 4E10 antibodies to a gp41 MPER peptide. (A) A biotinylated MPER peptide comprised of residues 656-683 of gp41 was immobilized on a streptavidin SA chip (GE Healthcare) and antibody Fabs flowed over as analyte at 2-fold serial increasing concentrations ranging from 3.9-125 nM (10E8), 0.49-31.25 nM (2F5), and 0.25 nM to 62.5 nM (4E10). Association and dissociation phases of three minutes and five minutes, respectively, were used, at a flow rate of 30 µl/minute, and each analyte concentration was performed in triplicate. (B) Binding constants, listed, were obtained by fitting sensograms with a 1:1 Langmuir model. The amino acid sequence of SEQ ID NO: 26 is shown.

Whether the greater neutralization potency of 10E8 compared to other MPER antibodies was a result of higher binding affinity to the MPER was next investigated. Capture of a biotinylated peptide encompassing the full MPER (656-683) to a surface-plasmon resonance chip allowed the binding kinetics of Fabs 10E8, 2F5 and 4E10 to be examined. In contrast to its higher neutralization potency, the $K_D$ of 10E8 to this MPER peptide was weaker than that of 2F5 and 4E10; 17 nM for 10E8 versus 3.8 nM for 2F5 and 0.74 nM for 4E10 (FIG. 9). Therefore, the affinity of 10E8 for the MPER in a soluble peptide format did not explain its greater neutralization potency compared to other MPER-specific antibodies.

Prevalence of 10E8-Like Antibodies.

Figure 10:
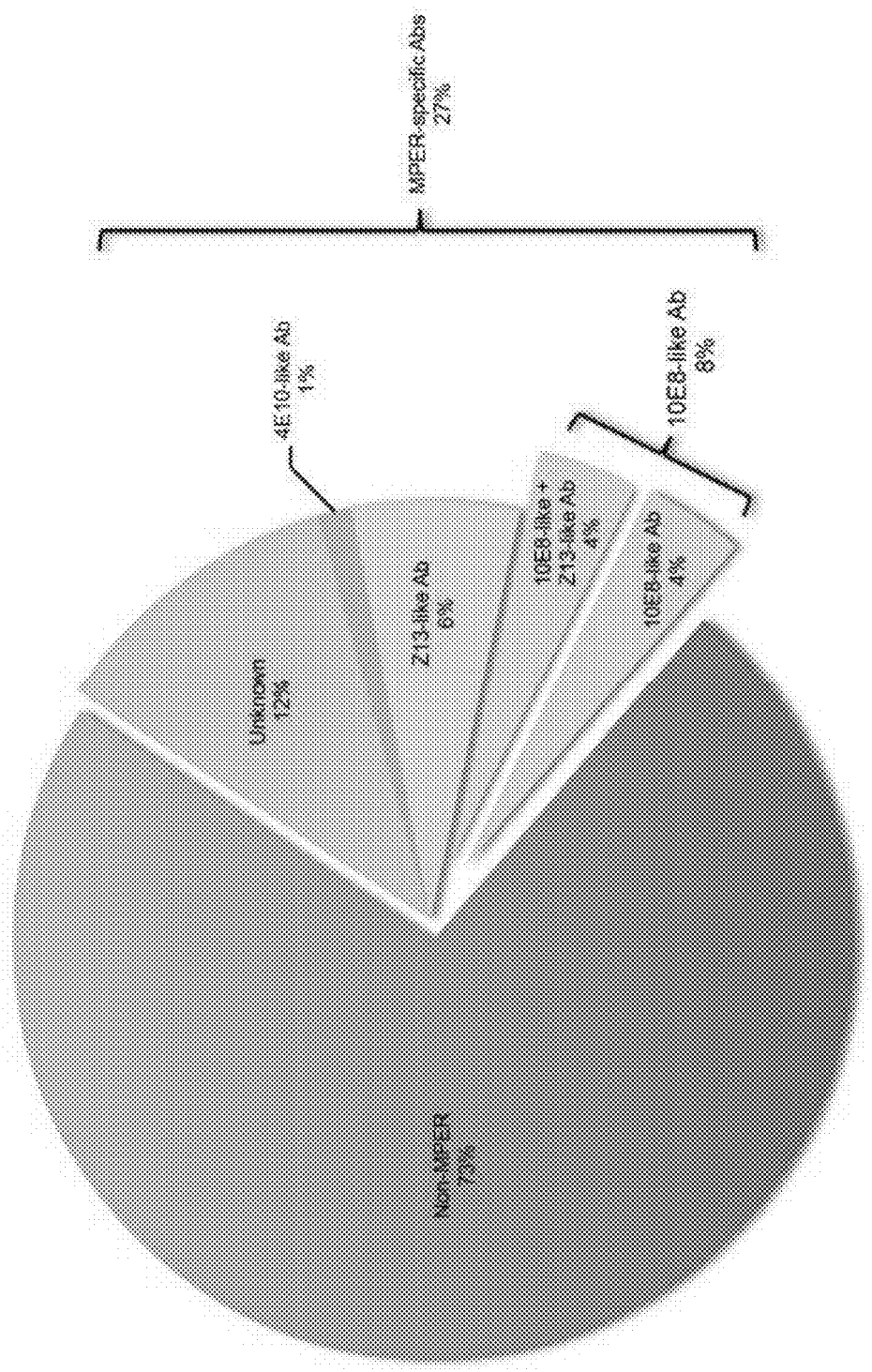
FIG. 10 is a pie chart illustrating the frequency of HIV-1+ sera with a given specificity. Sera from 78 healthy HIV-1-infected donors were used in this assay. Frequency measured by the ability of patient sera to neutralize HIV-2/HIV-1 chimeras containing portions of the MPER and confirmed with peptide blocking. Neutralization ID50s of sera are reported in FIG. 21. Fold changes of ID50 after peptide blocking are reported in FIG. 22. The six patients with sera containing 10E8-like antibodies were not different from the remaining 72 patients with regard to viral load (6748 copies per ml with 10E8 vs 5446 without; p>0.05), CD4 count (437 cells/µl vs. 557; p>0.05), years since diagnosis (20 years vs. 13; p>0.05), or median neutralization titer (302 vs. 156; p>0.05).

The prevalence of MPER-specific and 10E8-like neutralizing antibodies in the cohort of HIV-1-infected donors was next investigated. Next, 78 sera from the cohort with a neutralization ID50>100 against at least one pseudovirus in a 5-virus mini-panel were selected (Doria-Rose et al., *J Virol* 84, 1631-1636, 2010). The median time since diagnosis of these donors was 13.5 years, median CD4 count was 557 cells/µl, median plasma HIV RNA 5573 copies/ml, and they were not receiving antiretrovirals. Neutralization against the HIV-2/HIV-1 chimera C1 was tested (FIG. 20). Of 78 sera, 21 exhibited neutralization activity against the HIV-2/HIV-1 C1 virus (FIG. 21). To map the region that was targeted by these sera, neutralization was measured using 7 HIV-2/HIV-1 chimeras containing subdomains of the MPER (FIG. 20; Gray et al., *J Virol* 81, 6187-6196, 2007). Of the 21 sera with neutralization activity against the entire MPER, 8 exhibited a neutralization pattern similar to that observed for 10E8, which entailed neutralization of only those HIV-2/HIV-1 chimeric viruses that contained the terminal residue of the MPER Arg683 (C4, C4GW and C8; FIG. 21). To further confirm these results, peptides corresponding to different portions of the MPER to block sera neutralization of the HIV-2/HIV-1 chimera C1 were used (FIG. 22). Of the 8 sera found to have a 10E8-like pattern based upon neutralization of the chimeras, 3 were blocked by peptides consistent with 10E8-like activity. An additional 3 of the 8 10E8-like sera were blocked by peptides in a pattern consistent with a combination of 10E8 and Z13e1-like antibodies. The 6 patients whose sera had 10E8-like activity did not differ from the remaining 72 patients with regard to clinical course or HIV neutralization (legend; FIG. 10, legend). Overall, 27% of the tested patient sera exhibited anti-MPER neutralizing activity. This prevalence is considerably higher than observed in prior work, possibly related to selection of donors with known neutralizing activity (Gray et al., *J Virol* 83, 8925-8937, 2009; Tomaras et al., *J Virol* 85, 11502-11519, 2011; Morris et al., *PLoS ONE* 6, e23532, 2011; Gray et al., *J Virol* 83, 11265-11274, 2009). Further, 8% of the tested sera had 10E8-like antibodies (FIG. 10), suggesting that 10E8-like antibodies are not rare.

Analysis of 10E8 Autoreactivity.

Figure 3B:
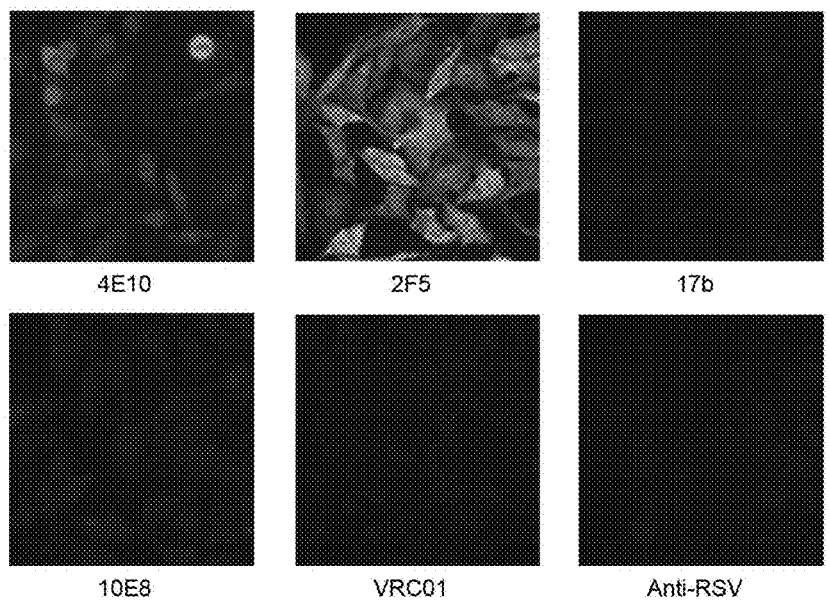

A property common to the previously characterized MPER mAbs 2F5 and 4E10 is that they cross-react with self-antigens (Haynes et al., *Science* 308, 1906-1908, 2005). In addition, binding to both the cell membrane and the Env trimer is thought to be important for optimal neutralization by these antibodies and this autoreactivity may be an obstacle to the elicitation of similar antibodies by a vaccine (Haynes et al., *Science* 308, 1906-1908, 2005; Alam et al., *Proceedings of the National Academy of Sciences of the United States of America* 106, 20234-20239, 2009). Surface plasmon resonance analysis showed that 10E8 did not bind to anionic phospholipids, such as phosphatidyl choline-cardiolipin (PC-CLP) and phosphatidyl choline-phosphatidyl serine (PC-PS) liposomes (FIG. 3A). 10E8 also did not bind HEp-2 epithelial cells, in contrast to 2F5 and 4E10 that bound in a cytoplasmic and nuclear pattern (FIG. 3B). Additionally, 10E8 did not bind autoantigens, such as Sjogren's syndrome antigens A and B, Smith antigen, ribonucleoprotein, scleroderma 70 antigen, Jo1 antigen, centromere B and histone (FIG. 23). Taken together, these results suggest that 10E8, in contrast to other MPER antibodies, is not autoreactive.

Virion Accessibility of 10E8.

Figure 11A:
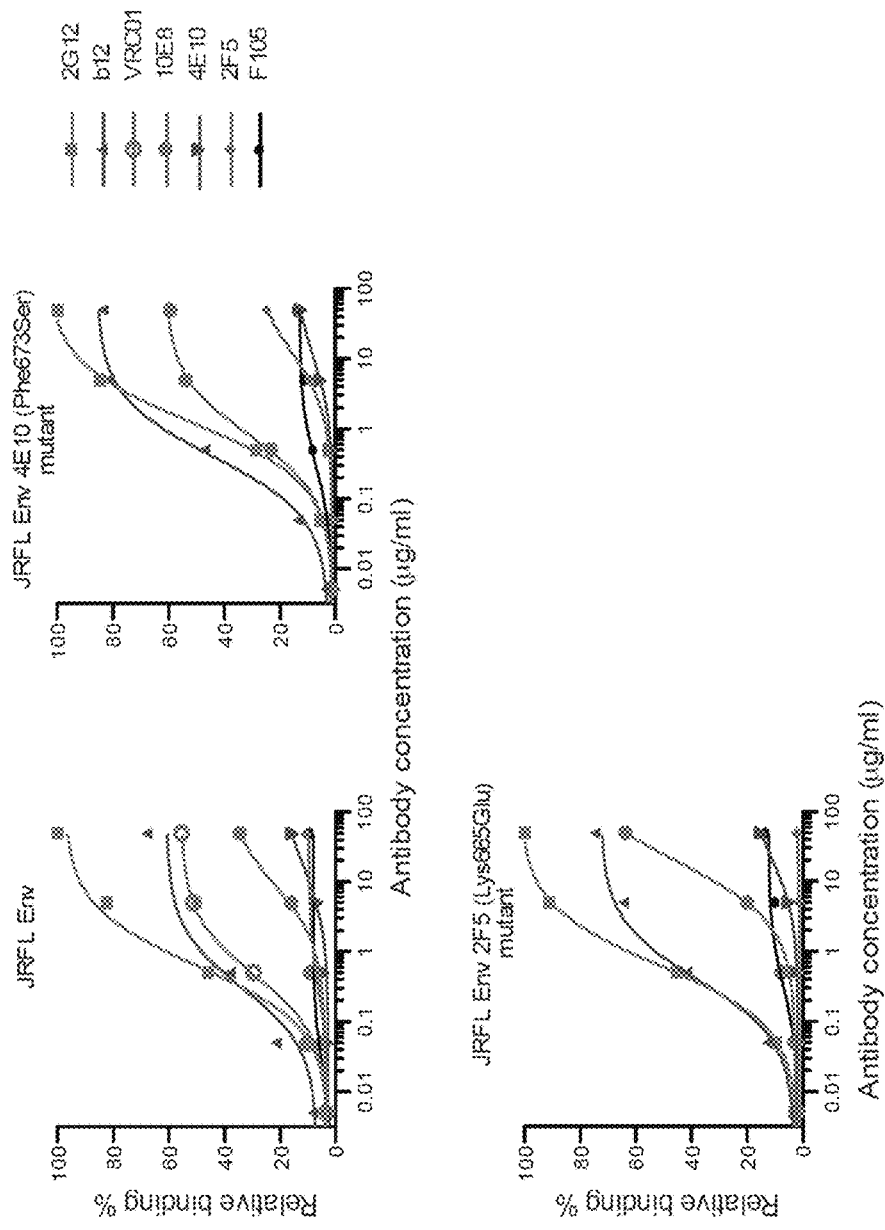

The 2F5 and 4E10 antibodies have been shown to bind relatively poorly to the HIV-1 envelope spike on the surface of infected cells or to cell-free virions, and react more efficiently after Env engagement of the CD4 receptor (Chakrabarti et al., *J Virol* 85, 8217-8226, 2011). Binding to cleaved, full-length envelope spikes on HIV$_{JRFL}$ transfected cells was measured (FIG. 11A). Although 10E8 bound less efficiently than other antibodies such as VRC01 or F105, where accessibility is not an issue, it bound more efficiently than either 2F5 or 4E10. In contrast to results of alanine substitution, a mutation in the 4E10 (F673S) region in full-length HIV$_{JRFL}$ envelope spikes enhanced 10E8 binding although the mechanism remains unclear. A mutation in the 2F5 (K665E) region had no influence on 10E8 binding. These data suggest that 10E8 has modestly greater access to the MPER epitope on the cell surface than either 2F5 or 4E10.

To assess binding to cell-free virus, virions were incubated with antibody, washed out unbound antibody, and tested neutralization (Chakrabarti et al., *J Virol* 85, 8217-8226, 2011; Frey et al., *Proceedings of the National Academy of Sciences of the United States of America* 105, 3739-3744, 2008; Rathinakumar et al., *J Virol* 86, 1820-1831, 2012). During washing, antibodies that cannot access their Env target on free virions will be largely removed and therefore neutralization will be diminished. As a control, neutralization of the HXBc2 isolate was not diminished by washing, because the MPER region is accessible on this laboratory adapted isolate (Chakrabarti et al., *J Virol* 85, 8217-8226, 2011). Washing also had little impact on neutralization of JRFL by VRC01. Consistent with prior work, 2F5 and 4E10 neutralization of most virus isolates tested was substantially diminished after washing (FIG. 11B). In contrast to 2F5 and 4E10, washing had a smaller effect on 10E8 neutralization of most viruses tested, as measured by the area under the curve or analysis of the fold-change in neutralization at a fixed inhibitory concentration (FIG. 11C). Although 10E8 is not fully able to access its epitope on the native viral spike similarly to VRC01, under most experimental conditions tested it was better able to access its epitope than either 2F5 or 4E10.

Structure of 10E8-Gp41 Complex.

Figure 4A:
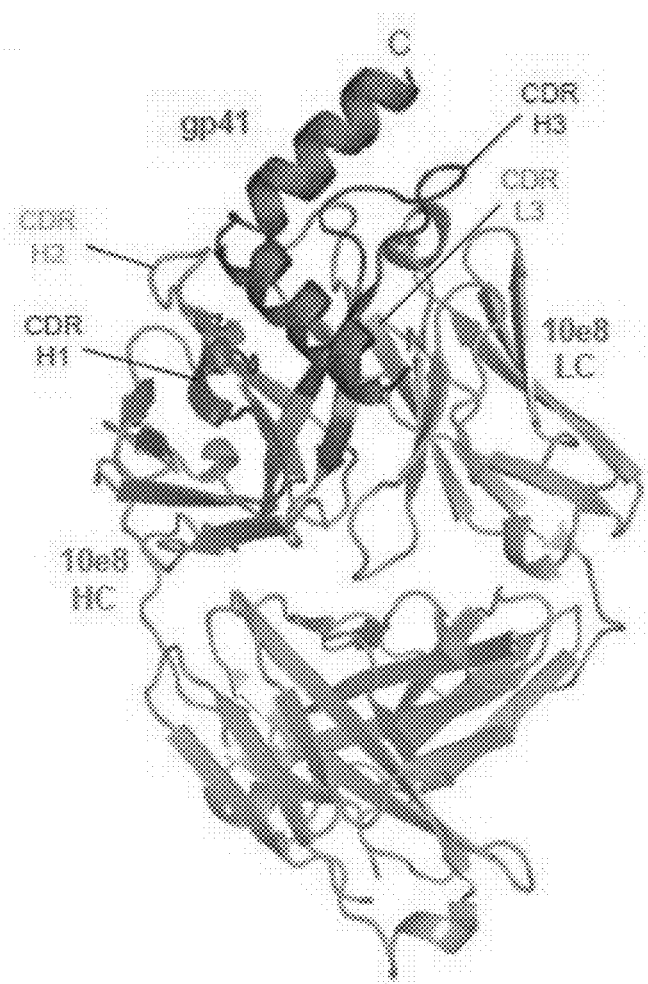
FIGS. 4A-4H are a set of ribbon diagrams illustrating the crystal structure of 10E8 antibody in complex with its gp41 MPER epitope. (A) 10E8 recognizes a highly conserved gp41 helix to neutralize HIV-1. Fab 10E8 is shown in ribbon representation (shades of dark grey for heavy chain and of light grey for light chain) in complex with a gp41 peptide (dark grey) that encompasses the MPER ($Asn_{656}$-$Arg_{683}$; NEQELLELDKWASLWNWFDITNWLWYIR (SEQ ID NO: 26)). (B) Interface between 10E8 and gp41 with select 10E8-side chains and gp41-side chains in stick representation. In analogy to a hand, the hinge can be viewed as being gripped by a thumb (represented by the CDR H2), the C-terminal helix as being suspended along a corresponding extended forefinger (represented by the CDR H3), and residues that commence the C-terminal helix as being caught in the cleft between the thumb and forefinger (represented by the juncture of the CDR loops). (C-D) Buried contact surfaces and epitope conservation. An examination of the buried contact surface on gp41 (grey; C) reveals that epitope residues (labeled, D) that are directly contacted by 10E8 are highly conserved across 2870 examined strains (conservation percentages provided in parentheses; see also FIGS. 26-28). E-H, Alanine mutagenesis of paratope and epitope. Residues at the tip of the 10E8 CDR H3 loop and within the hydrophobic cleft are crucial for recognition of gp41 and for virus neutralization (FIGS. 31-32), as mapped onto the buried 10E8-contact surface (E, G). These results mirror the effects of alanine scan mutations of the 10E8 epitope (FIGS. 18-19), as mapped onto the buried gp41-contact surface (F, H). A comparison of the effects of the alanine mutagenesis of the paratope and epitope reveal that residues of the epitope that are most crucial for 10E8 recognition and neutralization, are also the most highly conserved (D).
Figure 12A:
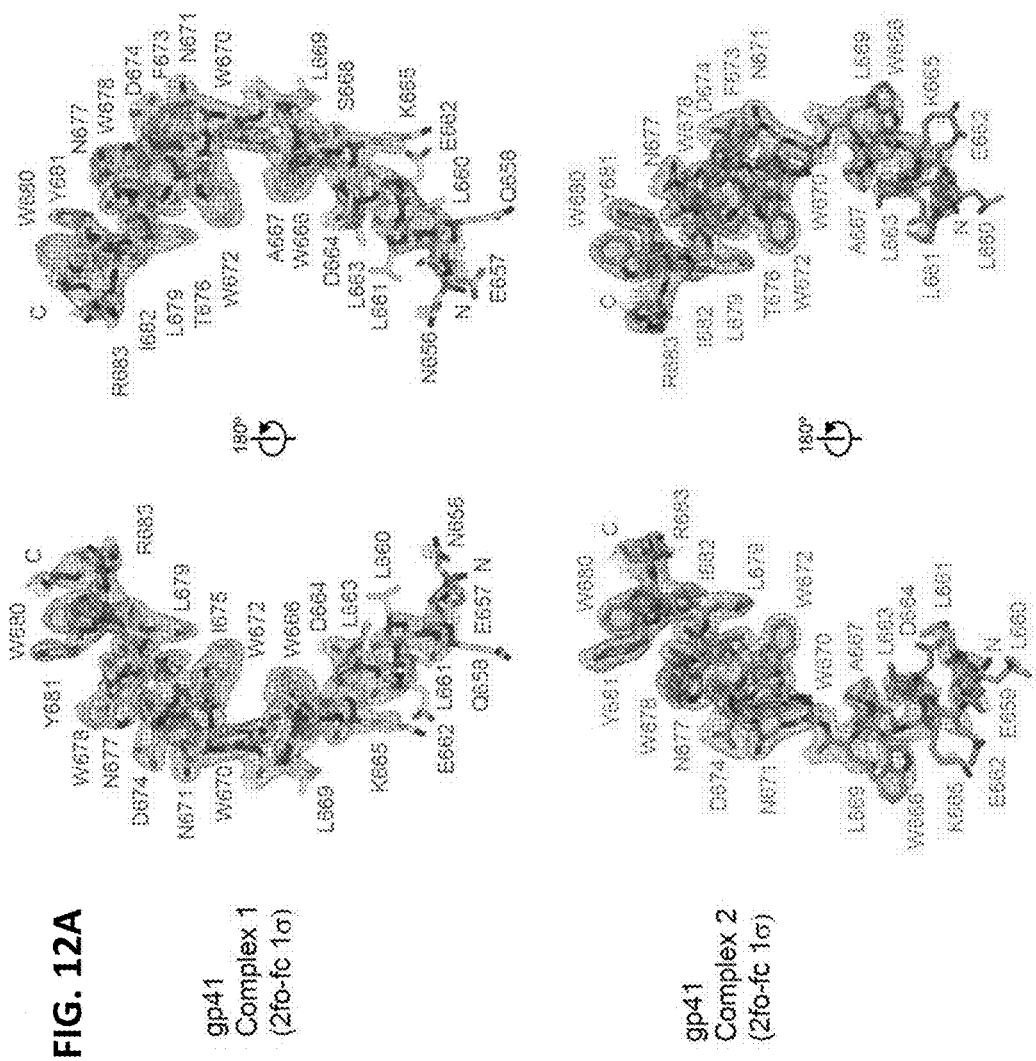
FIGS. 12A and 12B are schematic diagrams illustrating comparison of two copies of the gp41 MPER in the crystal asymmetric unit. (A) gp41 peptides from the two 10E8-gp41 complexes in the crystal asymmetric unit are shown in stick representation (complex 1, dark grey; complex 2, medium grey), surrounded by their 2fo-fc electron density contoured at 1σ (dark grey). Images shown are rotated 180° relative to each other, and are in the same orientation as in FIGS. 4C and 4D. (B) An alignment of the peptides in the two crystalline complexes. Shown, at 90° views, is a superposition of the two peptides in the asymmetric unit based on alignment of all atoms of residues 671-683. The N-terminal helix in complex 2 is shifted by 45° relative to the one in complex 1 in this alignment. While the differing orientations of the N-terminal helix in the two complexes suggests a degree of structural plasticity, residues of the hinge and C-terminal helix in the two complexes are highly conserved and are involved in the most critical interactions with the antibody.
Figure 12B:
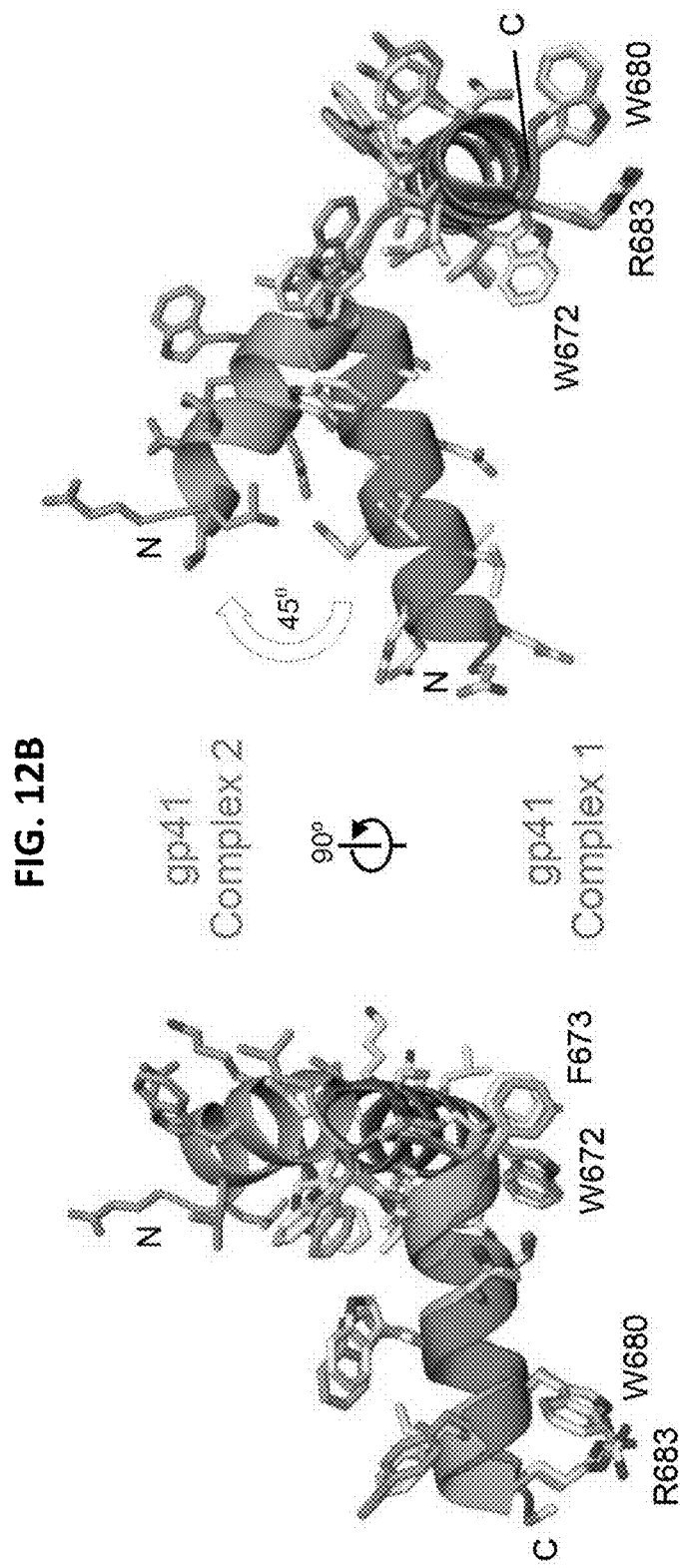
Figure 13A:
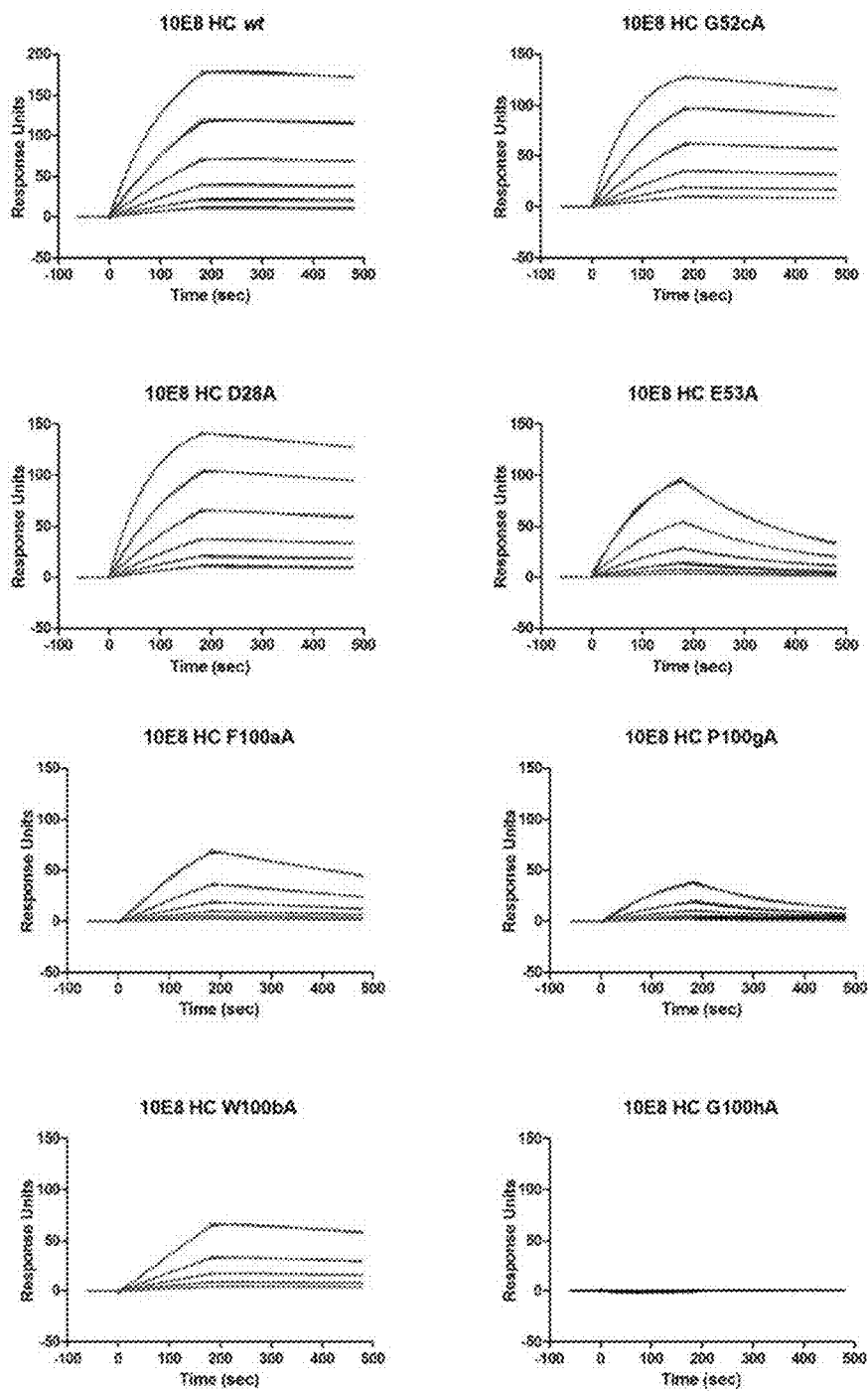
FIGS. 13A-13C are a set of graphs illustrating surface-Plasmon resonance analysis of 10E8 paratope alanine variants. Shown are binding sensograms of MPER peptide to 25 10E8 paratope variants, as well as to wild-type (wt) 10E8. Variant IgGs were captured on an anti-human IgG-coupled biosensor chip to surface densities of 1000-2000 response units and MPER peptide (listed) flowed over analyte at serial twofold dilutions starting at 500 nM (with the exception of HC D30A, W100bA, S100cA, P100fA, which started at 250 nM). Association and dissociation phases of three minutes and five minutes, respectively, were used, at flow rates of 30 µl/min. Sensograms were fit with a 1:1 Langmuir model using BIACORE® BIAEVALUATION® Software (GE Healthcare). Binding constants are reported in FIG. 31. The amino acid sequence of SEQ ID NO: 26 is shown in FIG. 13C.
Figure 13B:
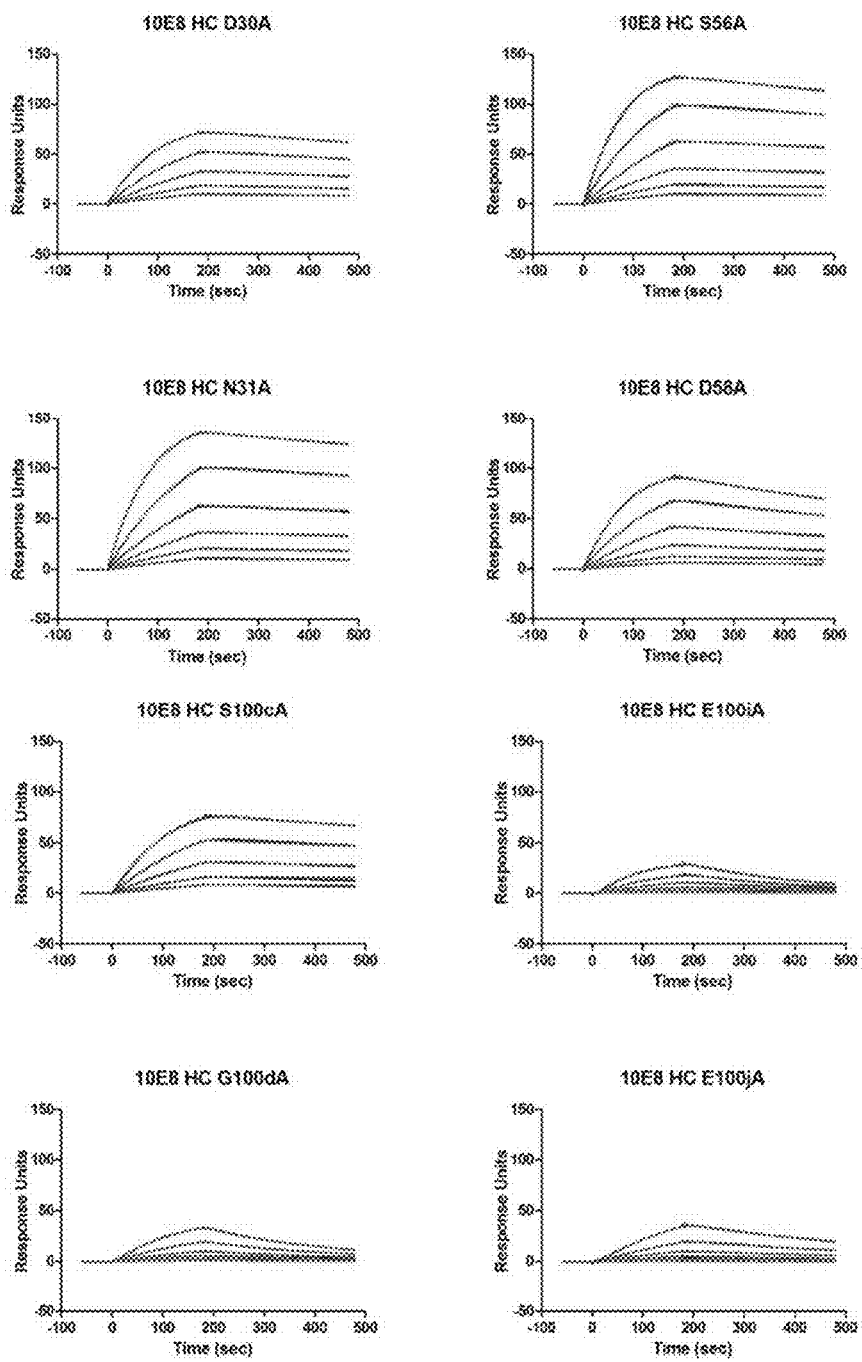
Figure 13C:
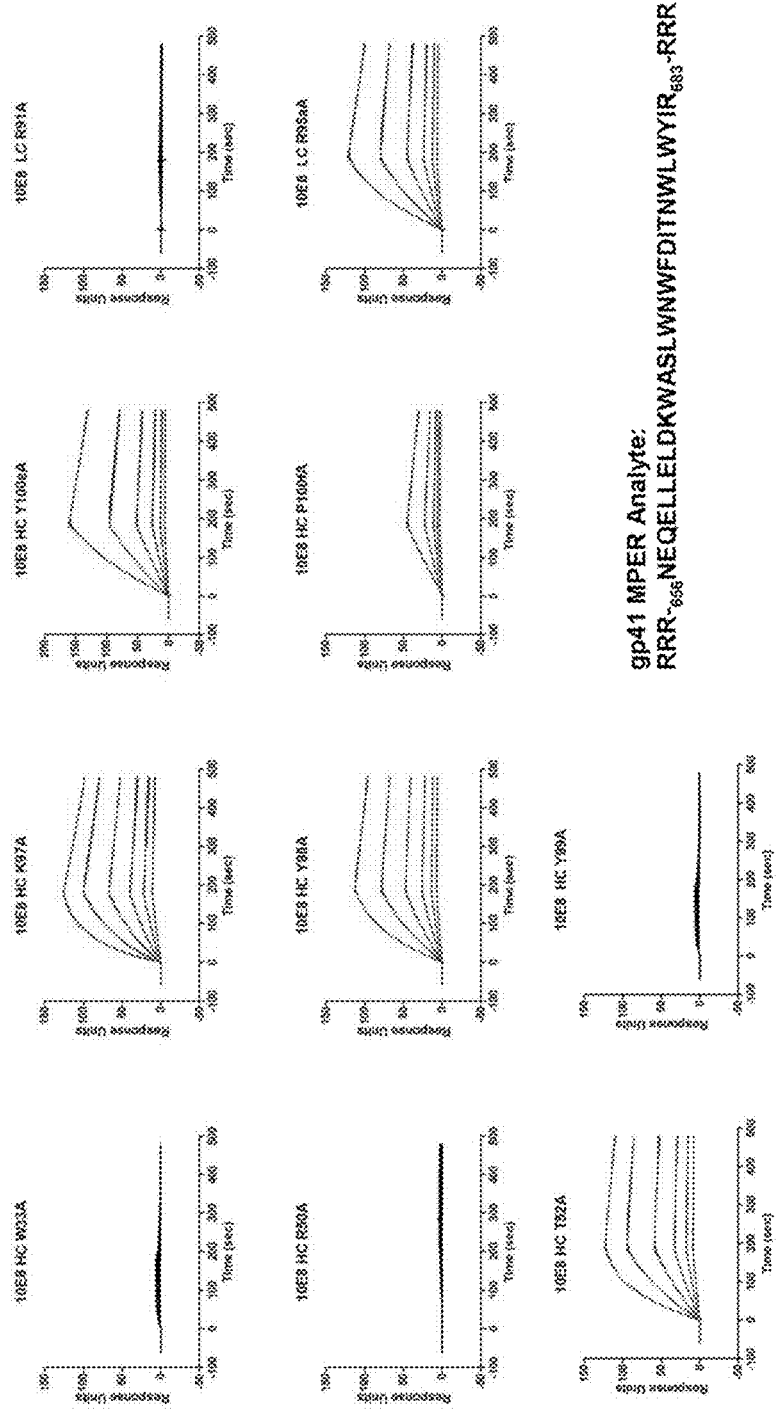
Figure 14:
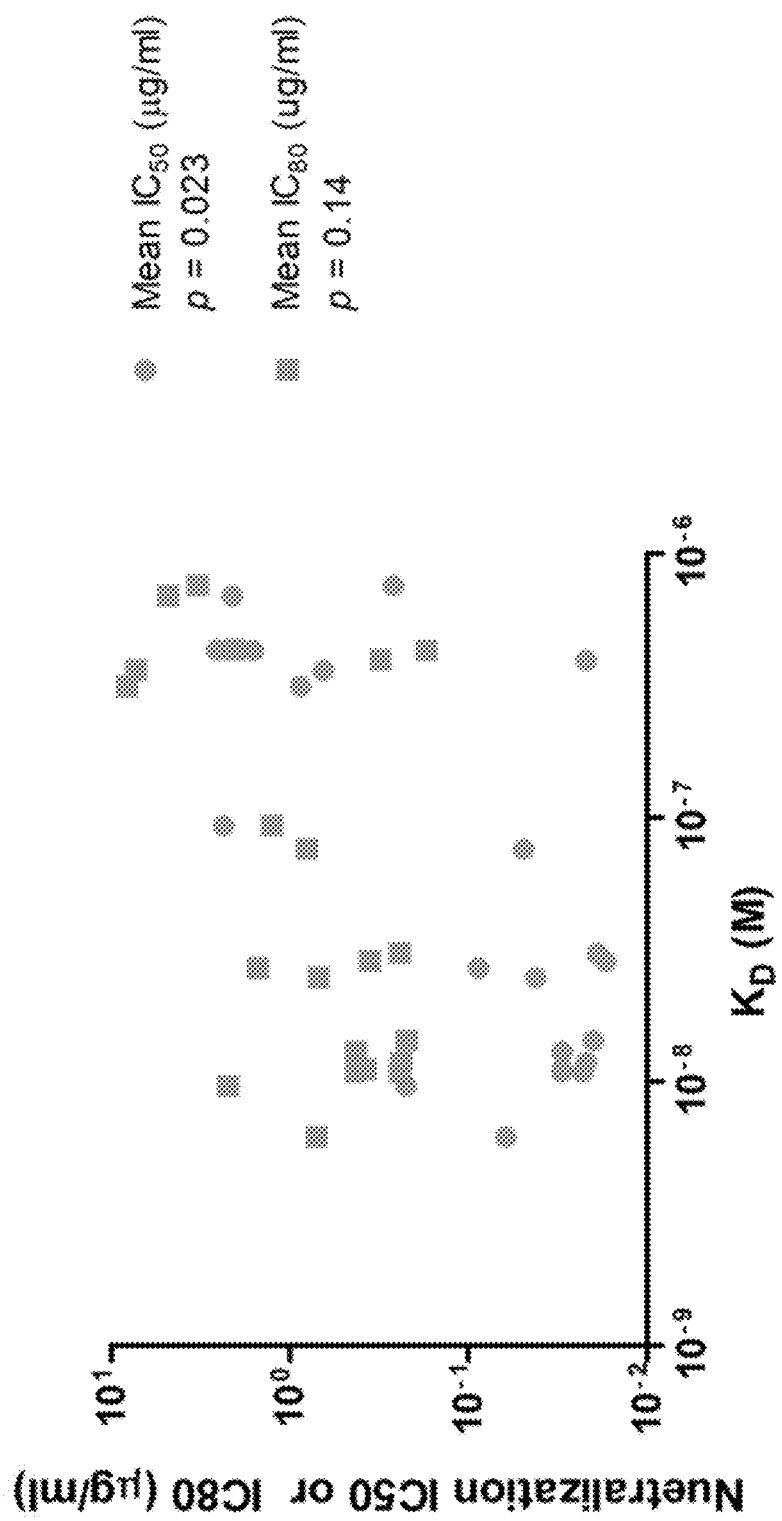
FIG. 14 shows a graph illustrating the correlation of 10E8 variant binding and neutralization. Binding K$_D$'s of the 10E8 alanine paratope variants plotted against their mean neutralization IC50s and IC80s. A nonparametric Spearman correlation was used to assess the relationship between binding and neutralization. K$_D$'s and neutralization IC50s and IC80s are reported in FIGS. 31-32.
Figure 15A:
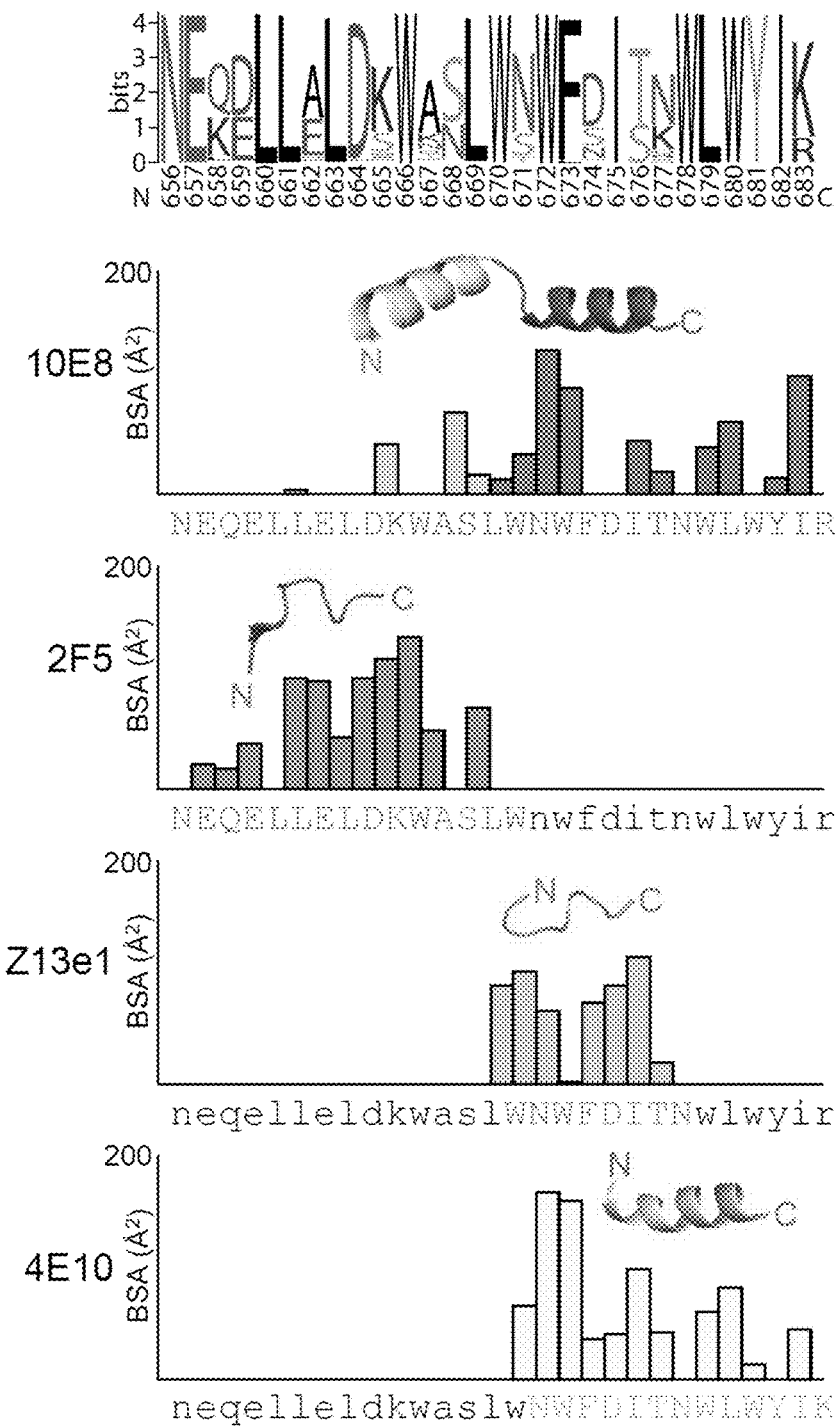
Figure 15B:
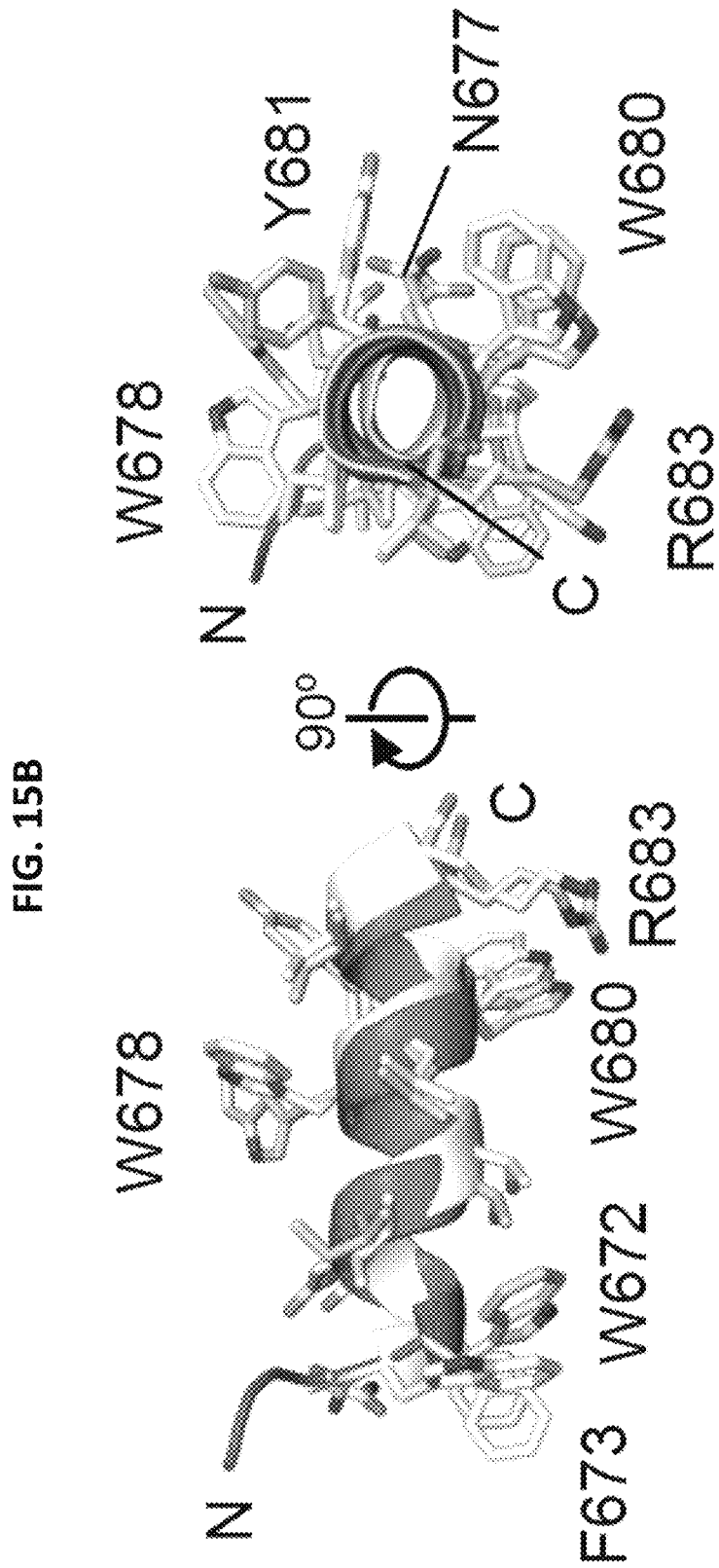
Figure 15D:
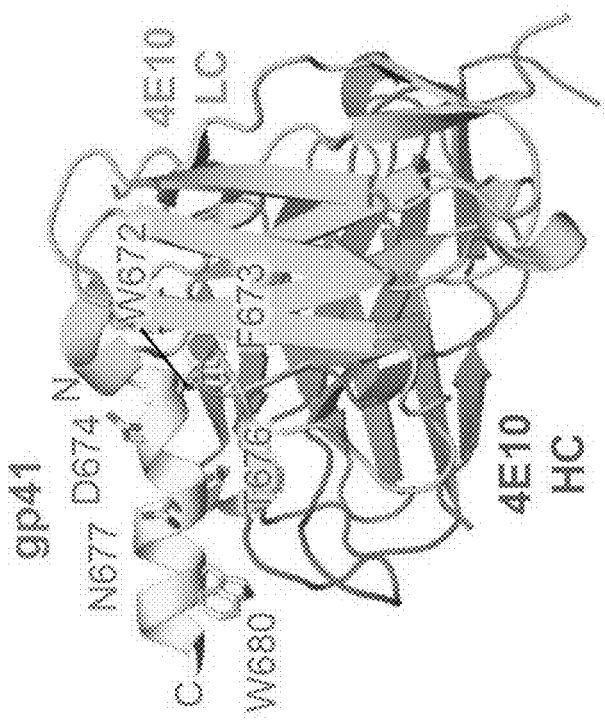
Figure 15C:
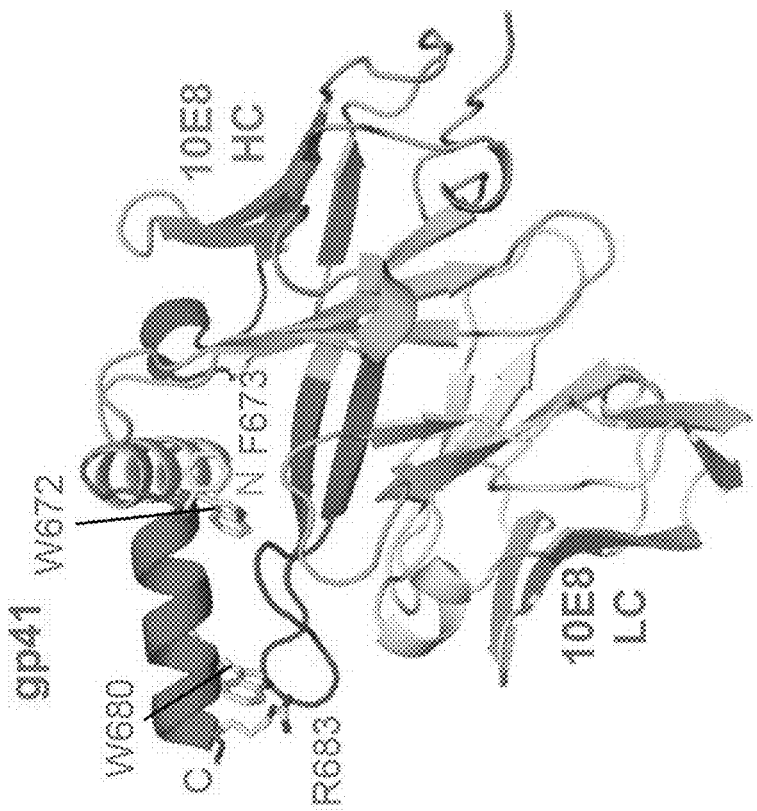
Figure 15H:
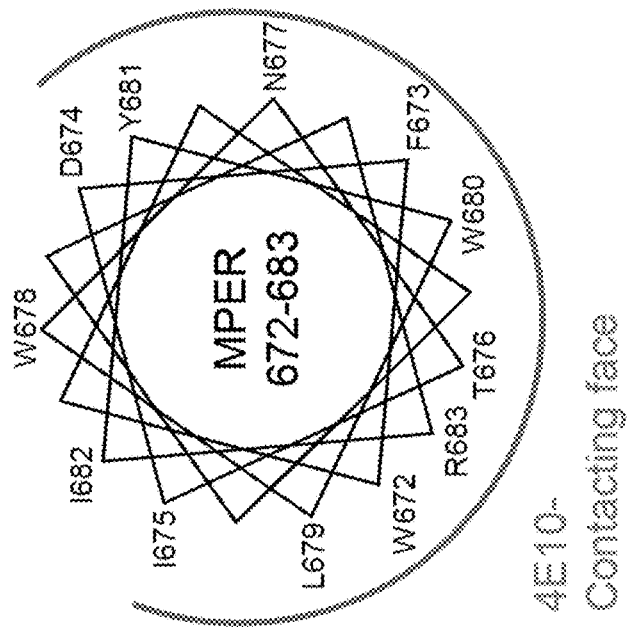
Figure 15G:
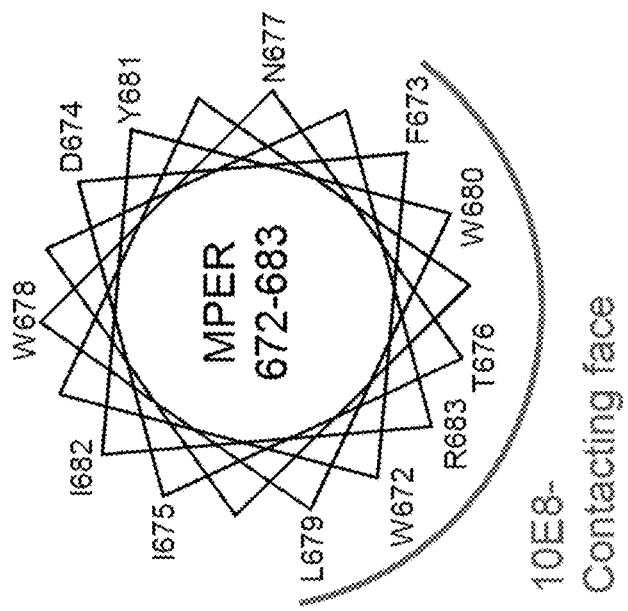
Figure 16:
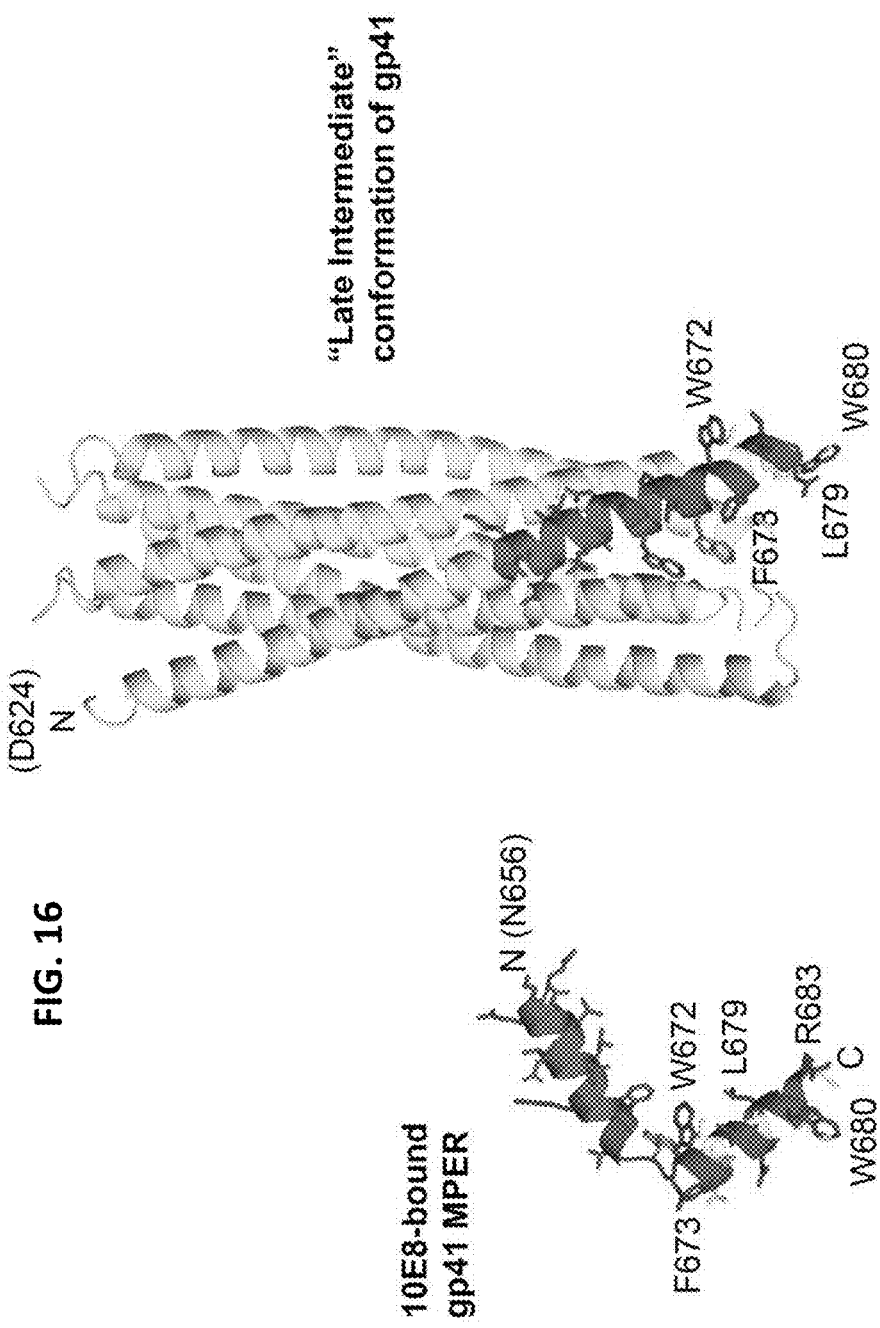
FIG. 16 shows a ribbon diagram illustrating the gp41 site of vulnerability mapped onto a "late intermediate" conformation of gp41. The gp41 site of vulnerability as defined by the contact footprint of antibody 10E8 on gp41 is shown mapped onto the 10E8-bound MPER peptide structure (left, similar orientation as FIG. 6B) and a late intermediate six-helix bundle conformation of gp41 (PDB ID No. 2XR7 (right), incorporated by reference herein as present in the database on Oct. 22, 2012). Atoms recognized by antibody 10E8 are shaded dark grey and shown in stick representation. Atom or residue contacts exclusive to antibodies 2F5, Z13e1, and 4E10, are shown as sticks, shaded light or medium grey. The 10E8-defined site of vulnerability faces outwards, away from the core axis of the bundle, and appears to be largely accessible in this conformation. A potential N-linked glycosylation site at position 674 would not be compatible with the late intermediate conformation since the sidechain of residue 674 faces the interior of the six-helix bundle.
Figure 38:
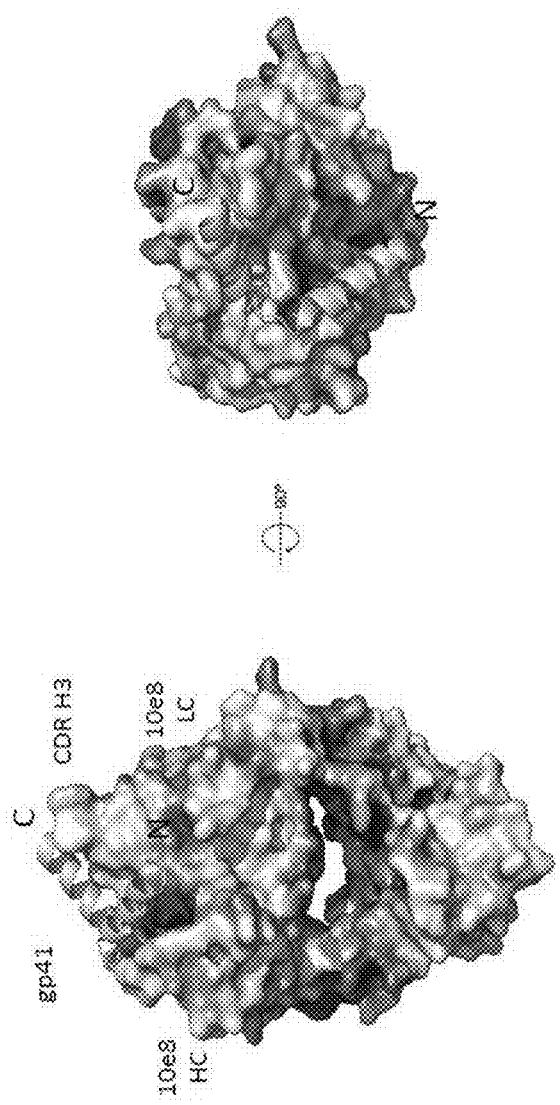
FIG. 38 is a schematic diagram of the crystal structure of the antibody 10E8 in complex with a gp41 peptide, showing the electrostatic surface charge of the antibody.
Figure 39:
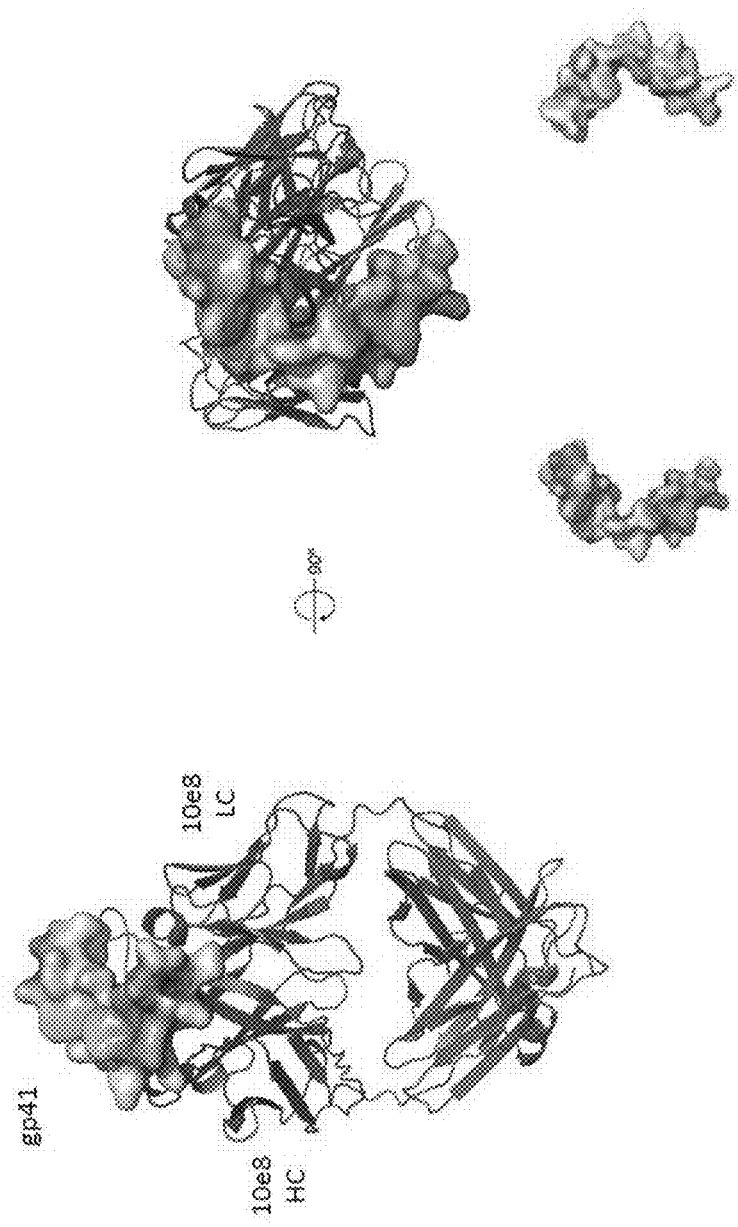
FIG. 39 is a schematic diagram of the crystal structure of the antibody 10E8 in complex with a gp41 peptide, showing the electrostatic surface charge of the peptide.
Figure 40:
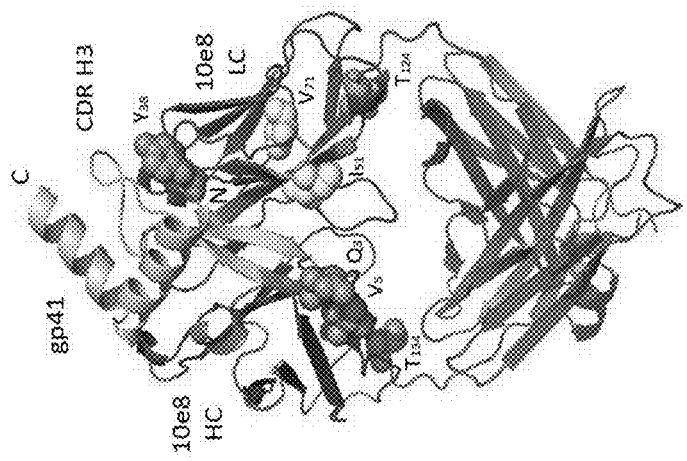
FIG. 40 is a schematic diagram of the crystal structure of the antibody 10E8 in complex with a gp41 peptide, showing the positions of the residue changes in the 10E8 variant antibodies 7H6 and 7N16.
Figure 41:
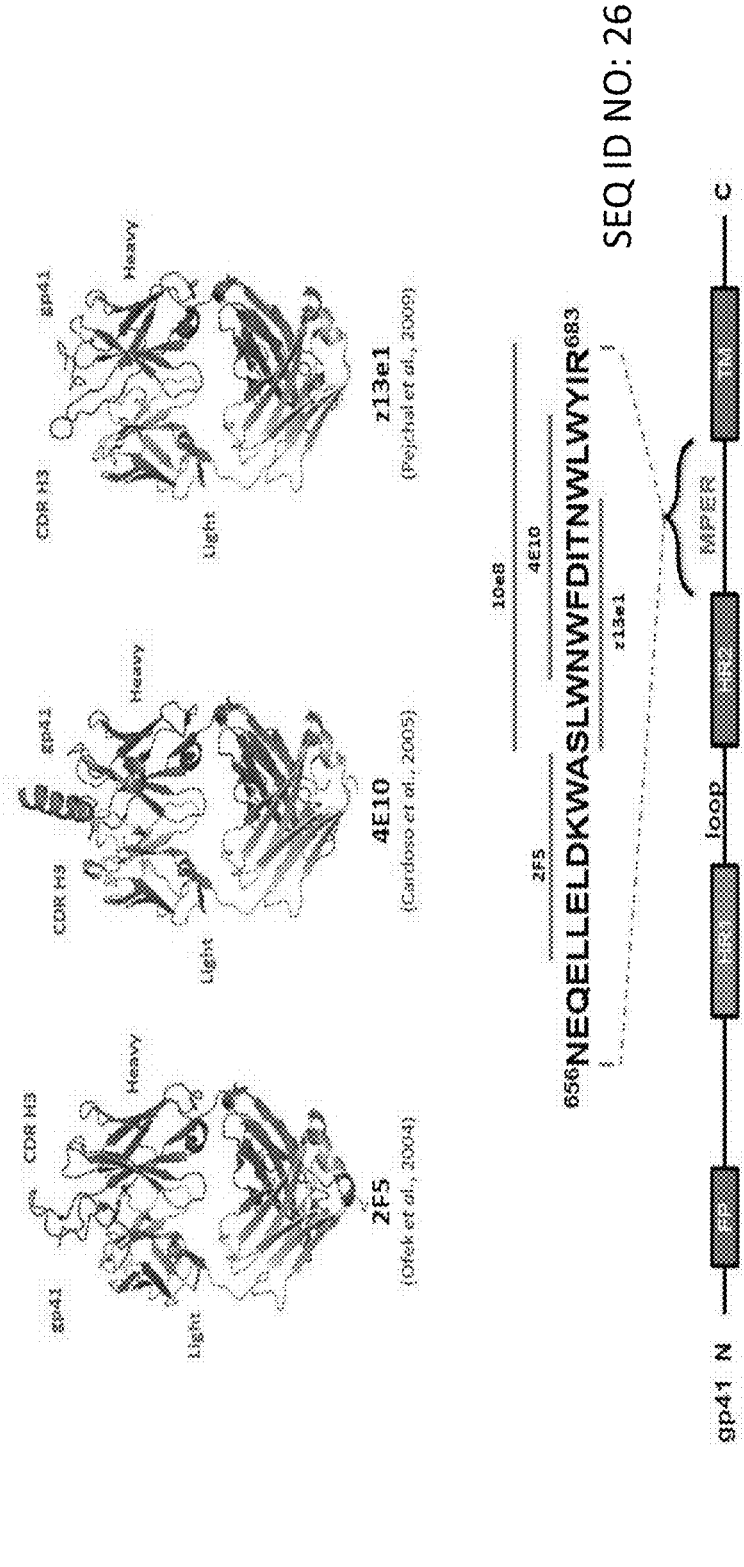
FIG. 41 is digital images of the crystal structures of the 2F5, 4E10 and Z13E1 antibodies in complex with gp41 peptides and a schematic of gp41 illustrating the relative biding sites of the 2F5, 4E10, Z13E1 and 10E8 antibodies. The amino acid sequence of SEQ ID NO: 26 is shown.

To provide an atomic-level understanding of the interaction of 10E8 with HIV-1, the antigen-binding fragment (Fab) of 10E8 in complex with a peptide encompassing the entire 28-residue gp41 MPER (residues 656-683) was crystallized. Monoclinic crystals diffracted to 2.1 Å resolution, and structure solution and refinement to $R_{cryst}$=18.01% ($R_{free}$=21.76%) revealed two complexes in the asymmetric unit (heretofore referred to as complexes 1 and 2) (FIG. 24). Overall, 10E8 bound to one face of the MPER peptide, which formed two helices, each 15-20 Å in length and oriented 100° relative to each other (FIG. 4A). Electron density was observed for the entire MPER, ranging from Asn656-Arg683 (Leu660-Arg683 for complex 2), with the highest degree of ordered density observed from residue Trp666 within the N-terminal helix through to Arg683 of the C-terminal helix (FIG. 12). Analysis of main-chain dihedral angles (FIG. 25) indicated that the N-terminal α-helix extends from residue Asn657 to Ala667, tightens into a $3_{10}$-helix between residues Ser668 and Leu669, before turning at residues Trp670 and Asn671. The C-terminal α-helix, capped by Asn671, starts at residue Trp672 and extends to residue Arg683, the final residue of the MPER (FIG. 4A,B).

Figure 4B:
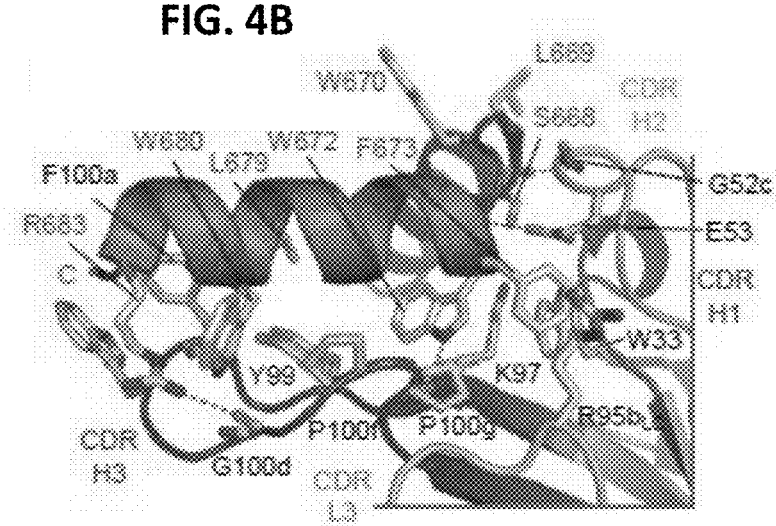
Figure 4C:
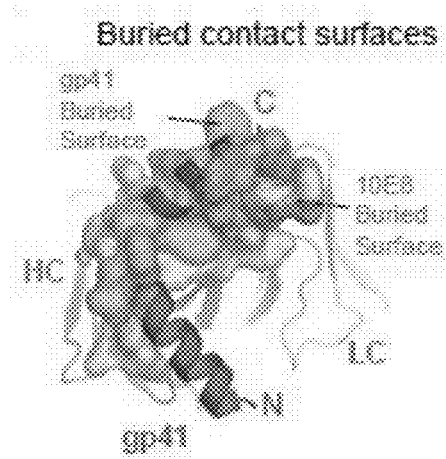
Figure 4D:
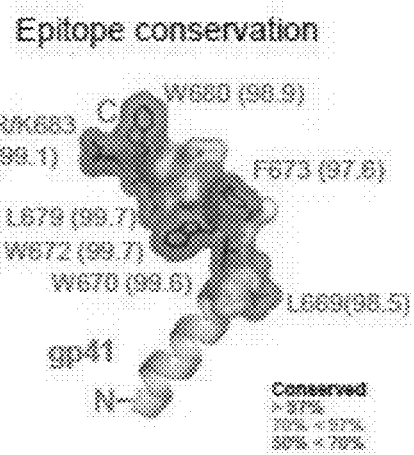
Figure 4E:
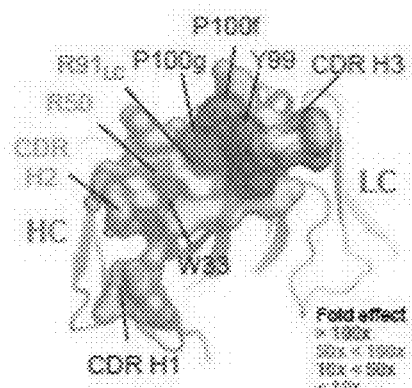
Figure 4F:
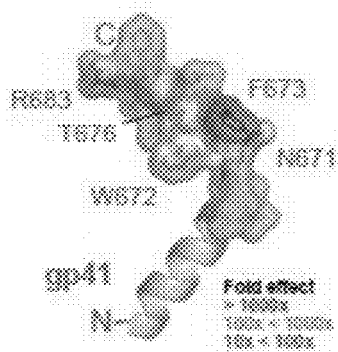
Figure 4G:
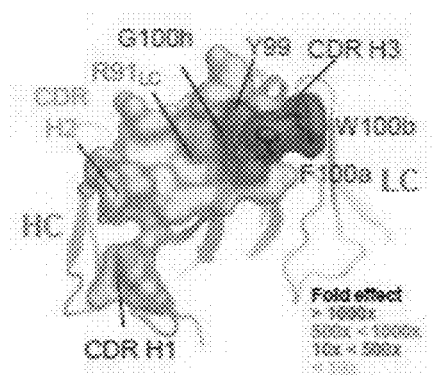
Figure 4H:
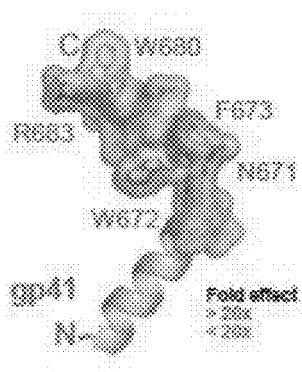
Figure 5A:
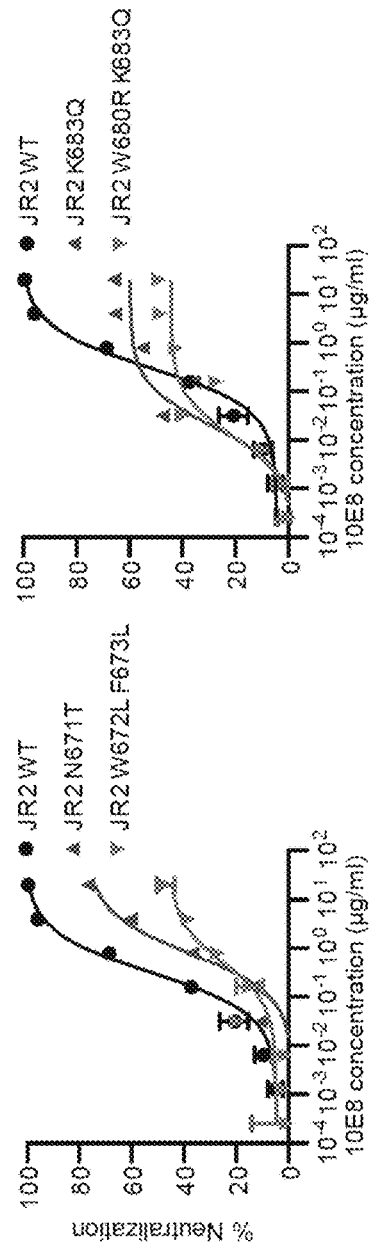

The 10E8 antibody contacts the gp41 MPER primarily through its heavy chain, although crucial contacts are also mediated by the light chain CDR L3 (FIGS. 4C and 26-28). Three predominant loci of interaction are observed between the antibody and gp41 (FIGS. 29-30): One between residues of the tip of the CDR H3 loop and the tip of the C-terminal helix of the peptide, a second between residues of the CDR H2 loop and residues of the hinge region of the peptide, and a third at the juncture of the three heavy chain CDR loops and the light chain CDR L3, which form a hydrophobic cleft that holds residues of the beginning of the MPER C-terminal helix (FIG. 4B).

10E8-Gp41 Interface.

To complement the results observed for the mutagenesis of the highly conserved 10E8 epitope (FIGS. 4D and 18), each residue of the 10E8 paratope, as determined from the crystal structure, was individually mutated to alanine and the resulting 25 10E8 variants assessed for affinity to a soluble MPER peptide. Overall, the most pronounced effects of the alanine mutations on the binding affinity of 10E8 to a soluble MPER peptide occurred within residues of the CDR H3 loop, though mutations within the hydrophobic cleft also showed substantial effect (FIGS. 4E, 13 and 31). 10E8 residues identified by alanine scan as critical for the interaction with gp41 stretched from the cleft all the way to the tip of the CDR H3 (FIG. 4E) and were mirrored by a corresponding stretch of gp41 residues which substantially affected 10E8 binding when mutated to alanine (FIG. 4F).

The same panel of 10E8 alanine mutations was tested for neutralization potency against a panel of five Env-pseudoviruses that included both Tier 1 and Tier 2 viruses (FIG. 32) Similar to the binding data, residues of the 10E8 CDR H3 had dramatic effects on neutralization, as did residues of the hydropohobic cleft (FIG. 4*g*). Generally, $K_D$s of paratope mutants correlated with neutralization (FIG. 14). Backbone interactions (on both 10E8 and gp41) also contribute to the interface, especially between the CDR H2 of 10E8 and the hinge region of the MPER, though these are silent in alanine scan analyses. Overall, 10E8 utilizes a narrow band of residues (~20×5 Å) that stretches from the CDR H1 and H2 and extends along most of the CDR H3 to recognize a string of highly conserved hydrophobic gp41 residues, and a critical charged residue, Arg/Lys683, that occurs just prior to the transmembrane region (FIG. 4F,H).

A Conserved Gp41-Neutralization Determinant.

Several structures of neutralizing antibodies in complex with the MPER of gp41 have been reported previously, including those for antibodies 2F5, Z13e1 and 4E10 (FIG. 15A; Julien et al., *J Mol Biol* 384, 377-392, 2008; Cardoso et al., *J Mol Biol* 365, 1533-1544, 2007; Cardoso et al., *Immunity* 22, 163-173, 2005; Ofek et al., *J Virol* 78, 10724-10737, 2004; Pejchal et al., *J Virol* 83, 8451-8462, 2009). The MPER adopts divergent loop conformations when bound by 2F5 and Z13e1 and an α-helix when bound by 4E10. Comparison of 2F5, Z13e1, and 4E10 epitopes with 10E8-bound gp41 revealed that only the 4E10 epitope has similar secondary structure, with superposition yielding an RMSD of 2.49 Å for all atoms of residues 671-683 and 0.98 Å for main-chain atoms (FIGS. 15B and 33).

To compare further the recognition of 10E8 and 4E10, their angles of epitope approach were examined. As shown in FIGS. 15C-15F, alignment of the recognized MPER helix places 10E8 and 4E10 into similar overall spatial positions. The relative orientations of the recognized helix and the heavy and light chains of the two antibodies, however, differ dramatically. With 10E8, the C-terminal helix is perpendicular to the plane bisecting heavy and light chains (FIGS. 15C,E); with 4E10, the recognized helix is at the interface between heavy and light chains (FIG. 15D,F). Perhaps relevant to this, 10E8 utilizes CDR loops almost exclusively in its recognition of gp41, while 4E10 incorporates substantial β-strand interactions with gp41 at the interface between the heavy and light chains.

The differing modes of 10E8 and 4E10 recognition of the conserved C-terminal MPER helix result in a substantial difference in the proportion of the recognized helical face: 10E8 contacts roughly a third of the helical face, while 4E10 contacts over half (FIGS. 15G, 15H and 34-35). The smaller contact surface of 10E8 may provide an explanation for the reduced recognition of lipid surfaces by 10E8 versus 4E10—providing a potential structure-based explanation for reduced autoreactivity of 10E8.

Sequence Variation and 10E8 Neutralization.

To place the specificity and structural data into the context of known variation of the MPER, viral sequences with resistance to neutralization by 10E8 were analyzed (FIG. 5A). Of the 183 viruses tested, only three were highly resistant to 10E8 with IC50>50 μg/ml. Each of these viruses had substitutions at positions found to affect neutralization by alanine scanning (Asn671, Trp672, Phe673, and Trp680). Plasma virus of the patient N152, from whom 10E8 was cloned, is also likely resistant to 10E8 mediated neutralization (Wu et al., *J Virol* 86, 5844-5856, 2012). Sequence analysis of plasma viral RNA revealed rare substitutions at positions Trp680 and Lys/Arg683 (FIG. 5A). These residues are typically highly conserved with variation only occurring in 1.17% of 3,730 HIV Env sequences in the Los Alamos Database (hiv.lanl.gov). When the substitutions for the 3 resistant viruses and the patient viruses were placed on the background of the sensitive JR2 virus, substitutions at Asn671Thr, Trp672Leu, and Phe673Leu had a modest effect on the IC50 but raised the IC80 above 20 μg/ml. In the structural analysis, direct contacts with 10E8 were not observed at position 671 suggesting the effects on neutralization of Thr or Ala substitutions at this position are mediated by conformational or other effects within gp41. The combination of Trp672Leu and Phe673Leu conferred high-level resistance at the IC50 and IC80 level. Changes corresponding to the patient's dominant circulating virus had a similar effect. Although Lys/Arg683Gln alone conferred resistance at the IC80 level, together Trp680Arg and Lys/Arg683Gln resulted in greater resistance to 10E8 (FIG. 5A). When taken together with the analysis of the 10E8 paratope, these data suggest that in addition to Trp672, Phe673, and Trp680 found in the 4E10 epitope, the additional 10E8-bound residue Lys/Arg683 is critical to neutralization. In addition to other differences in binding based upon structural analyses noted above, it is possible that the additional potency of 10E8 compared to 4E10 against naturally occurring viral variants may be mediated through binding of highly conserved residues Trp680 and Lys/Arg683 that directly interact with the 10E8 CDRH3.

Discussion.

10E8 is a broad and potent neutralizing antibody with important implications for efforts to stimulate such antibodies with vaccines. Previous MPER antibodies were somewhat limited in potency, and had a more limited ability to access MPER on Env of primary isolates. In addition, lipid binding and autoreactivity were thought to be characteristics of MPER antibodies and important obstacles to their elicitation by vaccines. However, 10E8 lacks each of these characteristics. In addition, antibodies with a similar specificity were not rare in the chronically infected cohort. This suggests that 10E8-like antibodies were not deleted from the repertoire because of autoreactivity. These results further suggest that 10E8-like antibodies might be raised in a larger fraction of HIV-uninfected persons receiving a vaccine designed to elicit these antibodies without the B cell defects of chronic HIV infection. Design of such a vaccine will likely require not only presentation of an intact 10E8 epitope but also use of a platform sufficiently immunogenic to drive the evolution of 10E8-like antibodies.

The extraordinary breadth and potency of 10E8 appears to be mediated by its ability to bind highly conserved residues within MPER. Although the epitope of 10E8 overlaps those of known mAbs such as 4E10, it differs in recognition surface, angle of approach, lipid binding, and self-reactivity. Alanine scanning, structural analysis, and paratope analysis each indicate that 10E8 makes crucial contacts with highly conserved residues Trp672, Phe673, Trp676 and Lys/Arg683. The extraordinary breadth of some potent mAbs, for example that bind the CD4 binding site, is thought to be conferred by blocking a functionally important site that is critical for viral entry. Whether 10E8 impairs Env function or simply acts by binding highly conserved residues remains to be determined. Nonetheless, the breadth and potency of 10E8 demonstrates a conserved site of gp41 vulnerability (FIG. 5B) that is an important target antigen for HIV neutralization and that will likely reinvigorate interest in MPER-based HIV vaccine design.

Methods

Methods Summary.

Peripheral blood CD19+IgM−IgD−IgA− B cells were sorted by flow cytometry, plated at 4 cells per well, and expanded with cytokines and feeder cells. B-cell culture supernatants were screened by microneutralization against $HIV_{MN.03}$ and $HIV_{Bal.26}$ pseudoviruses. IgG genes from wells with neutralization activity were cloned and re-expressed in 293T cells. Breadth of neutralizing activity was confirmed against a 181-isolate Env-pseudovirus panel. Specificity was determined by alanine scanning peptides and mutant-Env pseudoviruses. Lipid binding and autoreactivity of 10E8 were measured by surface plasmon resonance, indirect immunofluorescence on HEp-2 cells and bead arrays. Binding of HIV envelopes on transfected 293 cells was detected by flow cytometry. Following pre-incubation with antibody, the impact of washing virions prior to infecting TZM-b1 cells was used to measure access to viral MPER. The frequency of HIV-1$^+$ sera with a given specificity was measured by the ability to neutralize HIV-2/HIV-1 chimeras containing portions of the MPER. Successful co-crystallization of 10E8 with gp41 was obtained when a peptide encompassing the entire 28-residue gp41 MPER (residues 656-683). Structure determination revealed two complexes in the crystal asymmetric unit. Analysis of differences between the two complexes enabled essential interactions to be discerned. The paratope, as defined by residues in the antibody that showed reduced solvent accessibility when complexed by gp41, was subjected to comprehensive alanine scan, with each of the 25 10E8 alanine mutants assessed by SPR for recognition of gp41 and by neutralization on a panel of 5 pseudotyped viruses. The sequence of the patient plasma viral RNA was derived using limiting dilution RT-PCR.

Study Patients.

Plasma and peripheral blood mononuclear cells (PBMC) were selected from the HIV-1-infected patients enrolled in the National Institute of Health under a clinical protocol approved by the Investigational Review Board in the National Institute of Allergy and Infectious Diseases (NIAID-IRB). All participants signed informed consent approved by the NIAID-IRB. The criteria for enrollment were as follows: having a detectable viral load, a stable CD4 T-cell count above 400 cells/µl, being diagnosed with HIV infection for at least 4 years, and off ARV treatment for at least 5 years. Based on the locations of current and former residences, all patients were presumed to be infected with clade B virus. Donor N152 was selected for B cell sorting and antibody generation because his serum neutralizing activity is among the most potent and broad in the cohort. He is a slow progressor based on criteria described previously (Migueles et al., *Immunity* 29, 1009-1021, 2008). At the time of leukapheresis, he had been infected with HIV-1 for 20 years, with CD4 T-cell counts of 325 cells/µl, plasma HIV-1 RNA values of 3,811 copies/ml and was not on antiretroviral treatment.

Memory B-Cell Staining, Sorting and Antibody Cloning.

Staining and single-cell sorting of memory B cells were performed as follows. PBMCs from HIV-1 infected donor N152 were stained with antibody cocktail consisting of anti-CD19-PE-Cy7 (BD Bioscience), IgA-APC (Jackson ImmunoResearch Laboratories Inc.), IgD-FITC (BD Pharmingen), and IgM-PE (Jackson ImmunoResearch Laboratories Inc.) at 4° C. in dark for 30 min. The cells were then washed with 10 ml PBS-BSA buffer and resuspended in 500 µl PBS-BSA. 66,000 CD19+IgA−IgD−IgM− memory B cells were sorted using a FACSAria III cell sorter (Becton Dickinson) and resuspended in IMDM medium with 10% FBS containing 100 U/ml IL-2, 50 ng/ml IL-21 and $1 \times 10^5$/ml irradiated 3T3-msCD40L feeder cells (Kershaw et al., *Cancer Res* 61, 7920-7924, 2001). B cells were seeded into 384-well microtiter plates at a density of 4 cells/well in a final volume of 50 µl. After 13 days of incubation, 40 µl of culture supernatants from each well were collected and screened for neutralization activity using a high throughput micro-neutralization assay against HIV-1$_{MN.03}$ and HIV-1$_{Bal.26}$. B cells in each well were lysed with 20 µl lysis buffer containing 0.25 µl of RNase inhibitor (New England Biolabs Inc.), 0.3 µl of 1M Tris pH8 (Quality Biological Inc.) and 19.45 µl DEPC-treated $H_2O$. The plates with B cells were stored at −80° C.

The variable region of the heavy chain and the light chain of the immunoglobulin gene were amplified by RT-PCR from the wells that scored positive in both the HIV-1$_{MN.03}$ and HIV-1$_{Bal.26}$ neutralization assay. The cDNA product was used as template in the PCR reaction. In order to amplify the highly somatically mutated immunoglobulin gene, two sets of primers as described previously (Tiller et al., *Journal of immunological methods* 329, 112-124, 2008) were used in two independent PCRs. One set of primers consisted of the forward primers and the reverse primers specific for the leader region and constant region of IgH, Igκ or Igλ, respectively. The other set of primers consisted of the forward primer mixes specific for FWR1 and respective reverse primers specific for the IgH, Igκ and Igλ J genes. All PCRs were performed in 96-well PCR plates in a total volume of 50 µl containing 20 nM each primer or primer mix, 10 nM each dNTP (Invitrogen), 10 µl 5×Q-solution (Qiagen) and 1.2 U HotStar Taq DNA polymerase (Qiagen). From the positive PCR reactions, pools of the VH or VL-region DNA were ligated to a pCR2.1-Topo-TA vector (Invitrogen) for sequencing before cloning into the corresponding Igγ1, Igκ and Igλ expression vector. 10 µg of heavy and light chain plasmids, cloned from the same well and combined in all possible heavy and light chain pairs, were mixed with 40 µl FuGENE 6 (Roche) in 1500 µl DMEM (Gibco) and co-transfected into 293T cells. The full-length IgG was purified using a recombinant protein-A column (GE Healthcare).

Neutralization Assays.

Neutralization of the monoclonal antibodies was measured using single-round HIV-1 Env-pseudoviruses infection of TZM-b1 cells (Li et al., *J Virol* 79, 10108-10125, 2005). HIV-1 Env-pseudoviruses were generated by co-transfection of 293T cells with pSG3ΔEnv backbone containing a luciferase reporter gene and a second plasmid that expressed HIV-1 Env. At 72 hours post-transfection, supernatants containing pseudovirus were harvested and frozen at −80° C. until further use. In the neutralization assay, 10 μl of 5-fold serially diluted patient serum or mAb was incubated with 40 μl pseudovirus in a 96-well plate at 37° C. for 30 minutes before addition of TZM-b1 cells. After 2 days of incubation, cells were lysed and the viral infectivity was quantified by measuring luciferase activity with a Victor Light luminometer (Perkin Elmer). The 50% inhibitory concentration (IC50) was calculated as the antibody concentration that reduced infection by 50%. Antibody epitopes were mapped using HIV-1 JR2 MPER alanine mutant pseudoviruses in a TZM-b1 assay.

HIV-2/HIV-1 Chimera Neutralization.

HIV-2/HIV-1 C1 chimera (HIV-2 virus 7312A with HIV-1 gp41 MPER; Gray et al., *J Virol* 81, 6187-6196, 2007) was used in the competition assay. A fixed concentration of MPER peptide was incubated with serially diluted 2F5, 4E10, Z13e1 or 10E8 antibody at 37° C. for 30 minutes before incubation with HIV-2/HIV-1 C1 chimera. Wild-type HIV-2 virus 7312A was used as a control. Antibody epitope mapping was completed by adding 10 μl 10E8 mAb to 5 μl serial dilutions of 4E10 peptide or its alanine mutants at 37° C. for 30 minutes prior to the addition of HIV-2/HIV-1 C1 chimera. The degree to which peptides blocked antibody-mediated neutralization was calculated as the fold change in the IC50 value of the antibody in the presence of 4E10 alanine mutants compared to the wild-type peptide. The precise binding region within the MPER targeted by patient serum or antibodies was determined using the HIV-2/HIV-1 chimeras containing different portions of HIV-1 MPER, such as C1 (HIV-2 Env with HIV-1 MPER), C1C (HIV-2 Env with clade C MPER), C3 (HIV-2 Env with 2F5 epitope), C4 (HIV-2 Env with 4E10 epitope), C6 (HIV-2 Env with short 4E10 epitope NWFDIT), C7 (HIV-2 Env with short 2F5 epitope ALDKWA) and C8 (HIV-2 Env with both Z13 and 4E10 epitope). 5-fold diluted patient serum or mAb was incubated with chimera in a 96-well plate at 37° C. for 30 minutes before addition of TZM-b1 cells. The specificities within patient sera were confirmed by blocking neutralization of the C1 chimera with 25 μg/ml of 2F5, 4E10, MPER, Bal.V3, control peptide, or 50 μg/ml of Z13 peptide.

ELISA Assays.

Each antigen at 2 μg/ml was coated on 96-well plates overnight at 4° C. Plates were blocked with BLOTTO buffer (PBS, 1% FBS, 5% non-fat milk) for one hour at room temperature (RT), followed by incubation with antibody serially diluted in disruption buffer (PBS, 5% FBS, 2% BSA, 1% Tween-20) for one hour at room temperature. 1:10,000 dilution of horseradish peroxidase (HRP)-conjugated goat anti-human IgG antibody was added for one hour at room temperature. Plates were washed between each step with 0.2% Tween 20 in PBS. Plates were developed using 3,3', 5,5'-tetramethylbenzidine (TMB) (Sigma) and read at 450 nm.

Autoreactivity Assays.

Binding of 10E8 to phospholipid was measured by SPR conducted on a BIACORE® 3000 instrument and data analyses were performed using the BIAevaluation® 4.1 software (BIACORE®) as described previously (Alam et al., *Proc. Natl. Acad. Sci. U.S.A.*, 106, 20234-20239, 2009). Phospholipid-containing liposomes were captured on a BIACORE® L1 sensor chip, which uses an alkyl linker for anchoring lipids. Before capturing lipids, the surface of the L1 chip was cleaned with a 60-s injection of 40 mM octyl-β-D-glucopyranoside, at 100 μl/minute, and the chip and fluidics were washed with excess buffer to remove any traces of detergent. mAbs were then injected at 100 μg/ml at a flow rate of 30 μl/min. After each Ab injection, the surface was again cleaned with octyl β-D-glucopyranoside, and 5-s injections of each 5 mM HCl, then 5 mM NaOH, to clean any adherent protein from the chip.

Reactivity to HIV-1 negative human epithelial (HEp-2) cells was determined by indirect immunofluorescence on slides using Evans Blue as a counterstain and FITC-conjugated goat anti-human IgG (Zeus Scientific, Raritan N.J.; Haynes et al., *Science* 308, 1906-1908, 2005). Slides were photographed on a Nikon Optiphot fluorescence microscope. Regarding FIG. 3B, kodachrome slides were taken of each MAb binding to HEp-2 cells at a 32 second exposure, and the slides scanned into digital format. The Luminex AtheNA Multi-Lyte ANA test (Wampole Laboratories, Princeton, N.J.) was used to test for MAb reactivity to SSA/Ro, SS-B/La, Sm, ribonucleoprotein (RNP), Jo-1, double-stranded DNA (dsDNA), centromere B, and histone and was performed per the manufacturer's specifications and as previously described (Haynes et al., *Science* 308, 1906-1908, 2005). MAb concentrations assayed were 50, 25, 12.5 and 6.25 μg/ml. 10 μl of each concentration were incubated with the luminex fluorescent beads and the test performed per manufacturer's specifications.

Fluorescence-Activated Cell Sorting (FACS) Staining of Cell-Surface HIV-1 Env.

FACS staining was performed as previously described (Chakrabarti et al., *J Virol* 85, 8217-8226, 2011; Koch et al., *Virology* 313, 387-400, 2003). 48 hours following transfection, cells were harvested and washed in FACS buffer (PBS, 5% HIFBS, 0.02% azide) and stained with monoclonal antibodies. The transfected cells were suspended in FACS buffer and were incubated with the antibodies for one hour at room temperature. The monoclonal antibody-cell mixture was washed extensively in FACS buffer and phycoerythrin (PE)-conjugated goat anti-human secondary antibody (Sigma) was added for one hour at a 1:200 dilution, followed by extensive washing to remove unbound secondary antibody. The antibody-PE-stained cells were acquired on a BD LSRII instrument and analyzed by FlowJo.

Antibody-Virus Washout Experiments.

From a starting concentration of 2 mg/ml, 12.5 μl of 5-fold serially diluted antibodies in PBS were added to 487.5 μl of DMEM containing 10% HIFCS and 15 μl of pseudovirus such that the final concentrations of antibodies were 50 μg/ml to 0.08 μg/ml in a total volume of 500 μl. In the "no inhibitor" control, the same volume of PBS was added instead of antibody. The reaction mixture was incubated for 30 minutes at 37° C. The 250 μl reaction mixture was diluted to 10 ml with complete DMEM, centrifuged at 25,000 rpm in a SW41 rotor, for 2 hours at 4° C. The virus pellet was then washed two additional times with 10 ml of PBS. During the washing steps, the virus-antibody complex was centrifuged at 40,000 rpm for 20 minutes at 4° C. After the final wash, 250 μl of DMEM was added to the washed virus pellet and it was resuspended by gentle shaking at 4° C. for 30 min. 100 µl of the suspended virus was used to infect 100 µl of TZM-b1 cells (0.2 million/ml), in duplicate. From the remaining 250 µl of reaction mixture, an equal volume of the antibody virus mixture was used as a "no washout" control. Plates were incubated at 37° C. in a $CO_2$ incubator for 2 days. After 2 days, the luciferase assay was done as described previously (Mascola et al. *J Virol* 76, 4810-4821, 2002). The data was then plotted to determine the neutralization mediated by the antibodies in "wash" or "no wash" conditions Structure Determination and Analysis.

The antigen binding fragment of 10E8 (Fab) was prepared using LysC digestion, as previously described (Ofek et al., *Proc. Natl. Aca. Sci. U.S.A.*, 107, 17880-17887, 2010). The IgG was first reduced with 100 mM DTT for one hour at 37° C., followed by one hour of dialysis in Hepes, pH 7.6, to reduce the DTT concentration to 1 mM. Antibodies were then dialyzed against 2 mM iodoacetamide for 48 hours at 4° C., and subjected to a final dialysis against Hepes, pH 7.6, for 2 h. After reduction and alkylation, antibodies were cleaved with Lys-C(Roche), run over a Protein A column to segregate away the Fc fragment, and then subjected to ion exchange (Mono S) and size-exclusion chromatography (S200). Purified 10E8 Fab was incubated with 10-fold excess peptide RRR-NEQELLELDKWASLWNWFDIT-NWLWYIR(SEQ ID NO: 26)-RRR (American Peptide, CA) and the complex then set up set for 20° C. vapor diffusion sitting drop crystallizations on the Honeybee 963 robot. 576 initial conditions adapted from the commercially available Hampton (Hampton Research), Precipitant Synergy (Emerald Biosystems), and Wizard (Emerald Biosystems) crystallization screens were set up and imaged using the Rockimager (Formulatrix), followed by hand optimization of crystal hits. Crystals were grown in 40% PEG 400, 0.1 M NaCitrate, 0.1 M Tris pH 7.5 diffracted to 2.1 Å resolution in a cryoprotectant composed of mother liquor supplemented with 15% 2R-3R-butanediol and excess peptide. After mounting the crystals on a loop, they were flash cooled and data was collected at 1.00 Å wavelength at SER CAT ID-22 or BM-22 beamlines (APS) and processed using HKL-2000 (Otwinowski et al., *Macromolecular Crystallography, Pt A* 276, 307-326, 1997). Structures were solved through molecular replacement with Phaser (McCoy et al., *J Appl Crystallogr* 40, 658-674, 2007; Winn et al., *Acta Crystallogr D Biol Crystallogr* 67, 235-242, 2011), using a previously obtained free structure of 10E8 as a search model. Refinement of the structure was undertaken with Phenix (Adams et al., *Acta Crystallogr D Biol Crystallogr* 58, 1948-1954, 2002), with iterative model building using Coot (Emsley, P. & Cowtan, K. *Acta Crystallogr D Biol Crystallogr* 60, 2126-2132 (2004). The structure was validated with Mol-Probity (Davis et al., *Nucleic Acids Res* 35, W375-383, 2007), yielding 97% and 99.8% of residues falling within most favored Ramachandran regions and allowed Ramachandran regions, respectively. The structure was analyzed with APBS (Baker et al., *Proceedings of the National Academy of Sciences of the United States of America* 98, 10037-10041, 2001) for electrostatics (Ligplot; McDonald et al., *J Mol Biol* 238, 777-793, 1994), for direct contacts, PISA (Krissinel et al., *J Mol Biol* 372, 774-797, 2007), for buried surface areas, and LSQKAB (ccp4 Package; Winn, M. D. et al. *Acta Crystallogr D Biol Crystallogr,* 67, 235-242, 2011) for RMSD alignments. Helical wheels were generated using the program Pepwheel (150.185.138.86/cgi-bin/emboss/pepwheel). All graphics were prepared with Pymol (PyMOL Molecular Graphics System).

Assessment of Binding Affinities of 10E8 and 10E8 Variants to the Gp41 MPER.

Surface-Plasmon Resonance (SPR) (BIACORE® T200, GE Healthcare) was used to assess binding affinity of wild type 10E8 to a gp41 MPER peptide. A biotinylated peptide composed of residues 656-683 of the gp41 MPER (RRR-NEQELLELDKWASLWNWFDITNWLWYIR (SEQ ID NO: 26)-RRK-biotin; American Peptide, CA) was coupled to a BIACORE® SA chip to a surface density of 20-50 Response Units (RU). The 10E8 fragment of antigen binding (Fab) was then flowed over as analyte at concentrations ranging from 0.25 nM to 125 nM, at 2-fold serial dilutions, with association and dissociation phases of up to five minutes, at a flow rate of 30 ml/min. The binding of the 2F5 and 4E10 Fab controls to the same peptide were examined under identical conditions.

Binding affinities of the 10E8 paratope alanine mutants to the MPER were also assessed with SPR, but using an antibody capture method. A BIACORE® CM5 chip was amine-coupled with anti-human Fc antibody to high surface densities of ~10,000 RU. The 10E8 paratope variant IgGs were then captured to between 1500-2500 RU and a peptide composed of residues 656-683 of the gp41 MPER (RRR-NEQELLELDKWASLWNWFDITNWLWYIR(SEQ ID NO: 26)-RRR) flowed over as analyte at 2-fold serial dilutions starting at 500 nM (with the exception of HC D30A, W100bA, S100cA, P100fA, which started at 250 nM). Association and dissociation phases spanned three minutes and five minutes, respectively, at a flow rate of 30 µl/min. Binding sensograms were fit with 1:1 *Langmuir* models using BIACORE® BiaEvaluation® Software (GE Healthcare). In all cases, BIACORE® HBSEP+ buffer was used (10 mM Hepes, pH 7.4, 150 mM NaCl, 3 mM EDTA, 0.1% P-20).

PCR Amplification and Sequencing.

Extraction of viral RNA from plasma and cDNA synthesis were performed as previously described (Imamichi et al., *J Infect Dis* 183, 36-50, 2001). Single molecules of a 588 bp fragment, encompassing the MPER region of the HIV-1 envelope gene, obtained through limiting dilution, were PCR-amplified with the Expand High Fidelity PCR System (Roche Applied Science, Indianapolis, Ind.) using the following primer sets: +7789 (sense) 5'-TCTTAGGAGCA-GCAGGAAGCACTATGGG-3' (SEQI ID NO: 193) and −8524 (antisense) 5'-GTAAGTCTCTCAAGCGGTGG-TAGC-3' (SEQI ID NO: 194) in a first round reaction; +7850 (sense) 5'-ACAATTATTGTCTGGTATAGTGCAACA-GCA-3' (SEQI ID NO: 195) and −8413 (antisense) 5'-CCACCTTCTTCTTCGATTCCTTCGG-3' (SEQI ID NO: 196) in a second round reaction. Each round of PCR consisted of 25 cycles, with the initial denaturation at 94° C. for two minutes, followed by 25 cycles of denaturation at 94° C. for 15 seconds, annealing at 50° C. for 30 seconds, and extension at 72° C. for 1 minute, with the final extension at 72° C. for 7 min. The PCR products were purified with the QIA quick PCR purification kit (QIAGEN, Valencia, Calif.), and then cloned into pCR2.1-TOPO vector (TOPO TA Cloning it, Invitrogen, Carlsbad, Calif.) for sequence analysis of individual molecular clones. The DNAs from 18 independent clones were sequenced with the ABI BigDye Terminator v3.1 Ready Reaction Cycle Sequencing Kit (Applied Biosystems, Foster City, Calif.) and analyzed with the ABI PRISM 3130xl Genetic Analyzer (Applied Biosystems, Foster City, Calif.).

Statistical Analysis.

The relationship between the potency of N152 patient serum and 10E8, and the relationship between 10E8 variant binding and neutralization were evaluated by the Spearman rank method.

Deposits.

The nucleotide sequence of 10E8 heavy and light chains have been submitted to GenBank under accession numbers JX645769 and JX645770, each of which is incorporated by reference herein as present in GenBank on Sep. 18, 2012. Coordinates and structure factors for 10E8 Fab in complex with the gp41 MPER have been deposited with the Protein Data Bank under accession code 4G6F which is incorporated by reference herein as present in GenBank on Sep. 18, 2012.

Example 2

Neutralization Assays

This examples describes a method for testing of the neutralization breadth and potency of the antibodies disclosed herein.

Neutralization of the monoclonal antibodies was measured using a single round infection by HIV-1 Env-pseudoviruses and TZM-b1 target cells. HIV-1 Env-pseudoviruses were generated by co-transfection of 293T cells with pSG3ΔEnv backbone containing a luciferase reporter gene and a second plasmid that expressed HIV-1 Env. At 72 hours post-transfection, supernatant containing pseudoviruses were harvested and frozen at −80° C. until further use. Anti-gp41 membrane-proximal external region (MPER) specific activity of patient serum and antibodies was measured using the HIV-2/HIV-1 MPER chimeras. Wide-type HIV-2 7312A was used as a control. The 50% inhibitory concentration (IC50) was calculated as the antibody/inhibitor concentrations causing a 50% reduction of infection. For the competition assay, a fixed concentration of peptide was incubated with serially diluted 2F5, 4E10, Z13E1 or 10E8 Ab at 37° C. for 30 minutes before incubation of 7312A-C1 chimera. Epitope mapping assay was assessed by adding 0.5 μg/ml 10E8 Ab to serial dilutions of 4E10 peptide or its alanine mutants at 37° C. for 30 minutes prior to the addition of 7312A-C1 chimera. The neutralization blocking effect of the peptides was calculated as the fold change in the IC50 value of the antibody in the presence of 4E10 alanine mutants compared to the 4E10 wild-type peptide. Neutralization of 10E8 against HIV-1 COT6.15 alanine mutant pseudoviruses was also measured using a TZM-b1 assay (FIG. 36). Further neutralization of several HIV-1 strains was tested with 10E8 antibody as well as antibodies containing cross-complemented 10E8, 7H6, and 7N16 heavy and light chains (FIG. 37).

Example 3

ELISA Assays

Each antigen at 2 μg/ml was used to coat 96-well plates overnight at 4° C. Coated plates were blocked with BLOTTO buffer (PBS, 1% FBS, 5% non-fat milk) for one hour at room temperature, followed by incubation with antibody serially diluted in disruption buffer (PBS, 5% FBS, 2% BSA, 1% Tween-20) for one hour at room temperature. Horseradish peroxidase (HRP)-conjugated goat anti-human IgG antibody at 1:10,000 was added for one hour at room temperature. Plates were washed between each step with 0.2% Tween 20 in PBS. Plates were developed using 3,3', 5,5'-tetramethylbenzidine (TMB) (Sigma) and read at 450 nm.

Example 4

HIV-1 Monoclonal Neutralizing Antibodies Specific to Gp41 for Detecting HIV-1 in a Sample or a Subject This example describes the use of HIV-1 monoclonal neutralizing antibodies specific to gp41 for the detection of HIV-1 in a sample or a subject. This example further describes the use of these antibodies to confirm the diagnosis of HIV-1 in a subject.

A biological sample, such as a blood sample, is obtained from the patient diagnosed with, undergoing screening for, or suspected of having an HIV-1 infection. A blood sample taken from a patient who is not infected is used as a control, although a standard result can also be used as a control. An ELISA is performed to detect the presence of HIV-1 in the blood sample. Proteins present in the blood samples (the patient sample and control sample) are immobilized on a solid support, such as a 96-well plate, according to methods well known in the art (see, for example, Robinson et al., Lancet 362:1612-1616, 2003, incorporated herein by reference). Following immobilization, HIV-1 monoclonal neutralizing antibodies specific to gp41 that are directly labeled with a fluorescent marker are applied to the protein-immobilized plate. The plate is washed in an appropriate buffer, such as PBS, to remove any unbound antibody and to minimize non-specific binding of antibody. Fluorescence can be detected using a fluorometric plate reader according to standard methods. An increase in fluorescence intensity of the patient sample, relative to the control sample, indicates the gp41 antibody specifically bound proteins from the blood sample, thus detecting the presence of HIV-1 protein in the sample. Detection of HIV-1 protein in the patient sample indicates the patient has HIV-1, or confirms diagnosis of HIV-1 in the subject.

Example 5

HIV-1 Monoclonal Neutralizing Antibodies Specific for Gp41 for the Treatment of HIV-1

This example describes a particular method that can be used to treat HIV in a human subject by administration of one or more gp41-specific human neutralizing mAbs. Although particular methods, dosages, and modes of administrations are provided, one skilled in the art will appreciate that variations can be made without substantially affecting the treatment.

Based upon the teaching disclosed herein, HIV-1 can be treated by administering a therapeutically effective amount of one or more of the neutralizing mAbs described herein, thereby reducing or eliminating HIV infection.

Screening Subjects.

In particular examples, the subject is first screened to determine if they have an HIV infection. Examples of methods that can be used to screen for HIV infection include a combination of measuring a subject's CD4+ T cell count and the level of HIV in serum blood levels. Additional methods using the gp41-specific mAbs described herein can also be used to screen for HIV.

In some examples, HIV testing consists of initial screening with an enzyme-linked immunosorbent assay (ELISA)

to detect antibodies to HIV, such as to HIV-1. Specimens with a nonreactive result from the initial ELISA are considered HIV-negative unless new exposure to an infected partner or partner of unknown HIV status has occurred. Specimens with a reactive ELISA result are retested in duplicate. If the result of either duplicate test is reactive, the specimen is reported as repeatedly reactive and undergoes confirmatory testing with a more specific supplemental test (e.g., Western blot or an immunofluorescence assay (IFA)). Specimens that are repeatedly reactive by ELISA and positive by IFA or reactive by Western blot are considered HIV-positive and indicative of HIV infection. Specimens that are repeatedly ELISA-reactive occasionally provide an indeterminate Western blot result, which may be either an incomplete antibody response to HIV in an infected person, or nonspecific reactions in an uninfected person. IFA can be used to confirm infection in these ambiguous cases. In some instances, a second specimen will be collected more than a month later and retested for subjects with indeterminate Western blot results. In additional examples, nucleic acid testing (e.g., viral RNA or proviral DNA amplification method) can also help diagnosis in certain situations.

The detection of HIV in a subject's blood is indicative that the subject is infected with HIV and is a candidate for receiving the therapeutic compositions disclosed herein. Moreover, detection of a CD4+ T cell count below 350 per microliter, such as 200 cells per microliter, is also indicative that the subject is likely to have an HIV infection.

Pre-screening is not required prior to administration of the therapeutic compositions disclosed herein.

Pre-Treatment of Subjects.

In particular examples, the subject is treated prior to administration of a therapeutic agent that includes one or more antiretroviral therapies known to those of skill in the art. However, such pre-treatment is not always required, and can be determined by a skilled clinician.

Administration of Therapeutic Compositions.

Following subject selection, a therapeutically effective dose of a gp41-specific neutralizing mAb described herein is administered to the subject (such as an adult human or a newborn infant either at risk for contracting HIV or known to be infected with HIV). Additional agents, such as antiviral agents, can also be administered to the subject simultaneously or prior to or following administration of the disclosed agents. Administration can be achieved by any method known in the art, such as oral administration, inhalation, intravenous, intramuscular, intraperitoneal, or subcutaneous.

The amount of the composition administered to prevent, reduce, inhibit, and/or treat HIV or a condition associated with it depends on the subject being treated, the severity of the disorder, and the manner of administration of the therapeutic composition. Ideally, a therapeutically effective amount of an agent is the amount sufficient to prevent, reduce, and/or inhibit, and/or treat the condition (e.g., HIV) in a subject without causing a substantial cytotoxic effect in the subject. An effective amount can be readily determined by one skilled in the art, for example using routine trials establishing dose response curves. As such, these compositions may be formulated with an inert diluent or with an pharmaceutically acceptable carrier.

In one specific example, antibodies are administered at 5 mg per kg every two weeks or 10 mg per kg every two weeks depending upon the particular stage of HIV. In an example, the antibodies are administered continuously. In another example, antibodies or antibody fragments are administered at 50 µg per kg given twice a week for 2 to 3 weeks.

Administration of the therapeutic compositions can be taken long term (for example over a period of months or years).

Assessment.

Following the administration of one or more therapies, subjects with HIV can be monitored for reductions in HIV levels, increases in a subject's CD4+ T cell count, or reductions in one or more clinical symptoms associated with HIV. In particular examples, subjects are analyzed one or more times, starting 7 days following treatment. Subjects can be monitored using any method known in the art. For example, biological samples from the subject, including blood, can be obtained and alterations in HIV or CD4+ T cell levels evaluated.

Additional Treatments.

In particular examples, if subjects are stable or have a minor, mixed or partial response to treatment, they can be re-treated after re-evaluation with the same schedule and preparation of agents that they previously received for the desired amount of time, including the duration of a subject's lifetime. A partial response is a reduction, such as at least a 10%, at least 20%, at least 30%, at least 40%, at least 50%, or at least 70% in HIV infection, HIV replication or combination thereof. A partial response may also be an increase in CD4+ T cell count such as at least 350 T cells per microliter.

Example 6

PCR for 454 Sequencing of Patient N152 Cells

This example described a PCR assay for amplifying sample DNA for deep sequencing. Process included generation of cDNA from patient cells using RT PCR followed by amplification of VH3 and VL3 genes from the generated cDNA.

Sample of patient N152 had 33-36 million PBMCs/ml.

mRNA was prepared using Qiagen Oligotex Kit (as described in manufacturer's instructions).

RT PCR was performed on mRNA using Invitrogen reagents (which included oligo dT as primer, and Superscript II RT).

After RT PCR reactions, cDNA was then subjected to amplification using VH3 and VL3 gene specific primers meant to amplify from the leader sequences of the alleles IGHV3-15*05 and IGLV3-19*01, which are the putative precursors of 10E8.

The primers used were as follows:

```
5' Heavy Chain
>XLR-A_5L-VH3
                                      (SEQ ID NO: 28)
CCATCTCATCCCTGCGTGTCTCCGACTCAGAAGGTGTCCAGTGTGARGT

GCAG

>XLR-A_VH3-L1-MP
                                      (SEQ ID NO: 29)
CCATCTCATCCCTGCGTGTCTCCGACTCAGGCTATTTTAAAAGGTGTCC

AATGT

>XLR-A_VH3/4_L1_MP
                                      (SEQ ID NO: 30)
CCATCTCATCCCTGCGTGTCTCCGACTCAGGTGGCAGCTCCCAGATGGG

TCCTGTC
```

-continued

>XLR-A_VH3/4_L3_MP
(SEQ ID NO: 31)
CCATCTCATCCCTGCGTGTCTCCGACTCAGGTTGCAGTTTTAAAAGGTG

TCCAGTG

5' Light Chain
>XLR-A_5L-VL3
(SEQ ID NO: 32)
CCATCTCATCCCTGCGTGTCTCCGACTCCAGGCTCTGTGACCTCCTATG

AGCTG

>XLR-A_5MP-VL3-1
(SEQ ID NO: 33)
CCATCTCATCCCTGCGTGTCTCCGACTCAGGCTTACTGCACAGGATCCG

TGGCC

>XLR-A_5MP-VL3-19
(SEQ ID NO: 34)
CCATCTCATCCCTGCGTGTCTCCGACTCAGACTCTTTGCATAGGTTCTG

TGGTT

>XLR-A_5MP-VL3-21
(SEQ ID NO: 35)
CCATCTCATCCCTGCGTGTCTCCGACTCAGTCTCACTGCACAGGCTCTG

TGACC

Samples were gel extracted and purified by phenol-chloroform.
Final yield: 1.15 µg Heavy Chain; 0.9 µl Light Chain
0.5 µg of each chain was sent for 454 sequencing.
Total number of sequences obtained from a full 454 chip for each chain: Heavy Chain: 843084 raw sequences, 37669 sequences belonging to IGHV3-15 family; Light Chain: 1219214 raw sequences, 91951 sequences belonging to IGKV3-15 family Example 7

Method for Isolating and Producing Monoclonal Antibodies without Prior Knowledge of Antigen Specificity This example illustrates a method to isolate and produce all antibodies that an organism produces against a target antigen, such as a virions, cancers, or toxins. Current methods for the isolation and production of monoclonal antibodies rely upon specific, known epitopes to isolate and produce new monoclonal antibodies. Using these methods, B cells are sorted and immunoglobulin genes are isolated based on epitope specificity. These methodologies, however, may be biased because they rely upon previously known epitopes or antibody specificities. Additionally, because these methodologies rely upon previously known antibody specificities or epitopes, these methodologies do not permit the discovery of new monoclonal antibodies with unknown epitope specificities. Unlike current methodologies, this methodology starts with a population of B-cells from an organism which is representative of all B cells produced by the organism. This population is expanded and screened for activity against a functionality or antigen of interest such as a virion, toxin, protein, or cancer. This permits the isolation of a full repertoire of memory B-cells that an organism produces specific to an antigen without prior knowledge of specificity or binding characteristics. For example, memory B-cells in this repertoire can be screened for a functional activity (such as neutralization activity) and used to produce monoclonal antibodies specific to the antigen.

Methods

Staining and single-cell sorting of memory B cells are performed as follows.

Isolation of B Cells

Figure 42B:
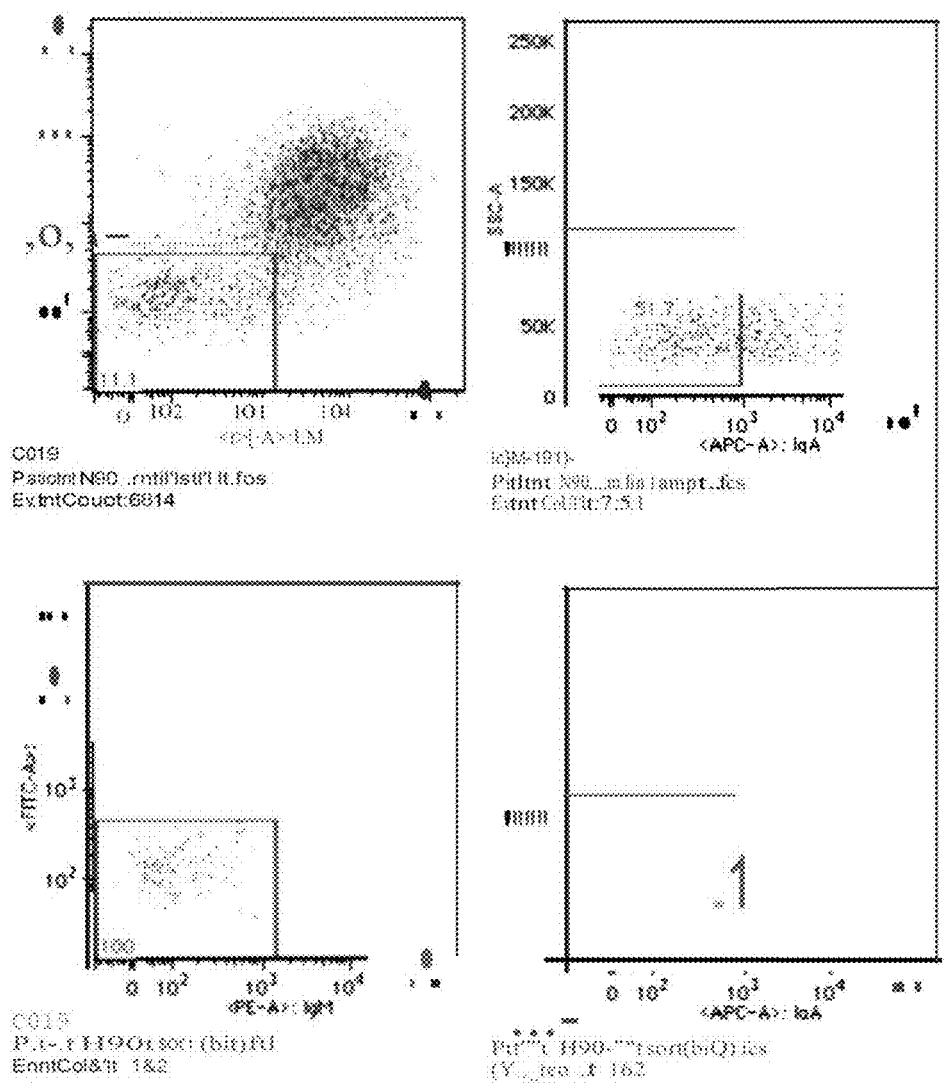

PBMCs from a subject previously exposed to the target antigen (such as a subject with HIV-1 infection, if the target antigen is an HIV-1 antigen) are stained with antibody cocktail consisting of anti-CD19-PE-Cy7 (BD Bioscience), IgA-APC (Jackson ImmunoResearch Laboratories Inc.), IgD-FITC (BD Pharmingen), and IgM-PE (Jackson ImmunoResearch Laboratories Inc.) at 4° C. in dark for 30 min. The cells are then washed with 10 ml PBS-BSA buffer and resuspended in 500 µl PBS-BSA. CD19+IgA-IgD-IgM- memory B cells are sorted using a FACSAria III cell sorter (Becton Dickinson). FIG. 42 illustrates results of FACS isolation of CD19$^+$IgA$^-$IgD$^-$IgM$^-$ B cells from a PBMC sample.

Additional Description of Isolation of B Cells

1. Prepare FACSARIA III® cell sorter (Becton Dickinson, Franklin Lakes, N.J.):
   a. turn on, warm up, and run CST; run Auto Drop delay (follow steps in manual);
   b. make a bottle of sterile PBS-BSA (or re-filter existing bottle)
   c. sterilize the tubing: (1) load a sample of 15% contrad and run for five minutes at flow rate 8; (2) load a sample of 10% bleach and run for five minutes at flow rate 8; (3) load a sample of sterile PBS-BSA (in sterile tube) and run for minutes at flow rate 8; (4) reset to flow rate 1
   d. aim the sort stream: (1) put an empty guava tube in sort block and attach the block; (2) open stream door; (3) Diva: in the sidestream window (called "70 micron"), open waste drawer; make sure sliders 1, 3, 4 are set to zero, slider 2 should be around 48; (4) click Voltage then Test Sort; (5) look in the stream door—is the sort stream hitting the center of the tube?; (6) use sliders on sidestream window to adjust stream so it's centered; (7) click Voltage to turn off; close waste drawer
   e. DIVA (Aria software): copy an old template by choosing a previous sort, then "Duplicate without data" or set up new experiment with gating as shown below
   f. Attach chiller tubing to sort block; turn on chiller
2. Prepare cells:
   a. thoroughly clean hood and pipets with ethanol before starting
   b. make at least 400 ml IMDM (with glutamax)/10% FBS/mycozap
   c. warm two 15 ml conical tube of 7.5 ml IMDM/10% FBS with 15 µl benzonase
   d. make staining master mix in eppindorf tube:
      spin IgM and IgA antibodies 1 min before aliquotting
      make master mix: 50 µl per 50 million cells antibody

|            | for 1x    | for 2.5x   |
|------------|-----------|------------|
| CD19-PE-Cy7| 0.5 µl    | 1.25 µl    |
| IgM-PE     | 1.0 µl    | 2.5 µl     |
| IgA-APC    | 2.5 µl    | 6.25 µl    |
| IgD-FITC   | 2.5 µl    | 6.25 µl    |
| PBS-BSA    | 43.5 µl   | 108.75 µl  | spin 20 minutes at 4° C. in microfuge; FACS Dyes (PE: Phycoerythrin; Cy7: a cyanine dye; APC: Allophycocyanin; FITC: fluorescein isothiocyanate; CD19-PE-Cy7 (anti-CD19 mAb conjugated with Dyes- specific to B-cells (except plasma b cells); IgA: and IgA mAb; IgD: anti-IgD mAb; IgM: anti-IgM mAb e. thaw 2 vials patient cells: (1) warm vial in water bath until floating ice is visible; (2) add 1 ml prewarmed medium/benzonase to vial, let sit 15 sec.; (3) move all vial contents to the 15 ml conical tube of warm medium; (4) pellet 1200 rpm 10 min; (5) resuspended each in 1 ml PBS-BSA, combine, move 50 µl to each of 5 conical tubes; (6) pellet all 6 conical tubes; (7) NOTE—if only one vial needed, you can skip steps v. and vi.

f. resuspended cell pellets: (1) main sample: in 100 µl master mix; (2) comps in 50 µl PBS-BSA, add single stains (0.5 µl CD19-PE-Cy7 etc)

g. 30 min 4° C. covered in foil h. wash: add 1000 µl PBS-BSA with P1000, mix well, add 2 ml more PBS-BSA i. pellet, meanwhile open new bag of filter cap tubes in hood and label them j. resuspended in 500 µl PBS-BSA and transfer to sterile filter-cap tubes by squirting cells thru the cap (touch tip to cap while squirting)

k. keep cold until ready to flow

3. Sort cells: (1) load on Aria, gate as shown in example; use old compensation if voltages look OK, otherwise, adjust voltages and run compensation; (2) adjust flow rate between 1-2 so that event rate is as high as possible but no more than 13,000 evt/sec. monitor this during sorts; (3) set up sort (Click on Sort >New sort layout; Purity 1.5; Sort: continuous; Choose gate P6 for sorting into on Left); (4) Put 250 µl medium into 2 ml o-ring tube, load into sort block e. Test sort 500 cells; (5) Unload sample, return to cold; (6) Run sample line backflush for 1-2 minutes, then load fresh tube of PBS-BSA at flow; (7) rate 8 for two minutes to clean out main sample; (8) Remove sort tube from sort block, use P1000 to gently wash down the sides using medium in tube; (9) Move all to a flow tube; (10) Flow and record the post sort purity; (12) Load main sample on Aria and sort 20000-30000 B cells; (13) Repeat steps 5-7; (14) Take 10 µl, add to 100 µl PBS-BSA in flow tube, flow and record the post sort purity; (15) Put 270 µl Guava ViaCount in a guava tube, add 30 µl sorted cells, two minutes, then count on Guava (record concentration only; it will not accept 0.25 ml as volume); (16) Calculate amount of cells needed to plate at desired density.

Treating the Cells with Growth Factors to Induce Cell Division

CD19+IgA−IgD−IgM− Memory B cells are resuspended in Iscove's Modified Dulbecco's Medium IMDM medium with 10% FBS containing 100 U/ml IL-2, 50 ng/ml IL-21 and $1 \times 10^5$/ml irradiated 3T3-msCD40L feeder cells produced as previously described (Kershaw et al., Cancer Res., 61: 7920-7924, 2001). B cells are seeded into 384-well microtiter plates at a density of 4 cells/well in a final volume of 50 µl.

Additional Description of Treating Cells with Growth Factors

1. Prepare plating conditions: (1) Thaw 1 vial of 35×106 irradiated 3T3-msCD40L cells (benzonase method), resuspended in 10 ml IMDM/10% FBS; (2) Calculate reagent amounts
    a. Concentrations (Feeder Mix): 3T3-msCD40L: 5000 cells/50 ul/well=$10^5$ cells/ml; IL2 100 u/ml; IL21 50 u/ml; In IMDM cell culture media/10% FBS (see above); For 20 plates=350 ml: 336 ml IMDM/10% FBS; 3.5 ml IL2 (10000 u/ml); 175 µl IL21; 10 ml 3T3msCD40L
    b. Make feeder mix as calculated; For 10 plates: set aside 12.5 ml for no-B cell control.

2. Plate cells: (1) Use 384-well white plates; label them on lid and on side of plate; (2) Use 12-channel pipets; (3) Angled plate holders may be useful; (4) Place 100 µl sterile dI-H2O with gent in outer wells (need 7.7 ml/plate); (5) Before adding b cells to mix, plate 50 µl/well feeders mix in row D of all plates (this is; (6) no-antibody control); (7) Add appropriate amount of B cells to remaining feeders mix (For 10 plates, 2.5 B cells/well=50 cells/ml, need 8125 B cells); (8) Move cell mix to large sterile basins, and plate 50 µl/well in inner 308 wells (except row D); (9) Be sure to mix the cells in the basin frequently; (10) Plate an extra quarter-plate for ELISA later; (11) Move to back of incubator, leave undisturbed for 13 days 3. Supplies: IL2-Roche-11147528001 (50 ml); IL21-Invitrogen-PHC0215 (25 ug); IMDM+Glutamax-Invitrogen-31980-097 (1×10 btls)

Incubation and Supernatant Neutralization Screening

After 13 days of incubation, 40 µl of culture supernatants from each well are collected and screened for neutralization activity using a functional target of the antigen of interest (for example, if an HIV-1 antigen is the target antigen, the neutralization assay can be a high throughput micro-neutralization assay against HIV-1MN.03 and HIV-1Bal.26).

Additional Description of Collection of Supernatant for Neutralization Assay

1. Collection of supernatant for Neutralization assay
    a. Prepare an ELISA plate beforehand (coat a Maxisorp™ plate with anti-IgG); Clean hood and pipets with ethanol and then RNaseAway™; label as many 384 well white plates as you have day 11 plates
    b. move 40 µl from each well of day 11 plate to corresponding well of fresh plate: (1) use a 12 channel pipette; (2) get tip as far down in well as possible—Ok to touch bottom lightly, move tip up slightly, then pull up; (3) dispense to new plate; (4) cover sups plates with foil sticker and put lid on; quarter-plate goes to 4° C.; (5) store sups plates at −80 and use as needed for neutralization assay
    c. make catch-lysis buffer—enough for 308 wells*1.15*number of plates: for 1 well (0.3 µl Tris, pH 8, 1M; 0.25 µl RNase Inhibitor; 19.45 µl depc-treated H2O); put 20 µl catch-lysis buffer onto all B cells wells (dispense with multi-channel pipette; cover with foil sticker and put lid on; store at −80° C.); perform ELISA using 10 µl of sup from quarter-plate to measure IgG concentration and hit rate Production of Monoclonal Antibodies B cells in each well are lysed with 20 µl lysis buffer containing 0.25 µl of RNase inhibitor (New England Biolabs Inc.), 0.3 µl of 1M Tris pH8 (Quality Biological Inc.) and 19.45 µl DEPC-treated H2O. The plates with B cells are stored at −80° C. The variable region of the heavy chain and the light chain of the immunoglobulin gene are amplified by RT-PCR from the wells that scored positive in the neutralization assay. The cDNA product is used as template in the PCR reaction. In order to amplify the highly somatically mutated immunoglobulin gene, two sets of primers as described previously (Tiller et al., J. Immunological Methods, 329:112-124, 2008) are used in two independent PCRs. One set of primers includes the forward primers and the reverse primers specific for the leader region and constant region of IgH, Igκ or Igλ, respectively. The other set of primers includes the forward primer mixes specific for FWR1 and respective reverse primers specific for the IgH, Igκ and Igλ J genes. All PCRs are performed in 96-well PCR plates in a total volume of 50 µl containing 20 nM each primer or primer mix, 10 nM each dNTP (Invitrogen), 10 μl 5×Q-solution (Qiagen) and 1.2 U HotStar Taq DNA polymerase (Qiagen). From the positive PCR reactions, pools of the VH or VL-region DNA are ligated to a pCR2.1-Topo-TA vector (Invitrogen) for sequencing before cloning into the corresponding Igγ1, Igκ and Igλ expression vector. 10 μg of heavy and light chain plasmids, cloned from the same well and combined in all possible heavy and light chain pairs, is mixed with 40 μl FUGENE® 6 (Roche) in 1500 μl DMEM (Gibco) and co-transfected into 293T cells. The full-length IgG is purified using a recombinant protein-A column (GE Healthcare).

Neutralization Assays for Monoclonal Antibodies

Following purification of full length IgG, the produced antibodies are tested for neutralization activity.

For example, if the antigen of interest is an HIV-1 antigen, the neutralization activity of the monoclonal antibodies can be measured using single-round HIV-1 Env-pseudoviruses infection of TZM-b1 cells. HIV-1 Env-pseudoviruses can be generated by co-transfection of 293T cells with pSG3 Env backbone and a second plasmid that expressed HIV-1 Env. At 72 hours post-transfection, supernatants containing pseudovirus are harvested and frozen at −80° C. until further use. In the neutralization assay, 10 μl of 5-fold serially diluted patient serum or mAb is incubated with 40 μl pseudovirus in a 96-well plate at 37° C. for 30 minutes before addition of TZM-b1 cells. After 2 days of incubation, cells are lysed and the viral infectivity quantified by measuring luciferase activity with a VICTOR® Light luminometer (Perkin Elmer). The 50% inhibitory concentration (IC50) is calculated as the antibody concentration that reduces infection by 50%.

Example 8

10E8 Modifications

This example illustrates modifications of the 10E8 antibody to increase affinity for gp120, without increasing autoreactivity. As described below, several approaches were undertaken to identify and design improvements to the 10E8 antibody, including Structure-based alanine scanning mutagenesis of 10E8 paratope; Structure-based mutagenesis to enhance hydrophobic interactions; Partial germline reversion; combination of these approaches, and 454 deep pyrosequencing of patient N152 B-cells to identify phylogenetic variants of 10E8 with improved potency. In addition, combinations of these four approaches were also undertaken, combining the best elements and results from each. Below is a summary of each of the four approaches with the rationale behind each.

(1) Structure-Based Alanine Scanning Mutagenesis of 10E8 Paratope

Figure 43:
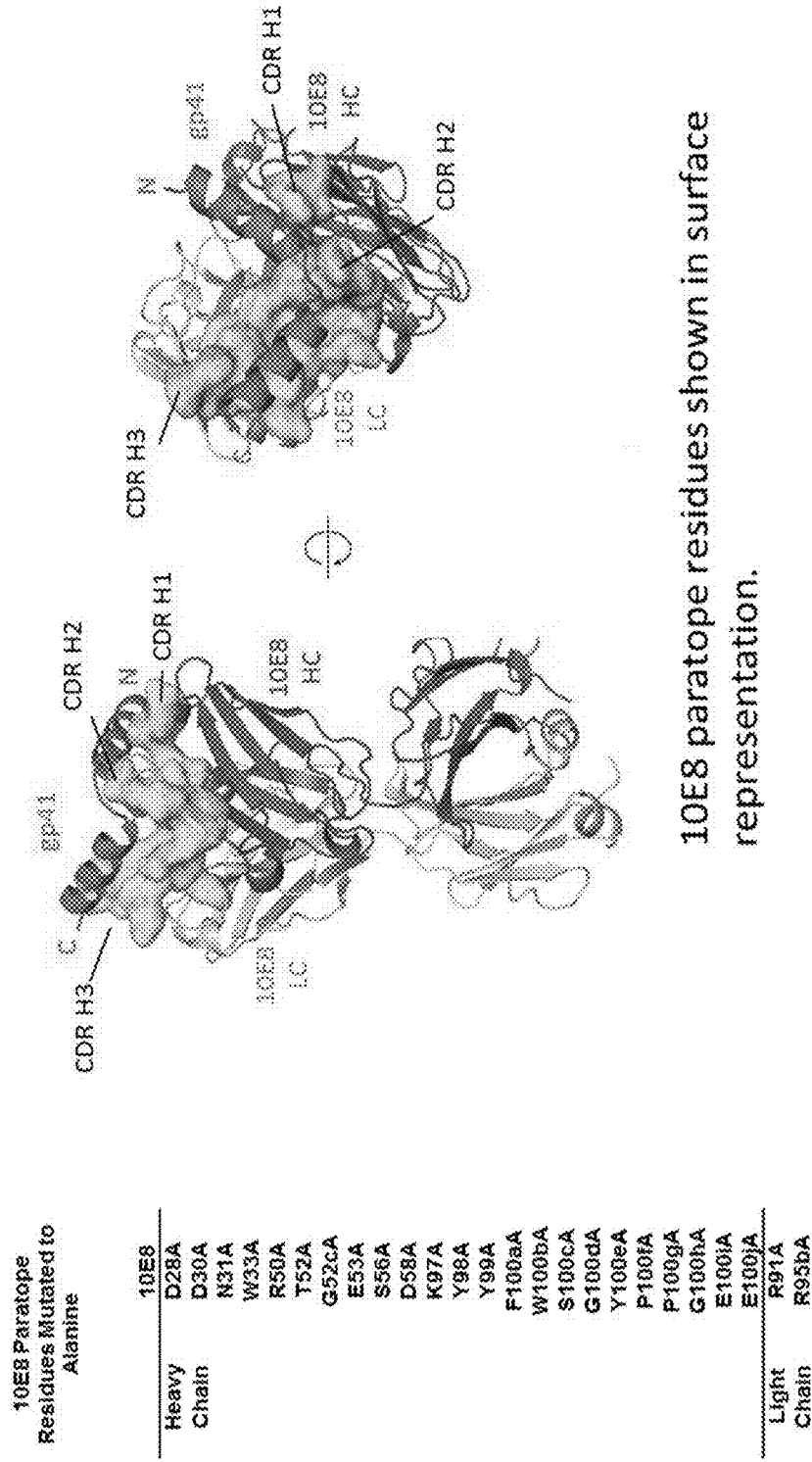
FIG. 43 is a table and a set of ribbon diagrams illustrating an alanine scan of the indicated 10E8 residues (Kabat positions) as described in Examples 1 and 8.

Based on the crystal structure of 10E8 Fab with the gp41 MPER (described above), heavy chain residues of the paratope of 10E8 were mutated to alanine. Mutant antibody constructs were generated using standard techniques, and the antibodies were expressed and purified as described in Example 1. All residues of the 10E8 paratope were mutated to alanine (see FIG. 43), and several residue positions led to enhanced 10E8-mediated virus neutralization (see FIGS. 32 and 49). These include 10E8 residues D28, D30, N31, T52, E53, S56, D58, and Y100e (Kabat numbering). Neutralization assays were performed as described in Example 2.

(2) Structure-Based Mutagenesis to Enhance Hydrophobic Interactions

Figure 44A:
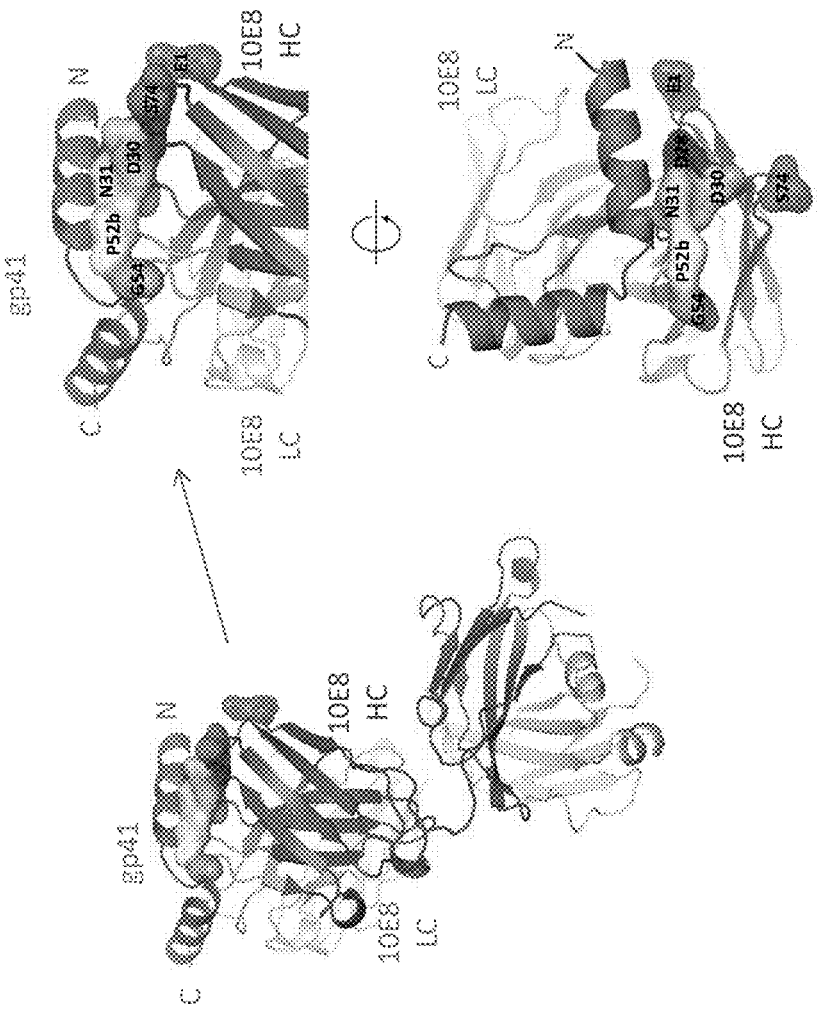
FIGS. 44A and 44B are a series of ribbon diagrams illustrating the structure-based mutagenesis of 10E8 to enhance hydrophobic interactions with gp41.
Figure 44B:
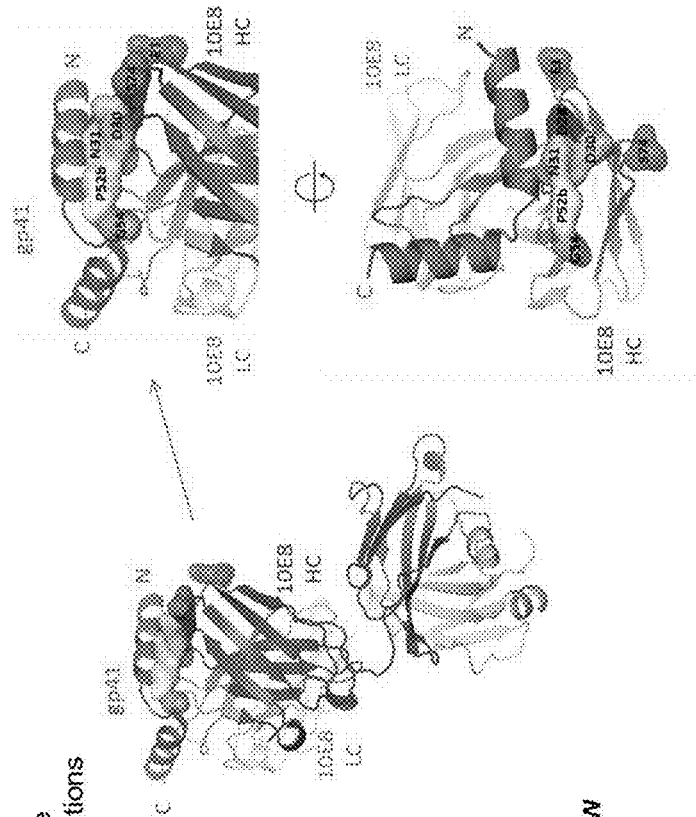
Figure 46:
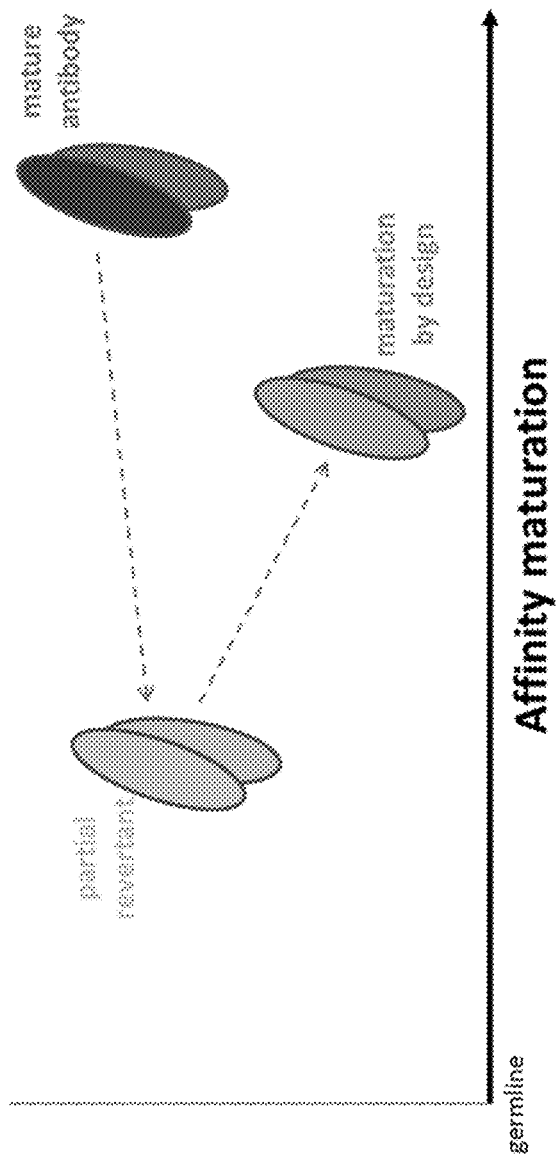
FIG. 46 is a schematic diagram illustrating design of partially-reverted antibody variants.

Based on the crystal structure of 10E8 Fab with the gp41 MPER, residues that were deemed to be co-planar with the 10E8 epitope were mutated to hydrophobic residues (see FIGS. 44A and 44B). Mutant antibody constructs were generated using standard techniques, and the antibodies were expressed and purified as described in Example 1. As shown in FIG. 45, several residue positions, both singly and in combination, resulted in increased neutralization potency of 10E8. Of the mutants listed in FIG. 45, mutation of residue S74 to tryptophan generated the greatest increase in neutralization, followed by the double mutant D30-N31 and the single mutant D28. Neutralization assays were performed as described in Example 2.

(3) Partial Germline Reversion

Figure 47:
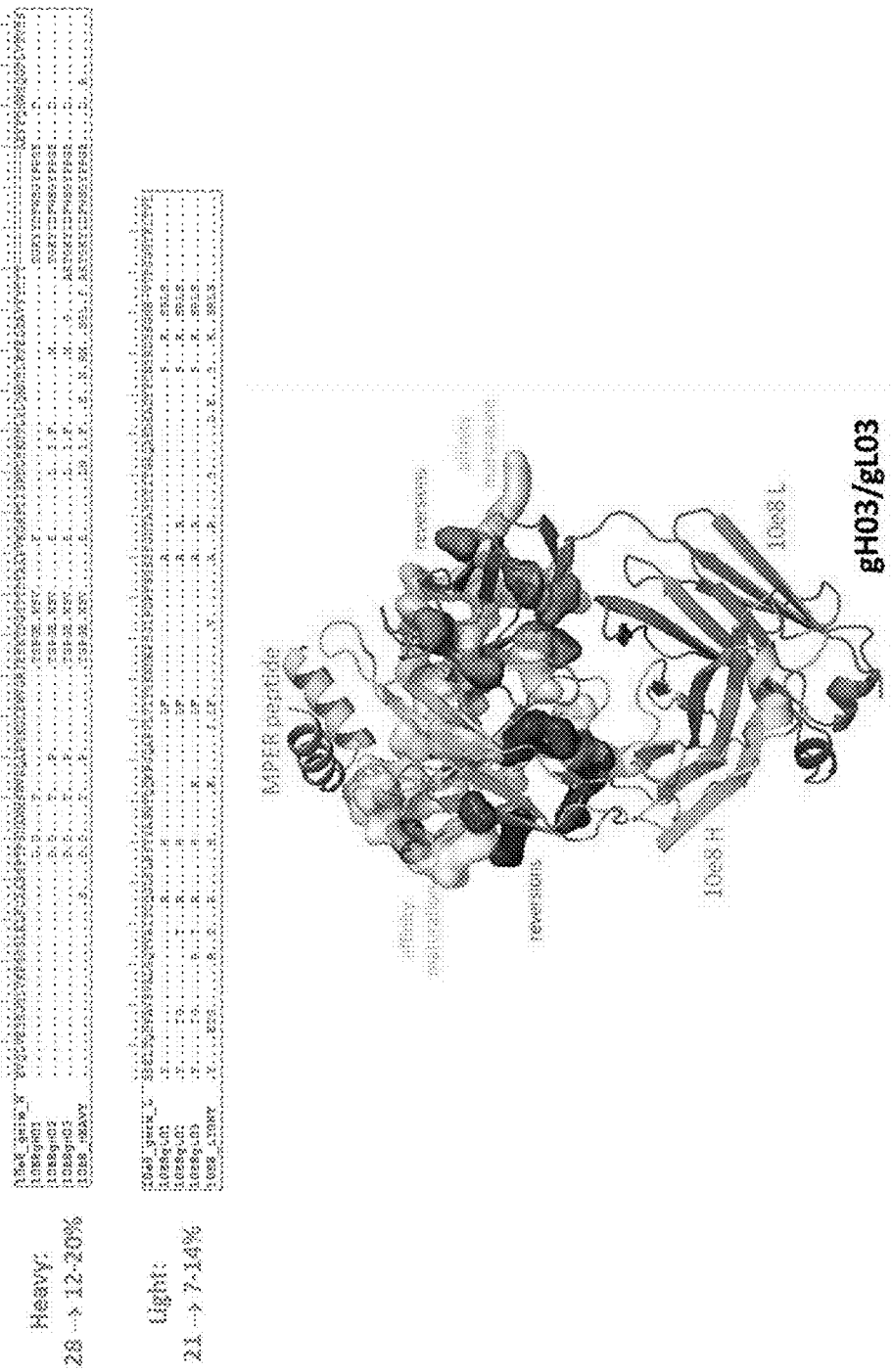
FIG. 47 is a sequence alignment and a ribbon diagram illustrating partial germline revertants of the 10E8 heavy and light chain. The sequences shown are SEQ ID NO: 7 (10E8_germ_H), SEQ ID NO: 147 (10E8gH01), SEQ ID NO: 148 (10E8gH02), SEQ ID NO: 149 (10E8gH03), SEQ ID NO: 1 (10E8_HEAVY), SEQ ID NO: 8 (10E8_germ_L), SEQ ID NO: 150 (10E8gL01), SEQ ID NO: 151 (10E8gL02), SEQ ID NO: 152 (10E8gL03), SEQ ID NO: 2 (10E8_LIGHT).

CDR grafting was used to revert a fraction of the 10E8 maturation changes back to the germline sequence. CDR grafting is a procedure that is typically used for humanization of antibodies from a non-human (e.g., mouse) source: the procedure uses a sequence alignment of the non-human antibody with a human counterpart (typically a human germline gene) and retains the original antibody CDR's but mutates selected framework residues to the respective human identities. Framework residues are selected for mutation based on structural and sequence analysis. In certain instances, not all of the observed maturation changes in an antibody may be beneficial, and partial reversion to germline may help improve certain antibody properties, such as increased half-life, decreased immunogenicity, or improved potency. By applying CDR grafting to 10E8, three different heavy chain revertants and three different light partially reverted chains were designed (see FIG. 47). At the amino acid level, the mutation rates were decreased from 28% to 12-20% for the heavy chain and from 21% to 7-14% for the light chain. The mutated antibodies were constructed and produced using standard methods as described in Example 1. Different combinations of heavy and light chain revertants were tested for binding to MPER and for neutralization (see FIG. 48). The largest improvement in neutralization (<2-fold) was observed for the revertant that included the heavy and light chain reversions closest to the mature antibody ("10E8-R3," which includes the 10E8gH03 heavy chain (SEQ ID NO: 149) and the 10E8gL03 light chain (SEQ ID NO: 152)). Additional improvements were observed when the revertants were paired with heavy/light chains from other sources (such as deep sequencing, discussed below).

(4) Additional Mutations

Figure 49:
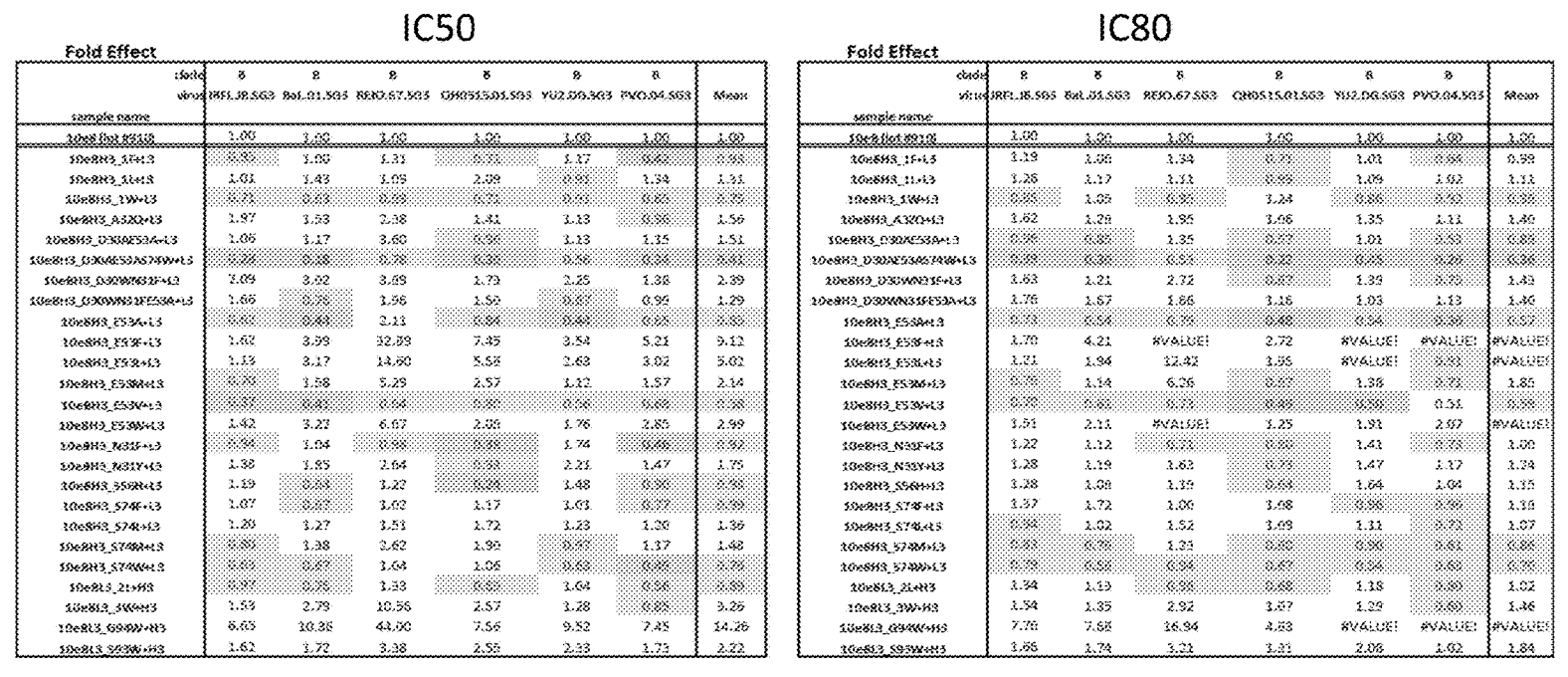

Based on neutralization data, revertant analysis, paratope alanine scanning, and enhanced hydrophobicity designs described above, the following additional mutations were introduced into the 10E8gH03 heavy chain variant of 10E8 and the 10E8gL03 light chain variant of 10E8, antibodies were constructed and produced according to standard methods as described in Example 1, and tested for neutralization activity according to methods described in Example 2 (FIG. 49)

TABLE 1

Additional 10E8 variant heavy and light chains

Figures 51A, 51B:
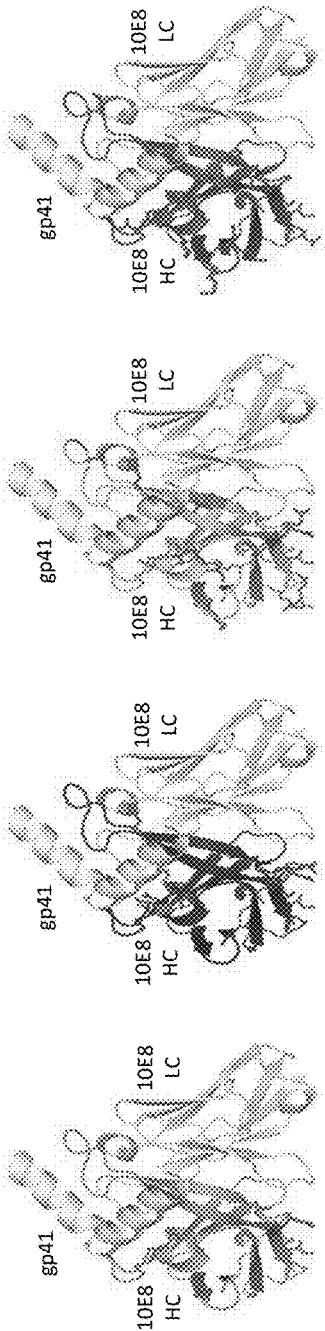
Figure 51C:
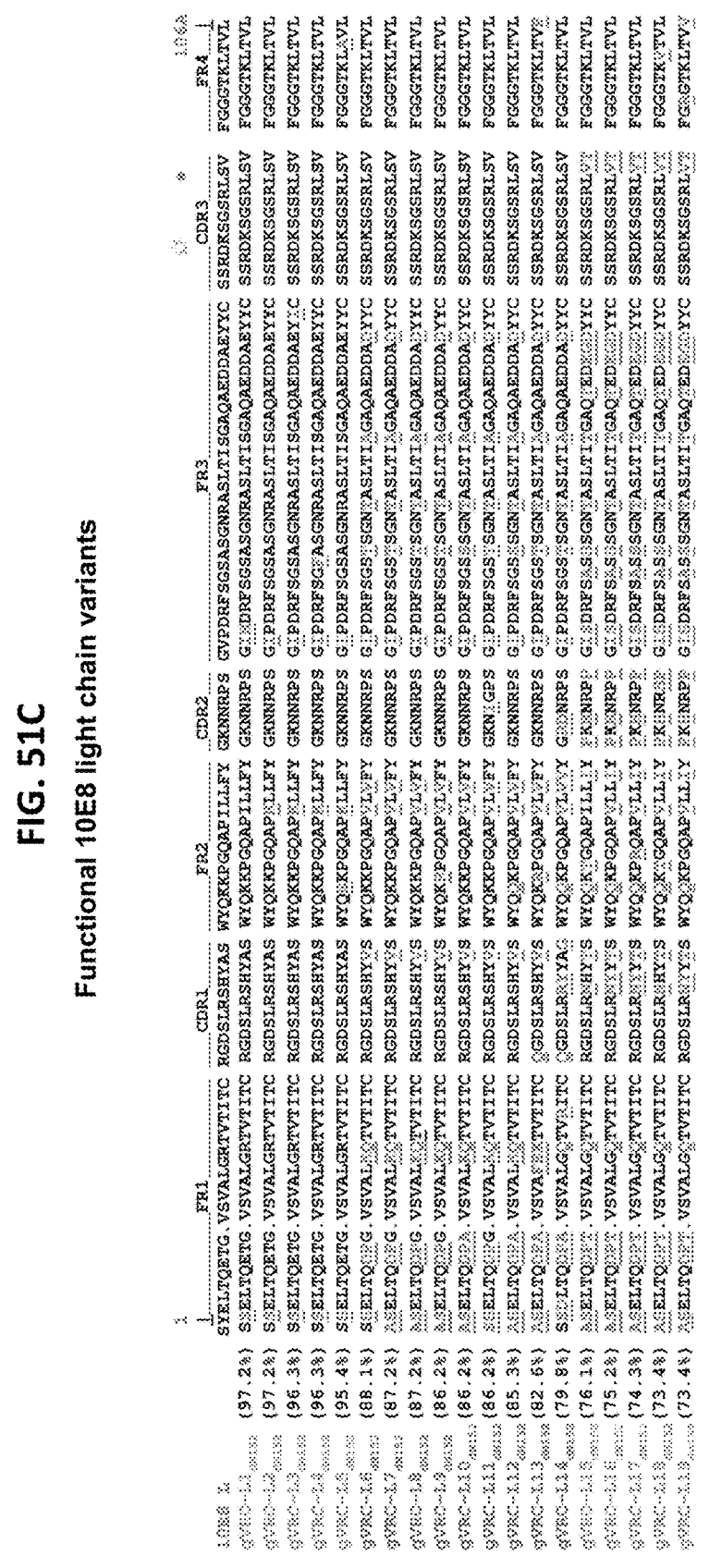
Figure 51D:
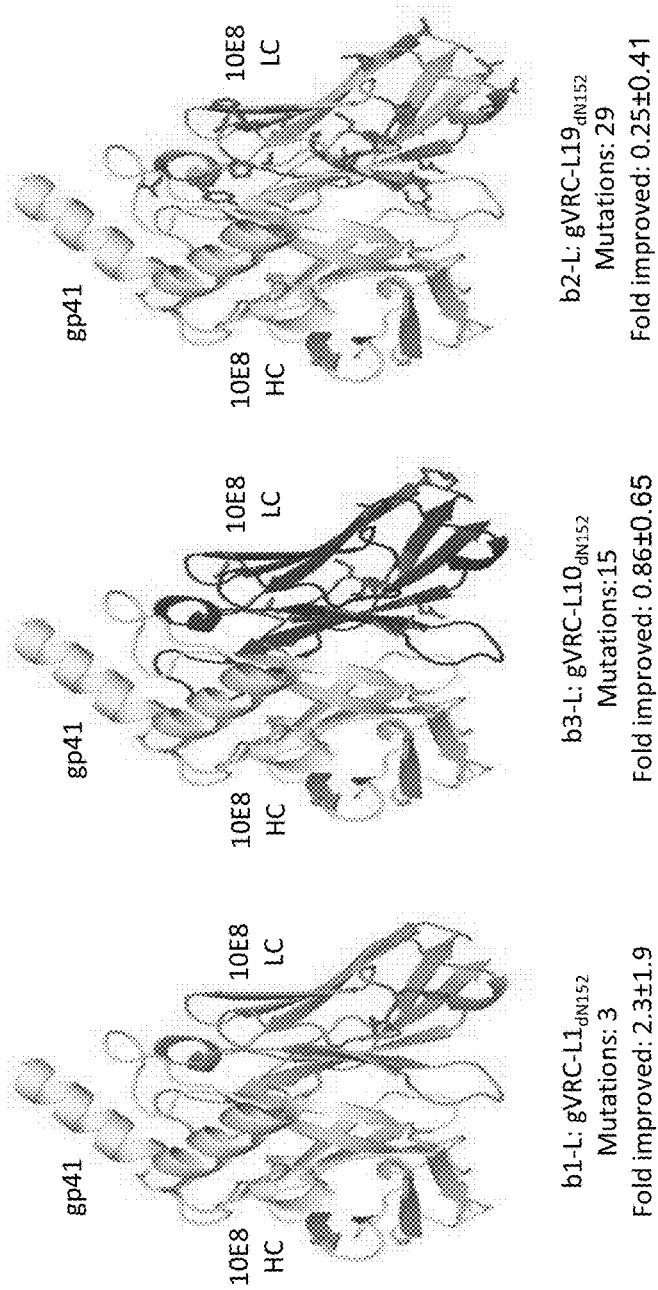

| Name in FIG. 51 | Heavy chain 10E8gH03 (SEQ ID NO: 149) with Additional mutants" | Light Chain 10E8gL03 (SEQ ID NO: 152) with Additional mutants |
|---|---|---|
| 10E8H3_1F + L3 | 1F | — |
| 10E8H3_1L + L3 | 1L | — |
| 10E8H3_1W + L3 | 1W | — |

TABLE 1-continued

Additional 10E8 variant heavy and light chains

| Name in FIG. 51 | Heavy chain 10E8gH03 (SEQ ID NO: 149) with Additional mutants" | Light Chain 10E8gL03 (SEQ ID NO: 152) with Additional mutants |
|---|---|---|
| 10E8H3_A32Q + L3 | A32Q | — |
| 10E8H3_D30AE56A + L3 | D30A + E53A | — |
| 10E8H3_D30AE56AS77W + L3 | D30A + E53A + S74W | — |
| 10E8H3_D30WN31F + L3 | D30W + N31F | — |
| 10E8H3_D30WN31FE56A + L3 | D30W + N31F + E53A | — |
| 10E8H3_E56A + L3 | E53A | — |
| 10E8H3_E56F + L3 | E53F | — |
| 10E8H3_E56L + L3 | E53L | — |
| 10E8H3_E56M + L3 | E53M | — |
| 10E8H3_E56V + L3 | E53V | — |
| 10E8H3_E56W + L3 | 1E53W | — |
| 10E8H3_N31F + L3 | 10N31F | — |
| 10E8H3_N31Y + L3 | N31Y | — |
| 10E8H3_S59H + L3 | S56H | — |
| 10E8H3_S77F + L3 | S74F | — |
| 10E8H3_S77L + L3 | S74L | — |
| 10E8H3_S77M + L3 | S74M | — |
| 10E8H3_S77W + L3 | S74W | — |
| 10E8L3_2L + H3 | — | 2L |
| 10E8L3_3W + H3 | — | 3W |
| 10E8L3_G94W + H3 | — | G94W |
| 10E8L3_S93W + H3 | — | S93W |

(5) 454 Deep Pyrosequencing to Identify Phylogenetic Variants of 10E8 with Improved Potency This example illustrates the identification and functional pairing of 10E8-like heavy and light chains sequences determined in separate 454 pyrosequencing reactions. Beginning from the wild-type sequence of 10E8 neutralizing antibody, clonal variants for heavy and light chain were identified and assessed for function by pairing with the wild-type 10E8 complementary chain. The phylogenetic trees of the heavy and light chains revealed similar branch topologies around the wild-type 10E8 sequences, allowing branches of the heavy- and light-chain phylogenetic trees to be matched based on their relative distances from 10E8. By assessing a matrix of antibodies reconstituted from matched and mismatched branches for neutralization of HIV-1 and reactivity with auto-antigens, the impact of phylogenetic pairing on function was quantified.

The broadly neutralizing antibody 10E8 was identified in the HIV-1-infected donor N152, and recognizes a helix in the membrane-proximal external region (MPER) just prior to the transmembrane-spanning region of the HIV-1 gp41 glycoprotein, and neutralizes 98% of diverse HIV-1 isolates at a 50% inhibitory concentration (IC50) of 0.32 ug/ml. The heavy chain of antibody 10E8 derives from IgHV3-15 and IgHJ1, has a third complementarity determining region (CDR H3) of 22 amino acids, and displays a somatic mutation rate of 21%. The light chain of antibody 10E8 derives from IgVL3-19 and IgLJ3, has a CDR L3 of 12 amino acids, and displays a somatic mutation rate of 14%. Deep sequencing of donor B cell transcripts using polymerase chain reaction (PCR) to amplify IgG heavy chain sequences from the IgHV3 family and to amplify IgG light chain sequences from the IgVL3 family was performed as described in Example 6. mRNA from an estimated 5 million peripheral blood mononuclear cells (PBMCs) was used for reverse transcription to produce template cDNA, and, in both cases, primers that were upstream from the start of the V-gene leader sequences and downstream from the end of J chain were used.

Roche 454 pyrosequencing provided 843,084 heavy chain reads and 1,219,214 light chain reads for donor N152 (see FIG. 50). After primary analysis using a bioinformatics pipeline 36,318 heavy chain sequences were assigned to the IgHV1-3 allelic family and 54,583 light chain sequences were assigned to the IgVL3-IgJ3 allelic families (see, e.g., Wu et al., Science, 333, 1593-1602, 2011, and Zhu et al., Frontiers in microbiology, 3, 315-315, 2012). Reads were analyzed for identity to 10E8 and divergence from the unmutated V-genes, and their frequencies plotted on identity/divergence grids (FIGS. 50A and 50B, left panels). Notably with the heavy chain several well-separated islands of high identify and about 25% divergence were observed, and with the light chain, a single well-separated island of high identify and about 15% divergence was observed. Grid-based sampling of the high identity-divergence region, selected 61 heavy chain sequences and 48 light chain sequences. The phylogenetic relationship of these sequences to 10E8 was analyzed (FIGS. 50C and 50D) and also synthesized, reconstituted with the complementary wild-type 10E8 chain, and expressed by transient transfection in a 96-well format. Enzyme-linked immunosorbent assays (ELISAs) of the expressed 10E8 variants identified 11 heavy chains and 24 light chains (the nomenclature and sequences of these heavy and light chains is shown in FIG. 51 and FIG. 59) which when paired with the partner 10E8 chains bound to a peptide corresponding to the entire MPER of HIV-1 gp41 (FIGS. 50A and 50B, right panels). On a 6-HIV-1-isolate panel, up to ~5-fold increases in neutralization potency were observed (FIGS. 50E and 50F).

Figure 50A:
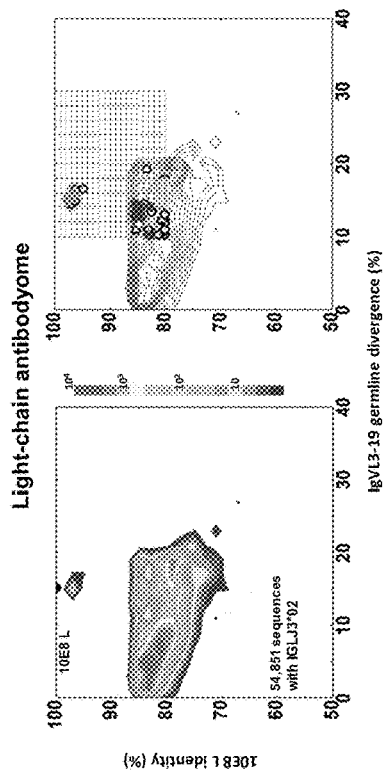
FIGS. 50A-50F are a series of charts illustrating identification of somatic variants of antibody 10E8 by deep sequencing and grid sampling. (A) 10E8-identity/divergence plots of donor N152 heavy-chain antibodyome (left), with grid sampling (right). Identity to 10E8 is shown on the vertical axis, and divergence from germline V-gene origin is plotted on the horizontal axis, with frequency of antibodies shown as a heat map. Grid sampling is shown, with selected antibodies that either did not express or bind to MPER in hollow circles and with selected antibodies that did bind in solid circles, shaded according to their phylogenetic distance from 10E8 in (C). (B) 10E8-identity/divergence plots of donor N152 light-chain antibodyome (left), with grid sampling (right). Axes and shading are the same as in (A). (C/D) Phylogenetic trees of grid-identified variant for heavy chain (C) and light chain (D). (E-F) Neutralization of 10E8 and 10E8 variants, assessed in duplicate on 6 HIV-1 isolates for heavy chain variants (E) and light chain variants (F). The average IC50s of gVRC-H1$_{dN152}$:10E8L and gVRC-H11$_{dN152}$:10E8L was roughly 6-fold improved over the original template 10E8. Variants are arranged and named by their genetic distance from 10E8, and shaded relative to their phylogenetic distance.
Figure 50B:
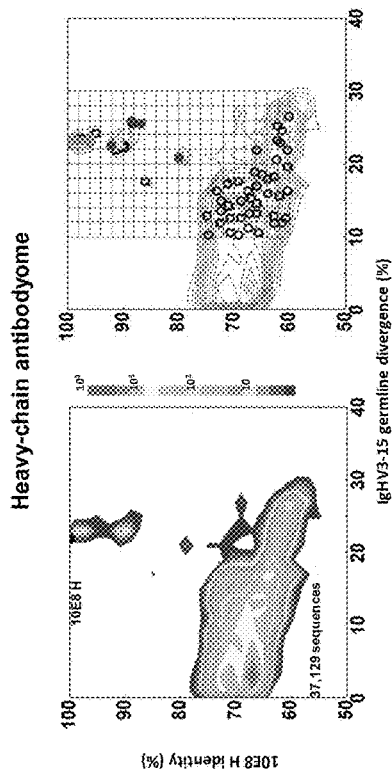

The functional 10E8 heavy chains derived from three distinct islands in the identity/divergence plots (FIG. 50A), and exhibited sequences and mutational patterns consistent with a common clonal origin (FIG. 51A). Mutations clustered in CDR H1 and H3, and also in the first, third and fourth framework regions (FR1, FR3 and FR4). The most divergent sequence, gVRC-H11$_{dN152}$, had 25 amino acid changes, corresponding to 19.1% difference from the wild-type 10E8 heavy chain. The functional 10E8 light chains derived from several regions of the identity/divergence plots, including a single distinct island and several regions overlapping the primary light chain population (FIG. 50B). Like heavy chain, the functional light chains exhibited mutational patterns consistent with a common clonal origin (FIG. 51C). Mutations clustered in CDR L1 and CDR L2 regions, and all of the framework regions. The most divergent sequence, gVRC-L23$_{dN152}$, had 33 amino acid changes, corresponding to 30.3% difference from the wild-type 10E8 light chain.

Although functional, the 10E8 variants reconstituted with 10E8 wild-type complementary chains do not represent natural pairs. A known drawback of the deep sequencing approach to antibody characterization is that separate sequencing reactions are required for heavy and light chains, and critical information related to natural ontogeny and functional phenotype is lost. Therefore, an evolution-based analysis was performed to provide sufficient information to recapitulate approximate natural pairings. The maturation/evolution of heavy and light chains should be linked because of their physical association as proteins, the presence of their evolving genes in the same cells subject to the same enzymatic mutation processes, and the requirement for cooperative structural change in response to the same immunogen. Furthermore, the sampling of paired heavy and light chains in a single cDNA library of mRNA population of antibody transcripts should be highly correlated because they originate from the same cells. In principle, this similarity in sampling should lead to correlations in frequencies of corresponding heavy- and light-chain branches of phylogenetic trees.

Figure 50C:
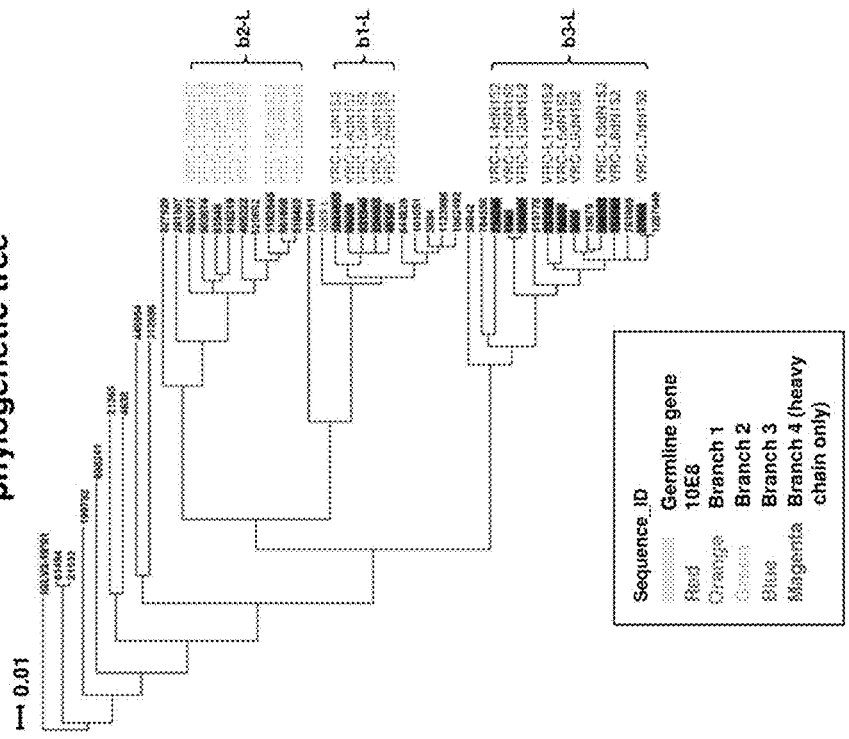
Figure 50D:
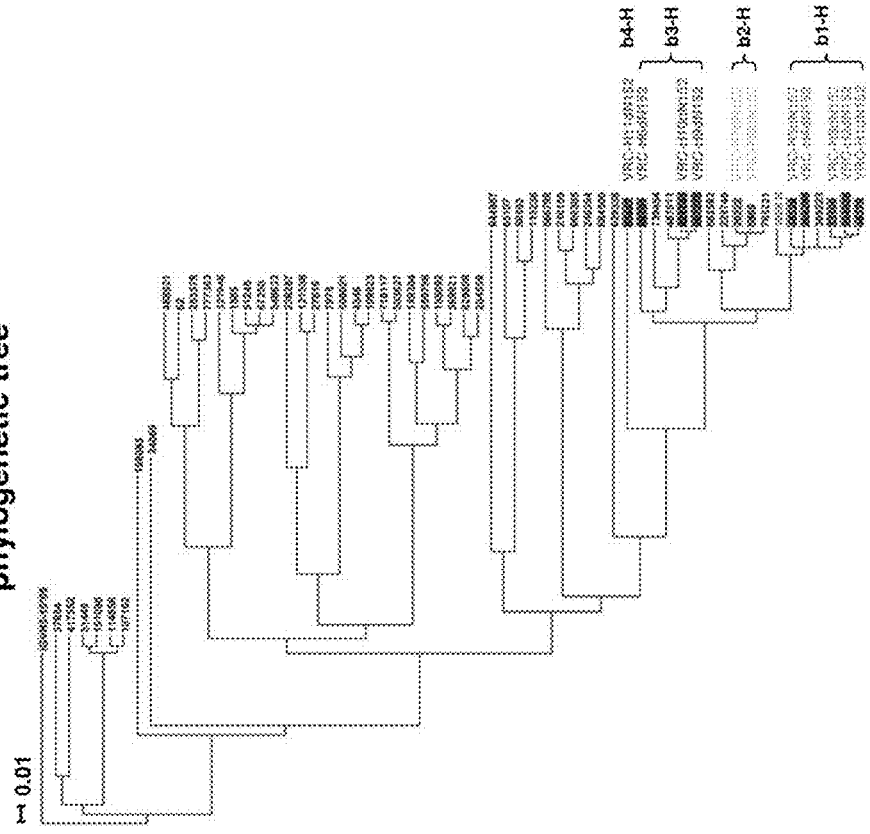
Figure 50E:
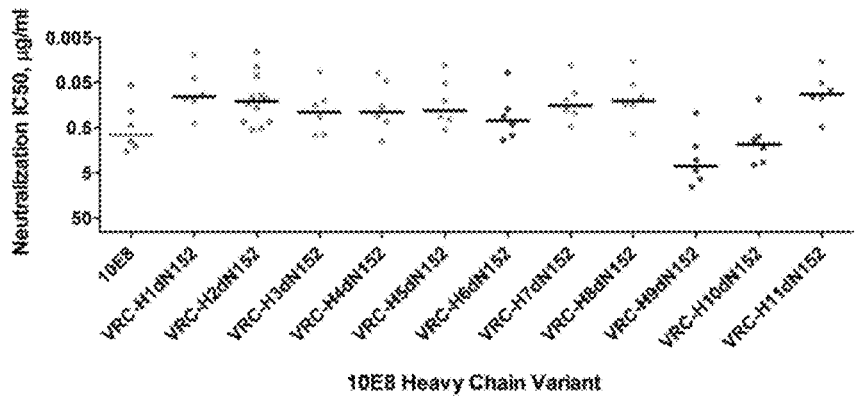
Figure 50F:
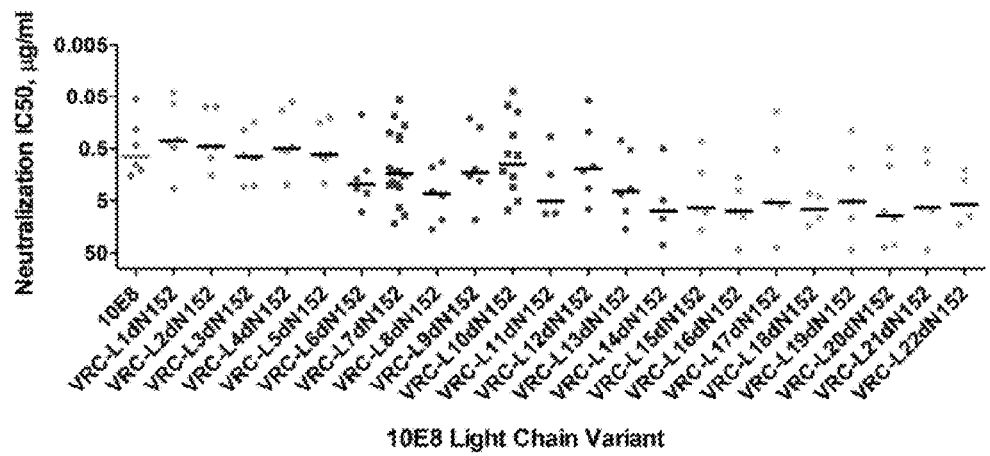

Phylogenetic analysis of the grid-selected experimentally-tested 10E8-heavy and -light chains found most of the neutralizing antibodies to populate three branches, close to and including the template 10E8 (FIGS. 50C and 50D). Branch b1-H for the heavy chain (or b1-L for the light chain) contained 10E8, branch b2-H (b2-L) was the closest branch to b1-H, and branch b3-H (b3-L) was the next closest branch. A single neutralizing sequence (gVRCH11$_{dN152}$) occupied a more distant branch (b4-H). Because 454 pyrosequencing produces on average about 5 errors per variable antibody domain, the most potent antibody from each branch was selected as representative, as the most functional antibody is likely to have the least 454-error-impaired function. Twelve antibodies were reconstituted, including a complete matrix of heavy-/light-chain pairing from the 4 heavy chain branches and the 3 light chain branches (FIG. 52A). 11 out of the 12 reconstituted antibodies expressed sufficient levels of IgG to assess neutralization, which was done on a panel of five HIV-1 isolates. All 11 expressed antibodies were neutralizing Heavy- and light-chain pairings that matched phylogenetic distance from 10E8 (e.g. b1-H to b1-L, b2-H to b2-L, and b3-H to b3-L), were slightly more potent on average than mismatched pairings, but the different was not statistically significant (FIG. 52B).

The reactivity of matched and mismatched pairing with auto-antigens was also tested. Notably, the matched pairing showed significantly lower Hep2 Staining (p=0.049) (FIG. 52C).

The results show with 10E8 and donor N152 (i) how identity/divergence-grid sampling can be used to identify somatic variants, (ii) how phylogenetic tree architecture can be used to approximate natural pairings, and (iii) that antibodies paired by phylogenetic matching show less auto-reactivity. Such reduced auto-reactivity is likely related to in vivo selection that natural antibodies undergo. With an antibody like 10E8, which may mechanistically be more prone to autoreactivity than other antibodies, such recapitulation of natural pairing may be useful. Although natural pairings are lost with deep sequencing, the above suggests that it is possible to approximate them using topological similarities between heavy and light chain phylogenetic trees. Thus, it may be possible to use phylogenetic similarity or lineage analysis as sieving methods, as these provide an exclusively computational means to identify somatic variants.

(5) Additional Variants and Combinations

Figure 56:
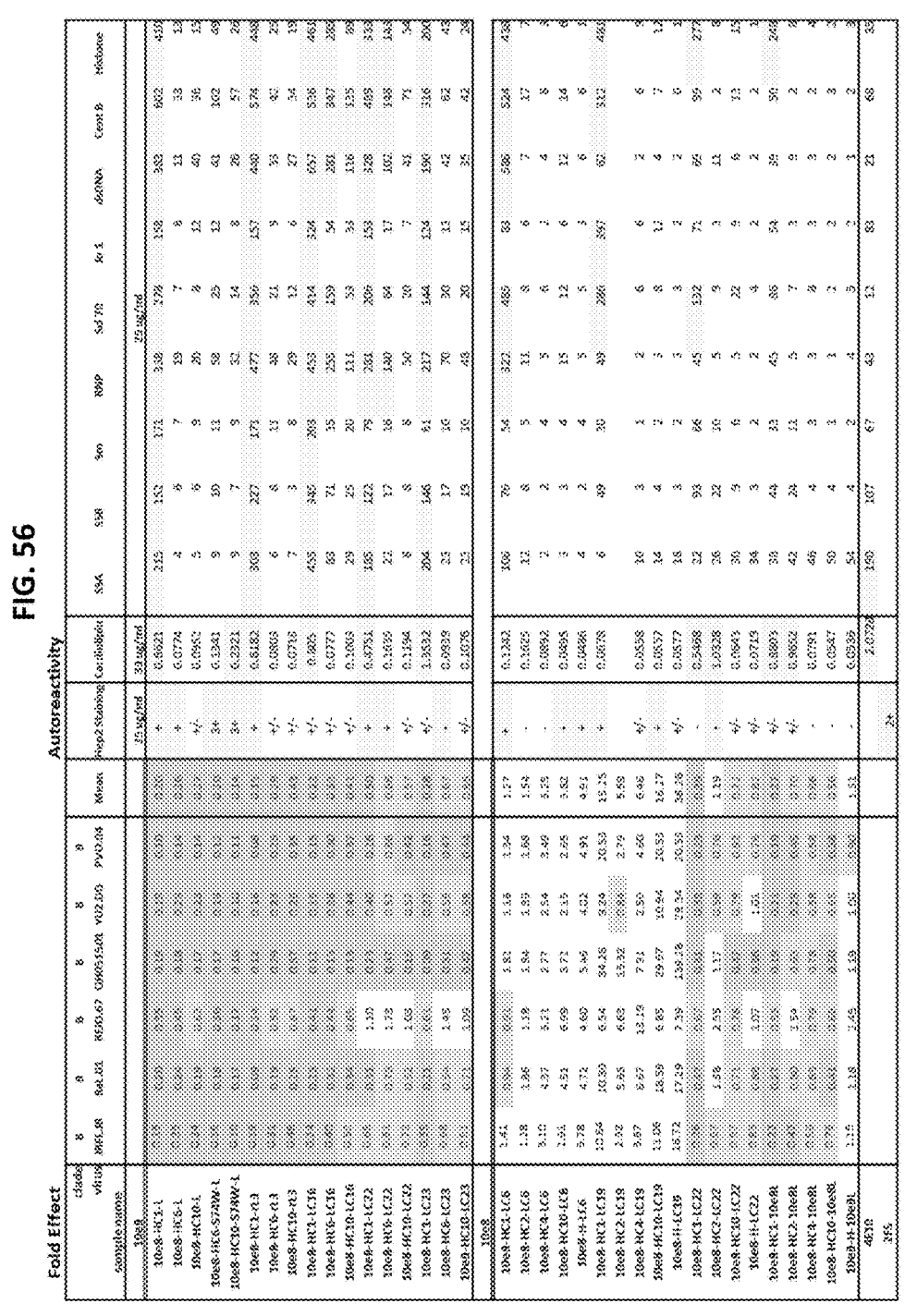
Figure 57:
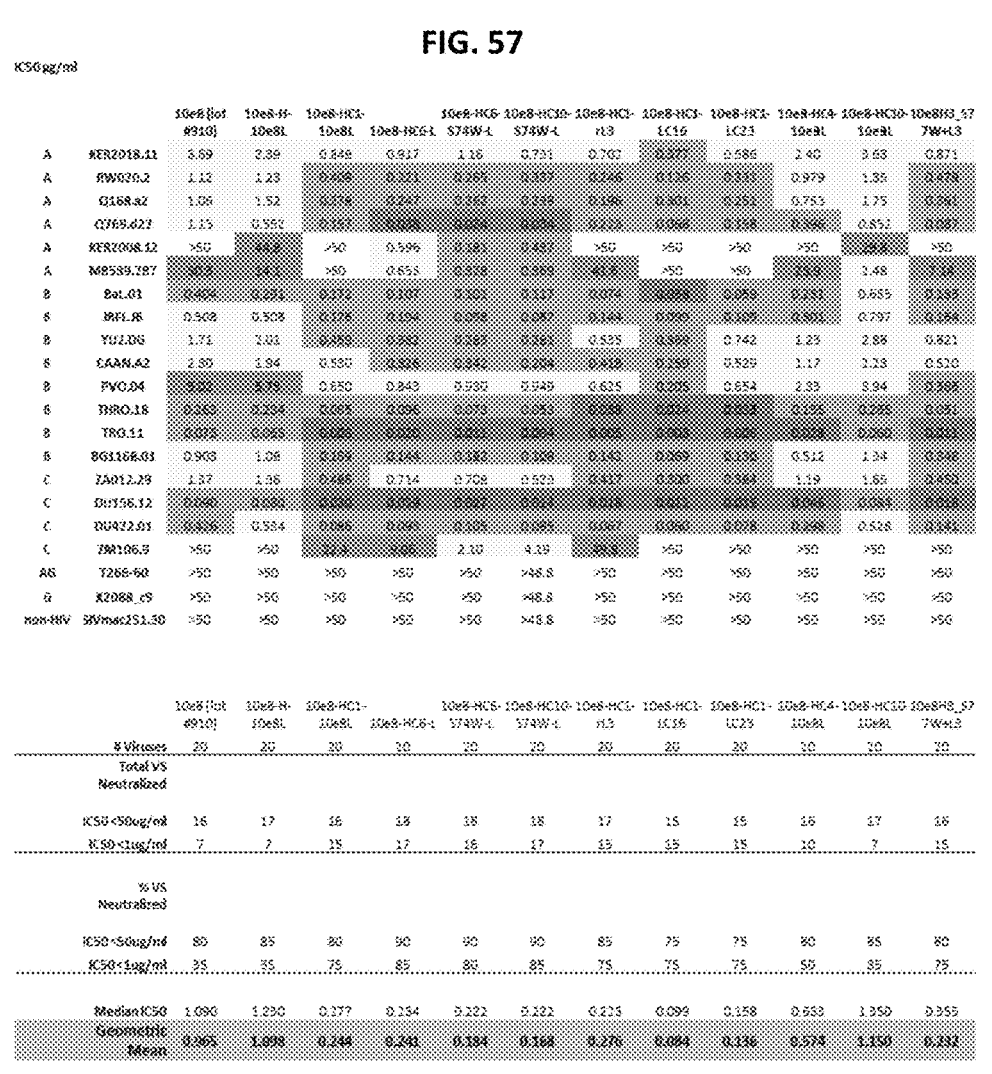

Additional combinations of the identified heavy and light chains, as well as the identified heavy and light chain variants were generated to test for neutralization and auto-reactivity. Combinations of certain heavy and light chains are indicated in FIGS. 53-54, including combinations based on neutralization in the context of the wild-type 10E8 complement chain, as well as combinations based on phylogenetic pairing. The nomenclature and sequence information for these pairings is shown in FIG. 59, except for "rL3" which corresponds to the 10E8gL03 light chain germline revertant shown in FIG. 47 and listed as SEQ ID NO: 149. Neutralization values (IC50 in µg/ml) against a six virus panel are presented in FIGS. 55A-55C, and autoreactivity values are presented in FIG. 56. Neutralization values (IC50 in µg/ml) against a twenty virus panel are presented in FIG. 57. The results indicate several heavy and light chain pairings that show increased neutralization activity compared to wild-type 10E8, but do not have increased autoactivity, including the pairing of heavy chain HC6 (gVRC-H2dn152; SEQ ID NO: 154) and light chain 10E8gL03 (rL3; SEQ ID NO: 152).

Figure 58B:
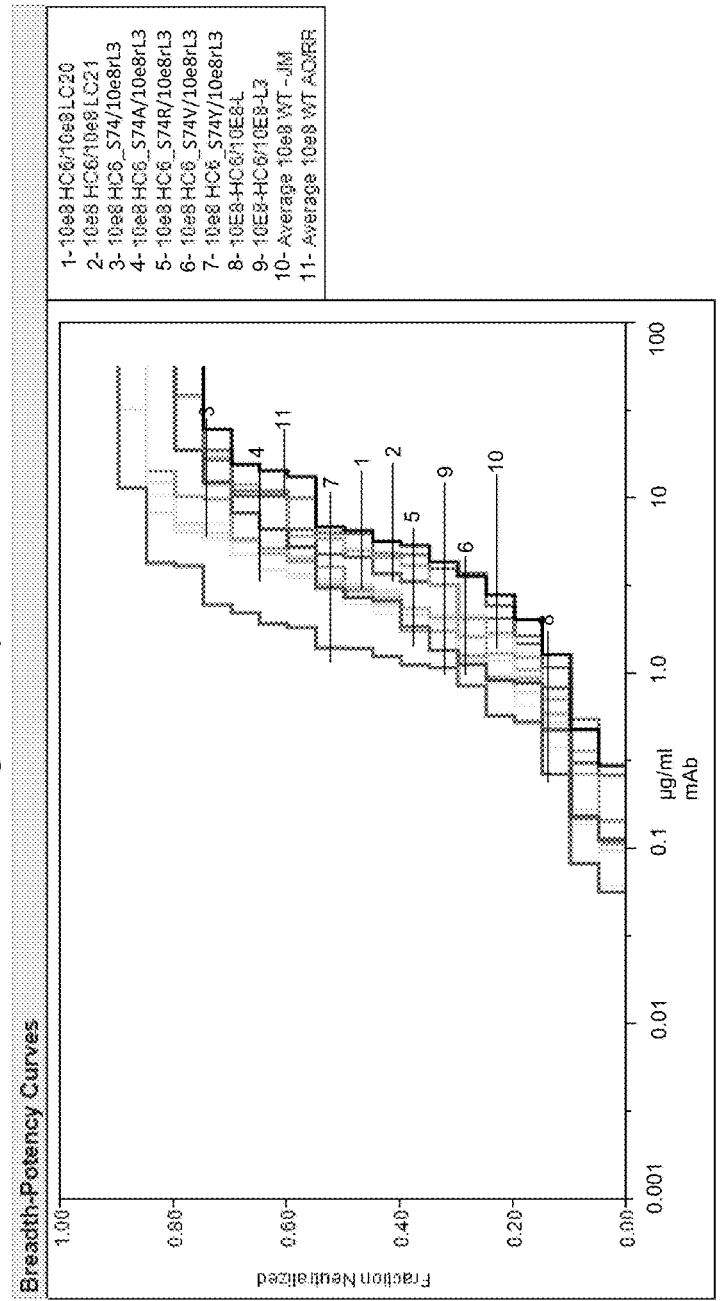

Further heavy chain variants were developed and complemented with 10E8 light chain or 10E8 light chain variants and tested for neutralization activity (see FIGS. 58A and 58B). The serine residue at position 74 (Kabat numbering) of the 10E8 variant heavy chain HC6 (gVRC-H2dn152; SEQ ID NO: 154) was additionally mutated to alanine, arginine, valine or tyrosine. The sequences of these variants are provided as SEQ ID NO: 189 (HC6 S74A), SEQ ID NO: 190 (HC6 S74R), SEQ ID NO: 191 (HC6 S74V), SEQ ID NO: 192 (HC6 S74Y). These 10E8 variant heavy chains were complemented with the "rL3" 10E8 light chain variant (10E8gL03; SEQ ID NO: 152) and the resulting antibody was tested for neutralization activity against a panel of 20 HIV viruses, including 6, 8, 4, 1 and 1 viruses from clades A, B, C, AG, and G, respectfully. Neutralization assays were performed as described in Example 1, and a graph summarizing the results of these assays is presented in FIG. 58A (showing IC50 values) and FIG. 58B (showing IC80 values Additional heavy chain and light chain mutants were developed to produce gp41 binding antibodies with increased solubility, by reducing the number of solvent exposed hydrophobic residues. Residues that are not required for epitope recognition (based on 454 deep sequencing data, as well as structure based protein redesign) were selected for substitution with polar or charged residues. The following 10E8-like heavy and light chains were constructed (Kabat amino acid substitutions with reference to the HC6 (SEQ ID NO: 154) and rL3 (SEQ ID NO: 152) heavy and light chains, respectively)

Light Chain:
10E8gL03_hp_L01 (SEQ ID NO: 197; I44K)
10E8gL03_hp_L02 (SEQ ID NO: 198; S2Y, V10T, L14A, I44V, L106P)
10E8gL03_hp_L03 (SEQ ID NO: 199; V10T, L14A, I44K, L106P)

Heavy Chain:
HC6_S77Y_hp_H01 (SEQ ID NO: 200; L18Q, S74Y)
HC6_S77Y_hp_H02 (SEQ ID NO: 201; L72D, S74Y, I75K, F77T, M84T)
HC6_S77Y_hp_H03 (SEQ ID NO: 202; L18Q, W55K, S74Y, M84T)
HC6_S77Y_hp_H04 (SEQ ID NO: 203; L18Q, W55K, L72D, S74Y, I75K, F77T, M84T)

A partial germline revertant construct of HC6 was also constructed: HC6rH03S77Y (SEQ ID NO: 204; S23A, N73D, S74Y, E81Q, N82bS, R83K, M84T, S87T, L89V, F91Y, R105Q)

Additional 10E8 light chain variants were constructed. These variants include variants of the 10E8 wildtype light chain, the 10E8 light chain partial germline revertant rL3, and the three light chain solubility mutants above. These constructs contain a single mutation R23Q that removes a potential integrin binding site. Q is the germline identity at position 23 in the 10E8 light chain. The additional mutants are set forth as: 10E8_L_R23Q (SEQ ID NO: 205); 10E8gL03_R23Q (SEQ ID NO: 206); 10E8gL03_hp_L01_R23Q (SEQ ID NO: 207); 10E8gL03_hp_L02_R23Q (SEQ ID NO: 208); 10E8gL03_hp_L03_R23Q (SEQ ID NO: 209).

The person of ordinary skill in the art will appreciate that the 10E8 or any of the 10E8 variant light chain variable regions disclosed herein can optionally include the R23Q substitution.

(6) Summary of 10E8 Mutations.

The 10E8 substitutions described above are summarized in the tables given as FIGS. 60A and 60B (heavy chain substitutions) and FIGS. 61A and 61B (light chain substitutions).

It will be apparent that the precise details of the methods or compositions described may be varied or modified without departing from the spirit of the described embodiments. We claim all such modifications and variations that fall within the scope and spirit of the claims below.

---

We claim:

1. A method of inhibiting an HIV-1 infection in a subject, comprising administering to the subject an effective amount of a monoclonal antibody, the monoclonal antibody comprising:
   a heavy chain variable region comprising a heavy chain complementarity determining region (HCDR)1, a HCDR2, and a HCDR3 comprising amino acids 26-33, 51-60, and 99-120 of SEQ ID NO: 1, respectively; and
   a light chain variable region comprising a light chain complementarity determining region (LCDR)1, a LCDR2, and a LCDR3, comprising amino acids 26-31, 49-51, and 88-99 of SEQ ID NO: 2, respectively;
   wherein the monoclonal antibody specifically binds gp41 and neutralizes HIV-1.

2. The method of claim 1, wherein the heavy chain variable region comprises the amino acid sequence set forth as one of SEQ ID NOs: 1, 3, 5, 149, 154, 189-192, 200-201, or 204, and further comprises at most ten amino acid substitutions in framework regions of the heavy chain variable region.

3. The method of claim 1, wherein the heavy chain variable region comprises the amino acid sequence set forth as SEQ ID NO: 11, wherein $X_1$ is Q or R, $X_2$ is V or A, $X_3$ is S or Y, and $X_4$ is T or I.

4. The method of claim 1, wherein the heavy chain variable region comprises the amino acid sequence set forth as one of SEQ ID NOs: 1, 3, 5, 149, 154, 189-192, 200-201, or 204.

5. The method of claim 1, wherein the light chain variable region comprises the amino acid sequence set forth as one of SEQ ID NOs: 2, 4, 150-152, or 164-168, and further comprises at most ten amino acid substitutions in framework regions of the light chain variable region.

6. The method of claim 1, wherein the light chain variable region comprises the amino acid sequence set forth as one of SEQ ID NOs: 2, 4, 150-152, or 164-168.

7. The method of claim 1, wherein the heavy chain variable region comprises the amino acid sequence set forth as one of SEQ ID NOs: 1, 3, 5, 149, 154, 189-192, 200-201, or 204, and the light chain variable region comprises the amino acid sequence set forth as one of SEQ ID NOs: 2, 4, 150-152, or 164-168.

8. The method of claim 1, wherein:
   the heavy chain variable region comprises the amino acid sequence set forth as SEQ ID NO: 154, and the light chain variable region comprises the amino acid sequence set forth as SEQ ID NO: 152; or
   the heavy chain variable region comprises the amino acid sequence set forth as SEQ ID NO: 192, and the light chain variable region comprises the amino acid sequence set forth as SEQ ID NO: 152.

9. The method of claim 1, wherein the heavy chain variable region comprises the amino acid sequence set forth as SEQ ID NO: 1.

10. The method of claim 1, wherein the light chain variable region comprises the amino acid sequence set forth as SEQ ID NO: 2.

11. The method of claim 1, wherein the heavy chain variable region comprises the amino acid sequence set forth as SEQ ID NO: 1 and further comprises at most ten amino acid substitutions in framework regions of the heavy chain variable region, and the light chain variable region comprises the amino acid sequence set forth as SEQ ID NO: 2 and further comprises at most ten amino acid substitutions in framework regions of the light chain variable region.

12. The method of claim 1, wherein the heavy chain variable region comprises the amino acid sequence set forth as SEQ ID NO: 1, and the light chain variable region comprises the amino acid sequence set forth as SEQ ID NO: 2.

13. The method of claim 1, wherein the antibody is an IgG, IgM or IgA.

14. The method of claim 1, wherein the antibody neutralizes at least 98% of the HIV-1 isolates listed in FIGS. 17C-17F with an inhibitory concentration (IC50) of less than 50 µg/ml.

15. The method of claim 1, wherein the antibody is a bispecific antibody.

16. The method of claim 1, wherein the method is a method for treating an HIV-1 infection, and wherein the subject has acquired immune deficiency syndrome (AIDS).

17. The method of claim 1, further comprising administering to the subject an additional anti-viral agent.

18. The method of claim 17, wherein the additional antiviral agent comprises a nucleoside analog reverse-transcriptase inhibitor, a nucleotide reverse transcriptase inhibitor, a non-nucleoside reverse transcriptase inhibitor, a protease inhibitor, an entry or fusion inhibitor, a maturation inhibitor, or a broad spectrum inhibitor or a combination thereof.

19. The method of claim 1, further comprising administering to the subject one or more additional antibodies, wherein the additional antibodies specifically bind to gp120 and/or gp41 and neutralize HIV-1.

20. A method of inhibiting HIV-1 infection in a subject, comprising administering to the subject an effective amount of an antigen binding fragment of a monoclonal antibody, the antigen binding fragment comprising:
a heavy chain variable region comprising a heavy chain complementarity determining region (HCDR)1, a HCDR2, and a HCDR3 comprising amino acids 26-33, 51-60, and 99-120 of SEQ ID NO: 1, respectively; and
a light chain variable region comprising a light chain complementarity determining region (LCDR)1, a LCDR2, and a LCDR3, comprising amino acids 26-31, 49-51, and 88-99 of SEQ ID NO: 2, respectively;
wherein the antigen binding fragment specifically binds gp41 and neutralizes HIV-1.

21. The method of claim 20, wherein the antigen binding fragment is a Fab fragment, a Fab' fragment, a F(ab)'2 fragment, a single chain Fv protein (scFv), or a disulfide stabilized Fv protein (dsFv).

22. The method of claim 20, wherein the heavy chain variable region comprises the amino acid sequence set forth as SEQ ID NO: 1.

23. The method of claim 20, wherein the light chain variable region comprises the amino acid sequence set forth as SEQ ID NO: 2.

24. The method of claim 20, wherein the heavy chain variable region comprises the amino acid sequence set forth as SEQ ID NO: 1 and further comprises at most ten amino acid substitutions in framework regions of the heavy chain variable region, and the light chain variable region comprises the amino acid sequence set forth as SEQ ID NO: 2 and further comprises at most ten amino acid substitutions in framework regions of the light chain variable region.

25. The method of claim 20, wherein the heavy chain variable region comprises the amino acid sequence set forth as SEQ ID NO: 1, and the light chain variable region comprises the amino acid sequence set forth as SEQ ID NO: 2.

* * * * *